(12) United States Patent
Oi et al.

(10) Patent No.: US 7,034,039 B2
(45) Date of Patent: Apr. 25, 2006

(54) FUSED HETEROCYCLIC COMPOUNDS

(75) Inventors: Satoru Oi, Nara (JP); Koji Ikedou, Himeji (JP); Koji Takeuchi, Chapel Hill, NC (US); Masaki Ogino, Nishinomiya (JP); Yoshihiro Banno, Suita (JP); Hiroyuki Tawada, Takatsuki (JP); Taihei Yamane, Takarazuka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 165 days.

(21) Appl. No.: 10/470,805

(22) PCT Filed: Feb. 1, 2002

(86) PCT No.: PCT/JP02/00831

§ 371 (c)(1),
(2), (4) Date: Aug. 1, 2003

(87) PCT Pub. No.: WO02/062764

PCT Pub. Date: Aug. 15, 2002

(65) Prior Publication Data

US 2004/0082607 A1    Apr. 29, 2004

(30) Foreign Application Priority Data

Feb. 2, 2001  (JP) .............................. 2001-027349
Sep. 25, 2001 (JP) .............................. 2001-292388
Dec. 14, 2001 (JP) .............................. 2001-382232

(51) Int. Cl.
*C07D 217/02*   (2006.01)
*A61K 31/47*    (2006.01)

(52) U.S. Cl. ..................... 514/307; 546/141
(58) Field of Classification Search ............... 546/141; 514/307
See application file for complete search history.

(56) References Cited

U.S. PATENT DOCUMENTS 6,090,786 A    7/2000   Augustyns et al. ........... 514/19

FOREIGN PATENT DOCUMENTS

| DE | 287 032  | 2/1991 |
| EP | 0 585 913 | 3/1994 |
| EP | 0 634 402 | 1/1995 |
| WO | 98/38168  | 3/1998 |
| WO | 98/18763  | 5/1998 |
| WO | 02/24655  | 3/2002 |

OTHER PUBLICATIONS

K. Unverferth et al., "Synthesis and anticonvulsant activity of 3-carbamoyl-4-arylisoquinolin-1(2H)-ones", Arch. Phar. vol. 324, pp. 809-814, 1991, (with English translation).

Y. Ikeura et al., "Potent NK₁ Receptor Antagonists: Synthesis and Antagonistic Activity of various Heterocycles with an N-[3,5-Bis (trifluoromethyl)benzyl]-N-methylcarbamoyl Substituent", Chem. Pharm. Bull., vol. 45, No. 10, pp. 1642-1652, 1997.

H. Natsugari et al., "Novel, Potent, and Orally Active Susbstance P Antagonists: Synthesis and Antagonist Activity of N-Benzylcarboxamide Derivatives of Pyrido[3,4-b]pyridine", J. Med. Chem., vol. 38, pp. 3106-3120, 1995.

*Primary Examiner*—Zinna Northington Davis
(74) *Attorney, Agent, or Firm*—Wenderoth, Lind & Ponack, L.L.P.

(57) ABSTRACT

The present invention provides a compound of the formula: wherein ring A is an optionally substituted 5 to 10-membered aromatic ring; $R^1$ and $R^2$ are the same or different and each is an optionally substituted hydrocarbon group or an optionally substituted heterocyclic group; X is a bond and the like; and L is a divalent hydrocarbon group, and a salt thereof, except 3-(aminomethyl)-2,6,7-trimethyl-4-phenyl-1(2H)-isoquinolinone, 3-(aminomethyl)-2-methyl-4-phenyl-1(2H)-isoquinolinone, 3-(aminomethyl)-6-chloro-2-methyl-4-phenyl-1(2H)-isoquinolinone and 3-(aminomethyl)-2-isopropyl-4-phenyl-1(2H)-isoquinolinone. The compound shows a superior peptidase-inhibitory activity and is useful as an agent for the prophylaxis or treatment of diabetes and the like.

(I)

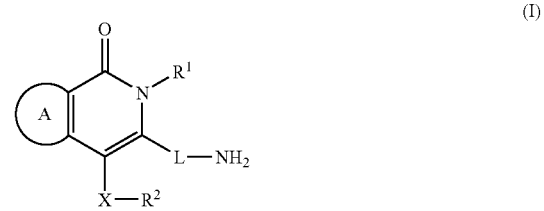

21 Claims, No Drawings

FUSED HETEROCYCLIC COMPOUNDS

TECHNICAL FIELD

The present invention relates to a novel fused heterocyclic compound having a peptidase (preferably dipeptidyl dipeptidase IV) inhibitory activity, which is useful as a prophylactic or therapeutic agent of diabetes and the like.

BACKGROUND ART

Peptidase is known to relate to various diseases. Dipeptidyl dipeptidase IV (hereinafter sometimes to be abbreviated as DPP-IV), which is one kind of peptidases, is serine protease that specifically binds with a peptide containing proline (or alanine) at the 2nd from the N terminal and cleaves the C-terminal side of the proline (or alanine) to produce dipeptide. DPP-IV has been shown to be the same molecule as CD26, and reported to be also involved in the immune system. While the role of DPP-IV in mammals has not been entirely clarified, it is considered to play an important role in the metabolism of neuropeptides, activation of T cells, adhesion of cancerous cells to endothelial cells, invasion of HIV into cells and the like. Particularly, from the aspect of glycometabolism, DPP-IV is involved in the inactivation of GLP-1 (glucagon-like peptide-1) and GIP (Gastric inhibitory peptide/Glucose-dependent insulinotropic peptide), which are incretins. With regard to GLP-1, moreover, its half-life in plasma is as short as 1–2 minutes, and GLP-1 is known to be degraded by DPP-IV and markedly lose its physiological activity because GLP-1 (9-36) amide, which is a degradation product by DPP-IV, acts on GLP-1 receptor as an antagonist. It is also known that suppression of degradation of GLP-1 by inhibiting activity of DPP-IV leads to potentiation of physiological activity that GLP-1 shows, such as glucose concentration-dependent insulinotropic effect and the like. From these facts, a compound having a DPP-IV inhibitory activity is expected to show effect on impaired glucose tolerance, postprandial hyperglycemia and fasting hyperglycemia observed in type I and type II diabetes and the like, , obesity or diabetic complications associated therewith and the like.

As therapeutic agents of diabetes now in use, a sulfonylurea, a biguanide, an α-glucosidase inhibitor and the like are known. While a sulfonylurea produce a potent hypoglycemic action, it sometimes causes serious hypoglycemia and requires attention during use. A biguanide easily causes lactic acidosis which is a relatively serious side effect. An α-glucosidase inhibitor delays digestion and absorption of glucose in the gastrointestinal tract and suppresses increase in the blood glucose level after meal, but side effects of sense of distension, diarrhea and the like are problematic (JOSLIN'S DIABETES MELLITUS 13Th Edition 521–522).

Isoquinolone compounds are described in the following publications.

(1) JP-A-7-76573 describes a compound of the formula

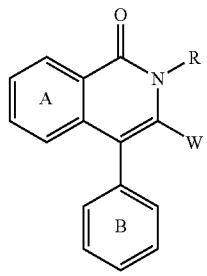

wherein ring A and ring B are optionally substituted benzene rings; Q is an oxygen atom or a sulfur atom; R is a hydrogen atom, an optionally substituted hydrocarbon group and the like; W is —$CH_2OH$, —$CH_2NHR^1$, — $CH_2CH_2NHR^1$ ($R^1$ is hydrogen atom or optionally substituted hydrocarbon group) and the like, as a starting material compound of a compound having a calcium antagonistic action and the like, wherein the specific examples are

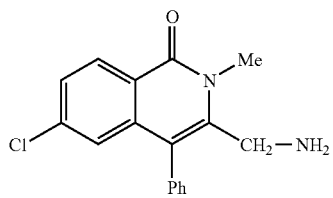

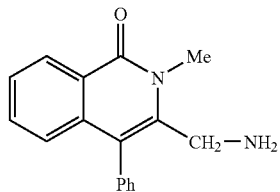

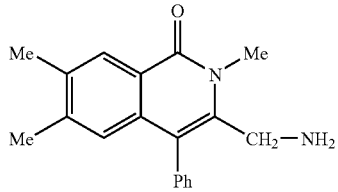

(2) Archiv der Pharmazie, vol. 324, pp. 809–814 (1991) describes a compound of the formula

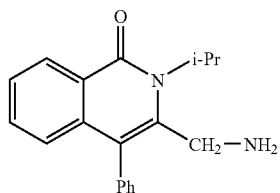

as a starting material compound of a compound having an anticonvulsant action.

(3) JP-A-7-10844 describes a compound of the formula

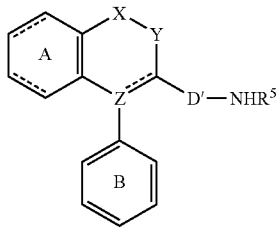

wherein ring A is optionally substituted; ring B is an optionally substituted benzene ring; one of X and Y is —NR$^1$— (R$^1$ is a hydrogen atom, an optionally substituted hydrocarbon group and the like), —O— or —S—, the other is —CO—, —CS— and the like; ===== is a single bond or a double bond; Z is a carbon atom and the like; D' is a C$_{1-3}$ alkylene group; and R$^5$ is a hydrogen atom or an optionally substituted hydrocarbon group] as a starting material compound of a compound having an acyl-CoA cholesterol acyl transferase (ACAT) inhibitory action and the like.

However, there is no report showing that these compounds have a peptidase (preferably DPP-IV) inhibitory activity.

There is a demand on the development of a compound having a peptidase (preferably DPP-IV) inhibitory activity, useful as a prophylactic or therapeutic drug of diabetes and the like and having superior properties in terms of efficacy, duration of action, specificity, low toxicity and the like.

SUMMARY OF THE INVENTION

The present inventors have first found that a compound of the formula

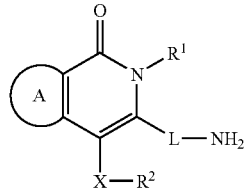

wherein
ring A is an optionally substituted 5 to 10-membered aromatic ring;
R$^1$ and R$^2$ are the same or different and each is an optionally substituted hydrocarbon group or an optionally substituted heterocyclic group;
X is a bond, —O—, —S—, —SO—, —SO$_2$— or —NR$^3$— (R$^3$ is a hydrogen atom or an optionally substituted hydrocarbon group); and
L is a divalent hydrocarbon group, and a salt thereof, which are characterized by the chemical structure where an amino group is bonded to a fused heterocycle via a divalent hydrocarbon group, have a superior peptidase (preferably DPP-IV) inhibitory activity and are useful as a prophylactic or therapeutic agent of diabetes and the like. Based on this finding, the present inventors have conducted intensive studies and completed the present invention.

Accordingly, the present invention relates to:
1) a compound of the formula (I) or a salt thereof except 3-(aminomethyl)-2,6,7-trimethyl-4-phenyl-1(2H)-isoquinolinone, 3-(aminomethyl)-2-methyl-4-phenyl-1(2H)-isoquinolinone, 3-(aminomethyl)-6-chloro-2-methyl-4-phenyl-1(2H)-isoquinolinone and 3-(aminomethyl)-2-isopropyl-4-phenyl-1(2H)-isoquinolinone,
2) the compound of 1), wherein the 5 to 10-membered aromatic ring for ring A is a benzene ring,
3) the compound of 1), wherein the ring A is a 5 to 10-membered aromatic ring optionally having 1 to 3 substituent(s) selected from
   a) a halogen atom,
   b) a nitro group,
   c) a cyano group,
   d) a C$_{1-3}$ alkylenedioxy group,
   e) a C$_{1-10}$ alkyl group or a C$_{2-10}$ alkenyl group, each optionally having 1 to 3 substituent(s) selected from a halogen atom, a hydroxy group, a carboxyl group, an alkoxycarbonyl group having 2 to 8 carbon atoms, a carbamoyl group, a cyano group, an amino group, an alkanoylamino group having 2 to 8 carbon atoms, an alkoxycarbonylamino group having 2 to 8 carbon atoms, an alkylsulfonylamino group having 1 to 8 carbon atoms,
   f) an optionally substituted hydroxy group,
   g) an acyl group,
   h) an optionally substituted amino group,
   i) an aryl group having 6 to 14 carbon atoms,
   j) an optionally substituted thiol group, and
   k) an optionally substituted heterocyclic group,
4) the compound of 1), wherein R$^1$ is an alkyl group having 1 to 10 carbon atom(s),
5) the compound of 1), wherein R$^1$ is an alkyl group having 4 to 10 carbon atoms,
6) the compound of 1), wherein X is a bond or —O—,
7) the compound of 1), wherein the divalent hydrocarbon group for L is an alkylene group having 1 to 10 carbon atom(s),
8) the compound of 1), wherein R$^2$ is an optionally substituted hydrocarbon group,
9) the compound of 1), wherein R$^2$ is an alkyl group having 1 to 10 carbon atom(s), an aryl group having 6 to 14 carbon atoms or an aralkyl group having 7 to 13 carbon atoms, each optionally having 1 to 3 substituent(s) selected from halogen atom, hydroxy group, nitro group, amino group, optionally halogenated alkyl group having 1 to 6 carbon atom(s), alkoxy group, having 1 to 6 carbon atom(s), aromatic heterocyclic group and cycloalkyl group having 3 to 10 carbon atoms,
10) the compound of 1), which is 2-[3-(aminomethyl)-4-butoxy-2-isobutyl-1-oxo-1,2-dihydro-6-isoquinolyl]-1,3-thiazole-4-carbonitrile, 2-[3-(aminomethyl)-4-butoxy-2-isobutyl-1-oxo-1,2-dihydro-6-isoquinolyl]-1,3-thiazole-4-carboxylic acid, 2-[3-(aminomethyl)-4-butoxy-2-isobutyl-1-oxo-1,2-dihydro-6-isoquinolyl]-1,3-thiazole-4-carboxamide, ethyl 2-[3-(aminomethyl)-4-butoxy-2-isobutyl-1-oxo-1,2-dihydro-6-isoquinolyl]-1,3-thiazole-4-carboxylate, (E)-3-[3-(aminomethyl,)-4-butoxy-2-isobutyl-1-oxo-1,2-dihydro-6-isoquinolyl]-2-propenamide, (E)-3-[3-(aminomethyl)-2-isobutyl-4-phenyl-1-oxo-1,2-dihydro-6-isoquinolyl]-2-propenamide, 3-(aminomethyl)-2-isobutyl-1-oxo-4- phenyl-1,2-dihydro-6-isoquinolinecarboxamide, 2-[[3-(aminomethyl)-2-isobutyl-4-phenyl-1-oxo-1,2-dihydro-6-isquinolyl]oxy]acetamide, or a salt thereof, 11) a crystal of 2-[3-(aminomethyl)-4-butoxy-2-isobutyl-1-oxo-1,2-dihydro-6-isoquinolyl]-1,3-thiazole-4-carbonritrile or a salt thereof, 12) a crystal of 2-[3-(aminomethyl)-4-butoxy-2-isobutyl-1-oxo-1,2-dihydro-6-isoquinolyl]-1,3-thiazole-4-carboxamide or a salt thereof, 13) a crystal of 2-[3-(aminomethyl)-4-butoxy-2-isobutyl-1-oxo-1,2-dihydro-6-isoquinolyl]-1,3-thiazole-4-carboxamide or a salt thereof, 14) a crystal of ethyl 2-[3-(aminomethyl)-4-butoxy-2-isobutyl-1-oxo-1,2-dihydro-6-isoquinolyl]-1,3-thiazole-4-carboxylate or a salt thereof, 15) a crystal of (E)-3-[3-(aminomethyl)-4-butoxy-2-isobutyl-1-oxo-1,2-dihydro-6-isoquinolyl]]-2-propenamide or a salt thereof, 16) a crystal of (E)-3-[3-(aminomethyl)-2-isobutyl-4-phenyl-1-oxo-1,2-dihydro-6-isoquiniolyl]]-2-propenamide or a salt thereof, 17) a crystal of 3-(aminomethyl)-2-isobutyl-1-oxo-4-phenyl-1,2-dihydro-6-isoquinolinecarboxamide or a salt thereof, 18) a crystal of 2-[[3-(aminomethyl)-2-isobutyl-4-phenyl-1-oxo-1,2-dihydro-6-isoquinolyl]oxy]acetamide or a salt thereof, 19) a pharmaceutical agent containing a compound of the formula (I) or a salt thereof, 20) a pharmaceutical agent comprising the pharmaceutical agent of 19) above in combination with at least one member selected from an insulin preparation, an insulin sensitizer, an α-glucosidase inhibitor, a biguanide and an insulin secretagogue, 21) an agent for prophylaxis or treatment of diabetes, which contains a compound of the formula (I), a salt thereof or a prodrug thereof, 22) an agent for prophylaxis or treatment of diabetic, complications, which contains a compound of the formula (I), a salt thereof or a prodrug thereof, 23) an agent for prophylaxis or treatment of impaired glucose tolerance, which contains a compound of the formula (I), a salt thereof or a prodrug thereof, 24) an agent for prophylaxis or treatment of obesity, which contains a compound of the formula (I), a salt thereof or a prodrug thereof, 25) a peptidase inhibitor containing a compound of the formula (I), a salt thereof or a prodrug thereof, 26) the inhibitor, of 25) above, wherein the peptidase is dipeptidyl dipeptidase IV, 27) a method of prophylaxis or treatment of diabetes in a mammal, which method comprising administering a compound of the formula (I), a salt thereof or a prodrug thereof to the mammal, 28) a method of prophylaxis or treatment of diabetic complications in a mammal, which method comprising administering a compound of the formula (I), a salt thereof or a prodrug thereof to the mammal, 29) a method of prophylaxis or treatment of impaired glucose tolerance in a mammal, which method comprising administering a compound of the formula(I), a salt thereof or a prodrug thereof to the mammal, 30) a method of prophylaxis or treatment of obesity in a mammal, which method comprising administering a compound of the formula (I), a salt thereof or a prodrug thereof to the mammal, 31) a method of inhibiting peptidase in a mammal, which method comprising administering a compound of the formula (I), a salt thereof or a prodrug thereof to the mammal, 32) use of a compound of the formula (I), a salt thereof or a prodrug thereof for production of an agent for prophylaxis or treatment of diabetes, 33) use of a compound of the formula (I), a salt thereof or a prodrug thereof for production of an agent for prophylaxis or treatment of diabetic complications, 34) use of a compound of the formula (I), a salt thereof or a prodrug thereof for production of an agent for prophylaxis or treatment of impaired glucose tolerance, 35) use of a compound of the formula (I), a salt thereof or a prodrug thereof for production of an agent for prophylaxis or treatment of obesity, 36) use of a compound of the formula (I), a salt thereof or a prodrug thereof for production of a peptidase inhibitor, 37) a production method of a compound of the formula

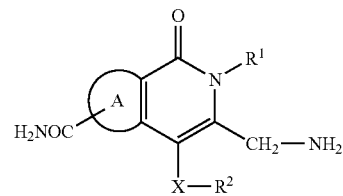

wherein
ring A is a 5 to 10-membered aromatic ring;
$R^1$ and $R^2$ are the same or different and each is an optionally substituted hydrocarbon group or an optionally substituted heterocyclic group; and
X is a bond, —O—, —S—, —SO—, —SO$_2$— or —NR$^3$— ($R^3$ is a hydrogen atom or an optionally substituted hydrocarbon group),
or a salt thereof, which method comprises subjecting a compound of the formula

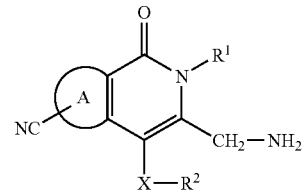

wherein the symbols are as defined above, or a salt thereof, to hydrolysis, 38) a compound of the formula

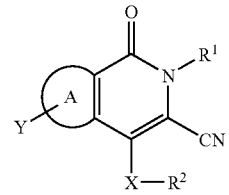

wherein
ring A is a 5 to 10-membered aromatic ring;
$R^1$ and $R^2$ are the same or different and each is an optionally substituted hydrocarbon group or an optionally substituted heterocyclic group;
X is a bond, —O—, —S—, —SO—, —SO$_2$— or —NR$^3$— ($R^3$ is a hydrogen atom or an optionally substituted hydrocarbon group); and
Y is a halogen atom,
or a salt thereof,
39) a compound of the formula $$\underset{Y}{\overset{}{\bigg\langle}} \overset{O}{\underset{X-R^2}{\overset{}{A}}} \overset{R^1}{\underset{O}{\overset{N}{\diagup}}} -CN$$

wherein
ring A is a 5 to 10-membered aromatic ring;
$R^1$ and $R^2$ are the same or different and each is an optionally substituted hydrocarbon group or an optionally substituted heterocyclic group;
X is a bond, —O—, —S—, —SO—, —SO$_2$— or, —NR$^3$— ($R^3$ is a hydrogen atom or an optionally substituted hydrocarbon group); and
Y is a halogen atom,
or a salt thereof, and the like.

DETAILED DESCRIPTION OF THE INVENTION

Each symbol of the formula (I) is described in detail in the following.

The "5 to 10-membered aromatic ring" of the "optionally substituted 5 to 10-membered aromatic ring" for ring A is, for example, a 5 to 10-membered aromatic hydrocarbon ring or a 5 to 10-membered aromatic heterocycle.

Preferable examples of the 5 to 10-membered aromatic hydrocarbon ring include benzene, naphthalene and the like.

Preferable examples of the 5 to 10-membered aromatic heterocycle include a 5 to 10-membered aromatic heterocycle containing 1 to 4 heteroatom(s) selected from an oxygen atom, a sulfur atom and a nitrogen atom as a ring-constituting atom, besides carbon atoms, such as furan, thiophene, pyrrole, oxazole, isoxazole, thiazole, isothiazole, imidazole, pyrazole, 1,2,3-oxadiazole, furazan, 1,2,3-thiadiazole, 1,2,3-triazole, pyridine, pyridazine, pyrimidine, triazine, benzofuran, isobenzofuran, benzo[b]thiophene, indole, isoindole, 1H-indazole, benzimidazole, benzoxazole, 1,2-benzoisoxazole, benzothiazole, 1,2-benzoisothiazole, 1H-benzotriazole, quinoline, isoquinoline and the like.

The "5 to 10-membered aromatic ring" is preferably a benzene ring, a naphthalene ring, a thiophene ring, a pyridine ring and the like. Of these, a benzene ring is preferable.

The "5 to 10-membered aromatic ring" optionally has 1 to 3 substituent(s) at substitutable position(s). Examples of the substituent include "halogen atom", "nitro group", "cyano group", "$C_{1-3}$ alkylenedioxy group", "optionally substituted alkyl group having 1 to 10 carbon atom(s)", "optionally substituted alkenyl group having 2 to 10 carbon atoms", "optionally substituted alkynyl group having 2 to 10 carbon atoms", "optionally substituted cycloalkyl group having 3 to 10 carbon atoms", "optionally substituted cycloalkenyl group having 3 to 10 carbon atoms", "optionally substituted cycloalkadienyl group having 4 to 10 carbon atoms", "optionally substituted aryl group having 6 to 14 carbon atoms", "optionally substituted heterocyclic group", "acyl group", "optionally substituted amino group", "optionally substituted hydroxy group", "optionally substituted thiol group", "amidino group" and the like.

As the "halogen atom", for example, fluorine, chlorine, bromine, iodine and the like can be used, with preference given to fluorine, chlorine and bromine.

Examples of the "$C_{1-3}$ alkylenedioxy group" include methylenedioxy, ethylenedioxy and the like.

As the "alkyl group having 1 to 10 carbon atom(s)" of the "optionally substituted alkyl group having 1 to 10 carbon atom(s)", for example, methyl, ethyl, propyl, isopropyl, butyl, isobutyl, sec.-butyl, t.-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be used.

As the "alkenyl group having 2 to 10 carbon atoms" of the "optionally substituted alkenyl group having 2 to 10 carbon atoms", for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be used.

As the "alkynyl group having 2 to 10 carbon atoms" of the "optionally substituted alkynyl group having 2 to 10 carbon atoms", for example, ethynyl, 1-propinyl, 2-propinyl, 1-butynyl, 2-butynyl, 3-butynyl, 1-pentinyl, 2-pentinyl, 3-pentinyl, 4-pentinyl, 1-hexynyl, 2-hexynyl, 3-hexynyl, 4-hexynyl, 5-hexynyl, 1-heptinyl, 1-octinyl and the like can be used.

The aforementioned "alkyl group having 1 to 10 carbon atom(s)", "alkenyl group having 2 to 10 carbon atoms" and "alkynyl group having 2 to 10 carbon atoms" optionally have 1 to 3 substituent(s) at substitutable position(s).

As these substituents, for example, cycloalkyl group having 3 to 10 carbon atoms, aryl group having 6 to 14 carbon atoms (e.g., phenyl, naphthyl and the like), aromatic heterocyclic group (e.g., thienyl, furyl, pyridyl, oxazolyl, thiazolyl, quinolyl and the like), non-aromatic heterocyclic group (e.g., tetrahydrofuryl, morpholino, thiomorpholino, piperidino, pyrrolizinyl, piperazinyl and the like), aralkyl group having 7 to 13 carbon atoms, amino group optionally mono or di-substituted by alkyl having 1 to 4 carbon atom(s) or acyl group having 2 to 8 carbon atoms (e.g., alkanoyl group, alkoxycarbonyl group and the like), alkylsulfonylamino group having 1 to 8 carbon atom(s), amidino group, acyl group having 2 to 8 carbon atoms (e.g., alkanoyl group, alkoxycarbonyl group and the like), alkylsulfonyl group having 1 to 8 carbon atom(s), carbamoyl group optionally mono or di-substituted by alkyl having 1 to 4 carbon atom(s), sulfamoyl group optionally mono or di-substituted by alkyl having 1 to 4 carbon atom(s), carboxyl group, hydroxy group, alkoxy group having 1 to 6 carbon atom(s) optionally substituted by 1 to 3 halogen atom(s) (e.g., fluorine, chlorine, bromine, iodine and the like), alkenyloxy group having 2 to 5 carbon atoms optionally substituted by 1 to 3 halogen atom(s,) (e.g., fluorine, chlorine, bromine, iodine and the like), cycloalkyloxy group having 3 to 7 carbon atoms, aralkyloxy group having 7 to 13 carbon atoms, aryloxy group having 6 to 14 carbon atoms (e.g., phenyloxy, naphthyloxy and the like), thiol group, alkylthio group having 1 to 6 carbon atom(s) optionally substituted by 1 to 3 halogen atom(s) (e.g., fluorine, chlorine, bromine, iodine and the like), aralkylthio group having 7 to 13 carbon atoms, arylthio group having 6 to 14 carbon atoms (e.g., phenylthio, naphthylthio and the like), sulfo group, cyano, group, azide group, nitro group, nitroso group, halogen atom (e.g., fluorine, chlorine, bromine, iodine) and the like can be used.

The "cycloalkyl group having 3 to 10 carbon atoms" of the "optionally substituted cycloalkyl group having 3 to 10 carbon atoms" is, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

The "cycloalkenyl group having 3 to 10 carbon atoms" of the "optionally substituted cycloalkenyl group having 3 to 10 carbon atoms" is, for example, 2-cyclopenten-1-yl, 3-cyclopenten-1-yl, 2-cyclohexen-1-yl, 3-cyclohexen-1-yl and the like.

The "optionally substituted cycloalkadienyl group having 4 to 10 carbon atoms" of the "optionally substituted cycloalkadienyl group having 4 to 10 carbon atoms" is, for example, 2,4-cyclopentadien-1-yl, 2,4-cyclohexadien-1-yl, 2,5-cyclohexadien-1-yl and the like.

The "aryl group having 6 to 14 carbon atoms" of the "optionally substituted aryl group having 6 to 14 carbon atoms" is, for example, phenyl, naphthyl, anthryl, phenanthryl, acenaphthylenyl, biphenylyl and the like. Of these, phenyl, 1-naphthyl, 2-naphthyl and the like are preferable.

The "heterocyclic group" of the "optionally substituted heterocyclic group" is exemplified by non-aromatic heterocyclic group and aromatic heterocyclic group.

The non-aromatic heterocyclic group is, for example, 5 to 7-membered monocyclic non-aromatic heterocyclic group or fused non-aromatic heterocyclic group, containing 1 to 4 heteroatom(s) selected from an oxygen atom, a sulfur atom and a nitrogen atom as a ring-constituting atom, besides carbon atoms. The non-aromatic fused heterocycle group is, for example, a group wherein these 5 to 7-membered monocyclic non-aromatic heterocyclic groups and a 6-membered ring containing 1 or 2 nitrogen atom(s), a benzene ring or a 5-membered ring containing one sulfur atom are fused and the like.

Preferable examples of the non-aromatic heterocyclic group include 1-pyrrolizinyl, piperidino, morpholino, thiomorpholino, 1-piperazinyl, hexamethylenimin-1-yl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxothiazolidin-3-yl, 1,3-dioxoisoindol-2-yl, 5-oxooxadiazol-3-yl, 5-oxothiadiazol-3-yl and the like.

The aromatic heterocyclic group is, for example, a 5 to 7-membered monocyclic aromatic heterocyclic group or fused aromatic heterocyclic group, containing 1 to 4 heteroatom(s) selected from an oxygen atom, a sulfur atom and a nitrogen atom as a ring-constituting atom, besides carbon atoms. The fused aromatic heterocyclic group is, for example, a group where these 5 to 7-membered monocyclic aromatic heterocyclic groups and a 6-membered ring containing 1 or 2 nitrogen atom(s), a benzene ring or a 5-membered ring, containing one sulfur atom are fused and the like.

Preferable examples of the aromatic heterocyclic group include 2-furyl, 3-furyl, 2-thienyl, -3-thienyl, 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,3,4-oxadiazol-2-yl, 1,3,4-thiadiazol-2-yl, 1,2,4-triazol-1-yl,-1,2,4-triazol-3-yl, 1,2,3-triazol-1-yl, 1,2,3-triazol-2-yl, 1,2,3-triazol-4-yl, tetrazol-4-yl, tetrazol-5-yl, 2-quinolyl, 3-quinolyl, 4-quinolyl, 2-quinazolyl, 4-quinazolyl, 2-quinoxalyl, 2-benzofuryl, 3-benzofuryl, 2-benzothienyl, 3-benzothienyl, 2-benzoxazolyl, 2-benzothiazolyl, benzimidazol-1-yl, benzimidazol-2-yl, indol-1-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and the like.

The substituent of the aforementioned "optionally substituted cycloalkyl group having 3 to 10 carbon atoms", "optionally substituted cycloalkenyl group having 3 to 10 carbon atoms", "optionally substituted cycloalkadienyl group having 4 to 10 carbon atoms", "optionally substituted aryl group having 6 to 14 carbon atoms" and "optionally substituted heterocyclic group" is, for example, alkyl group having 1 to 6 carbon atom(s) optionally substituted by 1 to 3 halogen atom(s) (e.g., fluorine, chlorine, bromine, iodine and the like); alkenyl group having 2 to 6 carbon atoms optionally substituted by 1 to 3 halogen atom(s) (e.g., fluorine, chlorine, bromine, iodine and the like); cycloalkyl group having 3 to 10 carbon atoms; aryl group having 6 to 14 carbon atoms (e.g., phenyl, naphthyl and the like); aromatic heterocyclic group (e.g., thienyl, furyl, pyridyl, oxazolyl, thiazolyl and the like); non-aromatic heterocyclic group (e.g., tetrahydrofuryl, morpholino, thiomorpholino, piperidino, pyrrolizinyl, piperazinyl and the like); aralkyl group having 7 to 13 carbon atoms; amino group optionally mono or di-substituted by alkyl group having 1 to 4 carbon atom(s) or acyl group having 1 to 15 carbon atom(s) (preferably having 2 to 8 carbon atoms) (e.g., alkanoyl group and the like), such as amino, mono- or di-$C_{2-10}$ alkanoylamino, $C_{1-10}$ alkoxy-carbonylamino, carbamoylamino, mono- or di-$C_{1-10}$ alkyl-carbamoylamino, $C_{6-14}$ aryl-carbonylamino, $C_{3-10}$ cycloalkyl-carbonylamino, $C_{7-13}$ aralkyloxy-carbonylamino, mono- or di-$C_{1-10}$ alkylsulfonylamino, $C_{6-14}$ arylsulfonylamino, $C_{1-6}$ alkoxy-carbamoylamino and the like; amidino group; acyl group having 2 to 8 carbon atoms (e.g., alkanoyl group and the like); carbamoyl group optionally mono or di-substituted by alkyl group having 1 to 4 carbon atom(s); sulfamoyl group optionally mono or di-substituted by alkyl group having 1 to 4 carbon atom(s); carboxyl group; alkoxycarbonyl group having 2 to 8 carbon atoms; hydroxy group; alkoxy group having 1 to 6 carbon atom(s) optionally substituted by 1 to 3 halogen atom(s) (e.g., fluorine, chlorine, bromine, iodine and the like); alkenyloxy group having 2 to 5 carbon atoms optionally substituted by 1 to 3 halogen atom(s) (e.g., fluorine, chlorine, bromine, iodine and the like); cycloalkyloxy group having 3 to 7 carbon atoms; aralkyloxy group having 7 to 13 carbon atoms; aryloxy group having 6 to 14 carbon atoms (e.g., phenyloxy, naphthyloxy and the like); thiol group; alkylthio group having 1 to 6 carbon atom(s) optionally substituted by 1 to 3 halogen atom(s) (e.g., fluorine, chlorine, bromine, iodine and the like); aralkylthio group having 7 to 13 carbon atoms; arylthio group having 6 to 14 carbon atoms (e.g., phenylthio, naphthylthio and the like); sulfo group; cyano group; azide group; nitro group; nitroso group; halogen atom (e.g., fluorine, chlorine, bromine, iodine and the like) and the like. The number of the substituent is, for example, 1 to 3.

The "acyl group" is, for example, a group of the formula: —COR$^4$, —CO—OR$^4$, —SO$_2$R$^4$, —SOR$^4$, —PO$_3$R$^4$R$^5$, —CO—NR$^{4a}$R$^{5a}$, —CS—NR$^{4a}$R$^{5a}$ wherein R$^4$ and R$^5$ are the same or different and each is hydrogen atom, optionally substituted hydrocarbon group or optionally substituted heterocyclic group. R$^{4a}$ and R$^{5a}$ are the same or different and each is hydrogen atom, optionally substituted hydrocarbon group or optionally substituted heterocyclic group and R$^{4a}$ and R$^{5a}$ may form, together with the adjacent nitrogen atom an optionally substituted, nitrogen-containing heterocycle, and the like.

The "optionally substituted hydrocarbon group" for R$^4$, R$^5$, R$^{4a}$ and R$^{5a}$ is exemplified by "optionally substituted alkyl group having 1 to 10 carbon atom(s)", "optionally substituted alkenyl group having 2 to 10 carbon atoms", "optionally substituted alkynyl group having 2 to 10 carbon atoms", "optionally substituted cycloalkyl group having 3 to 10 carbon atoms", "optionally substituted cycloalkenyl group having 3 to 10 carbon atoms", "optionally substituted cycloalkadienyl group having 4 to 10 carbon atoms", "optionally substituted aryl group having 6 to 14 carbon atoms", "optionally substituted aralkyl group having 7 to 13 carbon atoms", "optionally substituted arylalkenyl group having 8 to 13 carbon atoms" and the like, which are mentioned as the substituents in ring A.

The "aralkyl group having 7 to 13 carbon atoms" of the "optionally substituted aralkyl group having 7 to 13 carbon atoms" is, for example, benzyl, phenethyl, naphthylmethyl and the like.

The "arylalkenyl group having 8 to 13 carbon atoms" of the "optionally substituted arylalkenyl group having 8 to 13 carbon atoms" is, for example, styryl and the like.

The substituent of the "optionally substituted aralkyl group having 7 to 13 carbon atoms" and "optionally substituted arylalkenyl group having 8 to 13 carbon atoms" is exemplified by that mentioned as the substituent in the aforementioned "optionally substituted cycloalkyl group having 3 to 10 carbon atoms" and the like. The number of the substituent is, for example, 1 to 3.

The "optionally substituted heterocyclic group" for R$^4$, R$^5$, R$^{4a}$ or R$^{5a}$ is exemplified by that mentioned as the substituent in ring A.

The "nitrogen-containing heterocycle" of the "optionally substituted, nitrogen-containing heterocycle" formed by R$^{4a}$ and R$^{5a}$ together with the adjacent nitrogen atom is, for example, a 5 to 7-membered, nitrogen-containing heterocycle containing at least one nitrogen atom and further 1 or 2 heteroatom(s) selected from oxygen atom, sulfur atom and nitrogen atom as a ring-constituting atom, besides carbon atoms. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 or 2 substituent(s) at substitutable position(s). Examples of the substituent include hydroxy group, $C_{1-6}$ alkyl group optionally substituted by 1 to 3 halogen atom(s) (e.g., fluorine, chlorine, bromine, iodine and the like), $C_{7-13}$ aralkyl group (e.g., benzyl, diphenylmethyl and the like) and the like.

Preferable examples of the "acyl group" include formyl, carboxyl, carbamoyl, $C_{1-6}$ alkyl-carbonyl (e.g., acetyl, isobutanoyl, isopentanoyl and the like), $C_{1-6}$ alkoxy-carbonyl (e.g., methoxycarbonyl, ethoxycarbonyl, propoxycarbonyl, tert-butoxycarbonyl and the like), $C_{6-14}$ aryl-carbonyl (e.g., benzoyl, 1-naphthoyl, 2-naphthoyl and the like), $C_{6-14}$ aryloxy-carbonyl (e.g., phenyloxycarbonyl, naphthyloxycarbonyl and the like), $C_{7-13}$ aralkyloxy-carbonyl (e.g., benzyloxycarbonyl, phenethyloxycarbonyl and the like), mono- or di-($C_{1-6}$ alkyl optionally having 1 to 3 substituent(s) selected from halogen atom and $C_{1-6}$ alkoxy-carbonyl)-carbamoyl (e.g., methylcarbamoyl ethylcarbamoyl, dimethylcarbamoyl, diethylcarbamoyl, ethylmethylcarbamoyl, propylcarbamoyl, trifluoroethylcarbamoyl and the like), $C_{6-14}$ aryl-carbamoyl (e.g., phenylcarbamoyl and the like), $C_{3-10}$ cycloalkyl-carbamoyl (e.g., cyclopropylcarbamoyl and the like), $C_{7-13}$ aralkyl-carbamoyl (e. g., benzylcarbamoyl and the like), $C_{1-6}$ alkylsulfonyl (e.g., methylsulfonyl and the like), $C_{6-14}$ arylsulfonyl (e.g., phenylsulfonyl and the like), nitrogen-containing heterocycle-carbonyl optionally substituted by hydroxy (e.g., pyrrolidinylcarbonyl, piperidinocarbonyl and the like), $C_{1-6}$ alkylsulfinyl, (e.g., methylsulfinyl and the like), $C_{1-6}$ alkoxy-carbamoyl (e.g., methoxycarbamoyl), aminocarbamoyl, hydroxycarbamoyl, thiocarbamoyl and the like.

The "optionally substituted amino group" is, for example, amino group optionally substituted by 1 or 2 substituent(s) selected from alkyl group having 1 to 10 carbon atom(s), alkenyl group having 2 to 10 carbon atoms, cycloalkyl group having 3 to 10 carbon atoms, cycloalkenyl group having 3 to 10 carbon atoms, aryl group having 6 to 14 carbon atoms and acyl.

The "alkyl group having 1 to 10 carbon atom(s)", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms" and "acyl group" are exemplified by those mentioned as the substituent in ring A.

Preferable examples of the substituted amino group include mono- or di-$C_{1-10}$ alkylamino (e.g., methylamino, dimethylamino, ethylamino, diethylamino, propylamino, dibutylamino), mono- or di-$C_{2-10}$ alkenylamino (e.g., diallylamino), mono- or di-$C_{3-10}$ cycloalkylamino (e.g., cyclohexylamino), mono- or di-$C_{2-10}$ alkanoylamino (e.g., acetylamino, propionylamino, butanoylamino, isobutanoylamino, isopentanoylamino), $C_{6-14}$ aryl-carbonylamino (e.g., benzoylamino), $C_{6-14}$ arylamino (e.g., phenylamino), carbamoylamino, mono- or di-$C_{1-10}$ alkyl-carbamoylamino (e.g., methylcarbamoylamino, dimethylcarbamoylamino), $C_{1-10}$ alkoxy-carbonylamino (e.g., methoxycarbonylamino), $C_{7-13}$ aralkyloxy-carbonylamino (e.g., benzyloxycarbonylamino), $C_{3-10}$ cycloalkyl-carbonylamino (e.g., cyclopentylcarbonylamino, cyclohexylcarbonylamino), mono- or di-$C_{1-10}$ alkyl-sulfonylamino (e.g., methylsulfonylamino, dimethylsulfonylamino), $C_{6-14}$ arylsulfonylamino (e.g., phenylsulfonylamino), $C_{1-6}$ alkoxy-carbamoylamino (e.g., methoxycarbamoylamino) and the like.

The "optionally substituted hydroxy group" is, for example, hydroxy group optionally substituted by "alkyl group having 1 to 10 carbon atom(s)", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" or "aralkyl group having 7 to 13 carbon atoms", each of which is optionally substituted.

The "alkyl having 1 to 10 carbon atom(s)", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl having 7 to 13 carbon atoms" are exemplified by those mentioned as the aforementioned R$^4$ and the like.

These "alkyl group having 1 to 10 carbon atom(s)", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl group having 7 to 13 carbon atoms" each optionally have 1 to 3 substituent(s) at substitutable position(s). Such substituents are, for example, halogen atom (e.g., fluorine, chlorine, bromine, iodine and the like), alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, cycloalkyl group having 3 to 10 carbon atoms, carboxyl group, amino group, alkanoylamino group having 2 to 5 carbon atoms and the like.

The substituted hydroxy group is preferably "alkoxy group having 1 to 10 carbon atom(s)", "alkenyloxy group having 2 to 10 carbon atoms", "alkynyloxy group having 2 to 10 carbon atoms", "cycloalkyloxy group having 3 to 10 carbon atoms", "cycloalkenyloxy group having 3 to 10 carbon atoms", "aryloxy group having 6 to 14 carbon atoms", "aralkyloxy group having 7 to 13 carbon atoms" and the like, each optionally having 1 to 3 substituent(s) selected from halogen atom (e.g., fluorine, chlorine, bromine, iodine and the like), alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms.

The "alkoxy group having 1 to 10 carbon atom(s)" is, for example, methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy and the like.

The "alkenyloxy group having 2 to 10 carbon atoms" is, for example, allyloxy, crotyloxy, 2-pentenyloxy, 3-hexenyloxy and the like.

The "alkynyloxy group having 2 to 10 carbon atoms" is, for example, ethynyloxy, propinyloxy, pentinyloxy and the like.

The "cycloalkyloxy group having 3 to 10 carbon atoms" is, for example, cyclobutoxy, cyclopentyloxy, cyclohexyloxy and the like.

The "cycloalkenyloxy group having 3 to 10 carbon atoms" is, for example, 2-cyclopentenyloxy, 2-cyclohexenyloxy and the like.

The "aryloxy group having 6 to 14 carbon atoms" is, for example, phenoxy, naphthyloxy and the like.

The "aralkyloxy group having 7 to 13 carbon atoms" is, for example, benzyloxy, phenethyloxy, naphthylmethyloxy and the like.

The substituted hydroxy group is more preferably "alkoxy group having 1 to 10 carbon atom(s)", "cycloalkyloxy group having 3 to 10 carbon atoms" or "aralkyloxy group having 7 to 13 carbon atoms", each optionally having 1 to 3 substituent(s) selected from halogen atom (e.g., fluorine, chlorine, bromine, iodine and the like), alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms.

The "optionally substituted thiol group" is, for example, thiol group optionally substituted by "alkyl group having 1 to 10 carbon atom(s)", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" or "aralkyl group having 7 to 13 carbon atoms", each of which is optionally substituted.

These "alkyl group having 1 to 10 carbon atom(s)", "alkenyl group having 2 to 10 carbon atoms", "alkynyl group having 2 to 10 carbon atoms", "cycloalkenyl group having 3 to 10 carbon atoms", "cycloalkyl group having 3 to 10 carbon atoms", "aryl group having 6 to 14 carbon atoms" and "aralkyl group having 7 to 13 carbon atoms" are exemplified by those mentioned as the aforementioned $R^4$ and the like.

These "alkyl group having 1 to 10 carbon atom(s)", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl group having 7 to 13 carbon atoms" each optionally have 1 to 3 substituent(s) at substitutable position(s). These substituents are, for example, halogen atom (e.g., fluorine, chlorine, bromine, iodine and the like), alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, cycloalkyl group having 3 to 10 carbon atoms, carboxyl group, amino group, alkanoylamino group having 2 to 5 carbon atoms and the like.

The substituted thiol group is preferably "alkylthio group having 1 to 10 carbon atom(s)", "alkenylthio group having 2 to 10 carbon atom", "alkynylthio group having 2 to 10 carbon atoms", "cycloatlkylthio group having 3 to 10 carbon atoms", "cycloalkenylthio group having 3 to 10 carbon atoms", "arylthio group having 6 to 14 carbon atoms", "aralkylthio group having 7 to 13 carbon atoms" and the like, each optionally having 1 to 3 substituent(s) selected from halogen atom (e.g., fluorine, chlorine, bromine, iodine and the like), alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms.

The "alkylthio group having 1 to 10 carbon atom(s)" is, for example, methylthio, ethylthio, propylthio, isopropylthio, butylthio, isobutylthio, sec.-butylthio, t.-butylthio, pentylthio, isopentylthio, neopentylthio, hexylthio, heptylthio, nonylthio and the like.

The "alkenylthio group having 2 to 10 carbon atoms" is, for example, allylthio, crotylthio, 2-pentenylthio, 3-hexenylthio and the like.

The "alkynylthio group having 2 to 10 carbon atoms" is, for example, ethynylthio, propinylthio, pentinylthio and the like.

The "cycloalkylthio group having 3 to 10 carbon atoms" is, for example, cyclobutylthio, cyclopentylthio, cyclohexylthio and the like.

The "cycloalkenylthio group having 3 to 10 carbon atoms" is, for example, 2-cyclopentenylthio, 2-cyclohexenylthio and the like.

The "arylthio group having 6 to 14 carbon atoms" is, for example, phenylthio, naphthylthio and the like.

The "aralkylthio having 7 to 13 carbon atoms" is, for example, benzylthio, phenethylthio, naphthylmethylthio and the like.

The substituted thiol group is more preferably alkylthio group having 1 to 10 carbon atom(s) optionally substituted by carbamoyl group.

Preferable examples of the "substituent" of "5 to 10-membered aromatic ring" for ring A are (1) a halogen atom (e.g., fluorine, chlorine, bromine, iodine and the like);

(2) a nitro group;
(3) a cyano group;
(4) a $C_{1-3}$ alkylenedioxy group (e.g., methylenedioxy);
(5) a $C_{1-10}$ alkyl group (e.g., methyl, ethyl) or a $C_{2-10}$ alkenyl group (e.g., ethenyl), each optionally having 1 to 3 substituent(s) selected from halogen atom, hydroxy group, carboxyl group, alkoxycarbonyl group having 2 to 8 carbon atoms (e.g., ethoxycarbonyl), carbamoyl group, cyano group, amino group, alkanoylamino group having 2 to 8 carbon atoms (e.g., acetylamino, isobutanoylamino), alkoxycarbonylamino group having 2 to 8 carbon atoms (e.g., ethoxycarbonylamino) and alkylsulfonylamino group having 1 to 8 carbon atom(s) (e.g., methylsulfonylamino);
(6) an optionally substituted hydroxy group [e.g., alkoxy group having 1 to 10 carbon atom(s) (e.g., methoxy, ethoxy, propoxy, isopropoxy, butoxy, isobutoxy), cycloalkyloxy group having 3 to 10 carbon atoms (e.g., cyclopentyloxy) or aralkyloxy group having 7 to 13 carbon atoms (e.g., benzyloxy), each optionally having 1 to 3 substituent(s) selected from halogen atom, alkoxy group having 1 to 3 carbon atom(s) (e.g., methoxy), alkoxycarbonyl group having 2 to 5 carbon atoms (e.g., methoxycarbonyl, ethoxycarbonyl), alkanoyl group having 2 to 5 carbon atoms (e.g., pivaloyl), cyano group, carbamoyl group, hydroxy group, carboxyl group, amino group, alkanoylamino group having 2 to 5 carbon atoms (e.g., acetylamino) and cycloalkyl group having 3 to 10 carbon atoms (e.g., cyclopropyl, cyclohexyl); hydroxy group];
(7) an acyl group [e.g., formyl, carboxyl, $C_{1-6}$ alkyl-carbonyl (e.g., acetyl), $C_{1-6}$ alkoxy-carbonyl (e.g., methoxycarbonyl), carbamoyl, aminocarbamoyl, hydroxycarbamoyl, mono- or di-($C_{1-6}$ alkyl optionally having 1 to 3 substituent(s) selected from halogen atom and $C_{1-6}$ alkoxy-carbonyl (e.g., ethoxycarbonyl))-carbamoyl (e.g., methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (e.g., cyclopropylcarbamoyl), $C_{7-13}$ aralkyl-carbamoyl (e.g., benzylcarbamoyl), nitrogen-containing heterocycle-carbonyl optionally substituted by hydroxy. (e.g., pyrrolidinylcarbonyl, piperidinocarbonyl), $C_{1-6}$ alkylsulfonyl (e.g., methylsulfonyl), $C_{1-6}$ alkylsulfinyl (e.g., methylsulfinyl), thiocarbamoyl];
(8) an optionally substituted amino group [e.g., amino, mono- or di-$C_{2-10}$ alkanoylamino (e.g., acetylamino, propionylamino, isobutanoylamino, isopentanoylamino), $C_{1-10}$ alkoxy-carbonylamino (e.g., methoxycarbonylamino), carbamoylamino, mono- or di-$C_{1-10}$ alkyl-carbamoylamino (e.g., methylcarbamoylamino, dimethylcarbamoylamino), $C_{6-14}$ aryl-carbonylamino (e.g., benzoylamino), $C_{3-10}$ cycloalkyl-carbonylamino (e.g., cyclopentylcarbonylamino), $C_{7-13}$ aralkyloxy-carbonylamino (e.g., benzyloxycarbonylamino), mono- or di-$C_{1-10}$ alkylsulfonylamino (e.g., methylsulfonylamino, dimethylsulfonylamino), $C_{6-14}$ arylsulfonylamino (e.g., phenylsulfonylamino), $C_{1-6}$ alkoxy-carbamoylamino (e.g., methoxycarbamoylamino)];
(9) an aryl group having 6 to 14 carbon atoms (e.g., phenyl);
(10) an optionally substituted thiol group [e.g., alkylthio group having 1 to 10 carbon atom(s) optionally substituted by carbamoyl group (e.g., methylthio)];
(11) an optionally substituted heterocyclic group [e.g., aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindole, 5-oxooxadiazol-3-yl, 5-oxothiadiazol-3-yl), each optionally having 1 or 2 substituent(s) selected from $C_{1-6}$, alkyl group optionally substituted by 1 to 3 halogen atom(s) (e.g., methyl, trifluoromethyl), carboxyl group, alkoxycarbonyl group having 2 to 8 carbon atoms (preferably ethoxycarbonyl), cyano group, carbamoyl group, amino group, mono- or di-$C_{2-10}$ alkanoylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and $C_{1-6}$ alkoxy-carbamoylamino group (e.g., methoxycarbamoylamino)];
(12) an amidino group;

and the like.

The number of substituent is preferably 1 to 3, more preferably 1 or 2.

The "substituent" of the "5 to 10-membered aromatic ring" for ring A is preferably
(1) a halogen atom (e.g., fluorine, chlorine, bromine, iodine and the like);
(2) a nitro group;
(3) a cyano group;
(4) a $C_{1-3}$ alkylenedioxy group (e.g., methylenedioxy);
(5) a $C_{1-10}$ alkyl group or a $C_{2-10}$ alkenyl group, each optionally having 1 to 3 substituent(s) selected from halogen atom, hydroxy group, carboxyl group, alkoxycarbonyl group having 2 to 8 carbon atoms, carbamoyl group, cyano group, amino group, alkanoylamino group having 2 to 8 carbon atoms, alkoxycarbonylamino group having 2 to 8 carbon atoms, alkylsulfonylamino group having 1 to 8 carbon atoms;
(6) an optionally substituted hydroxy group (e.g., alkoxy group having 1 to 10 carbon atom(s), cycloalkyloxy group having 3 to 10 carbon atoms or aralkyloxy group having 7 to 13 carbon atoms each optionally having 1 to 3 substituent(s) selected from halogen atom, alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group and cycloalkyl group having 3 to 10 carbon atoms; hydroxy group);
(7) an acyl group (e.g., carboxyl, $C_{1-6}$ alkoxy-carbonyl, carbamoyl, mono- or di-($C_{1-6}$ alkyl optionally having 1 to 3 substituent(s) selected from halogen atom and $C_{1-6}$ alkoxy-carbonyl)-carbamoyl, $C_{3-10}$ cycloalkyl-carbamoyl, $C_{7-13}$ aralkyl-carbamoyl, nitrogen-containing heterocycle-carbonyl optionally substituted by hydroxy, $C_{1-6}$ alkyl-carbonyl, thiocarbamoyl, $C_{1-6}$ alkylsulfonyl, $C_{1-6}$ alkylsulfinyl);
(8) an optionally substituted amino group (e.g., amino, mono- or di-$C_{2-10}$ alkanoylamino, $C_{1-10}$ alkoxy-carbonylamino, mono- or di-$C_{1-10}$ alkyl-carbamoylamino, $C_{6-14}$ aryl-carbonylamino, $C_{3-10}$ cycloalkyl-carbonylamino, $C_{7-13}$ aralkyloxy-carbonylamino, mono- or di-$C_{1-10}$ alkylsulfonylamino, $C_{6-14}$ arylsulfonylamino, carbamoylamino); or
(9) an optionally substituted heterocyclic group [e.g., aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindole, 5-oxooxadiazol-3-yl, 5-oxothiadiazol-3-yl)], each optionally having 1 or 2 substituent(s) selected from $C_{1-6}$ alkyl group optionally substituted by 1 to 3 halogen atom(s), carboxyl group, alkoxycarbonyl group having 2 to 8 carbon atoms, cyano group, carbamoyl group, amino group, mono- or di-$C_{2-10}$ alkanoylamino group, $C_{1-10}$ alkoxy-carbonylamino group, carbamoylamino group, mono- or-di-$C_{1-10}$ alkyl-carbamoylamino group, $C_{6-14}$ aryl-carbonylamino group, $C_{3-10}$ cycloalkyl-carbonylamino,group, $C_{7-13}$ aralkyloxy-carbonylamino group, mono- or di-$C_{1-10}$ alkylsulfonylamino group, $C_{6-14}$ arylsulfonylamino group and $C_{1-6}$ alkoxy-carbamoylamino group.

The number of substituent is preferably 1 to 3, more preferably 1 or 2.

The "substituent" of the "5 to 10-membered aromatic ring" for ring A is more preferably (1) a halogen atom (e.g., fluorine, chlorine, bromine, iodine and the like);
(2) a nitro group;
(3) a cyano group;
(4) a $C_{1-3}$ alkylenedioxy group (e.g., methylenedioxy);
(5) an optionally substituted hydroxy group (preferably methoxy, carbamoylmethoxy and the like);
(6) an acyl group (preferably carbamoyl, methoxycarbonyl and the like);
(7) an optionally substituted amino group (preferably acetylamino and the like);
(8) a $C_{1-10}$ alkyl group (preferably ethyl) or a $C_{2-10}$ alkenyl group (preferably ethenyl), each optionally substituted by carbamoyl group;
(9) an optionally substituted heterocyclic group [e.g., aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindole, 5-oxooxadiazol-3-yl, 5-oxothiadiazol-3-yl), each optionally having 1 or 2 substituent(s) selected from $C_{1-6}$ alkyl group optionally substituted by 1 to 3 halogen atom(s), carboxyl group, alkoxycarbonyl group having 2 to 8 carbon atoms, cyano group, carbamoyl group, amino group, mono- or di-$C_{2-10}$ alkanoylamino group, $C_{1-10}$ alkoxy-carbonylamino group, carbamoylamino group, mono- or di-$C_{1-10}$ alkyl-carbamoylamino group, $C_{6-14}$ aryl-carbonylamino group, $C_{3-10}$ cycloalkyl-carbonylamino group, $C_{7-13}$ aralkyloxy-carbonylamino group, mono- or di-$C_{1-10}$ alkylsulfonylamino group, $C_{6-14}$ arylsulfonylamino group and $C_{1-6}$ alkoxy-carbamoylamino group]. The number of substituent is preferably 1 or 2.

The ring A is preferably benzene ring optionally having 1 or 2 substituent(s) selected from (1) a cyano group;
(2) a $C_{1-10}$ alkyl group (preferably ethyl) or a $C_{2-10}$ alkenyl group (preferably ethenyl), each optionally having 1 to 3 substituent(s) selected from carbamoyl group, carboxyl group and alkoxycarbonyl group having 2 to 8 carbon atoms (preferably methoxycarbonyl);
(3) an optionally substituted hydroxy group [preferably alkoxy group having 1 to 10 carbon atom(s) (preferably methoxy, isopropoxy) optionally having 1 to 3 substituent(s) selected from carbamoyl group, carboxyl group and alkoxycarbonyl group having 2 to 5 carbon atoms (preferably methoxycarbonyl); hydroxy group; aralkyloxy group having 7 to 13 carbon atoms (preferably benzyloxy)] [more preferably carbamoylmethoxy];
(4) an acyl group [preferably $C_{1-6}$ alkyl-carbonyl (preferably acetyl), carbamoyl, mono- or di-($C_{1-6}$ alkyl optionally having 1 to 3 substituent(s) selected from halogen atom and $C_{1-6}$ alkoxy-carbonyl)-carbamoyl (preferably methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl)];
(5) an optionally substituted amino group (preferably carbamoylamino);
(6) an optionally substituted thiol group [preferably alkylthio group having 1 to 10 carbon atom(s) optionally substituted by carbamoyl group (preferably methylthio)];
(7) an optionally substituted heterocyclic group [preferably aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindole, 5-oxooxadiazol-3-yl, 5-oxothiadiazol-3-yl), each optionally having 1 or 2 substituent(s) selected from $C_{1-6}$ alkyl group optionally substituted by 1 to 3 halogen atom(s) (preferably methyl, trifluoromethyl), carboxyl group, alkoxycarbonyl group having 2 to 8 carbon atoms (preferably ethoxycarbonyl), cyano group, carbamoyl group, amino group, mono- or di-$C_{2-10}$ alkanoylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and $C_{1-6}$ alkoxy, carbamoylamino group (e.g., methoxycarbamoylamino)]; and
(8) an amidino group.

The ring A is more preferably a benzene ring having 1 or 2 substituent(s) selected from (1) a $C_{1-10}$ alkyl group (preferably ethyl) or a $C_{2-10}$ alkenyl group (preferably ethenyl), each having 1 to 3 substituent(s) selected from carbamoyl group, carboxyl group and alkoxycarbonyl group having 2 to 8 carbon atoms (preferably methoxycarbonyl);
(2) an optionally substituted hydroxy group [preferably alkoxy group having 1 to 10 carbon atom(s) (preferably methoxy, isopropoxy) optionally having 1 to 3 substituent(s) selected from carbamoyl group, carboxyl group and alkoxycarbonyl group having 2 to 5 carbon atoms (preferably methoxycarbonyl); hydroxy group; aralkyloxy group having 7 to 13 carbon atom(s) (preferably benzyloxy)] [more preferably carbamoylmethoxy];
(3) an acyl group [preferably $C_{1-6}$ alkyl-carbonyl (preferably acetyl), carbamoyl, mono- or di-($C_{1-6}$ alkyl optionally having 1 to 3 substituent(s) selected from halogen atom and $C_{1-6}$ alkoxy-carbonyl)-carbamoyl (preferably methylcarbamoyl, ethylcarbamoyl propylcarbamoyl, dimethylcarbamoyl, trifluoroethylcarbamoyl ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl]; and (4) an optionally substituted heterocyclic group [preferably aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindole, 5-oxooxadiazol-3-yl, 5-oxothiadiazol-3-yl), each optionally having 1 or 2 substituent(s), selected from $C_{1-6}$ alkyl optionally substituted by 1 to 3 halogen atom(s) (preferably methyl, trifluoromethyl), carboxyl group alkoxycarbonyl group, having 2 to 8 carbon atoms (preferably ethoxycarbonyl), cyano group, carbamoyl group, amino, mono- or di-$C_{2-10}$ alkanoylamino (e.g., acetylamino, isopentanoylamino), $C_{1-10}$ alkoxy-carbonylamino (.e.g., methoxycarbonylamino), carbamoylamino, mono- or di-$C_{1-10}$ alkyl-carbamoylamino (e.g., methylcarbamoylamino, dimethylcarbamoylamino), $C_{6-14}$ arylcarbonylamino (e.g., benzoylamino), $C_{3-10}$ cycloalkylcarbonylamino, $C_{7-13}$ aralkyloxy-carbonylamino, mono- or di-$C_{1-10}$ alkylsulfonylamino (e.g., methylsulfonylamino, dimethylsulfonylamino), $C_{6-14}$ arylsulfonylamino, and $C_{1-6}$ alkoxy-carbamoylamino (e.g., methoxycarbamoylamino)].

Examples of the "optionally substituted hydrocarbon group" for $R^1$ and $R^2$ are those exemplified for the aforementioned $R^4$ and the like.

Examples of the "optionally substituted heterocyclic group" for $R^1$ and $R^2$ are those exemplified as the substituent in ring A.

$R^1$ is preferably an optionally substituted hydrocarbon and more preferably an alkyl group having 1 to 10 carbon atom(s) which is optionally substituted by cycloalkyl group having 3 to 10 carbon atoms (e.g., cyclopropyl and the like). $R^1$ is particularly preferably an alkyl group having 4 to 10 carbon atoms or a cycloalkylalkyl group having 4 to 10 carbon atoms (preferably cyclopropylmethyl). Of these, preferred is an alkyl group having 4 or 5 carbon atoms (e.g., butyl, isobutyl, sec.-butyl, t.-butyl, pentyl, isopentyl, neopentyl, 1-ethylpropyl and the like).

$R^2$ is preferably an optionally substituted hydrocarbon group. More preferably, $R^2$ is an alkyl group having 1 to 10 substituent(s) (e.g., methyl, ethyl, propyl, isopropyl, butyl, isobutyl, sec.-butyl, t.-butyl, pentyl and the like), aryl group having 6 to 14 carbon atoms (e.g., phenyl and the like) or aralkyl group having 7 to 13 carbon atoms (e.g., benzyl, phenethyl, naphthylmethyl and the like), each optionally having 1 to 3 (preferably 1 or 2) substituent(s) selected from halogen atom (e.g., fluorine, chlorine and the like), hydroxy group, nitro group, amino group, optionally halogenated alkyl group having 1 to 6 carbon atom(s) (e.g., trifluoromethyl, methyl and the like), alkoxy group having 1 to 6 carbon atom(s) (e.g., methoxy and the like), aromatic heterocyclic group (e.g., quinolyl, thienyl and the like) and cycloalkyl group having 3 to 10 carbon atoms (e.g., cyclopentyl and the like).

X is a bond, —O—, —S—, —SO—, —SO$_2$— or —NR$^3$— (R$^3$ is hydrogen atom or optionally substituted hydrocarbon group).

Examples of the "optionally substituted hydrocarbon group" for $R^3$ are those exemplified for the aforementioned $R^4$ and the like. The "optionally substituted hydrocarbon group" is preferably alkyl group having 1 to 10 carbon atom(s) (e.g., methyl, ethyl and the like) and the like.

In the formula (I), when X is a bond, $R^2$ is preferably an aryl group having 6 to 14 carbon atoms (e.g., phenyl and the like) optionally having 1 or 2 substituent(s) selected from halogen atom (e.g., fluorine, chlorine and the like), hydroxy group, nitro group, amino group, optionally halogenated alkyl group having 1 to 6 carbon atom(s) (e.g., trifluoromethyl, methyl and the like), alkoxy group having 1 to 6 carbon atom(s) (e.g., methoxy and the like), aromatic heterocyclic group (e.g., quinolyl, thienyl and the like) and cycloalkyl group having 3 to 10 carbon atoms (e.g., cyclopentyl and the like).

In the formula (I), when X is —O—, —S—, —SO—, —SO$_2$— or —NR$^3$—, $R^2$ is preferably an alkyl group having 1 to 10 carbon atom(s) (e.g., methyl, ethyl, propyl, isopropyl, butyl, isobutyl, sec.-butyl, t.-butyl, pentyl and the like) or an aralkyl group having 7 to 13 carbon atoms (e.g., benzyl and the like), each optionally having 1 to 3 (preferably 1 or 2) substituent(s) selected from halogen atom (e.g., fluorine and the like), hydroxy group, nitro group, optionally halogenated alkyl group having 1 to 6 carbon atom(s) (e.g., trifluoromethyl and the like), alkoxy group having 1 to 6 carbon atom(s) (e.g., methoxy and the like), aromatic heterocyclic group (e.g., quinolyl, thienyl and the like) and cycloalkyl group having 3 to 10 substituents (e.g., cyclopentyl and the like).

X is preferably a bond or —O—.

The "divalent hydrocarbon group" for L is, for example, (1) $C_{1-10}$ alkylene (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —CHCH$_3$—, —C(CH$_3$)$_2$—, —(CH(CH$_3$))$_2$—, —(CH$_2$)$_2$C(CH$_3$)$_2$—, —(CH$_2$)$_3$C(CH$_3$)$_2$— and the like);

(2) $C_{2-10}$ alkenylene (e.g., —CH=CH—, —CH$_2$—CH=CH—, —CH=CH—CH$_2$—, —CH=CH—CH$_2$—CH$_2$—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$— and the like); or (3) $C_{2-10}$ alkynylene (e.g., —C≡C—, —CH$_2$—C≡C—, —C$_2$—C≡C—CH$_2$—CH$_2$— and the like) and the like.

The "divalent hydrocarbon group" is preferably $C_{1-10}$ alkylene, more preferably, —CH$_2$—, —(CH$_2$)$_2$— and the like. Particularly, —CH$_2$— is preferable.

Preferable examples of compound (I) include the following compounds.

[Compound A]

A compound wherein ring A is a benzene ring, a naphthalene ring or a thiophene ring, each optionally having 1 or 2 substituent(s) selected from (1) a halogen atom;
(2) a nitro group;
(3) a cyano group;
(4) a $C_{1-3}$ alkylenedioxy group;
(5) an optionally substituted hydroxy group (preferably methoxy, carbamoylmethoxy and the like);
(6) an acyl group (preferably carbamoyl, methoxycarbonyl and the like); and
(7) an optionally substituted amino group (preferably acetylamino and the like);

$R^1$ is an alkyl group having 1 to 10 carbon atom(s) (preferably alkyl group having 4 to 10 carbon atom(s));

$R^2$ is an alkyl group having 1 to 10 carbon atom(s), an aryl group having 6 to 14 carbon atoms or an aralkyl group having 7 to 13 carbon atoms, each optionally having 1 or 2 substituent(s) selected from halogen atom, hydroxy group, nitro group, optionally halogenated alkyl group having 1 to 6 carbon atom(s), alkoxy groups having 1 to 6 carbon atom(s) aromatic heterocyclic group (e.g. quinolyl and the like) and cycloalkyl group having 3 to 10 carbon atoms;
X is a bond or —O—; and
L is $C_{1-10}$ alkylene.

[Compound B]
A compound wherein ring A is a benzene ring optionally having 1 or 2 substituent(s) selected from
(1) a cyano group;
(2) a $C_{1-10}$ alkyl group (preferably ethyl) or a $C_{2-10}$ alkenyl group (preferably ethenyl), each optionally substituted by carbamoyl group or carboxyl group;
(3) an optionally substituted hydroxy group [preferably alkoxy group having 1 to 10 carbon atom((s) (preferably methoxy, isopropoxy) optionally having 1 to 3 substituent(s) selected from carbamoyl group, carboxyl group and alkoxycarbonyl group having 2 to 5 carbon atoms (preferably methoxycarbonyl); hydroxy group; aralkyloxy group having 7 to 13 carbon atoms (preferably benzyloxy)] [more preferably carbamoylmethoxy];
(4) an acyl group [preferably $C_{1-6}$ alkyl-carbonyl (preferably acetyl), carbamoyl, mono- or di-($C_{1-6}$ alkyl optionally having 1 to 3 substituent(s) selected from halogen atom and $C_{1-6}$ alkoxy-carbonyl)-carbamoyl (preferably methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl];
(5) an optionally substituted amino group (preferably carbamoylamino);
(6) an optionally substituted thiol group [preferably alkylthio group having 1 to 10 carbon atom(s) optionally substituted by carbamoyl group (preferably methylthio);
(7) an optionally substituted heterocyclic group [preferably aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindole, 5-oxooxadiazol-3-yl, 5-oxothiadiazol-3-yl), each optionally having 1 or 2 substituent(s) selected from $C_{1-6}$ alkyl group optionally substituted by 1 to 3 halogen atom(s) (preferably methyl, trifluoromethyl), carboxyl group, alkoxycarbonyl group having 2 to 8 carbon atoms (preferably ethoxycarbonyl), cyano group, carbamoyl group, amino group, mono- or di-$C_{2-10}$ alkanoylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and, $C_{1-6}$ alkoxy-carbamoylamino group (e.g., methoxycarbamoylamino); and
(8) an amidino group;
$R^1$ is an alkyl group having 4 to 10 carbon atoms (preferably isobutyl, neopentyl) or a cycloalkylalkyl group having 4 to 10 carbon atom(s) (preferably cyclopropylmethyl);
$R^2$ is an aryl group having 6 to 14 carbon atoms (preferably phenyl) optionally having 1 or 2 substituent(s) selected from halogen atom (preferably fluorine, chlorine) and $C_{1-6}$ alkyl (preferably methyl);
X is a bond; and
L is $C_{1-10}$ alkylene (preferably —$CH_2$—).

[Compound C]
A compound wherein ring A is is a benzene ring optionally having 1 or 2 substituent(s) selected from
(1) a $C_{1-10}$ alkyl group (preferably ethyl) or a $C_{2-10}$ alkenyl group (preferably ethenyl), each optionally substituted by alkoxycarbonyl group having 2 to 8 carbon atoms (preferably ethoxycarbonyl) or carbamoyl group;
(2) an optionally substituted hydroxy group [preferably alkoxy group having 1 to 10 carbon atom(s) (preferably methoxy) optionally substituted by carbamoyl group; more preferably carbamoylmethoxy];
(3) an acyl group (preferably carbamoyl, thiocarbamoyl, carboxyl);
(4) an optionally substituted heterocyclic group [preferably aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably 5-oxooxadiazol-3-yl), each optionally having 1 or 2 substituent(s) selected from $C_{1-6}$ alkyl group (preferably methyl), carboxyl group, alkoxycarbonyl group having 2 to 8 carbon atoms (preferably ethoxycarbonyl), cyano group, carbamoyl group, amino group, mono- or di-$C_{2-10}$ alkanoylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and, $C_{1-6}$ alkoxy-carbamoylamino group (e.g., methoxycarbamoylamino)];
$R^1$ is an alkyl group having 4 to 10 carbon atoms (preferably isobutyl, neopentyl) or a cycloalkylalkyl group having 4 to 10 carbon atom(s) (preferably cyclopropylmethyl);
$R^2$ is an alkyl group having 1 to 10 carbon atom(s), which is optionally substituted by 1 to 3 halogen atom(s) (preferably butyl);
X is —O—; and
L is $C_{1-10}$ alkylene (preferably —$CH_2$—).

Preferable examples of compound (I) include compounds shown by the following formula.

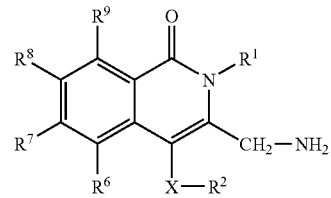

TABLE 1

| No. | X | $R^1$ | $R^2$ | $R^6$ | $R^7$ | $R^8$ | $R^9$ |
|---|---|---|---|---|---|---|---|
| 1 | O | neo-Pent | n-Bu | H | EtO— | H | H |
| 2 | O | neo-Pent | n-Bu | H | H | F | H |

TABLE 1-continued

| No. | X | R¹ | R² | R⁶ | R⁷ | R⁸ | R⁹ |
|---|---|---|---|---|---|---|---|
| 3 | O | neo-Pent | n-Bu | H | F | H | H |
| 4 | O | Me | Me | H | Cl | H | H |
| 5 | O | Me | Me | H | H | Cl | H |
| 6 | O | Me | i-Pr | H | Cl | H | H |
| 7 | O | Me | n-Bu | H | Cl | H | H |
| 8 | O | Me | PhCH₂— | H | Cl | H | H |
| 9 | O | Me | a) | H | Cl | H | H |
| 10 | O | Me | PhCH₂CH₂— | H | Cl | H | H |
| 11 | O | Me | b) | H | Cl | H | H |
| 12 | — | Me | Ph | H | H | Cl | H |
| 13 | O | Me | n-Pr | H | Cl | H | H |
| 14 | O | Me | c) | H | Cl | H | H |
| 15 | O | Me | 4-NO₂Ph | H | Cl | H | H |
| 16 | — | Me | 4-MeOph | H | Cl | H | H |
| 17 | — | Me | 3-MeOPh | H | Cl | H | H |
| 18 | — | Me | 4-HOPh | H | Cl | H | H |
| 19 | — | Me | 3-HOPh | H | Cl | H | H |
| 20 | — | Me | 4-FPh | H | Cl | H | H |
| 21 | — | Me | 4-F₃CPh | H | Cl | H | H |
| 22 | — | Me | Ph | H | Cl | Cl | H |
| 23 | — | Me | 3-NO₂Ph | H | Cl | H | H |
| 24 | — | Me | 3-NH₂Ph | H | Cl | H | H |
| 25 | O | n-Pr | n-Bu | H | Cl | H | H |

TABLE 2

| No. | X | R¹ | R² | R⁶ | R⁷ | R⁸ | R⁹ |
|---|---|---|---|---|---|---|---|
| 26 | O | i-Bu | n-Bu | H | Cl | Cl | H |
| 27 | O | neo-Pent | n-Bu | H | Cl | Cl | H |
| 28 | O | PhCH₂— | n-Bu | H | Cl | Cl | H |
| 29 | O | i-Bu | n-Pent | H | Cl | Cl | H |
| 30 | O | i-Pr | n-Bu | H | Cl | Cl | H |
| 31 | O | c-Pr | n-Bu | H | Cl | Cl | H |
| 32 | O | c-PrCH₂— | n-Bu | H | Cl | Cl | H |
| 33 | O | i-Pent | n-Bu | H | Cl | Cl | H |
| 34 | O | neo-Pent | i-Bu | H | Cl | Cl | H |
| 35 | O | d) | n-Bu | H | Cl | Cl | H |
| 36 | O | Me | n-Bu | H | Cl | Cl | H |
| 41 | O | e) | n-Bu | H | Cl | Cl | H |
| 42 | O | f) | n-Bu | H | Cl | Cl | H |
| 43 | O | g) | n-Bu | H | Cl | Cl | H |
| 44 | O | h) | n-Bu | H | Cl | Cl | H |
| 45 | O | i) | n-Bu | H | Cl | Cl | H |
| 46 | O | neo-Pent | n-Bu | H | H | H | H |
| 47 | O | j) | n-Bu | H | Cl | Cl | H |
| 48 | O | MeOCH₂CH₂— | n-Bu | H | Cl | Cl | H |
| 49 | O | neo-Pent | MeOCH₂CH₂— | H | H | H | H |
| 50 | O | neo-Pent | n-Bu | H | H | Me | H |

TABLE 3

| No. | X | R¹ | R² | R⁶ | R⁷ | R⁸ | R⁹ |
|---|---|---|---|---|---|---|---|
| 51 | O | neo-Pent | n-Bu | H | Me | H | H |
| 52 | O | neo-Pent | n-Bu | H | H | CF₃ | H |
| 53 | O | neo-Pent | n-Bu | H | CF₃ | H | H |
| 54 | O | k) | n-Bu | H | Cl | Cl | H |
| 55 | O | l) | n-Bu | H | Cl | Cl | H |
| 57 | O | neo-Pent | n-Bu | H | MeO— | H | H |
| 58 | O | neo-Pent | n-Bu | H | PhCH₂O— | H | H |
| 59 | O | neo-Pent | n-Bu | H | HO— | H | H |
| 60 | O | neo-Pent | n-Bu | H | n-PrO— | H | H |
| 61 | O | neo-Pent | n-Bu | H | n-BuO— | H | H |
| 62 | O | neo-Pent | n-Bu | H | MeOCH₂CH₂O— | H | H |
| 63 | O | neo-Pent | n-Bu | H | H | PhCH₂O | H |
| 64 | O | neo-Pent | n-Bu | H | H | HO— | H |
| 65 | O | neo-Pent | n-Bu | H | H | MeO— | H |
| 66 | O | neo-Pent | n-Bu | H | H | EtO— | H |
| 67 | O | neo-Pent | n-Bu | H | H | n-PrO— | H |
| 68 | O | neo-Pent | n-Bu | H | H | n-BuO— | H |
| 69 | O | neo-Pent | n-Bu | MeO | MeO— | H | H |
| 70 | O | neo-Pent | n-Bu | H | MeO— | MeO— | H |
| 74 | O | i-Bu | n-Bu | H | Br | H | H |

TABLE 3-continued

| No. | X | R¹ | R² | R⁶ | R⁷ | R⁸ | R⁹ |
|---|---|---|---|---|---|---|---|
| 75 | O | i-Bu | n-Bu | H | MeOCO— | H | H |

TABLE 4

| No. | X | R¹ | R² | R⁶ | R⁷ | R⁸ | R⁹ |
|---|---|---|---|---|---|---|---|
| 76 | O | i-Bu | n-Bu | H | HOCO— | H | H |
| 77 | O | i-Bu | n-Bu | H | H₂NCO— | H | H |
| 78 | O | i-Bu | n-Bu | H | NC— | H | H |
| 79 | O | i-Bu | n-Bu | H | HOCH₂— | H | H |
| 80 | O | i-Bu | n-Bu | H | MeNHCONH— | H | H |
| 81 | O | i-Bu | n-Bu | H | MeOCONH— | H | H |
| 82 | O | i-Bu | n-Bu | H | NH₂— | H | H |
| 83 | O | neo-Pent | n-Bu | H | Br | H | H |
| 84 | O | neo-Pent | n-Bu | H | MeOCO— | H | H |
| 85 | O | neo-Pent | n-Bu | H | HOCO— | H | H |
| 86 | O | neo-Pent | n-Bu | H | H₂NCO— | H | H |
| 87 | O | neo-Pent | n-Bu | H | NC— | H | H |
| 88 | O | i-Bu | n-Bu | H | AcNH— | H | H |
| 89 | O | i-Bu | n-Bu | H | EtCONH— | H | H |
| 90 | O | i-Bu | n-Bu | H | m) | H | H |
| 91 | O | i-Bu | n-Bu | H | n) | H | H |
| 92 | O | i-Bu | n-Bu | H | o) | H | H |
| 93 | O | i-Bu | n-Bu | H | MsNH— | H | H |
| 94 | O | i-Bu | n-Bu | H | PhSO₂NH— | H | H |
| 95 | O | nea-Pent | n-Bu | H | p) | H | H |
| 96 | O | neo-Pent | n-Bu | H | i-PrO— | H | H |
| 97 | O | neo-Pent | n-Bu | H | CF₃CH₂O— | H | H |
| 98 | O | neo-Pent | n-Bu | H | q) | H | H |
| 99 | O | neo-Pent | n-Bu | H | r) | H | H |
| 100 | O | neo-Pent | n-Bu | H | i-BuO— | H | H |

TABLE 5

| No. | X | R¹ | R² | R⁶ | R⁷ | R⁸ | R⁹ |
|---|---|---|---|---|---|---|---|
| 101 | O | neo-Pent | n-Bu | H | s) | H | H |
| 102 | O | neo-Pent | n-Bu | H | t) | H | H |
| 103 | O | neo-Pent | n-Bu | H | u) | H | H |
| 104 | O | neo-Pent | n-Bu | H | EtOCOCH₂O— | H | H |
| 105 | O | neo-Pent | n-Bu | H | v) | H | H |
| 106 | — | i-Bu | Ph | H | Br | H | H |
| 107 | — | i-Bu | Ph | H | MeOCO— | H | H |
| 108 | — | i-Bu | Ph | H | HOCO— | H | H |
| 109 | — | i-Bu | Ph | H | H₂NCO— | H | H |
| 110 | — | i-Bu | Ph | H | CbzNH— | H | H |
| 111 | — | i-Bu | Ph | H | NH₂— | H | H |
| 112 | — | i-Bu | Ph | H | AcNH— | H | H |
| 113 | — | Et | Ph | H | Cl | H | H |
| 114 | — | n-Pr | Ph | H | Cl | H | H |
| 115 | — | n-Bu | Ph | H | Cl | H | H |
| 116 | — | Me | Ph | H | Br | H | H |
| 117 | — | n-Pent | Ph | H | Cl | H | H |
| 118 | — | i-Bu | Ph | H | Cl | H | H |
| 119 | — | c-HexCH₂— | Ph | H | Cl | H | H |
| 120 | — | i-Bu | 4-FPh | H | Cl | Cl | H |
| 121 | — | i-Bu | Ph | H | Cl | Cl | H |
| 122 | — | neo-Pent | Ph | H | Cl | H | H |
| 123 | — | i-Bu | Ph | H | H | H | H |
| 124 | — | i-Bu | 4-ClPh | H | H | H | H |
| 125 | — | i-Bu | 4-MePh | H | H | H | H |

TABLE 6

| No. | X | R¹ | R² | R⁶ | R⁷ | R⁸ | R⁹ |
|-----|---|------|-----------------|---|------------|------|---|
| 126 | — | i-Bu | Ph | H | F | H | H |
| 127 | — | i-Bu | Ph | H | MeO— | H | H |
| 128 | — | i-Bu | Ph | H | EtO— | H | H |
| 129 | — | i-Bu | Ph | H | n-PrO— | H | H |
| 130 | — | i-Bu | Ph | H | MeO— | MeO— | H |
| 131 | — | i-Bu | 4-FPh | H | MeOCO— | H | H |
| 132 | — | i-Bu | 4-FPh | H | HOCO— | H | H |
| 133 | — | i-Bu | 4-FPh | H | H₂NCO— | H | H |
| 134 | — | i-Bu | 4-FPh | H | AcNH— | H | H |
| 135 | — | i-Bu | 4-FPh | H | EtO— | H | H |
| 136 | — | i-Bu | 4-FPh | H | p) | H | H |
| 137 | — | i-Bu | 2-FPh | H | MeOCO— | H | H |
| 138 | — | i-Bu | 2-FPh | H | HOCO— | H | H |
| 139 | — | i-Bu | 2-FPh | H | H₂NCO— | H | H |
| 140 | — | i-Bu | 2-FPh | H | AcNH— | H | H |
| 141 | — | i-Bu | 2-FPh | H | p) | H | H |
| 142 | — | i-Bu | 3-FPh | H | MeOCO— | H | H |
| 143 | — | i-Bu | 3-FPh | H | HOCO— | H | H |
| 144 | — | i-Bu | 3-FPh | H | H₂NCO— | H | H |
| 145 | — | i-Bu | 3-FPh | H | AcNH— | H | H |
| 146 | — | i-Bu | 3-FPh | H | EtO— | H | H |
| 147 | — | i-Bu | Ph | H | MeNHCONH— | H | H |
| 148 | — | i-Bu | Ph | H | Me₂NCONH— | H | H |
| 149 | — | i-Bu | Ph | H | H₂NCONH— | H | H |
| 150 | O | i-Bu | CF₃CH₂CH₂CH₂— | H | p) | H | H |

TABLE 7

| No. | X | R¹ | R² | R⁶ | R⁷ | R⁸ | R⁹ |
|-----|---|---------|--------|---|----------|---|---|
| 151 | O | c-PrCH₂— | n-Bu | H | H₂NCO— | H | H |
| 152 | O | c-PrCH₂— | n-Bu | H | p) | H | H |
| 153 | O | c-PrCH₂— | n-Bu | H | w) | H | H |
| 154 | O | i-Bu | n-Bu | H | p) | H | H |
| 155 | O | i-Bu | n-Bu | H | w) | H | H |
| 156 | — | i-Bu | Ph | H | NC— | H | H |
| 157 | — | i-Bu | Ph | H | MeNHCO— | H | H |
| 158 | — | i-Bu | Ph | H | p) | H | H |
| 159 | — | i-Bu | Ph | H | w) | H | H |
| 160 | O | neo-Pent | n-Bu | H | w) | H | H |
| 161 | O | c-PrCH₂— | n-Bu | H | x) | H | H |
| 162 | O | i-Bu | n-Bu | H | x) | H | H |
| 163 | — | i-Bu | Ph | H | x) | H | H |
| 164 | O | i-Bu | n-Bu | H | y) | H | H |
| 165 | — | i-Bu | Ph | H | y) | H | H |
| 166 | O | i-Bu | n-Bu | H | z) | H | H |
| 167 | — | i-Bu | Ph | H | z) | H | H |
| 168 | O | i-Bu | n-Bu | H | aa) | H | H |
| 169 | — | i-Bu | Ph | H | aa) | H | H |
| 170 | O | i-Bu | n-Bu | H | ab) | H | H |
| 171 | — | i-Bu | Ph | H | ab) | H | H |
| 172 | — | i-Bu | 4-MePh | H | p) | H | H |
| 173 | — | i-Bu | 4-ClPh | H | p) | H | H |
| 174 | — | i-Bu | 4-MePh | H | z) | H | H |
| 175 | — | i-Bu | 4-ClPh | H | z) | H | H |
| 176 | — | i-Bu | 4-MePh | H | ac) | H | H |

The symbols in the Tables mean the following:

a) : 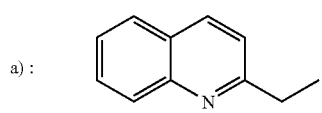

b) : 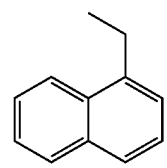

c) : 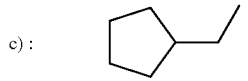

d) : 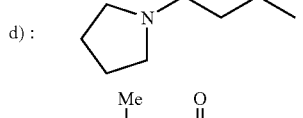

e) : 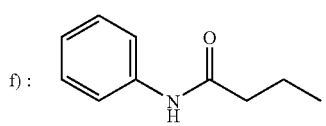

f) : 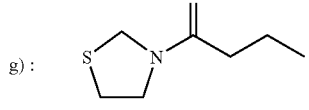

g) : 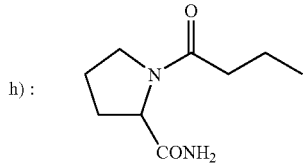

h) :

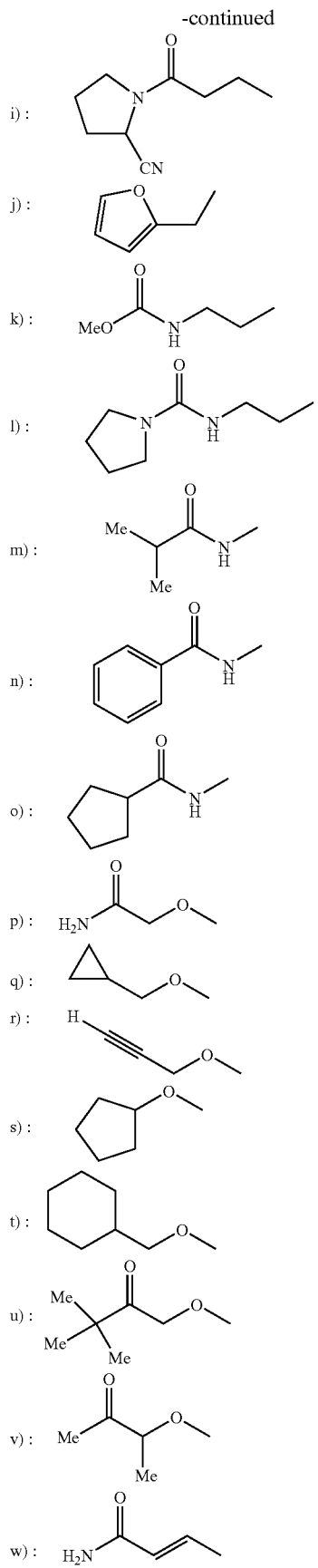

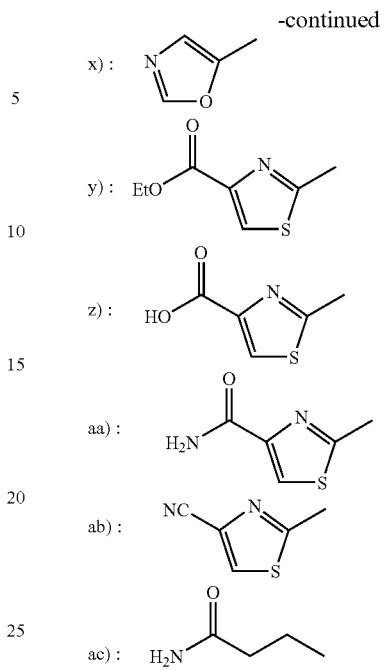

Me: methyl, Et: ethyl, CF$_3$: trifluoromethyl, neo-Pent: neopentyl, n-Bu: n-butyl, i-Bu: isobutyl, i-Pr: isopropyl, Ph: phenyl, n-Pr: n-propyl, 4-NO$_2$Ph: 4-nitrophenyl, 4-MeOPh: 4-methoxyphenyl, 4-MePh: 4-methylphenyl, 4-HOPh: 4-hydroxyphenyl, 3-MeOPh: 3-methoxyphenyl, 3-HOPh: 3-hydroxyphenyl, 4-FPh: 4-fluorophenyl, 4-CF$_3$Ph: 4-trifluoromethylphenyl, 3-NO$_2$Ph: 3-nitrophenyl, 3-NH$_2$Ph: 3-aminophenyl, n-Pent: n-pentyl, i-Pent: isopentyl, c-Pr: cyclopropyl, c-Hex: cyclohexyl, 4-ClPh: 4-chlorophenyl, 2-FPh: 2-fluorophenyl, 3-FPh: 3-fluorophenyl, Cbz: benzyloxycarbonyl, Ac: acetyl, Ms: methanesulfonyl More Preferable examples of compound (I) include:
2-[3-(aminomethyl)-4-butoxy-2-isobutyl-1-oxo-1,2-dihydro-6-isoquinolyl]-1,3-thiazole-4-carbonitrile;
2-[3-(aminomethyl)-4-butoxy-2-isobutyl-1-oxo-1,2-dihydro-6-isoquinolyl]-1,3-thiazole-4-carboxylic acid;
2-[3-(aminomethyl)-4-butoxy-2-isobutyl-1-oxo-1,2-dihydro-6-isoquinolyl]-1,3-thiazole-4-carboxamide;
ethyl 2-[3-(aminomethyl)-4-butoxy-2-isobutyl-1-oxo-1,2-dihydro-6-isoquinolyl]-1,3-thiazole-4-carboxylate;
(E)-3-[3-(aminomethyl)-4-butoxy-2-isobutyl-1-oxo-1,2-dihydro-6-isoquinolyl]-2-propenamide;
(E)-3-[3-(aminomethyl)-2-isobutyl-4-phenyl-1-oxo-1,2-dihydro-6-isoquinolyl]-2-propenamide;
3-(aminomethyl)-2-isobutyl-1-oxo-4-phenyl-1,2-dihydro-6-isoquinolinecarboxamide;
2-[[3-(aminomethyl)-2-isobutyl-4-phenyl-1-oxo-1,2-dihydro-6-isoquinolyl]oxy]acetamide; and the like.

As a salt of the compound of the formula (I) (hereinafter sometimes to be abbreviated as compound (I)), pharmacologically acceptable salt is preferable. Examples of such salt include salt with inorganic base, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include a salt with trimethylamine, triethylamine, pyridine, picoline, ethanolamine, diethanolamine, triethanolamine, dicyclohexylamine, N,N-dibenzylethylenediamine or the like.

Preferable examples of the salt with inorganic acid include a salt with hydrochloric acid, hydrobromic acid, nitric acid, sulfuric acid, phosphoric acid or the like.

Preferable examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like.

Preferable examples of the salt with basic amino acid include a salt with arginine, lysin, ornithine or the like.

Preferable examples of the salt with acidic amino acid include a salt with aspartic acid, glutamic acid or the like.

Of the above-mentioned salts, sodium salt, potassium salt, hydrochloride and the like are preferable.

A prodrug of compound (I) is a compound that converts to compound (I) due to the reaction of enzyme, gastric acid and the like under the physiological conditions in the body. That is, a compound that converts to compound (I) by enzymatic oxidation, reduction, hydrolysis and the like, and a compound that converts to compound (I) by hydrolysis and the like by gastric acid and the like. A prodrug of compound (I) is exemplified by a compound wherein an amino group of compound (I) is acylated, alkylated, phosphorylated (e.g., compound where amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); compound wherein a hydroxy group of compound (I) is acylated, alkylated, phosphorinated, borated (e.g., compound where hydroxy group of, compound (I) is acetylated, palmitoylated, propanoylated, pivaloylated, succinilated, fumarinated, alanilated, dimethylaminomethylcarbonylated and the like); compound wherein a carboxyl group of compound (I) is esterified or amidated (e.g., compound where carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3dioxolen-4-yl)methyl esterified, cyclohexyloxycarbonyethyl esterified, methylamidated and the like) and the like. These compounds can be produced from compound (I) by a method known per se.

A prodrug of compound (I) may be a compound that converts to compound (I) under physiological conditions as described in Development of pharmaceutical products, vol. 7, Molecule Design, 163–198, Hirokawa Shoten (1990).

The compound (I) may be labeled with isotope (e.g., $^3$H, $^{14}$C, $^{35}$S, $^{125}$I and the like) and the like.

The compound (I) may be an anhydride or a hydrate.

The compound (I), a salt thereof and a prodrug thereof (hereinafter sometimes to be simply referred to as the compound of the present invention) show low toxicity and can be used as an agent for the prophylaxis or treatment of various diseases to be mentioned later for mammal (e.g., human, mouse, rat, rabbit, dog, cat, cattle, horse, swine, simian and the like) by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder, disintegrant for solid preparations; and solvent, dissolution aids, suspending agent, isotonicity agent, buffer, soothing agent and the like for liquid preparations. Where necessary, additive for pharmaceutical preparations such as preservative, antioxidant, coloring agent, sweetening agent and the like can be used.

Preferable examples of the excipient include lactose, sucrose, D-mannitol, D-sorbitol, pregelatinized starch, dextrin, crystalline cellulose, low-substituted hydroxypropylcellulose, sodium carboxymethylcellulose, gum arabic, dextrin, pullulan, light silicic anhydride, synthetic aluminumsilicate, magnesium aluminate metasilicate and the like.

Preferable examples of the lubricant include magnesium stearate, calcium stearate, talc, colloidal silica and the like.

Preferable examples of the binder include pregelatinized starch, saccharose, gelatin, gum arabic, methylcellulose, carboxymethylcellulose, sodium carboxymethylcellulose, crystalline cellulose, sucrose, D-mannitol, trehalose, dextrin, pullulan, hydroxypropyl cellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium crosscarmellose, sodium carboxymethyl starch, light silicic anhydride, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferable examples of the dissolution aids include polyethylene glycol, propylene glycol, D-mannitol, trehalose, benzyl benzoate, ethanol, Tris aminomethane, cholesterol, triethanolamine, sodium carbonate, sodium citrate, sodium salicylate, sodium acetate and the like.

Preferable examples of the suspending agent include surfactants such as stearyltriethanolamine, sodium lauryl sulfate, lauryl aminopropionate, lecithin, benzalkonium chloride, benzethonium chloride, monostearic glyceride and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferable examples of the isotonicity agent include sodium chloride, glycerol, D-mannitol, D-sorbitol, glucose and the like.

Preferable examples of the buffer include phosphate buffer, acetate buffer, carbonate buffer, citrate buffer, and the like.

Preferable examples of the soothing agent include benzyl alcohol and the like.

Preferable examples of the preservative include p-oxybenzoic acid esters, chlorobutanol, benzyl alcohol, phenethyl alcohol, dehydroacetic acid, sorbic acid and the like.

Preferable examples of the antioxidant include sulfite, ascorbate and the like.

Preferable examples of the coloring agent include water-soluble edible tar pigment (.e.g., foodcolors such as Food Color Red Nos. 2 and 3, Food Color Yellow Nos. 4 and 5, Food Color Blue Nos. 1 and 2 and the like, water insoluble lake pigment (e.g., aluminum salt of the aforementioned water-soluble edible tar pigment and the like), natural pigments (e.g., beta carotene, chlorophil, red iron oxide etc.) and the like.

Preferable examples of the sweetening agent include saccharin sodium, dipotassium glycyrrhizinate, aspartame, stevia and the like.

The dosage form of the aforementioned pharmaceutical composition may be, for example, oral agents such as tablets (inclusive of sublingual tablets and orally disintegrable tablets), capsules (inclusive of soft capsules and micro capsules), granules, powders, troches, syrups, emulsions, suspensions and the like; or parenteral agents such as injections (e.g., subcutaneous injections, intravenous injections, intramuscular injections, intraperitoneal injections, drip infusions and the like), external agents (e.g., transdermal preparations, ointments and the like), suppositories (e.g., rectal suppositories, vaginal suppositories and the like), pellets, nasal preparations, pulmonary preparations (inhalations), ophthalmic preparations and the like. These may be administered safely via oral or parenteral route. These agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. The specific production methods of the pharmaceutical preparation are described in detail in the following.

While the content of the compound of the present invention in the pharmaceutical composition varies depending on dosage form, dose of the compound of the present invention and the like, it is, for example, about 0.1–100 wt %.

For example, an oral agent is produced by adding, to the active ingredient, excipient (e.g., lactose, sucrose, starch, D-mannitol and the like), disintegrant (e.g., calcium carboxymethylcellulose and the like), binder (e.g., pregelatinated starch, gum arabic, carboxymethylcellulose, hydroxypropylcellulose, polyvinylpyrrolidone and the like), lubricant (e.g., talc, magnesium stearate, polyethylene glycol 6000 and the like) and the like, compression-shaping the mixture, and where necessary, coating the same using a coating base for masking of taste, enteric property or sustained release according to a method known per se.

Examples of the coating base include a sugar-coating base, a water-soluble film coating base, an enteric film coating base, a sustained release film coating base and the like.

As a sugar-coating base, sucrose may be used, along with one or two species selected from talc, precipitated calcium carbonate, gelatin, gum arabic, pullulan, carnauba wax and the like.

As a water-soluble film coating, base, for example, cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkyl methacrylate copolymer E [Eudragit E, trademark, Rohm Pharma], polyvinylpyrrolidone and the like; polysaccharides such as pullulan and the like; and the like are used.

As a enteric film coating base, for example, cellulose polymers such as hydroxypropylmethylcellulose phthalate, hydroxypropylmethylcellulose acetate succinate, carboxymethylethylcellulose, acetic phthalic cellulose and the like; acrylic acid polymers, such as methacrylic acid copolymer L [Eudragit L, trademark, Rohm Pharma], methacrylic acid copolymer LD [Eudragit L-30D55, trademark, Rohm Pharma], methacrylic acid copolymer S [Eudragit S, trademark, Rohm Pharma] and the like; naturally occurring substance such as shellac and the like; and the like are used.

As a sustained release film coating base, for example, cellulose polymers such as ethylcellulose and the like; acrylic acid polymers such as aminoalkyl methacrylate copolymer RS [Eudragit RS, trademark, Rohm Pharma], ethyl acrylate methyl methacrylate copolymer suspension [Eudragit NE, trademark, Rohm Pharma] and the like, and the like are used.

Two or more kinds of the above-mentioned coating bases may be mixed in an appropriate ratio for use. In addition, a light shielding agent such as titanium oxide, iron tri or dioxide and the like may be used during coating.

An injection is produced by dissolving, suspending or emulsifying an active ingredient in an aqueous solvent (e.g., distilled water, physiological saline, Ringer's solution and the like) or an oily solvent (e.g., plant oil such as olive oil, sesame oil, cottonseed oil, corn oil and the like, propylene glycol and the like) and the like, together with a dipersing agent (eg., polysorbate 80, polyoxyethylene hydrogenated castor oil 60 and the like), polyethylene glycol, carboxymethylcellulose, sodium alginate and the like), preservative (e.g., methylparaben, propylparaben, benzyl alcohol, chlorobutanol, phenol and the like), isotonicity agent (e.g., sodium chloride, glycerol, D-mannitol, D-sorbitol, glucose and the like) and the like. In this step, dissolution aids (e.g., sodium salicylate, sodium acetate and the like), stabilizers (e.g., human serum albumin and the like), soothing agents (e.g., benzyl alcohol and the like) and the like may be used on demand.

The compound of the present invention and the pharmaceutical agent of the present invention show low toxicity, cause fewer side effects and can be used as an agent for the prophylaxis or treatment or diagnosis of various diseases to be mentioned later for mammal (e.g., human, cattle, horse, dog, cat, simian, mouse, rat, especially human).

The compound of the present invention and the pharmaceutical agent of the present invention have a superior peptidase inhibitory activity and can suppress peptidase-caused degradation of a physiologically active substance such as peptide hormones, cytokines, neurotransmitters and the like.

Examples of the peptide hormones include glucagon-like peptide-1 (GLP-1), glucagon-like peptide-2 (GLP-2), GIP, growth hormone release hormone (GHRH) and the like.

Examples of the cytokines include chemokine such as RANTES and the like.

Examples of the neurotransmitters include neuropeptide Y and the like.

Examples of the peptidase include EC 3.4.11.1 (Leucyl aminopeptidase), EC 3.4.11.2 (Membrane alanine aminopeptidase), EC 3.4.11.3 (Cystinyl aminopeptidase), EC 3.4.11.4 (Tripeptide aminopeptidase), EC 3.4.11.5 (Prolyl aminopeptidase), EC 3.4.11.6 (Aminopeptidase B), EC 3.4.11.7 (Glutamyl aminopeptidase), EC 3.4.11.9 (Xaa-Pro aminopeptidase), EC 3.4.11.10 (Bacterial leucyl aminopeptidase), EC 3.4.11.13 (Clostridial aminopeptidase), EC 3.4.11.14 (Cytosol alanyl aminopeptidase), EC 3.4.11.15 (Lysyl aminopeptidase), EC 3.4.11.16 (Xaa-Trp aminopeptidase), EC 3.4.11.17 (Tryptophanyl aminopeptidase), EC 3.4.11.18 (Methionyl aminopeptidase), EC 3.4.11.19 (D-stereospecific aminopeptidase), EC 3.4.11.20 (Aminopeptidase Ey), EC 3.4.11.21 (Aspartyl aminopeptidase), EC 3.4.11.22 (Aminopeptidase I), EC 3.4.13.3 (Xaa-His dipeptidase), EC 3.4.13.4 (Xaa-Arg dipeptidase), EC 3.4.13.5 (Xaa-methyl-His dipeptidase), EC 3.4.13.7 (Glu-Glu dipeptidase), EC 3.4.13.9 (Xaa-Pro dipeptidase), EC 3.4.13.12 (Met-Xaa dipeptidase), EC 3.4.13.17 (Non-stereospecific dipeptidase), EC 3.4.13.18 (Cytsol nonspecific dipeptidase), EC 3.4.13.19 (Membrane dipeptidase), EC 3.4.13.20 (Beta-Ala-His dipeptidase), EC 3.4.14.1 (Dipeptidyl-peptidase I), EC 3.4.14.2 (Dipeptidyl-peptidase II), EC 3.4.14.4 (Dipeptidylpeptidase III), EC 3.4.14.5 (Dipeptidyl-peptidase IV), EC 3.4.14.6 (Dipeptidyl-dipeptidase), EC 3.4.14.9 (Tripeptidyl-peptidase I), EC 3.4.14.10 (Tripeptidyl-peptidase II) and EC 3.4.14.11 (Xaa-Pro dipeptidyl-peptidase) as classified by International Union of Biochemistry and Molecular Biology (IUBMB), and the like.

Of these, EC 3.4.14.1, EC 3.4.14.2, EC 3.4.14.4, EC 3.4.14.5, EC 3.4.14.6, EC 3.4.14.9, EC 3.4.14.10 and EC 3.4.14.11 are preferable. Especially preferred is EC 3.4.14.5.

The compound of the present invention and the pharmaceutical agent of the present invention are useful as a prophylactic and therapeutic agent of diabetes (e.g., type 1 diabetes, type 2 diabetes, gestational diabetes and the like); prophylactic and therapeutic agent of hyperlipidemia (e.g., hypertriglyceridemia, hypercholesterolemia, low HDL lipemia, postprandial lipemia and the like); prophylactic and therapeutic agent of arteriosclerosis; prophylactic and therapeutic agent of impaired glucose tolerance [IGT]; an insulin secretagogue; and an agent for suppressing progress of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, a non-fasting blood glucose level (glucose concentration of intravenous plasma) of not less than 200 mg/dl. A condition not falling under the above-mentioned diabetes, or "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Academy) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG, (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention and the pharmaceutical agent of the present invention can be also used as a prophylactic and therapeutic agent of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention and the pharmaceutical agent of the present invention can prevent progress of borderline type, impaired glucose tolerance, IFG (Impaired Fasting Glucose) or IFG (Impaired Fasting Glycemia) into diabetes.

The compound of the present invention and the pharmaceutical agent of the present invention can be also used as a prophylactic and therapeutic agent of, for example, diabetic complications [e.g., neuropathy, nephropathy, retinopathy, cataract, macroangiopathy, osteopenia, hyperosmolar diabetic coma, infectious disease (respiratory infection, urinary tract infection, gastrointestinal infection, dermal soft tissue infections, inferior limb infection and the like), diabetic gangrene, xerostomia, hypacusis, cerebrovascular disorder, peripheral blood circulation disorder and the like], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease and the like), muscular dystrophy, myocardial infarction, angina pectoris, cerebrovascular accident (e.g., cerebral infarction, cerebral apoplexy), insulin resistance syndrome, Syndrome X, hyperinsulinemia, hyperinsulinemia-induced sensory disorder, tumor (e.g., leukemia, breast cancer, prostatic cancer, skin cancer and the like), irritable bowel syndrome, acute or chronic diarrhea, inflammatory diseases (e.g., chronic rheumatoid arthritis, spondylitis deformans, arthritis cleformans, lumbar pain, gout, postoperative or traumatic inflammation, remission of tumentia, neuralgia, pharyngolaryngitis, cystitis, hepatitis (inclusive of nonalcoholic steatohepatitis), pneumonia, pancreatitis, inflammatory bowel disease, ulcerative colitis, gastric mucosal injury (inclusive of gastric mucosal injury caused by aspirin) and the like), visceral obesity syndrome and the like.

The compound of the present invention and the pharmaceutical agent of the present invention can be also used for decreasing visceral, fat, suppressing visceral fat accumulation, improving glycometabolism, improving lipid metabolism, suppressing production of oxidized LDL, improving lipoprotein metabolism, improving coronary artery metabolism, prophylaxis and treatment of cardiovascular complication, prophylaxis and treatment of heart failure complication, lowering blood remnant, prophylaxis and treatment of anovulation, prophylaxis and treatment of hypertrichosis, prophylaxis and treatment of hyperandrogenemia, improving pancreatic (β cell) function, regeneration of pancreatic (β cell), promotion of pancreatic (β cell) regeneration, and the like.

The compound of the present invention and the pharmaceutical agent of the present invention can be also used for secondary prophylaxis and suppression of progression of the above-mentioned various diseases (e.g., cardiovascular event such as myocardial infarction and the like).

The compound of the present invention and the pharmaceutical agent of the present invention is a glucose dependent insulin secretagogue that selectively promotes insulin secretion in hyperglycemic patients (e.g., patients showing fasting blood glucose level of not less than 126 mg/dl or 75 g oral glucose tolerance test (75 g OGTT) 2 h level of not less than 140 mg/dl and the like). Therefore, the compound of the present invention and the pharmaceutical agent of the present invention are useful as a safe prophylactic or therapeutic agent of diabetes with a low risk of vascular complications, hypoglycemia induction and the like caused by insulin.

While the dose of the compound of the present invention and the pharmaceutical agent of the present invention varies depending on the administration subject, administration route, target disease, condition and the like, the compound of the present invention as an active ingredient is generally given in a single dose of about 0.01–100 mg/kg body weight, preferably 0.05–30 mg/kg body weight, more preferably 0.1–10 mg/kg body weight, in the case of, for example, oral administration to adult diabetic patients. This dose is desirably given 1 to 3 times a day.

The compound of the present invention can be used in combination with therapeutic agents such as a therapeutic agent of diabetes, a therapeutic agent of diabetic complications, an antihyperlipemia agent, an antihypertensive agent, an antiobestic agent, a diuretic, a chemotherapeutic agent, an immunotherapeutic agent, an antithrombotic agent, a therapeutic agent of osteoporosis, an antidementia agent, an agent for the improvement of erectile dysfunction, a therapeutic agent of incontinentia or pollakiuria and the like (hereinafter to be referred to as a combination drug). In this case, the timing of administration of the compound of the present invention and a combination drug is not limited. These may be simultaneously administered to an administration object or administered in a staggered manner. Moreover, the compound of the present invention and a combination drug may be administered as two kinds of preparations each containing an active ingredient, or may be administered as a single preparation containing both active ingredients.

The dose of the combination drug can be determined as appropriate based on the dose clinically employed. The proportion of the compound of the present invention and combination drug can be appropriately determined depending on the administration subject, administration route, target disease, condition, combination and the like. When, for example, the administration subject is human, a combination drug is used in an amount of 0.01–100 parts by weight per 1 part by weight of the compound of the present invention.

Examples of the therapeutic agent of diabetes include insulin preparations (e.g., animal insulin preparations extracted from pancreas of cattle, swine; human insulin preparations synthesized by genetic engineering techniques using *Escherichia coli* or yeast; zinc insulin; protamine zinc insulin; fragments or derivatives of insulin (e.g., INS-1 and the like) and the like), insulin sensitizers (e.g., pioglitazone hydrochloride, rosiglitazone (maleate), GI-262570, JTT-501, MCC-555, YM-440, KRP-297, CS-011, FK-614, NN-622, AZ-242, BMS-298585, EML-16336, compounds described in WO99/58510 (e.g., (E)-4-[4-(5-methyl-2-phenyl-4-oxazolylmethoxy)benzyloxyimino]-4-phenylbutyric acid) and the like), PPARγ agonists, PPARγ antagonists, PPARγ/α dual agonists, α-glucosidase inhibitors (e.g., voglibose, acarbose, miglitol, emiglitate and the like), biguanides (e.g., phenformin, metformin, buformin and the like), insulin secretagogues [sulfonylureas (e.g., tolbutamide, glibenclamide, gliclazide, chlorpropamide, tolazamide, acetohexamide, gyclopyramide, glimepiride, glipizide, glybuzole and the like), repaglinide, senaglinide, nateglinide, mitiglinide or calcium salt hydrate thereof], GLP-1 receptor agonists [e.g., GLP-1, NN-2211, AC-2993 (exendin-4), BIM-51077, Aib(8,35)hGLP-1(7,37)NH$_2$ and the like], amyrin agonists (e.g., pramlintide and the like), phosphotyrosine phosphatase inhibitors (e.g., vanadic acid and the like), dipeptidylpeptidase IV inhibitors (e.g., NVP-DPP-278, PT-100, P32/98, LAF-237 and the like), β3 agonists (e.g., CL-316243, SR-58611-A, UL-TG-307, SB-226552, AJ-9677, BMS-196085, AZ40140 and the like), gluconeogenesis inhibitors (e.g., glycogen phosphorylase inhibitors, glucose-6-phosphatase inhibitors, glucagon antagonists, somatostatin receptor agonists and the like), SGLT (sodium-glucose cotransporter);inhibitors (e.g., T-1095 and the like) and the like.

Examples of the therapeutic agent of diabetic complications include aldose reductase inhibitors (e.g., Tolrestat, Epalrestat, Zenarestat, Zopolrestat, Minalrestat, Fidarestat, SNK-860, CT-112 and the like), neurotrophic factors and increasing drugs thereof (e.g., NGF, NT-3, BDNF, neurotrophin production secretion promoters described in WO01/14372 (e.g., 4-(4-chlorophenyl)-2-(2methyl-1-imidazolyl)-5-[3-(2-methylphenoxy)propyl]oxazole and the like) and the like), neuranagenesis stimulators (e.g., Y-128 and the like), PKC inhibitors (e.g., LY-333531 and the like), AGE inhibitors (e.g., ALT946, pimagedine, pyratoxanthine, N-phenacylthiazolium bromide (ALT766), EXO-226 and the like), active oxygen scavengers (e.g., thioctic acid and the like), cerebral vasodilators (e.g., tiapride, mexiletine and the like), and the like.

Examples of the antihyperlipemia agent include statin compounds which are cholesterol synthesis inhibitors (e.g., cerivastatin, pravastatin, simvastatin, lovastatin, atorvastatin, fluvastatin, itavastatin and salts thereof (e.g., sodium salt) and the like), squalene synthase inhibitors (e.g., compounds described in WO97/10224, such as N-[-[(3R,5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]-piperidine-4-acetic acid and the like) or fibrate compounds having a triglyceride lowering action (e.g., bezafibrate, clofibrate, simfibrate, clinofibrate and the like), ACAT inhibitors (e.g., Avasimibe, Eflucimibe and the like), anion exchange resins (e.g., colestyramine and the like), probucol, nicotinic acid drugs (e.g., nicomol, niceritrol and the like), ethyl icosapentate, plant sterols (e.g., soysterol, γ-oryzanol and the like) and the like.

Examples of the antihypertensive agent include angiotensin converting enzyme inhibitors (e.g., captopril, enalapril, delapril and the like) or angiotensin II antagonists (e.g., candesartan cilexetil, losartan, eprosartan, valsartan, telmisartan, irbesartan, tasosartan and the like), calcium antagonists (e.g., manidipine, nifedipine, amlodipine, efonidipine, nicardipine and the like), potassium channel, openers (e.g., levcromakalim, L-27152, AL 0671, NIP-121 and the like), Clonidine and the like.

Examples of the antiobestic agent include central antiobestic agents (e.g., Dexfenfluramine, fenfluramine, phentermine, Sibutramine, amfepramone, dexamphetamine, Mazindol, phenylpropanolamine, clobenzorex and the like), pancreatic lipase inhibitors (e.g., orlistat and the like), β3 agonists (e.g., CL-316243, SR-58611-A, UL-TG-307, SB-226552, AJ-9677, BMS-196085, AZ40140and the like), peptide anorexiants (e.g., leptin, CNTF (Ciliary Neurotropic Factor) and the like), cholecystokinin agonists (e.g., lintitript, FPL-15849 and the like) and the like.

Examples of the diuretic include xanthine derivatives (e.g., sodium salicylate and theobromine, calcium salicylate and theobromine and the like), thiazide preparations (e.g., ethiazide, cyclopenthiazide, trichloromethyazide, hydrochlorothiazide, hydroflumethiazide, benzylhydrochlorothiazide, penflutizide, polythiazide, methylcothiazide and the like), antialdosterone agents (e.g., spironolactone, triamterene and the like), carbonate dehydrating enzyme inhibitors (e.g., acetazolamide and the like), chlorobenzene-sulfonamide agents (e.g., chlortalidone, mefruside, indapamide and the like), azosemide, isosorbide, etacrynic acid, piretanide, bumetanide, furosemide and the like.

Examples of the chemotherapeutic agent include alkylation agents (e.g., cyclophosphamide, ifosfamide and the like), metabolic antagonists (e.g., methotrexate, 5-fluorouracil and the like), anti-cancer antibiotics (e.g., mitomycin, adriamycin and the like), plant-derived anti-cancer agents (e.g., vincristin, vindesine, taxol and the like), cisplatin, carboplatin, etopoxide and the like. Of these, furtulon and neofurtulon which are 5-fluorouracil derivatives and the like are preferable.

Examples of the immunotherapeutic agent include microorganism or bacterial components (e.g., muramyl dipeptide derivative, picibanil and the like), polysaccharides having immunity potentiating activity (e.g., lentinan, sizofiran, krestin and the like), cytokines obtained by genetic engineering techniques (e.g., interferon, interleukin (IL) and the like), colony stimulating factors (e.g., granulocyte stimulating factor, erythropoietin and the like) and the like, with preference given to IL-1, IL-2, IL-12 and the like.

Examples of the antithrombotic agent include heparin (e.g., heparin sodium, heparin calcium, dalteparin sodium and the like), warfarin (e.g., warfarin potassium and the like), anti-thrombin drugs (e.g. aragatroban and the like), thrombolytic agents (eg., urokinase, tisokinase, alteplase, nateplase, monteplase, pamiteplase and the like), platelet aggregation inhibitors (e.g., ticlopidine hydrochloride, cilostazol, ethyl icosapentate, beraprost sodium, sarpogrelate hydrochloride and the like) and the like.

Examples of the therapeutic agent of osteoporosis include alfacalcidol, calcitriol, elcaltonin, calcitonin salmon, estriol, ipriflavone, papidronate disodium, alendronate sodium hydrate, incadronate disodium and the like.

Examples of the antidementia agent include tacrine, donepezil, rivastigmine, galantamine and the like.

Examples of the agent for improving erectile, dysfunction include apomorphine, sildenafil citrate and the like.

Examples of the therapeutic agent of incontinentia or pollakiuria include flavoxate hydrochloride, oxybutynin hydrochloride, propiverine hydrochloride and the like.

Furthermore, drugs having a cachexia-improving action established in animal models and clinical situations, such as cyclooxygenase inhibitors (e.g., Indometacin and the like) [Cancer Research, vol. 49, 5935–5939, 1989], Progesterone derivatives (e.g., Megesterol acetate) [Journal of Clinical Oncology, vol. 12, 213–225, 1994], glucosteroid (e.g., dexamethasone and the like), metoclopramide agents, tetrahydrocannabinol agents (ibid.), fat metabolism improving agents (e.g., eicosapentaenoic acid and the like) [British Journal of Cancer, vol. 68, 314–318, 1993], growth hormones, IGF-1, or antibodies to a cachexia-induced factor such as TNF-α, LIF, IL-6, Oncostatin M and the like, can be used in combination with the compound of the present invention.

The combination drug is preferably an insulin preparation, an insulin sensitizer, an α-glucosidase inhibitor, a biguanide, an insulin secretagogue (preferably a sulfonylurea) or the like.

Two or more of the above-mentioned combination drugs can be used in combination in an appropriate ratio. Preferable combinations in the case of using two or more combination drugs are, for example, as shown in the following.
(1) an insulin secretagogue (preferably a sulfonylurea) and an α-glucosidase inhibitor;
(2) an insulin secretagogue (preferably a sulfonylurea) and a biguanide;
(3) an insulin secretagogue (preferably a sulfonylurea), a biguanide and an α-glucosidase inhibitor;
(4) an insulin sensitizer and an a-glucosidase inhibitor;
(5) an insulin sensitizer and a biguanide;
(6) an insulin sensitizer, a biguanide and an α-glucosidase inhibitor.

When the compound of the present invention or the pharmaceutical agent of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent of diabetic complications, antihyperlipemia agent and antihypertensive agent can be reduced whereby an adverse effect which may be caused by these agents can be prevented effectively.

Hereinafter the production methods of the compound of the present invention are explained.

The compound of the present invention can be produced according to a method known per se, such as a method to be described in detail in the following, or an analogous method thereto.

For example, compound (I-a) of the formula (I) wherein L is alkylene can be produced according to the following Method A or an analogous method thereto.

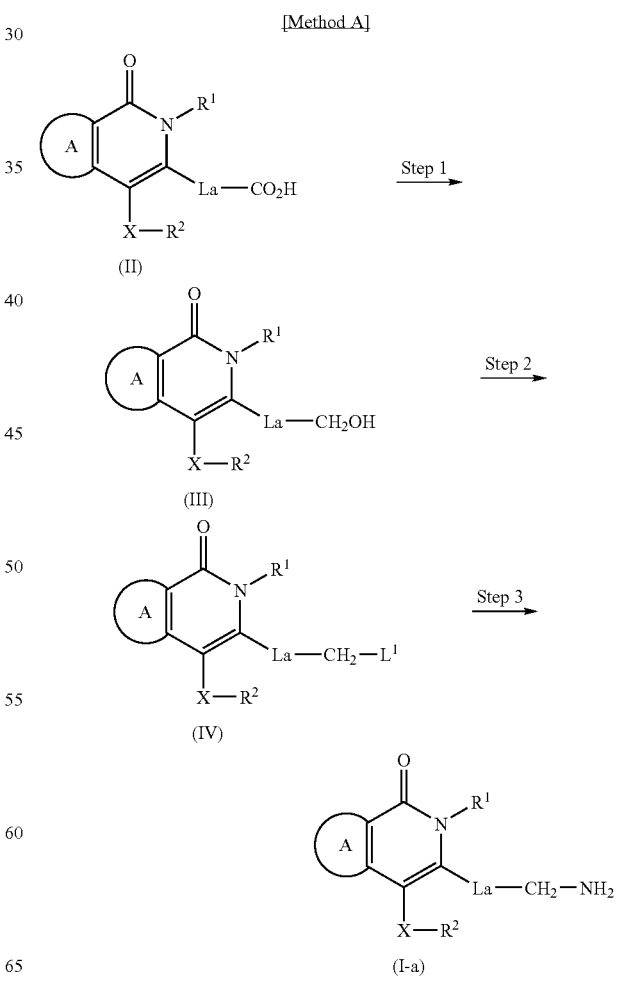

wherein La is a bond or alkylene, $L^1$ is a leaving group, and other symbols are as defined above.

The alkylene for La is exemplified by that mentioned as the aforementioned L. When L is alkylene, L is the same as La(CH$_2$).

The leaving group for $L^1$ may be, for example, halogen atom (e.g., chlorine, bromine, iodine and the like), optionally halogenated $C_{1-6}$ alkylsulfonyloxy (e.g., methanesulfonyloxy, ethanesulfonyloxy, trifluoromethanesulfonyloxy and the like), optionally substituted $C_{6-10}$ arylsulfonyloxy, hydroxy and the like.

Examples of the substituent in the "optionally substituted $C_{6-10}$ arylsulfonyloxy" include halogen atom (e.g., chlorine, bromine, iodine and the like), optionally halogenated $C_{1-6}$ alkyl or $C_{1-6}$ alkoxy and the like. The number of the substituent(s) is, for example, 1 to 3. Specific examples of the "optionally substituted $C_{6-10}$ arylsulfonyloxy" include benzenesulfonyloxy, p-toluenesulfonyloxy, 1-naphthalenesulfonyloxy, 2-naphthalenesulfonyloxy and the like.

The "leaving group" is preferably halogen atom (e.g., chlorine, bromine, iodine and the like), methanesulfonyloxy, trifluoromethanesulfonyloxy, p-toluenesulfonyloxy and the like.

(Step 1)

This reaction is carried out by directly reducing with a reducing agent (e.g., borane, lithium aluminum hydride and the like) in a solvent that does not adversely influence the reaction, or converting a carboxyl group to its reactive derivative (e.g., acid halide, mixed acid anhydride, active ester, ester and the like) and reducing with a reducing agent (e.g., sodium borohydride, sodium lithium borohydride, lithium aluminum hydride, diisobutyl aluminum hydride and the like).

The amount of the reducing agent to be used is preferably from about 0.5 to about 10 molar equivalents per compound (II).

The solvent that does not adversely influence the reaction varies depending on the reducing agent. Examples thereof include aromatic hydrocarbons such as benzene, toluene, xylene and the like; halogenated hydrocarbons such as chloroform, dichlordmethane and the like; ethers such as tetrahydrofuran, 1,2-dimethoxyethane, dioxane, diethyl ether and the like; water; alcohols such as methanol, ethanol, isopropanol and the like; and the like. Two or more of these solvents may be used upon mixing at a suitable ratio.

The reaction temperature is generally from about –50° C. to about 150° C., preferably about –10° C. to about 100° C.

The reaction time is generally from about 0.5 to about 20 hours.

The compound (III) thus obtained can be isolated and purified by a known separation and purification means, such as concentration, concentration under reduced pressure, solvent extraction, crystallization, recrystallization, phase transfer, chromatography and the like.

(Step 2)

When $L^1$ is a halogen atom, this reaction is carried out using a halogenating agent in a solvent that does not adversely influence the reaction.

Examples of the halogenating agent include thionyl chloride, phosphorus tribromide and the like.

The amount of the halogenating agent to be used is preferably 1 to about 20 molar equivalents per compound (III).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like, and the like. Two or more of these solvents may be used upon mixing at a suitable ratio. It is also possible to use an excess halogenating agent as a solvent.

The reaction temperature is generally from about –20° C. to about 150° C., preferably about 0° C. to about 100° C.

The reaction time is generally from about 0.1 to about 20 hours.

When $L^1$ is an optionally halogenated $C_{1-6}$ alkylsulfonyloxy or an optionally substituted $C_{6-10}$ arylsulfonyloxy, this reaction is carried out using a sulfonylating agent in the presence of a base in a solvent that does not adversely influence the reaction.

Examples of the sulfonylating agent include mesyl chloride, tosyl chloride, benzenesulfonyl chloride and the like.

Examples of the base include amines such as triethylamine, N-methylmorpholine, N,N-dimethylaniline and the like; alkali metal salts such as sodium hydrogencarbonate, sodium carbonate, potassium carbonate and the like; and the like.

The amount of the sulfonylating agent and the base to be used is preferably 1 to about 2 molar equivalents per compound (III).

Examples of the solvent that does not adversely influence the reaction include aromatic hydrocarbons such as benzene, toluene, xylene and the like; ethers such as tetrahydrofuran, dioxane diethyl ether and the like; halogenated hydrocarbons such as chloroform, dichloromethane and the like; ethyl acetate and the like.

Two or more of these solvents may be used upon mixing at a suitable ratio.

The reaction temperature is generally about –20° C. to about 150° C., preferably about 0° C. to about 100° C.

The reaction time is generally from about 0.1 to about 20 hours.

The thus-obtained compound (IV) can be isolated and purified by a known separation and purification means, such as concentration, concentration under reduced pressure, solvent extraction, crystallization, recrystallization, phase transfer, chromatography and the like.

(Step 3)

This reaction is carried out by reacting compound (IV) and an aminating agent in a solvent that does not adversely influence the reactions and subjecting the obtained compound to deprotection of an amino group as necessary.

Examples of the aminating agent include ammonia, hexamethylenetetramine, potassium phthalimide, di-t-butyl dicarboxylimide and the like.

The amount of the aminating agent to be used is preferably about 1 to about 5 molar equivalents per compound (IV).

Examples of the solvent that does not adversely influence the reaction include aromatic hydrocarbons such as benzene, toluene, xylene, and the like; ethers such as tetrahydrofuran, dioxane, diethyl ether and the like; halogenated hydrocarbons such as chloroform, dichloromethane and the like; alcohols such as methanol, ethanol, isopropanol and the like; ketones such as acetone, 2-butanone and the like; amides such as N,N-dimethylformamide and the like; sulfoxides such as dimethyl sulfoxide and the like; and the like. Two or more of these solvents may be used upon mixing at a suitable ratio.

The reaction temperature is about 0° C. to about 200° C., preferably about 20° C. to about 120° C.

The reaction time is generally from about 0.5 to about 20 hours.

The amino group is deprotected according to a method known per se.

The thus obtained compound (I-a) can be isolated and purified by a known separation and purification means, such as concentration, concentration under reduced pressure, solvent extraction, crystallization, recrystallization, phase transfer, chromatography and the like.

The compound (II) used as a starting material compound in Method A can be produced according to a method known per se, for example, the methods detailed in the following or analogous methods thereto.

The compound (II-a) which is a compound of the formula (II) wherein La is a bond and X is —O— can be produced according to the method described in, for example, Journal of Heterocyclic chemistry, vol. 7, 1057 (1970), the following Method B, or analogous methods thereto.

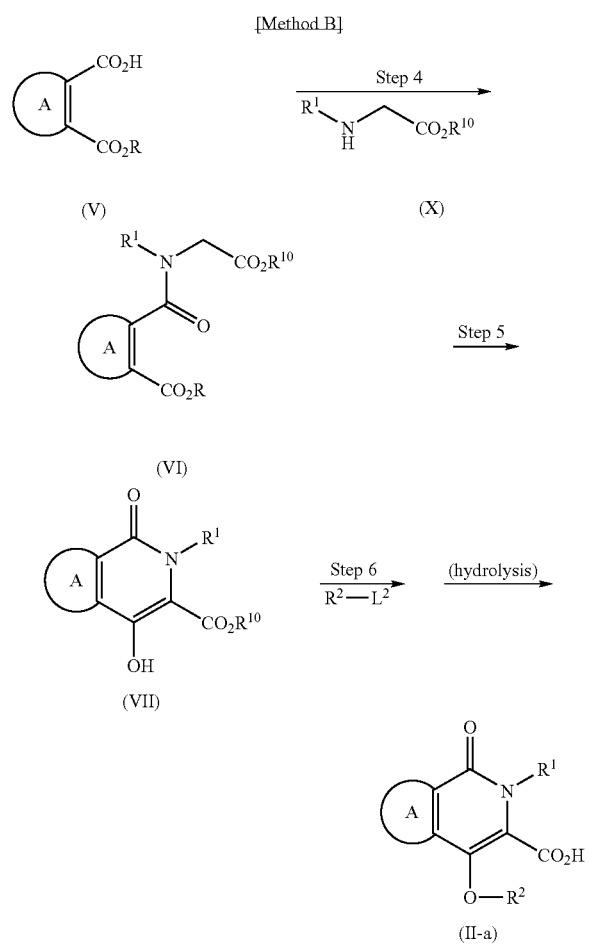

wherein R is a $C_{1-6}$ alkyl group, $R^{10}$ is a hydrogen atom or an optionally substituted hydrocarbon group, $L^2$ is a leaving group and other symbols are as defined above.

Examples of the $C_{1-6}$ alkyl group for R include methyl, ethyl and the like.

The "optionally substituted hydrocarbon group" for $R^{10}$ is exemplified by that mentioned as the aforementioned $R^3$.

The leaving group for $L^2$ is exemplified by that mentioned as the aforementioned $L^1$. The leaving group for $L^2$ maybe a hydroxy group.

(Step 4)

This reaction is carried out according to, for example a method comprising direct condensation of compound (V) and glycine derivative (X) using a condensation agent (e.g., dicyclohexylcarbodiimide and the like), or a method comprising appropriately reacting a reactive derivative of compound (V) and a glycine derivative and the like. Examples of the reactive derivative include acid anhydride, acid halide (e.g., acid chloride, acid bromide), imidazolide, or mixed acid anhydride (e.g., anhydride with methyl carbonate, ethyl carbonate or isobutyl carbonate and the like) and the like.

When, for example, acid halide is used as a reactive derivative of compound (V), the reaction is carried out in the presence of a base in a solvent that does not adversely influence the reaction.

Examples of the base include amines such as triethylamine, N-methylmorpholine, N,N-dimethylaniline and the like; alkali metal salts such as sodium hydrogencarbonate, sodium carbonate, potassium carbonate and the like; and the like.

Examples of the solvent that does not adversely influence the reaction include halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like. Two or more of these solvents may be used upon mixing at a suitable ratio.

The amount of the glycine derivative (X) to be used is 0.1 to 10 molar equivalents preferably 1 to 3 molar equivalents, per compound (V).

The reaction temperature is about –30° C. to about 100° C.

The reaction time is generally 0.5 to 20 hours.

When a mixed acid anhydride is used as a reactive derivative of compound (V), compound (V) and chlorocarbonate ester (e.g., methyl chlorocarbonate, ethyl chlorocarbonate, isobutyl chlorocarbonate and the like) are reacted in the presence of a base and then reacted with glycine derivative (X).

Examples of the base include amines such as triethylamine, N-methylmorpholine, N,N-dimethylaniline and the like; alkali metal salts such as sodium hydrogencarbonate, sodium carbonate, potassium carbonate and the like; and the like.

The amount of the glycine derivative (X) to be used is generally 0.1 to 10 molar equivalents, preferably 0.3 to 3 molar equivalents, per compound (V).

The reaction temperature is generally from about –30° C. to about 100° C.

The reaction time is generally from 0.5 to 20 hours.

The thus-obtained compound (VI) can be isolated and purified by a known separation and purification means, such as concentration, concentration under reduced pressure, solvent extraction, crystallization, recrystallization, phase transfer, chromatography and the like.

The compound (V) and glycine derivative (X) used as a starting material compound in step 4 can be produced according to a method known per se.

(Step 5)

This reaction is carried out according to a conventional method in the presence of a base in a solvent that does not adversely influence the reaction.

Examples of the base include metalhydrides such as sodium hydride, potassium hydride and the like; alkali metal alkoxides such as sodium methoxide, sodium ethoxide, potassium t-butoxide and the like; alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undeca-7-ene and the like.

The amount of the base to be used is preferably about 0.1 to about 2 molar equivalents per compound(VI).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; water; alcohols such as methanol, ethanol, isopropanol and the like; ketones such as acetone, 2-butanone and the like; amides such as N,N-dimethylformamide and the like; sulfoxides such as dimethyl sulfoxide and the like; and the like. Two or more of these solvents may be used upon mixing at a suitable ratio.

The reaction temperature is about −10° C. to about 150° C., preferably about 0° C. to about 110° C.

The reaction time is generally from about 0.5 to about 20 hours.

The thus-obtained compound (VII) can be isolated and purified by a known separation and purification means, such as concentration, concentration under reduced pressure, solvent extraction, crystallization, recrystallization, phase transfer, chromatography and the like.

(Step 6)

When $L^2$ is a hydroxy group, this reaction is carried out by a method known per se, such as a method described in Synthesis, page 1 (1981), or an analogous method thereto.

This reaction is generally carried out in the presence of an organic phosphorus compound and electrophil in a solvent that does not adversely influence the reaction.

Examples of the organic phosphorus compound include triphenylphosphine, tributylphosphine and the like.

Examples of the electrophil include diethyl azodicarboxylate, diisopropyl azodicarboxylate, azodicarbonyldipiperazine and the like.

The amount of the organic phosphorus compound and electrophil to be used is preferably about 1 to about 5 molar equivalents per compound (VII).

Examples of the solvent that does not adversely influence the reaction include ethers such as diethyl ether, tetrahydrofuran, dioxane and the like; halogenated hydrocarbons such as chloroform, dichloromethane, and the like; aromatic hydrocarbons such as benzene, toluene, xylene and the like; amides such as N,N-dimethylformamide and the like; sulfoxides such as dimethyl sulfoxide and the like; and the like. Two or more of these solvents may be used upon mixing at a suitable ratio.

The reaction temperature is about −50° C. to about 150° C., preferably about −10° C. to about 100° C.

The reaction time is generally from about 0.5 to about 20 hours.

When $L^2$ is a halogen atom, an optionally halogenated $C_{1-6}$ alkylsulfonyloxy or an optionally substituted $C_{6-10}$ arylsulfonyloxy, this reaction is carried out according to a conventional method in the presence of a base in a solvent that does not adversely influence the reaction.

Examples of the base include alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undeca-7-ene and the like; metalhydrides such as potassium hydride, sodium hydride and the like; alkali metal alkoxides such as sodium methoxide, sodium ethoxide, potassium t.-butoxide and the like; and the like.

The amount of the base to be used is preferably about 1 to about 5 molar equivalents per compound (VII).

Examples of the solvent that does not adversely influence the reaction include aromatic hydrocarbons such as benzene, toluene, xylene and the like; ethers such as tetrahydrofuran, dioxane, diethyl, ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like. Two or more of these solvents may be used upon mixing at a suitable ratio.

The reaction temperature is generally about −50° C. to about 150° C., preferably about −10° C. to about 100° C.

The reaction time is generally from about 0.5 to about 20 hours.

The compound obtained from the aforementioned step 6 is hydrolyzed, where necessary, by a method known per se to give compound (II-a).

The thus-obtained compound (II-a) can be isolated and purified by a known separation and purification means, such as concentration, concentration under reduced pressure, solvent extraction, crystallization, recrystallization, phase transfer, chromatography and the like.

The compound (VI) to be used in the aforementioned Method B can be also produced according to the following Method C.

[Method C]

wherein the symbols are as defined above.

(Step 7)

This reaction is carried out according to a conventional method in a solvent that does not adversely influence the reaction.

Examples of the solvent that does not adversely influence the reaction include halogenated hydrocarbons such as chloroform, dichloromethane and the like; aromatic, hydrocarbons such as benzene, toluene and the like; ethers such as tetrahydrofuran, dioxane, diethyl ether and the like; ethyl acetate and the like. Two or more of these solvents may be used upon mixing at a suitable ratio.

The amount of the glycine derivative (X) to be used is about 1 to about 10 molar equivalents; preferably 1 to 3 molar equivalents per compound (VIII).

The reaction temperature is generally from −30° C. to 100° C.

The reaction time is generally from 0.5 to 20 hours.

The thus-obtained compound (IX) can be isolated and purified by a known separation and purification means, such as concentration, concentration under reduced, pressure, solvent extraction, crystallization, recrystallization, phase transfer, chromatography and the like.

The compound (VIII) used as a starting material compound in Step 7 can be produced according to a method known per se.

(Step 8)

This reaction is carried out according to a conventional method in the presence of a base and a $C_{1-6}$ alkyl halide in a solvent that does not adversely influence the reaction.

Examples of the base include alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undeca-7-ene and the like.

The amount of the base to be used is preferably about 1 to about 2 molar equivalents per compound (IX).

Examples of the $C_{1-6}$ alkyl halide include iodomethane, iodoethane and the like.

The amount of the $C_{1-6}$ alkyl halide to be used is preferably about 1 to about 2 molar equivalents per compound (IX).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane, and the like; ketones such as acetone, 2-butanone and the like; amides such as N,N-dimethylformamide and the like; sulfoxides such as dimethyl sulfoxide and the like; and the like. Two or more of these solvents may be used upon mixing at a suitable ratio.

The reaction temperature is generally from about −10° C. to about 150° C., preferably 0° C., to 110° C.

The reaction time is generally from about 0.5 to about 20 hours.

The thus-obtained compound (VI) can be isolated and purified by a known separation and purification means, such as concentration, concentration under reduced pressure, solvent extraction, crystallization, recrystallization, phase transfer, chromatography and the like.

The compound (II-b) which is a compound of the formula (II) wherein La is a bond and X is a bond can be produced by a method described in, for example, JP-A-7-76573, JP-A-2000-72751 or JP-A-2000-72675, the following Method D or analogous methods thereto.

[Method D]

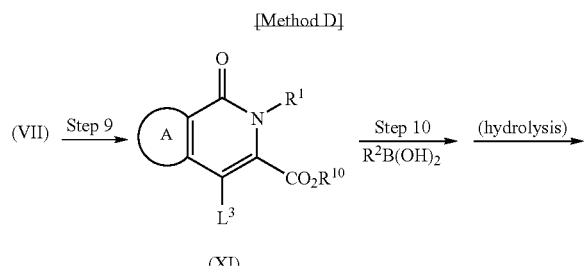

(XI)

-continued

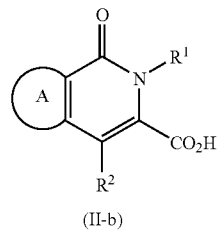

(II-b)

wherein $L^3$ is a leaving group, and other symbols are as defined above.

The leaving group for $L^3$ is exemplified by that mentioned as the aforementioned $L^1$.

(Step 9)

When, for example, $L^3$ is an optionally halogenated $C_{1-6}$ alkylsulfonyloxy or an optionally substituted $C_{6-10}$ arylsulfonyloxy, this reaction is carried out according to a conventional method in the presence of a base and a sulfonylating agent in a solvent that does not adversely influence the reaction.

Examples of the base include metalhydrides such as sodium hydride, potassium hydride and the like; alkali metal alkoxides such as sodium methoxide, sodium ethoxide, potassium t-butoxide and the like; alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undeca-7-ene and the like.

The amount of the base to be used is preferably about 1 to about 5 molar equivalents per compound (VII).

Examples of the sulfonylating agent include N-phenyltrifluoromethanesulfonimide, anhydrous trifluoromethanesulfonic acid and the like.

The amount of the sulfonylating agent to be used is preferably about 1 to about 5 molar equivalents per compound (VII).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; and the like. Two or more of these solvents may be used upon mixing at a suitable ratio.

The reaction temperature is generally from about −50° C. to about 150° C., preferably about −10° C. to about 20° C.

The reaction time is generally from about 0.5 to about 20 hours.

The thus-obtained compound (XI) can be isolated and purified by a known separation and purification means, such as concentration, concentration under reduced pressure, solvent extraction, crystallization, recrystallization, phase transfer, chromatography and the like.

(Step 10)

This reaction is carried out according to a conventional method in the presence of a base, and a metal catalyst in a solvent that does not adversely influence the reaction under an inert gas atmosphere.

Examples of the base include metalhydrides such as sodium hydride, potassium hydride and the like; akali metal alkoxides such as sodium methoxide, sodium ethoxide, potassium t-butoxide and the like; alkali metal salts such as potassium hydroxide, sodium hydroxide, sodium hydrogencarbonate, sodium carbonate, potassium carbonate and the like; amines such as pyridine, triethylamine, N,N-dimethylaniline, 1,8-diazabicyclo[5.4.0]undeca-7-ene and the like. Of these, alkali metal salts such as sodium hydrogencarbonate, sodium carbonate, potassium carbonate and the like are preferable.

The amount of the base to be used is preferably about 1 to about 5 molar equivalents per compound (XI).

Examples of the metal catalyst include palladium complex such as tetrakis(triphenylphosphine)palladium(0) and the like.

The amount of use of the metal catalyst is preferably about 0.01 to about 0.5 molar equivalents per compound (XI).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; water; alcohols such as methanol, ethanol, isopropanol and the like; ketones such as acetone, 2-butanone and the like; amides such as N,N-dimethylformamide and the like; sulfoxides such as dimethyl sulfoxide and the like; and the like. Two or more of these solvents may be used upon mixing at a suitable ratio.

Examples of the inert gas include argon, nitrogen and the like.

The reaction temperature is generally from about −10° C. to about 150° C., preferably about 0° C. to about 100° C.

The reaction time is generally from about 0.5 to about 20 hours.

The compound obtained from Step 10 is hydrolyzed according to a method known per se to give compound (II-b).

The compound (II-b) can be isolated and purified by a known separation and purification means, such as concentration, concentration under reduced pressure, solvent extraction, crystallization, recrystallization, phase transfer, chromatography and the like.

The compound (I-aa) wherein ring A has a group of the formula: —CO—OR$^4$ (R$^4$ is as defined above) as a substituent can be also produced by the following Method E.

[Method E]

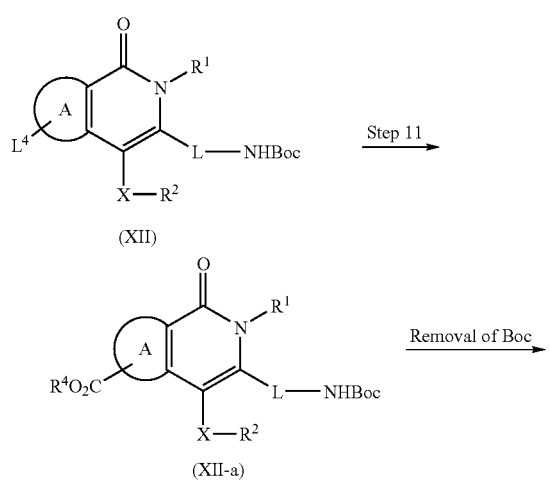

(XII)

(XII-a)

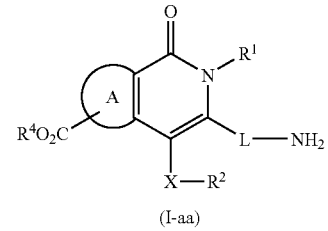

(I-aa)

wherein L$^4$ is a leaving group, Boc is a t-butoxycarbonyl group and other symbols are as defined above.

The leaving group for L$^4$ is exemplified by that mentioned as the aforementioned L$^1$.

(Step 11)

This reaction is carried out in the presence of carbon monoxide, a metal catalyst, a reaction reagent and an alcohol in a solvent that does not adversely influence the reaction.

The metal catalyst is, for example, a palladium catalyst (e.g., palladium acetate and the like).

The amount of the metal catalyst to be used is preferably about 0.01 to about 1 molar equivalent per compound (XII).

The reaction reagent is, for example, an organic phosphorus compound (e.g., 1,3-bis(diphenylphosphino)propane and the like), a base (e.g., amines such as pyridine, triethylamine, N,N-dimethylaniline etc., and the like), and the like.

The amount of the reaction reagent to be used is preferably about 1 to about 5 molar equivalents per compound (XII).

As the alcohol, an excess amount of ethanol or methanol is generally used.

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; and the like. Two or more of these solvents may be used upon mixing at a suitable ratio.

The reaction temperature is generally from about 0° C. to about 150° C., preferably about 50° C. to about 100° C.

The reaction time is generally from about 0.5 to about 20 hours.

From compound (XII-a) obtained from Step 11, Boc group is removed by a method known per se to give compound (I-aa).

The thus-obtained compound (I-aa) can be isolated and purified by a known separation and purification means, such as concentration, concentration under reduced pressure, solvent extraction, crystallization, recrystallization, phase transfer, chromatography and the like.

The compound (XII) used as a starting material compound in Method E can be produced according to, for example, the aforementioned Method A or an analogous method thereto.

The compound (I-ab) wherein ring A has an optionally substituted hydroxy group as a substituent can be also produced by the following Method F.

[Method F]

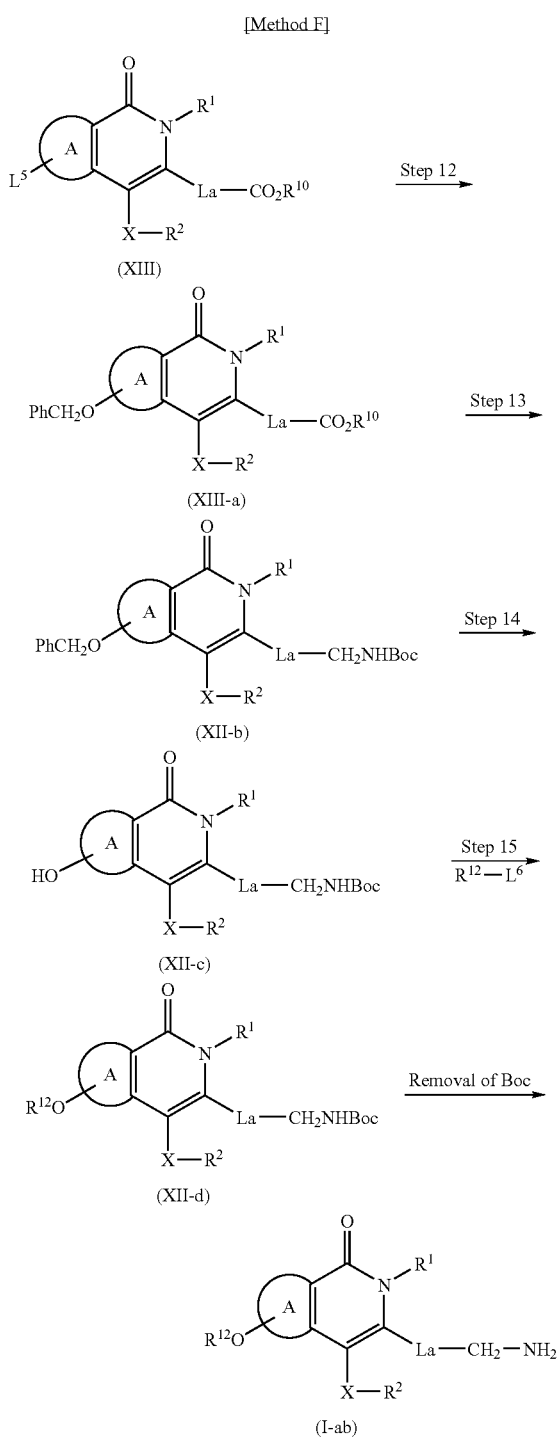

wherein $L^5$ and $L^6$ are leaving group, $R^{12}$ is an optionally substituted hydrocarbon group and other symbols are as defined above.

The leaving group for $L^5$ and $L^6$ are exemplified by that mentioned as the aforementioned $L^1$.

Examples of the "optionally substituted hydrocarbon group" for $R^{12}$ include each optionally substituted "alkyl group having 1 to 10 carbon atom(s)", "alkenyl group having 2 to 10 carbon atoms", "alkynyl group having 2 to 10 carbon atoms", "cycloalkyl group, having 3 to 10 carbon atoms", "cycloalkenyl group having 3 to 10 carbon atoms", "aryl group having 6 to 14 carbon atoms" and "aralkyl having 7 to 13 carbon atoms" mentioned in the "optionally substituted hydroxy group" as the substituent in ring A.

(Step 12)

This reaction is carried out using benzyl alcohol in the presence of a base in a solvent that does not adversely influence the reaction.

Examples of the base include alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undeca-7-ene and the like; metalhydrides such as potassium hydride, sodium hydride and the like; alkali metal alkoxides such as sodium methoxide, sodium ethoxide, potassium t.-butoxide and the like; and the like.

The amount of the base to be used is preferably about 1 to about 5molar equivalents per compound (XII).

The amount of benzyl alcohol to be used is preferably about 1 to about 3 molar equivalents per compound (XIII).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; and the like. Two or more of these solvents may be used upon mixing at a suitable ratio.

The reaction temperature is generally from about 0° C. to about 150° C., preferably about 50° C. to about 100° C.

The reaction time is generally from about 0.5 to about 20 hours.

The thus-obtained compound (XIII-a) can be isolated and purified by a known separation and purification means, such as concentration, concentration under reduced pressure, solvent extraction, crystallization, recrystallization, phase transfer, chromatography and the like.

(Step 13)

This reaction is carried out by introducing a Boc group according to a method known per se after reaction in the same manner as in the aforementioned Steps 1 to 3.

The thus-obtained compound (XII-b) can be isolated and purified by a known separation and purification means, such as concentration, concentration under reduced pressure, solvent extraction, crystallization, recrystallization, phase transfer, chromatography and the like.

(Step 14)

This reaction is carried out according to a per se known hydrogenation under a hydrogen atmosphere or in the presence of a hydrogen source, such as formic acid and the like and a metal catalyst in a solvent that does not adversely influence the reaction.

Examples of the metal catalyst include a transition metal catalyst such as palladium-carbon, palladium black, platinum oxide, Raney-nickel, Wilkinson's catalyst etc., and the like.

The amount of the metal catalyst to be used is preferably about 0.01 to about 10 molar equivalents per compound (XII-b).

Examples of the solvent that does not adversely influence the reaction include lower organic acids such as acetic acid and the like; ethers such as tetrahydrofuran, dioxane, diethyl ether and the like; amides such as N,N-dimethylformamide and the like; alcohols such as methanol, ethanol, isopropanol and the like; and the like. Two or more of these solvents may be used upon mixing at a suitable ratio.

The reaction temperature is generally from about 0° C. to about 150° C., preferably about 0° C. to about 100° C.

The reaction time is generally from about 0.5 to about 20 hours.

The thus-obtained compound (XII-c) can be isolated and purified by a known separation and purification means, such as concentration, concentration under reduced pressure, solvent extraction, crystallization, recrystallization, phase transfer, chromatography and the like.

(Step 15)

This Step is carried out by the reaction in the same manner as in the aforementioned Step 8.

The thus-obtained compound (XII-d) can be isolated and purified by a known separation and purification means, such as concentration, concentration under reduced pressure, solvent extraction, crystallization, recrystallization, phase transfer, chromatography and the like.

The compound (I-ab,) can be produced by removing a Boc group from compound (XII-d) according to a method known per se.

The compound (I-ab) can be isolated and purified by a known separation and purification means, such as concentration, concentration under reduced pressure, solvent extraction, crystallization, recrystallization, phase transfer, chromatography and the like.

The compound (XIII) used as a starting material compound in Method F can be produced according to, for example, the aforementioned Method A or an analogous method thereto.

The compound (I-ac) wherein ring A has an optionally substituted amino group as a substituent can be also produced according to the following Method G.

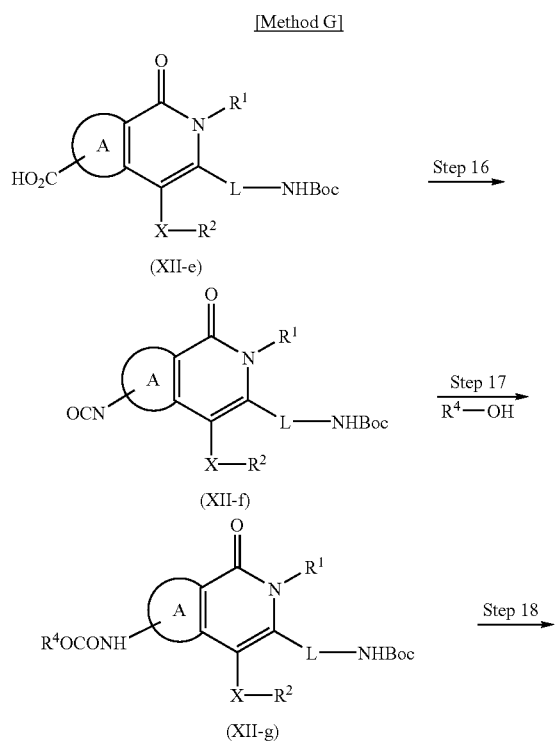

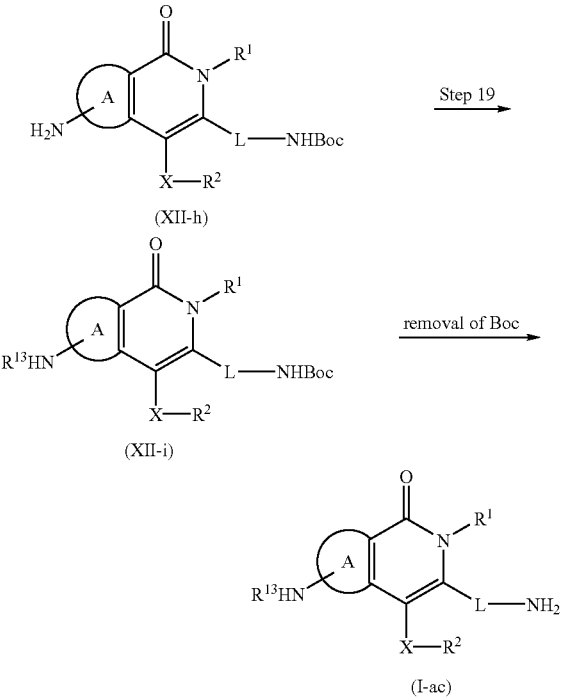

wherein $R^{13}$ is a hydrocarbon group or an acyl group and other symbols are as defined above.

Examples of the "hydrocarbon group" for $R^{13}$ include "alkyl group having 1 to 10 carbon atom(s)", "alkenyl group having 2 to 10 carbon atoms", "cycloalkyl group having 3 to 10 carbon atoms", "cycloalkenyl group having 3 to 10 carbon atoms" and "aryl group having 6 to 14 carbon atoms" mentioned in the "optionally substituted amino group" as the substituent in ring A. Examples of the acyl group for $R^{13}$ is exemplified by that mentioned as the substituent in ring A.

(Step 16)

In this Step, compound (XII-e) and diphenylphosphoryl azide are reacted in the presence of a base in a solvent that does not adversely influence the reaction to give an acyl azide compound, which is subjected to Curtius rearrangement reaction to give isocyanic acid derivative (XII-f).

The amount of the diphenylphosphoryl azide to be used is 1 to 10 molar equivalent(s), preferably 1.5 to 3 molar equivalents, per compound (XII-e).

Examples of the base include amines such as triethylamine, 4-dimethylaminopyridine, triethylenediamine, tetramethylethylenediamine and the like.

The amount of the base to be used is preferably about 1 to about 5 molar equivalents per compound (XII-e).

Examples of the solvent that does not adversely influence the reaction include ethers such as diethyl ether, tetrahydrofuran, dioxane and the like; halogenated hydrocarbons such as dichloromethane, dichloroethane, chloroform and the like; dimethylformamide and the like. Two or more of these solvents may be used upon mixing at a suitable ratio.

The reaction temperature is −20° C. to 50° C., preferably 0° C. to 20° C.

The reaction time is from 0.5 to 5 hours, preferably from 1 to 2 hours.

The Curtius rearrangement reaction is carried out according to a method known per se in a solvent that does not adversely influence the reaction.

Examples of the solvent that does not adversely influence the reaction include hydrocarbons such as benzene, toluene, xylene and the like; ethers such as diethyl ether, tetrahydrofuran, dioxane and the like; halogenated hydrocarbons such as dichloromethane, dichloroethane, chloroform and the like; amides such as dimethylformamide and the like; and the like. Two or more of these solvents may be used upon mixing at a suitable ratio.

The reaction temperature is generally from 50° C. to 200° C., preferably 80° C. to 150° C.

The reaction time is generally from 0.5 to 12 hours, preferably from 1 to 3 hours.

The thus-obtained compound (XII-f) can be isolated and purified by a known separation and purification means, such as concentration, concentration under reduced pressure, solvent extraction, crystallization, recrystallization, phase transfer, chromatography and the like.

(Step 17)

This reaction is carried out in a solvent that does not adversely influence the reaction.

The amount of a compound of the formula: $R^4$—OH (wherein the symbols are as defined above) to be used is preferably about 1 to about 5 molar equivalents per compound (XII-f).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; and the like. Two or more of these solvents may be used upon mixing at a suitable ratio.

The reaction temperature is generally from about 0° C. to about 150° C., preferably about 50° C. to about 100° C.

The reaction time is generally from about 5 to about 20 hours.

This reaction may be carried out in the presence of a catalytic amount of N,N-dimethylaminopyridine and the like.

The thus-obtained compound (XII-g) can be isolated and purified by a known separation and purification means, such as concentration, concentration under reduced pressure, solvent extraction, crystallization, recrystallization, phase transfer, chromatography and the like.

By using a compound of the formula: $HNR^{4a}R^{5a}$ (wherein the symbols are as defined above) instead of a compound of the above-mentioned formula: $R^4$—OH (wherein the symbols are as defined above), a compound (XII-g) wherein the substituent: $R^4OCONH$— is replaced by $R^{4a}R^{5a}NCONH$— can be produced.

(Step 18)

This reaction is carried out by deprotection (e.g., catalytic reduction, piperidine treatment and the like) generally employed in peptide chemistry and the like.

The thus-obtained compound (XII-h) can be isolated and purified by a known separation and purification means, such as concentration, concentration under reduced pressure, solvent extraction, crystallization, recrystallization, phase transfer, chromatography and the like.

(Step 19)

This reaction is carried out according to a conventional method using an alkylation agent, an acylation agent and the like in the presence of a condensation agent or a base in a solvent that does not adversely influence the reaction.

The alkylation agent is exemplified by alkyl halides, alkylsulfonates and the like.

The amount of the alkylation agent to be used is preferably about 1 to about 5 molar equivalents per compound (XII-h).

The acylation agent is exemplified by carboxylic acid sulfonic acid, phosphoric acid, carbonic acid or reactive derivatives thereof (e.g., acid halide, acid anhydride, mixed acid anhydride, active ester and the like), isocyanide, isothiocyanide and the like.

The amount of the acylating agent to be used is preferably about 1 to about 5 molar equivalents per compound (XII-h).

The condensation agent is exemplified by dicyclohexylcarbodiimide, diethyl cyanophosphate, 1-ethyl-3-(3-dimethylaminopropyl)carbodiimide and the like.

The amount of the condensation agent to be used is preferably about 1 to about 5 molar equivalents per compound (XII-h).

Examples of the base include alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undeca-7-ene and the like; metalhydrides such as potassium hydride, sodium hydride and the like; alkali metal alkoxides such as sodium methoxide, sodium ethoxide, potassium t.-butoxide and the like; and the like.

The amount of the base to be used is preferably about 1 to about 5 molar equivalents per compound (XII-h).

Examples of the solvent that does not adversely influence the reaction include aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane, and the like; amides such as N,N-dimethylformamide and the like; sulfoxides such as dimethyl sulfoxide and the like; and the like. Two or more of these solvents may be used upon mixing at a suitable ratio.

The reaction temperature is generally from about −50° C. to about 50° C., preferably about −10° C. to about 100° C.

The reaction time is generally from about 0.5 to about 20 hours.

The thus-obtained compound (XII-i) can be isolated and purified by a known separation and purification means, such as concentration, concentration under reduced pressure, solvent extraction, crystallization, recrystallization, phase transfer, chromatography and the like.

By removing a Boc group from the thus-obtained compound (XII-i) according to a method known per se, compound (I-ac) can be produced.

The compound (I-Ac) can be isolated and purified by a known separation and purification means, such as concentration, concentration under reduced pressure, solvent extraction, crystallization, recrystallization, phase transfer, chromatography and the like.

Furthermore, by removing a Boc group from the aforementioned compound (XII-g) and compound (XII-h) according to a method known per se, a compound (I-ac) wherein the substituent: $R^{13}HN$— is respectively substituted by $R^4OCONH$— or amino can be produced.

The compound (XII-e) used as a starting material in Method G can be produced according to, for example, the aforementioned Method A, Method E or analogous methods thereto.

The compound (I-ae) which is a compound of the formula (I) wherein ring A has a carbamoyl group as a substituent and L is methylene can be also produced by, for example, the following Method H.

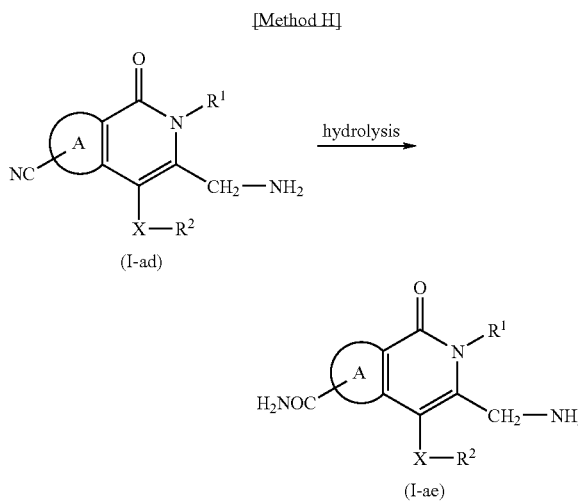

(I-ad)

(I-ae)

wherein the symbols are as defined above.

The hydrolysis can be generally carried out in the presence of an acid or a base.

Examples of the acid include mineral acids (e.g., hydrochloric acid, hydrobromic acid, sulfuric acid, phosphoric acid and the like), carboxylic acids (e.g., formic acid, acetic acid, propionic acid and the like), and the like. Of these, hydrochloric acid, sulfuric acid and the like are preferable.

Examples of the base include alkali metal salts such as lithium hydroxide, potassium hydroxide, sodium hydroxide, potassium carbonate, sodium carbonate, potassium hydrogencarbonate, sodium hydrogencarbonate and the like; alkaline earth metal salts such as calcium hydroxide, barium hydroxide and the like; amines such as trimethylamine, triethylamine, ethyldiisopropylamine, N-methylmorpholine and the like; and the like. Of these, potassium hydroxide, sodium hydroxide and the like are preferable.

The amount of the acid or base to be used is, for example, 0.01 to 100 molar equivalents, preferably 0.1 to 50 molar equivalents per compound (I-ad).

Hydrolysis is generally conducted in a solvent that does not adversely influence the reaction. Examples of the solvent include alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; amides such as dimethylformamide, dimethylacetamide and the like; sulfoxides such as dimethyl sulfoxide and the like; water and the like. Two or more of these solvents may be used upon mixing at a suitable ratio.

The reaction temperature is generally from 0° C. to 150° C., preferably 10° C. to 100° C.

The reaction time is generally from 0.1 to about 100 hours, preferably from 0.1 to 10 hours.

The thus-obtained compound (I-ae) can be isolated and purified by a known separation and purification means, such as concentration, concentration under reduced pressure, solvent extraction, crystallization, recrystallization, phase transfer, chromatography and the like.

The compound (I-ad) used as a starting material compound in Method H can be produced according to, for example, the following Method I.

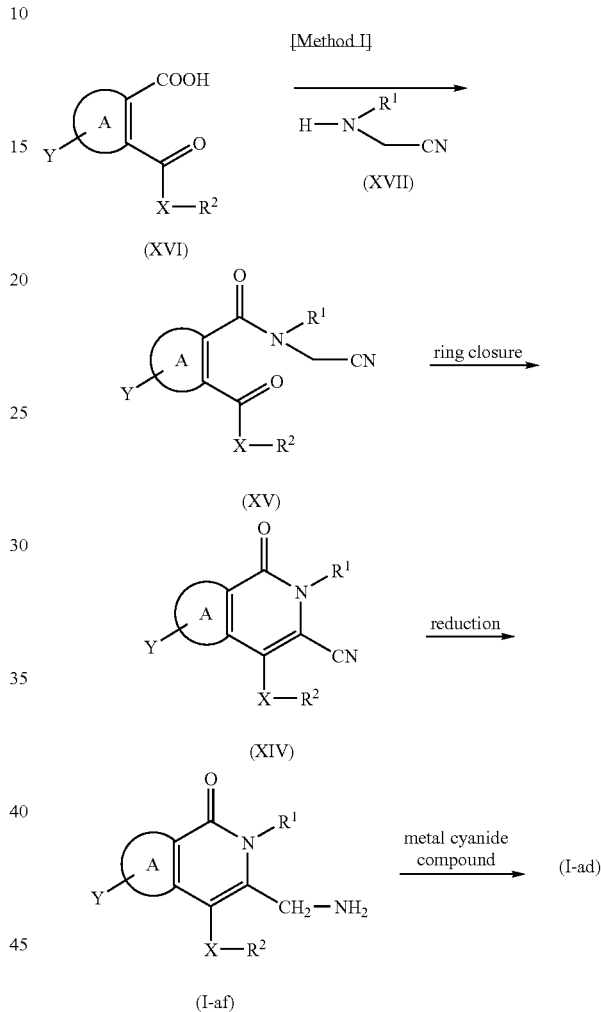

wherein the symbols are as defined above.

In this method, compound (XVI) and compound (XVII) are reacted to give compound (XV).

This reaction is carried out according to a per se known amidation reaction. This method may be, for example, a method comprising direct condensation of compound (XVI) and compound (XVII) using a condensation agent, a method comprising reacting a reactive derivative of compound (XVI) and compound (XVII), and the like.

Examples of the condensation agent include carbodiimide condensation reagents such as dicyclohexylcarbodiimide, diisopropylcarbodiimide, 1-ethyl-3-(3-dimethylaminopropyl)carbodiimide and its hydrochloride, and the like; phosphoric acid condensation reagents such as diethyl cyanophosphate, diphenylphosphoryl azide and the like; carbonyldiimidazole, 2-chloro-1,3-dimethylimidazolium tetrafluoroborate and the like.

Examples of the solvent to be used for a reaction using a condensation agent include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. Two or more of these solvents may be used upon mixing at a suitable ratio.

The amount of the compound (XVII) to be used is generally 1 to 10 molar equivalents, preferably 1 to 3 molar equivalents, per compound (XVI).

The amount of the condensation agent to be used is generally 0.1 to 10 molar equivalents, preferably 0.3 to 3 molar equivalents, per compound (XVI).

When a carbodiimide condensation reagent is used as a condensation agent, the reaction efficiency can be increased by the use of a suitable condensation promoter (e.g., 1-hydroxy-7-azabenzotriazole, 1-hydroxybenzotriazole, N-hydroxysuccinimide, N-hydroxyphthalimide and the like) as necessary. When a phosphoric condensation reagent is used as a condensation agent, the reaction efficiency can be increased by the use of an organic amine base such as triethylamine and the like.

The amount of the above-mentioned condensation promoter and organic amine base to be used is generally 0.1 to 10 molar equivalents, preferably 0.3 to 3 molar equivalents, per compound (XVI).

The reaction temperature is generally from −30° C. to 120° C., preferably −10° C. to 100° C.

The reaction time is generally from 0.5 to 60 hours.

The reactive derivative of compound (XVI) may be, for example, acid anhydride, acid halide (acid chloride, acid bromide), imidazolide, mixed acid anhydride (e.g., anhydride with methylcarbonate, ethylcarbonate or isobutylcarbonate and the like) and the like.

When, for example, an acid anhydride or an acid halide is used, the reaction is generally carried out in the presence of a base in a solvent that does not adversely influence the reaction.

Examples of the base include amines such as triethylamine, pyridine, N-methylmorpholine, N,N-dimethylaniline, 4-dimethylaminopyridine and the like; alkali metal salts such as lithium hydroxide, sodium hydroxide, potassium hydroxide, sodium hydrogencarbonate, sodium carbonate, potassium carbonate and the like; and the like.

Examples of the solvent that does not adversely influence the reaction include amides such as N,N-dimethylformamide, N,N-dimethylacetamide, N-methylpyrrolidone and the like, sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. Two or more of these solvents may be used upon mixing at a suitable ratio.

When the above-mentioned amides are used as the solvent that does not adversely influence the reaction, the reaction may be carried out in the absence of a base.

The amount of the compound (XVII) to be used is generally 1 to 10 molar equivalents, preferably 1 to 5 molar equivalents, per compound (XVI).

The amount of the base to be used is generally 1 to 10 molar equivalents, preferably 1 to 5 molar equivalents per compound (XVI).

The reaction temperature is generally from −30° C. to 100° C., preferably −10° C. to 100° C.

The reaction time is generally from 0.5 to 30 hours.

When a mixed acid anhydride is used, compound (XVI) and chlorocarbonate (e.g., methyl chlorocarbonate, ethyl chlorocarbonate, isobutyl chlorocarbonate and the like) are reacted in the presence of a base, and the obtained compound is reacted with compound (XVII).

Examples of the base include amines such as triethylamine, aniline, N-methylmorpholine, N,N-dimethylaniline, 4-dimethylaminopyridine and the like; alkali metal salts such as sodium hydroxide, potassium hydroxide, lithium hydroxide, sodium hydrogencarbonate, sodium carbonate, potassium carbonate and the like; and the like.

The amount of the compound (XVII) to be used is generally 1 to 10 molar equivalents, preferably 1 to 5 molar equivalents, per compound (XVI).

The amount of the base to be used is generally 1 to 10 molar equivalents, preferably 1 to 3 molar equivalents per compound (XVI).

The reaction temperature is generally from −30° C. to 120° C., preferably −10° C. to 100° C.

The reaction time is generally from 0.5 to 20 hours.

The thus-obtained compound (XV) can be isolated and purified by a known separation and purification means such as concentration, concentration under reduced pressure, solvent extraction, crystallization, recrystallization, phase transfer, chromatography and the like. It is also possible to subject a reaction mixture containing compound (XV) to the next reaction without isolating compound (XV).

The compound (XIV) is produced by subjecting the compound (XV) to a ring closure reaction.

The ring closure reaction is generally carried out in the presence of a base in a solvent that does not adversely influence the reaction.

Examples of the base include amines such as triethylamine, pyridine, N-methylmorpholine, N,N-dimethylaniline, 4-dimethylaminopyridine, 1,5-diazabicyclo[4.3.0]-5-nonene (DBN), 1,8-diazabicyclo[5.4.0]-7-undecene (DBU) and the like; alkali metal salts such as lithium hydroxide, sodium hydroxide, potassium hydroxide, sodium hydrogencarbonate, sodium carbonate, potassium carbonate and the like; and the like.

Examples of the solvent that does not adversely influence the reaction include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. Two or more of these solvents may be used upon mixing at a suitable ratio.

The amount of the base to be used is generally 0.01 to 10 molar equivalents, preferably 0.1 to 3 molar equivalents per compound (XV).

The reaction temperature is generally from −30° C. to 120° C., preferably −10° C. to 100° C.

The reaction time is generally from 0.5 to 40 hours.

The thus-obtained compound (XIV) can be isolated and purified by a known separation and purification means, such as concentration, concentration under reduced pressure, solvent extraction, crystallization, recrystallization, phase transfer, chromatography and the like. It is also possible to subject a reaction mixture containing compound (XIV) to the next reaction without isolating compound (XIV).

The compound (I-af) is produced by reducing compound (XIV).

The reduction is performed according to a conventional method in the presence of a reducing agent in a solvent that does not adversely influence the reaction.

Examples of the reducing agent include metal hydrogen compounds such as bis(2-methoxyethoxy)aluminum sodium hydride, diisobutyl aluminum hydride and the like; metal hydrogen complex compounds such as sodium borohydride, sodium cyanide borohydride, aluminum lithium hydride, aluminum sodium hydride and the like; and the like.

The amount of the reducing agent to be used is generally 0.1 to 20 molar equivalents per compound (XIV).

Examples of the solvent that does not adversely influence the reaction include alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimeithoxyethane and the like; esters such as methyl acetate, ethyl acetate, n-butyl acetate, tert-butyl acetate and the like; amides such as dimethylformamide, dimethylacetamide, N-methylpyrrolidone and the like. Two or more of these solvents may be used upon mixing at a suitable ratio.

The reaction temperature is generally from $-70°$ C. to $150°$ C., preferably $-20°$ C. to $100°$ C.

The reaction time is generally from 0.1 to 100 hours, preferably from 0.1 to 40 hours.

The reduction reaction can be also conducted in the presence of a metal catalyst such as palladium-carbon, palladium black, palladium chloride, platinum oxide, platinum black, platinum-palladium, Raney-nickel, Raney-cobalt and the like, and a hydrogen source in a solvent that does not adversely influence the reaction.

The amount of the metal catalyst to be used is generally 0.001 to 1000 molar equivalents, preferably 0.01 to 100 molar equivalents, per compound (XIV).

Examples of the hydrogen source include hydrogen gas, formic acid, formic acid amine salt, phosphinate, hydrazine and the like.

The solvent that does not adversely influence the reaction is that employed for reduction using the aforementioned reducing agent.

The reaction temperature and reaction time are the same as those for reduction using the aforementioned reducing agent.

This reaction may be carried out in the presence of ammonia (e.g., aqueous ammonia, ammonia-ethanol and the like) as necessary. By reacting in the presence of ammonia, side reaction is suppressed and compound (I-af) can be produced in a high yield.

The thus-obtained compound (I-af) can be isolated and purified by a known separation and purification means, such as concentration, concentration under reduced pressure, solvent extraction, crystallization, recrystallization, phase transfer, chromatography and the like. It is also possible to subject a reaction mixture containing compound (I-af) to the next reaction without isolating compound (I-af).

The compound (I-ad) is produced by reacting compound (I-af)and a metal cyanide.

Examples of the metal cyanide include potassium cyanide, sodium cyanide, zinc cyanide and the like.

The reaction is generally carried out in a solvent that does not adversely influence the reaction.

Examples of the solvent that does not adversely influence the reaction include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. Two or more of these solvents may be used upon mixing at a suitable ratio.

In this reaction, a catalyst may be used where necessary. Examples of the catalyst include transition metal compounds such as rhodium, palladium-carbon, tetrakis(triphenylphosphine)palladium, tetrakis(tri-(2-toryl)phosphine)palladium, tetrakis(tri-(2-furyl)phosphine)palladium, bis(acetylacetone)nickel, dichlorobis(triphenylphosphine)nickel, bis(1,5-cyclooctadiene)nickel, bis(1,10-phenanthroline)nickel, Raney-nickel, Raney-cobalt and the like.

The amount of the metal cyanide to be used is generally 1 to 100 molar equivalents, preferably 1 to 10 molar equivalents, per compound(I-af).

The amount of the catalyst to be used is generally 0.00001 to 10 molar equivalents, preferably 0.001 to 1 molar equivalent, per compound (I-af).

The reaction temperature is generally from, $-10°$ C. to $250°$ C., preferably $0°$ C. to $150°$ C.

The reaction time is generally from 0.1 to 100 hours, preferably 0.1 to 40 hours.

The thus-obtained compound (I-ad) can be isolated and purified by a known separation and purification means, such as concentration, concentration under reduced pressure, solvent extraction, crystallization, recrystallization, phase transfer, chromatography and the like.

The compound (XVI) used as a starting material compound in Method I can be produced according to a method known per se.

In each of the aforementioned reactions, when the starting material compound has amino, carboxy, hydroxy or carbonyl as a substituent, a protecting group generally known in peptide chemistry and the like may be introduced into these groups. By removing the protecting group as necessary after the reaction, the objective compound can be obtained.

The amino-protecting group includes, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-13}$ aralkyl-carbonyl (e.g., benzylcarbonyl and the like), $C_{7-13}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldimethylsilyl and the like), $C_{2-6}$ alkenyl(e.g., 1-allyl and the like) and the like. These groups are optionally substituted by 1 to 3 halogen atom(s) (e.g., fluorine, chlorine, bromine, iodine and the like), $C_{1-6}$ alkoxy (e.g., methoxy, ethoxy, propoxy and the like) or nitro and the like.

The carboxy-protecting group is, for example, $C_{1-6}$ alkyl (e.g., methyl, ethyl, propyl, isopropyl, butyl, tert-butyl and the like), $C_{7-13}$ aralkyl (e.g., benzyl and the like), phenyl, trityl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like.

These groups are optionally substituted by 1 to 3 halogen atom(s) (e.g., fluorine, chlorine, bromine, iodine and the like), $C_{1-6}$ alkoxy (e.g., methoxy, ethoxy, propoxy and the like) or nitro and the like.

The hydroxy-protecting group is, for example, $C_{1-6}$ alkyl (e.g., methyl, ethyl, propyl, isopropyl, butyl, tert-butyl and the like), phenyl, trityl, $C_{7-13}$ aralkyl (e.g., benzyl and the like), formyl, $C_{1-6}$ alkyl-carbonyl (e.g., acetyl, propionyl and the like), benzoyl, $C_{7-13}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 halogen atom(s) (e.g., fluorine, chlorine, bromine, iodine and the like), $C_{1-6}$ alkyl (e.g., methyl, ethyl, propyl and the like), $C_{1-6}$ alkoxy (e.g., methoxy, ethoxy, propoxy and the like) or nitro and the like.

The carbonyl-protecting group is, for example, cyclic acetal (e.g., 1,3-dioxane and the like), non-cyclic acetal (e.g., di-$C_{1-6}$ alkyl acetal and the like) and the like.

Introduction and removal of these protecting groups can follow a method known per se, for example, a method described in Protective Groups in Organic Synthesis, John Wiley and Sons (1980) and the like. For example, employed is a method using acid, base, UV light, hydrazine, phenyl hydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction and the like.

When the starting material compound can form a salt in each of the aforementioned reactions, the compound in the form of a salt may be used. The salt is, for example the salt of compound (I) exemplified above.

When compound (I) contains an optical isomer, a stereoisomer, a positional isomer or a rotational isomer, these are also encompassed compound (I), and can be obtained as a single product according to a synthetic method and separation method known per se. For example, when compound (I) contains an optical isomer, an optical isomer resolved from this compound is also encompassed in compound (I).

The optical isomer can be produced by a method known per se. To be specific, an optically active synthetic, intermediate used, or the final racemate product is subjected to optical resolution according to a conventional method to give an optical isomer.

The method of optical resolution may be a method known per se, such as a fractional recrystallization method, a chiral column method, a diastereomer method and the like.

1) Fractional Recrystallization Method

A salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine and the like) is formed, which is separated by a fractional recrystallization method, and a free optical isomer is obtained by a neutralization step where desired.

2) Chiral Column Method

A racemate or a salt thereof is applied to a column for separation of an optical isomer (chiral column) to allow separation. In the case of a liquid chromatography, for example, a mixture of an optical isomer is applied to a chiral column such as ENANTIO-OVM (manufactured by Tosoh Corporation) or CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine and the like) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A racemate mixture is prepared into a diastereomer mixture by chemical reaction with an optically active reagent, which is prepared into a homogeneous substance by a typical separation means (e.g., fractional recrystallization, chromatography method and the like), and the like, and subjected to a chemical treatment such as hydrolysis and the like to separate the optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid and the like) and the like are subjected to condensation to give an ester form or amide form diastereomer. When compound (I) has a carboxylic acid group, this compound and an optically active amine or an alcohol reagent are subjected to condensation to give an ester form or amide form diastereomer. The separated diastereomer is converted to an optical isomer of the original compound by acid hydrolysis or base hydrolysis.

The compound (I) and a salt thereof may be in the form of a crystal.

The crystal of compound (I) or a salt thereof (hereinafter sometimes to be referred to as crystal of the present invention) can be produced by crystallization of compound (I) or a salt thereof by a crystallization method known per se.

Examples of the crystallization method include crystallization from a solution, crystallization from vapor, crystallization from a molten form and the like.

The "crystallization method from a solution" is typically a method including shifting a non-saturation state to hyper-saturation state by varying factors involved in solubility of compounds (solvent composition, pH, temperature, ionic strength, oxidation-reduction state and the like) or the amount of solvent. To be specific, for example, concentration method, annealing method, reaction method (diffusion method, electrolysis method), hydrothermal growth method, fusing agent method and the like can be mentioned. Examples of the solvent to be used include aromatic hydrocarbons (e.g., benzene, toluene, xylene and the like), halogenated hydrocarbons (e.g., dichloromethane, chloroform and the like), saturated hydrocarbons (e.g., hexane, heptane, cyclohexane and the like), ethers (e.g., diethyl ether, diisopropyl ether, tetrahydrofuran, dioxane and the like), nitriles (e.g., acetonitrile and the like), ketones (e.g., acetone and the like), sulfoxides (e.g., dimethyl sulfoxide and the like), acid amides (e.g., N,N-dimethylformamide and the like), esters (e.g., ethyl acetate and the like), alcohols (e.g., methanol, ethanol, isopropyl alcohol and the like), water and the like. These solvents are used alone or in combination of two or more at a suitable ratio (e.g., 1:1 to 1:100 (volume ratio)).

The "crystallization method from vapor" is, for example, vaporization method (sealed tube method, gas stream method), gas phase reaction method, chemical transportation method and the like.

The "crystallization method from a molten form" is, for example, normal freezing method (Czockralski method, temperature gradient method, Bridgman method), zone melting method (zone leveling method, floating zone method), special growth method (VLS method, liquid phase epitaxy method) and the like.

Preferable examples of the crystallization method include a method including dissolving compound (I) or a salt thereof in a suitable solvent (e.g., alcohols such as methanol, ethanol etc., and the like) at a temperature of 20–120° C. and cooling the resulting solution to a temperature not higher than a the temperature of dissolution (e.g., 0–50° C., preferably 0–20° C.) and the like.

The thus-obtained crystals of the present invention can be isolated by, for example, filtration and the like.

In the present specification, the melting point refers to that measured using, for example, micromelting point measuring apparatus (Yanako, MP-500D) or DSC (differential scanning calorimetry) device (SEIKO, EXSTAR6000) and the like.

In the present specification, moreover, a peak by powder X-ray diffraction refers to that measured using, for example, RINT2100 (Rigaku Industrial Corporation) and the like using Cu-Kα1 ray (tube voltage: 40 KV; tube current: 50 mA) as a ray source.

In general, melting points and peaks by powder X-ray diffraction vary depending on measurement apparatuses, measurement conditions and the like. The crystal in the present specification may show a different melting point or a peak by powder X-ray diffraction described in the present specification, as long as it is within general error range.

The crystal of the present invention is superior in physicochemical properties (e.g., melting point, solubility, stability and the like) and biological properties (e.g., pharmacokinetics (absorption, distribution, metabolism, excretion), efficacy expression and the like), and is extremely useful as a pharmaceutical agent.

The present invention is explained in more detail by the following Examples, Reference Examples, Experimental Examples and Formulation Examples. These do not limit the present invention and the present invention can be modified within the range that does not, deviate from the scope of the invention.

The abbreviations in Examples and Reference Examples mean the following. s: singlet, d: doublet, t: triplet, q: quartet, dd: double doublet, dt: double triplet, m: multiplet, bs: broad singlet, tt: triple triplet, J: coupling constant, room temperature: 0–30° C.

EXAMPLES

Example 1

3-(Aminomethyl)-4-butoxy-6-ethoxy-2-neopentyl-1 (2H)-isoquinolinone hydrochloride (1) A solution of 4-fluorophthalic anhydride (8.31 g, 50 mmol) and ethyl 2-(neopentylamino)acetate (10.40 g, 60 mmol) in tetrahydrofuran (50 ml) was stirred at room temperature for 1 h. The reaction mixture was poured into water and extracted with ethyl acetate. The extract was washed with brine, dried over anhydrous magnesium sulfate and concentrated under reduced pressure. The residue was dissolved in N,N-dimethylformamide (50 ml), and potassium carbonate (6.91 g, 50 mmol) and ethyl iodide (4.8 ml, 60 mmol) were added. The mixture was stirred at room temperature for 3 h. The reaction mixture was poured into water and extracted with ethyl acetate. The extract was washed with brine, dried over anhydrous magnesium sulfate and concentrated under reduced pressure. The residue was dissolved in ethanol (50 ml) and 20% sodium ethoxide ethanol solution (34.04 g, 100 mmol) was added. The mixture was stirred at room temperature for 1 h. The reaction mixture was poured into 1N hydrochloric acid (150 ml) and extracted with ethyl acetate. The extract was washed with brine, dried over anhydrous magnesium sulfate and concentrated under reduced pressure. The residue, was purified by silica gel column chromatography and the component eluted earlier was concentrated to give ethyl 7-fluoro-4-hydroxy-2-neopentyl-1-oxo-1,2-dihydro-3-isoquinolinecarboxylate (5.12 g, 31.9%) as crystals.

Melting point 92–93° C. Elemental analysis for $C_{17}H_{20}NO_4F$ Calculated: C, 63.54; H, 6.27; N, 4.36. Found: C, 63.56; H, 6.19; N, 4.16. $^1$H-NMR(CDCl$_3$) δ: 0.85 (9H, s), 1.47 (3H, t, J=7.1 Hz), 4.48 (2H, q, J=7.1 Hz), 4.54 (2H, bs), 7.42–7.52 (1H, m), 8.10 (1H, dd, J=2.7, 9.2 Hz), 8.17 (1H, dd, J=5.5, 9.2 Hz), 10.19 (1H, s).

The component eluted later was concentrated to give ethyl 6-fluoro-4-hydroxy-2-neopentyl-1-oxo-1,2-dihydro-3-isoquinolinecarboxylate (3.85 g, 24.0%) as crystals.

Melting point 115–115.5° C. Elemental analysis for $C_{17}H_{20}NO_4F$ Calculated: C, 63.54; H, 6.27; N, 4.36. Found: C, 63.54; H, 6.19; N, 4.11. $^1$H-NMR(CDCl$_3$) δ: 0.85 (9H, s), 1.47 (3H, t, J=7.2 Hz), 4.49 (2H, q, J=7.2 Hz), 4.54 (2H, bs), 7.32–7.42 (1H, m), 7.72 (1H, dd, J=2.9, 9.2 Hz), 8.47 (1H, dd, J=5.5, 9.2 Hz), 10.70 (1H, s).

(2) To a solution of ethyl 6-fluoro-4-hydroxy-2-neopentyl-1-oxo-1,2-dihydro-3-isoquinolinecarboxylate (3.21 g, 10 mmol), 1-butanol (1.4 ml, 15 mmol) and tributylphosphine (5.0 ml, 20 mmol) in tetrahydrofuran (30 ml) was added 1,1'-azodicarbonylpiperidine (5.05 g, 20 mmol) and the mixture was stirred at room temperature for 3 h. The reaction mixture was concentrated under reduced pressure and the residue was purified by silica gel column chromatography to give ethyl 4-butoxy-6-fluoro-2-neopentyl-1-oxo-1,2-dihydro-3-isoquinolinecarboxylate (3.55 g, 94.2%) as an oil.

$^1$H-NMR(CDCl$_3$) δ: 0.94 (9H, s), 1.01. (3H, t, J=7.4 Hz), 1.44 (3H, t, J=7.1 Hz), 1.48–1.59 (2H, m), 1.73–1.89 (2H, m), 3.94 (2H, t, J=6.5 Hz), 4.07 (2H, bs), 4.44 (2H, q, J=7.1 Hz), 7.21–7.31 (1H, m), 7.38(1H, dd, J=2.5, 9.1 Hz), 8.45 (1H, dd, J=5.6, 8.8 Hz).

(3) To a solution of ethyl 4-butoxy-6-fluoro-2-neopentyl-1-oxo-1,2-dihydro-3-isoquinolinecarboxylate (3.40 g, 9 mmol) in tetrahydrofuran (20 ml) and ethanol (20 ml) was added sodium hydroxide (1.08 g, 27 mmol). The obtained mixture was refluxed under heating for 12 h. The reaction mixture was poured into water and acidified with 1N hydrochloric acid and extracted with ethyl acetate. The extract was washed with brine, dried over anhydrous magnesium sulfate and concentrated under reduced pressure. The residue was dissolved in tetrahydrofuran (20 ml) and oxalyl chloride (0.9 ml, 10.8 mmol) and N,N-dimethylformamide (2 drops) were added thereto. The mixture was stirred at room temperature for 1 h. The reaction mixture was concentrated under reduced pressure, and the residue was dissolved in tetrahydrofuran (20 ml). The obtained solution was added dropwise to a suspension of sodium tetrahydroborate (1.13 g, 30 mmol) in 1,2-dimethoxyethane (20 ml) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The residue was purified by silica gel column chromatography and the component eluted earlier was concentrated to give 4-butoxy-6-fluoro-3-hydroxymethyl-2-neopentyl-1(2H)-isoquinolinone (1.72 g, 57.1%) as crystals.

Melting point 143–143.5° C. Elemental analysis for $C_{19}H_{26}NO_3F$ Calculated: C, 68.04; H, 7.81; N, 4.18. Found:

C, 67.85; H, 7.72; N, 4.20. $^1$H-NMR(CDCl$_3$) δ: 96 (9H, s), 1.00 (3H, t, J=7.3 Hz), 1.50–1.68 (2H, m), 1.79–1.93 (2H, m), 2.46 (1H, bs), 3.88 (2H, t, J=6.6 Hz), 4.17 (2H, bs), 4.87 (2H, bs), 7.08–7.18 (1H, m), 7.24–7.30 (1H, m), 8.28–8.37 (1H, m).

The component eluted later was concentrated to give 4-butoxy-6-ethoxy-3-hydroxymethyl-2-neopentyl-1(2H)-isoquinolinone (0.51 g, 15.7%) as crystals.

Melting point 92.5–93.0° C. Elemental analysis for C$_{21}$H$_{31}$NO$_4$ Calculated: C, 69.78; H, 8.64; N, 3.87. Found: C, 69.84; H, 8.65; N, 3.68. 1H-NMR(CDCl$_3$) δ: 0.95 (9H, s), 1.03 (3H, t, J=7.3 Hz), 1.48 (3H, t, J=7.0 Hz), 1.54–1.66 (2H, m), 1.79–1.89 (2H, m), 2.77 (1H, bs), 3.89 (2H, t, J=6.4 Hz), 4.13 (2H, q, J=7.0 Hz), 4.18 (2H, bs), 4.85 (2H, bs), 6.93–6.98 (2H, m), 8.17–8.22 (1H, m).

(4) To a solution of 4-butoxy-6-ethoxy-3-hydroxymethyl-2-neopentyl-1(2H)-isoquinolinone (0.43 g, 1.2 mmol) in tetrahydrofuran (10 ml) and toluene (10 ml) was added thionyl chloride (0.18 ml, 2.4 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 4-butoxy-6-ethoxy-3-chloromethyl-2-neopentyl-1(2H)-isoquinolinone (0.41 g, 91.1%) as an oil.

$^1$H-NMR(CDCl$_3$) δ: 0.98 (9H, s), 1.04 (3H, t, J=7.3 Hz), 1.48 (3H, t, J=7.0 Hz), 1.55–1.70 (2H, m), 1.81–1.91 (2H, m), 3.95 (2H, t, J=6.5 Hz), 4.10 (2H, bs), 4.15 (2H, q, J=7.0 Hz), 4.87 (2H, bs), 7.05–7.30 (2H, m), 8.34 (1H, d, J=9.4 Hz).

(5) A solution of 4-butoxy-6-ethoxy-3-chloromethyl-2-neopentyl-1(2H)-isoquinolinone (0.38 g, 1 mmol) and potassium phthalimide (0.28 g, 1.5 mmol) in N,N-dimethylformamide (10 ml) was stirred at room temperature for 6 h. The reaction mixture was poured into water and extracted with ethyl acetate. After washing the extract with water, the extract was dried over anhydrous magnesium sulfate and concentrated under reduced pressure. The residue was purified by silica gel column chromatography to give 2-{(4-butoxy-6-ethoxy-2-neopentyl-1-oxo-1,2-dihydro-3-isoquinolinyl)methyl}-1H-isoindole-1,3(2H)-dione (0.48 g, 98.0%) as an amorphous.

Elemental analysis for C$_{29}$H$_{34}$N$_2$O$_5$ Calculated: C, 71.00; H, 6.99; N, 5.71. Found: C, 71.41; H, 7.15; N, 5.64. $^1$H-NMR(CDCl$_3$) δ: 1.00 (9H, s), 1.01 (3H, t, J=7.3 Hz), 1.48 (3H, t, J=7.0 Hz), 1.50–1.61 (2H, m), 1.81–1.94 (2H, m), 3.99 (2H, bs), 4.02 (2H, t, J=6.8 Hz), 4.15 (2H, q, J=7.0 Hz), 5.07 (2H, s), 7.02–7.10 (2H, m), 7.69–7.80 (1H, m), 8.31 (1H, d, J=8.8 Hz).

(6) To a solution of 2-{(4-butoxy-6-ethoxy-2-neopentyl-1-oxo-1,2-dihydro-3-isoquinolinyl)methyl}-1H-isoindole-1,3(2H)-dione (0.43 g, 1.2 mmol) in ethanol (20 ml) was added hydrazine monohydrate (0.13 ml, 2.7 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (20 ml) and di-t-butyl dicarbonate (0.31 g, 1.4 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl(4-butoxy-6-ethoxy-2-neopentyl-1-oxo-1,2-dihydro-3-isoquinolinyl)methyl carbamate (0.36 g, 87.8%) as crystals.

Melting point 138–139° C. Elemental analysis for C$_{26}$H$_{40}$N$_2$O$_5$ Calculated: C, 67.80; H, 8.75; N, 6.08. Found: C, 67.76; H, 8.91; N, 5.87. $^1$H-NMR(CDCl$_3$) δ: 0.99 (9H, s), 1.03 (3H, t, J=7.0 Hz), 1.45 (9H, s), 1.49 (3H, t, J=7.0 Hz), 1.52–1.64 (2H, m), 1.79–1.91 (2H, m), 3.96 (2H, t, J=6.4 Hz), 4.10 (2H, bs), 4.15 (2H, q, J=7.0 Hz), 4.55 (2H, d, J=5.6 Hz), 4.67 (1H, bs), 7.02–7.08 (2H, m), 8.29–8.34 (1H, m).

(7) To a solution of tert-butyl(4-butoxy-6-ethoxy-2neopentyl-1-oxo-1,2-dihydro-3-isoquinolinyl)methylcarbamate (0.28 g, 0.6 mmol) in ethyl acetate (5 ml) was added a solution of 4N hydrogen chloride in ethyl acetate (5 ml), and the obtained solution was stirred at room temperature for 2 h. The reaction mixture was concentrated under reduced pressure, and the precipitated crystals were recrystallized from methanol-diisopropyl ether to give 3-(aminomethyl)-4-butoxy-6-ethoxy-2-neopentyl-1(2H)-isoquinolinone hydrochloride (0.23 g, 95.8%) as crystals.

Melting point 195.5–201° C. Elemental analysis for C$_{21}$H$_{33}$N$_2$O$_3$Cl ¼H$_2$O Calculated: C, 62.83; H, 8.41; N, 6.98. Found: C, 62.79; H, 8.52; N, 6.72. $^1$H-NMR(DMSO-d$_6$) δ: 0.90 (9H, s), 1.00 (3H, t, J=7.3 Hz), 1.41 (3H, t, J=7.0 Hz), 1.51–1.63 (2H, m), 1.77–1.91 (2H, m), 3.93 (2H, t, J=6.4 Hz), 4.09 (2H, bs), 4.20 (2H, q, J=7.0 Hz), 4.22 (2H, s), 7.07 (1H, d, J=2.2 Hz), 7.18 (1H, dd, J=2.2, 8.8 Hz), 8.18 (1H, d, J=8.8 Hz), 8.56 (3H, bs).

Example 2

3-(Aminomethyl)-4-butoxy-7-fluoro-2-neopentyl-1 (2H)-isoquinolinone hydrochloride (1) To a solution of ethyl 7-fluoro-4-hydroxy-2-neopentyl-1-oxo-1,2-dihydro-3-isoquinolinecarboxylate (5.12 g, 31.9%) (from Example 1(1), 3.21 g, 10 mmol), 1-butanol (1.4 ml, 15 mmol) and tributylphosphine (5.0 ml, 20 mmol) in tetrahydrofuran (30 ml) was added 1,1'-(azodicarbonyl) dipiperidine (5.05. g, 20 mmol) and the mixture was stirred at room temperature for 3 h. The reaction mixture was concentrated, under reduced pressure and the residue was purified by silica gel column chromatography to give ethyl 4-butoxy-7-fluoro-2-neopentyl-1-oxo-1,2-dihydro-3-isoquinolinecarboxylate (3.55 g, 94.2%) as an oil.

$^1$H-NMR(CDCl$_3$) δ: 0.94 (9H, s), 1.01 (3H, t, J=7.1 Hz), 1.44 (3H, t, J=7.1 Hz), 1.51–1.63 (2H, m), 1.73–1.87 (2H, m), 3.95 (2H, t, J=6.4 Hz), 4.11 (2H, bs), 4.43 (2H, q, J=7.1 Hz), 7.40–7.50 (1H, m), 7.79 (1H, dd, J=5.2, 8.8 Hz), 8.09 (1H, dd, J=2.8, 9.4 Hz).

(2) To a solution of 4-butoxy-7-fluoro-2-neopentyl-1-oxo-1,2-dihydro-3-isoquinolinecarboxylate (3.40 g, 9 mmol) in tetrahydrofuran (20 ml) and ethanol (20 ml) was added sodium hydroxide (1.08 g, 27 mmol). The obtained mixture was refluxed under heating for 3 h. The reaction mixture was pouted into water, and, after making the mixture acidic with 1N hydrochloric acid, extracted with ethyl acetate. The extract was washed with brine, dried over anhydrous magnesium sulfate and concentrated under reduced pressure. The obtained crystals were recrystallized from tetrahydrofuran-diisopropyl ether to give 4-butoxy-7-fluoro-2-neopentyl-1-oxo-1,2-dihydro-3-isoquinolinecarboxylic acid (3.04 g, 96.8%) as crystals.

Melting point 184–185° C. Elemental analysis for C$_{19}$H$_{24}$NO$_4$F Calculated: C, 65.31; H, 6.92; N, 4.01. Found: C, 65.49; H, 7.11; N, 3.77. $^1$H-NMR(CDCl$_3$) δ: 0.94 (9H, s), 0.99 (3H, t, J=7.5 Hz), 1.45–1.64 (2H, m), 1.77–1.91 (2H, m), 4.03 (2H, t, J=6.6 Hz), 4.30 (2H, bs), 5.67 (1H, bs), 7.42–7.52 (1H, m), 7.80 (1H, dd, J=5.2, 8.8 Hz), 8.09 (1H, dd, J=2.6, 9.2 Hz).

(3) 4-Butoxy-7-fluoro-2-neopentyl-1-oxo-1,2-dihydro-3-isoquinolinecarboxylic acid (2.97 g, 8.5 mmol) was dissolved in tetrahydrofuran (30 ml) and oxalyl chloride (0.9 ml, 10.2 mmol) and N,N-dimethylformamide (2 drops) were added thereto. The mixture was stirred at room temperature for 1 h. The reaction mixture was concentrated under reduced pressure and the residue was dissolved in tetrahydrofuran (20 ml). The obtained solution was added dropwise to sodium tetrahydroborate (1.13 g, 30 mmol) in dimethoxyethane (20 ml) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from tetrahydrofuran-diisopropyl ether to give 4-butoxy-7-fluoro-3-hydroxymethyl-2-neopentyl-1(2H)-isoquinolinone (2.52 g, 88.4%) as crystals.

Melting point 149–150° C. Elemental analysis for $C_{19}H_{26}NO_3F$ Calculated: C, 68.04; H, 7.81; N, 4.18. Found: C, 67.80; H, 8.00; N, 4.19. $^1$H-NMR(CDCl$_3$) δ: 0.95 (9H, s), 1.04 (3H, t, J=7.1 Hz), 1.50–1.69 (2H, m), 1.71–1.94 (2H, m), 2.93 (1H, bs), 3.91 (2H, t, J=6.6 Hz), 4.21 (2H, bs), 4.87 (2H, bs), 7.27–7.36 (1H, m), 7.65 (1H, dd, J=5.0, 8.8 Hz), 7.86 (1H, dd, J=2.4, 9.2 Hz).

(4) To a solution of 4-butoxy-7-fluoro-3-hydroxymethyl-2-neopentyl-1(2H)-isoquinolinone (2.35g, 7 mmol) in tetrahydrofuran (10 ml) and toluene (10 ml) was added thionyl chloride (1.0 ml, 14 mmol) and the obtained mixture was refluxed under heating for 2 h. The reaction mixture was poured into saturated aqueous sodium hydrogencarbonate solution and extracted with ethyl acetate. The extract was washed with brine dried over anhydrous magnesium sulfate and concentrated under reduced pressure to give 4-butoxy-7-fluoro-3-chloromethyl-2-neopentyl-1(2H)-isoquinolinone (2.04 g, 82.6%) as an oil.

$^1$H-NMR(CDCl$_3$) δ: 0.99 (9H, s), 1.04 (3H, t, J=7.3 Hz), 1.51–1.69 (2H, m), 1.81–1.91 (2H, m), 3.94 (2H, t, J=6.4 Hz), 4.20 (2H, bs), 4.88 (2H, bs), 7.38–7.48 (1H, m), 7.75 (1H, dd, J=5.0, 8.8 Hz), 8.09 (1H, dd, J=2.6, 9.0 Hz).

(5) A solution of 4-butoxy-7-fluoro-3-chloromethyl-2-neopentyl-1(2H)-isoquinolinone (1.95 g, 5.5 mmol) and potassium phthalimide (1.54 g, 8.3 mmol) in N,N-dimethylformamide (20 ml) was stirred at room temperature for 6 h. The reaction mixture was poured into water and extracted with ethyl acetate. After washing the extract with water, the extract was dried over anhydrous magnesium sulfate and concentrated under reduced pressure. The obtained crystals were recrystallized from ethyl acetate-diisopropyl ether to give 2-{(4-butoxy-7-fluoro-2-neopentyl-1-oxo-1,2-dihydro-3-isoquinolinyl)methyl}-1H-isoindole-1,3(2H)-dione (2.46 g, 96.5%) as crystals.

Melting point 155–156° C. Elemental analysis for $C_{27}H_{29}N_2O_4F$ Calculated: C, 69.81; H, 6.29; N, 6.03. Found: C, 69.84; H, 6.17; N, 5.88. $^1$H-NMR(CDCl$_3$) δ: 1.00 (3H, t, J=7.3 Hz), 1.01 (9H, s), 1.45–1.62 (2H, m), 1.81–1.95 (2H, m), 4.02 (2H, t, J=6.7 Hz), 4.13 (2H, bs), 5.07 (2H, bs), 7.36–7.45 (1H, m), 7.69–7.83 (5H, m), 8.05 (1H, dd, J=2.6, 9.4 Hz).

(6) To a suspension of 2-{(4-butoxy-7-fluoro-2-neopentyl-1-oxo-1,2-dihydro-3-isoquinolinyl)methyl}-1H-isoindole-1,3(2H)-dione (2.32 g, 5 mmol) in ethanol (20 ml) was added hydrazine monohydrate (0.73 ml, 15 mmol). The obtained mixture was refluxed under heating for 2 h. The reaction mixture was poured into saturated aqueous sodium hydrogencarbonate solution and extracted with ethyl acetate. The extract was washed with brine dried over anhydrous magnesium sulfate and concentrated under reduced pressure. The residue was dissolved in tetrahydrofuran (20 ml) and di-t-butyl dicarbonate (1.64 g, 7.5 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl(4-butoxy-7-fluoro-2-neopentyl-1-oxo-1,2-dihydro-3-isoquinolinyl)methylcarbamate (1.93 g, 88.9%) as crystals.

Melting point 149–150° C. Elemental analysis for $C_{24}H_{35}N_2O_4F$ Calculated: C, 66.34; H, 8.12; N, 6.45. Found: C, 66.33; H, 8.14; N, 6.33. $^1$H-NMR(CDCl$_3$) δ: 0.99 (9H, s), 1.03 (3H, t, J=7.4 Hz), 1.45 (9H, s), 1.52–1.67 (2H, m), 1.79–1.93 (2H, m), 3.86 (2H, t, J=6.4 Hz), 4.13 (2H, bs), 4.57 (2H, d, J=5.6 Hz), 4.68 (1H, bs), 7.36–7.45 (1H, m), 7.70 (1H, dd, J=5.1, 8.7 Hz), 8.05 (1H, dd, J=2.7, 9.3 Hz).

(7) To a solution of tert-butyl(4-butoxy-7-fluoro-2-neopentyl-1-oxo-1,2-dihydro-3-isoquinolinyl)methylcarbamate (1.74 g, 4 mmol) in ethyl acetate (5 ml) was added a solution of 4N hydrogen chloride in ethyl acetate(5 ml), and the obtained solution was stirred at room temperature for 2 h. The reaction mixture was concentrated under reduced pressure and the precipitated crystals were, recrystallized from methanol-diisopropyl ether to give 3-(aminomethyl)-4butoxy-7-fluoro-2-neopentyl-1(2H)-isoquinolinone hydrochloride (1.42 g, 95.9%) as crystals.

Melting point 198–199° C. Elemental analysis for $C_{19}H_{28}N_2O_2ClF$ ½$H_2O$ Calculated: C, 60.07; H, 7.69; N, 7.37. Found: C, 60.33; H, 7.57; N, 7.42. $^1$H-NMR(DMSO-d$_6$) δ: 0.91 (9H, s), 0.99 (3H, t, J=7.4 Hz), 1.45–1.64 (2H, m), 1.78–1.92 (2H, m), 3.94 (2H, t, J=6.4 Hz), 4.12 (2H, bs), 4.25 (2H, bs), 7.70–7.80 (1H, m), 7.87 (1H, dd, J=5.4, 9.0 Hz), 7.95. (1H, dd, J=2.5, 9.5 Hz), 8.60 (3H, bs).

Example 3

3-(Aminomethyl)-4-butoxy-6-fluoro-2-neopentyl-1 (2H)-isoquinolinone hydrochloride (1) To a solution of 4-butoxy-6-fluoro-3-hydroxymethyl-2-neopentyl-1(2H)-isoquinolinone (from Example 1(3), 1.68 g, 5 mmol) in tetrahydrofuran (10 ml) and toluene (10 ml) was added thionylchloride (0.73 ml, 10 mmol), and the resulting mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 4-butoxy-6-fluoro-3-chloromethyl-2-neopentyl-1 (2H)-isoquinolinone (1.62 g, 92.0%) as an oil.

$^1$H-NMR(CDCl$_3$) δ: 0.98 (9H, s), 1.04 (3H, t, J=7.4 Hz), 1.51–1.69 (2H, m), 1.81–1.95 (2H, m), 3.94 (2H, t, J=6.6 Hz), 4.17 (2H, bs), 4.87 (2H, bs), 7.12–7.30 (1H, m), 7.35 (1H, dd, J=2.6, 9.6 Hz), 8.09 (1H, dd, J=5.8, 9.0 Hz).

(2) A solution of 4-butoxy-6-fluoro-3-chloromethyl-2-neopentyl-1(2H)-isoquinolinone (1.59 g, 4.5 mmol) and potassium phthalimide (1.26 g, 6.8 mmol) in N,N-dimethylformamide (20 ml) was stirred at room temperature for 6 h. The reaction mixture was poured into water and extracted with ethyl acetate. After washing the extract with water, the extract was dried over anhydrous magnesium sulfate and concentrated under reduced pressure. The obtained crystals were recrystallized from ethyl acetate-diisopropyl ether to give 2-{(4-butoxy-6-fluoro-2-neopentyl-1-oxo-1,2-dihydro-3-isoquinolinyl)methyl}-1H-isoindole-1,3(2H)-dione (1.81 g, 86.6%) as crystals.

Melting point 162–164° C. Elemental analysis for $C_{27}H_{29}N_2O_4F$ Calculated: C, 69.81; H,6.29; N, 6.03. Found: C, 69.47; H, 6.10; N, 6.02. $^1$H-NMR(CDCl$_3$) δ: 1.00 (9H, s), 1.01 (3H, t, J=7.3 Hz), 1.48–1.62 (2H, m), 1.81–1.95 (2H, m), 4.01 (2H, t, J=6.8 Hz), 4.04 (2H, bs), 5.07 (2H, bs), 7.13–7.23 (1H, m), 7.34 (1H, dd, J=2.4, 9.8 Hz), 7.70–7.86 (4H, m), 8.42 (1H, dd, J=5.6, 8.8 Hz).

(3) To a suspension of 2-{(4-butoxy-6-fluoro-2-neopentyl-1-oxo-1,2-dihydro-3-isoquinolinyl)methyl}-1H-isoindole-1,3(2H)-dione (1.71 g, 3.7 mmol) in ethanol (20 ml) was added hydrazine monohydrate (0.54 ml, 11.1 mmol). The resulting mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (20 ml) and di-t-butyl dicarbonate (1.22 g, 5.6 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The resulting crystals were recrystallized from ethyl acetate-n-hexane to give tert-butyl(4-butoxy-6-fluoro-2-neopentyl-1-oxo-1,2-dihydro-3-isoquinolinyl)methylcarbamate (1.35 g, 83.9%) as crystals.

Melting point 168–169° C. Elemental analysis for $C_{24}H_{35}N_2O_4F$ Calculated: C, 66.34; H, 18.12; N, 6.45. Found: C, 66.18; H, 8.26; N, 6.34. $^1$H-NMR(CDCl$_3$) δ: 1.00 (9H, s), 1.04 (3H, t, J=7.0 Hz), 1.45 (9H, s), 1.52–1.67 (2H, m), 1.79–1.93 (2H, m), 3.85. (2H, t, J=6.4 Hz), 4.11 (2H, bs), 4.56 (2H, d, J=5.2 Hz), 4.68 (1H, bs), 7.14–7.24 (1H, m), 7.30 (1H, dd, J=2.6, 10.0 Hz), 8.42 (1H, dd, J=5.4, 8.8 Hz).

(4) To a solution of tert-butyl(4-butoxy-6-fluoro-2-neopentyl-1-oxo-1,2-dihydro-3-isoquinolinyl)methylcarbamate (1.22 g, 2.8 mmol) in ethyl acetate (5 ml) was added a solution of 4N hydrogen chloride in ethyl acetate (5 ml) and the obtained solution was stirred at room temperature for 2 h. The reaction mixture was concentrated under reduced pressure, and the precipitated crystals were recrystallized from methanol-diisopropyl ether to give 3-(aminomethyl)-4-butoxy-6-fluoro-2-neopentyl-1(2H)-isoquinoline hydrochloride (1.01 g, 98.1%) as crystals.

Melting point 195.5–201° C. Elemental analysis for $C_{19}H_{28}N_2O_2ClF$ ¼$H_2O$ Calculated: C, 62.83; H, 8.41; N, 6.98. Found: C, 62.79; H, 8.52; N, 6.72. $^1$H-NMR(DMSO-d$_6$) δ: 0.90 (9H, s), 1.00 (3H, t, J=7.3 Hz), 1.41 (3H, t, J=7.0 Hz), 1.51–1.63 (2H, m), 1.77–1.91 (2H, m), 3.93 (2H, t, J=6.4 Hz), 4.09 (2H, bs), 4.20(2H, q, J=7.0 Hz), 4.22 (2H, s), 7.07 (1H, d, J=2.2 Hz), 7.18 (1H, dd, J=2.2, 8.8 Hz), 8.18 (1H, d, J=8.8 Hz), 8.56 (3H, bs).

Example 4

3-(Aminomethyl)-6-chloro-4-methoxy-2-methyl-1(2H)-isoquinolinone hydrochloride (1) To a solution of 4-chlorophthalic anhydride (9.13 g, 50 mmol) in tetrahydrofuran (50 ml) was added 28% sodium methoxide-methanol solution (11.6 ml, 60 mmol), and the mixture was stirred at room temperature for 30 min. The reaction mixture was poured into water, and, after making the mixture acidic with 1N hydrochloric acid, extracted with ethyl acetate. The extract was washed with brine, dried over anhydrous magnesium sulfate and concentrated under reduced pressure. The residue was dissolved in tetrahydrofuran (100 ml) and oxalyl chloride (5.2 ml, 60 mmol) and N,N-dimethylformamide (3 drops) were added thereto. The mixture was stirred at room temperature for 30 min. The reaction mixture was concentrated under reduced pressure, and the residue was dissolved in N,N-dimethylacetamide (100 ml). To the obtained solution was added ethyl sarcosinate hydrochloride (9.22 g, 60 mmol). The obtained mixture was stirred at room temperature for 2 h. The reaction mixture was poured into 1N hydrochloric acid and extracted with ethyl acetate. The extract was washed with brine, dried over anhydrous magnesium sulfate and concentrated under reduced pressure. The residue was dissolved in ethanol (100 ml) and 20% sodium ethoxide ethanol solution (27.2 g, 80 mmol) was added. The mixture was stirred at room temperature for 1 h. The reaction mixture was poured into 1N hydrochloric acid (100 ml) and extracted with ethyl acetate. The extract was washed with brine, dried over anhydrous magnesium sulfate and concentrated under reduced pressure. The residue was purified by silica gel column chromatography and the component eluted earlier was concentrated to give ethyl 7-chloro-4-hydroxy-2-methyl-1-oxo-1,2-dihydro-3-isoquinolinecarboxylate (2.24 g, 20.9%) as crystals.

Melting point 109–110° C. Elemental analysis for $C_{13}H_{12}NO_4Cl$ Calculated: C, 55.43; H, 4.29; N, 4.97. Found: C, 55.54; H, 4.22; N, 5.12. $^1$H-NMR(CDCl$_3$) δ: 1.46 (3H, t, J=7 Hz), 3.68 (3H, s), 4.50 (2H, q, J=7.0 Hz), 7.70 (1H, dd, J=2.0, 8.6 Hz), 8.09 (1H, d, J=8.6 Hz), 8.43 (1H, d, J=2.0 Hz), 11.25 (1H, s).

The component eluted later was concentrated to give ethyl 6-chloro-4-hydroxy-2-methyl-1-oxo-1,2-dihydro-3-isoquinolinecarboxylate (2.82 g, 26.4%) as crystals.

Melting point 110–111° C. Elemental analysis for $C_{13}H_{12}NO_4Cl$ Calculated: C, 55.43; H, 4.29; N, 4.97. Found: C, 55.49; H, 4.30; N, 5.11. $^1$H-NMR(CDCl$_3$) δ: 1.46 (3H, t, J=7.0 Hz), 3.68 (3H, s), 4.50 (2H, q, J=7.0 Hz), 7.63 (1H, dd, J=1.9, 8.7 Hz), 8.17 (1H, d, J=1.9 Hz), 8.38 (1H, d, J=8.7 Hz), 11.16 (1H, s).

(2) A suspension of ethyl 6-chloro-4-hydroxy-2-methyl-1-oxo-1,2-dihydro-3-isoquinolinecarboxylate (1.41 g, 5 mmol), methyl iodide (0.47 ml, 7.5 mmol) and potassium carbonate (1.04 g, 7.5 mmol) in N,N-dimethylformamide (10 ml) was stirred at room temperature for 4 h. The reaction mixture was concentrated under reduced pressure, and the residue was purified by silica gel column chromatography to give ethyl 6-chloro-4-methoxy-2-methyl-1-oxo-1,2-dihydro-3-isoquinolinecarboxylate (1.11 g, 75.5%) as crystals.

Melting point 122–123° C. Elemental analysis for $C_{14}H_{14}NO_4Cl$ Calculated: C, 56.86; H, 4.77; N, 4.74. Found: C, 56.85; H, 4.76; N, 4.57. $^1$H-NMR(CDCl$_3$) δ: 1.45 (3H, t, J=7.2 Hz), 3.52 (3H, s), 3.89 (3H, s), 4.49 (2H, q, J=7.2 Hz), 7.51 (1H, dd, J=2.2, 8.8 Hz), 7.74 (1H, d, J=2.2 Hz), 8.38 (1H, d, J=8.8 Hz).

(3) To a solution of ethyl 6-chloro-4-methoxy-2-methyl-1-oxo-1,2-dihydro-3-isoquinolinecarboxylate (1.03 g, 3.5 mmol) in tetrahydrofuran (10 ml) and ethanol (10 ml) was added 1N sodium hydroxide (5 ml). The obtained mixture was refluxed under stirring at 50° C. for 3 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate diethyl ether to give 6-chloro-4-methoxy-2-methyl-1-oxo-1,2-dihydro-3-isoquinolinecarboxylic acid (0.72 g, 77.4%) as crystals.

Melting point 216–217° C. Elemental analysis for $C_{12}H_{10}NO_4Cl$ Calculated: C, 53.85; H, 3.77; N, 5.23. Found: C, 53.78; H, 3.74; N, 5.03. $^1$H-NMR(CDCl$_3$) δ: 3.58 (3H, s), 3.91 (3H, s), 4.78 (1H, bs), 7.49 (1H, dd, J=2.0, 8.6 Hz), 7.75 (1H, d, J=2.0 Hz), 8.36 (1H, d, J=8.6 Hz).

(4) 6-Chloro-4-methoxy-2-methyl-1-oxo-1,2-dihydro-3-isoquinolinecarboxylic acid (0.67 g, 2.5 mmol) was dissolved in tetrahydrofuran (10 ml) and oxalyl chloride (0.26 ml, 3 mmol) and N,N-dimethylformamide (2 drops) were added thereto. The mixture was stirred at room temperature for 1 h. The reaction mixture was concentrated under reduced pressure, and the residue was dissolved in tetrahydrofuran (10 ml). The obtained solution was added dropwise to a suspension of sodium tetrahydroborate (0.33 g, 8.8 mmol) in 1,2-dimethoxyethane (20 ml) at 0° C. The obtained mixture was stirred at 0° C. for 1 h, and the reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-chloro-3-hydroxymethyl-4-methoxy-2-methyl-1(2H)-isoquinolinone (0.42 g, 66.7%) as crystals.

Melting point 195–196° C. Elemental analysis for $C_{12}H_{12}NO_3Cl$ Calculated: C, 56.81; H, 4.77; N, 5.52. Found: C, 56.69; H, 4.88; N, 5.44. $^1$H-NMR(CDCl$_3$) δ: 2.70 (1H, bs), 3.71 (3H, s), 3.82 (3H, s), 4.82 (2H, s), 7.40 (1H, dd, J=2.0, 8.6 Hz), 7.61 (1H, d, J=2.0 Hz), 8.26 (1H, d, J=8.6 Hz).

(5) To a solution of 6-chloro-3-hydroxymethyl-4-methoxy-2-methyl-1(2H)-isoquinolinone (0.76 g, 3 mmol) in tetrahydrofuran (20 ml) was added thionyl chloride (0.26 ml, 3.6 mmol). The obtained mixture was refluxed under heating for 2 h. The reaction mixture was poured into saturated aqueous sodium hydrogencarbonate solution, extracted with ethyl acetate. The extract was washed with brine, dried over anhydrous magnesium sulfate and concentrated under reduced pressure to give 6-chloro-3-chloromethyl-4-methoxy-2-methyl-1(2H)-isoquinolinone (0.73 g, 90.1%) as crystals.

$^1$H-NMR(CDCl$_3$) δ: 3.73 (3H, s), 3.93 (3H, s), 4.80 (2H, s), 7.49 (1H, dd, J=2.0, 8.6 Hz), 7.74 (1H, d, J=2.0 Hz), 8.38 (1H, d, J=8.6 Hz).

(6) A solution of 6-chloro-3-chloromethyl-4-methoxy-2-methyl-1(2H)-isoquinolinone (0.81 g, 3 mmol) and potassium phthalimide (0.83 g, 4.5 mmol) in N,N-dimethylformamide (20 ml) was stirred at room temperature for 4 h. The reaction mixture was poured into water and extracted with ethyl acetate. After washing the extract with water, the extract was dried over anhydrous magnesium sulfate and concentrated under reduced pressure. The residue was purified by silica gel column chromatography to give 2-{(6-chloro-4methoxy-2-methyl-1-oxo-1,2-dihydro-3-isoquinolinyl)methyl}-1H-isoindole-1,3(2H)-dione (0.59 g, 51.8%) as crystals.

Melting point 248–249° C. Elemental analysis for $C_{20}H_{15}N_2O_4Cl$ Calculated: C, 62.75; H, 3.95; N, 7.32. Found: C, 62.73; H, 3.94; N, 7.32. $^1$H-NMR(CDCl$_3$) δ: 3.61 (3H, s), 3.96 (3H, s), 5.07 (2H, s), 7.45 (1H, dd, J=2.0, 8.6 Hz), 7.73–7.88 (5H, m), 8.36 (1H, d, J=8.6 Hz).

(7) To a solution of 2-{(6-chloro-4-methoxy-2-methyl-1oxo-1,2-dihydro-3-isoquinolinyl)methyl}-1H-isoindole-1,3(2H)-dione (0.38 g, 1 mmol) in ethanol (10 ml) and tetrahydrofuran (10 ml) was added hydrazine monohydrate (0.14 ml, 3 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. To the residue was added a solution of 4N hydrogen chloride in ethyl acetate (2 ml), and the precipitated crystals were recrystallized from methanol-diethyl ether to give 3-(aminomethyl)-6-chloro-4-methoxy-2-methyl-1(2H)-isoquinolinone hydrochloride (0.08 g, 28.6%) as crystals.

Melting point 236–237° C. Elemental analysis for $C_{12}H_{14}N_2O_2Cl_2$ Calculated: C, 49.84; H, 4.88; N, 9.69. Found: C, 49.67; H, 4.71; N, 9.48. $^1$H-NMR(DMSO-d$_6$) δ: 3.61 (3H, s), 3.85 (3H, s), 4.24 (2H, s), 7.66 (1H, dd, J=2.0, 8.6 Hz), 7.81 (1H, d, J=2.0 Hz), 8.28 (1H, d, J=8.6 Hz), 8.75 (3H, bs).

Example 5

3-(Aminomethyl)-7-chloro-4-methoxy-2-methyl-1(2H)-isoquinolinone hydrochloride (1) Ethyl 7-chloro-4-methoxy-2-methyl-1-oxo-1,2-dihydro-3-isoquinolinecarboxylate (synthesized according to the method similar to that in Example 4 (2))

Melting point 114–115° C. Elemental analysis for $C_{14}H_{14}NO_4Cl$ Calculated: C, 56.86; H, 4.77; N, 4.74. Found: C, 56.77; H, 4.74; N, 4.64. $^1$H-NMR(CDCl$_3$) δ: 1.45 (3H, t, J=7.1 Hz), 3.53 (3H, s), 3.89 (3H, s), 4.49 (2H, q, J=7.1 Hz), 7.67 (1H, dd, J=2.0, 8.6 Hz), 7.74 (1H, d, J=8.0 Hz), 8.38 (1H, d, J=2.0 Hz).

(2) 7-Chloro-4-methoxy-2-methyl-1-oxo-1,2-dihydro-3-isoquinolinecarboxylic acid (synthesized according to the method similar to that in Example 4 (3))

Melting point 163–164° C. Elemental analysis for $C_{12}H_{10}NO_4Cl$ Calculated: C, 53.85; H, 3.77; N, 5.23. Found: C, 53.78; H, 3.74; N, 5.03. $^1$H-NMR(CDCl$_3$) δ: 3.60 (3H, s), 3.91 (3H, s), 7.66 (1H, dd, J=2.2, 8.8 Hz), 7.76 (1H, d, J=2.2 Hz), 8.40 (1H, d, J=2.2 Hz).

(3) 7-Chloro-3-hydroxymethyl-4-methoxy-2-methyl-1(2H)-isoquinolinone (synthesized according to the method similar to that in Example 4 (4))

Melting point 151–152° C. Elemental analysis for $C_{12}H_{12}NO_3Cl$ ¼H$_2$O Calculated: C, 55.83; H, 4.88; N, 5.43. Found: C, 55.88; H, 4.84; N, 5.55. $^1$H-NMR(CDCl$_3$) δ: 2.57 (1H, bs), 3.73 (3H, s), 3.84 (3H, s), 4.83 (2H, s), 7.59 (1H, dd, J=2.0, 8.6 Hz), 7.66 (1H, d, J=8.6 Hz), 8.33 (1H, d, J=2.0 Hz).

(4) 7-Chloro-3-chloromethyl-4-methoxy-2-methyl-1(2H)-isoquinolinone (synthesized according to the method similar to that in Example 4 (5))

$^1$H-NMR(CDCl$_3$) δ: 3.74 (3H, s), 3.93 (3H, s), 4.81 (2H, s), 7.66 (1H, dd, J=2.2, 8.6 Hz), 7.66 (1H, d, J=8.6 Hz), 8.33 (1H, d, J=2.2 Hz).

(5) 2-{(7-Chloro-4-methoxy-2-methyl-1-oxo-1,2-dihydro-3-isoquinolinyl)methyl}-1H-isoindole-1,3(2H)-dione (synthesized according to the method similar to that in Example 4 (6))

Melting point 262–263° C. Elemental analysis for $C_{20}H_{15}N_2O_4Cl$ Calculated: C, 62.75; H, 3.95; N, 7.32. Found: C, 62.41; H, 3.91; N, 7.20. $^1$H-NMR(CDCl$_3$) δ: 3.56 (3H, s), 3.82 (3H, s), 5.02 (2H, s), 7.81–7.86 (6H, m), 8.18 (1H, s).

(6) 3-(Aminomethyl)-7-chloro-4-methoxy-2-methyl-1(2H)-isoquinolinone hydrochloride (synthesized according to the method similar to that in Example 4 (7))

Melting point 225–226° C. Elemental analysis for $C_{12}H_{14}N_2O_2Cl_2$ Calculated: C, 49.84; H, 4.88; N, 9.69. Found: C, 49.82; H, 4.88; N, 10.12. $^1$H-NMR(DMSO-$d_6$) δ: 3.62 (3H, s), 3.84 (3H, s), 4.23 (2H, d, J=4.4 Hz), 7.83–7.88 (2H, m), 8.22 (1H, d, J=0.8 Hz), 8.72 (3H, bs).

Example 6

3-(Aminomethyl)-6-chloro-4-isopropoxy-2-methyl-1 (2H)-isoquinolinone hydrochloride (1) Ethyl 6-chloro-4-isopropoxy-2-methyl-1-oxo-1,2-dihydro-3-isoquinolinecarboxylate (synthesized according to the method similar to that in Example 4 (2))

Melting point 66–67° C. Elemental analysis for $C_{16}H_{18}NO_4Cl$ Calculated: C, 59.35; H, 5.60; N, 4.33. Found: C, 59.22; H, 5.56; N, 4.33. $^1$H-NMR(CDCl$_3$) δ: 1.32 (6H, d, J=6.2 Hz), 1.45 (3H, t, J=7.2 Hz), 3.52 (3H, s), 4.28–4.40 (1H, m) 4.47 (2H, q, J=7.2 Hz), 7.50 (1H, dd, J=2.9, 8.6 Hz), 7.75 (1H, d, J=2.0 Hz), 8.37 (1H, d, J=8.6 Hz).

(2) 6-Chloro-4-isopropoxy-2-methyl-1-oxo-1,2-dihydro-3-isoquinolinecarboxylic acid (synthesized according to the method similar to that in Example 4 (3))

Melting point 229–230° C. Elemental analysis for $C_{14}H_{14}NO_4Cl$ Calculated: C, 56.86; H, 4.77; N, 4.74. Found: C, 56.86; H, 4.79; N, 4.48. $^1$H-NMR(CDCl$_3$) δ: 1.34 (6H, d, J=6.2 Hz), 3.60 (3H, s), 4.34–4.46 (1H, m), 7.48 (1H, dd, J=2.2, 8.4 Hz), 7.77 (1H, d, J=2.2 Hz), 8.36 (1H, d, J=8.4 Hz).

(3) 6-Chloro-3-hydroxymethyl-4-isopropoxy-2-methyl-1 (2H)-isoquinolinone (synthesized according to the method similar to that in Example 4 (4))

Melting point 146–147° C. Elemental analysis for $C_{14}H_{16}NO_3Cl$ Calculated: C, 59.68; H, 5.72; N, 4.97. Found: C, 59.43; H, 5.70; N, 5.06. $^1$H-NMR(CDCl$_3$) δ: 1.35 (6H, d, J=6.2 Hz), 2.34 (1H, bs), 3.74 (3H, s), 4.12–4.24 (1H, m), 4.83 (2H, d, J=4.8 Hz), 7.41 (1H, d, J=8.6 Hz), 7.61 (1H, s), 8.30 (1H, d, J=8.6 Hz).

(4) 2-{(6-Chloro-4-isopropoxy-2-methyl-1-oxo-1,2-dihydro-3-isoquinolinyl)methyl}-1H-isoindole-1,3(2H)-dione (synthesized according to the method similar to that in Example 4 (6))

Melting point 175–176° C. Elemental analysis for $C_{22}H_{19}N_2O_4Cl$ ½$H_2O$ Calculated: C, 62.93; H, 4.80; N, 6.67. Found: C, 62.78; H, 4.65; N, 6.41. $^1$H-NMR(CDCl$_3$) δ: 1.41 (6H, d, J=5.8 Hz), 3.60 (3H, s), 4.27–4.39 (1H, m), 5.08 (2H, s), 7.43 (1H, dd, J=2.0, 8.6 Hz), 7.68–7.90 (5H, m), 8.34 (1H, d, J=8.6 Hz).

(5) 3-(Aminomethyl)-6-chloro-4-isopropoxy-2-methyl-1 (2H)-isoquinolinone hydrochloride (synthesized according to the method similar to that in Example 4 (7))

Melting point 218–220° C. Elemental analysis for $C_{14}H_{18}N_2O_2Cl_2$ ½$H_2O$ Calculated: C, 52.27; H, 5.80; N, 8.71. Found: C, 52.37; H, 5.84; N, 8.70. $^1$H-NMR(DMSO-$d_6$) δ: 1.34 (6H, d, J=5.8 Hz), 3.61 (3H, s), 4.21–4.30 (3H, m), 7.65 (1H, dd, J=1.8, 8.6 Hz), 7.72 (1H, d, J=1.8 Hz), 8.28 (1H, d, J=8.6 Hz), 8.73 (3H, bs).

Example 7

3-(Aminomethyl)-4-butoxy-6-chloro-2-methyl-1 (2H)-isoquinolinone hydrochloride (1) Ethyl 4-butoxy-6-chloro-2-methyl-1-oxo-1,2-dihydro-3-isoquinolinecarboxylate (synthesized according to the method similar to that in Example 4 (2))

$^1$H-NMR(CDCl$_3$) δ: 1.01 (3H, t, J=7.3 Hz), 1.45 (3H, t, J=7.2 Hz), 1.51–1.63 (2H, m), 1.73–1.87 (2H, m), 3.52 (3H, s), 3.97 (2H, t, J=6.4 Hz), 4.48 (2H, q, J=7.2 Hz), 7.50 (1H, dd, J=2.0, 8.6 Hz), 7.71 (1H, d, J=2.0 Hz), 8.38 (1H, d, J=8.6 Hz).

(2) 4-Butoxy-6-chloro-2-methyl-1-oxo-1,2-dihydro-3-isoquinolinecarboxylic acid (synthesized according to the method similar to that in Example 4 (3))

Melting point 160–161° C. Elemental analysis for $C_{15}H_{16}NO_4Cl$ Calculated: C, 58.16; H, 5.21; N, 4.52. Found: C, 58.34; H, 5.42; N, 4.58. $^1$H-NMR(CDCl$_3$) δ: 0.95 (3H, t, J=7.2 Hz), 1.39–1.57 (2H, m), 1.67–1.80 (2H, m), 3.43 (3H, s), 3.95 (2H, t, J=6.4 Hz), 7.65 (1H, dd, J=2.0, 8.6 Hz), 7.73 (1H, d, J=2.0 Hz), 8.26 (1H, d, J=8.6 Hz).

(3) 4-Butoxy-6-chloro-3-hydroxymethyl-2-methyl-1 (2H)-isoquinolinone (synthesized according to the method similar to that in Example 4 (4))

Melting point 110–111° C. Elemental analysis for $C_{15}H_{18}NO_3Cl$ Calculated: C, 60.91; H, 6.18; N, 4.74. Found: C, 61.06; H, 6.09; N, 4.92. $^1$H-NMR(CDCl$_3$) δ: 1.03 (3H, t, J 7.3 Hz), 1.50–1.65 (2H, m), 1.76–1.90 (2H, m), 2.82 (1H, bs), 3.69 (3H, s), 3.82 (2H, t, J=6.4 Hz), 4.79 (2H, d, J=5.4 Hz), 7.39 (1H, dd, J=2.1, 8.5 Hz), 7.54 (1H, d, J=2.1 Hz), 8.24 (1H, d, J=8.5 Hz).

(4) 4-Butoxy-6-chloro-3-chloromethyl-2-methyl-1(2H)-isoquinolinone (synthesized according to the method similar to that in Example 4 (5))

$^1$H-NMR(CDCl$_3$) δ: 1.05 (3H, t, J=7.3 Hz), 1.56–1.71 (2H, m), 1.83–1.97 (2H, m), 3.73 (3H, s), 3.99 (2H, t, J=6.4 Hz), 4.80 (2H, s), 7.46 (1H, dd, J=2.2, 8.6 Hz), 7.71 (1H, d, J=2.2 Hz), 8.38 (1H, d, J=8.6 Hz).

(5) 2-{(4-Butoxy-6-chloro-2-methyl-1-oxo-1,2-dihydro-3-isoquinolinyl)}-1H-isoindole-1,3(2H)-dione (synthesized according to the method similar to that in Example 4 (6)).

Melting point 200–201° C. Elemental analysis for $C_{23}H_{21}N_2O_4Cl$ Calculated: C, 65.02; H, 4.98; N, 6.59. Found: C, 64.85; H, 5.07; N, 6.60. $^1$H-NMR(DMSO-$d_6$) δ: 0.93 (3H, t, J=7.4 Hz), 1.40–1.51 (2H, m), 1.70–1.81 (2H, m), 3.52 (3H, s), 3.93 (2H, t, J=6.6 Hz), 5.03 (2H, s), 7.59 (1H, dd, J=2.0, 8.4 Hz), 7.67 (1H, d, J=2.0 Hz), 7.87 (4H, s), 8.25 (1H, d, J=8.4 Hz).

(6) 3-(Aminomethyl)-4-butoxy-6-chloro-2-methyl-1 (2H)-isoquinolinone hydrochloride (synthesized according to the method similar to that in Example 4 (7))

Melting point 222–223° C. Elemental analysis for $C_{15}H_{20}N_2O_2Cl_2$ ½$H_2O$ Calculated: C, 60.91; H, 6.13; N, 4.74. Found: C, 61.06; H, 6.09; N, 4.92. $^1$H-NMR(DMSO-$d_6$) δ: 1.00 (3H, t, J=7.3 Hz), 1.46–1.64 (2H, m), 1.77–1.99 (2H, m), 3.61 (3H, s), 3.91 (2H, t, J=6.4 Hz), 4.23 (2H, bs), 7.65 (1H, dd, J=2.0, 8.6 Hz), 7.72 (1H, d, J=2.0 Hz), 8.28 (1H, d, J=8.6 Hz), 8.74 (3H, bs).

Example 8

3-(Aminomethyl)-4-benzyloxy-6-chloro-2-methyl-1 (2H)-isoquinolinone hydrochloride (1) Ethyl 4-benzyloxy-6-chloro-2-methyl-1-oxo-1,2-dihydro-3-isoquinolinecarboxylate (synthesized according to the method similar to that in Example 4 (2))

Melting point 114–115° C. Elemental analysis for $C_{20}H_{18}NO_4Cl$ Calculated: C, 64.61; H, 4.88; N, 3.77. Found: C, 64.67; H, 5.04; N, 4.00. $^1$H-NMR(CDCl$_3$) δ: 1.35 (3H, t, J=7.2 Hz), 3.54 (3H, s), 3.97 (2H, q, J=7.2 Hz), 5.03 (2H, s), 7.39–7.54 (6H, m), 7.72 (1H, d, J=1.8 Hz), 8.39 (1H, d, J=8.8 Hz).

(2) 4-Benzyloxy-6-chloro-2-methyl-1-oxo-1,2-dihydro-3-isoquinolinecarboxylic acid (synthesized according to the method similar to that in Example 4 (3))

Melting point 226–227° C. Elemental analysis for $C_{18}H_{14}NO_4Cl$ Calculated: C, 62.89; H, 4.10; N, 4.07. Found: C; 62.84; H, 4.16; N, 4.20. $^1$H-NMR(CDCl$_3$) δ: 3.61 (3H, s), 5.07 (2H, s), 6.36 (1H, bs), 7.32–7.54 (6H, m), 7.72 (1H, d, J=8 Hz), 8.37 (1H, d, J=8.4 Hz).

(3) 4-Benzyloxy-6-chloro-3-hydroxymethyl-2-methyl-1 (2H)-isoquinolinone (synthesized according to the method similar to that in Example 4 (4))

Melting point 207–208° C. Elemental analysis for $C_{18}H_{16}NO_3Cl$ Calculated: C, 65.56; H, 4.89; N, 4.25. Found: C, 65.48; H, 4.96; N, 4.39. $^1$H-NMR(CDCl$_3$) δ: 1.22 (1H, t, J=5.8 Hz), 3.64 (3H, s), 4.52 (2H, d, J=5.8 Hz), 4.96 ((2H, s), 7.35–7.48 (6H, m), 7.72 (1H, d, J=2.2 Hz), 8.36 (1H, d, J=8.4 Hz).

(4) 4-Benzyloxy-6-chloro-3-chloromethyl-2-methyl-1 (2H)-isoquinolinone (synthesized according to the method similar to that in Example 4 (5))

$^1$H-NMR(CDCl$_3$) δ: 3.74 (3H, s), 4.76 (2H, s), 5.04 (2H, s), 7.43–7.52 (6H, m), 7.75 (1H, d, J=2.2 Hz), 8.40 (1H, d, J=8.8 Hz).

(5) 2-(4-Benzyloxy-6-chloro-2-methyl-1-oxo-1,2-dihydro-3-isoquinolinyl)-1H-isoindole-1,3(2H)-dione (synthesized according to the method similar to that in Example 4 (6))

Melting point 243–244° C. Elemental analysis for $C_{26}H_{19}N_2O_4Cl$ $H_2O$ Calculated: C, 65.48; H, 4.44; N, 5.87. Found: C, 65.27; H, 4.22; N, 5.99. $^1$H-NMR(DMSO-d$_6$) δ: 3.48 (3H, s), 5.06 (4H, s), 7.38–7.64 (7H, m), 7.85 (4H, s), 8.25 (1H, d, J=8.6 Hz).

(6) 3-(Aminomethyl)-4-benzyloxy-6-chloro-2-methyl-1 (2H)-isoquinolinone hydrochloride (synthesized according to the method similar to that in Example 4 (7))

Melting point 221–223° C. Elemental analysis for $C_{18}H_{18}N_2O_2Cl_2$ ½$H_2O$ Calculated: C, 52.95; H, 6.22; N, 8.23. Found: C, 53.21; H, 6.25; N, 8.28. $^1$H-NMR(DMSO-d$_6$) δ: 3.62 (3H, s), 4.25 (2H, s), 5.02 (2H, s), 7.42–7.52 (7H, m), 7.59–7.69 (4H, m),8.29 (1H, d, J=8.4 Hz), 8.72 (3H, bs).

Example 9

3-(Aminomethyl)-6-chloro-2-methyl-4-(2-quinolinylmethoxy)-1(2H)-isoquinolinone hydrochloride (1) Ethyl 6-chloro-2-methyl-1-oxo-4-(2-quinolinylmethoxy)-1,2-dihydro-3-isoquinolinecarboxylate (synthesized according to the method similar to that in Example 4 (2))

Melting point 164–165° C. Elemental analysis for $C_{23}H_{19}N_2O_4Cl$ Calculated: C, 65.33; H, 4.53; N, 6.62. Found: C, 65.29; H, 4.52; N, 6.33. $^1$H-NMR(CDCl$_3$) δ: 1.31 (3H, t, J=7.1 Hz), 3.56 (3H, s), 4.39 (2H, q, J=7.1 Hz), 5.33 (2H, s), 7.52 (1H, dd, J=1.9, 8.6 Hz), 7.55–7.63 (1H, m), 7.72–7.82 (2H, m), 7.88 (1H, d, J=8.4 Hz), 7.93 (1H, d, J=1.9 Hz), 8.11 (1H, d, J=8.6 Hz), 8.29 (1H, d, J=8.4 Hz), 8.41 (1H, d, J=8.4 Hz).

(2) 6-Chloro-2-methyl-1-oxo-4-(2-quinolinylmethoxy)-1,2-dihydro-3-isoquinolinecarboxylic acid (synthesized according to the method similar to that in Example 4 (3))

Melting point 268-268° C. $^1$H-NMR(DMSO-d$_6$) δ: 3.51 (3H, s), 5.29 (2H, s), 7.43 (1H, dd, J=2.0, 8.8 Hz), 7.59–7.67 (1H, m), 7.75–7.84 (2H, m), 7.87 (1H, d, J=8.6 Hz), 8.00–8.06 (2H, m), 8.19 (1H, d, J=8.6 Hz), 8.46 (1H, d, J=8.8 Hz).

(3) 6-Chloro-3-hydroxymethyl-2-methyl-4-(2-quinolinylmethoxy)-1(2H)-isoquinolinone (synthesized according to the method similar to that in Example 4 (4))

Melting point 206–207° C. Elemental analysis for $C_{21}H_{17}N_2O_3Cl$ ¼$H_2O$ Calculated: C, 65.46; H, 4.58; N, 7.27. Found: C, 65.40; H, 4.47; N, 7.23. $^1$H-NMR(CDCl$_3$) δ: 3.78 (3H, s), 4.80 (2H, s), 5.27 (2H, s), 7.42 (1H, dd, J=2.0, 8.6 Hz), 7.57–7.93 (5H, m), 8.12 (1H, d, J=8.8 Hz), 8.30 (1H, d, J=8.6 Hz), 8.36 (1H, d, J=8.8 Hz).

(4) 6Chloro-3-chloromethyl-2-methyl-4-(2-quinolinylmethoxy)-1(2H)-isoquinolinone (synthesized according to the method similar to that in Example 4 (5))

H-NMR(CDCl$_3$) δ: 3.76 (3H, s), 4.89 (2H, s), 5.33 (2H, s), 7.50 (1H, dd, J=2.0, 8.4 Hz), 7.57–7.65 (1H, m), 7.74–7.92 (3H, m), 7.95 (1H, d, J=2.0 Hz), 8.16 (1H, d, J=8.4 Hz), 8.31 (1H, d, J=8.4 Hz), 8.41 (1H, d, J=8.4 Hz).

(5) 2-{(6-Chloro-2-methyl-1-oxo-4-(2-quinolinylmethoxy)-1,2-dihydro-3-isoquinolinyl)methyl}-1H-isoindole-1,3 (2H)-dione (synthesized according to the method similar to that in Example 4 (6))

Melting point 249–250° C. $^1$H-NMR(DMSO-d$_6$) δ: 3.53 (3H, s), 5.16 (2H, s), 5.30 (2H, s), 7.59–7.67 (2H, m), 7.80–7.83 (6H, m), 8.00–8.08 (3H, m), 8.27 (1H, d, J=9.0 Hz), 8.46 (1H, d, J=8.4 Hz).

(6) 3-(Aminomethyl)-6-chloro-2-methyl-4-(2-quinolinylmethoxy)-1(2H)-isoquinolinone dihydrochloride (synthesized according to the method similar to that in Example 4 (7))

Melting point 236° C. Elemental analysis for $C_{21}H_{20}N_3O_2Cl_3$ ¼$H_2O$ Calculated: C, 55.16; H, 4.52; N, 9.19. Found: C, 55.29; H, 4.54; N, 9.12. $^1$H-NMR(DMSO-d$_6$) δ: 3.65 (3H, s), 4.41 (2H, d, J=4.8 Hz), 5.44 (2H, s), 7.67 (1H, dd, J=2.0, 8.8 Hz), 7.17 (1H, t, J=7.3 Hz), 7.96 (1H, t, J=7.3 Hz), 8.07 (1H, d, J=8.6 Hz), 8.15–8.20 (2H, m), 8.30 (1H, d, J=8.8 Hz), 8.33 (1H, d, J=8.4 Hz), 8.75 (1H, d, J=8.4 Hz), 8.87 (3H, bs).

Example 10

3-(Aminomethyl)-6-chloro-2-methyl-4-(2-phenylethoxy)-1(2H)-isoquinolinone hydrochloride (1) Ethyl 6-chloro-2-methyl-1-oxo-4-(2-phenylethoxy)-1,2-dihydro-3-isoquinolinecarboxylate (synthesized according to the method similar to that in Example 1 (2))

$^1$H-NMR(CDCl$_3$) δ: 1.38 (3H, t, J=7.2 Hz), 3.09 (2H, t, J=6.4 Hz), 3.49 (3H, s), 4.17 (2H, t, J=6.4 Hz), 4.33 (2H, q, J=7.2 Hz), 7.24–7.40 (6H, m), 7.44 (1H, dd, J=2.1, 8.5 Hz), 8.33 (1H, d, J=8.5 Hz).

(2) 6-Chloro-2-methyl-1-oxo-4-(2-phenylethoxy)-1,2-dihydro- 3-isoquinolinecarboxylic acid (synthesized according to the method similar to that in Example 4 (3))

Melting point 168–169° C. Elemental analysis for $C_{19}H_{16}NO_4Cl$ Calculated: C, 63.78; H, 4.51; N 3.91. Found: C, 63.73; H, 4.56; N, 3.86. $^1$H-NMR(DMSO-d$_6$) δ: 3.06 (2H, t, J=6.4 Hz), 3.43 (3H, s), 4.16 (2H, t, J=6.4 Hz), 7.19 (1H, dd, J=2.0 Hz), 7.28–7.36 (5H, m), 7.58 (1H, dd, J=2.0, 8.6 Hz), 8.20 (1H, d, J=8.6 Hz).

(3) 6-Chloro-3-hydroxymethyl-2-methyl-4-(2-phenylethoxy)-1(2H)-isoquinolinone (synthesized according to the method similar to that in Example 4 (4))

Melting point 170–171° C. Elemental analysis for $C_{19}H_{18}NO_3Cl$ Calculated: C, 66.38; H, 5.28; N, 4.07. Found: C, 66.18; H, 5.20; N, 3.93. $^1$H-NMR(CDCl$_3$) δ: 2.08 (1H, bs), 3.14 (2H, t, J=6.2 Hz), 3.67 (3H, s), 4.08 (2H, t, J=6.2 Hz), 4.59 (2H, d, J=5.8 Hz), 7.26–7.43 (7H, m), 8.27 (1H, d, J=8.4 Hz).

(4) 6-Chloro-3-chloromethyl-2-methyl-4-(2-phenylethoxy)-1(2H)-isoquinolinone (synthesized according to the method similar to that in Example 4 (5))

$^1$H-NMR(CDCl$_3$) δ: 3.19 (2H, t, J=6.4 Hz), 3.69 (3H, s), 4.20 (2H, t, J=6.4 Hz), 4.58 (2H, s), 7.34–7.42 (6H, m), 7.46 (1H, d, J=2.2 Hz), 8.34 (1H, d, J=8.0 Hz).

(5) 2-{(6-Chloro-2-methyl-1-oxo-4-(2-phenylethoxy)-1,2-dihydro-3-isoquinolinyl)methyl}-1H-isoindole-1,3(2H)-dione (synthesized according to the method similar to that in Example 4 (6))

Melting point 219–220° C. Elemental analysis for C$_{27}$H$_{21}$N$_2$O$_4$Cl Calculated: C, 68.57; H, 4.48; N, 5.92. Found: C, 68.29; H, 4.54; N, 5.97. $^1$H-NMR(DMSO-d$_6$) δ: 3.06 (2H, t, J=6.4 Hz), 3.49 (3H, s), 4.14 (2H, t, J=6.4 Hz), 4.96 (2H, s), 7.19–7.30 (6H, m), 7.52 (1H, dd, J=2.2, 8.6 Hz), 7.89 (4H, s), 8.19 (1H, d, J=8.6 Hz).

(6) Tert-butyl(6-chloro-2-methyl-1-oxo-4-(2-phenylethoxy)-1,2-dihydro-3-isoquinolinyl)methylcarbamate (synthesized according to the method similar to that in Example 1 (6))

Melting point 163–164° C. Elemental analysis for C$_{24}$H$_{27}$N$_2$O$_4$Cl Calculated: C, 65.08; H, 6.14; N, 6.32. Found: C, 65.16; H, 6.32; N, 6.15. $^1$H-NMR(CDCl$_3$) δ: 1.47 (9H, s), 3.15 (2H, t, J=6.4 Hz), 3.59 (3H, s), 4.04 (2H, t, J=6.4 Hz), 4.34 (2H, d, J=6.0 Hz), 4.60 (1H, bs), 7.27–7.41 (7H, m), 8.29 (1H, d, J=8.8 Hz).

(7) 3-(Aminomethyl)-6-chloro-2-methyl-4-(2-phenylethoxy)-1(2H)-isoquinolinone hydrochloride (synthesized according to the method similar to that in Example 1 (7))

Melting point 200–201° C. Elemental analysis for C$_{19}$H$_{20}$N$_2$O$_2$Cl$_2$ ¾H$_2$O Calculated: C, 58.10; H, 5.52; N, 7.13. Found: C, 58.23; H, 5.77; N, 7.11. $^1$H-NMR(DMSO-d$_6$) δ: 3.16 (2H, t, J=6.4 Hz), 3.58 (3H, s), 4.11 (2H, t, J=6.4 Hz), 4.25 (2H, d, J=5.6 Hz), 7.21 (1H, d, J=2.0 Hz), 7.29–7.45 (5H, m), 7.58 (1H, dd, J=2.0, 8.6 Hz), 8.22 (1H, d, J=8.6 Hz), 8.68 (3H, bs).

Example 11

3-(Aminomethyl)-6-chloro-2-methyl-4-(1-naphthylmethoxy)-1(2H)-isoquinolinone hydrochloride (1) Ethyl 6-chloro-2-methyl-4-(1-naphthylmethoxy)-1-oxo-1,2-dihydro-3-isoquinolinecarboxylate (synthesized according to the method similar to that in Example 1 (2))

Melting point 158–159° C. Elemental analysis for C$_{24}$H$_{20}$NO$_4$Cl Calculated: C, 68.33; H, 4.78; N, 3.32. Found: C, 68.25; H, 4.559; N, 3.21. $^1$H-NMR(CDCl$_3$) δ: 1.24 (3H, t, J=7.2 Hz), 3.53 (3H, s), 4.19 (2H, q, J=7.2 Hz), 5.50 (2H, s), 7.45–7.63 (5H, m), 7.68 (1H, d, J=2.2 Hz), 7.87–7.95 (2H, m), 8.09–8.14 (1H, m), 8.39 (1H, d, J=8.4 Hz).

(2) 6-Chloro-2-methyl-4-(1-naphthylmethoxy)-1-oxo-1,2-dihydro-3-isoquinolinecarboxylic acid (synthesized according to the method similar to that in Example 4 (3))

Melting point 166–167° C. Elemental analysis for C$_{22}$H$_{16}$NO$_4$Cl Calculated: C, 67.10; H, 4.10; N, 3.56. Found: C, 66.93; H, 3.95; N, 3.49. $^1$H-NMR(DMSO-d$_6$) δ: 3.50 (3H, s), 5.49 (2H, s), 7.51–7.68 (6H, m), 7.96–8.04 (2H, m), 8.20–8.28 (2H, m).

(3) 6-Chloro-3-hydroxymethyl-2-methyl-4-(1-naphthylmethoxy)-1(2H)-isoquinolinone (synthesized according to the method similar to that in Example 4 (4))

Melting point 202–203° C. Elemental analysis for C$_{22}$H$_{18}$NO$_3$Cl Calculated: C, 69.57; H, 4.78; N, 3.69. Found: C, 69.18; H, 5.11; N, 3.61. $^1$H-NMR(DMSO-d$_6$) δ: 3.64 (3H, s), 4.63 (2H, d, J=5.0 Hz), 5.47 (2H, s), 5.59 (1H, t, J=5.0 Hz), 7.50–7.69 (6H, m) 7.96–8.04 (2H, m), 8.21–8.25 (2H, m).

(4) 6-Chloro-3-chloromethyl-2-methyl-4-(1-naphthylmethoxy)-1(2H)-isoquinolinone (synthesized according to the method similar to that in Example 4 (5))

$^1$H-NMR(CDCl$_3$) δ: 3.72 (3H, s), 4.67 (2H, s), 5.52 (2H, s), 7.45–7.67 (6H, m), 7.71 (1H, d, J=1.8 Hz), 7.89–7.97 (2H, m), 8.16 (1H, d, J=8.0 Hz), 8.39 (1H, d, J=8.4 Hz).

(5) 2-{(6-Chloro-2-methyl-4-(1-naphthylmethoxy)-1-oxo-1,2-dihydro-3-isoquinolinyl)methyl}-1H-isoindole-1,3(2H)-dione (synthesized according to the method similar to that in Example 4 (6))

Melting point 211–212° C. $^1$H-NMR(DMSO-d$_6$) δ: 3.49 (3H, s), 5.09 (2H, s), 5.58 (2H, s), 7.45–7.68 (6H, m), 7.84 (4H, s), 7.91–8.01 (2H, m) 8.14–8.19 (1H, m), 8.23 (1H, d J=8.8 Hz).

(6) Tert-butyl(6-chloro-2-methyl-4-(1-naphthylmethoxy)-1-oxo-1,2-dihydro-3-isoquinolinyl)methylcarbamate (synthesized according to the method similar to that in Example 1 (6))

Melting point 205–206° C. Elemental analysis for C$_{27}$H$_{27}$N$_2$O$_4$Cl Calculated: C, 67.71; H, 5.68; N, 5.85. Found: C, 67.50; H, 5.90; N, 5.70. $^1$H-NMR(CDCl$_3$) δ: 1.37 (9H, s), 3.14 (1H, bs), 3.45 (3H, s), 4.02 (2H, d, J=6.2 Hz), 5.44 (2H, s), 7.29 (1H, d, J=7.2 Hz), 7.41–7.51 (2H, m), 7.72 (1H, d, J=2.0 Hz), 7.55–7.69 (2H, m), 7.81 (1H, d, J=1.8 Hz), 7.91–7.95 (2H, m), 8.24 (1H, d, J=8.2 Hz), 8.39 (1H, d, J=8.8 Hz).

(7) 3-(Aminomethyl)-6-chloro-2-methyl-4(1-naphthylmethoxy)-1(2H)-isoquinolinone hydrochloride (synthesized according to the method similar to that in Example 1 (7))

Melting point 226–227° C. Elemental analysis for C$_{22}$H$_{20}$N$_2$O$_2$Cl$_2$ ¼H$_2$O Calculated C, 62.94; H, 4.92; N, 6.67. Found: C, 63.01; H, 4.79; N, 6.59. $^1$H-NMR(DMSO-d$_6$) δ: 3.65 (3H, s), 4.29 (2H, d, J=4.2 Hz), 5.55 (2H, s), 7.52–7.78 (6H, m), 7.98–8.06 (2H, m), 8.22–8.30 (2H, m), 8.81 (3H, bs).

Example 12

3-(Aminomethyl)-7-chloro-2-methyl-4-phenyl-1(2H)-isoquinolinone hydrochloride (1) To a solution of ethyl 7-chloro-4-hydroxy-2-methyl-1-oxo-1,2-dihydro-3-isoquinolinecarboxylate (synthesized according to the method similar to that in Example 5 (1)) (2.82 g, 10 mmol) in tetrahydrofuran (20 ml) was added sodium hydride (0.48 g, 12 mmol)(60% in oil) at 0° C. and the mixture was stirred at 0° C. for 30 min. To the obtained mixture was added N-phenyltrifluoromethane sulfonimide (4.29 g, 12 mmol) and the mixture was stirred at room temperature for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give ethyl 7-chloro-2-methyl-1-oxo-4-trifluoromethane-sulfonyloxy-1,2-dihydro-3-isoquinolinecarboxylate (2.95 g, 71.4%) as an oil.

$^1$H-NMR(CDCl$_3$) δ: 1.45 (3H, d, J=7.2 Hz), 3.61 (3H, s), 4.49 (2H, q, J=7.2 Hz), 7.75–7.76 (2H, m), 8.44–8.45 (1H, m).

(2) A mixture of ethyl 7-chloro-2-methyl-1-oxo-4-trifluoromethanesulfonyloxy-1,2-dihydro-3-isoquinolinecarboxylate (2.90 g, 7 mmol), phenylboronic acid (1.02 g, 8.4 mmol)

and sodium carbonate (1.85 g, 17.5 mmol) in toluene (20 ml), ethanol (4 ml) and water (4 ml) was stirred under an argon atmosphere at room temperature for 30 min. To the obtained mixture was added tetrakis(triphenylphosphine)palladium (0.46. g, 4 mmol) and the mixture was refluxed under heating under an argon atmosphere for 12 h. The reaction mixture was poured into water and extracted with ethyl acetate. After washing the extract with water, the extract was dried over anhydrous magnesium sulfate and concentrated under reduced pressure. The residue was purified by silica gel column chromatography to give ethyl 7-chloro-2-methyl-1-oxo-4-phenyl-1,2-dihydro-3-isoquinolinecarboxylate (1.70 g, 71.1%) as crystals.

Melting point 152–153° C. $^1$H-NMR(CDCl$_3$) δ: 0.92 (3H, t, J=7.1 Hz), 3.62 (3H, s), 4.02 (2H, q, J=7.1 Hz), 7.17 (1H, dd, J=8.8 Hz), 7.28–7.33 (2H, m), 7.41–7.53 (4H, m), 8.48 (1H, d, J=2.2 Hz).

(3) 7-Chloro-2-methyl-1-oxo-4-phenyl-1,2-dihydro-3-isoquinolinecarboxylic acid (synthesized according to the method similar to that in Example 4 (3))

Melting point 261–262° C. $^1$H-NMR(CDCl$_3$) δ: 3.68 (3H, s), 7.13 (1H, d, J=8.8 Hz), 7.32–7.51 (6H, m), 8.45 (1H, d, J=2.2 Hz).

(4) 7-Chloro-3-hydroxymethyl-2-methyl-4-phenyl-1(2H)-isoquinolinone (synthesized according to the method similar to that in Example 4 (4))

Melting point 199–200° C. Elemental analysis for $C_{17}H_{14}NO_2Cl$ Calculated: C, 68.12; H, 4.71; N, 4.67. Found: C, 68.25; H, 4.71; N, 4.49. $^1$H-NMR(CDCl$_3$) δ: 2.17 (1H, t, J=5.5 Hz), 3.82 (3H, s), 4.40 (2H, d, J=5.5 Hz), 6.96 (1H, d, J=8.8 Hz), 7.26–7.33 (2H, m), 7.39 (1H, dd, J=2.2, 8.8 Hz), 7.45–7.54 (3H, m), 8.39 (1H, d, J=2.2 Hz).

(5) 7-Chloro-3-chloromethyl-2-methyl-4-phenyl-1(2H)-isoquinolinone (synthesized according to the method similar to that in Example 4 (5))

$^1$H-NMR(CDCl$_3$) δ: 3.84 (3H,), 4.40 (2H, s), 6.99 (1H, d, J=8.4 Hz), 7.31–7.35 (2H, m), 7.42–7.56 (4H, m), 8.47 (1H, d, J=2.2 Hz).

(6) 2-{(7-Chloro-2-methyl-1-oxo-4-phenyl-1,2-dihydro-3-isoquinolinyl)methyl}-1H-isoindole-1,3(2H)-dione (synthesized according to the method similar to that in Example 4 (6))

Melting point 241–242° C. Elemental analysis for $C_{25}H_{17}N_2O_3Cl$ Calculated: C, 70.01; H, 4.00; N, 6.53. Found: C, 69.69; H, 4.13; N, 6.56. $^1$H-NMR(DMSO-d$_6$) δ: 3.61 (3H, s), 4.76 (2H, s), 6.89 (1H, d, J=8.8 Hz), 7.26–7.31 (2H, m), 7.40–7.43 (3H, m), 7.66 (1H, dd, J=2.2, 8.8 Hz), 7.74–7.83 (4H, m), 8.23 (1H, d, J=2.2 Hz).

(7) 3-(Aminomethyl)-7-chloro-2-methyl-4-phenyl-1(2H)-isoquinolinone hydrochloride (synthesized according to the method similar to that in Example 4 (7))

Melting point 242–243° C. Elemental analysis for $C_{17}H_{16}N_2OCl_2$ ½$H_2O$ Calculated: C, 59.31; H, 4.98; N, 8.14. Found: C, 59.50; H, 4.97; N, 8.14. $^1$H-NMR(DMSO-d$_6$) δ: 3.72 (3H, s), 3.93 (2H, s), 6.94 (1H, d, J=8.6 Hz), 7.37–7.41 (2H, m), 7.56–7.59 (3H, m), 7.72 (1H, dd, J=2.4, 8.6 Hz), 8.27 (1H, d, J=2.4 Hz), 8.65 (3H, bs).

Example 13

3-(Aminomethyl)-6-chloro-2-methyl-4-propoxy-1(2H)-isoquinolinone hydrochloride (1) Ethyl 6-chloro-2-methyl-4-propoxy-1-oxo-1,2-dihydro-3-isoquinolinecarboxylate (synthesized according to the method similar to that in Example 1 (2))

$^1$H-NMR(CDCl$_3$) δ: 1.08 (3H, t, J=7.3 Hz), 1.45 (3H, t, J=7.2 Hz), 1.76–1.89 (2H, m), 3.51 (3H, s), 3.93 (2H, t, J=6.6 Hz), 4.48. (2H, q, J=7.2 Hz), 7.49 (1H, dd, J=2.0, 8.6 Hz), 7.71 (1H, d, J=2.0 Hz), 8.37 (1H, d, J=8.6 Hz).

(2) 6-Chloro-2-methyl-1-oxo-4-propoxy-1,2-dihydro-3-isoquinolinecarboxylic acid (synthesized according to the method similar to that in Example 4 (3))

Melting point 1.64–165° C. Elemental analysis for $C_{14}H_{14}NO_4Cl$ Calculated: C, 56.86; H, 4.77; N, 4.74. Found: C, 56.82; H, 4.70; N, 4.52. $^1$H-NMR(CDCl$_3$) δ: 1.08 (3H, t, J=7.3 Hz), 1.77–1.95 (2H, m), 3.65 (3H, s), 3.97 (2H, t, J=6.6 Hz), 7.51 (1H, dd, J=2.0, 8.6 Hz), 7.64 (1H, d, J=2.0 Hz), 7.67 (1H, bs), 8.31 (1H, d, J=8.6 Hz).

(3) 6-Chloro-3-hydroxymethyl-2-methyl-4-propoxy-1(2H)-isoquinolinone (synthesized according to the method similar to that in Example 4 (4))

Melting point 95.5–96.5° C. Elemental analysis for $C_{14}H_{16}NO_3Cl$ Calculated: C, 59.68; H, 5.72; N, 4.97. Found: C, 59.38; H, 5.69; N, 4.87. $^1$H-NMR(CDCl$_3$) δ: 1.14 (3H, t, J=7.3 Hz), 1.79–1.93 (2H, m), 2.89 (1H, bs), 3.69 (3H, s), 3.79 (2H, t, J=6.6 Hz), 4.79 (2H, d, J=4.8 Hz), 7.39 (1H, dd, J=2.0, 8.6 Hz), 7.55 (1H, d, J=2.0 Hz), 8.24 (1H, dd, J=3.8, 8.6 Hz).

(4) 6-Chloro-3-chloromethyl-2-methyl-4-propoxy-1(2H)-isoquinolinone (synthesized according to the method similar to that in Example 4 (5))

$^1$H-NMR(CDCl$_3$) δ: 1.16 (3H, t, J=7.3 Hz), 1.86–2.00 (2H, m), 3.73 (3H, s), 3.95 (2H, t, J=6.6 Hz), 4.80 (2H, s), 7.48 (1H, dd, J=2.0, 8.6 Hz), 7.71 (1H, d, J=2.0 Hz), 8.38 (1H, d, J=8.6 Hz).

(5) 2-{(6-Chloro-2-methyl-4-propoxy-1-oxo-1,2-dihydro-3-isoquinolinyl)methyl}-1H-isoindole-1,3(2H)-dione (synthesized according to the method similar to that in Example 4 (6))

Melting point 193–194° C. Elemental analysis for $C_{22}H_{19}N_2O_4Cl$ Calculated: C, 64.31; H, 4.66; N, 6.82. Found: C, 63.96; H, 4.51; N, 6.48. $^1$H-NMR(DMSO-d$_6$) δ: 1.00 (3H, t, J=7.4 Hz), 1.72–1.86 (2H, m), 3.51 (3H, s), 3.90 (2H, t, J=6.7 Hz), 5.03 (2H, s), 7.59 (1H, dd, J=1.8, 8.4 Hz), 7.68 (1H, d, J=1.8 Hz), 7.86 (4H, s), 8.24 (1H, d, J=8.4 Hz).

(6) Tert-butyl(6-chloro-2-methyl-4-propoxy-1-oxo-1,2-dihydro-3-isoquinolinyl)methylcarbamate (synthesized according to the method similar to that in Example 1 (6))

Melting point 104–105° C. Elemental analysis for $C_{19}H_{25}N_2O_4Cl$ Calculated: C, 59.92; H, 6.62; N, 7.36. Found: C, 59.87; H, 6.34; N, 7.23. $^1$H-NMR(CDCl$_3$) δ: 1.13 (3H, t, J=7.4 Hz), 1.47 (9H, s), 1.85–1.96 (2H, m), 3.62 (3H, s), 3.80 (2H, t, J=6.6 Hz), 4.53 (2H, d, J=6.0 Hz), 4.77 (1H, bs), 7.43 (1H, dd, J=2.0, 8.6 Hz), 7.65 (1H, d, J=2.0 Hz), 8.33 (1H, d, J=8.6 Hz).

(7) 3-(Aminomethyl)-6-chloro-2-methyl-4-propoxy-1(2H)-isoquinolinone hydrochloride (synthesized according to the method similar to that in Example 1 (7))

Melting point 226–227° C. Elemental analysis for $C_{14}H_{18}N_2O_2Cl_2$ ½$H_2O$ Calculated: C, 51.55; H, 5.87; N 8.59. Found: C, 51.61; H, 6.13; N, 8.44. $^1$H-NMR(DMSO-d$_6$) δ: 1.09 (3H, t, J=7.4 Hz), 1.79–1.93 (2H, m), 3.39 (3H, s), 3.88 (2H, t, J=6.4 Hz), 4.24 (2H, s), 7.66 (1H, dd, J=2.0, 8.6 Hz), 7.74 (1H, d, J=2.0 Hz), 8.28 (1H, d, J=8.6 Hz), 8.78 (3H, bs).

Example 14

3-(Aminomethyl)-6-chloro-4-cyclopentylmethoxy-2-methyl-1(2H)-isoquinolinone hydrochloride (1) Ethyl 6-chloro-4-cyclopentylmethoxy-2-methyl-1-oxo-1,2-dihydro-3-isoquinolinecarboxylate (synthesized according to the method similar to that in Example 1 (2))

Melting point 89–90° C. Elemental analysis for $C_{19}H_{22}NO_4Cl$ ¼$H_2O$ Calculated: C, 61.96; H, 6.15; N, 3.80. Found: C, 61.91; H, 6.03; N, 3.93. $^1$H-NMR(CDCl$_3$) δ: 1.33–1.43 (2H, m), 1.45 (3H, t, J=7.2 Hz), 1.61–1.72 (4H, m), 1.89–1.93 (2H, m), 2.32–2.47 (1H, m), 3.51 (3H, s), 3.85 (2H, d, J=6.8 Hz), 4.47 (2H, q, J=7.2 Hz), 7.50 (1H, dd, J=2.0, 8.6 Hz), 7.72 (1H, d, J=2.0 Hz), 8.37 (1H, d, J=8.6 Hz).

(2) 6-Chloro-4-cyclopentylmethoxy-2-methyl-1-oxo-1,2-dihydro-3-isoquinolinecarboxylic acid (synthesized according to the method similar to that in Example 4 (3))

Melting point 191–192° C. Elemental analysis for $C_{17}H_{18}NO_4Cl$ ¼$H_2O$ Calculated: C, 60.00; H, 5.48; N, 4.12. Found: C, 60.20; H, 5.28; N, 4.09. $^1$H-NMR(DMSO-d$_6$) δ: 1.33–1.46 (2H, m), 1.58–1.60 (4H, m), 1.71–1.86 (2H, m), 2.30–2.45 (1H, m), 3.43 (3H, s), 3.82 (2H, d, J=6.8 Hz), 7.65 (1H, dd, J=2.0, 8.6 Hz), 7.71 (1H, d, J=2.0 Hz), 8.26 (1H, d, J=8.6 Hz)

(3) 6-Chloro-4-cyclopentylmethoxy-3-hydroxymethyl-2-methyl-1(2H)-isoquinolinone (synthesized according to the method similar to that in Example 4 (4))

Melting point 127–128° C. Elemental analysis for $C_{17}H_{20}NO_3Cl$ ¼$H_2O$ Calculated: C, 62.57; H, 6.33; N, 4.29. Found: C, 62.61; H, 6.21; N, 4.23. $^1$H-NMR(CDCl$_3$) δ: 1.35–1.51 (2H, m), 1.61–1.74 (4H, m), 1.84–1.97 (2H, m), 2.36–2.51 (1H, m), 3.71 (5H, s), 4.81 (2H, d, J=5.0 Hz), 7.40 (1H, dd, J=2.0, 8.6 Hz), 7.60 (1H, d, J=2.0 Hz), 8.28 (1H, d, J=8.6 Hz).

(4) 6-Chloro-3-chloromethyl-4-cyclopentylmethoxy-2-methyl-1(2H)-isoquinolinone (synthesized according to the method similar to that in Example 4 (5))

$^1$H-NMR(CDCl$_3$) δ: 1.36–1.71 (6H, m), 1.85–1.97 (2H, m), 2.37–2.57 (1H, m), 3.73 (3H, s), 3.87 (2H, d, J=7.0 Hz), 4.80 (2H,), 7.48 (1H, dd, J=2.2, 8.8 Hz), 7.72 (1H, d, J=2.2 Hz), 8.37 (1H, d, J=8.8 Hz).

(5) 2-{(6-Chloro-4-cyclopentylmethoxy-2-methyl-1-oxo-1,2-dihydro-3-isoquinolinyl)methyl}-1H-isoindole-1,3(2H)-dione (synthesized according to the method similar to that in Example 4 (6))

Melting point 204–205° C. Elemental analysis for $C_{25}H_{23}N_2O_4Cl$ 3/4$H_2O$ Calculated: C, 64.65; H, 5.32; N, 6.03. Found: C, 64.85; H, 5.08; N, 6.09. $^1$H-NMR(DMSO-d$_6$) δ: 1.23–1.63 (6H,m), 1.72–1.84 (2H, m), 2.33–2.46 (1H, m), 3.48 (3H, s), 3.83 (2H, d, J=6.8 Hz), 7.59 (1H, dd, J=2.0, 8.6 Hz), 7.68. (1H, d, J=2.0 Hz), 7.82–7.91 (4H, m), 8.37(1H, d, J=8.8 Hz).

(6) Tert-butyl(6-chloro-4-cyclopentylmethoxy-2-methyl-1-oxo-1,2-dihydro-3-isoquinolinyl)methylcarbamate (synthesized according to the method similar to that in Example 1 (6))

Melting point 161–162° C. Elemental analysis for $C_{22}H_{29}N_2O_4Cl$ Calculated: C, 62.77; H, 6.94; N, 6.66. Found: C, 62.49; H, 7.15; N, 6.60. $^1$H-NMR(CDCl$_3$) δ: 1.26–1.44 (2H, m), 1.47 (9H, s), 1.60–1.71 (4H, m), 1.87–1.99 (2H, m), 2.38–2.53 (1H,m), 3.62 (3H, s), 3.72 (2H, d, J=6.8 Hz), 4.53 (2H, d, J=5.8 Hz), 7.43 (1H, dd, J=1.8, 8.6 Hz), 7.66 (1H, d, J=1.8 Hz), 8.33 (1H, d, J=8.6 Hz).

(7) 3-(Aminomethyl)-6-chloro-4-cyclopentylmethoxy-2-methyl-1(2H)-isoquinolinone hydrochloride (synthesized according to the method similar to that in Example 1 (7))

Melting point 211–219° C. Elemental analysis for $C_{17}H_{22}N_2O_2Cl_2$ ½$H_2O$ Calculated: C,55.74; H, 6.33; N, 7.65. Found: C, 55.75; H 6.32; N, 7.69. $^1$H-NMR(DMSO-d$_6$) δ: 1.37–1.68 (6H, m), 1.81–1.93 (2H, m), 2.39–2.54 (1H, m), 3.61 (3H, s), 3.80 (2H, d, J=6.8 Hz), 4.24 (2H, d, J=5.2.Hz), 7.65 (1H, dd, J=2.0, 8.4 Hz), 7.72 (1H, d, J=2.0 Hz), 8.28 (1H, d, J=8.4 Hz), 8.77 (3H, bs).

Example 15

3-(Aminomethyl)-6-chloro-2-methyl-4-(4-nitrophenoxy)-1(2H)-isoquinolinone hydrochloride (1) Ethyl 6-chloro-2-methyl-4-(4-nitrophenoxy)-1-oxo-1,2-dihydro-3-isoquinolinecarboxylate (synthesized according to the method similar to that in Example 4 (2))

Melting point 184–185° C. Elemental analysis for $C_{19}H_{15}N_2O_6Cl$ ¼$H_2O$ Calculated: C, 56.66; H, 3.75; N, 6.95. Found: C, 56.70; H, 3.85; N, 6.81. $^1$H-NMR(CDCl$_3$) δ: 1.12 (3H, t, J=7.2 Hz), 3.60 (3H, s), 4.28 (2H, q, J=7.2 Hz), 7.05 (2H, d, J=9.2 Hz), 7.35 (1H, d, J=2.0 Hz), 7.55 (1H, dd, J=2.0, 8.8 Hz), 8.24 (2H, d, J=9.2 Hz), 8.44 (1H, d, J=8.8 Hz).

(2) 6-Chloro-2-methyl-4-(4-nitrophenoxy)-1-oxo-1,2-dihydro-3-isoquinolinecarboxylic acid (synthesized according to the method similar to that in Example 4 (3)).

Melting point 240–241° C. Elemental analysis for $C_{17}H_{11}N_2O_6Cl$ ½AcOEt Calculated: C, 54.49; H, 3.61; N, 6.69. Found: C, 54.63; H, 3.64; N, 6.69. $^1$H-NMR(CDCl$_3$) δ: 3.51 (3H, s), 7.28 (2H, d, J=9.2 Hz), 7.36 (1H, d, J=2.0 Hz), 7.68 (1H, d, J=2.0, 8.6 Hz), 8.22 (2H, d, J=9.2 Hz), 8.33 (1H, d, J=8.6 Hz).

(3) 6-Chloro-3-hydroxymethyl-2-methyl-4-(4nitrophenoxy)-1(2H)-isoquinolinone (synthesized according to the method similar to that in Example 4 (4))

Melting point 249–250° C. Elemental analysis for $C_{17}H_{13}N_2O_5Cl$ Calculated: C, 56.60; H, 3.63; N, 7.77. Found: C, 56.68; H, 3.83; N, 7.65. $^1$H-NMR(CDCl$_3$) δ: 3.80 (3H, s), 4.35 (1H, bs), 4.64 (2H, d, J=5.2 Hz), 7.07 (2H, d, J=9.1 Hz), 7.32 (1H, d, J2.0 Hz), 7.47 (1H, dd, J=2.0, 8.6 Hz), 8.22 (2H, d, J=9.1 Hz), 8.40 (1H, d, J=8.6 Hz).

(4) 6-Chloro-3-chloromethyl-2-methyl-4-(4-nitrophenoxy)-1(2H)-isoquinolinone (synthesized according to the method similar to that in Example 4 (5))

$^1$H-NMR(CDCl$_3$) δ: 3.79 (3H, s), 4.65 (2H, s), 7.06 (2H, d, J=9.1 Hz), 7.34 (1H, d, J=1.8 Hz), 7.52 (1H, dd, J=1.8, 8.8 Hz), 8.24 (2H, d, J=9.1 Hz), 8.44 (1H, d, J=8.8 Hz).

(5) 2-{(6-Chloro-2-methyl-4-(4-nitrophenoxy)-1-oxo-1,2-dihydro-3-isoquinolinyl)methyl}-1H-isoindole-1,3(2H)-dione (synthesized according to the method similar to that in Example 4(6))

Melting point 257–258° C. Elemental analysis for $C_{25}H_{16}N_3O_6Cl$ Calculated: C, 61.30; H, 3.29; N, 8.58. Found: C, 61.10; H, 3.38; N, 8.41. $^1$H-NMR(DMSO-d$_6$) δ: 3.81 (3H, s), 4.94 (2H, s), 6.92 (2H, d, J=9.4 Hz), 7.24 (1H, d, J=1.8 Hz), 7.60–7.72 :(5H, m), 7.88 (2H, d, J=9.4 Hz), 8.33 (1H, d, J=8.4 Hz).

(6) Tert-butyl[6-chloro-2-methyl-4-(4-nitrophenoxy)-1-oxo-1,2-dihydro-3-isoquinolinyl]methylcarbamate (synthesized according to the method similar to that in Example 1 (6))

Melting point 198–199° C. Elemental analysis for $C_{22}H_{22}N_3O_6Cl$ Calculated: C, 57.46; H, 4.82; N, 9.14. Found: C, 57.44; H, 4.80; N, 9.25. $^1$H-NMR(:CDCl$_3$) δ: 1.41

(9H, s), 3.70 (3H, s), 4.41 (2H, d, J=5.8 Hz), 4.64 (1H, bs), 7.03 (2H, d, J=9.4 Hz), 7.29 (1H, d, J=2.0 Hz), 7.48 (1H, d, J=2.0, 8.6 Hz), 8.24 (2H, d, J=9.4 Hz), 8.40 (1H, d, J=8.6 Hz).

(7) 3-(Aminomethyl)-6-chloro-2-methyl-4-(4nitrophenoxy)-1(2H)-isoquinolinone hydrochloride (synthesized according to the method similar to that in Example 1 (7))

Melting point 242–243° C. Elemental analysis for $C_{17}H_{15}N_3O_4Cl_2$ ¼$H_2O$ Calculated: C, 50.95; H, 3.90; N, 10.49. Found: C, 51.05; H, 3.92; N, 10.23. $^1$H-NMR (DMSO-$d_6$) δ: 3.68 (3H, s), 4.08 (2H, bs), 7.35 (2H, d, J=9.4 Hz), 7.38 (1H, d, J=2.0 Hz), 7.68 (1H, d, J=2.0, 8.6 Hz), 8.26 (2H, d, J=9.4 Hz), 8.34 (1H, d, J=8.6 Hz), 8.83 (3H, bs).

Example 16

3-(Aminomethyl)-6-Chloro-4-methoxyphenyl)-2-methyl-1(2H)-isoquinolinone hydrochloride (1) To a solution of ethyl 6-Chloro-4-hydroxy-2-methyl-1-oxo-1,2-dihydro-3-isoquinolinecarboxylate (synthesized according to the method similar to that in Example 5 (1)) (8.45 g, 30 mmol) in tetrahydrofuran (100 ml) was added sodium hydride (1.44 g, 36 mmol)(60% in oil) at 0° C. and the mixture was stirred at 0° C. for 30 min. To the obtained mixture was added N-phenyltrifluoromethane sulfonimide (12.86 g, 36 mmol) and the mixture was stirred at room temperature for 2 h. The reaction mixture was poured, into water and extracted with ethyl acetate. After washing the extract with water, the extract was dried over anhydrous-magnesium sulfate and concentrated under reduced pressure. The residue was purified by silica gel column chromatography to give ethyl 6-chloro-2-methyl-1-oxo-4-trifluoromethane-sulfonyloxy-1,2-dihydro-3-isoquinolinecarboxylate (8.54 g, 68.8%) as crystals.

$^1$H-NMR(CDCl$_3$) δ: 1.45 (3H, t, J=7.0 Hz), 3.60 (3H, s), 4.49 (2H, q, J=7.0 Hz), 7.60 (1H, dd, J=2.0, 8.6 Hz), 7.75 (1H, d, J=2.0 Hz), 8.40 (1H, d, J=8. 6 Hz). (2) Ethyl 6-chloro-4-(4-methoxyphenyl)-2-methyl-1-oxo-1,2-dihydro-3-isoquinolinecarboxylate (synthesized according to the method similar to that in Example 12 (2))

Melting point 135–136° C. Elemental analysis for $C_{20}H_{18}NO_4Cl$ Calculated: C, 64.61; H, 4.88; N, 3.77. Found: C, 64.81; H, 4.87; N, 3.57. $^1$H-NMR(CDCl$_3$) δ: 1.00 (3H, t, J=7.2 Hz), 3.59 (3H, s), 3.88 (3H, s), 4.07 (2H, q, J=7.2 Hz), 6.98 (2H, d, J=8.8 Hz), 7.232 (2H, d, J=8.8 Hz), 7.24 (1H, d, J=2.0 Hz), 7.47 (1H, d, J=2.0, 8.6 Hz), 8.34 (1H, d, J=8.6 Hz). (3) 6-Chloro-4-(4-methoxyphenyl)-2-methyl-1-oxo-1,2-dihydro-3-isoquinolinecarboxylic acid (synthesized according to the method similar to that in Example 4 (3))

Melting point 242–243° C. Elemental analysis for $C_{16}H_{14}NO_4Cl$ Calculated: C, 62.89; H, 4.10; N, 4.07. Found: C, 63.06; H, 4.18; N, 4.01. $^1$H-NMR(CDCl$_3$) δ: 3.52 (3H, s), 3.83 (3H, s), 7.04 (1H, d, J=2.2 Hz), 7.06 (2H, d, J=8.6 Hz), 7.26(2H, d, J=8.6 Hz), 7.62 (1H, d, J=2.2, 8.6 Hz), 8.32 (1H, d, J=8.6 Hz).

(4) 6-Chloro-4-(4-methoxyphenyl)-3-hydroxymethyl-2methyl-1(2H)-isoquinolinone (synthesized according to the method similar to that in Example 4 (4))

Melting point 187–188° C. Elemental analysis for $C_{18}H_{16}NO_3Cl$ Calculated: C, 65.56; H, 4.89; N, 4.25. Found: C, 65.62; H, 5.04; N, 4.09. $^1$H-NMR(CDCl$_3$) δ: 2.26 (1H, bs), 3.80 (3H,s), 3.90 (3H, s), 4.47 (2H, d, J=5.6 Hz), 7.01–7.06 (3H, m), 7.18–7.25.(3H, m), 7.35 (1H, dd, J=1.8, 8.6 Hz), 8.33 (1H, d, J=8.6 Hz).

(5) 6-Chloro-3-chloromethyl-4-(4-methoxyphenyl-)-2-methyl-1(2H)-isoquinolinone (synthesized according to the method similar to that in Example 4 (5))

$^1$H-NMR(CDCl$_3$) δ: 3.82 (3H, s), 3.91 (3H, s), 4.41 (2H, s), 7.03–7.08 (3H, m), 7.24 (22H, d, J=8.0 Hz), 7.43 (1H, dd, J=2.0, 8.6 Hz), 8.42(1H, d, J=8.6 Hz).

(6) 2-{(6-Chloro-4-(4-methoxyphenyl)-2-methyl-1-oxo-1,2-dihydro-3-isoquinolinyl)methyl}-1H-1,3(2H)-dione (synthesized according to the method similar to that in Example 4 (6))

Melting point 207–208° C. Elemental analysis for $C_{26}H_{19}N_2O_4Cl$ Calculated: C, 68.05; H, 4.17; N, 6.10. Found: C, 68.24; H, 4.25; N, 5.96. $^1$H-NMR(DMSO-$d_6$) δ: 3.58 (3H, s), 3.77 (3H, s), 4.77 (2H, s), 6.83 (1H, d, J=2.0 Hz), 6.98 (2H, d, J=8.8: Hz), 7.20 (2H, d, J=8.8 Hz), 7.55 (1H, dd, J=2.0, 8.6 Hz), 7.75–7.85 (4H, m), 8.29 (1H, d, J=8.6 Hz).

(7) Tert-butyl{6-chloro-4-(4-methoxyphenyl)-2-methyl-1-oxo-1,2-dihydro-3-isoquinolinyl}methylcarbamate (synthesized according to the method similar to that in Example 1 (6))

Melting point 187–188° C. Elemental analysis for $C_{23}H_{25}N_2O_4Cl$ Calculated: C, 64.41; H, 5.88; N, 6.53. Found: C, 64.72; H, 5.96;N, 6.51. $^1$H-NMR(CDCl$_3$) δ: 1.43 (9H, s), 3.69 (3H, s), 3.91 (3H, s), 4.21 (2H, d, J=5.8 Hz), 4.65 (1H, bs), 6.95 (1H, d, J=2.0 Hz), 7.02 (2H, d, J=8.9 Hz), 7.15 (2H, d, J=8.9 Hz), 7.36 (1H, dd, J=2.0, 8.6 Hz), 8.35 (1H, d, J=8.6 Hz).

(8) 3-(Aminomethyl)-6-chloro-4-(4-methoxyphenyl)-2methyl-1(2H)-isoquinolinone hydrochloride (synthesized according to the method similar to that in Example 1: (7))

Melting point 249–250° C. Elemental analysis for $C_{18}H_{18}N_2O_2Cl_2$ Calculated: C, 59.19; H, 4.97; N, 7.67.Found: C, 59.23; H, 4.81; N, 7.30. $^1$H-NMR(DMSO-$d_6$) δ: 3.71 (3H, s), 3.87 (3H, s), 3.95 (2H, bs), 6.88 (1H, d, J=2.0 Hz), 7.14 (2H, d, J=8.8 Hz), 7.32 (2H, d, J=8.8 Hz), 7.62 (1H, dd, J=2.0, 8.6 Hz), 8.33 (1H, d, J=8.6 Hz), 8.66 (3H, bs).

Example 17

3-(Aminomethyl)-6-chloro-4-(3-methoxyphenyl)-2-methyl-1(2H)-isoquinolinone hydrochloride (1) Ethyl 6-chloro-4-(3-methoxyphenyl)-2-methyl-1-oxo-1,2-dihydro-3-isoquinolinecarboxylate (synthesized according to the method similar to that in Example 12 (2))

Melting point 146–147° C. Elemental analysis for $C_{20}H_{18}NO_4Cl$ Calculated: C, 64.61; H, 4.88; N, 3.77. Found: C, 64.55; H, 4.84; N, 3.69. $^1$H-NMR(CDCl$_3$) δ: 0.97 (3H, t, J=7.2 Hz), 3.60 (3H, s), 3.83 (3H, s), 4.06 (2H, q, J=7.2 Hz), 6.84–7.09 (3H, m), 7.23 (1H, d, J=2.0 Hz), 7.37 (1H, t, J=7.91 Hz), 7.47 (1H, dd, J=2.0, 8.6 Hz), 8.44 (1H, d, J=8.6 Hz).

(2) 6-Chloro-4-(3-methoxyphenyl)-2-methyl-1-oxo-1,2-dihydro-3-isoquinolinecarboxylic acid (synthesized according to the method similar to that-in Example 4 (3).

Melting point 212–213° C. Elemental analysis for $C_{18}H_{14}NO_4Cl$ Calculated: C, 62.89; H, 4.10; N, 4.07. Found: C, 63.14; H, 4.22; N, 3.90. $^1$H-NMR(DMSO-$d_6$) δ: 3.52 (3H, s), 3.78 (3H, s), 6.90–6.94 (2H, m), 7.03–7.07. (2H, m), 7.44 (1H, t, J=8.1 Hz), 7.62 (1H, dd, J=2.0, 8.6 Hz), 8.32 (1H, d, J=8.6 Hz)

(3) 6-Chloro-4-(3-methoxyphenyl)-3-hydroxymethyl-2methyl-1(2H)-isoquinolinone (synthesized according to the method similar to that in Example 4 (4))

Melting point 127–128° C. Elemental analysis for $C_{18}H_{16}NO_3Cl$ Calculated: C, 65.56; H, 4.89; N, 4.25. Found: C, 65.72; H, 5.14; N, 4.04. $^1$H-NMR(CDCl$_3$) δ: 2.00 (1H, bs), 3.81 (3H, s), 3.86 (3H, s), 4.47 (2H, s), 6.82–6.89 (2H, m), 6.99–7.04 (2H, m), 7.38 (1H, dd, J=2.1, 8.6 Hz), 7.43 (1H, t, J=7.9 Hz), 8.37 (1H, d, J=8.6 Hz).

(4) 6-Chloro-3-chloromethyl-4-(3-methoxyphenyl)-2-methyl-1 (2H)-isoquinolinone (synthesized according to the method similar to that in Example 4 (5))

$^1$H-NMR(CDCl$_3$) δ: 3.82 (3H, s), 3.86 (3H, s), 4.40 (2H, s), 6.88–6.92 (1H, m), 7.01–7.07 (2H, m), 7.44 (1H, dd, J=2.0, 8.6 Hz), 7.45(1H, t, J=8.0 Hz), 8.42 (1H, d, J=8.6 Hz).

(5) 2-{(6-Chloro-4-(3-methoxyphenyl)-2-methyl-1-oxo-1,2-dihydro- 3-isoquinolinyl)methyl}-1H-isoindole-1,3 (2H)-dione (synthesized according to the method similar to that in Example 4 (6))

Melting point 184–185° C. Elemental analysis for $C_{26}H_{19}N_2O_4Cl$ Calculated: C, 68.05; H, 4.17; N, 6.10. Found: C, 67.69; H 4.40; N, 5.82. $^1$H-NMR(DMSO-d$_6$) δ: 3.61 (3H, s), 3.63 (3H, s), 4.78 (2H, s), 6.08–6.84 (3H, m), 6.90–6.95 (1H, m), 7.33 (1H, t, J=8.1 Hz), 7.55 (1H, dd, J=2.0, 8.6 Hz), 7.74–7.84 (4H, m), 8.30 (1H, d, J=8.6 Hz).

(6) Tert-butyl{6-chloro-4.4(3-methoxyphenyl)-2-methyl-1-oxo-1,2-dihydro-3-isoquinolinyl}methylcarbamate (synthesized according to the method similar to that in Example 1 (6))

Melting point 231–232° C. Elemental analysis for $C_{23}H_{25}N_2O_4Cl$ Calculated: C, 64.41; H, 5.88; N, 6.53. Found: C, 64.25; H, 5.49; N,6.34. $^1$H-NMR(CDCl$_3$) δ: 1.43 (9H, s), 3.70 (3H, s), 3.86 (3H, s), 4.21–4.23 (2H, m), 4.60, (1H, bs), 6.77–6.84 (2H,m), 6.96 (1H, d, J=1.8 Hz), 6.99–7.05 (1H, m), 7.35–7.48 (2H, m), 8.37 (1H, d, J=8.8 Hz).

(7) 3-(Aminomethyl)-6-chloro-4-(3-methoxyphenyl)-2-methyl-1(2H)-isoquinolinone hydrochloride (synthesized according to the method similar to that in Example 1 (7))

Melting point. 237–238° C. Elemental analysis for $C_{18}H_{18}N_2O_2Cl_2$ ½H$_2$O Calculated: C, 5.77; H, 5.12; N, 7.67. Found: C, 57.62; H, 5.23; N, 7.40. $^1$H-NMR(DMSO-d$_6$) δ: 3.71 (3H, s), 3.82 (3H, s), 3.92–3.98 (2H, m), 6.87 (1H, d, J=2.0 Hz), 6.94 (1H, d, J=7.5 Hz), 7.01 (1H, bs), 7.11 (1H, dd, J=2.6, 8.1 Hz), 7.51 (1H, dd, J=7.5, 8.1 Hz), 7.62 (1H, dd, J=2.0, 8.6 Hz), 8.33 (11H, d, J=8.6 Hz), 8.63 (3H, bs).

Example 18

3-(Aminomethyl)-6-chloro-4-(4-hydroxyphenyl)-2-methyl-1(2H)-isoquinolinone hydrochloride (1) To a solution of 2-{[6-chloro-4-(4-methoxyphenyl)-2-methyl-1-oxo-1,2-dihydro-3-isoquinolinyl]methyl}-1H-isoindole-1,3(2H)-dione (synthesized according to the method similar to that in Example 16(7)) (0.92 g, 2 mmol) in dichloromethane (10 ml) was added boron tribromide, (76 ml, 36 mmol) at 0° C. and the mixture was stirred at 0° C. for 1 h. The reaction mixture was poured into water and extracted with ethyl acetate. After washing the extract with water, the extract was dried over anhydrous magnesium sulfate and concentrated under reduced pressure. The residue was recrystallized from tetrahydrofuran-diisopropyl ether to give 2-{[6chloro-4-(4-hydroxyphenyl)-2-methyl-1-oxo-1,2-dihydro-3-isoquinolinyl]methyl}-1H-isoindole-1,3 (2H)-dione (0.83 g, 94.3%) as crystals.

Melting point 307–308° C. Elemental analysis for $C_{25}H_{17}N_2O_4Cl$ H$_2$O Calculated: C, 64.87; H, 4.14.; N, 6.05. Found: C, 64,44; H, 3.88; N, 5.66. $^1$H-NMR(DMSO-d$_6$) δ: 3.67 (3H, s), 4.76 (2H, s), 6.81. (2H, d, J=8.6 Hz), 6.86 (1H, d, J=2.0 Hz), 7.08 (2H, d, J=8.6 2,5 Hz), 7.54 (H, dd, J=2.0, 8.6 Hz), 7.75–7.85 (4H, m), 8.28 (1H, dd, J=8.6 Hz), 9.60 (1H, s).

(2) Tert-butyl 4-{3-{{(tertbutoxycarbonyl) amino}methyl}-6-chloro-2-methyl-1-oxo-1,2-dihydro-3-isoquinolinyl}phenylcarbonate (synthesized according to the method similar to that in Example 1 (6))

Melting point 195–196° C. Elemental analysis for $C_{27}H_{31}N_2O_6Cl$ Calculated: C, 62.97; H, 6.07; N, 5.44. Found: C, 63.02; H, 6.28; N, 5.34. $^1$H-NMR(CDCl$_3$) δ: 1.41 (9H, s), 1.61 (9H, s), 3.69 (3H, s), 4.20 (2H, d, J=6.0 Hz), 4.62 (1H, bs), 6.92 (1H, d, J=1.8 Hz), 7.24–7.40 (5H, m), 8.35 (1H, d, J=8.6 Hz).

(3) 3-(Aminomethyl)-6-chloro-4-(4-hydroxyphenyl)-2-methyl-1(2H)-isoquinolinone hydrochloride (synthesized according to the method similar to that in Example 1 (7))

Melting point 253–254° C. Elemental analysis for $C_{17}H_{16}N_2O_2Cl_2$ Calculated: C, 58.13; H, 4.59; N, >7.98. Found: C, 57.99; H, 4.57; N, 7.88. $^1$H-NMR(DMSO-d$_6$) δ: 3.70 (3H, s), 3.97 (2H, bs), 6.92 (1H, d, J=2.0 Hz), 6.97 (2H, d, J=8.4 Hz), 7.17 (2H, d, J=8.4 Hz), 7.60 (1H, dd, J=2.0, 8.6 Hz), 8.32 (1H, d, J=8.6 Hz), 8.62 (3H, bs), 9.89 (1H, bs).

Example 19

3-(Aminomethyl)-6-chloro-4-(3-hydroxyphenyl)-2-methyl-1(2H)-isoquinolinone hydrochloride (1) 2-{[6-Chloro-4-(3-hydroxyphenyl)-2-methyl-1-oxo-1,2-dihydro-3-isoquinolinyl]methyl}-1H-isoindole-1,3 (2H)-dione (synthesized according to the method similar to that in Example 18,(1))

Melting point 297–298° C. Elemental analysis for $C_{25}H_{17}N_2O_4Cl$ ¼H$_2$O Calculated: C, 66.82; H, 4.00; N, 6.23. Found: C, 66.52; H, 4.34; N, 5.85. $^1$H-NMR(DMSO-d$_6$) δ: 3.58 (3H, s), 4.73 (1H, d, J=15.8 Hz), 4.82 (1H, d, J=15.8 Hz), 6.65–6.70 (2H, m), 6.76–6.80 (1H, m), 6.85 (1H, d, J=2.0 Hz), 7.20 (1H, t, J=7.7 Hz), 7.55 (1H, dd, J=2.0, 8.6, Hz), 7.75–7.85 (4H, m), 8.29 (1H, d, J=8.6 Hz), 9.57 (1H, s).

(2) Tert-butyl{6-chloro-4-(3-hydroxyphenyl)-2-methyl-1-oxo-1,2-dihydro-3-isoquinolinyl}methylcarbamate (synthesized according to the method similar to that in Example 1 (6))

Melting point 244–2450° C. Elemental analysis for $C_{22}H_{23}N_2O_4Cl$ Calculated: C, 63.69; H, 5.59; N, 6.75.Found: C, 63.76; H, 5.75; N, 6.52. $^1$H-NMR(CDCl$_3$) δ: 1.44 (9H, s), 3.69 (3H, s), 4.23 (2H, d, J=5.6 Hz) 4.86 (1H, bs), 6.69–6.75 (2H, m), 6.95–7.00(1H, m), 7.02 (1H, d, J=2.0 Hz), 7.33 (1H, t, J=7.7 Hz), 7.37 (1H, dd, J=2.0, 8.6 Hz), 8.36 (1H, d, J=8.6 Hz), 8.87 (1H, s).

(3) 3-(Aminomethyl)-6-chloro-4-(3-hydroxyphenyl)-2-methyl-1(2H)-isoquinolinone hydrochloride (synthesized according to the method similar to that in Example 1(7))

Melting point 277° C. Elemental analysis for $C_{17}H_{16}N_2O_2Cl_2$ Calculated: C, 58.13; H, 4.59; N, 7.98. Found: C, 57.96; H, 4.66; N, 8.01. $^1$H-NMR(DMSO-d$_6$) δ: 3.69 (3H, s), 3.97 (2H, bs), 6.78–6.81 (2H, m), 6.90 (1H, d, J=2.0 Hz), 6.94–6.99 (1H, m), 7.38 (1H, t, J=7.9 Hz), 7.62 (1H, dd, J=2.0, 8.6.Hz), 8.32(1H, d, J=8.6 Hz), 8.60(3H, bs), 9.87(1H, bs).

Example 20

3-(Aminomethyl)-6-chloro-4-(4-fluorophenyl)-2-methyl-1(2H)-isoquinolinone hydrochloride (1) Ethyl 6-chloro-4-(4-fluorophenyl)-2-methyl-1-oxo-1,2-dihydro-3-isoquinolinecarboxylate (synthesized according to the method similar to that in Example 12 (2))

Melting point 159–160° C. Elemental analysis for $C_{19}H_{15}NO_3ClF$ Calculated: C, 63.43; H, 4.20; N, 3.89. Found: C, 63.56; H, 3.96; N, 3.66. $^1$H-NMR(CDCl$_3$) δ: 1.00 (3H, t, J=7.0 Hz), 3.59 (3H, s), 4.07 (2H, q, J=7.0 Hz), 7.12 (1H, d, J=2.0 Hz), 7.17–7.21. (2H, m), 7.27–7.347 (2H, m), 7.48 (1H, dd, J=2.0, 8.6 Hz), 8.44 (1H, d, J=8.6, Hz).

(2) 6-Chloro-4-(4-fluorophenyl)-2-methyl-1-oxo-1,2-dihydro-3-isoquinolinecarboxylic acid (synthesized according to the method similar to that in Example 4 (3))

Melting point 239–240° C. Elemental analysis for $C_{17}H_{11}NO_3ClF$ Calculated: C, 61.55; H, 3.34; N, 4.22. Found: C, 61.82; H, 3.52; N, 4.02. $^1$H-NMR(DMSO-d$_6$) δ: 3.52,(3H, s), 6.99 (1H, d, J=2.0 Hz), 7.30–7.45 (4H, m), 7.63 (1H, dd, J=2.0, 8.6 Hz), 8.33 (1H, d, J=8.6 Hz).

(3) 6-Chloro-4-(4-fluorophenyl)-3-hydroxymethyl-2-methyl-1(2H)-isoquinolinone (synthesized according to the method similar to that in Example 4 (4))

Melting point 167–168° C. Elemental analysis for $C_{17}H_{13}NO_2ClF$ Calculated: C, 64.26; H, 4.12; N, 4.41. Found: C, 64.33; H, 4.08; N, 4.36. $^1$H-NMR(CDCl$_3$) δ: 2.08 (1H, bs), 3.81 (3H, s), 4.45 (2H, d, J=5.2 Hz), 6.94 (1H, d, J=2.0 Hz), 7.1.7–7.33 (4H, m), 7.38 (1H, d, J=2.0, 8.6 Hz), 8.36 (1H, d, J=8.6 Hz).

(4) 6-Chloro-3-chloromethyl-4-(4-fluorophenyl)-2-methyl-1(2H)-isoquinolinone (synthesized according to the method similar to that in Example 4 (5))

$^1$H-NMR(CDCl$_3$) δ: 382 (3H, s), 4.37 (2H, s), 6.97 (1H, d, J=2.0 Hz), 7.20–7.37 (4H, m), 7.45 (1H, dd, J=2.0, 8.6 Hz), 8.43 (1H, d, J=8.6 Hz).

(5) 2-{[6-Chloro-4-(4-fluorophenyl)-2-methyl-1-oxo-1,2-dihydro-3-isoquinolinyl]methyl}-1H-isoindole-1,3(2H)-dione (synthesized according to the method similar to that in Example 4 (6))

Melting point 190–191° C. Elemental analysis for $C_{25}H_{16}N_2O_3ClF$ Calculated: C, 67.20; H, 3.61; N, 6.27. Found: C, 67.40; H, 3.42; N, 6.24. $^1$H-NMR(DMSO-d$_6$) δ: 3.61 (3H, S), 4.75 (2H, s), 6.78 (1H, d, J=2.0 Hz), 7.23–7.39 (4H, m), 7.57 (1H, dd, J=2.0, 8.6 Hz), 7.76–7.85 (4H, m), 7.86 (4H, s), 8.31 (1H, d, J=8.6 Hz).

(6) Tert-butyl{6-chloro-4-(4-fluorophenyl)-2-methyl-1-oxo-1,2-dihydro-3-isoquinolinyl}methylcarbamate (synthesized according to the method similar to that in Example 1 (6))

Melting point 2.06–207° C. Elemental analysis for $C_{22}H_{22}N_2O_3ClF$ Calculated: C, 63.39; H, 5.32; N, 6.72. Found: C, 63.56; H, 5.27; N, 6.61. $^1$H-NMR(CDCl$_3$) δ: 1.44 (9H, s), 3.69 (3H; s), 4.19 (2H, d, J=5.6 Hz), 4.67 (1H, bs), 6.8–8 (1H, d, J=2.6 Hz), 7.22–7.27 (4H, m), 7.38 (1H, dd; J=2.0, 8.6 Hz), 8.35 (1H, d, J=8.6 Hz).

(7) 3-(Aminomethyl)-6-chloro-4-(4-fluorophenyl)-2-methyl-1 (2H)-isoquinolinone hydrochloride (synthesized according to the method similar to that in Example 1 (7))

Melting point 277–278° C. Elemental analysis for $C_{17}H_5N_2OCl_2F$ Calculated: C, 57.81; H, 4.28; N, 7.93. Found: C, 5,7.98; H, 4.29; N, 7.84. $^1$H-NMR(DMSO-d$_6$) δ: 3.71 (3H, s), 3.92 (2H, s), 6.–83 (1H, d, J=2.0 Hz), 7.37–7.46 (4H, m), 7.62 (1H, d, J=2.0, 8.6 Hz), 8.34 (1H, d, J=8.6 Hz), 8.73 (3H, bs).

Example 21

3-(Aminomethyl)-6-chloro-2-methyl-4-(4trifluoromethylphenyl)-1(2H)-isoquinolinone hydrochloride (1) 6-Chloro-2-methyl-1-oxo-4-(4-trifluoromethylphenyl)-1,2-dihydro-3-isoquinolinecarboxylate, ethyl (synthesized according to the method similar to that in Example 12 (2))

Melting point 170–171° C. Elemental analysis for $C_{20}H_{15}NO_3ClF_3$ Calculated: C, 58.62; H, 3.69; N, 3.40. Found: C, 58.83; H, 3.71; N, 3.22. $^1$H-NMR(CDCl$_3$) δ: 0.93 (3H, t, J=7.2 Hz), 3.60 (3H, s), 4.05 (2H, q, J=7.2 Hz), 7.09 (1H, d, J=2.0 Hz)., 7.46 (2H, d, J=7.8 Hz), 7.50 (1H, dd, J=2.0, 8.4 Hz), 7.75 (2H, d, J=7.8 Hz), 8.46 (1H, d, J=8.4 Hz).

(2) 6-Chloro-2-methyl-1-oxo-4-(4-trifluoromethylphenyl)-1,2-dihydro-3-isoquinolinecarboxylic acid (synthesized according to the method similar to that in Example 4 (3))

Melting point 285–28.6° C. Elemental analysis for $C_{18}H_{11}NO_3ClF_3$ Calculated: C, 56.63; H, 2.90; N, 3.67. Found: C, 56.73; H, 2.68; N, 3.49. $^1$H-NMR(DMSO-d$_6$) δ: 3.53 (3H, s), 6.99 (1H, d, J2.2 Hz), 7.60 (2H, d, J=8.0 Hz), 7.65 (1H, dd, J=2.2, 8.4 Hz), 7.89 (2H, d, J=,8.34 (1H, d, J=8.4 Hz).

(3) 6-Chloro-3-hydroxymethyl-2-methyl-4-(4-trifluoromethylphenyl)-1(2H)-isoquinolinone (synthesized according to the method similar to that in Example 4 (4))

Melting point 219–220° C. Elemental analysis for $C_{18}H_{13}NO_2ClF_3$ Calculated: C, 58.79; H, 3.56; N, 3.81. Found: C, 58.94; H, 3.52; N, 3.65. $^1$H-NMR(CDCl$_3$) δ: 2.13 (1H, bs) 3.82 (3H, s), 4.43. (2H, d, j=5 0 Hz), 7.40 (1H, dd, J=2.0, 8.6 Hz), 7.47 (2H, d, J=7.9 Hz), 7.80 (2H, d, J=7.9 Hz), 8.37 (1H, d, J8.6 Hz).

(4) 6-Chloro-3-chloromethyl-2-methyl-4-(4-trifluoromethylphenyl)-1(2H)-isoquinolinone (synthesized according to the method similar to that in Example-4 (5))

$^1$H-NMR(CDCl$_3$) δ: 3.83 (3H, s), 4.33 (2H, s), 6.91 (1H, d, J=1.8 Hz), 7.47 (1H, dd, J=1.8, 8.6 Hz), 7.50 (2H, d, J=7.5 Hz), 7.83 (2H, d, J=7.5 Hz), 8.45 (1H, d, J=8.6 35 Hz).

(5) 2-{(6-Chloro-2-methyl-1-oxo-4-(4-trifluoromethylphenyl)- 1,2-dihydro-3-isoquinolinyl)methyl}-1H-isoindole-1,3(2H)-dione (synthesized according to the method similar to that in Example 4 (6))

Melting point 236–237° C. Elemental analysis for $C_{26}H_6N_2O_3ClF_3$ Calculated: C, 62.85; H, 3.25; N, 5.64. Found: C, 62.92; H, 3.07; N, 5.52. $^1$H-NMR(DMSO-d$_6$) δ: 3.62 (3H, s), 4.76 (2H, s), 6.73 (1H, d, J=1.8 Hz), 7.54 (2H, d, J=7.6 Hz), 7.58 (1H, dd, J=1.8, 8.4 Hz), 7.73–7.84 (6H, m), 8.32(1H, d, J=8.4 Hz).

(6) Tert-butyl{6-chloro-2-methyl-1-oxo-4-(4-trifluoromethylphenyl)-1,2-dihydro-3-isoquinolinyl}-methylcarbamate (synthesized according to the method similar to that in Example 1 (6))

Melting point 193–194° C. Elemental analysis for $C_{23}H_{22}N_2O_3ClF_3$ Calculated: C, 59.17; H, 4.75; N, 6.00. Found: C, 59.35; H, 4.76; N, 5.92. $^1$H-NMR(CDCl$_3$) δ: 1.43 (9H, s), 3.70 (3H, s), 4.16 (2H, d, J=5.8 Hz), 4.67 (1H, bs), 6.82 (1H, d, J=2.0 Hz), 7.39(1H, dd, J=2.0, 8.6 Hz), 7.42 (2H, d, J=7.9 Hz), 7.81 (2H, d, J=7.9 Hz), 8.36 (1H;, d, J=8.6 Hz).

(7) 3-(Aminomethyl)-6-chloro-2-methyl-4-(4-trifluoromethylphenyl)-1(2H)-isoquinolinone hydrochloride (synthesized according to the method similar to that in Example 1 (7))

Melting point 261–262° C. Elemental analysis for $C_{18}H_{15}N_2OCl_2F_3$ ½$H_2O$ Calculated: C, 52.44; H, 3.91; N, 6.80. Found: C, 52.57; H, 4.09; N, 7.02. $^1$H-NMR(DMSO-$d_6$) δ: 3.71 (3H, s), 3.90(2H, s), 6.79 (1H, d, J=2.0 Hz), 7.64 (1H, dd, J=2.0, 8.8 Hz), 7.65 (2H, d, J=8.2 Hz), 7.96 (2H, d, J=8.2 Hz), 8.35 (1H, d, J=8.8 Hz), 8.70 (3H, bs).

Example 22

3-(Aminomethyl)-6,7-dichloro-2-methyl-4-phenyl-1 (2H)-isoquinolinone hydrochloride (1) ethyl 6,7-dichloro-4-hydroxy-2-methyl-1-oxo-1,2-dihydro-3-isoquinolinecarboxylate (synthesized according to the method similar to that in Example 4 (1))

Melting point 127–128° C. Elemental analysis for $C_{13}H_{11}NO_4Cl_2$ Calculated: C, 49.39; H, 3.51; N, 4.43. Found: C, 49.31; H, 3.50; N, 4.36. $^1$H-NMR;(CDCl$_3$) δ: 1.47 (3H, t, J=7.2 Hz), 3.68 (3H, s), 4.51 (2H, q, J=7.2 Hz), 8.21, (1H, s), 8.51 (1H, bs), 11.17 (1H, s).

(2) Ethyl 6,7-dichloro-2-methyl-1-oxo-4-trifluoromethanesulfonyloxy-1,2-dihydro-3-isoquinolinecarboxylate (synthesized according to the method similar to that in Example 12 (1))

$^1$H-NMR(CDCl$_3$) δ: 1.45 (3H, t, J=7.2 Hz), 3.60 (3H, s), 4.49 (2H, q, J=7.2 Hz), 7.86 (1H, s), 8.53.(1H, s).

(3) Ethyl 6,7-dichloro-2-methyl-1-oxo-4-phenyl-1,2-dihydro-3-isoquinolinecarboxylate (synthesized according to the method similar to that in Example 12 (2))

Melting point 288–289° C. Elemental analysis for $C_{19}H_{15}NO_3Cl_2$ Calculated: C, 60.65; H, 4.02; N, 3.72. Found: C, 60.96; H, 4.04; N, 3.62. $^1$H-NMR(CDCl$_3$) δ: 0.92 (3H, t, J=7.2 Hz), 3.60 (3H, s), 4.02 (2H, q, J=7.2 Hz), 7.28–7.32 (3H, m), 7.45–7.48 (3H, m), 8.57 (1H, s).

(4) 6,7-Dichloro-2-methyl-1-oxo-4-phenyl-1,2-dihydro-3-isoquinolinecarboxylic acid (synthesized according to the method similar to that in Example 4 (3))

Melting point 261–262° C. $^1$H-NMR(CDCl$_3$) δ: 3.68 (3H, s), 7.13 (1H, d, J=8.8 Hz), 7.32–7.51.(6H, m), 8.45 (1H, d, J=2.2 Hz).

(5) 6,7-Dichloro-3-hydroxymethyl-2-methyl-4-phenyl-1(2H)-isoquinolinone (synthesized according to the method similar to that in Example 4 (4))

Melting point 211–212° C. Elemental analysis for $C_{17}H_{13}NO_2Cl_2$ Calculated: C, 61.10;H, 3.92;N, 4.19. Found: C, 61.21; H, 3.80; N, 4.12. $^1$H-NMR(CDCl$_3$) δ: 2.22 (1H, t, J=5.8 Hz), 3.81 (3H, s), 4.45 (2H, d, J=5.8 Hz), 7.09 (1H, s), 7.27–7.33, (2H, m), 7.48–7.56 (3H, m), 8.47 (1H, s).

(6) 6,7-Dichloro-3-chloromethyl-2-methyl-4-phenyl-1 (2H)-isoquinolinone (synthesized according to the method similar to that in Example 4 (5))

$^1$H-NMR(CDCl$_3$) δ: 3.82 (3H, s), 4.36 (2H, s), 7.11 (1H, s), 7.31–7.34 (2H, m), 7.49–7.56 (3H, m), 8.57 (1H, s).

(7) 2-{(6,7-Dichloro-2-methyl-1oxo-4-phenyl-1,2-dihydro-3-isoquinolinyl)methyl}-1-isoindole-1,2-dione (synthesized according to the method similar to that in Example 4 (6))

Melting point 234–235° C. Elemental analysis for $C_{25}H_{16}N_2O_3Cl_2$ Calculated: C, 64.81; H, 3.48; N, 6.05. Found: C, 64.68; H, 3.56; N, 5.86. $^1$H-NMR(DMSO-$d_6$) δ: 3.61 (3H, s), 4.76 (2H, s), 6.94 (1H, s), 7.28–7.32 (2H, m), 7.41–7.48 (3H, m), 8.40 (1H, s).

(8) Tert-butyl{6,7-dichloro-2-methyl-1-oxo-4-phenyl-1, 2-dihydro-3-isoquinolinyl}methylcarbamate (Synthesized according to the method similar to that in Example 1 (6))

Melting point 226–227° C. Elemental analysis for $C_{22}H_{22}N_2O_3Cl_2$ Calculated: C, 60.98; H, 5.12; N, 6.46. Found: C, 61.10; H, 5.30; N, 6.37. $^1$H-NMR(CDCl$_3$) δ: 1.43 (9H, s), 3.70 (3H, s), 4.19 (2H, d, J=5.4, Hz), 4.77 (1H, bs), 7.02 (1H, s), 7.22–7.27 (2H, m), 7.49–7.53 (3H, m), 8.47 (1H, s).

(9) 3-(Aminomethyl)-6,7-dichloro-2-methyl-4-phenyl-1(2H)-isoquinolinone hydrochloride (synthesized according to the method similar to that in Example 4 (7))

Melting point 266–267° C. Elemental analysis for $C_{17}H_{15}N_2OCl_3$ Calculated: C, 55.23; H, 4.09; N, 7.58. Found: C, 55.40; H, 4.21; N, 7.33. $^1$H-NMR(DMSO-$d_6$) δ: 3.72. (3H, s), 3.93 (2H, bs), 6.99 (1H, s), 7.39–7.44. (2H, m), 7.55–7.64 (3H, m), 8.43 (1H, s), 8.73 (3H, bs).

Example 23

3-(Aminomethyl)-6-chloro-2-methyl-4-(3-nitrophenyl)-1(2H)-isoquinolinone hydrochloride (1) Ethyl 6-chloro-2-methyl-1-oxo-4-(3-nitrophenyl)-1,2-dihydro-3-isoquinolinecarboxylate (synthesized according to the method similar to that in Example 12 (2))

Melting point 211–212° C. Elemental analysis for $C_{19}H_{15}N_2O_5Cl$ Calculated: C, 59.00; H, 3.91; N, 7.24. Found: C, 59.13; H, 3.86; N, 7.32. $^1$H-NMR(CDCl$_3$) δ: 1.02 (3H, t, J=7.2 Hz), 3.61 (3H, s), 4.09. (2H, q, J=7.2 Hz), 7.02 (1H, d, J=2.0 Hz), 7.52 (1H, dd, J=2.0, 8.6 Hz), 7.68–7.71 (2H, m), 8.23–8.25 (1H, m), 8.32–8.38 (1H, m), 8.47 (1H, d, J=8.6 Hz), (2) 6-Chloro-2-methyl-1-oxo-4-(3-nitrophenyl)-1,2-dihydro-3-isoquinolinecarboxylic acid (synthesized according to the method similar to that in Example 4

Melting point 259–260° C. $^1$H-NMR(CDCl$_3$) δ: 3.54 (3H, s), 7.04 (1H, d, J=2.0 Hz), 7.65 (1H, dd, J=2.0, 8.6 Hz), 7.82–7.85 (2H, m), 8.19–8.21 (1H, m), 8.33–8.39 (2H, m).

(3) 6-Chloro-3-hydroxymethyl-2-methyl-4-(3-nitrophenyl)-1(2H)-isoquinolinone (synthesized according to the method similar to that in Example 4 (4))

Melting point 227–228° C. Elemental analysis for $C_{17}H_{13}N_2O_4Cl$ ½$H_2O$ Calculated: C, 57.72; H, 3.99; N, 7.92. Found: C, 57.96; H, 3.88; N, 7.63. $^1$H-NMR(CDCl$_3$) δ: 3.85 (3H, s), 4.34 (2H, d, J=3.2 Hz), 4.80 (1H, bs), 6.86 (1H, d, J=2.0 Hz), 7.42 (1H, dd, J=2.0, 8.6 Hz), 7.69–7.73 (2H, m), 8.27–8.38 (2H, m), 8.43 (1H, d, J=8.6 Hz).

(4) 6-Chloro-3-chloromethyl-2-methyl-4-(3-nitrophenyl)-1(2H)-isoquinolinone (synthesized according to the method similar to that in Example 4 (5))

$^1$H-NMR(CDCl$_3$) δ: 3.84 (3H, s), 4.32 (2H, s), 6.86 (1H, d, J=2.0 Hz), 7.49 (1H, dd, J=2.0, 8.6 Hz), 7.73–7.79 (2H, m), 8.25–8.26 (1H, m), 8.39–8.43 (1H, m), 8.46 (1H, d, J=8.6 Hz).

(5) 2-{(6-Chloro-2-methyl-1-oxo-4-(3-nitrophenyl)-1,2-dihydro-3-isoquinolinyl)methyl}-1H-isoindole-1,3(2H)-dione (synthesized according to the method similar to that in Example 4 (6))

Melting point 246–247° C. Elemental analysis for $C_{25}H_{16}N_3O_5Cl$ Calculated: C, 63.37; H, 3.40; N, 8.87. Found C, 63.14; H, 3.33; N, 8.50. $^1$H-NMR(DMSO-$d_6$) δ: 3.65 (3H, s), 4.71 (1H, d, J=16.3 Hz), 4.80 (1H, d, J=16.3 Hz) 6.79 (1H, d, J=2.0 Hz), 7.59 (1H, d, J=2.0, 8.6 Hz), 7.69–7.84 (5H, m), 8.13–8.14 (1H, m), 8.23–8.29.(4H, m),8.33 (1H, d, J=8.6 Hz).

(6) Tert-butyl{6-chloro-2-methyl-1-oxo-4-(3-nitrophenyl)-1,2-dihydro-3-isoquinolinyl}methylcarbamate (synthesized according to the, method similar to that in Example 1 (6))

Melting point 231–232° C. Elemental analysis for $C_{22}H_{22}N_3O_5Cl$ Calculated: C, 59.53; H, 5.00; N, 9.47.

Found: C, 59.51; H, 5.01; N, 9.25. $^1$H-NMR(CDCl$_3$) δ: 1.42 (9H, s), 3.71 (3H, s), 4.14–4.17 (2H, m), 4.81 (1H, bs), 6.77 (1H, s), 7.18–7.23 (1H, m), 7.62 (1H, d, J=7.8 Hz), 7.76 (1H, t, J=7.8 Hz), 8.17 (1H, s), 8.36–8.42 (2H, m).

(7) 3-(Aminomethyl)-6-chloro-2-methyl-4-(3-nitrophenyl)-1(2H)-isoquinolinone hydrochloride (synthesized according to the method similar to that in Example 1 (7))

Melting point 263–264° C. Elemental analysis for C$_{17}$H$_{15}$N$_3$O$_3$Cl$_2$ Calculated: C, 53.70; H, 3.98; N, 11.05. Found: C, 53.56; H, 4.09; N, 10.95. $^1$H-NMR(DMSO-d$_6$) δ: 3.71 (3H, s), 3.83–3.93 (2H, m), 36.86 (1H, d, J=2.0 Hz), 7.65 (1H, dd, J=2.0, 8.6 Hz), 7.82–7.93 (2H, m), 8.23–8.25 (1H, m), 8.35 (1H, d, J=8.6 Hz), 8.39–8.44 (1H, m), 8.66 (3H, bs).

Example 24

3-(Aminomethyl)-4-(3-aminophenyl)-6-chloro-2-methyl-1(2H)-isoquinolinone hydrochloride (1) Tert-butyl{6-chloro-2-methyl-1-oxo-4-(3-nitrophenyl)-1,2-dihydro-3-isoquinolinyl}methylcarbamate (synthesized according to the method similar to that in Example 23 (6)) (0.89 g, 2 mmol) was added to an aqueous solution (10 ml) of potassium carbonate (2.90 g, 21 mmol) and sodium hydrosulfite (2.44 g, 14 mmol) and the mixture was stirred at room temperature for 1 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl{4-(3-aminophenyl)-6-chloro-2-methyl-1-oxo-1,2-dihydro-3-isoquinolinyl}methylcarbamate (0.48 g, 58.5%) as crystals.

Melting point 157–158° C. $^1$H-NMR(CDCl$_3$) δ: 1.43 (9H, s), 3.69 (3H, s), 4.22 (2H, d, J=5.6 Hz), 4.65 (1H, bs), 6.54–6.62 (1H, m), 6.76–6.83 (1H, m), 6.90–7.03 (1H, m), 7.08 (1H, dd, J=2.0, 8.0 Hz), 7.34–7.45 (2H, m), 8.35 (1H, d, J=8.0 Hz).

(2) 3-(Aminomethyl)-4-(3-aminophenyl)-6-chloro-2-methyl-1(2H)-isoquinolinone hydrochloride (synthesized according to the method similar to that in Example 1 (7))

Melting point 255° C. Elemental analysis for C$_{17}$H$_{18}$N$_3$OCl$_3$ ½H$_2$O Calculated: C, 51.60; H, 4.84; N, 10.62. Found: C, 51.76; H, 4.64; N, 10.29. $^1$H-NMR (DMSO-d$_6$) δ: 3.70 (3H, s), 3.91 (2H,bs), 6.87–6.93 (2H,m), 7.38–7.46 (1H, m), 7.57–7.75 (3H, m), 8.35(1H, d, J=8.8 Hz), 8.73–8.87 (6H, m).

Example 25

3-(Aminomethyl)-4-butoxy-6-chloro-2-propyl-1-(2H)-isoquinolinone hydrochloride (1) Ethyl 6-chloro-4-hydroxy-1-oxo-2-propyl-1,2-dihydro-3-isoquinolinecarboxylate (synthesized according to the method similar to that in Example 1 (1))

Melting point 61–62° C. Elemental analysis for C$_{15}$H$_{16}$NO$_4$Cl Calculated: C, 58.16; H, 5.21; N, 4.52. Found: C, 58.22; H, 5.28; N, 4.45. $^1$H-NMR(CDCl$_3$) δ: 0.93 (3H, t, J=7.3 Hz), 1.47 (3H, t, J=7.2 Hz), 1.69–1.84 (2H, m), 4.17–4.24 (2H, m), 4.51 (2H, q, J=7.2 Hz), 7.62 (1H, dd, J=2.2, 8.6 Hz), 8.11 (1H, d, J=2.2 Hz), 8.37 (1H, d, J=2.2 Hz), 11.28 (1H, s).

(2) Ethyl 4-butoxy-6-chloro-1-oxo-2-propyl-1,2-dihydro-3-isoquinolinecarboxylate (synthesized according to the method similar to that in Example 1 (2))

Melting point 72–73° C. Elemental analysis for C$_{19}$H$_{24}$NO$_4$Cl Calculated: C, 62.38; H, 6.61; N, 3.83. Found: C, 62.32; H, 6.55; N, 3.56. $^1$H-NMR(CDCl$_3$) δ: 0.94 (3H, t, J=7.3 Hz), 1.01 (3H, t, J=7.3 Hz), 1.43 (3H, t, J=7–1 Hz), 1.48–1.62 (2H, m), 1.68–1.86 (4H, m), 3.85–3.98 (4H, m), 4.47 (2H, q, J=7.1 Hz), 7.49 (1H, dd, J=2.0, 8.7 Hz), 7.69 (1H, d, J=2.0 Hz), 8.37 (1H, d, J=8.7 Hz).

(3) 4-Butoxy-6-chloro-1-oxo-2-propyl-1,2-dihydro-3-isoquinolinecarboxylic acid (synthesized according to the method similar to that in Example 4 (3))

Melting point 175–176° C. Elemental analysis for C$_{17}$H$_{20}$NO$_4$Cl Calculated: C, 60.45; H, 5.97; N, 4.15. Found: C, 60.45; H, 6.27; N, 3.98. $^1$H-NMR(CDCl$_3$) δ: 0.91–1.06 (6H, m), 1.50–1.65 (2H, m), 1.80–1.85 (4H, m), 3.95–4.04 (4H, m), 7.46 (1H, dd, J=2.0, 8.6 Hz), 7.70 (1H, d, J=2.0 Hz), 8.36 (1H, d, J8.6 Hz).

(4) 4-Butoxy-6-chloro-3-hydroxymethyl-2-propyl-1 (2H)-isoquinolinone (synthesized according to the method similar to that in Example 4 (4))

Melting point 108–109° C. Elemental analysis for C$_{17}$H$_{22}$NO$_3$Cl Calculated: C, 63.06; H, 6.85; N, 4.33. Found: C, 62.75; H, 6.89; N, 4.12. $^1$H-NMR(CDCl$_3$) δ: 1.00(3H, t, J=7.6 Hz), 1.04 (3H, t, J=7.0 Hz), 1.49–1.92 (6H, m), 2.43 (2H, t, J=6.6 Hz), 4.79 (1H, t, J=5.6 Hz), 3.87 (2H, t, J=6.6 Hz), 4.12–4.20 (2H, m), 4.79 (2H, d, J=5.6 Hz), 7.41 (1H, dd, J=2.0, 8.6 Hz), 7.61 (1H, d, J=2.0 Hz), 8.29(1H, d, J=8.6 Hz).

(5) 4-Butoxy-6-chloro-3-chloromethyl-2-propyl-1(2H) isoquinolinone (synthesized according to the method similar to that in Example 4 (5))

$^1$H-NMR(CDCl$_3$) δ: 1.02 (3H, t, J=7.4 Hz), 1.05 (3H, t, J=7.2 Hz), 1.56–1.97 (6H, m), 3.99 (2H, t, J=6–5 Hz), 4.11–4.19 (2H, m), 4.78 (2H, s), 7.47 (1H, dd, J=2.2, 8.6 Hz), 7.70 (1H, d, J=2.2 Hz), 8.37 (1H, d, J=8.6 Hz).

(6) 2-{(4-Butoxy-6-chloro-1-oxo-2-propyl-1,2-dihydro-3-isoquinolinyl)methyl}-1H-isoindole-3(2H)-dione (synthesized according to the method similar to that in Example 4 (6))

Melting point 153–154° C. Elemental analysis for C$_{25}$H$_{25}$N$_2$O$_4$Cl Calculated: C, 66.29; H, 5.56; N, 6.18. Found: C, 66.31; H, 5.48; N, 6.08. $^1$H-NMR(DMSO-d$_6$) δ: 0.80 (3H, t, J=7.3 Hz), 0.92 (3H, t, J=7.4 Hz), 1.38–1.58 (4H, m), 1.69–1.82 (2H, m), 3.89–4.02 (4H, m), 5.02 (2H, s), 7.59, (H, dd, J=2.0, 8.6 Hz), 7.65 (1H, d, J=2.0 Hz), 7.83–7.92 (4H, m), 8.24 (1H, d, J=8.6 Hz).

(7) Tert-butyl(4-butoxy-6-chloro-1-oxo-2-propyl-1,2-dihydro-3-isoquinolinyl)methylcarbamate (synthesized according to the method similar to that in Example 1 (6))

Melting point 120–121° C. Elemental analysis for C$_{22}$H$_{31}$N$_2$O$_4$Cl Calculated: C, 62.48; H, 7.39; N, 6.62. Found: C, 62.53; H, 7.40; N, 6.49. $^1$H-NMR(CDCl$_3$) δ: 1.01 (3H, t, J=7.4 Hz), 1.04 (3H, t, J=6.8 Hz), 1.47 (9H, s), 1.52–1.90 (4H, m), 3.84 (2H, t, J=6.6 Hz), 4.01–4.08 (2H, m), 4.50 (2H, d, J=5.6 Hz), 4.77 (1H, bs), 7.43 (1H, dd, J=2.0, 8.6 Hz), 7.64, (1H, d, J=2.0 Hz), 8.34 (1H, d, J=8.6 Hz).

(8) 3-(Aminomethyl)-4-butoxy-6-chloro-2-propyl-1(2H)-isoquinolinone hydrochloride (synthesized according to the method similar to that in Example 1 (7))

Melting point 124–125° C. Elemental analysis for C$_{17}$H$_{24}$N$_2$O$_2$Cl$_2$ ¼H$_2$O Calculated: C, 56.13; H, 6.79; N, 7.70. Found: C, 56.15; H, 6.82; N, 7.53. $^1$H-NMR(DMSO-d$_6$) δ: 0.95 (3H, t, J7.4 Hz), 1.00 (3H, t, J=7.3 Hz), 1.46–1.68 (4H, m), 1.78–1.92 (2H, m), 3.93 (2H, t, J=6.6 Hz), 3.93–4.02 (2H, m), 4.16 (2H, s), 7.66 (1H, dd, J=2.0, 8.4 Hz), 7.72 (1H, d, J=2.0 Hz), 8.28 (1H, d, J=8.4 Hz), 8.75 (3H, bs).

Example 26

3-(Aminomethyl)-4-butoxy-6,7-dichloro-2-isobutyl-1(2H)isoquinolinone hydrochloride (1) Ethyl 6,7-dichloro-4-hydroxy-2-isobutyl-1-oxo-1,2-dihydro-3-isoquinolinecarboxylate (synthesized according to the method similar to that in Example 1 (1))

Melting point 111–112° C. Elemental analysis is for $C_{16}H_{17}NO_4Cl_2$ Calculated: C, 53.65; H, 4.78; N, 3.91. Found: C, 53.62; H, 4.65;N, 3.66. $^1$H-NMR(CDCl$_3$) δ: 0.82 (6H, d, J=6.6 Hz), 1.46 (3H, t, J=7.2 Hz), 1.73–1.87 (1H, m), 4.38 (2H, d, J=7.8 Hz), 4.50 (2H, q, J=7.2 Hz), 8.23 (1H, s), 8.53 (1H, s), 11.16 (1H, s).

(2) Ethyl 4-butoxy-6,7-dichloro-2-isobutyl-1-oxo-1,2-dihydro-3-isoquinolinecarboxylate (synthesized according to the method similar to that in Example 1 (2))

$^1$H-NMR(CDCl$_3$) δ: 0.90 (6H, d, J=6.8 Hz), 1.01 (3H, t, J=7.4 Hz), 1.44 (3H, t, J=7.1 Hz), 1.48–1.62 (2H, m), 1.72–1.8.5 (2H, m), 2.05–2.17 (1H, m), 3.88 (2H, d, J=7.6 Hz), 3.94 (2H, t, J=6.5 Hz), 4–46 (2H, q, J=7.1 Hz), 7.81 (1H, s), 8.51 (1H, s).

(3) 4-Butoxy-6,7-dichloro-2-isobutyl-1-oxo-1,2-dihydro-3-isoquinolinecarboxylic acid (synthesized according to the method similar to that in Example 4 (3))

Melting point 104–105° C. Elemental analysis for $C_{18}H_{21}NO_4Cl_2$ Calculated: C, 55.97; H, 5.48; N, 3.63. Found: C, 55.82; H, 5.43; N, 3.46. $^1$H-NMR(CDCl$_3$) δ: 0.91 (6H, d, J=6.6 Hz), 1.00 (3H, t, J=7.3 Hz), 1.45–1.64 (2H, m), 1.75–1.86 (2H, m), 2.08–2.22 (1H, m), 3.97–4.05 (4H, m), 7.65 (1H, s), 8.45 (1H, s).

(4) 4-Butoxy-6,7-dichloro-3-hydroxymethyl-2-isobutyl-1(2H)-isoquinolinone (synthesized according to the method similar to that in Example 4 (4))

Melting point 99–100° C. Elemental analysis for $C_{18}H_{23}NO_3Cl_2$ Calculated: C, 58.07; H, 6.23; N, 3.76. Found: C, 57.90; H, 6.09; N, 3.46. $^1$H-NMR(CDCl$_3$) δ: 0.92 (6H, d, J=6.6 Hz), 1.05 (3H, t, J=7.3 Hz), 1.50–1.69 (2H, m), 1.80–1.94 (2H, m), 2.04–2.21 (1H, m), 2.57 (1H, bs), 3.88 (2H, t, J=6.6 Hz), 4.09 (2H, d, J=7.8 Hz), 4.79 (2H, d, J=4.8 Hz), 7.69 (1H, d, J=2.0 Hz), 8.35 (1H, d, J=2.0 Hz).

(5) 4-Butoxy-3-chloromethyl-6,7-dichloro-2-isobutyl-1(2H)-isoquinolinone (synthesized according to the method similar to that in Example 4 (5))

$^1$H-NMR(CDCl$_3$) δ: 0.95 (6H, d, J=7.0 Hz), 1.05 (3H, t, J=7.3 Hz), 1.51–1.66 (2H, m), 1.82–1.96 (2H, m), 2.04–2.21 (1H, m), 3.97 (2H, t, J=6.5 Hz), 4.06 (2H, d, J=5.8 Hz), 4.77(2H, s), 7.81 (1H, s), 8.50 (1H, s).

(6) 2-{(4-Butoxy-6,7-dichloro-2-isobutyl-1-oxo-1,2-dihydro-3-isoquinolinyl)methyl}-1H-isoindole-1,3(2H)-dione (synthesized according to the method similar to that in Example 4 (6))

Melting point 103–104° C. Elemental analysis for $C_{26}H_{26}N_2O_4Cl_2$ Calculated: C, 62.28; H, 5.23; N, 5.59. Found: C, 62.18; H, 5.03; N, 5.53. $^1$H-NMR(CDCl$_3$) δ: 0.95 (6H, d, J=6.6 Hz), 1.00 (3H, t, J=7.4 Hz), 1.43–1.58 (2H, m), 1.79–1.92 (2H, m), 2.07–2.21 (1H, m), 3.94–4.04 (4H, m), 5.01 (2H, s), 7.7.0–7.90 (5H, m), 8.49 (1H s).

(7) Tert-butyl(4-butoxy-6,7-dichloro-2-isobutyl-1-oxo-1,2-dihydro-3-isoquinolinyl)methylcarbamate (synthesized according to the method similar to that in Example 1 (6))

Melting point 138–139° C. Elemental analysis for $C_{23}H_{32}N_2O_4Cl_2$ Calculated: C, 58.85; H, 6.44; N, 5.97. Found: C, 58.60; H, 6.64; N, 5.72. $^1$H-NMR(CDCl$_3$) δ: 0.95 (6H, d, J=6.6 Hz), 1.04 (3H, t, J=7.3 Hz), 1.47 (9H, s), 1.47–1.67 (2H, m), 1.79–1.93 (2H, m), 2.07–2.21 (1H, m), 3.84 (2H, t, J=6.5 Hz), 3.98 (2H, d, J=7.4 Hz), 4.49 (2H, d, J=5.4 Hz), 4.80 (1H, bs), 7.75 (1H, s), 8.45 (1H, s).

(8) 3-(Aminomethyl)-4-butoxy-6,7-dichloro-2-isobutyl-1(2H)-isoquinoline hydrochloride (synthesized according to the method similar to that in Example 1 (7))

Melting point 168–170° C. Elemental analysis for $C_{18}H_{25}N_2O_2Cl_3$ Calculated: C, 53.02; H, 6.18; N, 6.87. Found: C, 53.28; H, 6.13; N, 6.76. $^1$H-NMR(DMSO-d$_6$) δ: 0.88 (6H, d, J=6.6 Hz), 1.00 (3H, t, J=7.1 Hz), 1.45–1.63 (2H, m), 1.78–1.96 (2H, i), 1.99–2.09 (1H, m), 3.91–3.99 (4H, m), 4.17 (2H, s), 7.92 (1H, s), 8.38 (1H, s), 8.68 (3H, bs).

Example 27

3-(Aminomethyl)-4-butoxy-6,7-dichloro-2-neopentyl-1(2H)-isoquinolinone hydrochloride (1) Ethyl 6,7-dichloro-4-hydroxy-2-neopentyl-1-oxo-1,2-dihydro-3-isoquinolinecarboxylate (synthesized according to the method similar to that in Example 1 (1))

Melting point 117–118° C. Elemental analysis for $C_{17}H_{19}NO_4Cl_2$ Calculated: C, 54.85; H, 5.14; N, 3.76. Found: C, 54.89; H, 5.14; N, 3.62. $^1$H-NMR(CDCl$_3$) δ: 0.84 (9H, s), 1.47 (3H, t, J=7.1 Hz), 4.49 (2H, q, J=7.1 Hz), 4.51 (2H, bs), 8.22 (1H, s), 8.52 (1H, s), 10.73 (1H, s).

(2) Ethyl 4-butoxy-6,7-dichloro-2-neopentyl-1-oxo-1,2-dihydro-3-isoquinolinecarboxylate (synthesized according to the method similar to that in Example 1 (2))

$^1$H-NMR(CDCl$_3$) δ: 0.93 (9H, s), 1.02 (3H, t, J=7.3 Hz), 1.44 (3H, t, J=7.1 Hz), 1.48–1.59 (2H, m), 1.73–83 (2H, m), 3.94 (2H, t, J=6.6 Hz), 4.07 (2H, bs), 4.43 (2H, q, J=7.1 Hz), 7.83 (1H, s), 8.51 (1H, s).

(3) 4-Butoxy-6,7-dichloro-2-neopentyl-1-oxo-1,2-dihydro-3-isoquinolinecarboxylic acid (synthesized according to the method similar to that in Example 4 (3))

Melting point 138–139° C. Elemental analysis for $Cl_{19}H_{23}NO_4Cl_2$ Calculated: C, 57.01; H, 5.79; N, 3.50. Found: C, 57.03; H 5.86; N, 3.30. $^1$H-NMR(CDCl$_3$) δ: 0.93 (9H, s), 1.01 (3H, t, J=7.1 Hz), 1.40–1.64 (2H, m), 1.77–1.91 (2H, m), 4.00 (2H, t, J=6.6 Hz), 4.23 (2H, bs), 5.81 (1H, bs), 7.77 (1H, s), 8.45

(4) 4-Butoxy-6,7-dichloro-3-hydroxymethyl-2-neopentyl-1(2H)-isoquinolinone (synthesized according to the method similar to that in Example 4 (4))

Melting point 178–179° C. Elemental analysis for $Cl_{19}H_{25}NO_3Cl_2$ Calculated: C, 59.07; H, 6.52; N, 3.63. Found: C, 59.00 H, 6.39; N, 3.33. $^1$H-NMR(CDCl$_3$) δ: 0.93 (9H, s), 1.06 (3H, t, J=7.3 Hz), 1.56–1.67 (2H, m), 1.81–1.92 (2H, m), 3.08 (1H, t, J=5.9 Hz), 3.90 (2H, t, J=6.4, Hz), 4.20 (2H, bs), 4.84 (2H, bs), 7.66 (1H, s), 8.22 (1H, s).

(5) 4-Butoxy-3-chloromethyl-6,7-dichloro-2-neopentyl-1(2H)-isoquinolinone (synthesized according to the method similar to that in Example 4 (5))

$^1$H-NMR(CDCl$_3$) δ: 0.98 (9H, s), 1.05 (3H, t, J7.3 Hz), 1.55–1.70 (2H, m), 1.82–1.95. (2H, m), 3.93 (2H, t, J=6.6 Hz), 4.17. (2H, bs), 4.84 (2H, bs), 7.80 (1H, s), 8.50 (1H, s).

(6) 2-{(4-Butoxy-6,7-dichloro-2-neopentyl-1-oxo-1,2-dihydro-3-isoquinolinyl)methyl}-1H-isoindole-1,3(2H)-dione (synthesized according to the method similar to that in Example 4 (6))

Melting point 145–146° C. Elemental analysis for $C_{27}H_{28}N_2O_4Cl_2$ Calculated: C, 62.92; H, 5.48; N, 5.43. Found: C, 62.76; H, 5.76; N, 5.22. $^1$H-NMR(CDCl$_3$) δ: 1.00 (9H, s), 1.01 (3H, t, J=7.1 Hz), 1.49–1.61 (2H, m), 1.81–1.95 (2H, m), 4.00 (2H, t, J=6.8 Hz), 4.07 (2H, bs), 5.05 (,2H, s), 7.70–7.86 (5H, m), 8.47 (1H, s).

(7) Tert-butyl(4-butoxy-6,7-dichloro-2-neopentyl-1-oxo-1,2-dihydro-3-isoquinolinyl)methylcarbamate (synthesized according to the method similar to that in Example 1 (6))

Melting point 152–153° C. Elemental analysis for $C_{24}H_{34}N_2O_4Cl_2$ Calculated: C, 59.39; H, 7.06; N, 5.77. Found: C, 59.15; H, 7.10; N, 5.54. $^1$H-NMR(CDCl$_3$) δ: 0.98 (9H, s), 1.01 (3H, t, J=7.0 Hz), 1.46 (9H, s), 1.53–1.68 (2H, m), 1.80–1.94 (2H, m), 3.85 (2H, t, J=6.6 Hz), 4.11–4.28 (2H, m), 4.55 (2H, d, J=5.4 Hz), 4.83 (1H, bs), 7.74 (1H, d, J=1.7 Hz), 8.41 (1H, d, J=1.7 Hz).

(3-(Aminomethyl)-4-butoxy-6,7-dichloro-2-neopentyl-1 (2H)-isoquinolinone hydrochloride (synthesized according to the method similar to that in Example 1 (7))

Melting point 157–158° C. Elemental analysis for $C_{19}H_2N_2O_2Cl_3$ ½$H_2O$ Calculated: C, 52.97; H, 6.55; N, 6.50. Found: C, 53.04; H, 6.59; N, 6.46. $^1$H-NMR(DMSO-d$_6$) δ: 0.91 (9H, s), 0.99 (3H, t, J=7.1 Hz), 1.45–1.60 (2H, m), 1.77–1.91 (2H, m), 3.95 (2H, t, J=6.4 Hz), 4.11 (2H, bs), 4.24 (2H, bs), 7.92 (1H, s), 8.38 (1H, s), 8.62 (3H, bs).

Example 28

3-(Aminomethyl)-2-benzyl-4-butoxy-6,7-dichloro-1 (2H) isoquinolinone hydrochloride (1) Ethyl 2-benzyl-6,7-dichloro-4-hydroxy-1-oxo-1,2-dihydro-3-isoquinolinecarboxylate (synthesized according to the method similar to that in Example 1 (1))

Melting point 140–141° C. Elemental analysis for $C_{19}H_{15}NO_4Cl_2$ Calculated: C, 58.18; H, 3.85; N, 3.57. Found: C, 58.22; H, 3.98; N, 3.27. $^1$H-NMR(CDCl$_3$) δ: 1.18 (3H, t, J=7.2 Hz), 4.28 (2H, q, J=7.2 Hz), 5.60 (2H, s), 7.03–7.07 (2H, m), 7.20–7.32 (3H, m), 8.26 (1H, s), 8.57 (1H, s), 11.20 (1H, s).

(2) Ethyl 2-benzyl-4-butoxy-6,7-dichloro-1-oxo-1,2-dihydro-3-isoquinolinecarboxylate (synthesized according to the method similar to that in Example 1 (2))

$^1$H-NMR(CDCl$_3$) δ: 0.98 (3H, t, J=7.3 Hz), 1.13 (3H, t, J=7.2 Hz), 1.40–1.59 (2H, m), 1.70–1.83 (2H, m), 3.92 (2H, t, J=6.4 Hz), 4.17 (2H, q, J=7.2 Hz), 5.34 (2H, s), 7.16–7.31 (5H, m), 7.83. (1H, s), 8.56 (1H, s).

(3) 2-Benzyl-4-butoxy-6,7-dichloro-1-oxo-1,2-dihydro-3isoquinolinecarboxylic acid (synthesized according to the method similar to that in Example 4 (3))

Melting point 128–129° C. Elemental analysis for $C_{21}H_{19}NO_4Cl_2$ Calculated: C, 60.01; H, 4.59; N, 3.33. Found: C, 60.00; H, 4.40; N, 3.11. $^1$H-NMR(CDCl$_3$) δ: 0.97 (3H, t, J=7.3 Hz), 1.41–1.60 (2H, m), 1.72–1.86 (2H, m), 3.97 (2H, t, J=6.4 Hz), 4.83 (1H, bs), 5.42 (2H, s), 7.18–7.26 (5H, m), 7.83 (.1H, s), 8.53 (1H, s).

(4) 2-Benzyl-4-butoxy-6,7-dichloro-3-hydroxymethyl-1 (2H)-isoquinolinone (synthesized according to the method similar to that in Example 4 (4))

Melting point 110–111° C. Elemental analysis for $C_{21}H_2NO_3Cl_2$ Calculated: C, 62.08; H, 5.21; N, 3.45. Found: C, 62.01; H, 5.28; N, 3.25. $^1$H-NMR(CDCl$_3$) δ: 1.02 (3H, t, J=7.1 Hz), 1.47–1.65 (2H, m), 1.77–1.91 (2H, m), 2.23 (1H, bs), 3.87 (2H, t, J=6.6 Hz), 4.65 (2H, d, J=5.6 Hz), 5.9 (2H, s), 7.12–7.16 (2H, m), 7.25–7.34(3H, m), 7.78 (1H, d, J=1.7 Hz), 8.50 (1H, d, J=1.7 Hz).

(5) 2-Benzyl-4-butoxy-3-chloromethyl-6,7-dichloro-1 (2H)-isoquinolinone (synthesized according to the method similar to that in Example 4 (5))

$^1$H-NMR(CDCl$_3$) δ: 1.03 (3H, d, J=7.2 Hz), 1.53–1.64 (2H, m), 1.80–1.95 (2H, m), 4.00 (2H, t, J=6.4 Hz), 4.60 (2H, s), 5.60 (2H, s), 7.10–7.34 (5H, m), 7.85 (11H, s), 8.58 (1H, s).

(6) 2-{(2-Benzyl-4-butoxy-6,7-dichloro-1-oxo-1,2-dihydro-3-isoquinolinyl)methyl}-1H-isoindole-1,3(2H)-dione (synthesized according to the method similar to that in Example 4 (6))

Melting point 161–162° C. Elemental analysis for $C_{29}H_{28}N_2O_4Cl_2$ Calculated: C, 65.05; H, 4.52; N, 5.23. Found: C, 64.98; H, 4.64; N, 5.07. $^1$H-NMR(CDCl$_3$) δ: 1.01 (3H, t, J=7.3, Hz), 1.47–1.65. (2H, m), 1.80–1.94 (2H, m), 4.12 (2H, t, J=6.7 Hz), 5.02 (2H, s), 5.37 (2H, s), 6.65–6.72 (1H, m), 6.78–6.92 (4H, m), 7.51–7.60 (4H, m), 7.90 (1H, s), 8.53 (1H, s).

(7) Tert-butyl(2-benzyl-4-butoxy-6,7-dichloro-1-oxo-1,2-dihydro-3-isoquinolinyl)methylcarbamate (synthesized according to the method similar to that in Example 1 (6))

Melting point 151–152° C. Elemental analysis for $C_{26}H_{30}N_2O_4Cl_2$ Calculated: C, 61.78; H, 5.98; N, 5.54. Found: C, 61.73; H, 6.17; N, 5.45. $^1$H-NMR(CDCl$_3$) δ: 1.02 (3H, t, J=7.3 Hz), 1.42 (9H, s), 1.47–1.60 (2H, m), 1.76–1.87 (2H, m), 3.83 (2H, t, J=6.6. Hz), 4.38 (2H, d, J=6.0 Hz), 4.74 (1H, bs), 5.45 (2H, s), 7.19–7.35 (5H, m), 7.78(1H, s), 8.53 (1H, s).

(8) 3-(Aminomethyl)-2-benzyl-4-butoxy-6,7-dichloro-1 (2H)-isoquinoline hydrochloride (synthesized according to the method similar to that in Example 1 (7))

Melting point 191–192° C. Elemental analysis for $C_{21}H_{23}N_2O_2Cl_3$ Calculated: C, 57.09; H, 5.25; N, 6.34. Found: C, 56.77; H, 5.14; N, 6.04. $^1$H-NMR(DMSO-d$_6$) δ: 0.97 (3H, t, J=7.3 Hz), 1.43–1.59 (2H, m), 1.76–1.90 (2H, m), 3.91–3.98 (4H, m), 5.47 (2H, s), 7.18–7.22 (2H, m), 7.28–7.39 (3H, m), 7.96 (1H, s), 8.43 (1H, s), 8.89 (3H, bs).

Example 29

3-(Aminomethyl)-6,7-dichloro-2-isobutyl-4-pentyloxy-1(2H)-isoquinolinone hydrochloride (1) Ethyl 6,7-dichloro-2-isobutyl-1-oxo-4-pentyloxy-1,2-dihydro-3-isoquinolinecarboxylate synthesized according to the method similar to that in Example 1 (2))

$^1$H-NMR(CDCl$_3$) δ: 0.90 (6H, d, J=6.6 Hz), 0.96 (3H, t, J=6.6 Hz), 1.29–1.54 (7H, m), 1.74–1.87 (2H, m), 2.05–2.17 (1H, m), 3.90 (2H, d, J=5.8 Hz), 3.93 (2H, t, J=6.6 Hz), 4.46 (2H, q, J=7.1 Hz), 7.81 (1H, s), 8.51 (1H, s).

(2) 6,7-Dichloro-2-isobutyl-1-oxo-4-pentyloxy-1,2-dihydro-3-isoquinolinecarboxylic acid (synthesized according to the method similar to that in Example 4 (3))

Melting point 124–125° C. Elemental analysis for $Cl_{19}H_{23}NO_4Cl_2$ Calculated: C, 57.01; H, 5.79; N, 3.50. Found: C, 57.13; H, 5.72 N, 3.40. $^1$H-NMR(CDCl$_3$) δ: 0.90 (6H, d, J=6.6 Hz), 0.95 (3H, t, J=6.6 Hz), 1.31–1.57 (4H, m), 1.7–1.91 (2H, m), 2.07–2.21 (1H, m), 3.95–4.04 (4H, m), 4.35 (1H, bs), 7.75 (1H, s), 8.45 (1H, s).

(3) 6,7-Dichloro-3-hydroxymethyl-2-isobutyl-4-pentyloxy-1(2H)-isoquinolinone (synthesized according to the method similar to that in Example 4 (4))

Melting point 86–87° C. Elemental analysis for $C_{19}H_{25}NO_3Cl_2$ Calculated: C, 59.07; H, 6.52; N, 3.63. Found: C, 58.91; H, 6.65; N, 3.48. $^1$H-NMR(CDCl$_3$) δ: 0.82 (6H, d, J=6.6 Hz), 0.99 (3H, t, J=7.0 Hz), 1.39–1.59 (4H, m), 1.82–1.92 (2H, m), 2.07–2.17 (1H, m), 2.67 (1H, bs), 3.87 (2H, t, J=6.4 Hz), 4.09 (2H, d, J=7.6 Hz), 4.78 (2H, d, J=4.8 Hz), 7.69 (1H, s), 8.35 (1H, s).

(4) 3-Chloromethyl-6,7-dichloro-2-isobutyl-4–4pentyloxy-1(2H)-isoquinoline (synthesized according to the method similar to that in Example 4,(5))

$^1$H-NMR(CDCl$_3$) δ: 0.96 (6H, d, J=6.6 Hz), 0.99 (3H, t, J=7.0 Hz), 1.36–1.61 (4H, m), 1.84–1.98 (2H, m), 2.05–2.22

(1H, m), 3.96 (2H, t, J=6.4 Hz), 4.07 (2H, d, J=7.6 Hz), 4.78 (2H, s), 7.81 (1H, s), 8.51 (1H, s).

(5) 2-{(6,7-Dichloro-2-isobutyl-1-oxo-4-pentyloxy-1,2-dihydro-3-isoquinolinyl)methyl}-1H-isoindole-1,3(2H)-dione (synthesized according to the method similar to that in Example 4 (6))

Melting point 119–120° C. Elemental analysis for $C_{27}H_{28}N_2O_4Cl_2$ Calculated: C, 62.92; H, 5.48; N, 5.43. Found: C, 62.95; H, 5.43; N, 5.55. $^1$H-NMR(CDCl$_3$) δ: 0.88–1.04 (9H, m), 1.30–1.54 (4H, m), 1.80–1.90 (2H, m), 2.05–2.17 (1H, m), 3.90–4.05 (4H, m), 5.06 (2H, s), 7.70–7.89 (5H, m), 8.49 (1H, s).

(6) Tert-butyl(6,7-dichloro-2-isobutyl-1-oxo-4-pentyloxy-1,2-dihydro-3-isoquinolinyl)methylcarbamate (synthesized according to the method similar to that in Example 1 (6))

Melting point 113–114° C. Elemental analysis for $C_{24}H_{34}N_2O_4Cl_2$ Calculated: C, 59.39; H, 7.06; N, 5.77. Found: C, 59.39; H, 7.00; N, 5.67. $^1$H-NMR(CDCl$_3$) δ: 0.95 (6H, d, J=6.6 Hz), 0.98 (3H, t, J=7.1 Hz), 1.38–1.57 (13H, m), 1.81–1.95 (2H, m), 2.07–2.21 (1H, m), 3.84 (2H, t, J=6.6 Hz), 3.97 (2H, d, J=7.4 Hz), 4.49 (2H, d, J=5.4 Hz), 4.81 (1H, bs), 7.75 (1H, s), 8.46 (1H, s).

(7) 3-(Aminomethyl)-6,7-dichloro-2-isobutyl-4-pentyloxy- 1(2H)-isoquinolinone, hydrochloride (synthesized according to the method similar to that in Example 1 (7))

Melting point 167–169° C. Elemental analysis for $C_{19}H_{27}N_2O_2Cl_3$ Calculated: C, 54.10; H, 6.45; N, 6.64. Found: C, 54.09; H, 6.45; N, 6.54. $^1$H-NMR(DMSO-d$_6$) δ: 0.88 (6H, d, J=7.0 Hz), 0.95,(3H, t, J=7.0 Hz), 1.31–1.57 (4H, m), 1.80–2.10 (3H, m), 3.91–3.99 (4H, m), 4.17 (2H, s), 7.92 (1H, s), 8.38 (1H, s), 8.72 (3H, bs).

Example 30

3-(Aminomethyl)-4-butoxy-6,7-dichloro-2-isopropyl-1(2H)-isoquinolinone hydrochloride (1) Ethyl 6,7-dichloro-4-hydroxy-2-isopropyl-1-oxo-1,2-dihydro-3-isoquinolinecarboxylate (synthesized according to the method similar to that in Example 1 (1))

Melting point 124–125° C. Elemental analysis for $C_{15}H_{15}NO_4Cl_2 \cdot ½H_2O$ Calculated: C, 51.01; H, 4.57; N, 3.97. Found: C, 51.23; H, 4.25; N, 3.86. $^1$H-NMR(CDCl$_3$) δ: 1.45 (3H, t, J=7.1 Hz), 1.62 (6H, d, J=6.6 Hz), 4.19–4.33: (1H, m), 4.47 (2H, q, J=7.17 Hz), 8.17 (1H, s), 8.46 (1H, s), 10.64 (1H, s).

(2) Ethyl 4-butoxy-6,7-dichloro-2-isopropyl-1-oxo-1,2-dihydro-3-isoquinolinecarboxylate (synthesized according to the method similar to that in Example 1 (2))

$^1$H-NMR(CDCl$_3$) δ: 1.01 (3H, t, J=7.1 Hz), 1.44 (3H, t, J=7.2 Hz), 1.46–1.59 (2H, m), 1.64 (6H, d, J=6.6 Hz), 1.71–1.85 (2H, m), 3.93 (2H, t, J=6.4 Hz), 4.01–4.18 (1H, m), 4.45 (2H, q, J=7.2 Hz), 7.77 (1H, s), 8.47 (1H, s).

(3) 4-Butoxy-6,7,-dichloro-2-isopropyl-1-oxo-1,2-dihydro-3-isoquinolinecarboxylic acid (synthesized according to the method similar to that in Example 4 (3))

Melting point 186–187° C. Elemental analysis for $C_{17}H_{19}NO_4Cl_2$ Calculated: C, 54.85; H, 5.14; N, 3.76. Found: C, 54.90; H, 5.12; N, 3.68. $^1$H-NMR(CDCl$_3$) δ: 0.99 (3H, t, J=7.3 Hz), 1.44–1.62 (2H, m), 1.68 (6H, d, J=6.6 Hz), 1.74–1.88 (2H, m), 4.00 (2H, t, J=6.4 Hz), 4.21–4.34 (1H, m), 5.11 (1H, bs), 7.80 (1H, s), 8.51 (1H, s).

(4) 4-Butoxy-6,7-dichloro-3-hydroxymethyl-2-isopropyl-1(2H)-isoquinolinone (synthesized according to the method similar to that in Example 4 (4))

Melting point 150–151° C. Elemental analysis for $C_{17}H_{21}NO_3Cl_2 \cdot ¼H_2O$ Calculated: C, 56.29; H, 5.97, N, 3.86. Found: C, 56.53; H, 6.01; N, 3.96. $^1$H-NMR(CDCl$_3$) δ: 1.03 (3H, t, J=7.4 Hz), 1.44–1.66 (2H, m), 1.67 (6H, d, J=7.0 Hz), 1.78–1.92 (2H, m), 2.04 (1H, bs), 3.85 (2H, t, J=6.6 Hz), 4.64–4.74 (1H, m), 4.81 (2H, s), 7.73 (1H, s), 8.44 (1H, s).

(5) 4-Butoxy-3-chloromethyl-6,7-dichloro-2-isopropyl-1 (2H)-isoquinolinone (synthesized according to the method similar to that in Example 4 (5))

$^1$H-NMR(CDCl$_3$) δ: 1.05 (3H, t, J=7.1 Hz), 1.51–1.66 (2H, m), 1.70 (6H, d, J=6.6 Hz), 1.78–1.95 (2H, m), 3.96 (2H, t, J=6.4 Hz), 4.47–4.60 (1H, m), 4.77 (2H, s), 7.77 (1H, s), 8.46 (1H, s). (6) 2-[(4-Butoxy-6,7-dichloro-2-isopropyl-1-oxo-1,2-dihydro-3-isoquinolinyl)methyl]-1H-isoindole-1,3 (2H)-dione (synthesized according to the method similar to that in Example 4 (6))

Melting point 185–186° C. Elemental analysis for $C_{25}H_{24}N_2O_4Cl_2$ Calculated: C, 61.61; H, 4.96; N, 5.75. Found: C, 61.71; H, 4.89; N, 5.66. $^1$H-NMR(CDCl$_3$) δ: 1.01 (3H, t, J=7.4 Hz), 1.47 (6H, d, J=6.6 Hz), 1.48–1.68 (2H, m), 1.80–1.94 (2H, m), 4.05 (2H, t, J=6.6 Hz), 4.19–4.32 (1H, m), 5.09 (2H, s), 7.73–7.89 (5H, m), 8.43 (1H, s). (7) Tert-butyl(4-butoxy-6.7-dichloro-2-isopropyl-1-oxo-1,2-dihydro-3-isoquinolinyl)methylcarbamate (synthesized according to the method similar to that in Example 1 (6))

Melting point 169.5–170° C. Elemental analysis for $C_{22}H_{30}N_2O_4Cl_2$ Calculated: C, 57.77; H, 6.61; N, 6.12. Found: C, 57.74; H, 6.76; N, 6.13. $^1$H-NMR(CDCl$_3$) δ: 1.03 (3H, t, J=7.4 Hz), 1–47 (9H, s), 1.48–1.62 (2H, m), 1.63, (6H, d, J=6.6 Hz), 1.71–1.92 (2H, m), 3.81 (2H, t, J=6–4 Hz), 4.41–4.52 (1H, m), 4.53 (2H, d, J=5.4 Hz), 4.67 (1H, bs), 7.73 (1H, s), 8.45 (1H, s).

(8) 3-(Aminomethyl)-4-butoxy-6,7-dichloro-2-isopropyl-1(2H)-isoquinolinone hydrochloride (synthesized according to the method similar to that in Example 1 (7)

Melting point 264–265° C. Elemental analysis for $C_{17}H_{23}N_2O_2Cl_3$ Calculated: C, 51.86; H, 5.89; N, 7.11. Found: C, 52.00; H, 5.70; N, 7.18. $^1$H-NMR(DMSO-d$_6$) δ: 0.99 (3H, t, J=7.1 Hz), 1.45–1.56 (2H, m), 1.57 (6H, d, J=6.6 Hz), 1.77–1.91 (2H, m), 3.90 (2H, t, J=6.4 Hz), 4.23 (2H, s), 4.36–4.49 (1H, m), 7.87 (1H, s), 8.34 (1H, s), 8.85 (3H, bs).

Example 31

3-(Aminomethyl)-4-butoxy-6,7-dichloro-2-cyclopropyl-1(2H)-isoquinolinone hydrochloride (1) Ethyl 2-cyclopropyl-6,7-dichloro-4-hydroxy-1-oxo-1, 2-dihydro-3-isoquinolinecarboxylate (synthesized according to the method similar to that in Example 1 (1)

Melting point 119.5–120° C. Elemental analysis for $C_{15}H_{13}NO_4C_2$ Calculated: C, 52.63; H, 3.83; N, 4.09. Found: C, 52.97; H, 3.90; N, 3.78. $^1$H-NMR(CDCl$_3$) δ: 0.62–0.70 (2H, m), 1.05–1.16 (2H, m), 1.44 (3H, t, J=7.2 Hz), 3.33–3.44 (1H, m), 4.48 (2H, q, J=7.2Hz), 8.16 (1H, s), 8.47 (1H, s), 10.58 (1H, s).

(2) Ethyl 4-butoxy-6,7-dichloro-2-cyclopropyl-1-oxo-1, 2-dihydro-3-isoquinolinecarboxylate (synthesized according to the method similar to that in,Example 1 (2))

Melting point 72.5–73.5° C. Elemental analysis for $C_{19}H_{21}NO_4Cl_2$ Calculated: C, 57.30; H, 5.31; N, 3.52. Found: C, 57.24; H, 5.24; N, 3.47. $^1$H-NMR(CDCl$_3$) δ: 0.82–0.91 (2H, m), 1.01 (3H, t, J=7.3 Hz), 1.01–1.15 (2H, m), 1.44 (3H, t, J=7.2 Hz), 1.43–1.60 (2H, m), 1.72–1.86 (2H, m), 3.10–3.22 (1H, m), 3.94 (2H, t, J=6.5 Hz), 4.46 (2H, q, J=7.2 Hz), 7.80 (1H, s), 8.47 (1H, s).

(3) 4-Butoxy-6,7-dichloro-2-cyclopropyl-1oxo-1,2-dihydro-3-isoquinolinecarboxylic acid (synthesized according to the method similar to that in Example 4

Melting point 198–201° C. Elemental analysis for $C_{17}H_{17}NO_4Cl_2$ Calculated: C, 55.15; H, 4.68; N, 3.78. Found: C, 55.14; H, 4.47; N, 3.73. $^1$H-NMR(CDCl$_3$) δ: 0.85–0.94 (2H, m), 1.00(3H, t, J=7.3 Hz), 1.14–1.30 (2H, m), 1.42–1.63 (2H, m), 1.75–1.89 (2H, m), 3.26–3.35 (1H, m), 4.00 (2H, t, J=6.4 Hz), 5.55 (1H, bs), 7.75 (1H, s), 8.41 (1H, s).

(4), 4-Butoxy-6,7-dichloro-2-cyclopropyl-3-hydroxyethyl-1(2H)-isoquinolinone (synthesized according to the method similar to that in Example 4 (4))

Melting point 145–146° C. Elemental analysis for $C_{17}H_{19}NO_3Cl_2$ Calculated: C, 57.32; H, 5.38; N, 3.93. Found: C, 57.28; H, 5.17; N, 3.97. $^1$H-NMR(CDCl$_3$) δ: 0.82–0.91 (2H, m), 1.06 (3H, t, J=7.2 Hz), 1.21–1.32 (2H, m), 1.51–1.70 (2H, m), 1.80–1.94 (2H, m), 3.04 (1H, bs), 3.13–3.22 (1H, m), 3.90 (2H, t, J=6.4 Hz), 4.98 (2H, d, J=5.8 Hz), 7.65 (1H, s), 8.25 (1H, s).

(5) 4-Butoxy-3-chloromethyl-6,7-dichloro-2-cyclopropyl-1(2H)-isoquinolinone (synthesized according to the method similar to that in Example 4 (5))

$^1$H-NMR(CDCl$_3$) δ: 0.87–0.95 (2H, m), 1.04 (3H, t, J=7.4 Hz), 1.22–1.37 (2H, m), 1.50–1.69 (2H, m), 1.80–1.95 (2H, m), 3.14–3.25 (1H, m), 3.93 (2H, t, J=6.6 Hz), 5.03 (2H, s), 7.76 (1H, s), 8.45 (1H, s).

(6) 2-(4-Butoxy-6,7-dichloro-2-cyclopropyl-1-oxo-1,2-dihydro-3-isoquinolinyl)methyl-1H-isoindole-1,3(2H)-dione (synthesized according to the method similar to that in Example 4 (6))

Melting point 197–198° C. Elemental analysis for $C_{25}H_{22}N_2O_4Cl_2$ Calculated: C, 61.87; H, 4.57; N, 5.77. Found: C, 61.93; H, 4.50; N, 5.84. $^1$H-NMR(-CDCl$_3$) δ: 0.82–0.91 (2H, m), 1.00 (3H, t, J=7.3 Hz), 1.26–1.37 (2H, m), 1.43–1.61 (2H, m), 1.75–1.90 (2H, m), 2.84–2.95 (1H, m), 3.98 (2H, t, J=6.8 Hz), 5.25 (2H, s), 7.69–7.84 (5H, m), 8.42 (1H, s).

(7) Tert-butyl(4-butoxy-6,7-dichloro-2-cyclopropyl-1-oxo-1,2-dihydro-3-isoquinolinyl)methylcarbamate (synthesized according to the method similar to that in Example 1 (6))

Melting point 143–144° C. Elemental analysis for $C_{22}H_{28}N_2O_4Cl_2$ Calculated: C, 58.03; H, 6.20; N, 6.15. Found: C, 58.09; H, 6.33; N, 5.95. $^1$H-NMR(CDCl$_3$) δ: 0.79–0.88 (2H, m), 1.04 (3H, t, J=7.3 Hz), 1.25–1.39 (2H, m), 1.44 (9H, s), 1.48–1.67 (2H, m) 1.76–1.93 (2H, m), 2.97–3.08 (1H, m), 3.86 (2H, t, J=6.6 Hz), 4.73 (2H, d, J=5.6 Hz), 4.95 (1H, bs), 7.71 (1H, s), 838 (1H, s).

(8) 3-(Aminomethyl)-4-butoxy-6,7-dichloro-2-cyclopropyl-1(2H)-isoquinoline hydrochloride (synthesized according to the method similar to that in Example 1 (7))

Melting point 238° C. Elemental analysis for $C_{17}H_{21}N_2O_2Cl_3$ Calculated: C, 52.12; H, 5.40; N, 7.15. Found: C, 51.96; H, 5.30; N, 6.99. $^1$H-NMR(DMSO-d$_6$) δ: 0.84–0.92 (2H, m), 0.99 (3H, t, J7.3 Hz), 1.19–1.30 (2H, m), 1.44–1.63 (2H, m), 1.77–1.91 (2H, m), 3.13–3.21 (1H, m), 3.93 (2H, t, J=6.0 Hz), 4.38 (2H, bs), 7.85 (1H, s), 8.30 (1H, s), 8.78 (3H, bs).

Example 32

3-(Aminomethyl)-4-butoxy-6,7-dichloro-2-cyclopropylmethyl-1(2H)-isoquinoline hydrochloride (1) Ethyl 6,7-dichloro-2-cyclopropylmethyl-4-hydroxy-1-oxo-1,2-dihydro-3-isoquinolinecarboxylate (synthesized according to the method similar to-that in Example 1 (1))

Melting point 109.5–110° C. Elemental analysis for $C_{16}H_{15}NO_4Cl_2$ Calculated: C, 53.95; H, 4.24; N, 3.93. Found: C, 54.03; H, 4.04; N, 3.95. $^1$H-NMR(CDCl$_3$) δ: 0.32–0.54 (4H, m), 0.96–1.16 (1H, m), 1.48 (3H, t, J=7.2 Hz), 4.33 (2H, d, J=6.8 Hz), 4.52 (2H, q, J=7.2 Hz), 8.23 (1H, s), 8.51 (1H, s), 11.17 (1H, s).

(2) Ethyl 4-butoxy-6,7-dichloro-2-cyclopropylmethyl-1-oxo-1,2-dihydro-3-isoquinolinecarboxylate (synthesized according to the method similar to that in Example 1 (2)

$^1$H-NMR(CDCl$_3$) δ: 0.38–0.57 (4H, m):, 1.01 (3H1, t, J=7.4 Hz), 1.16–1.26 (1H, m), 1.45 (3H, t, J=7.4 Hz), 1.47–1.62 (2H, m), 1.68–1.86 (2H, m), 3.89–3.99 (4H, m), 4.47 (2H, q, J=7.4 Hz), 7.81 (1H, s), 8.51 (1H, s).

(3) 4-Butoxy-6,7-dichloro-2-cyclopropylmethyl-1-oxo-1,2-dihydro-3-isoquinolinecarboxylic acid (synthesized according to the method similar to that in Example 4 (3))

Melting point 150–151° C. Elemental analysis for $C_{18}H_{19}NO_4Cl_2$ Calculated: C, 56.26; H, 4.98; N, 3.65. Found: C, 56.45; H, 5.02; N, 3.67. $^1$H-NMR(CDCl$_3$) δ: 0.41–0.58 (4H, m), 1.00 (3H, t, J=7.3 Hz), 1.20–1.33 (1H, m), 1.45–1.64 (2H, m), 1.76–1.90 (2H, m), 4.01 (2H, t, J=6.5 Hz), 4.06 (2H, d, J=7.4 Hz), 7.74 (1H, s), 8.46 (1H, s).

(4) 4-Butoxy-6,7-dichloro-2-cyclopropylmethyl-3-hydroxymethyl-1(-2H)-isoquinoline (synthesized according to the method similar to that in Example 4 (4))

Melting point 130–130.5° C. Elemental analysis for $C_{18}H_{21}NO_3Cl_2$ Calculated: C, 58.39; H, 5.72; N, 3.78. Found: C, 58.46; H, 5.84; N, 3.77. $^1$H-NMR(CDCl$_3$) δ: 0.46–0.58 (4H, m), 1.04(3H, t, J=7.4 Hz), 1.08–1.24 (1H, m), 1.50–1.68 (2H, m), 1.79–1.94 (2H, m), 2.33 (1H, bs), 3.88 (2H, t, J=6.8 Hz), 4.19 (2H, d, J=7.0 Hz), 4.83 (2H, d, J=5.6 Hz), 7.72 (1H, s), 8.42 (1H, s).

(5) 4-Butoxy-3-chloromethyl-6,7-dichloro-2-cyclopropylmethyl-1(2H)-isoquinolinone (synthesized according to the method similar to that in Example 4

$^1$H-NMR(CDCl$_3$) δ: 0.44–0.62 (4H, m), 1.02–1.15 (4H, m), 1.52–1.71 (2H, m), 1.83–1.97 (2H, m), 3.99 (2H, t, J=6.6 Hz), 4.20 (2H, d, J=6.6 Hz), 4.83 (2H, s), 7.81 (1H, s), 8.51 (1H, s).

(6) 2-(4-Butoxy-6,7-dichloro-2-cyclopropylmethyl-1-oxo-1,2-dihydro-3-isoquinolinyl)methyl-1H-isoindole-1,3 (2H)-dione (synthesized according to the method similar to that in Example 4 (6))

Melting point 162–163° C. Elemental analysis for $C_{26}H_{24}N_2O_4Cl_2$ Calculated: C, 62.53; H, 4.84; N, 5.61. Found: C, 62.64; H, 4.77; N, 5.61. $^1$H-NMR(CDCl$_3$) δ: 0.47–0.50 (4H, m), 0.95–1–08 (4H, m), 1.43–1.62 (2H, m), 1.78–1.92 (2H, m), 3.98 (2H, t, J=6.7 Hz), 4.15 (2H, d, J=6.6 Hz), 5.05 (2H, s), 7.71–7.86 (5H, m), 8.49 (1H, s).

(7) Tert-butyl(4-butoxy-6,7-dichloro-2-cyclopropylmethyl-1-oxo-1,2-dihydro-3-isoquinolinyl)methylcarbamate (synthesized according to the method similar to that in Example 1 (6))

Melting point 1.41.5–142.5° C. Elemental analysis for $C_{23}H_{30}N_2O_4Cl_2$ Calculated: C, 58.85; H, 6.44; N, 5.97. Found: C, 58.84; H, 6.32; N, 6.04. $^1$H-NMR(CDCl$_3$) δ: 0.50–0.59 (4H, m), 1.04 (3H, t, J=7.4 Hz), 1.08–1.28 (1H, m), 1.47 (9H, s), 1.53–1.6.8 (2H, m), 1.80–1.94 (2H, m), 3.86 (2H, t, J=6.4 Hz), 4.08 (2H, d, J=6.6 Hz), 4.52 (2H, d, J=5.8 Hz), 4.87 (11H bs), 7.74 (1H, s), 8.45. (1H, s).

(8) 3-(Aminomethyl)-4-butoxy-6,7-dichloro-2cyclopropylmethyl-1(2H)-isoquinoline hydrochloride (synthesized according to the method similar to that in Example 1 (7))

Melting point 227–228° C. Elemental analysis for $C_{18}H_{23}N_2O_2Cl_3$ Calculated: C, 53.28; H, 5.71; N, 6.90. Found: C, 53.18; H, 5.71; N, 6.75. $^1$H-NMR(DMSO-d$_6$) δ: 0.47 (4H, d, J=6.6 Hz), 1.00 (3H, t, J=7.3 Hz), 1.13–1.26 (1H, m), 1.45–1.64 (2H, m), 1.78–1.92(4H, m), 3.96 (3H, t, J=6.4 Hz), 4.06 (6H, d,: J=6.6 Hz), 4.20 (2H, d, J=4.0 Hz), 7.92 (1H, s), 8.39 (1H, s), 8.72 (3H, bs).

Example 33

3-(Aminomethyl)-4-butoxy-6,7-dichloro-2-isopentyl-1(2H)-isoquinolinone hydrochloride (1) Ethyl 6,7-dichloro-4-hydroxy-2-isopentyl-1-oxo-1,2-dihydro-3-isoquinolinecarboxylate (synthesized according to the method similar to that in Example 1 (1))

Melting point 118–120° C. Elemental analysis for $C_{16}H_{15}NO_4Cl_2$ Calculated: C, 54.85; H, 5.14; N, 3.76. Found: C, 54.63; H, 5.03; N, 3.52. $^1$H-NMR(CDCl$_3$) δ: 0.96 (6H, d, J=6.2 Hz), 1.47 (3H, t, J=7.2 Hz), 1.58–1.65 (3H, m), 4.26–4.34 (2H, m), 4.52 (2H, q, J=7.2 Hz), 8.22 (1H, s), 8.51 (1H, s), 11.24 (1H, s).

(2) Ethyl 4-butoxy-6,7-dichloro-2-isopentyl-1-oxo-1,2-dihydro-3-isoquinolinecarboxylate (synthesized according to the method similar to that in Example 1 (2))

$^1$H-NMR(CDCl$_3$) δ: 0.95 (6H, d, J=6.2 Hz), 1.01 (3H, t, J=7.0 Hz), 1.39–1.86 (10H, m), 3.91–3.98 (4H, m), 4.46 (2H, q, J=7.2 Hz), 7.80 (1H, s), 8.50 (1H, s).

(3) 4-Butoxy-6,7-dichloro-2-isopentyl-1-oxo-1,2-dihydro-3-isoquinolinecarboxylic acid (synthesized according to the method similar to that in Example 4 (3))

Melting point 100–101° C. Elemental analysis for $C_{19}H_{23}NO_4Cl_2$ Calculated: C, 5.7.01; H, 5.79; N, 3.50. Found: C, 56.83; H, 5.88; N, 3.51. $^1$H-NMR(CDCl$_3$) δ: 0.94–1.03 (98H, m), 45–1.88 (7H, m), 3.99 (2H, t, J=6.4 Hz), 4.04–4.11 (2H, m), 5.59 (1H, bs), 7.76 (1H, s), 8.46 (1H, s).

(4-Butoxy-6,7-dichloro-3-hydroxymethyl-2-isopentyl-1 (2H)-isoquinolinone (synthesized according to the method similar to that in Example 4 (4))

Melting point 102–103.5° C. Elemental analysis for $C_{19}H_{25}NO_3Cl_2$ Calculated: C, 59.07; H, 6.52; N, 3.63. Found: C, 58.78; H, 6.64; N, 3.60. $^1$H-NMR(CDCl$_3$) δ: 0.99 (6H, d, J=6.6 Hz), 1.04 (3H, t, J=7.4 Hz), 1.49–1.92 (7H, m), 2.56 (1H, bs), 3.86 (2H, t, J=6.5 Hz), 4.18–4.26 (21H, m), 4.76 (2H, s), 7.69 (1H, s), (5) 4-Butoxy-3-chloromethyl-6,7-dichloro-2-isopentyl-1(2H)-isoquinolinone (synthesized according to the method similar to that in Example 4 (5))

$^1$H-NMR(CDCl$_3$) δ: 1.01 (6H, d, J=6.2 Hz), 1.05 (3H, t, J=7.3 Hz), 1.52–1.96 (7H, m), 3.98 (2H, t, J=6.4 Hz), 4.10–4.25 (2H, m), 4.75 (2H, s), 7.81 (1H, s), 8.50 (1H, s).

(6) 2-[(4-Butoxy-6,7-dichloro-2-isopentyl-1-oxo-1,2-dihydro-3-isoquinolinyl)methyl]-1H-isoindole-1,3(2H)-dione (synthesized according to the method similar to that in Example 4 (6))

Melting point 115–119° C. Elemental analysis for $C_{27}H_{26}N_2O_4Cl_2$ Calculated: C, 62.92;H, 5.48; N, 5.43. Found: C, 63.10; H, 5.30; N, 5.76. $^1$H-NMR(CDCl$_3$) δ: 0.85 (6H, d, J=6.4 Hz), 1.00 (3H, t, J=7.2 Hz), 1.38–1.63 (5H, m), 1.78–1.92 (2H, m), 3.99 (2H, t, J=6.8 Hz), 4.07–4.15 (2H, m), 5.02 (2H, s), 7.73–7.90 (5H, m), 8.48 (1H, s).

(7) Tert-butyl(4-butoxy-6,7-dichloro-2-isopentyl-1-oxo-1,2-dihydro-3-isoquinolinyl)methylcarbamate (synthesized according to the method similar to that in Example 1 (6))

Melting point 129–129° C. Elemental analysis for $C_{24}H_{34}N_2O_4Cl_2$ Calculated: C, 59.38; H, 7.06; N, 5.77. Found: C, 59.48; H, 7.32; N, 5.80. $^1$H-NMR(CDCl$_3$) δ: 0.99 (6H, d, J=6.6 Hz), 1.04 (3H, t, J=7.3 Hz), 1.47 (9H, s), 1.52–1.699 (4H, m), 1.73–1.93 (3H, m), 3.83 (2H, t, J=6.5 Hz), 4.06–4.14 (2H, m), 4.47 (2H, d, J=6.4 Hz), 4.72 (1H, bs), 7.75 (1H, s), 8.47 (1H, s).

(8) 3-(Aminomethyl)-4-butoxy-6,7-dichloro-2-isopentyl-1(2H)-isoquinolinone hydrochloride (synthesized according to the method similar to that in Example 1 (7))

Melting point 251–253° C. Elemental analysis for $C_{19}H_{27}N_2O_2Cl_3$ Calculated: C, 54.10; H, 6.4.5; N, 6.64. Found: C, 54.13; H, 6.44; N, 6.64. $^1$H-NMR(DMSO-d$_6$) δ: 0.96 (6H, d, J=6.6 Hz), 1.00 (3H, t, J=7.3 Hz), 1.42–1.92 (7H, m), 3.94 (2H, t, J=6.6 Hz), 4.05–4.13 (4H, m), 7.91 (1H, s), 8.38 (1H, s), 8.79 (3H, bs).

Example 34

3-(Aminomethyl)-6,7-dichloro-4-isobutoxy-2-neopentyl-1(2H)-isoquinolinone hydrochloride (1) Ethyl 6,7-dichloro-4-isobutoxy-2-neopentyl-1-oxo-1, 2-dihydro-3-isoquinolinecarboxylate (synthesized according to the method similar to that in Example 1 (2))

$^1$H-NMR(CDCl$_3$) δ: 0.93 (9H, s), 1.08 (6H, d, J=6.6 Hz), 1.43 (3H, t, J=7.1 Hz), 2.04–2.19 (1H, m), 3.70 (2H, d, J=6.6 Hz), 4.04 (2H, bs), 4.42 (2H, q, J=7.1 Hz), 7.83. (1H, s), 8.51 (1H, s).

(2) 6,7-Dichloro-4-isobutoxy-2neopentyl-1-oxo-1,2-dihydro-3-isoquinolinecarboxylic acid (synthesized according to the method similar to that in Example 4 (3))

Melting point 156–157° C. Elemental analysis for $C_{19}H_{23}NO_4Cl_2$ Calculated: C, 57.01; H, 5.79; N, 3.50. Found: C, 57.14; H, 5.55; N, 3.58. $^1$H-NMR(CDCl$_3$) δ: 0.93 (9H, s), 1.10 (6H, d, J=6.6 Hz), 2.11–2.24 (1H, m), 3.78 (22H, d, J=6.2 Hz), 4.21 (2H, bs), 7.76(1H, s), 8.43 (1H, s).

(3) 6,7-Dichloro-3-hydroxyethyl-4-isobutoxy-2neopentyl-1 (2H)-isoquinolinone (synthesized according to the method similar to that in Example 4 (4))

Melting point 180–180.5° C. Elemental analysis for $C_{19}H_{25}NO_3Cl_2$ ½H$_2$O Calculated: C, 58.39; H, 6.58; N, 3.58 Found: C, 58.52; H, 6.68; N, 3.57. $^1$H-NMR(CDCl$_3$) δ: 0.94 (9H, s), 1.16 (6H, d, J=6.6 Hz), 2.12–2.29 (1H, m), 3.09 (1H, bs), 3.67 (2H, d, J=6.2 Hz), 4.21 (2H, bs), 4.83 (2H, bs), 7.67–7.68 (1H, m), 8.22–8.26 (1H, m).

(4) 3-Chloromethyl-6,7-dichloro-4-isobutoxy-2-neopentyl-1(2H)-isoquinolinone (synthesized according to the method similar to that in Example 4 (5))

$^1$H-NMR(CDCl$_3$) δ: 0.98 (9H, s), 1.15 (6H, d, J=6.6 Hz), 2.15–2.25 (1H, m), 3.71 (2H, d, J=6.2 Hz), 4.19 (2H, bs), 4.85 (2H, bs), 7.81 (1H, s), 8.50 (1H, s).

(5) 2-(6,7-Dichloro-1-oxo-4-isobutoxy-2-neopentyl-1,2-dihydro-3-isoquinolinyl)methyl-1H-isoindole-1,3(2H)-dione (synthesized according to the method similar to that in Example 4 (6))

Melting point 147–148° C. Elemental analysis for $C_{27}H_{28}N_2O_4Cl_2$ Calculated: C, 62.92; H, 5.48; N, 5.43.Found: C, 62.85; H, 5.59; N, 5.42. $^1$H-NMR(CDCl$_3$) δ: 100 (9H, s), 1.11 (6H, d, J=6.6 Hz), 2.17–2.31 (1H, m), 3.76 (2H, d, J=6.6 Hz), 4.03 (2H, bs), 5.05 (2H, s), 7.71–7.84 (5H, m), 8.47 (1H, s).

(6) Tert-butyl(6,7-dichloro-4-isobutoxy-2-neopentyl-1-oxo-1,2-dihydro-3-isoquinolinyl)methylcarbamate (synthesized according to the method similar to that in Example 1 (6))

Melting point 171–172° C. Elemental analysis for $C_{24}H_{34}N_2O_4Cl_2$ Calculated: C, 59.38; H, 7.06; N, 5.77. Found: C, 59.49; H, 6.96; N, 5.91. $^1$H-NMR(CDCl$_3$) δ: 0.98 (9H, s), 1.13 (6H, d, J=6.6 Hz), 1.46 (9H, s), 2.13–2.27 (11, m), 3.61 (2H, d, J=6.2 Hz), 4.12 (2H, bs), 4.54 (2H, d, J=5.4 Hz), 4.77(1H, bs), 7.76 (1H, s), 8.45 (1H, s).

(7) 3-(Aminomethyl)-6,7-dichloro-4-isobutoxy-2neopentyl-1(2H)-isoquinolinone hydrochloride (synthesized according to the method similar to that in Example 1 (7))

Melting point 254–256° C. Elemental analysis for $C_{19}H_{27}N_2O_2Cl_3$ Calculated: C, 54.10; H, 6.45; N, 6.64. Found: C, 53.76; H, 6.40; N, 6.47. $^1$H-NMR(DMSO-d$_6$) δ: 0.91 (9H, s), 1.10 (6H, d, J=6.6 Hz), 2.14–2.27 (1H, m), 3.73 (2H, d, J=6.6 Hz), 4.11 (2H, bs), 4.24 (2H, s), 7.89 (1H, s), 8.38 (1H, s), 8.63 (3H, bs).

Example 35

3-(Aminomethyl)-4-butoxy-6,7-dichloro-2-[3oxo-(1pyrrolidinyl)propyl]-1(2H)-isoquinolinone hydrochloride (1) tert-butyl 6,7-dichloro-2-(3-ethoxy-3-oxypropyl)-4-hydroxy-1-oxo-1,2-dihydro-3-isoquinolinecarboxylate (synthesized according to the method similar to that in Example 1(1))

Melting point 114–115° C. Elemental analysis for $C_{19}H_{21}NO_6Cl_2$ Calculated: C, 53.04; H, 4.92; N, 3.26. Found: C, 53.04; H, 4.94; N, 3.16. $^1$H-NMR(CDCl$_3$) δ: 1.24 (3H, t, J=7.2 Hz), 1.66 (9H, s), 2.86–2.93 (2H, m), 4.15 (2H, q, J=7.2 Hz), 4.39–4.47 (2H, m), 8.22 (1H, s), 8.49 (1H, s), 11.30 (1H, s).

(2) Tert-butyl 4-butoxy-6,7-dichloro-2-(3-ethoxy-3-oxypropyl)-1-oxo-1,2-dihydro-3-isoquinolinecarboxylate (synthesized according to the method similar to that in Example 1 (2))

Melting point 89–90° C. Elemental analysis for $C_{23}H_{29}NO_6Cl_2$ Calculated: C, 56.80; H, 6.01; N, 2.88. Found: C, 56.84; H, 5.93; N, 2.92. $^1$H-NMR(CDCl$_3$) δ: 1.01 (3H, t, J=7.4 Hz), 1.26 (3H, t, J=7.1 Hz), 1.48–1.61 (2H, m), 1.64 (9H, s), 1.74–1.85 (2H, m), 2.82–2.90 (2H, m), 3.95 (2H, t, J=6.4 Hz), 4.12–4.22(4H, m), 7.80(1H, s), 8.48 (1H, s).

(3) A solution of tert-butyl 4-butoxy-6,7-dichloro-2-(3ethoxy-3-oxypropyl)-1-oxo-1,2-dihydro-3-isoquinolinecarboxylate (2.43 g, 5 mmol) in trifluoroacetic acid (10 ml) was stirred at room temperature for 2 h. The reaction mixture was concentrated under reduced pressure and the residue was recrystallized from ethyl acetate -diisopropyl ether to give 4-butoxy-6,7-dichloro-2-(3-ethoxy-3-oxypropyl)-1-oxo-1,2-dihydro-3-isoquinolinecarboxylic acid (2.06 g, 95.8%) as crystals.

Melting point 117.5–118° C. Elemental analysis for $C_{19}H_{21}NO_6Cl_2$ Calculated: 53.304; H, 4.92; N, 3.26. Found: C, 53.20; H, 4.83; N, 3.30. $^1$H-NMR(CDCl$_3$) δ: 1.00 (3H, t, J=7.3 Hz), 1.24 (3H, t, J=7.2 Hz), 1.44–1.63 (2H, m), 1.75–1.89 (2H, m), 2.96 (2H, t, J=7.3.Hz), 4.00 (2H, t, J=6.4 Hz), 4.15 (2H, t, J=7.2 Hz), 4.30 (2H, t, J=7.2 Hz), 5.01 (1H, bs), 7.83 (1H, s), 8.50 (1H, s).

(4) Ethyl 3-[4-butoxy-6,7-dichloro-3-hydroxymethyl-1oxo-2(1H)-isoquinolinyl]propionate (synthesized according to the method similar to that in Example 4 (4))

Melting point 122–123° C. Elemental analysis for $C_{19}H_{23}NO_5Cl_2$ Calculated: C, 544.82; H, 5.57; N, 3.36. Found: C, 54.71; H, 5.51; N, 3.37. $^1$H-NMR(CDCl$_3$) δ: 1.03 (3H, t, J=7.4 Hz), 1.23 (3H, t, J=7.2 Hz), 1.49–1.67 (2H, m), 1.78–1.92 (2H, m), 2.82. (1H, bs), 2.92 (2H, t, J=6.9 Hz), 3.89 (2H, t, J=6.4 Hz), 4.13 (2H, q, J=7.2 Hz), 4.43 (2H, t, J=6.9 Hz), 4.86 (2H, s), 7.78 (1H, s), 8.44 (1H, s).

(5) Ethyl 3-[4-butoxy-3-chloromethyl-6,7-dichloro-1-oxo-2(1H)-isoquinolinyl]propionate (synthesized according to the method similar to that in Example 4 (5))

$^1$H-NMR(CDCl$_3$) δ: 1.05 (3H, t, J=7.1 Hz), 1.22 (3H, t, J=7.0 Hz), 1.51–1.66 (2H, m), 1.70–1.95 (2H, m), 2.89 (2H, t, J=6.8 Hz), 3.96 (2H, t, J=6.6 Hz), 4.11 (2H, q, J=7.0 Hz), 4.42 (2H, t, J=6.8 Hz), 4.95 (2H, s), 7.81 (1H, s), 8.49 (1H, s).

(6) Ethyl 3-[4-butoxy-6,7-dichloro-3-[(1,3-dioxo-1,3-dihydro-2H-isoindol-2-yl)methyl]-1-oxo-2(1H)-isoquinolinyl]propionate Melting point 167–169° C. Elemental analysis for $C_{27}H_{26}N_2O_6Cl_2$ Calculated: C, 59.46; H, 4.80; N, 5.14. Found: C, 59.54; H, 4.66; N, 5.11. $^1$H-NMR(CDCl$_3$) δ: 1.00 (3H, t, J=7.1 Hz), 1.19 (3H, t, J=7.1 Hz), 1.47–1.61 (2H, m), 1.78–1.93 (2H, m), 2.77 (2H, t, J=7.0 Hz), 3.97 (2H, t, J=6.7 Hz), 4.07 (2H, q, J=7.1 Hz), 4.39 (2H, t, J=7.0 Hz), 5.13 (2H, s), 7.72–7.87(5H, m), 8.47 (1H, s).

(7) A mixture of ethyl 3-[4-butoxy-6,7-dichloro-3-[(1,3-dioxo-1,3-dihydro-2H-isoindol-2-yl)methyl]-1-oxo-2 (1H) isoquinolinyl]propionate (1.36 g, 2.5 mmol) in 6N hydrochloric acid (15 ml) and acetic acid (15 ml) was refluxed with stirring for 2 h. The reaction mixture was concentrated under reduced pressure, and the residue was recrystallized from tetrahydrofuran-diisopropyl ether to give 3-[4-butoxy-6,7-dichloro-3-[(1,3-dioxo-1,3-dihydro-2H-isoindol-2-yl)methyl]-1-oxo-2(1H)-isoquinolinyl]propionic acid (1.08 g, 83.7%) as crystals.

Melting point 196–197° C. Elemental analysis for $C_{26}H_{22}N_2C_6Cl_2 \cdot 2H_2O$ Calculated: C, 54.26; H, 4.74; N, 5.06. Found: C, 54.32; H, 4.38; N, 5.13. $^1$H-NMR(CDCl$_3$) δ: 0.99 (3H, t, J=7.1 Hz), 1.42–1.60 (2H, m), 1.77–1.91 (2H, m), 2.76 (2H, t, J=7.1 Hz), 3.94 (2H, t, J=6.8 Hz), 4.41 (2H, t, J=7.1 Hz), 5.13 (2H, s), 7.73–7.86 (5H, m), 8.44 (1H, s).

(8) A solution of 3-[4-butoxy-6,7-dichloro-3-[(1,3-dioxo-1,3-dihydro-2H-isoindol-2-yl)methyl]-1-oxo-2(1H)isoquinolinyl]propionic acid (1.03 g, 2.4 mmol), pyrrolidine (0.20 ml, 2.4 mmol), 1-ethyl-3-(3-dimethylaminopropyl) carbodiimide hydrochloride (0.46 g, 2.4 mmol) and 1-hydroxybenzotriazole (0.37 g, 2.4 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was recrystallized from tetrahydrofuran-diisopropyl ether to give 2-[[4-butoxy-6,7-dichloro-1-oxo-2-[3-oxo-3-(1-pyrrolidinyl)propyl]-1,2-dihydro-3-isoquinolinyl]-methyl]-1H-isoindole-1,3(2H)-dione (0.72 g, 66.1%) as crystals.

Melting point 222–222.5° C. Elemental analysis for $C_{29}H_{29}N_3O_5Cl_2$ Calculated: C, 61.01; H, 5.12; N, 7.37. Found: C, 60.91; H, 5.16; N, 7.21. $^1$H-NMR(CDCl$_3$) δ: 0.98 (3H, t, J=7.1 Hz), 1.41–1.59 (2H, m), 1.74–1.92 (6H, m), 2.78 (2H, t, J=7.0 Hz), 3.25–3.38(4H, m), 3.94 (2H, t, J=6.8 Hz), 4.46 (2H, t, J=7.0 Hz), 5.23 (2H, s), 7.70–7.85 (5H, m), 8.47 (1H, s).

(9), Tert-butyl{4-butoxy-6,7-dichloro-1-oxo-{3-oxo-3-(1pyrrolidinyl)propyl}-1,2-dihydro-3-isoquinolinyl}-methylcarbamate (synthesized according to the method similar to that in Example 1 (6))

Melting point 215–217° C. Elemental analysis for $C_{26}H_{35}N_3O_5Cl_2$ Calculated: C, 57.78; H, 6.53; N, 7.77. Found: C, 57.95; H, 6.43; N, 7.60. $^1$H-NMR(CDCl$_3$) δ: 1.03 (3H, t, J=7.3 Hz), 1.44 (9H, s), 1.51–1.62 (2H, m), 1.79–1.95 (6H, m), 2.86 (2H, t, J=6.8 Hz), 3.36–3.45 (4H, m), 3.88 (2H, t, J=6.6 Hz), 4.73 (2H, t, J=6.8 Hz), 4.60 (2H, d, J=5.4 Hz), 5.80 (1H, bs), 7.79 (1H, s), 8.45 (1H, s).

(10) 3-(Aminomethyl)-4-butoxy-6,7-dichloro-2-{3-oxo-(1-pyrrolidinyl)propyl}-1(2H)-isoquinolinone hydrochloride (synthesized according to the method similar to that in Example 1 (7))

Melting point 206–206.5° C. Elemental analysis for $C_{21}H_{28}N_3O_3Cl_3$ ½$H_2O$ Calculated: C, 50.06; H, 6.20; N, 8.34. Found: C, 49.72; H, 6.02; N, 8.23. $^1$H-NMR(DMSO-$_6$) δ: 0.99 (3H, d, J=7.4 Hz), 1.45–1.63 (2H, m), 1.71–1.883 (6H, m), 2.76 (2H, t, J=6.6 Hz), 3.23–3.38 (4H, m), 3.93 (2H, t, J=6.4 Hz), 4.21–4.28 (4H, m), 7.91 (1H, s), 8.36 (1H, s), 8.79 (3H, bs).

Example 36

3-(Aminomethyl)-4-butoxy-6,7-dichloro-2-methyl-1 (2H)-isoquinolinone hydrochloride (1) Ethyl 4-butoxy-6,7-dichloro-4-hydroxy-2-methyl-1oxo-1,2-dihydro-3-isoquinolinecarboxylate (synthesized according to the method similar to that in Example 1 (1))

Melting point 78–80° C. Elemental analysis for $C_{17}H_{19}NO_6Cl_2$¼$H_2O$ Calculated: C, 54.20; H, 5.22; N, 3.72 Found: C, 54.16; H, 5.06; N, 3.61. $^1$H-NMR(CDCl$_3$) δ: 1.01 (3H, t, J=7.1 Hz), 1.44 (3H, t, J=7.2 Hz), 1.47–1.58 (2H, m), 1.72–1.86 (2H, m), 3.51 (3H, s), 3.95 (2H, t, J=6.5 Hz), 4.47 (2H, q, J=7.2 Hz), 7.82 (1H, s), 8.51 (1H, s).

(2) 4-Butoxy-6,7-dichloro-2-methyl-1-oxo-1,2-dihydro-3-isoquinolinecarboxylic acid (synthesized according to the method similar to that in Example 4 (3))

Melting point 209–210° C. Elemental analysis for $C_{15}H_{15}NO_4Cl_2$ Calculated: C, 52.34; H, 4.39; N, 4.07. Found: C, 52.21; H, 4.27; N, 3.78. $^1$H-NMR(CDCl$_3$) δ: 1.01 (3H, t, J=7.3 Hz), 1.49–1.60 (2H, m), 1.74–1.84 (2H, m), 3.58 (3H, s), 3.99 (2H, t, J=6.6 Hz), 5.03 (1H, bs), 7.83 (1H, s), 8.49 (1H, s).

(3) 4-Butoxy-6,7-dichloro-3-hydroxymethyl-2-methyl-1 (2H)-isoquinolinone (synthesized according to the method similar to that in Example 4 (4))

Melting point 146–147° C. Elemental analysis for $C_{15}H_{17}NO_3Cl_2$ Calculated: C, 54.56; H, 5.19; N, 4.24. Found: C, 54.32; H, 4.98; N, 4.14. $^1$H-NMR(CDCl$_3$) δ: 1.04 (3H, t, J=7.3 Hz), 1.44–1.67 (2H, m), 1.77–1.91 (2H, m), 2.52 (1H, bs), 3.71 (3H, s), 3.83 (2H, t, J=6.6 Hz), 4.79 (2H, s), 7.66 (1H, s), 8.38 (1H, s).

(4) 4-Butoxy-3-chloromethyl-6,7-dichloro-2-methyl-1 (2H)-isoquinolinone (synthesized according to the method similar to that in Example 4 (5))

$^1$H-NMR(CDCl$_3$) δ: 1.05 (3H, t, J=7.1 Hz), 1.52–1.76 (2H, m), 1.82–1.96 (2H, m), 3.72 (3H, s), 3.97 (22H, t, J=6.5 Hz), 4.77 (2H, s), 7.81 (1H, s), 8.51 (1H, s).

(5) 2-[(4-Butoxy-6,7-dichloro-2-methyl-1-oxo-1,2-dihydro-3-isoquinolinyl)methyl]-1H-isoindole-1,3(2H)-dione (synthesized according to the method similar to that in Example 4 (6))

Melting point 228–228.5° C. Elemental analysis for $C_{23}H_{20}N_2O_4Cl_2$ Calculated: C, 60.14; H, 4.39; N, 6.10. Found: C, 59.92; H, 4.35; N, 6.13. $^1$H-NMR(CDCl$_3$) δ: 1.01 (3H, t, J=7.2 Hz), 1.46–1.64 (2H, m), 1.80–1.94 (2H, m), 3.56 (3H, s), 4.03 (2H, t, J=6.8 Hz), 5.06 (2H, s), 7.73–7.88 (5H, m), 8.48 (1H, s).

(6) Tert-butyl(4-butoxy-6,7-dichloro-2-methyl-1-oxo-1, 2-dihydro-3-isoquinolinyl)methylcarbamate (synthesized according to the method similar to that in Example 1 (6))

Melting point 159.5–160° C. Elemental analysis for $C_{20}H_{26}N_2O_4Cl_2$ Calculated: C, 55.95; H, 6.10; N, 6.52. Found: C, 55.93; H, 6.18; N, 6.29. $^1$H-NMR(CDCl$_3$) δ: 1.04 (3H, t, J=7.1 Hz), 1.47 (9H, s), 1.49–1.63 (2H, m), 1.73–1.93 (2H, m), 3.62 (3H, s), 3.83 (2H, t, J=6.6 Hz), 4.52 (2H, d, J=5.4 Hz), 4.82 (1H, bs), 7.75 (1H, s), 8.46 (1H, s).

(7) 3-(Aminomethyl)_4-butoxy-6,7-dichloro-2-mehtyl-1 (2H)-isoquinolinone hydrochloride (synthesized according to the method similar to that in Example 1 (7))

Melting point 251–252° C. Calculated: C, 48.67; H, 5.31; N, 7.57. Found: C, 48.69; H, 5.37; N, 7.79. $^1$H-NMR (DMSO-d$_6$) δ: 0.99 (3H, t, J=7.3 Hz), 1.45–1.63 (2H, m), 1.77–1.91 (2H, m), 3.61 (3H, s), 3.92 (2H, t, J=6.4 Hz), 4.23 (2H, s), 7.91 (1H, s), 8.36 (1H, s), 8.79 (3H, bs).

Example 37

3-(1-Aminoethyl)-4-butoxy-6,7-dichloro-2-methyl-1 (2H)-isoquinolinone hydrochloride (1) To a solution of dimethyl sulfoxide;(1.7 ml, 24 mmol) in tetrahydrofuran (10 mmol) was added oxalyl chloride (1.05 ml, 12 mmol) at −78° C. and the obtained mixture was stirred at −78° C. for 15 min. To the mixture was added 4-butoxy-6,7-dichloro-3-hydroxymethyl-2-methyl-1(2H)-isoquinolinone (synthesized according to the method similar to that in Example 36 (3)) (2.43 g, 5mmol) and the obtained mixture was stirred at −78° C. for 5 min. To the mixture was added triethylamine (5.6 ml, 40mmol) and the obtained mixture was stirred at room temperature for 30 min. The reaction mixture was poured into water and extracted with ethyl acetate. The extract was washed with brine, dried over anhydrous magnesium sulfate and concentrated under reduced pressure. The residue was recrystallized from tetrahydrofuran-diisopropyl ether to give 4-butoxy-6,7-dichloro-2-methyl-1-oxo-1,2-dihydro-3-isoquinolinealdehyde (2.14 g, 81.7%) as crystals.

Melting point 114–115° C. Elemental analysis for $C_{15}H_{15}NO_3Cl_2$ Calculated: C, 54.90; H, 4.61; N, 4.27. Found: C, 54.71; H, 4.39; N, 4.21. $^1$H-NMR(CDCl$_3$) δ: 1.04 (3H, t, J=7.3 Hz), 1.49–1.68 (2H, m), 1.84–1.98 (2H, m), 3.82 (3H, s), 4.05 (2H, t, J=6.6 Hz), 7.96 (2H, s), 8.56 (1H, s), 10.24 (1H, s).

(2) To a solution of 4-butoxy-6,7-dichloro-2-methyl-1-oxo-1,2-dihydro-3-isoquinolinealdehyde (0.98 g, 24 mmol) in tetrahydrofuran (20 mmol) was added 3N methylmagnesium bromide tetrahydrofuran solution (1.5 ml, 4.5 mmol) at 0° C. and the obtained mixture was stirred at 0° C. for 1 h. The reaction mixture was poured into water and extracted with ethyl acetate. The extract was washed with brine, dried over anhydrous magnesium sulfate and concentrated under reduced pressure. The residue was recrystallized from ethyl acetate-n-hexane to give 4-butoxy-6,7-dichloro-3-(1-hydroxyethyl)-2-methyl-1(2H)-isoquinolinone (0.95 g, 92.2%) as crystals.

Melting point 123–123.5° C. Elemental analysis for $C_{16}H_{19}NO_3Cl_2$ Calculated: C, 55.83; H, 5.56; N, 4.07. Found: C, 55.81; H, 5.59; N, 3.86. $^1$H-NMR(CDCl$_3$) δ: 1.04 (3H, t, J=7.3 Hz), 1.49–1.63 (2H, m), 1.64 (3H, d, J=7.0 Hz), 1.78–1.92 (2H, m), 3.26 (1H, bs), 3.70–3.84 (5H, m), 5.63 (1H, q, J=7.0 Hz), 7.59 (1H, s), 8.36 (1H, s).

(3) 4-Butoxy-3-(1-chloroethyl)-6,7-dichloro-2-methyl-1 (2H)-isoquinolinone (synthesized according to the method similar to that in Example 4 (5))

¹H-NMR(CDCl₃) δ: 1.05 (3H, t, J=7.3 Hz), 1.51–1.69 (2H, m), 1.82–1.92 (2H, m), 1.96 (3H, d, J=7.2 Hz), 3.83 (3H, s), 3.88–3.96 (2H, m), 5.92–6.00 (1H, m), 7.81 (1H, s), 8.50 (1H, s).

(4) 2-[1-(4-Butoxy-6,7-dichloro-2-methyl-1-oxo-1,2-dihydro-3-isoquinolinyl)ethyl]-1H-isoindole-1,3(2H)-dione (synthesized according to the method similar to that in Example 4 (6))

Elemental analysis for $C_{24}H_{22}N_2O_4Cl_2$ Calculated: C, 60.90; H, 4.68; N, 5.92. Found: C, 60.76; H, 4.38; N, 5.72. ¹H-NMR(CDCl₃) δ: 0.99 (3H, t, J=7.3 Hz), 1.41–1.52 (2H, m), 1.77–1.87 (2H, m), 2.08 (3H, d, J=7.6 Hz), 3.67 (3H, s), 3.84–3.95 (1H, m), 4.405–4.16 (1H, m), 5.81 (1H, q, J=7.6 Hz), 7.72–7.87 (5H, m), 8.47 (1H, s).

(5) Tert-butyl 1-(4-butoxy-6,7-dichloro-2-methyl-1-oxo-1,2-dihydro-3-isoquinolinyl)ethylcarbamate (synthesized according to the method similar to that in Example 1 (6))

Melting point 118–118.5° C. Elemental analysis for $C_{21}H_{28}N_2O_4Cl_2$ Calculated: C, 5:6.89; H, 6.3.7; N, 6.32. Found: C, 57.11; H, 6.58; N, 6.13. ¹H-NMR(CDCl₃) δ: 1.04 (3H, t, J=7.4 Hz), 1.43 (9H, s), 1.54 (3H, d, J=7.0 Hz), 1.56–1.74 (2H, m), 1.84–1.98 (2H, m), 3.73 (3H, s), 3.82–4.03 (2H, m), 5.20–5.29 (1H, m), 5.57 (1H, bs), 7.72 (1H, s), 8.48 (1H, s).

(6) 3-(1-Aminobutyl)-4-butoxy-6,7-dichloro-2-methyl-1(2H)-isoquinolinone hydrochloride (synthesized according to the method similar to that in Example 1 (7))

Melting point 224–225° C. Elemental analysis for $C_{16}H_{21}N_2O_2Cl_3$ Calculated: C, 50.61; H, 5.57; N, 7.38. Found: C, 50.38; H, 5.63; N, 7.28. ¹H-NMR(DMSO-d₆) δ: 0.99 (3H, t J=7.3 Hz), 1.44–1.62 (2H, m), 1.69 (3H, d, J=7.4 Hz), 1.81–1.92 (2H, m), 3.61 (3H, s), 3.92 (2H, t, J=6.8 Hz), 4.95 (2H, bs), 7.87 (1H, s), 8.36 (1H, s), 8.87 (3H, bs).

Example 38

3-(1-Aminobutyl)-4-butoxy-6,7-dichloro-2-methyl-1(2H)-isoquinolinone hydrochloride (1) 4-Butoxy-6,7-dichloro-3-(1-hydroxybutyl)-2-methyl-1(2H)-isoquinolinone (synthesized according to the method similar to that in Example 37 (2))

Melting point 105.5–106° C. Elemental analysis for $C_{18}H_{23}NO_3Cl_2$ Calculated: C, 58.07; H, 6.23; N, 3.76. Found: C, 58.09; H, 6.53; N, 3.57. ¹H-NMR(CDCl₃) δ: 1.00 (3H, t, J=7.3 Hz), 1.04 (3H, t, J=7.3 Hz), 1.31–2.10 (8H, m), 2.98 (1H, bs), 3.75 (3H, s), 3.82 (2H, t, J=6.4 Hz), 5.31–5.40 (1H, m), 7.66 (1H, s), 8.41 (1H, s).

(2) 4-Butoxy-3-(1-chlorobutyl)-6,7-dichloro-2-methyl-1(2H)-isoquinolinone (synthesized according to the method similar to that in Example 4 (5))

¹H-NMR(CDCl₃) δ: 0.97 (3H, t, J=7.4 Hz), 1.05 (3H, t, J=7.3 Hz), 1.22–1.76 (4H, m), 1.80–1.95 (2H, m), 2.17–2.35 (2H, m), 3.79 (3H, s), 3.91 (2H, t, J=6.2 Hz), 5.79 (1H, bs), 7.81 (1H, s), 8.50 (1H, s).

(3) 2-[1-(4-Butoxy-6,7-dichloro-2-methyl-1-oxo-1,2-dihydro-3-isoquinolinyl)butyl]-1H-isoindole-1,3(2H)-dione (synthesized according to the method similar to that in Example 4 (6))

Elemental analysis for $C_{26}H_{26}N_2O_4Cl_2$ Calculated: C, 62.28; H, 5.23; N, 5.59. Found: C, 62.05; H, 5.02; N, 5.60. ¹H-NMR(CDCl₃) δ: 1.00 (3H, t, J=7.2 Hz), 1.03 (3H, t, J=7.2 Hz), 1.37–1.62 (4H, m), 1.78–1.91 (2H, m), 1.99–2.17 (1H, m), 2.89–3.08 (1H, m), 3.65 (3H, s), 3.75–3.93 (1H, m), 4.08–4.19 (1H, m), 5.64–5.72 (1H, m), 7.70–7.90 (5H, m), 8.47 (1H, s).

(4) Tert-butyl 1-(4-butoxy-6,7-dichloro-2-methyl-1-oxo-1,2-dihydro-3-isoquinolinyl)butylcarbamate (synthesized according to the method similar to that in Example 1 (6))

Elemental analysis for $C_{23}H_{32}N_2O_4Cl_2$ Calculated: C, 58.60; H, 6.84; N, 5.94. Found: C, 58.67; H, 6.62; N, 5.82. ¹H-NMR(CDCl₃) δ: 0.87 (3H, t, J=7.1 Hz), 1.07 (3H, t, J=7.4 Hz), 1.43 (9H, s), 1.44–1.98 (8H, m), 3.74 (3H, s), 3.82–3.97 (2H, m), 5.12 (1H, bs), 5.37 (1H, bs), 7.71 (1H, s), 8.48 (1H, s).

(5) 3-(1-Aminobutyl)-4-butoxy-6,7-dichloro-2-methyl-1(2H)-isoquinoline hydrochloride (synthesized according to the method similar to that in Example 1 (7))

Melting point 217–218° C. Elemental analysis for $C_{18}H_{25}N_2O_2Cl_3$ ½H₂O Calculated: C, 51.87; H, 6.29; N, 6.72. Found: C, 51.66; H, 6.44; N, 6.62. ¹H-NMR(DMSO-d₆) δ: 0.92 (3H, t, J=7.4 Hz), 0.99 (3H, t, J=7.4 Hz), 1.26–1.59 (4H, m), 1.83–2.21 (4H, m), 3.59 (3H, s), 3.82–3.93 (2H, m), 4.88 (1H, bs), 7.88 (1H, s), 8.36 (1H, s), 9.06 (3H, bs).

Example 39

3-(1-Amino-3-methylbutyl)-4-butoxy-6,7-dichloro-2-methyl-1(2H)-isoquinolinone hydrochloride (1) 4-Butoxy-6,7-dichloro-3-(1-hydroxy-3-methylbutyl)-2-methyl-1(2H)-isoquinolinone (synthesized according to the method similar to that in Example 37 (2))

Melting point 121–122° C. Elemental analysis for $C_{19}H_{25}NO_3Cl_2$ Calculated: C, 59.07; H, 6.52; N, 3.63. Found: C, 59.13; H, 6.54; N, 3.51. ¹H-NMR(CDCl₃) δ: 1.02 (6H, d, J=6.6 Hz), 1.04 (3H, t, J=7.4 Hz), 1.50–1.67 (3H, m), 1.79–2.04 (4H m), 2.90 (1H, bs), 3.74 (3H, s), 3.77–3.89 (2H, m), 5.39–5.46 (1H, m), 7.66 (1H, s), 8.41 (1H, s).

(2) 4-Butoxy-3-(1-chloro-3-methylbutyl)-6,7-dichloro-2-methyl-1(2H)-isoquinoline (synthesized according to the method similar to that in Example 4 (5))

¹H-NMR(CDCl₃) δ: 0.95 (3H, d, J=6.6 Hz), 0.97 (3H, d, J=6.6 Hz), 1.05 (3H, t, J=7.3 Hz), 1.52–1.99 (5H, m), 2.13–2.26 (2H, m), 3.79 (3H, s), 3.93 (2H, t, J=6.6 Hz), 5.90 (1H, bs), 7.81 (1H, s), 8.50 (1H, s).

(3) 2-[1-(4-Butoxy-6,7-dichloro-2-methyl-1-oxo-1,2-dihydro-3-isquinolinyl)-3-methylbutyl]-1H-isoindole-1,3(2H)-dione (synthesized according to the method similar to that in Example 4 (6))

Elemental analysis for $C_{27}H_{28}N_2O_4Cl_2$ Calculated: C, 62.69; H, 5.48; N, 5.43. Found: C, 62.92; H, 5.29; N, 5.39. ¹H-NMR(CDCl₃) δ: 0.81–1.07 (9H, m), 1.40–1.54 (2H, m), 1.63–1.92 (4H, m), 3.03–3.15 (1H, m), 3.72 (3H, s), 3.79–3.90 (1H, m), 4.07–4.19 (1H, m), 5.74–5.82 (1H, m), 7.72–7.85 (5H, m), 8.47 (1H, s).

(4) Tert-butyl 1-(4-butoxy-6,7-dichloro-2-methyl-1-oxo-1,2-dihydro-3-isoquinolinyl)-3methylbutylcarbamate (synthesized according to the method similar to that in Example 1 (6))

Elemental analysis for $C_{24}H_{34}N_2O_4Cl_2$ Calculated: C, 59.38; H, 7.06; N, 5.77. Found: C, 59.31; H, 6.96; N, 5.53. ¹H-NMR(CDCl₃) δ: 0.99 (3H, d, J=6.6 Hz), 1.01 (3H, d, J=6.6 Hz), 1.06 (3H, t, J=7.4 Hz), 1.43 (9H, s), 1.46–1.69 (4H, m), 1.74–1.95 (3H, m), 3.73 (3H, s), 3.83–3.98 (2H, m), 5.21 (1H, bs), 5.31 (1H, bs), 7.71 (1H, s), 8.48 (1H, s).

(5) 3-(1-Amino-3-methylbutyl)-4-butoxy-6,7-dichloro-2-methyl-1(2H)-isoquinolinone hydrochloride (synthesized according to the method similar to that in Example 1 (7))

Melting point 212.5–213.5° C. Elemental analysis for $C_{19}H_{27}N_2O_2Cl_3$ Calculated: C, 54.10; H, 6.45; N, 6.64. Found: C, 53.92; H, 6.55; N, 6.47. ¹H-NMR(DMSO-d₆) δ:

0.93–0.97 (6H, m), 0.99 (3H, t, J=7.4 Hz), 1.42–2.18 (7H, m), 3.59 (3H, s), 3.89 (2H, bs), 5.05 (1H, bs), 7.89 (1H, s), 8.36 (1H, s), 9.18 (3H, bs).

Example 40

3-(1-Aminohexyl)-4-butoxy-6,7-dichloro-2-methyl-1(2H)-isoquinolinone hydrochloride (1) 4-Butoxy-6,7-dichloro-3-(1-hydroxyhexyl)-2-methyl-1(2H)-isoquinoline (synthesized according to the method similar to that in Example 37 (2))

Melting point 95–96° C. Elemental analysis for $C_{20}H_{27}NO_3Cl_2$ Calculated: C, 60.00; H, 6.80; N, 3.50. Found: C, 59.90; H, 6.75; N, 3.45. $^1$H-NMR(CDCl$_3$) δ: 0.87–0.93(3H, m), 1.04 (3H, t, J=7.2 Hz), 1.33–1.35 (4H, m), 1.49–2.05 (8H, m), 2.99 (1H, bs), 3.74 (3H, s), 3.81 (2H, t, J=6.4 Hz), 5.28–5.38 (1H, m), 7.64 (1H, s), 8.40 (1H, s).

(2) 4-Butoxy-3-(1-chlorohexyl)-6,7-dichloro-2-methyl-1(2H)-isoquinolinone (synthesized according to the method similar to that in Example 4 (5))

$^1$H-NMR(CDCl$_3$) δ: 0.82–0.91 (3H, m), 1.05 (3H, t, J=7.3 Hz), 1.22–1.39 (6H, m), 1.51–1.76 (4H, m), 1.80–1.95 (2H, m), 3.79 (3H, s), 3.91 (2H, t, J=6.2 Hz), 5.78 (1H, bs), 7.81 (1H, s), 8.50 (1H, s).

(3) 2-[1-(4-Butoxy-6,7-dichloro-2-methyl-1-oxo-1,2-dihydro-3-isoquinolinyl)hexyl]-1H-isoindole-1,3(2H)-dione (synthesized according to the method similar to that in Example 4 (6))

Elemental analysis for $C_{28}H_{30}N_2O_4Cl_2$ Calculated: C, 63.52; H, 5.71; N, 5.29. Found: C, 63.25; H, 5.78; N, 5.03. $^1$H-NMR(CDCl$_3$) δ: 0.90 (3H, t, J=7.0 Hz), 1.00 (3H, t, J=7.3 Hz), 1.30–1.59 (8H, m), 1.77–1.91 (2H, m), 2.01–2.14 (1H, m), 2.97–3.04 (1H, m), 3.70 (3H, s), 3.80–3.92 (1H, m), 4.07–4.18 (1H, m), 5.61–5.69 (1H, m), 7.72–7.85 (5H, m), 8.47 (1H, s).

(4) Tert-butyl 1-(4-butoxy-6,7-dichloro-2-methyl-1-oxo-1,2-dihydro-3-isoquinolinyl)hexylcarbamate (synthesized according to the method similar to that in Example 1 (6))

Elemental analysis for $C_{25}H_{36}N_2O_4Cl_2$ Calculated: C, 60.12; H, 7.26; N, 5.61. Found: C, 59.95; H, 7.04; N, 5.53. $^1$H-NMR(CDCl$_3$) δ: 0.88 (3H, t, J=6.0 Hz), 1.06 (3H, t, J=7.4 Hz), 1.22–1.32 (4H, m), 1.43 (9H, s), 1.50–1.69 (4H, m), 1.74–1.98 (4H, m), 3.73 (3H, s), 3.82–3.96 (2H, m), 5.10–5.12 (1H, m), 5.37 (1H, bs), 7.71 (1H, s), 8.48 (1H, s).

(5) 3-(1-Aminohexyl)-4-butoxy-6,7-dichloro-2-methyl-1(2H)-isoquinolinone hydrochloride (synthesized according to the method similar to that in Example 1 (7))

Melting point 199.5–200° C. Elemental analysis for $C_{20}H_{29}N_2O_2Cl_3$ ½$H_2O$ Calculated: C, 54.00; H, 6.80; N, 6.30. Found: C, 54.18; H, 6.87; N, 6.14. $^1$H-NMR(DMSO-d$_6$) δ: 0.85–0.88 (3H, m), 0.99 (3H, t, J=7.3. Hz), 1.26–1.62 (7H, m), 1.83–2.18 (4H, m), 3.59 (3H, s), 3.81–3.92 (2H, m), 4.87 (1H, bs), 7.89 (1H, s), 8.36 (1H, s), 9.09 (3H, bs).

Example 41

3-[(Aminomethyl)-4-butoxy-6,7-dichloro-1-oxo-2(1H)-isoquinolinyl]-N-isopropylpropanamide hydrochloride (1) 3-[4-Butoxy-6,7-dichloro-3-[(1,3-dioxo-1,3-dihydro-2H-isoindol-2-yl)methyl]-1-oxo-1,2-dihydro-3-isoquinolinyl]-N-isopropylpropanamide (synthesized according to the method similar to that in Example 35 (8))

Melting point 232–232.5° C. Elemental analysis for $C_{28}H_{29}N_3O_5Cl_2$ Calculated: C, 60.22; H, 5.23; N, 7.52. Found: C, 59.98; H, 5.48; N, 7.41. $^1$H-NMR(CDCl$_3$) δ: 0.99 (3H, t, J=7.3 Hz), 1.05 (6H, d, J=6.6 Hz), 1.44–1.59 (2H, m), 1.74–1.91 (2H, m), 2.6.6 (2H, t, J=6.8 Hz), 3.92 (2H, t, J=6.8 Hz), 3.92–4.02 (1H, m), 4.47 (2H, t, J=7.0 Hz), 5.15 (2H, s), 5.76 (2H, d, J=7.6 Hz), 7.70–7.86 (5H, m), 8.43 (1H, s).

(2) Tert-butyl{4-butoxy-6,7-dichloro-2-{3-(isopropylamino)-3-oxypropyl}-1-oxo-1,2-dihydro-3-isoquinolinyl}methylcarbamate (synthesized according to the method similar to that in Example 1 (6))

Melting point 221–221.5° C. Elemental analysis for $C_{25}H_{35}N_3O_5Cl_2$ Calculated: C, 56.82; H, 6.68; N, 7.95. Found: C, 56.72; H, 6.51; N, 7.93. $^1$H-NMR(CDCl$_3$) δ: 1.03 (3H, t, J=7.1 Hz), 1.06 (6H, d, J=6.6 Hz), 1.46 (9H, s), 1.51–1.66 (2H, m), 1.74–1.94 (2H, m), 2.71 (2H, t, J=7.0 Hz), 3.87 (3H, t, J=6.6 Hz), 3.94–4.08 (1H, m), 4.35 (2H, t, J=7.0 Hz), 4.56 (2H, d, J=5.8 Hz), 5.69 (1 H, bs), 6.01 (1H, bs), 7.79 (1H, s), 8.43 (1H, s).

(3) 3-[(Aminomethyl)-4-butoxy-6,7-dichloro-1-oxo-2(1H)-isoquinolinyl]-N-isopropylpropanamide hydrochloride (synthesized according to the method similar to that in Example 1 (7))

Melting point 189–191° C. Elemental analysis for $C_{20}H_{28}N_3O_3Cl_3$ 2$H_2O$ Calculated: C, 47.96; H, 6.44; N, 8.39. Found: C, 48.07; H, 6.05; N, 8.36. $^1$H-NMR(DMSO-d$_6$) δ: 0.95 (6H, d, J=6.6 Hz) 0.99 (3H, t, J=7.3 Hz), 1.44–1.63 (2H, m), 1.77–1.91 (2H, m), 2.56 (2H, t, J=6.6 Hz), 3.71–3.82 (1H, m), 3.91 (2H, t, J=6.6 Hz), 4.20–4.31 (4H, m), 4.84 (2H, s), 7.92 (1H, s), 8.02 (1H, d, J=7.4 Hz), 8.38 (1H, s), 8.75 (3H, bs).

Example 42

3-{3-(Aminomethyl)-4-butoxy-6,7-dichloro-1-oxo-2(1H)-isoquinolinyl}-N-phenylpropanamide hydrochloride (1) 3-[4-Butoxy-6,7-dichloro-3-[(1,3-dioxo-1,3-dihydro-2H-isoindol-2-yl)methyl]-1-oxo-1,2-dihydro-3-isoquinolinyl]-N-phenylpropanamide (synthesized according to the method similar to that in Example 35 (8))

Melting point 204–206° C. Elemental analysis for $C_{31}H_{27}N_3O_5Cl_2$ Calculated: C, 62.84; H, 4.59; N, 7.09. Found: C, 62.46; H, 4.66; N, 7.08. $^1$H-NMR(CDCl$_3$) δ: 0.97 (3H, t, J=7.3 Hz), 1.38–1.57 (2H, m), 1.78–1.89 (2H, m), 2.88 (2H, t, J=6.8 Hz), 3.87 (2H, t, J=6.8 Hz), 4.57 (2H, t, J=6.6 Hz), 5.16 (2H, s), 7.03–7.10 (1H, m), 7.23–7.31 (2H, m), 7.46–7.51 (2H, m), 7.69–7.85 (5H, m), 8.34 (1H, s), 8.52 (1H, s).

(2) Tert-butyl{2-(2-anilino-3-oxopropyl)-4-butoxy-6,7-dichloro-1-oxo-1,2-dihydro-3-isoquinolinyl}methylcarbamate (synthesized according to the method similar to that in Example 1 (6))

Melting point 219–220° C. Elemental analysis for $C_{28}H_{33}N_3O_5Cl_2$ Calculated: C, 59.79; H, 5.91; N, 7.47. Found: C, 59.92; H, 5.84; N, 7.42. $^1$H-NMR(CDCl$_3$) δ: 1.03 (3H, t, J=7.3 Hz), 1.46 (9H, s), 1.47–1.65 (2H, m), 1.78–1.93 (2H, m), 2.90 (2H, t, J=7.2 Hz), 3.83 (2H, t, J=6.6 Hz), 4.48 (2H, t, J=7.2 Hz), 4.60 (2H, d, J=5.8 Hz), 5.34 (1H, bs), 7.04–7.11 (1H, m), 7.25–7.33 (2H, m), 7.55–7.59 (2H, m), 7.76 (1H, s), 8.41 (1H, s), 8.72 (1H, bs).

(3) 3-{3-(Aminomethyl)-4-butoxy-6,7-dichloro-1-oxo-2(1H)-isoquinolinyl}-N-phenylpropanamide hydrochloride (synthesized according to the method similar to that in Example 1 (7))

Melting point 243–244° C. Elemental analysis, for $C_{23}H_{26}N_3O_3Cl_3$ Calculated: C, 55.38; H, 5.25; N, 8.42. Found: C, 55.31; H, 5.45; N, 8.27. $^1$H-NMR(DMSO-d$_6$) δ:

0.97 (3H, t, J=7.3 Hz), 1.40–1.60 (2H, m), 1.73–1.87 (2H, m), 2.83 (2H, t, J=6.4 Hz), 3.84 (2H, t, J=6.4 Hz), 4.31–4.34 (4H, m), 6.99–7.06 (1H, m), 7.23–7.31 (2H, m), 7.54–7.58 (2H, m), 7.91 (1H, s), 8.40 (1H, s), 8.65 (3H, bs), 10.23 (1H, s),

Example 43

3-(Aminomethyl)-4-butoxy-6,7-dichloro-2-{3-oxo-3-(1,3-thiazolidin- 3-yl)propyl}-1(2H)-isoquinolinone hydrochloride (1) 2-[4-Butoxy-6,7-dichloro-1-oxo-2-{3-oxo-3-(1,3-thiazolidin-3-yl)propyl}methyl]-1H-isoindole-1,3(2H)-dione (synthesized according to the method similar to that in Example 35 (8))

Melting point 218–220° C. Elemental analysis for $C_{28}H_{27}N_3O_5Cl_2S$ ¼$H_2O$ Calculated: C, 56.71; H, 4.67; N, 7.09. Found: C, 56.66; H, 4.58; N, 6.92. $^1$H-NMR(CDCl$_3$) δ: 0.99 (3H, t, J=7.2 Hz), 1.42–1.60 (2H, m), 1.77–1.91 (2H, m), 2.80–2.94 (2H, m), 2.98 (2H, t, J=6.3 Hz), 3.60 (1H, t, J=6.2 Hz), 3.72 (1H, t, J=6.2 Hz), 3.95 (2H, t, J=6.3 Hz), 4.35–4.47 (4H, m), 5.21 (2H, s), 7.71–7.86 (5H, m), 8.46 (1H, s).

(2) Tert-butyl{4-butoxy-6,7-dichloro-1-oxo-2-{(3-oxo-3-(1,3-thiazolidin-3-yl)propyl}-1,2-dihydro-3-isoquinolinyl}methylcarbamate (synthesized according to the method similar to that in Example 1 (6))

Melting point 218–218.5° C. Elemental analysis for $C_{25}H_{33}N_3O_5Cl_2S$ Calculated: C, 53.71; H, 5.96; N, 7.52. Found: C, 54.08; H, 6.20; N, 7.35. $^1$H-NMR(CDCl$_3$) δ: 1.03 (3H, t, J=7.3 Hz), 1.45 (9H, s), 1.51–1.63 (2H, m), 1.80–1.94 (2H, m), 2.89–3.00 (2H, m), 3.06 (2H, t, J=6.2 Hz), 3.69–3.91 (4H, m), 4.38 (2H, t, J=6.8 Hz), 4.46 (1H, s) 4.54 (1H, s), 4.61 (2H, d, J=5.6 Hz), 5.40 (1H, bs), 7.79 (1H, s), 8.45 (1H, s).

(3) 3-(Aminomethyl)-4-butoxy-6,7-dichloro-2-{3-oxo-3-(1,3-thiazolidin-3-yl)propyl}-1(2H)-isoquinolinone hydrochloride (synthesized according to the method similar to that in Example 1 (7))

Melting point 206–207° C. Elemental analysis for $C_{20}H_{26}N_3O_3Cl_3S$ Calculated: C, 48.54; H, 5.30; N, 8.49. Found: C, 48.19; H, 5.19; N, 8.36. $^1$H-NMR(DMSO-d$_6$) δ: 0.99 (3H, t, J=7.3 Hz), 1.45–1.64 (2H, m), 1.78–1.92 (2H, m), 2.84 (2H, bs), 2.97 (1H, t, J=6.2 Hz), 3.06 (1H, t, J=6.2 Hz), 3.46 (2H, s), 3.65 (2H, q, J=6.2 Hz), 3.93 (2H, t, J=6.4 Hz), 4.27 (2H, d, J=6.6 Hz), 4.44 (1H, s), 4.50 (1H, s), 7.92 (1H, s), 8.38 (1H, s), 8.66 (3H, bs).

Example 44

(2S)-1-[3-[3-(Aminomethyl)-4-butoxy-6,7-dichloro-1-oxo-2(1H)-isoquinolinyl]propanoyl]-2-pyrrolidinecarboxamide hydrochloride (1) (2S)-1-[3-[4-Butoxy-6,7-dichloro-3-[(1,3-dioxo-1,3-dihydro-2H-isoindol-2-yl)methyl]-1-oxo-2(1H)-isoquinolinyl]propanoyl]-2-pyrrolidinecarboxamide (synthesized according to the method similar to that in Example 35 (8))

Melting point 235–236.5° C. Elemental analysis for $C_{30}H_{30}N_4O_6Cl_2$ ½$H_2O$ Calculated: C, 57.88; H, 5.02; N, 9.00. Found: C, 57.86; H, 4.94; N, 8.90. $^1$H-NMR(CDCl$_3$) δ: 1.00 (3H, t, J=7.3 Hz), 1.43.–1.62 (2H, m), 1.69–1.99 (4H, m), 2.33–2.42 (1H, m), 2.67–2.89 (2H, m), 3.22–3.29 (2H, m), 3.98 (2H, t, J=,6.6 Hz), 4.35–4.49 (2H, m), 5.16 (2H, d, J=2.2 Hz), 5.37 (1H, bs), 7.06 (1H, bs), 7.72–7.86 (5H, m), 8.44 (1H, s).

(2) Tert-butyl(2-{3-[(2S)-2-(aminocarbonyl)pyrrolizinyl]-3-oxopropyl}-4-butoxy-6,7-dichloro-1-oxo-1,2-dihydro-3-isoquinolinyl)methylcarbamate (synthesized according to the method similar to that in Example 1 (6))

Melting point 159–160° C. Elemental analysis for $C_{26}H_{35}N_3O_5Cl_2$ Calculated: C, 57.78; H, 6.53; N, 7.77. Found: C, 57.95; H, 6.43; N, 7.60. $^1$H-NMR(CDCl$_3$) δ: 1.03 (3H, t, J=7.2 Hz), 1.43,(9H, s), 1.53–1.73 (4H, m), 1.83–2.00 (4H, m), 2.33–2.42 (1H, m), 2.79–2.98 (2H, m), 3.37–3.65 (2H, m), 3.87 (2H, t, J=6.5 Hz), 4.24–4.44 (2H, m), 4.55 (2H, d, J=6.4 Hz), 5.34 (1H, bs), 5.41 (11H, bs), 7.13 (1H, bs), 7.79 (1H, s), 8.42 (1H, s).

(3) (2S)-1-[3-[3-(Aminomethyl)-4-butoxy-6,7-dichloro-1-oxo-2(1H)-isoquinolinyl]propanoyl]-2-pyrrolidinecarboxamide hydrochloride (synthesized according to the method similar to that in Example 1 (7))

Melting point 185–185.5° C. Elemental analysis for $C_{22}H_{29}N_4O_4Cl_3$ ½$H_2O$ Calculated: C, 49.96; H, 5.72; N, 10.59. Found: C, 50.12; H, 5.79; N, 10.29. $^1$H-NMR(DMSO-d$_6$) δ: 1.00 (3H, t, J=7.3 Hz), 1.45–1.64 (2H, m), 1.72–1.99 (5H, m), 2.65–2.83 (2H, m), 3.33–3.55 (4H, m), 3.93 (2H, t, J=6.4 Hz), 4.08–4.28 (4H, m), 6.94 (1H, bs), 7.35 (1H, bs), 7.92 (1H, s), 8.38 (1H, s), 8.72 (3H, bs).

Example 45

(2S)-1-[3-[3-(Aminomethyl)-4-butoxy-6,7-dichloro-1-oxo-2(1H)-isoquinolinyl]propanoyl]-2-pyrrolidine carbonitrile hydrochloride (1) A solution of tert-butyl(2-{3-[(2S)-2-(aminocarbonyl)pyrrolizinyl]-3-oxopropyl}-4-butoxy-6,7-dichloro-1-oxo-1,2-dihydro-3-isoquinolinyl)-methylcarbamate (Example 44 (1)) (0.58 g, 1 mmol) and cyanuric chloride (0.54 g, 3 mmol) in N,N-dimethylformamide (50 mmol) was stirred at 0° C. for 1 h. The reaction mixture was poured into water and extracted with ethyl acetate. The extract was washed with brine, dried over anhydrous magnesium sulfate and concentrated under reduced pressure. The residue was recrystallized from tetrahydrofuran diisopropyl ether to give tert-butyl (4-butoxy-6,7-dichloro-2-{3-[(2S)-2-cyanopyrrolizinyl]-3-oxopropyl}-1oxo-1,2-dihydro-3-isoquinolinyl)methylcarbamate (0.39 g, 69.6%) as crystals.

Melting point 181–183° C. Elemental analysis $C_{27}H_{34}N_4O_5Cl_2$ Calculated: C, 57.35; H, 6.06; N, 9.91. Found: C, 57.16; H, 6.24; N, 9.61. $^1$H-NMR(CDCl$_3$) δ: 1.03 (3H, t, J=7.4 Hz), 1.45 (9H, s), 1.51–1.63 (2H, m), 1.76–1.94 (2H, m), 2.11–2.32 (4H, m), 2.91 (2H, t, J=6.8 Hz), 3.44–3.51 (1H, m), 3.62–3.67, (1H, m), 3.88 (2H, t, J=6.6 Hz), 4.40 (2H, t, J=6.8 Hz), 4.61 (2H, d, J=5.6 Hz), 4.63–4.72 (1H, m), 5.38 (1H, s), 7.79 (1H, s), 8.44 (1H, s).

(2) (2S)-1-[3-[3-(Aminomethyl)-4-butoxy-6,7-dichloro-1-oxo-2(1H)-isoquinolinyl]propanoyl]-2-pyrrolidine carbonitrile hydrochloride (synthesized according to the method similar to that in Example 1 (7))

$^1$H-NMR(DMSO-d$_6$) δ: 0.99 (3H, t, J=7.3 Hz), 1.47–1.64 (2H, m), 1.71–2.19 (6H, m), 2.78–2.88 (2H, m), 3.36–3.82 (2H, m), 3.93 (2H, t, J=6.4 Hz), 4.16–4.58 (5H, m), 7.93 (1H, s), 8.38 (1H, s), 8.64 (3H, bs).

Example 46

3-(Aminomethyl)-4-butoxy-2-neopentyl-1(2H)-isoquinolinone hydrochloride (1) Ethyl 4-hydroxy-2-neopentyl-1-oxo-1,2-dihydro-3-isoquinolinecarboxylate (synthesized according to the method similar to that in Example 1 (1))

Melting point 72–72.5° C. Elemental analysis for C$_{17}$H$_{21}$NO$_4$ ¼H$_2$O Calculated: C, 66.32; H, 7.04; N, 4.55. Found: C, 66.40; H, 7.14; N, 4.54. $^1$H-NMR(CDCl$_3$) δ: 0.85 (9H, s), 1.47 (3H, t, J=7.2 Hz), 4.48 (2H, q, J=7.2 Hz), 4.54 (2H, bs), 7.69–7.80 (2H, m), 8.13–8.18 (1H, m), 8.44–8.749 (1H, m), 10.85 (1H, s).

(2) Ethyl 4-butoxy-2-neopentyl-1-oxo-1,2-dihydro-3-isoquinolinecarboxylate (synthesized according to the method similar to that in Example 1 (2))

$^1$H-NMR(CDCl$_3$) δ: 0.94 (9H, s), 1.01 (3H, t, J=7.3 Hz), 1.44 (3H, t, J=7.2 Hz), 1.44–1.60 (2H, m), 1.74–1.84 (2H, m), 3.96 (2H, t, J=6.6 Hz), 4.11 (2H, bs), 4.43 (2H, q, J=7.2 Hz), 7.51–7.61 (1H, m), 7.68–7.81 (2H, m), 8.43–8.47 (1H, m).

(3) 4-Butoxy-2-neopentyl-1-oxo-1,2-dihydro-3-isoquinolinecarboxylic acid (synthesized according to the method similar to that in Example 4 (3))

Melting point 146–148° C. $^1$H-NMR(CDCl$_3$) δ: 0.96 (9H, s), 1.00 (3H, t, J=7.4 Hz), 1.46–1.65 (2H, m), 1.76–1.90 (2H, m), 4.01 (2H, t, J=6.6 Hz), 4.19 (2H, bs), 5.71 (1H, bs), 7.51–7.60 (1H, m), 7.67–7.86 (2H, m), 8.41–8.45 (1H, m).

(4) 4-Butoxy-3-hydroxymethyl-2-neopentyl-1(2H)-isoquinolinone (synthesized according to the method similar to that in Example 4 (4))

Melting point 123–124° C. Elemental analysis for C$_{19}$H$_{27}$NO$_3$ Calculated: C, 70.89; H, 8.61; N, 4.35. Found: C, 71.29; H, 8.23; N, 4.36. $^1$H-NMR(CDCl$_3$) δ: 1.00 (9H, s), 1.07 (3H, t, J=7.3 Hz), 1.50–1.68 (2H, m), 1.80–1.94 (2H, m), 2.35 (1H, bs), 3.91 (2H, t, J=6.4 Hz), 4.22 (2H, bs), 4.89 (2H, bs), 7.42–7.50 (1H, m), 7.60–7.72 (2H, m), 8.35 (1H, d, J=8.1 Hz).

(5) 4-Butoxy-3-chloromethyl-2-neopentyl-1(2H)-isoquinolinone (synthesized according to the method similar to that in Example 4 (5))

$^1$H-NMR(CDCl$_3$) δ: 0.99 (9H, s), 1.04 (3H, t, J=7.1 Hz), 1.52–1.69 (2H, m), 1.82–1.96 (2H, m), 3.96 (2H, t, J=6.6 Hz), 4.18 (2H bs), 4.90 (2H, bs), 7.50–7.58 (1H, m), 7.66–7.78 (2H, m), 8.42–8.46 (1H, m).

(6) 2-{(4-Butoxy-2-neopentyl-1-oxo-1,2-dihydro-3-isoquinolinyl)methyl}-1H-isoindole-1,3(2H)-dione (synthesized according to the method similar to that in Example 4 (6))

Melting point 132.5–133° C. Elemental analysis for C$_{27}$H$_{30}$N$_2$O$_4$ ¼H$_2$O Calculated: C, 71.90; H, 6.82; N, 6.21. Found: C, 72.18; H, 6.73; N, 6.12. $^1$H-NMR(CDCl$_3$) δ: 1.00 (3H, t, J=7.3 Hz), 1.01 (9H, s), 1.45–1.60 (2H, m), 1.82–1.96 (2H, m), 4.03 (2H, t, J=6.8 Hz), 4.14 (2H, bs), 5.09 (2H, s), 7.46–7.54 (1H, m), 7.64–7.83 (6H, m), 8.39–8.43 (1H, m).

(7) Tert-butyl(4-butoxy-2neopentyl-1-oxo-1,2-dihydro-3-isoquinolinyl)methylcarbamate (synthesized according to the method similar to that in Example 1 (6))

Melting point 138–139° C. Elemental analysis for C$_{24}$H$_{36}$N$_2$O$_4$ Calculated: C, 69.20; H, 8.71; N, 6.73. Found: C, 69.30; H, 8.80; N, 6.70. $^1$H-NMR(CDCl$_3$) δ: 1.00 (9H, s), 1.03 (3H, t, J=7.4 Hz), 1.45 (9H, s), 1.53–1.65 (2H, m), 1.76–1.94 (2H, m), 3.87 (2H, t, J=6.6 Hz), 4.14 (2H, bs), 4.58 (2H, d, J=5.2 Hz), 4.66 (1H, bs), 7.46–7.54 (1H, m), 7.64–7.73 (2H, m), 8.40–8.44 (1H, m).

(8) 3-(Aminomethyl)-4-butoxy-2-neopentyl-1(2H)-isoquinolinone hydrochloride (synthesized according to the method similar to that in Example 1 (7))

Melting point 231–232° C. Elemental analysis for C$_{19}$H$_{29}$N$_2$O$_2$Cl Calculated: C, 64.67; H, 8.28; N, 7.94. Found: C, 64.61; H, 8.44; N, 7.76. $^1$H-NMR(DMSO-d$_6$) δ: 0.91 (9H, s), 0.99 (3H, t, J=7.3 Hz), 1.48–1.62 (2H, m), 1.78–1.92 (2H, m), 3.94 (2H, t, J=6.4 Hz), 4.11 (2H, bs), 4.25 (2H, bs), 7.58–7.67 (1H, m), 7.77–7.90 (2H, m), 8.27–8.30 (1H, m), 8.59 (3H, bs).

Example 47

3-(Aminomethyl)-4-butoxy-6,7-dichloro-2-(2-furylmethyl)-1(2H)-isoquinolinone hydrochloride (1) Ethyl 6,7-dichloro-2-(2-furylmethyl)-4-hydroxy-1-oxo-1,2-dihydro-3-isoquinolinecarboxylate (synthesized according to the method similar to that in Example 1 (1))

Melting point 134–135° C. Elemental analysis for C$_{17}$H$_{13}$NO$_5$Cl$_2$ calculated: C, 53.42; H, 3.43; N, 3.66. Found: C, 53.84; H, 3.53; N, 3.44. $^1$H-NMR(CDCl$_3$) δ: 1.42 (3H, t, J=7.2 Hz), 4.42 (2H, q, J=7.2 Hz), 5.68 (2H, s), 6.16 (1H, dd, J=0.8, 3.1 Hz), 6.27 (1H, dd, J=2.0, 3.1 Hz), 7.28 (1H, dd, J=0.8, 2.0 Hz), 8.21 (1H, s), 8.54 (1H, s), 11.11 (1H, s).

(2) Ethyl 4-butoxy-6,7-dichloro-2-(2-furylmethyl)-1-oxo-1,2-dihydro-3-isoquinolinecarboxylate (synthesized according to the method similar to that in Example 1 (2))

$^1$H-NMR(CDCl$_3$) δ: 1.00 (3H, t, J=7.4 Hz), 1.37 (3H, t, J=7.1 Hz), 1.42–1.61 (2H, m), 1.71–1.85 (2H, m), 3.92 (2H, t, J=6.4 Hz), 4.39 (2H, q, J=7.1 Hz), 5.36 (2H, s), 6.28–6.32 (2H, m), 7.32 (1H, d, J=1.5 Hz), 7.81 (1H, s), 8.53 (1H, s).

(3) 4-Butoxy-6,7-dichloro-2-(2-furylmethyl)-1-oxo-1,2-dihydro-3-isoquinolinecarboxylic acid (synthesized according to the method similar to that in Example 4 (3))

Melting point 147.5–148° C. Elemental analysis for C$_{19}$H$_{17}$NO$_5$Cl$_2$ Calculated: C, 57.59; H, 4.83; N, 3.53. Found: C, 57.40; H, 4.79; N, 3.37. $^1$H-NMR(CDCl$_3$) δ: 0.99 (3H, t, J=7.3 Hz), 1.47–1.62 (2H, m), 1.75–1.89 (2H, m), 4.00 (2H, t, J=6.6 Hz), 5.16 (1H, bs), 5.52 (2H, s), 6.28 (1H, dd, J=1.8, 3.2 Hz), 6.35 (1H, dd, J=0.8, 3.2 Hz), 7.30 (1H, dd, J=0.8, 1.8 Hz), 7.82 (1H, s), 8.54 (1H, s).

(4) 4-Butoxy-6,7-dichloro-2-(2-furylmethyl)-3-hydroxymethyl-1(2H)-isoquinolinone (synthesized according to the method similar to that in Example 4 (4))

Melting point 120–121° C. Elemental analysis for C$_{19}$H$_{19}$NO$_5$Cl$_2$ Calculated: C, 57.59; H, 4.83; N, 3.53. Found: C, 57.40; H, 4.79; N, 3.37. $^1$H-NMR(CDCl$_3$) δ: 1.04 (3H, t, J=7.3 Hz), 1.49–1.62 (2H, m), 1.78–1.92 (2H, m), 3.88 (2H, t, J=6.5 Hz), 4.97 (2H, d, J=5.4 Hz), 5.49 (2H, s), 6.32 (1H, dd, J=1.8, 2.9 Hz), 6.40 (1H, dd, J=0.8, 2.9 Hz), 7.31 (1H, dd, J=0.8, 1.8 Hz), 7.75 (1H, s), 8.45 (1H, s).

(5) 4-Butoxy-3-chloromethyl-6,7-dichloro-2-(2-furylmethyl)-1(2H)-isoquinoline (synthesized according to the method similar to that in Example 4 (5))

$^1$H-NMR(CDCl$_3$) δ: 1.05 (3H, t, J=7.3 Hz), 1.55–1.79 (2H, m), 1.82–1.93 (2H, m), 3.99 (2H, t, J=6.6 Hz), 5.00 (2H, s), 5.46 (2H, s), 6.31 (1H, dd, J=1.9, 3.2 Hz), 6.41 (1H, dd, J=1.1, 3.2 Hz), 7.31 (1H, dd, J=1.1, 1.9 Hz), 7.81 (1H, s), 8.51 (1H, s).

(6) 2-{(4-Butoxy-6,7-dichloro-2-(2-furylmethyl)-1-oxo-1,2-dihydro-3-isoquinolinyl)methyl}-1H-isoindole-1,3 (2H)-dione (synthesized according to the method similar to that in Example 4 (6))

Melting point 148–149° C. Elemental analysis for C$_{27}$H$_{22}$N$_2$O$_5$Cl$_2$ Calculated: C, 61.72; H, 4.22; N, 5.33. Found: C, 61.95; H, 4.51; N, 5.47. $^1$H-NMR(CDCl$_3$) δ: 1.01 (3H, t, J=7.3 Hz), 1.45–1.63 (2H, m), 1.80–1.94 (2H, m), 4.02 (2H, t, J=6.8 Hz), 5.15 (2H, s), 5.36 (2H, s), 6.05 (1H, dd, J=1.8, 3.2 Hz), 6.17 (1H, dd, J=0.8, 3.2 Hz), 6.89 (1H, dd, J=0.8, 1.8 Hz), 7.69–7.80 (4H, bs), 7.82 (1H, s), 8.49 (1H, s).

(7) Tert-butyl(4-butoxy-6,7-dichloro-2-(2-furylmethyl)-1-oxo-1,2-dihydro-3-isoquinolinyl)methylcarbamate (synthesized according to the method similar to that in Example 1 (6))

Melting point 143–144° C. Elemental analysis for $C_{24}H_{28}N_2O_5Cl_2$ Calculated: C, 58.19; H, 5.70; N, 5.65. Found: C, 58.31; H, 5.53; N, 5.70. $^1$H-NMR(CDCl$_3$) δ: 1.04 (3H, t, J=7.3 Hz), 1.46 (9H, s), 1.51–1.67 (2H, m), 1.79–1.93 (2H, m), 3.84 (2H, t, J=6.5 Hz), 4.66 (2H, d, J=5.8 Hz), 4.91 (1H, bs), 5.37 (2H, s), 6.30 (1H, dd, J=2.0, 3.4 Hz), 6.44 (1H, d, J=3.4 Hz), 7.32 (1H, d, J=2.0 Hz), 7.75 (1H, s), 8.47 (1H, s).

(8) 3-(Aminomethyl)-4-butoxy-6,7-dichloro-2-(2-furylmethyl)-1(2H)-isoquinolinone hydrochloride (synthesized according to the method similar to that in Example 1 (7))

Melting point 223–224° C. Elemental analysis for $C_{19}H_{21}N_2O_3Cl_3$ Calculated: C, 52.86; H, 4.90; N, 6.49. Found: C, 52.55; H, 4.97; N, 6.58. $^1$H-NMR(DMSO-d$_6$) δ: 0.99 (3H, t, J=7.3 Hz), 1.44–1.63 (2H, m), 1.77–1.92 (2H, m), 3.94 (2H, t, J=6.4 Hz), 4.26 (2H, s), 5.40 (2H, s), 6.42 (1H, dd, J=1.8, 3.2 Hz), 6.45 (1H, dd, J=1.0, 3.2 Hz), 7.61 (1H, dd, J=1.0, 1.8 Hz), 7.93 (1H, s) 8.39 (1H, s), 8.82 (3H, bs).

Example 48

3-(Aminomethyl)-4-butoxy-6,7-dichloro-2-(2methoxyethyl)-1(2H)-isoquinolinone hydrochloride (1) ethyl 6,7-dichloro-4-hydroxy-2-(2methoxyethyl)-1-oxo-1,2-dihydro-3-isoquinolinecarboxylate (synthesized according to the method similar to that in Example 1 (1))

Melting point 110.5–111° C. Elemental analysis for $C_{15}H_{15}NO_5Cl_2$ Calculated: C, 50.02; H, 4.20; N, 3.89. Found: C, 49.86; H, 4.44; N, 3.76. $^1$H-NMR(CDCl$_3$) δ: 1.46 (3H, t, J=7.1 Hz), 3.30 (3H, s), 3.62 (2H, d, J=5.8 Hz), 4.49 (2H, q, J=7.1 Hz), 4.61 (2H, t, J=5.8 Hz), 8.22 (1H, s), 8.51 (1H, s), 10.95 (1H, s).

(2) Ethyl 4-butoxy-6,7-dichloro-2-(2-methoxyethyl)-1-oxo-1,2-dihydro-3-isoquinolinecarboxylate (synthesized according to the method similar to that in Example 1 (2))

Melting point 102–103° C. Elemental analysis for $C_{19}H_{23}NO_5Cl_2$ Calculated: C, 54.82; H, 5.57; N, 3.36. Found: C, 54.81; H, 5.35; N, 3.36. $^1$H-NMR(CDCl$_3$) δ: 1.01 (3H, t, J=7.3 Hz), 1.44 (3H, t, J=7.2 Hz), 1.50–1.62 (2H, m), 1.72–1.86 (2H, m), 3.31 (3H, s), 3.63 (2H, t, J=5.9 Hz), 3.94 (2H, t, J=6.4 Hz), 4.26 (2H, t, J=5.9 Hz), 4.45 (2H, q, J=7.2 Hz), 7.82 (1H, s), 8.50 (1H, s).

(3) 4-Butoxy-6,7-dichloro-2-(2-methoxyethyl)-1-oxo-1,2-dihydro-3-isoquinolinecarboxylic acid (synthesized according to the method similar to that in Example 4 (3))

Melting point 142–143° C. Elemental analysis for $C_{17}H_{19}NO_5Cl_2$ Calculated: C, 52.59; H, 4.93; N, 3.61. Found: C, 52.58; H, 4.94; N, 3.41. $^1$H-NMR(CDCl$_3$) δ: 1.00 (3H, t, J=7.2 Hz), 1.44–1.63 (2H, m), 1.74–1.89 (2H, m), 3.41 (3H, s), 3.85 (2H, t, J=5.3 Hz), 4.00 (2H, t, J=6.4 Hz), 4.37–4.40 (2H, m), 7.82 (1H, s), 8.48 (1H, s).

(4) 4-Butoxy-6,7-dichloro-3-hydroxymethyl-2-(2-methoxyethyl)-1(2H)-isoquinolinone (synthesized according to the method similar to that in Example 4 (4))

Melting point 122–123° C. Elemental analysis for $C_{17}H_{21}NO_4Cl_2$ Calculated: C, 54.56; H, 5.66; N, 3.74. Found: C, 54.34; H, 5.59; N, 3.57. $^1$H-NMR(CDCl$_3$) δ: 1.04 (3H, t, J=7.3 Hz), 1.50–1.69 (2H, m), 1.80–1.94 (2H, m), 3.34 (3H, s), 3.83 (2H, t, J=5.5 Hz), 3.96 (2H, t, J=6.6 Hz), 4.38 (2H, t, J=5.5 Hz), 4.46 (2H, t, J=6.4 Hz), 4.79 (2H, d, J=6.4 Hz), 7.84 (1H, s), 8.47 (1H, s).

(5) 4-Butoxy-3-chloromethyl-6,7-dichloro-2-(2-methoxyethyl)-1(2H)-isoquinolinone (synthesized according to the method similar to that in Example 4 (5))

$^1$H-NMR(CDCl$_3$) δ: 1.05 (3H, t, J=7.3 Hz), 1.55–1.70 (2H, m), 1.82–1.96 (2H, m), 3.26 (3H, s), 3.69 (2H, t, J=4.8 Hz), 3.98 (2H, t, J=6.4 Hz), 4.43 (2H, t, J=4.8 Hz), 4.99 (2H, s), 7.82 (1H, s), 8.50 (1H, s).

(6) 2-{(4-Butoxy-6,7-dichloro-2-(2-methoxyethyl)-1-oxo-1,2-dihydro-3-isoquinolinyl)methyl}-1H-isoindole-1,3 (2H)-dione (synthesized according to the method similar to that in Example 4 (6))

Melting point 151–152° C. Elemental analysis for $C_{25}H_{24}N_2O_5Cl_2$ Calculated: C, 59.65; H, 4.81; N, 5.57. Found: C, 59.52; H, 4.85; N, 5.55. $^1$H-NMR(CDCl$_3$) δ: 1.00 (3H, t, J=7.3 Hz), 1.44–1.62 (2H, m), 1.79–1.93 (2H, m), 2.97 (3H, s), 3.64 (2H, t, J=4.9 Hz), 3.98 (2H, t, J=6.6 Hz), 4.37 (2H, t, J=4.9 Hz), 5.10 (2H, s), 7.68–7.87 (5H, m), 8.47 (1H, s).

(7) Tert-butyl{4-butoxy-6,7-dichloro-2-(2-methoxyethyl)-1-oxo-1,2-dihydro-3-isoquinolinyl}methylcarbamate (synthesized according to the method similar to that in Example 1 (6))

Melting point 137–138° C. Elemental analysis for $C_{22}H_{30}N_2O_5Cl_2$ Calculated: C, 55.82; H, 6.39; N, 5.92. Found: C, 55.99; H, 6.33; N, 5.76. $^1$H-NMR(CDCl$_3$) δ: 1.03 (3H, t, J=7.3 Hz), 1.46 (9H, s), 1.51–1.64 (2H, m), 1.81–1.95 (2H, m), 3.33 (3H, s), 3.80 (2H, t, J=4.5 Hz), 3.85 (2H, t, J=6.6 Hz), 4.30 (2H, t, J=4.5 Hz), 4.54 (2H, d, J=5.2 Hz), 6.15 (1H, bs), 7.80 (1H, s), 8.46 (1H, s).

(8) 3-(Aminomethyl)-4-butoxy-6,7-dichloro-2-(2-methoxyethyl)-1(2H)-isoquinolinone hydrochloride (synthesized according to the method similar to that in Example 1 (7))

Melting point 241.5–242° C. Elemental analysis for $C_{17}H_{23}N_2O_3Cl_3$ Calculated: C, 49.83; H, 5.66; N, 6.84. Found: C, 49.80; H, 5.91; N, 6.81. $^1$H-NMR(DMSO-d$_6$) δ: 0.99 (3H, t, J=7.3 Hz), 1.45–1.63 (2H, m), 1.77–1.91 (2H, m), 3.24 (3H, s), 3.61 (2H, d, J=4.9 Hz), 3.93 (2H, t, J=6.6 Hz), 4.23–4.32 (4H, m), 7.91 (1H, s), 8.38 (1H, s), 8.68 (3H, bs).

Example 49

3-(Aminomethyl)-4-(2-methoxyethoxy)-2-neopentyl-1(2H)-isoquinolinone hydrochloride (1) Ethyl 4-(2-methoxyethoxy)-2-neopentyl-1-oxo-1,2-dihydro-3-isoquinolinecarboxylate (synthesized according to the method similar to that in Example 1 (2))

$^1$H-NMR(CDCl$_3$) δ: 0.94 (9H, s), 1.43 (3H, t, J=7.2 Hz), 3.48 (3H, s), 3.71–3.75 (2H, m), 4.07–4.17 (2H, m), 4.43 (2H, q, J=7.2 Hz), 7.53–7.61 (1H, m), 7.69–7.77 (1H, m), 7.93–7.97 (1H, m), 8.42–8.47 (1H, m).

(2) 4-(2-Methoxyethoxy)-2-neopentyl-1-oxo-1,2-dihydro-3-isoquinolinecarboxylic acid (synthesized according to the method similar to that in Example 4 (3))

Melting point 148–149° C. Elemental analysis for $C_{18}H_{23}NO_5$ Calculated: C, 64.85; H, 6.95; N, 4.20. Found: C, 64.79; H, 6.96; N, 4.09. $^1$H-NMR(CDCl$_3$) δ: 0.94 (9H, s), 3.49 (3H, s), 3.76–3.81 (2H, m), 4.27–4.32 (4H, m), 7.56–7.64 (1H, m), 7.70–7.78 (1H, m), 7.89 (1H, dd, J=0.8, 8.0 Hz), 8.44 (1H, dd, J=1.0, 8.0 Hz), 9.79 (1H, bs).

(3) 3-Hydroxymethyl-4-(2-methoxyethoxy)-2-neopentyl-1(2H)-isoquinolinone (synthesized according to the method similar to that in Example 4 (4))

Melting point 145–145.5° C. Elemental analysis for $C_{18}H_{25}NO_4$ Calculated: C, 67.69; H, 7.89; N, 4.39. Found: C, 67.54; H, 8.06; N, 4.28. $^1$H-NMR(CDCl$_3$) δ: 0.98 (9H, s), 3.45 (3H, s), 3.58 (1H, t, J=6.8 Hz), 3.75–3.79 (2H, m), 4.14–4.18 (2H, m), 4.23 (2H, bs), 4.90 (2H, bs), 7.44–7.52 (1H, m), 7.63–7.76 (2H, m), 8.40 (1H, dd, J=0.8, 8.0 Hz).

(4) 3-Chloromethyl-4-(2-methoxyethoxy)-2-neopentyl-1(2H)-isoquinolinone (synthesized according to the method similar to that in Example 4 (5))

$^1$H-NMR(CDCl$_3$) δ: 0.98 (9H, s), 3.52 (3H, s), 3.76–3.82 (2H, m), 4.11–4.18 (2H, m), 4.21 (2H, bs), 4.96 (2H, bs), 7.50–7.58 (1H, m), 7.67–7.76 (1H, m), 7.87 (1H, dd, J=0.8, 8.0 Hz), 8.44 (1H, dd, J=0.8, 8.0 Hz).

(5) 2-{{4-(2-Methoxyethoxy)-2-neopentyl-1-oxo-1,2-dihydro-3-isoquinolinyl}methyl}-1H-isoindole-1,3(2H)-dione (synthesized according to the method similar to that in Example 4 (6))

Melting point 145–146° C. Elemental analysis for $C_{26}H_{28}N_2O_5$ Calculated: C, 68.93; H, 6.34; N, 6.18. Found: C, 69.07; H, 6.06; N, 6.53. $^1$H-NMR(CDCl$_3$) δ: 1.00 (9H, s), 3.47 (3H, s), 3.78–3.82 (2H, m), 4.24–4.29 (2H, m), 4.31 (2H, bs), 5.12 (2H, bs), 7.45–7.54 (1H, m), 7.65–7.92 (6H, m), 8.41 (1H, dd, J=0.7, 8.1 Hz).

(6) Tert-butyl{4-(2-methoxyethoxy)-2-neopentyl-1-oxo-1,2-dihydro-3-isoquinolinyl}methylcarbamate (synthesized according to the method similar to that in Example 1 (6))

Melting point 143–144° C. Elemental analysis for $C_{23}H_{34}N_2O_5$ Calculated: C, 66.06; H, 8.19; N, 6.69. Found: C, 65.73; H, 8.14; N, 6.78. $^1$H-NMR(CDCl$_3$) δ: 0.99 (9H, s), 1.44 (9H, s), 3.48 (3H, s), 3.74–3.79 (2H, m), 4.07–4.12 (2H, m), 4.19 (2H, bs), 4.61 (2H, d, J=6.0 Hz), 5.17 (1H, bs), 7.46–7.54 (1H, m), 7.65–7.73 (1H, m), 7.79 (1H, d, J=8.2 Hz), 8.42 (1H, dd, J=0.7, 8.2 Hz).

(7) 3-(Aminomethyl)-4-(2-methoxyethoxy)-2-neopentyl-1(2H)-isoquinolinone hydrochloride (synthesized according to the method similar to that in Example 1 (7))

Melting point 205–206° C. Elemental analysis for $C_{18}H_{27}N_2O_3Cl$ ¼H$_2$O Calculated: C, 60.16; H, 7.71; N, 7.80. Found: C, 59.84; H, 7.52; N, 7.82. $^1$H-NMR(DMSO-d$_6$) δ: 0.91 (9H, s), 1.10 (6H, d, J=6.6 Hz), 2.14–2.27 (1H, m), 3.73 (2H, d, J=6.6 Hz), 4.11 (2H, bs), 4.24 (2H, s), 7.89 (1H, s), 8.38 (1H, s), 8.63 (3H, bs).

Example 50

3-(Aminomethyl)-4-butoxy-7-methyl-2-neopentyl-1(2H)-isoquinolinone hydrochloride (1) Ethyl 4-hydroxy-7-methyl-2-neopentyl-1-oxo-1,2-dihydro-3-isoquinolinecarboxylate (synthesized according to the method similar to that in Example 1 (1))

Melting point 90–91° C. Elemental analysis for $C_{18}H_{23}NO_4$ Calculated: C, 68.12; H, 7.30; N, 4.41. Found: C, 67.98; H, 7.10; N, 4.22. $^1$H-NMR(CDCl$_3$) δ: 0.84 (9H, s), 1.46 (3H, t, J=7.1 Hz), 2.54 (3H, s), 4.42 (2H, bs), 4.49 (2H, q, J=7.1 Hz), 7.57 (1H, dd, J=1.9, 8.0 Hz), 8.04 (1H, d, J=8.0 Hz), 8.26 (1H, d, J=1.9 Hz), 10.90 (1H, s).

(2) Ethyl 4-butoxy-7-methyl-2-neopentyl-1-oxo-1,2-dihydro-3-isoquinolinecarboxylate (synthesized according to the method similar to that in Example 1 (2))

$^1$H-NMR (CDCl$_3$) δ: 0.93 (9H, s), 1.00 (3H, t, J=7.3 Hz), 1.44 (3H, t, J=7.0 Hz), 1.47–1.62 (2H, m), 1.73–1.87 (2H, m), 2.51 (3H, s), 3.95 (2H, t, J=6.6 Hz), 4.11 (2H, bs), 4.42 (2H, q, J=7.0 Hz), 7.54 (1H, dd, J=1.7, 8.0 Hz), 7.68 (1H, d, J=8.0 Hz), 8.26 (1H, d, J=1.7 Hz).

(3) 4-Butoxy-7-methyl-2-neopentyl-1-oxo-1,2-dihydro-3-isoquinolinecarboxylic acid (synthesized according to the method similar to that in Example 4 (3))

Melting point 160.5–161° C. Elemental analysis for $C_{20}H_{27}NO_4$ Calculated: C, 69.54; H, 7.88; N, 4.05. Found: C, 69.45; H, 8.10; N, 3.98. $^1$H-NMR(CDCl$_3$) δ: 0.91 (9H, s), 0.99 (3H, t, J=7.1 Hz), 1.44–1.63 (2H, m), 1.76–1.90 (2H, m), 2.50 (3H, s), 4.00 (2H, t, J=6.6 Hz), 4.26 (2H, bs), 5.92 (1H, bs), 7.45–7.56 (2H, m), 8.13 (1H, s).

(4) 4-Butoxy-3-hydroxymethyl-7-methyl-2-neopentyl-1(2H)-isoquinoline (synthesized according to the method similar to that in Example 4 (4))

Melting point 109–110° C. Elemental analysis for $C_{20}H_{29}NO_3$ Calculated: C, 72.47; H, 8.82; N, 4.23. Found: C, 72.18; H, 8.75; N, 4.26. $^1$H-NMR(CDCl$_3$) δ: 0.96 (9H, s), 1.03 (3H, t, J=7.4 Hz), 1.49–1.68 (2H, m), 1.79–1.93 (2H, m), 2.45 (3H, s), 2.61 (1H, bs), 3.90 (2H, t, J=6.6 Hz), 4.22 (2H, bs), 4.87 (2H, bs), 7.43 (1H, dd, J=1.8, 8.0 Hz), 7.56 (1H, d, J=8.0 Hz), 8.09 (1H, d, J=1.8 Hz).

(5) 4-Butoxy-3-chloromethyl-7-methyl-2-neopentyl-1(2H)-isoquinoline (synthesized according to the method similar to that in Example 4 (5))

$^1$H-NMR(CDCl$_3$) δ: 0.98 (9H, s), 1.04 (3H, t, J=7.3 Hz), 1.51–1.69 (2H, m), 1.81–1.95 (2H, m), 2.50 (3H, s), 3.95 (2H, t, J=6.4 Hz), 4.18 (2H, bs), 4.90 (2H, bs), 7.52 (1H, dd, J=1.8, 8.1 Hz), 7.65 (1H, d, J=8.1 Hz), 8.24 (1H, d, J=1.8 Hz).

(6) 2-{(4-Butoxy-7-methyl-2-neopentyl-1-oxo-1,2-dihydro-3-isoquinolinyl)methyl}-1H-isoindole-1,3(2H)-dione (synthesized according to the method similar to that in Example 4 (6))

Melting point 174–175° C. Elemental analysis for $C_{28}H_{32}N_2O_4$ ¼H$_2$O Calculated: C, 72.31; H, 7.04; N, 6.02. Found: C, 72.57; H, 7.35; N, 6.04. $^1$H-NMR(CDCl$_3$) δ: 1.00 (9H, s), 1.01 (3H, t, J=7.3 Hz), 1.44–1.59 (2H, m), 1.81–1.95 (2H, m), 2.48 (3H, s), 4.02 (2H, t, J=6.8 Hz), 4.10 (2H, bs), 5.08 (2H, s), 7.50 (1H, dd, J=1.7, 8.3 Hz), 7.63–7.82 (5H, m), 8.22 (1H, d, J=1.7 Hz).

(7) Tert-butyl(4-butoxy-7-methyl-2-neopentyl-1-oxo-1,2-dihydro-3-isoquinolinyl)methylcarbamate (synthesized according to the method similar to that in Example 1 (6))

Melting point 153–154° C. Elemental analysis for $C_{25}H_{38}N_2O_4$ Calculated: C, 69.74; H, 8.90; N, 6.51. Found: C, 69.65; H, 9.13; N, 6.56. $^1$H-NMR(CDCl$_3$) δ: 0.99 (9H, s), 1.03 (3H, t, J=7.2 Hz), 1.45 (9H, s), 1.52–1.63 (2H, m), 1.79–1.93 (2H, m), 2.49 (3H, s), 3.86 (2H, t, J=6.5 Hz), 4.18 (2H, bs), 4.56 (2H, t, J=5.4 Hz), 4.68 (1H, bs), 7.50 (1H, dd, J=1.8, 8.0 Hz), 7.60 (1H, d, J=8.0 Hz), 8.21 (1H, d, J=1.8 Hz).

(8) 3-(Aminomethyl)-4-butoxy-7-methyl-2-neopentyl-1(2H)-isoquinolinone hydrochloride (synthesized according to the method similar to that in-Example 1 (7))

Melting point 231–233° C. Elemental analysis for $C_{20}H_{31}N_2O_2Cl$ Calculated: C, 65.47; H, 8.52; N, 7.63. Found: C, 65.44; H, 8.53; N, 7.86. $^1$H-NMR(DMSO-d$_6$) δ: 0.99 (9H, s), 0.99 (3H, t, J=7.2 Hz), 1.45–1.64 (2H, m), 1.77–1.91 (2H, m), 2.47 (3H, s), 3.92 (2H, t, J=6.6 Hz), 4.10 (2H, bs), 4.23 (2H, d, J=5.2 Hz), 7.63–7.72 (2H, m), 8.09 (1H, s), 8.56 (3H, bs).

Example 51

3-(Aminomethyl)-4-butoxy-6-methyl-2-neopentyl-1(2H)-isoquinolinone hydrochloride (1) Ethyl 4-hydroxy-6-methyl-2-neopentyl-1-oxo-1,2-dihydro-3-isoquinolinecarboxylate (synthesized according to the method similar to that in Example 1 (1))

$^1$H-NMR(CDCl$_3$) δ: 0.84 (9H, s), 1.46 (3H, t, J=7.2 Hz), 2.54 (3H, s), 4.42 (2H, bs), 4.47 (2H, q, J=7.2 Hz), 7.51 (1H, dd, J=1.9, 8.0 Hz), 7.93 (1H, d, J=1.9 Hz), 8.33 (1H, d, J=8.0 Hz), 10.86 (1H, s).

(2) Ethyl 4-butoxy-6-methyl-2-neopentyl-1-oxo-1,2-dihydro-3-isoquinolinecarboxylate (synthesized according to the method similar to that in Example 1 (2))

$^1$H-NMR(CDCl$_3$) δ: 0.94 (9H, s), 1.00 (3H, t, J=7.2 Hz), 1.44 (3H, t, J=7.2 Hz), 1.47–1.60 (2H, m), 1.74–1.91 (2H, m), 2.52 (3H, s), 3.96 (2H, t, J=6.4 Hz), 4.07 (2H, bs), 4.43 (2H, q, J=7.2 Hz), 7.38 (1H, dd, J=1.0, 8.0 Hz), 7.68 (1H, d, J=1.0 Hz), 8.26 (1H, d, J=8.0 Hz).

(3) 4-Butoxy-6-methyl-2-neopentyl-1-oxo-1,2-dihydro-3-isoquinolinecarboxylic acid (synthesized according to the method similar to that in Example 4 (3))

Melting point 153–154° C. Elemental analysis for C$_{20}$H$_{27}$NO$_4$ Calculated: C, 69.54; H, 7.88; N, 4.05. Found: C, 69.59; H, 8.16; N, 4.06. $^1$H-NMR(CDCl$_3$) δ: 0.91 (9H, s), 1.01 (3H, t, J=7.1 Hz), 1.48–1.65 (2H, m), 1.77–1.88 (2H, m), 2.52 (3H, s), 4.02 (2H, t, J=6.4 Hz), 4.22 (2H, bs), 6.42 (1H, bs), 7.38 (1H, dd, J=1.3, 8.2 Hz), 7.45 (1H, d, J=1.3 Hz), 8.25 (1H, d, J=8.2 Hz).

(4) 4-Butoxy-3-hydroxymethyl-6-methyl-2-neopentyl-1(2H)-isoquinolinone (synthesized according to the method similar to that in Example 4 (4))

Melting point 133–134° C. Elemental analysis for C$_{20}$H$_{29}$NO$_3$ Calculated: C, 72.47; H, 8.82; N, 4.23. Found: C, 72.43; H, 8.80; N, 4.24. $^1$H-NMR(CDCl$_3$) δ: 0.97 (9H, s), 1.04 (3H, t, J=7.2 Hz), 1.51–1.69 (2H, m), 1.80–1.94 (2H, m), 2.38 (1H, bs), 2.49 (3H, s), 3.90 (2H, t, J=6.6 Hz), 4.20 (2H, bs), 4.86 (2H, bs), 7.27 (1H, dd, J=1.6, 8.0 Hz), 7.45 (1H, d, J=1.6 Hz), 8.22 (1H, d, J=8.0 Hz).

(5) 4-Butoxy-3-chloromethyl-6-methyl-2-neopentyl-1(2H)-isoquinolinone (synthesized according to the method similar to that in Example 4 (5))

$^1$H-NMR(CDCl$_3$) δ: 0.98 (9H, s), 1.05 (3H, t, J=7.1 Hz), 1.56–1.71 (2H, m), 1.82–1.92 (2H, m), 2.52 (3H, s), 3.95 (2H, t, J=6.5 Hz), 4.14 (2H, bs), 4.88 (2H, bs), 7.35 (1H, dd, J=1.8, 8.0 Hz), 7.51 (1H, d, J=1.8 Hz), 8.32 (1H, d, J=8.0 Hz).

(6) 2-{(4-Butoxy-6-methyl-2-neopentyl-1-oxo-1,2-dihydro-3-isoquinolinyl)methyl}-1H-isoindole-1,3(2H)-dione (synthesized according to the method similar to that in Example 4 (6))

Melting point 170–172° C. Elemental analysis for C$_{28}$H$_{32}$N$_2$O$_4$ Calculated: C, 73.02; H, 7.00; N, 6.08. Found: C, 72.72; H, 7.05; N, 6.25. $^1$H-NMR(CDCl$_3$) δ: 1.00 (9H, s), 1.01 (3H, t, J=7.2 Hz), 1.50–1.65 (2H, m), 1.82–1.93 (2H, m), 2.50 (3H, s), 4.03 (2H, t, J=6.8 Hz), 4.06 (2H, bs), 5.08 (2H, s), 7.31 (1H, dd, J=1.4, 8.2 Hz), 7.53 (1H, d, J=1.4 Hz), 7.68–7.82 (4H, m), 8.29 (1H, d, J=8.2 Hz).

(7) Tert-butyl(4-butoxy-6-methyl-2-neopentyl-1-oxo-1,2-dihydro-3-isoquinolinyl)methylcarbamate (synthesized according to the method similar to that in Example 1 (6))

Melting point 127–129° C. Elemental analysis for C$_{25}$H$_{38}$N$_2$O$_4$ Calculated: C, 69.74; H, 8.90; N, 6.51. Found: C, 69.80; H, 8.75; N, 6.46. $^1$H-NMR(CDCl$_3$) δ: 0.99 (9H, s), 1.00 (3H, t, J=7.6 Hz), 1.45 (9H, s), 1.53–1.68 (2H, m), 1.75–1.94 (2H, m), 2.51 (3H, s), 3.87 (2H, t, J=6.6 Hz), 4.14 (2H, bs), 4.56 (2H, d, J=5.2 Hz), 4.65 (1H, bs), 7.32 (1H, dd, J=1.4, 8.4 Hz), 7.47 (1H, d, J=1.4 Hz), 8.30 (1H, d, J=8.4 Hz).

(8) 3-(Aminomethyl)-4-butoxy-6-methyl-2-neopentyl-1(2H)-isoquinolinone hydrochloride (synthesized according to the method similar to that in Example 1 (7))

Melting point 201–203° C. Elemental analysis for C$_{20}$H$_{31}$N$_2$O$_2$Cl Calculated: C, 65.47; H, 8.52; N, 7.63. Found: C, 65.50; H, 8.59; N, 7.56. $^1$H-NMR(DMSO-d$_6$) δ: 0.90 (9H, s), 1.00 (3H, t, J=7.3 Hz), 1.50–1.65 (2H, m), 1.78–1.91 (2H, m), 2.50 (3H, s), 3.93 (2H, t, J=6.2 Hz), 4.09 (2H, bs), 4.23 (2H, bs), 7.31 (1H, d, J=8.0 Hz), 7.55 (1H, s), 8.16 (1H, d, J=8.0 Hz), 8.58 (3H, bs).

Example 52

3-(Aminomethyl)-4-butoxy-2-neopentyl-7-trifluoromethyl-1(2H)-isoquinolinone hydrochloride (1) Ethyl 4-hydroxy-2-neopentyl-1-oxo-7-trifluoromethyl-1,2-dihydro-3-isoquinolinecarboxylate (synthesized according to the method similar to that in Example 1 (1))

Melting point 133.5–134° C. Elemental analysis for C$_{18}$H$_{20}$NO$_4$F$_3$ Calculated: C, 58.22; H, 5.43; N, 3.77. Found: C, 58.24; H, 5.48; N, 3.76. $^1$H-NMR(CDCl$_3$) δ: 0.86 (9H, s), 1.48 (3H, t, J=7.2 Hz), 4.45 (2H, bs), 4.50 (2H, q, J=7.2 Hz), 7.96 (1H, dd, J=1.8, 8.4 Hz), 8.27 (1H, d, J=8.4 Hz), 8.75 (1H, d, J=1.8 Hz), 10.71 (1H, s).

(2) Ethyl 4-butoxy-2-neopentyl-1-oxo-7-trifluoromethyl-1,2-dihydro-3-isoquinolinecarboxylate (synthesized according to the method similar to that in Example 1 (2))

$^1$H-NMR(CDCl$_3$) δ: 0.95 (9H, s), 1.01 (3H, t, J=7.3 Hz), 1.45 (3H, t, J=7.1 Hz), 1.52–1.63 (2H, m), 1.74–1.88 (2H, m), 3.96 (2H, t, J=6.6 Hz), 4.09 (2H, bs), 4.45 (2H, q, J=7.1 Hz), 7.90–7.94 (2H, m), 8.73–8.75 (1H, m).

(3) 4-Butoxy-2-neopentyl-1-oxo-7-trifluoromethyl-1,2-dihydro-3-isoquinolinecarboxylic acid (synthesized according to the method similar to that in Example 4 (3))

Melting point 169–170° C. Elemental analysis for C$_{20}$H$_{24}$NO$_4$F$_3$ Calculated: C, 60.14; H, 6.06; N, 3.51. Found: C, 60.17; H, 5.94; N, 3.45. $^1$H-NMR(CDCl$_3$) δ: 0.95 (9H, s), 1.00 (3H, t, J=7.4 Hz), 1.45–1.64 (2H, m), 1.78–1.92 (2H, m), 4.03 (2H, t, J=6.6 Hz), 4.26 (2H, bs), 5.02 (1H, bs), 7.84–7.95 (2H, m), 8.70 (1H, s).

(4) 4-Butoxy-3-hydroxymethyl-2-neopentyl-7-trifluoromethyl-1(2H)-isoquinolinone (synthesized according to the method similar to that in Example 4 (4))

Melting point 98–99° C. Elemental analysis for C$_{20}$H$_{26}$NO$_3$F$_3$ ¼H$_2$O Calculated: C, 61.31; H, 6.85; N, 3.59. Found: C, 61.54; H, 6.83; N, 3.79. $^1$H-NMR(CDCl$_3$) δ: 0.95 (9H, s), 1.05 (3H, t, J=7.3 Hz), 1.51–1.70 (2H, m), 1.81–1.95 (2H, m), 3.02 (1H, bs), 3.91 (2H, t, J=6.4 Hz), 4.25 (2H, bs), 4.89 (2H, bs), 7.70–7.75 (2H, m), 8.45 (1H, s).

(5) 4-Butoxy-3-chloromethyl-2-neopentyl-7-trifluoromethyl-1(2H)-isoquinolinone (synthesized according to the method similar to that in Example 4 (5))

$^1$H-NMR(CDCl$_3$) δ: 0.99 (9H, s), 1.04 (3H, t, J=7.4 Hz), 1.52–1.76 (2H, m), 1.82–1.96 (2H, m), 3.95 (2H, t, J=6.4 Hz), 4.22 (2H, bs), 4.89 (2H, bs), 7.83–7.93 (2H, m), 8.72–8.74 (1H, m).

(6) 2-{(4-Butoxy-2-neopentyl-1-oxo-7-trifluoromethyl-1,2-dihydro-3-isoquinolinyl)methyl}-1H-isoindole-1,3(2H)-dione (synthesized according to the method similar to that in Example 4 (6))

Melting point 132–133° C. Elemental analysis for C$_{28}$H$_{29}$N$_2$O$_4$F$_3$ Calculated: C, 65.36; H, 5.68; N, 5.44. Found: C, 65.34; H, 5.38; N, 5.49. $^1$H-NMR(CDCl$_3$) δ: 1.01 (3H, t, J=7.3 Hz), 1.02 (9H, s), 1.46–1.62 (2H, m), 1.82–1.93 (2H, m), 4.02 (2H, t, J=6.8 Hz), 4.05 (2H, bs), 5.09 (2H, s), 7.70–7.86 (6H, m), 8.70 (1H, s).

(7) Tert-butyl(4-butoxy-2-neopentyl-1-oxo-7-trifluoromethyl-1,2-dihydro-3-isoquinolinyl)methylcarbamate (synthesized according to the method similar to that in Example 1 (6))

Elemental analysis for C$_{25}$H$_{35}$N$_2$O$_4$F$_3$ Calculated: C, 61.97; H, 7.28; N, 5.78. Found: C, 61.86; H, 7.38; N, 5.73. $^1$H-NMR(CDCl$_3$) δ: 1.00 (9H, s), 1.04 (3H, t, J=7.4 Hz), 1.46 (9H, s), 1.53–1.68 (2H, m), 1.81–1.95 (2H, m), 3.87

(2H, t, J=6.6 Hz), 4.14 (2H, bs), 4.59 (2H, d, J=5.0 Hz), 4.82 (1H, bs), 7.77–7.88 (2H, m), 8.66(1H, d, J=0.6 Hz).

(8) 3-(Aminomethyl)-4-butoxy-2-neopentyl-7-trifluoromethyl-1(2H)-isoquinolinone hydrochloride (synthesized according to the method similar to that in Example 1 (7))

Melting point 224–225° C. Elemental analysis for $C_{20}H_{28}N_2O_2ClF_3$ Calculated: C, 57.07; H, 6.71; N, 6.66. Found: C, 56.77; H, 6.69; N, 6.73. $^1$H-NMR(DMSO-$d_6$) δ: 0.92 (9H, s), 1.00 (3H, t, J=7.3 Hz), 1.50–1.61 (2H, m), 1.80–1.92 (2H, m), 3.96 (2H, t, J=6.4 Hz), 4.15 (2H, bs), 4.29 (2H, bs), 8.00 (1H, d, J=8.4 Hz), 8.17 (1H, dd, J=1.8, 8.4 Hz), 8.52 (1H, d, J=1.8 Hz), 8.66 (3H, bs).

Example 53

3-(Aminomethyl)-4-butoxy-2-neopentyl-6-trifluoromethyl-1(2H)-isoquinolinone hydrochloride (1) Ethyl 4-hydroxy-2-neopentyl-1-oxo-6-trifluoromethyl-1,2-dihydro-3-isoquinolinecarboxylate (synthesized according to the method similar to that in Example 1 (1))

$^1$H-NMR(CDCl$_3$) δ: 0.86 (9H, s), 1.49 (3H, t, J=7.2 Hz), 4.46 (2H, bs), 4.51 (2H, q, J=7.2 Hz), 7.89 (1H, dd, J=2.0, 8.4 Hz), 8.43 (1H, d, J=2.0 Hz), 8.57 (1H, d, J=8.4 Hz), 10.79 (1H, s).

(2) Ethyl 4-butoxy-2-neopentyl-1-oxo-6-trifluoromethyl-1,2-dihydro-3-isoquinolinecarboxylate (synthesized according to the method similar to that in Example 1 (2))

$^1$H-NMR (CDCl$_3$) δ: 0.95 (9H, s), 1.02 (3H, t, J=7.4 Hz), 1.45 (3H, t, J=7.1 Hz), 1.49–1.66 (2H, m), 1.76–1.90 (2H, m), 3.98 (2H, t, J=6.4 Hz), 4.11 (2H, bs), 4.46 (2H, q, J=7.1 Hz), 7.78 (1H, dd, J=1.6, 8.4 Hz), 8.05 (1H, d, J=1.6 Hz), 8.57 (1H, d, J=8.4 Hz).

(3) 4-Butoxy-2-neopentyl-1-oxo-6-trifluoromethyl-1,2-dihydro-3-isoquinolinecarboxylic acid (synthesized according to the method similar to that in Example 4 (3))

Melting point 164–166° C. Elemental analysis for $C_{20}H_{24}NO_4F_3$ Calculated: C, 60.14; H, 6.06; N, 3.51. Found: C, 60.15; H, 5.86; N, 3.43. $^1$H-NMR(CDCl$_3$) δ: 0.95 (9H, s), 1.01 (3H, t, J=7.2 Hz), 1.48–1.66 (2H, m), 1.78–1.92 (2H, m), 4.04 (2H, t, J=6.4 Hz), 4.28 (2H, bs), 5.01 (1H, bs), 7.79 (1H, dd, J=1.4, 8.6 Hz), 8.00 (1H, d, J=1.4 Hz), 8.54 (1H, d, J=8.6 Hz).

(4) 4-Butoxy-3-hydroxymethyl-2-neopentyl-6-trifluoromethyl-1(2H)-isoquinolinone (synthesized according to the method similar to that in Example 4 (4))

Melting point 107–108° C. Elemental analysis for $C_{20}H_{26}NO_3F_3$ Calculated: C, 62.33; H, 6.80; N, 3.63. Found: C, 62.31; H, 6.74; N, 3.74. $^1$H-NMR(CDCl$_3$) δ: 0.97 (9H, s), 1.08 (3H, t, J=6.9 Hz), 1.52–1.71 (2H, m), 1.81–1.95 (2H, m), 2.48 (1H, bs), 3.91 (2H, t, J=6.4 Hz), 4.23 (2H, bs), 4.89 (2H, bs), 7.63 (1H, d, J=8.5 Hz), 7.94 (1H, s), 8.42 (1H, d, J=8.5 Hz).

(5) 4-Butoxy-3-chloromethyl-2-neopentyl-6-trifluoromethyl-1(2H)-isoquinolinone (synthesized according to the method similar to that in Example 4 (5))

$^1$H-NMR(CDCl$_3$) δ: 0.99 (9H, s), 1.05 (3H, t, J=7.3 Hz), 1.54–1.72 (2H, m), 1.83–1.97 (2H, m), 3.96 (2H, t, J=6.4 Hz), 4.22 (2H, bs), 4.89 (2H, bs), 7.74 (1H, dd, J=1.6, 8.6 Hz), 8.02 (1H, d, J=1.6 Hz), 8.55 (1H, d, J=8.6 Hz).

(6) 2-{(4-Butoxy-2-neopentyl-1-oxo-6-trifluoromethyl-1,2-dihydro-3-isoquinolinyl)methyl}-1H-isoindole-1,3(2H)-dione (synthesized according to the method similar to that in Example 4 (6))

Melting point 123–124° C. Elemental analysis for $C_{28}H_{29}N_2O_4F_3$ Calculated: C, 65.36; H, 5.68; N, 5.44. Found: C, 65.44; H, 5.77; N, 5.48. $^1$H-NMR(CDCl$_3$) δ: 1.01 (9H, s), 1.02 (3H, t, J=7.3 Hz), 1.48–1.67 (2H, m), 1.83–1.97 (2H, m), 4.04 (2H, t, J=6.6 Hz), 4.07 (2H, bs), 5.09 (2H, s), 7.67–7.84 (5H, m), 8.03 (1H, s), 8.52 (1H, d, J=8.4 Hz).

(7) Tert-butyl(4-butoxy-2-neopentyl-1-oxo-6-trifluoromethyl-1,2-dihydro-3-isoquinolinyl)methylcarbamate (synthesized according to the method similar to that in Example 1 (6))

Melting point 153–154° C. Elemental analysis for $C_{25}H_{35}N_2O_4F_3$ Calculated: C, 61.97; H, 7.28; N, 5.78. Found: C, 61.71; H, 7.09; N, 5.75. $^1$H-NMR(CDCl$_3$) δ: 1.00 (9H, s), 1.04 (3H, t, J=7.4 Hz), 1.45 (9H, s), 1.51–1.70 (2H, m), 1.81–1.95 (2H, m), 3.88 (2H, t, J=6.4 Hz), 4.14 (2H, bs), 4.59 (2H, d, J=5.8 Hz), 4.73 (1H, bs), 7.69 (1H, dd, J=1.6, 8.2 Hz), 7.96 (1H, d, J=1.6 Hz), 8.52 (1H, d, J=8.2 Hz).

(8) 3-(Aminomethyl)-4-butoxy-2-neopentyl-6-trifluoromethyl-1(2H)-isoquinolinone hydrochloride (synthesized according to the method similar to that in Example 1 (7))

Melting point 206–208° C. Elemental analysis for $C_{20}H_{28}N_2O_2ClF_3$ ½$H_2O$ Calculated: C, 55.88; H, 6.80; N, 6.52. Found: C, 55.71; H, 6.58; N, 6.19. $^1$H-NMR(DMSO-$d_6$) δ: 0.92 (9H, s), 1.00 (3H, t, J=7.4 Hz), 1.52–1.64 (2H, m), 1.78–1.92 (2H, m), 3.97 (2H, t, J=6.5 Hz), 4.14 (2H, bs), 4.29 (2H, bs), 7.94 (1H, d, J=8.6 Hz), 8.00 (1H, s), 8.49 (1H, d, J=8.6 Hz), 8.61 (3H, bs).

Example 54

Methyl 3-{2-{3-(aminomethyl)-4-butoxy-6,7-dichloro-1-oxo-2(1H)-isoquinolinyl}ethylcarbamate hydrochloride (1) A solution of 3-[4-butoxy-6,7-dichloro-3-[(1,3-dioxo-1,3-dihydro-2H-isoindol-2-yl)methyl]-1-oxo-2(1H)-isoquinolinyl]propionic acid (0.78 g, 1.5 mmol), diphenylphosphoryl azide (0.39 ml, 1.8 mmol) and triethylamine (0.25 ml, 1.8 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was dissolved in toluene (20 ml) and the mixture was refluxed with stirring. To the obtained mixture was added methanol (1 ml) and the mixture was refluxed with stirring for 1 h. The reaction mixture was poured into water and extracted with ethyl acetate. The extract was washed with brine, dried over anhydrous magnesium sulfate and concentrated under reduced pressure. The residue was recrystallized from tetrahydrofuran-diisopropyl ether to give methyl 2-[4-butoxy-6,7-dichloro-3-[(1,3-dioxo-1,3-dihydro-2H-isoindol-2-yl)methyl]-1-oxo-2(1H)-isoquinolinyl]ethylcarbamate (0.30 g, 36.6%) as crystals.

Melting point 241–243° C. $^1$H-NMR(CDCl$_3$) δ: 0.99 (3H, t, J=7.3 Hz), 1.43–1.58 (2H, m), 1.72–1.91 (2H, m), 3.51 (2H, q, J=6.6 Hz), 3.61 (3H, s), 3.91 (2H, t, J=6.8 Hz), 4.45 (2H, t, J=6.6 Hz), 5.07 (2H, s), 5.47 (1H, bs), 7.71–7.88 (5H, m), 8.47 (1H, s).

(2) Methyl 2-{4-butoxy-3-{{(tert-butoxycarbonyl)amino}methyl}-6,7-dichloro-1-oxo-2(1H)-isoquinolinyl}ethylcarbamate (synthesized according to the method similar to that in Example 1 (6))

Melting point 185.5–186° C. Elemental analysis for $C_{23}H_{31}N_3O_6Cl_2$ Calculated: C, 53.49; H, 6.05; N, 8.14. Found: C, 53.64; H, 6.11; N, 8.30. $^1$H-NMR(CDCl$_3$) δ: 1.04 (3H, t, J=7.3 Hz), 1.46 (9H, s), 1.52–1.67 (2H, m), 1.80–1.94 (2H, m), 3.54 (2H, t, J=6.2 Hz), 3.59 (3H, s), 3.85 (2H, t, J=6.5 Hz), 4.29 (2H, t, J=6.2 Hz), 4.52 (2H, d, J=5.8 Hz), 5.34 (1H, s), 5.51 (1H, bs), 7.78 (1H, s), 8.46 (1H, s).

(3) Methyl 3-{2-{3-(aminomethyl)-4-butoxy-6,7-dichloro-1-oxo-2(1H)-isoquinolinyl}ethylcarbamate hydrochloride (synthesized according to the method similar to that in Example 1 (7))

Melting point 230–231° C. Elemental analysis for $C_{18}H_{24}N_3O_4Cl_3$ Calculated: C, 47.75; H, 5.34; N, 9.28. Found: C, 47.47; H, 5.47; N, 9.10. $^1$H-NMR(DMSO-d$_6$) δ: 0.99 (3H, t, J=7.3 Hz), 1.45–1.63 (2H, m), 1.76–1.91 (2H, m), 3.29 (2H, q, J=6.4 Hz), 3.47 (3H, s), 3.91 (2H, t, J=6.4 Hz), 4.12 (2H, t, J=6.4 Hz), 4.23 (2H, d, J=4.4 Hz), 7.44 (1H, bs), 7.93 (1H, s), 8.39 (1H, s), 8.72 (3H, bs).

Example 55

N-{2-{3-(Aminomethyl)-4-butoxy-6,7-dichloro-1-oxo-2(1H)-isoquinolinyl}ethyl}-1-pyrrolidinecarboxamide hydrochloride (1) N-{2-{4-Butoxy-6,7-dichloro-3-[(1,3-dioxo-1,3-dihydro-2H-isoindol-2-yl)methyl]-1-oxo-2(1H)-isoquinolinyl}ethyl}-1-pyrrolidinecarboxamide (synthesized according to the method similar to that in Example 4 (6))

Melting point 197–198° C. Elemental analysis for $C_{29}H_{30}N_4O_5Cl_2$ ½$H_2O$ Calculated: C, 58.59; H, 5.26; N, 9.42. Found: C, 58.59; H, 5.54; N, 9.32. $^1$H-NMR(CDCl$_3$) δ: 0.98 (3H, t, J=7.3 Hz), 1.38–1.57 (2H, m), 1.76–1.89 (6H, m), 3.23–3.30 (4H, m), 3.56 (2H, q, J=6.6 Hz), 3.89 (2H, t, J=6.8 Hz), 4.53 (2H, t, J=6.6 Hz), 5.08 (1H, bs), 5.12 (2H, s), 7.70–7.85 (5H, m), 8.47 (1H, s).

(2) Tert-butyl{4-butoxy-6,7-dichloro-1-oxo-2-{2-(1-pyrrolidinylcarbonyl)amino}ethyl}-1,2-dihydro-3-isoquinolinyl}methylcarbamate (synthesized according to the method similar to that in Example (6))

Melting point 161–162° C. Elemental analysis for $C_{26}H_{36}N_4O_5Cl_2$ Calculated: C, 56.22; H, 6.53; N, 10.09. Found: C, 56.61; H, 6.24; N, 9.99. $^1$H-NMR(CDCl$_3$) δ: 1.03 (3H, t, J=7.3 Hz), 1.45 (9H, s), 1.52–1.66 (2H, m), 1.80–1.91 (8H, m), 3.17–3.24 (4H, m), 3.61 (2H, q, J=6.3 Hz), 3.88 (2H, t, J=6.6 Hz), 4.32 (2H, t, J=6.3 Hz), 4.53 (2H, d, J=6.0 Hz), 5.09 (1H, bs), 6.07 (1H, bs), 7.81 (1H, s), 8.44 (1H, s).

(3) N-{2-{3-(Aminomethyl)-4-butoxy-6,7-dichloro-1-oxo-2(1H)-isoquinolinyl}ethyl}-1-pyrrolidinecarboxylic acid hydrochloride (synthesized according to the method similar to that in Example 1 (7))

Melting point 190–192° C. Elemental analysis for $C_{21}H_{29}N_4O_3Cl_3$ ³⁄₂$H_2O$ Calculated: C, 48.61; H, 6.17; N, 10.80. Found: C, 48.85; H, 6.06; N, 10.81. $^1$H-NMR (DMSO-d$_6$) δ: 0.99 (3H, t, J=7.3 Hz), 1.48–1.63 (2H, m), 1.79–1.91 (6H, m), 3.16–3.28 (6H, m), 3.92 (2H, t, J=6.4 Hz), 4.09 (2H, t, J=6.8 Hz), 4.31 (2H, bs), 6.80 (1H, bs), 7.92 (1H, s), 8.38 (1H, s), 8.95 (3H, bs).

Example 56

3-(Aminomethyl)-4-butoxy-2-neopentylbenzo{g}isoquinolin-1(2H)-one hydrochloride (1) Ethyl 4-hydroxy-2-neopentyl-1-oxo-1,2-dihydrobenzo-{g}isoquinoline-3-carboxylate (synthesized according to the method similar to that in Example 1 (1))

Melting point 140–141.5° C. Elemental analysis for $C_{21}H_{23}NO_4$ Calculated: C, 71.37; H, 6.56; N, 3.96. Found: C, 71.08; H, 6.36; N, 3.72. $^1$H-NMR(CDCl$_3$) δ: 0.87 (9H, s), 1.48 (3H, t, J=7.2 Hz), 4.50 (2H, q, J=7.2 Hz), 4.55 (2H, bs), 7.59–7.69 (2H, m), 8.05–8.12 (2H, m), 8.67 (1H, s), 9.03 (1H, s) 11.11 (1H, s).

(2) Ethyl 4-butoxy-2-neopentyl-1-oxo-1,2-dihydrobenzo{g}isoquinoline-3-carboxylate (synthesized according to the method similar to that in Example 1 (2))

$^1$H-NMR(CDCl$_3$) δ: 0.96 (9H, s), 1.05 (3H, t, J=7.3 Hz), 1.48 (3H, t, J=7.1 Hz), 1.55–1.66 (2H, m), 1.74–1.95 (2H, m), 4.06 (2H, t, J=6.4 Hz), 4.11 (2H, bs), 4.46 (2H, q, J=7.1 Hz), 7.52–7.67 (2H, m), 7.98–8.09 (2H, m), 8.24 (1H, s), 9.05 (1H, s).

(3) 4-Butoxy-2-neopentyl-1-oxo-1,2-dihydrobenzo{g}isoquinoline-3-carboxylic acid (synthesized according to the method similar to that in Example 4 (3))

Melting point 203–205° C. Elemental analysis for $C_{23}H_{27}NO_4$ Calculated: C, 72.42; H, 7.13; N, 3.67. Found: C, 72.39; H, 7.05; N, 3.53. $^1$H-NMR(CDCl$_3$) δ: 0.94 (9H, s), 1.03 (3H, t, J=7.1 Hz), 1.48–1.66 (2H, m), 1.79–1.93 (2H, m), 4.06 (2H, t, J=6.6 Hz), 4.28 (2H, bs), 7.55–7.67 (2H, m), 7.74–7.82 (2H, m), 8.03–8.08 (1H, m), 8.89 (1H, s).

(4) 4-Butoxy-3-hydroxymethyl-2-neopentyl-benzo{g}isoquinolin-1(2H)-one (synthesized according to the method similar to that in Example 4 (4))

Melting point 147–148° C. Elemental analysis for $C_{23}H_{29}NO_3$ Calculated: C, 75.17; H, 7.95; N, 3.81. Found: C, 75.12; H, 8.10; N, 3.65. $^1$H-NMR(CDCl$_3$) δ: 0.98 (9H, s), 1.08 (3H, t, J=7.3 Hz), 1.56–1.75 (2H, m), 1.86–1.99 (2H, m), 2.73 (1H, bs), 3.97 (2H, t, J=6.6 Hz), 4.25 (2H, bs), 4.92 (2H, bs), 7.45–7.57 (2H, m), 7.76–7.80 (1H, m), 7.91 (1H, s), 7.94–7.99 (1H, m), 8.85 (1H, s).

(5) 4-Butoxy-3-chloromethyl-2-neopentyl-benzo{g}isoquinolin-1(2H)-one (synthesized according to the method similar to that in Example 4 (5))

$^1$H-NMR(CDCl$_3$) δ: 1.00 (9H, s), 1.08 (3H, t, J=7.2 Hz), 1.57–1.76 (2H, m), 1.89–2.02 (2H, m), 4.05 (2H, t, J=6.5 Hz), 4.21 (2H, bs), 4.95 (2H, bs), 7.50–7.66 (2H, m), 7.98–8.09 (2H, m), 8.20 (1H, s), 9.04 (1H, s).

(6) 2-{(4-Butoxy-2-neopentyl-1-oxo-1,2-dihydrobenzo{g}-isoquilinon-3-yl)methyl}-1H-isoindole-1,3(2H)-dione (synthesized according to the method similar to that in Example 4 (6))

Melting point 244–245° C. Elemental analysis for $C_{31}H_{32}N_2O_4$ Calculated: C, 74.98; H, 6.50; N, 5.64. Found: C, 74.73; H, 6.58; N, 5.60. $^1$H-NMR(CDCl$_3$) δ: 1.02 (9H, s), 1.05 (3H, t, J=7.2 Hz), 1.53–1.71 (2H, m), 1.90–2.04 (2H, m), 4.12 (2H, bs), 4.15 (2H, t, J=6.8 Hz), 5.14 (2H, s), 7.48–7.64 (2H, m), 7.68–7.83 (4H, m), 7.96–8.06 (2H, m), 8.21 (1H, s), 9.01 (1H, s)

(7) Tert-butyl(4-butoxy-2-neopentyl-1-oxo-1,2-dihydrobenzo{g}isoquinolin-3-yl)methylcarbamate (synthesized according to the method similar to that in Example 1 (6))

$^1$H-NMR(CDCl$_3$) δ: 1.01 (9H, s), 1.07 (3H, t, J=7.3 Hz), 1.47 (9H, s), 1.50–1.73 (2H, m), 1.87–2.01 (2H, m), 3.96 (2H, t, J=6.4 Hz), 4.14 (2H, bs), 4.62 (2H, d, J=5.2 Hz), 4.73 (1H, bs), 7.48–7.64 (2H, m), 7.94–8.06 (2H, m), 8.11 (1H, s), 9.00 (1H, s).

(8) 3-(Aminomethyl)-4-butoxy-2-neopentylbenzo{g}isoquinolin-1(2H)-one hydrochloride (synthesized according to the method similar to that in Example 1 (7))

Melting point 231–232° C. Elemental analysis for $C_{23}H_{31}N_2O_2Cl$ Calculated: C, 68.55; H, 7.55; N, 6.95. Found: C, 68.30; H, 7.80; N, 7.02. $^1$H-NMR(DMSO-d$_6$) δ: 0.93 (9H, s), 1.04 (3H, t, J=7.1 Hz), 1.56–1.67 (2H, m), 1.90–1.97 (2H, m), 4.05 (2H, bs), 4.14 (2H, bs), 4.30 (2H, bs), 7.64–7.75 (2H, m), 8.19–8.27 (2H, m), 8.32 (1H, s), 8.63 (3H, bs), 8.99 (1H, s).

Example 57

3-(Aminomethyl)-4-butoxy-6-methoxy-2-neopentyl-1(2H)-isoquinolinone hydrochloride (1)-Tert-butyl 4-hydroxy-2-neopentyl-6-fluoro-1-oxo-1,2-dihydro-3-isoquinoline-3-carboxylate (synthesized according to the method similar to that in Example 1 (1))

Melting point 130–131° C. Elemental analysis for $C_{19}H_{24}NO_4F$ Calculated: C, 65.31; H, 6.92; N, 4.01. Found: C, 65.32; H, 7.19; N, 3.92. $^1$H-NMR(CDCl$_3$) δ: 0.86 (9H, s), 1.65 (9H, s), 4.51 (2H, bs), 7.30–7.40 (1H, m), 7.74 (1H, dd, J=2.6, 9.0 Hz), 8.46 (1H, dd, J=5.4, 9.0 Hz), 10.68 (1H, s).

(2) Tert-butyl 4-butoxy-2-neopentyl-6-fluoro-1-oxo-1,2-dihydro-3-isoquinoline-3-carboxylate (synthesized according to the method similar to that in Example 1 (2))

$^1$H-NMR(CDCl$_3$) δ: 0.97 (9H, s), 1.01 (3H, t, J=6.8 Hz), 1.49–1.60 (2H, m), 1.63 (9H, s), 1.73–1.86 (2H, m), 3.96 (2H, t, J=6.6 Hz), 4.00 (2H, bs), 7.18–7.27 (1H, m), 7.35 (1H, dd, J=2.4, 9.4 Hz), 8.43 (1H, dd, J=5.4, 8.8 Hz).

(3) A solution of tert-butyl 4-butoxy-2-neopentyl-6fluoro-1-oxo-1,2-dihydro-3-isoquinoline-3-carboxylate (6.08 g, 15 mmol) in trifluoroacetic acid (20 ml) was stirred at room temperature for 2 h. The reaction mixture was concentrated under reduced pressure, and the residue was recrystallized from ethyl acetate-n-hexane to give 4-butoxy-2-neopentyl-6-fluoro-1-oxo-1,2-dihydro-3-isoquinoline-3-carboxylic acid (4.98 g, 95.0%) as crystals.

Melting point 141–142° C. Elemental analysis for $C_{19}H_{24}NO_4F$ Calculated: C, 65.31; H, 6.92; N, 4.01. Found: C, 65.38; H, 6.86; N, 3.90. $^1$H-NMR(CDCl$_3$) δ: 0.95 (9H, s), 0.99 (3H, t, J=7.2 Hz), 1.48–1.60 (2H, m), 1.76–1.87 (2H, m), 4.02 (2H, t, J=6.5 Hz), 4.23 (2H, bs), 7.23–7.38 (2H, m), 8.43 (1H, dd, J=5.5, 9.1 Hz).

(4) A solution (8.68 g, 45 mmol) of 4-butoxy-2-neopentyl-6-fluoro-1-oxo-1,2-dihydro-3-isoquinoline-3carboxylic acid (1.05 g, 3 mmol) and 20% sodium methoxide in methanol was refluxed under heating for 6 h. The reaction mixture was poured into water, and, after making the mixture acidic with 1N hydrochloric acid, extracted with ethyl acetate. The extract was washed with brine, dried over anhydrous magnesium sulfate and concentrated under reduced pressure. The residue was recrystallized from tetrahydrofuran-diethyl ether to give 4-butoxy-6-methoxy-2-neopentyl-1-oxo-1,2-dihydro-3-isoquinoline-3-carboxylic acid (0.96 g, 88.9%) as crystals.

Melting point 194–196° C. Elemental analysis for $C_{20}H_{27}NO_5$ Calculated: C, 66.46; H, 7.53; N, 3.88. Found: C, 66.39; H, 7.45; N, 3.88. $^1$H-NMR(CDCl$_3$) δ: 0.91 (9H, s), 1.01 (3H, t, J=7.2 Hz), 1.51–1.62 (2H, m), 1.76–1.87 (2H, m), 3.91 (3H, s), 4.01 (2H, t, J=6.4 Hz), 4.13 (2H, bs), 6.91 (1H, d, J=2.4 Hz), 7.08 (1H, dd, J=2.4, 8.8 Hz), 8.17 (1H, d, J=8.8 Hz).

(5) 4-Butoxy-3-hydroxymethyl-6-methoxy-2-neopentyl-1(2H)-isoquinolinone (synthesized according to the method similar to that in Example 4 (4))

Melting point 124–125° C. Elemental analysis for $C_{20}H_{29}NO_4$ Calculated: C, 69.14; H, 8.41; N, 4.03. Found: C, 69.06; H, 8.41; N, 3.96. $^1$H-NMR(CDCl$_3$) δ: 0.94 (9H, s), 1.04 (3H, t, J=7.3 Hz), 1.56–1.67 (2H, m), 1.79–1.93 (2H, m), 3.01 (1H, bs), 3.89 (2H, t, J=6.2 Hz), 3.90 (3H, s), 4.17 (2H, bs), 4.85 (2H, bs), 6.94–6.98 (2H, m), 8.15–8.21 (1H, m).

(6) 4-Butoxy-3-chloromethyl-6-methoxy-2-neopentyl-1(2H)-isoquinolinone (synthesized according to the method similar to that in Example 4 (5))

$^1$H-NMR(CDCl$_3$) δ: 0.98 (9H, s), 1.04 (3H, t, J=7.4 Hz), 1.53–1.71 (2H, m), 1.82–1.95 (2H, m), 3.93 (3H, s), 3.96 (2H, t, J=6.2 Hz), 4.24 (2H, bs), 4.88 (2H, bs), 7.07–7.30 (2H, m), 8.33–8.38 (1H, m).

(7) 2-{(4-Butoxy-6-methoxy-2-neopentyl-1-oxo-1,2-dihydro-3-isoquinolinyl)methyl}-1H-isoindole-1,3(2H)-dione (synthesized according to the method similar to that in Example 4 (6))

Melting point 145–146° C. Elemental analysis for $C_{28}H_{32}N_2O_5$ Calculated: C, 70.57; H, 6.77; N, 5.88. Found: C, 70.60; H, 6.83; N, 5.93. $^1$H-NMR(CDCl$_3$) δ: 1.00 (9H, s), 1.01 (3H, t, J=7.3 Hz), 1.51–1.66 (2H, m), 1.82–1.96 (2H, m), 3.92 (3H, s), 4.03 (2H, t, J=6.7 Hz), 4.24 (2H, bs), 5.07 (2H, bs), 7.06 (1H, dd, J=2.4, 8.8 Hz), 7.11 (1H, d, J=2.4 Hz), 7.63–7.83 (4H, m), 8.32 (1H, d, J=8.8 Hz).

(8) Tert-butyl(4-butoxy-6-methoxy-2-neopentyl-1-oxo-1,2-dihydro-3-isoquinolinyl)methylcarbamate (synthesized according to the method similar to that in Example 1 (6))

Melting point 138.5–139° C. Elemental analysis for $C_{25}H_{38}N_2O_5$ Calculated: C, 67.24; H, 8.58; N, 6.27. Found: C, 67.31; H, 8.85; N, 6.43. $^1$H-NMR(CDCl$_3$) δ: 0.99 (9H, s), 1.04 (3H, t, J=7.4 Hz), 1.45 (9H, s), 1.51–1.64 (2H, m), 1.79–1.93 (2H, m), 3.87 (2H, t, J=6.4 Hz), 3.93 (3H, s), 4.11 (2H, bs), 4.56 (2H, t, J=5.0 Hz), 4.68 (1H, bs), 7.03–7.09 (2H, m), 8.33 (1H, d, J=9.6 Hz).

(9) 3-(Aminomethyl)-4-butoxy-6-methoxy-2-neopentyl-1(2H)-1-oxo-isoquinolinone hydrochloride (synthesized according to the method similar to that in Example 1 (7))

Melting point 172–174° C. Elemental analysis for $C_{20}H_{31}N_2O_3Cl$ ¼$H_2O$ Calculated: C, 62.00; H, 8.20; N, 7.23. Found: C, 61.90; H, 8.11; N, 7.35. $^1$H-NMR(DMSO-d$_6$) δ: 0.90 (9H, s), 1.00 (3H, t, J=7.1 Hz), 1.52–1.64 (2H, m), 1.77–1.92 (2H, m) 3.93 (3H, s), 3.94 (2H, t, J=6.4 Hz), 4.08 (2H, bs), 4.23 (2H, bs), 7.09 (1H, d, J=2.4 Hz), 7.20 (1H, dd, J=2.4, 8.8 Hz), 8.20 (1H, d, J=8.8 Hz), 8.59 (3H, bs).

Example 58

3-(Aminomethyl)-6-benzyloxy-4-butoxy-2-neopentyl-1(2H)-isoquinolinone hydrochloride (1) 6-Benzyloxy-4-butoxy-2-neopentyl-1-oxo-1,2-dihydro-3-isoquinoline-3-carboxylic acid (synthesized according to the method similar to that in Example 57 (4))

Melting point 163–164° C. Elemental analysis for $C_{26}H_{31}NO_5$ Calculated: C, 71.37; H, 7.14; N, 3.20. Found: C, 71.13; H, 7.10; N, 2.94. $^1$H-NMR(CDCl$_3$) δ: 0.89 (9H, s), 0.99 (3H, t, J=7.1 Hz), 1.41–1.59 (2H, m), 1.69–1.84 (2H, m), 3.91 (2H, t, J=6.4 Hz), 4.13 (2H, bs), 5.17 (2H, s), 7.01 (1H, d, J=2.4 Hz), 7.18 (1H, dd, J=2.4, 9.0 Hz), 7.33–7.44 (5H, m), 8.22 (1H, d, J=9.0 Hz).

(2) 6-Benzyloxy-4-butoxy-3-hydroxymethyl-2-neopentyl-1(2H)-isoquinolinone (synthesized according to the method similar to that in Example 4 (4))

Melting point 95–95.5° C. Elemental analysis for $C_{26}H_{33}NO_4$ Calculated: C, 73.73; H, 7.85; N, 3.31. Found: C, 73.44; H, 7.77; N, 3.38. $^1$H-NMR(CDCl$_3$) δ: 0.95 (9H, s), 1.02 (3H, t, J=7.4 Hz), 1.45–1.64 (2H, m), 1.73–1.86 (2H, m) 2.57 (1H, bs), 3.80 (2H, t, J=6.4 Hz), 4.18 (2H, bs), 4.84 (2H, bs), 5.18 (2H, s), 7.06–7.11 (2H, m), 7.31–7.47 (5H, m), 8.23 (1H, d, J=8.0 Hz).

(3) 6-Benzyloxy-4-butoxy-3-chloromethyl-2-neopentyl-1 (2H)-isoquinolinone (synthesized according to the method similar to that in Example 4 (5))

¹H-NMR(CDCl₃) δ: 0.97 (9H, s), 1.03 (3H, t, J=7.1 Hz), 1.46–1.65 (2H, m), 1.74–1.88 (2H, m), 3.84 (2H, t, J=6.4 Hz), 4.14 (2H, bs), 4.86 (2H, bs), 5.21 (2H, s), 7.12–7.48 (7H, m), 8.36 (1H, d, J=9.2 Hz).

(4) 2-{(6-Benzyloxy-4-butoxy-2-neopentyl-1-oxo-1,2-dihydro-3-isoquinolinyl)methyl}-1H-isoindole-1,3(2H)-dione (synthesized according to the method similar to that in Example 4 (6))

Elemental analysis for C₃₄H₃₆N₂O₅ ½H₂O Calculated: C, 72.71; H, 6.64; N, 4.99. Found: C, 72.74; H, 6.42; N, 5.26. ¹H-NMR(CDCl₃) δ: 0.99 (3H, t, J=7.3 Hz), 1.00 (9H, s), 1.39–1.58 (2H, m), 1.64–1.89 (2H, m), 3.92 (2H, t, J=6.7 Hz), 4.10 (2H, bs), 5.06 (2H, bs), 5.20 (2H, s), 7.11–7.17 (2H, m), 7.31–7.47 (5H, m), 7.70–7.90 (4H, m), 8.30–8.35 (1H, m).

(5) Tert-butyl(6-benzyloxy-4-butoxy-2-neopentyl-1-oxo-1,2-dihydro-3-isoquinolinyl)methylcarbamate (synthesized according to the method similar to that in Example 1 (6))

Melting point 114–115° C. Elemental analysis for C₃₁H₄₂N₂O₅ Calculated: C, 71.42; H, 8.10; N, 5.36. Found: C, 71.34; H, 8.40; N, 5.39. ¹H-NMR(CDCl₃) δ: 0.98 (9H, s), 1.02 (3H, t, J=7.4 Hz), 1.45 (9H, s), 1.46–1.59 (2H, m), 1.73–1.87 (2H, m), 3.76 (2H, t, J=6.4 Hz), 4.11 (2H, bs), 4.54 (2H, d, J=5.2 Hz), 4.66 (1H, bs), 5.21 (2H, s), 7.08 (1H, d, J=2.6 Hz), 7.14 (1H, dd, J=2.6, 8.8 Hz), 7.32–7.48 (5H, m), 8.33 (1H, d, J=8.8 Hz).

(6) 3-(Aminomethyl)-6-benzyloxy-4-butoxy-2-neopentyl-1(2H)-1-oxo-isoquinolinone hydrochloride (synthesized according to the method similar to that in Example 1 (7))

Melting point 234–236° C. Elemental analysis for C₂₆H₃₅N₂O₃Cl Calculated: C, 68.03; H, 7.69; N, 6.10. Found: C, 67.96; H, 7.64; N, 5.93. ¹H-NMR(DMSO-d₆) δ: 0.89 (9H, s), 0.98 (3H, t, J=7.5 Hz), 1.45–1.56 (2H, m), 1.71–1.82 (2H, m), 3.84 (2H, t, J=6.2 Hz), 4.07 (2H, bs), 4.21 (2H, bs), 5.33 (2H, bs), 7.11 (1H, d, J=2.2 Hz), 7.27 (1H, dd, J=2.2, 8.8 Hz), 7.34–7.50 (5H, m), 8.19 (1H, d, J=8.8 Hz), 8.52 (3H, bs).

Example 59

3-(Aminomethyl)-4-butoxy-6-hydroxy-2-neopentyl-1(2H)-isoquinolinone hydrochloride (1) A suspension of tert-butyl(6-benzyloxy-4-butoxy-2-neopentyl-1-oxo-1,2-dihydro-3-isoquinolinyl)methylcarbamate (2.61 g, 5 mmol) and 5% palladium carbon (1.5 g) in tetrahydrofuran (10 ml) and ethanol (10 ml) was stirred under a hydrogen atmosphere at room temperature for 2 h. After filtering off 5% palladium carbon, the filtrate was concentrated under reduced pressure. The residue was recrystallized from ethyl acetate-n-hexane to give tert-butyl (4-butoxy-6-hydroxy-2-neopentyl-1-oxo-1,2-dihydro-3-isoquinolinyl)-methylcarbamate (4.98 g, 95.0%) as crystals.

Melting point 195.5–197° C. Elemental analysis for C₂₄H₃₆N₂O₅ Calculated: C, 66.64; H, 8.39; N, 6.48. Found: C, 66.57; H, 8.58; N, 6.49. ¹H-NMR(CDCl₃) δ: 0.96 (3H, t, J=7.4 Hz), 0.99 (9H, s), 1.45 (9H, s), 1.46–1.55 (2H, m), 1.72–1.81 (2H, m), 3.82 (2H, t, J=6.6 Hz), 4.11 (2H, bs), 4.56 (2H, d, J=5.2 Hz), 4.78 (1H, bs), 7.06–7.11 (2H, m), 8.26 (1H, d, J=9.2 Hz), 8.79 (1H, bs).

(2) 3-(Aminomethyl)-4-butoxy-6-hydroxy-2-neopentyl-1 (2H)-1-oxo-isoquinolinone hydrochloride (synthesized according to the method similar to that in Example 1 (7))

Melting point 264–266° C. Elemental analysis for C₁₉H₂₉N₂O₃Cl ¼H₂O Calculated: C, 61.11; H, 7.96; N, 7.50. Found: C, 61.22; H, 7.77; N, 7.56. ¹H-NMR(DMSO-d₆) δ: 0.89 (9H, s), 1.00 (3H, t, J=7.1 Hz), 1.50–1.61 (2H, m), 1.77–1.92 (2H, m), 3.89 (2H, t, J=6.2 Hz), 4.05 (2H, bs), 4.20 (2H, bs), 7.03–7.08 (2H, m), 8.11 (1H, d, J=8.2 Hz), 8.50 (1H, s), 10.67 (1H, bs).

Example 60

3-(Aminomethyl)-4-butoxy-2-neopentyl-6-propoxy-1(2H)-isoquinolinone hydrochloride (1) A solution of tert-butyl(4-butoxy-6-hydroxy-2-neopentyl-1-oxo-1,2-dihydro-3-isoquinolinyl)methylcarbamate (0.52 g, 1.2 mmol), 1-bromopropane (0.16 ml, 1.2 mmol) and potassium carbonate (0.16 g, 1.2 mmol) in N,N-dimethylformamide (10 ml) was stirred at room temperature for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl(4-butoxy-2-neopentyl-1-oxo-6-propoxy-1,2-dihydro-3-isoquinolinyl)methylcarbamate (0.50 g, 89.3%) as an amorphous.

Elemental analysis for C₂₇H₄₂N₂O₅ ¼H₂O Calculated: C, 67.68; H, 8.94; N, 5.85. Found: C, 67.87; H, 8.89; N, 5.95. ¹H-NMR(CDCl₃) δ: 0.99 (9H, s), 1.04 (3H, t, J=7.2 Hz), 1.08 (3H, t, J=7.4 Hz), 1.45 (9H, s), 1.50–1.65 (2H, m), 1.79–1.93 (4H, m), 3.83 (2H, t, J=6.6 Hz) 4.01 (2H, bs), 4.04 (2H, t, J=6.4 Hz), 4.55 (2H, d, J=5.2 Hz), 4.67 (1H, bs), 7.02–7.08 (2H, m), 8.31 (1H, d, J=9.6 Hz).

(2) 3-(Aminomethyl)-4-butoxy-2-neopentyl-6-propoxy-1 (2H)-1-oxo-isoquinoline hydrochloride (synthesized according to the method similar to that in Example 1 (7))

Melting point 202–204° C. Elemental analysis for C₂₂H₃₅N₂O₃Cl Calculated: C, 64.29; H, 8.58; N, 6.82. Found: C, 64.05; H, 8.29; N, 6.64. ¹H-NMR(DMSO-d₆) δ: 0.90 (9H, s), 1.00 (3H, t, J=7.4 Hz), 1.02 (3H, t, J=7.3 Hz), 1.53–1.63 (2H, m), 1.72–1.86 (4H, m), 3.94 (2H, t, J=6.2 Hz), 4.07 (2H, bs), 4.10 (2H, t, J=6.5 Hz), 4.23 (2H, bs), 7.07 (1H, d, J=2.5 Hz), 7.19 (1H, dd, J=2.5, 8.8 Hz), 8.18 (1H, d, J=8.8 Hz), 8.51 (3H, bs).

Example 61

3-(Aminomethyl)-4,6-dibutoxy-2-neopentyl-1(2H)-isoquinolinone hydrochloride (1) Tert-butyl(4,6-dibutoxy-2-neopentyl-1-oxo-1,2-dihydro-3-isoquinolinyl))methylcarbamate (synthesized according to the method similar to that in Example 60 (1))

Elemental analysis for C₂₈H₄₄N₂O₅ Calculated: C, 68.82; H, 9.08; N, 5.73. Found: C, 68.66; H, 8.87; N, 5.54. ¹H-NMR(CDCl₃) δ: 0.99 (9H, s), 1.00 (3H, t, J=7.4 Hz), 1.04 (3H, t, J=7.0 Hz), 1.45 (9H, s), 1.51–1.64 (4H, m), 1.77–1.90 (4H, m), 3.86 (2H, t, J=6.4 Hz), 4.08 (2H, t, J=6.5 Hz), 4.14 (2H, bs), 4.56 (2H, d, J=5.2 Hz), 4.67 (1H, bs), 7.02–7.08 (2H, m), 8.32 (1H, d, J=9.4 Hz).

(2) 3-(Aminomethyl)-4,6-dibutoxy-2-neopentyl-1(2H)-1-oxo-isoquinolinone hydrochloride (synthesized according to the method similar to that in Example 1 (7))

Melting point 184–186° C. Elemental analysis for C₂₃H₃₇N₂O₃Cl ¾H₂O Calculated: C, 63.00; H, 8.85; N, 6.39. Found: C, 62.85; H, 8.88; N, 6.14. ¹H-NMR(DMSO-d₆) δ: 0.90 (9H, s), 0.96 (3H, t, J=7.8 Hz), 1.00 (3H, t, J=7.4

Hz), 1.42–1.60 (4H, m), 1.63–1.92 (4H, m), 3.94 (2H, t, J=6.2 Hz), 4.11 (2H, bs), 4.15 (2H, t, J=6.5 Hz), 4.23 (2H, bs), 7.07 (1H, d, J=2.4 Hz), 7.18 (1H, dd, J=2.4, 8.8 Hz), 8.18 (1H, d, J=8.8 Hz), 8.57 (3H, bs).

Example 62

3-(Aminomethyl)-4-butoxy-6-(2-methoxyethoxy)-2-neopentyl-1(2H)-isoquinolinone hydrochloride (1) Tert-butyl{4-butoxy-6-(2-methoxyethoxy)-2-neopentyl-1-oxo-1,2-dihydro-3-isoquinolinyl}methylcarbamate (synthesized according to the method similar to that in Example 60 (1))

Elemental analysis for $C_{27}H_{42}N_2O_6$ Calculated: C, 66.10; H, 8.63; N, 5.71. Found: C, 66.22; H, 8.59; N, 5.41. $^1$H-NMR(CDCl$_3$) δ: 0.99 (9H, s), 1.03 (3H, t, J=7.4 Hz), 1.45 (9H, s), 1.52–1.64 (2H, m), 1.78–1.89 (2H, m), 3.49 (3H, s), 3.80–3.88 (4H, m), 4.20 (2H, bs), 4.22–4.25 (2H, m), 4.55 (2H, d, J=5.4 Hz), 4.66 (1H, bs), 7.08–7.13 (2H, m), 8.30–8.35 (1H, m).

(2) 3-(Aminomethyl)-4-butoxy-6-(2-methoxyethoxy)-2-neopentyl-1(2H)-1-oxo-isoquinolinone hydrochloride (synthesized according to the method similar to that in Example 1 (7))

Melting point 188–189° C. Elemental analysis for $C_{22}H_{35}N_2O_4Cl$ Calculated: C, 61.89; H, 8.26; N, 6.56. Found: C, 61.55; H, 8.34; N, 6.59. $^1$H-NMR(DMSO-d$_6$) δ: 0.90 (9H, s), 1.00 (3H, t, J=7.3 Hz), 1.51–1.62 (2H, m), 1.77–1.88 (2H, m), 3.33 (3H, s), 3.71–3.75 (2H, m), 3.94 (2H, t, J=6.4 Hz), 4.07 (2H, bs), 4.25–4.30 (4H, m), 7.09 (1H, d, J=2.4 Hz), 7.21 (1H, dd, J=2.4, 8.8 Hz), 8.18 (1H, d, J=8.8 Hz), 8.55 (3H, bs).

Example 63

3-(Aminomethyl)-7-benzyloxy-4-butoxy-2-neopentyl-1(2H)-isoquinolinone hydrochloride (1) A solution of 5-benzyloxy-2-(ethoxycarbonyl)benzoic acid (21.86 g, 120 mmol), ethyl 2-(neopentylamino)acetate (20.79 g, 120 mmol), 1-ethyl-3-(3-dimethylaminopropyl) carbodiimide hydrochloride (28.76 g, 150 mmol) and 1-hydroxybenzotriazole (22.97 g, 150 mmol) in N,N-dimethylformamide (200 ml) was stirred at room temperature for 3 h. The reaction mixture was poured into water and extracted with ethyl acetate. The extract was washed with brine, dried over anhydrous magnesium sulfate and concentrated under reduced pressure. The residue was dissolved in N,N-dimethylformamide (300 ml), and potassium carbonate (33.17 g, 240 mmol) and benzyl bromide (35.7 ml, 300 mmol) were added. The mixture was stirred at room temperature for 12 h. The reaction mixture was poured into water and extracted with ethyl acetate. The extract was washed with brine, dried over anhydrous magnesium sulfate and concentrated under reduced pressure. The residue was dissolved in ethanol (50 ml) and 20% sodium ethoxide ethanol solution (34.04 g, 100 mmol) was added. The mixture was stirred at room temperature for 1 h. The reaction mixture was poured into 1N hydrochloric acid (150 ml) and extracted with ethyl acetate. The extract was washed with brine, dried over anhydrous magnesium sulfate and concentrated under reduced pressure. The residue was purified by silica gel column chromatography and the component eluted earlier was concentrated to give ethyl 7-benzyloxy-4-hydroxy-2-neopentyl-1-oxo-1,2-dihydro-3-isoquinolinecarboxylate as an oil. To a solution of the obtained ethyl 7-benzyloxy-4-hydroxy-2-neopentyl-1-oxo-1,2-dihydro-3-isoquinolinecarboxylate (3.26 g, 8 mmol), 1-butanol (1.1 ml, 12 mmol) and tributylphosphine (4.0 ml, 16 mmol) in tetrahydrofuran (30 ml) was added 1,1'-(azodicarbonyl)dipiperidine (4.04 g, 16 mmol) and the mixture was stirred at room temperature for 3 h. The reaction mixture was concentrated under reduced pressure and the residue was purified by silica gel column chromatography to give ethyl 7-benzyloxy-4-butoxy-2-neopentyl-1-oxo-1,2-dihydro-3-isoquinolinecarboxylate (3.61 g, 97.0%) as an oil.

$^1$H-NMR(CDCl$_3$) δ: 0.94 (9H, s), 1.00 (3H, t, J=7.4 Hz), 1.43 (3H, t, J=7.2 Hz), 1.51–1.66 (2H, m), 1.73–1.87 (2H, m), 3.94 (2H, t, J=6.5 Hz), 4.14 (2H, bs), 4.42 (2H, q, J=7.2 Hz), 5.20 (2H, bs), 7.34–7.50 (6H, m), 7.73 (1H, d, J=8.8 Hz), 7.96 (1H, d, J=2.6 Hz).

(2) 7-Benzyloxy-4-butoxy-2-neopentyl-1-oxo-1,2-dihydro-3-isoquinoline-3-carboxylic acid (synthesized according to the method similar to that in Example 57 (4))

Elemental analysis for $C_{26}H_{31}NO_5$ Calculated: C, 71.37; H, 7.14; N, 3.20. Found: C, 71.11; H, 7.35; N, 3.08. $^1$H-NMR(CDCl$_3$) δ: 0.91 (9H, s), 0.95 (3H, t, J=7.4 Hz), 1.44–1.59 (2H, m), 1.74–1.89 (2H, m), 4.00 (2H, t, J=6.6 Hz), 4.35 (2H, bs), 5.20 (2H, s), 7.31–7.51 (6H, m), 7.60 (1H, d, J=8.8 Hz), 7.84 (1H, d, J=2.6 Hz).

(3) 7-Benzyloxy-4-butoxy-3-hydroxymethyl-2-neopentyl-1(2H)-isoquinolinone (synthesized according to the method similar to that in Example 4 (4))

Melting point 156.5–157° C. Elemental analysis for $C_{26}H_{33}NO_4$ Calculated: C, 73.73; H, 7.85; N, 3.31. Found: C, 73.76; H, 7.62; N, 3.42. $^1$H-NMR(CDCl$_3$) δ: 0.98 (9H, s), 1.00 (3H, t, J=7.4 Hz), 1.47–1.64 (2H, m), 1.76–1.90 (2H, m), 2.57 (1H, bs), 3.87 (2H, t, J=6.4 Hz), 4.23 (2H, bs), 4.86 (2H, bs), 5.17 (2H, s), 7.25–7.51 (6H, m), 7.59 (1H, d, J=8.8 Hz), 7.82 (1H, d, J=2.2 Hz).

(4) 7-Benzyloxy-4-butoxy-3-chloromethyl-2-neopentyl-1(2H)-isoquinolinone (synthesized according to the method similar to that in Example 4 (5))

$^1$H-NMR(CDCl$_3$) δ: 0.99 (9H, s), 1.03 (3H, t, J=7.4 Hz), 1.54–1.69 (2H, m), 1.80–1.94 (2H, m), 3.94 (2H, t, J=6.4 Hz), 4.17 (2H, bs), 4.90 (2H, bs), 5.20 (2H, s), 7.33–7.50 (6H, m), 7.69 (1H, d, J=8.8 Hz), 7.96 (1H, d, J=2.4 Hz).

(5) 2-{(7-Benzyloxy-4-butoxy-2-neopentyl-1-oxo-1,2-dihydro-3-isoquinolinyl)methyl}-1H-isoindole 1,3(2H)-dione (synthesized according to the method similar to that in Example 4 (6))

Melting point 120–121° C. Elemental analysis for $C_{34}H_{36}N_2O_5$ Calculated: C, 73.89; H, 6.57; N, 5.07. Found: C, 73.77; H, 6.28; N, 5.29. $^1$H-NMR(CDCl$_3$) δ: 1.00 (3H, t, J=7.2 Hz), 1.02 (9H, s), 1.44–1.62 (2H, m), 1.81–1.95 (2H, m), 4.02 (2H, t, J=6.8 Hz), 4.06 (2H, bs), 5.08 (2H, bs), 5.18 (2H, s), 7.30–7.50 (6H, m), 7.67–7.90 (5H, m), 7.93 (1H, d, J=2.6 Hz).

(6) Tert-butyl(7-benzyloxy-4-butoxy-2-neopentyl-1-oxo-1,2-dihydro-3-isoquinolinyl)methylcarbamate (synthesized according to the method similar to that in Example 1 (6))

Melting point 122–123° C. Elemental analysis for $C_{31}H_{42}N_2O_5$ Calculated: C, 71.42; H, 8.10; N, 5.36. Found: C, 71.31; H, 8.19; N, 5.39. $^1$H-NMR(CDCl$_3$) δ: 1.00 (9H, s), 1.02 (3H, t, J=7.2 Hz), 1.45 (9H, s), 1.46–1.64 (2H, m), 1.78–1.92 (2H, m), 3.86 (2H, t, J=6.6 Hz), 4.17 (2H, bs), 4.56 (2H, t, J=5.2 Hz), 4.65 (1H, bs), 5.19 (2H, s), 7.30–7.50 (6H, m), 7.64 (1H, d, J=8.6 Hz), 7.93 (1H, d, J=2.6 Hz).

(7) 3-(Aminomethyl)-7-benzyloxy-4-butoxy-2-neopentyl-1(2H)-1-oxo-isoquinoline hydrochloride (synthesized according to the method similar to that in Example 1 (7))

Melting point 202–204° C. Elemental analysis for $C_{26}H_{35}N_2O_3Cl\ H_2O$ Calculated: C, 65.46; H, 7.82; N, 5.87. Found: C, 65.57; H, 7.47; N, 5.49. $^1$H-NMR(DMSO-$d_6$) δ: 0.91 (9H, s), 0.99 (3H, t, J=7.3 Hz), 1.48–1.60 (2H, m), 1.76–1.91 (2H, m), 3.92 (2H, t, J=6.4 Hz), 4.08 (2H, bs), 4.23 (2 H, bs), 5.27 (2H, s), 7.31–7.55 (6H, m), 7.74 (1H, d, J=8.6 Hz), 7.80 (1H, d, J=2.6 Hz), 8.51 (3H, bs).

Example 64

3-(Aminomethyl)-4-butoxy-7-hydroxy-2-neopentyl-1(2H)-isoquinolinone hydrochloride (1) Tert-butyl(4-butoxy-7-hydroxy-2-neopentyl-1-oxo-1,2-dihydro-3-isoquinolinyl)methylcarbamate (synthesized according to the method similar to that in Example 59 (1))

Melting point 237–238° C. Elemental analysis for $C_{24}H_{36}N_2O_5$ Calculated: C, 66.64; H, 8.39; N, 6.48. Found: C, 66.54; H, 8.41; N, 6.36. $^1$H-NMR(CDCl$_3$) δ: 0.88 (9H, s), 0.96 (3H, t, J=7.2 Hz), 1.40 (2H, m), 1.44–1.59 (9H, s), 1.40–1.55 (2H, m), 1.69–1.79 (2H, m), 3.80 (2H, t, J=6.2 Hz), 3.94 (2H, bs), 4.39 (2H, d, J=4.8 Hz), 7.21 (1H, bs), 7.24 (1H, dd, J=2.4, 8.4 Hz), 7.56 (1H, d, J=2.4 Hz), 7.58 (1H, d, J=8.4 Hz), 10.15 (1H, s).

(2) 3-(Aminomethyl)-4-butoxy-7-hydroxy-2-neopentyl-1(2H)-1-oxo-isoquinolinone hydrochloride (synthesized according to the method similar to that in Example 1 (7))

Melting point 238–239° C. Elemental analysis for $C_{19}H_{29}N_2O_3Cl$ Calculated: C, 61.86; H, 7.92; N, 7.59. Found: C, 61.80; H, 7.84; N, 7.52. $^1$H-NMR(DMSO-$d_6$) δ: 0.89 (9H, s), 0.98 (3H, t, J=7.3 Hz), 1.44–1.63 (2H, m), 1.75–1.89 (2H, m), 3.91 (2H, t, J=6.5 Hz), 4.08 (2H, bs), 4.20 (2H, bs), 7.31 (1H, dd, J=2.8, 8.6 Hz), 7.62 (1H, d, J=2.8 Hz), 7.64 (1H, d, J=8.6 Hz), 8.43 (3H, bs), 10.33 (1H, s).

Example 65

3-(Aminomethyl)-4-butoxy-7-methoxy-2-neopentyl-1(2H)-isoquinolinone hydrochloride (1) Tert-butyl(4-butoxy-7-methoxy-2-neopentyl-1-oxo-1,2-dihydro-3-isoquinolinyl)methylcarbamate (synthesized according to the method similar to that in Example 60 (1))

Melting point 171–172° C. Elemental analysis for $C_{25}H_{38}N_2O_5\ ¼H_2O$ Calculated: C, 66.57; H, 8.60; N, 6.21. Found: C, 66.65; H, 8.77; N, 6.15. $^1$H-NMR(CDCl$_3$) δ: 1.00 (9H, s), 1.02 (3H, t, J=7.4 Hz), 1.45 (9H, s), 1.51–1.66 (2H, m), 1.78–1.92 (2H, m), 3.86 (2H, t, J=6.4 Hz), 3.93 (3H, s), 4.14 (2H, bs), 4.56 (2H, d, J=4.8 Hz), 4.66 (1H, bs), 7.28 (1H, dd, J=2.6, 8.8 Hz), 7.63 (1H, d, J=8.8 Hz), 7.82 (1H, d, J=2.6 Hz).

(2) 3-(Aminomethyl)-4-butoxy-7-methoxy-2-neopentyl-1(2H)-1-oxo-isoquinolinone hydrochloride (synthesized according to the method similar to that in Example 1 (7))

Melting point 210–212° C. Elemental analysis for $C_{20}H_{31}N_2O_3Cl$ Calculated: C, 62.00; H, 8.20; N, 7.23. Found: C, 61.97; H, 8.07; N, 7.28. $^1$H-NMR(DMSO-$d_6$) δ: 0.91 (9H, s), 0.99 (3H, t, J=7.3 Hz), 1.45–1.64 (2H, m), 1.77–1.91 (2H, m), 3.90 (3H, s), 3.92 (2H, t, J=6.2 Hz), 4.10 (2H, bs), 4.23 (2H, bs), 7.45 (1H, dd, J=2.6, 8.8 Hz), 7.70 (1H, d, J=2.6 Hz), 7.73 (1H, d, J=8.8 Hz), 8.52 (3H, bs).

Example 66

3-(Aminomethyl)-4-butoxy-7-ethoxy-2-neopentyl-1(2H)-isoquinolinone hydrochloride (1) Tert-butyl(4-butoxy-7-ethoxy-2-neopentyl-1-oxo-1,2-dihydro-3-isoquinolinyl)methylcarbamate (synthesized according to the method similar to that in Example 60 (1))

Melting point 140–142° C. Elemental analysis for $C_{26}H_{40}N_2O_5$ Calculated: C, 67.80; H, 8.75; N, 6.08. Found: C, 67.57; H, 8.51; N, 6.10. $^1$H-NMR(CDCl$_3$) δ: 1.00 (9H, s), 1.02 (3H, t, J=7.4 Hz), 1.44 (9H, s), 1.45 (3H, t, J=7.0 Hz), 1.49–1.67 (2H, m), 1.78–1.92 (2H, m), 3.85 (2H, t, J=6.6 Hz), 4.11 (2H, bs), 4.16 (2H, q, J=7.0 Hz), 4.56 (2H, d, J=5.2 Hz), 4.65 (1H, bs), 7.27 (1H, dd, J=2.4, 8.8 Hz), 7.62 (1H, d, J=8.8 Hz), 7.80 (1H, d, J=2.4 Hz).

(2) 3-(Aminomethyl)-4-butoxy-7-ethoxy-2-neopentyl-1(2H)-1-oxo-isoquinoline hydrochloride (synthesized according to the method similar to that in Example 1 (7))

Elemental analysis for $C_{21}H_{33}N_2O_3Cl\ ½H_2O$ Calculated: C, 62.13; H, 8.44; N, 6.90. Found: C, 62.21; H, 8.40; N, 7.15. $^1$H-NMR(DMSO-$d_6$) δ: 0.91 (9H, s), 0.99 (3H, t, J=7.3 Hz), 1.38 (3H, t, J=6.8 Hz), 1.49–1.60 (2H, m), 1.69–1.92 (2H, m), 3.92 (2H, bs), 4.12–4.22 (6H, m), 7.44 (1H, dd, J=2.6, 8.8 Hz), 7.62–7.75 (2H, m), 8.54 (3H, bs).

Example 67

3-(Aminomethyl)-4-butoxy-2-neopentyl-7-propoxy-1(2H)-isoquinolinone hydrochloride.

(1) Tert-butyl(4-butoxy-2-neopentyl-1-oxo-7-propoxy-1,2-dihydro-3-isoquinolinyl)methylcarbamate (synthesized according to the method similar to that in Example 60 (1))

Melting point 143.5–144.5° C. Elemental analysis for $C_{27}H_{42}N_2O_5$ Calculated: C, 68.32; H, 8.92; N, 5.90. Found: C, 68.30; H, 8.95; N, 6.02. $^1$H-NMR(CDCl$_3$) δ: 1.00 (9H, s), 1.02 (3H, t, J=7.4 Hz), 1.06 (3H, t, J=7.4 Hz), 1.45 (9H, s), 1.51–1.65 (2H, m), 1.76–1.92 (4H, m), 3.85 (2H, t, J=6.6 Hz), 4.06 (2H, t, J=6.8 Hz), 4.09 (2H, bs), 4.56 (2H, d, J=4.4 Hz), 4.62 (1H, bs), 7.28 (1H, dd, J=2.7, 8.8 Hz), 7.62 (1H, d, J=8.8 Hz), 7.80 (1H, d, J=2.7 Hz).

(2) 3-(Aminomethyl)-4-butoxy-2-neopentyl-7-propoxy-1(2H)-1-oxo-isoquinolinone hydrochloride (synthesized according to the method similar to that in Example 1 (7))

Melting point 216–218° C. Elemental analysis for $C_{22}H_{35}N_2O_3Cl\ ¼H_2O$ Calculated: C, 63.60; H, 8.61; N, 6.74. Found: C, 63.84; H, 8.67; N, 6.80. $^1$H-NMR(DMSO-$d_6$) δ: 0.90 (9H, s), 0.99 (3H, t, J=7.4 Hz), 1.01 (3H, t, J=7.3 Hz), 1.49–1.70 (2H, m), 1.73–1.90 (4H, m), 3.92 (2H, t, J=6.6 Hz), 4.07 (2H, t, J=6.4 Hz), 4.10 (2H, bs), 4.23 (2H, bs), 7.45 (1H, dd, J=2.8, 8.8 Hz), 7.68 (1H, d, J=2.8 Hz), 7.72 (1H, d, J=8.8 Hz), 8.51 (3H, bs).

Example 68

3-(Aminomethyl)-4,7-dibutoxy-2-neopentyl-1(2H)-isoquinoline hydrochloride (1) Tert-butyl(4-butoxy-7-butoxy-2-neopentyl-1-oxo-1,2-dihydro- 3-isoquinolinyl)methylcarbamate (synthesized according to the method similar to that in Example 60 (1))

Elemental analysis for $C_{28}H_{44}N_2O_5$ Calculated: C, 68.82; H, 9.08; N, 5.73 Found: C, 68.79; H, 9.34; N, 5.72. $^1$-NMR (CDCl$_3$) δ: 0.99 (3H, t, J=7.2 Hz), 1.00 (9H, s), 1.02 (3H, t, J=7.2 Hz), 1.45 (9H, s), 1.46–1.64 (4H, m), 1.74–1.89 (4H, m), 3.85 (2H, t, J=6.4 Hz), 4.07 (2H, bs), 4.10 (2H, t, J=6.4

Hz), 4.55 (2H, d, J=4.4 Hz), 4.61 (1H, bs), 7.28 (1H, dd, J=2.8, 8.8 Hz), 7.62 (1H, d, J=8.8 Hz), 7.80 (1H, d, J=2.8 Hz).

(2) 3-(Aminomethyl)-4,7-dibutoxy-2-neopentyl-1(2H)-1-oxo-isoquinolinone hydrochloride (synthesized according to the method similar to that in Example 1 (7))

Melting point 192.5–193° C. Elemental analysis for $C_{23}H_{37}N_2O_3Cl$ ¼$H_2O$ Calculated: C, 64.32; H, 8.80; N, 6.52. Found: C, 64.38; H, 8.83; N, 6.49. $^1$H-NMR(DMSO-$d_6$) δ: 0.91 (9H, s), 0.95–1.02 (6H, m), 1.41–1.60 (4H, m), 1.68–1.87 (4H, m), 3.92 (2H, t, J=6.1 Hz), 4.11 (2H, t, J=6.2 Hz), 4.14 (2H, bs), 4.23 (2H, bs), 7.44 (1H, dd, J=2.6, 8.8 Hz), 7.68 (1H, d, J=2.6 Hz), 7.72 (1H, d, J=8.8 Hz), 8.54 (3H, bs).

Example 69

3-(Aminomethyl)-4-butoxy-5,6-dimethoxy-2-neopentyl-1(2H)-isoquinolinone hydrochloride (1) A solution of ethyl 6-formyl-2,3-dimethoxybenzoate (5.24 g, 22 mmol), sodium dihydrogen phosphate (3.60 g, 30 mmol) and 2-methyl-2-butene (10.3 ml, 96.8 mmol) in t-butanol (20 ml), tetrahydrofuran (20 ml) and water (20 ml) was stirred at room temperature for 10 min. To the obtained mixture was added sodium chlorite (6.76 g, 74.8 mmol) and the mixture was stirred at room temperature for 1 h. The reaction mixture was poured into water and extracted with ethyl acetate. The extract was washed with brine, dried over anhydrous magnesium sulfate and concentrated under reduced pressure. The residue was recrystallized from ethyl acetate-n-hexane to give 2-(ethoxycarbonyl)-3,4-dimethoxybenzoic acid (4.51 g, 80.7%) as crystals.

Melting point 148–149° C. Elemental analysis for $C_{12}H_{14}O_6$ Calculated: C, 56.69; H, 5.55. Found: C, 56.52; H, 5.64. $^1$H-NMR(CDCl$_3$) δ: 1.38 (3H, t, J=7.2 Hz), 3.87 (3H, s), 3.95 (3H, s), 4.43 (2H, q, J=7.2 Hz), 6.97 (1H, d, J=8.8 Hz), 7.88 (1H, d, J=8.8 Hz).

(2) A solution of 2-(ethoxycarbonyl)-3,4-dimethoxybenzoic acid (4.45 g, 17.5 mmol), ethyl 2-(neopentylamino)acetate (3.47 g, 20 mmol) and 1-ethyl-3-(3-dimethylaminopropyl)carbodiimide hydrochloride (3.83 g, 20 mmol) in N,N-dimethylformamide (50 ml) was stirred at room temperature for 3 h. The reactions mixture was poured into water and extracted with ethyl acetate. The extract was washed with brine, dried over anhydrous magnesium sulfate and concentrated under reduced pressure. The residue was dissolved in ethanol (50 ml) and 20% sodium ethoxide ethanol solution (34.04 g, 100 mmol) was added thereto. The mixture was stirred at room temperature for 1 h. The reaction mixture was poured into 1N hydrochloric acid (150 ml) and extracted with ethyl acetate. The extract was washed with brine, dried over anhydrous magnesium sulfate and concentrated under reduced pressure. The residue was purified by silica gel column chromatography to give ethyl 5,6-dimethoxy-4-hydroxy-2-neopentyl-1-oxo-1,2-dihydro-3-isoquinolinecarboxylate (3.21 g, 50.6%) as an oil.

Elemental analysis for $C_{19}H_{25}NO_6$ ½$H_2O$ Calculated: C, 61.28; H, 7.04; N, 3.76. Found: C, 61.61; H, 6.67; N, 3.85. $^1$H-NMR(CDCl$_3$) δ: 0.90 (9H, s), 1.43 (3H, t, J=7.2 Hz), 4.01 (3H, s), 4.04 (3H, s), 4.21 (2H, bs), 4.44 (2H, q, J=7.2 Hz), 7.24 (1H, d, J=9.2 Hz), 8.28. (1H, d, J=9.2 Hz), 9.56 (1H, s).

(3) Ethyl 4-butoxy-5,6-dimethoxy-2-neopentyl-1-oxo-1,2-dihydro-3-isoquinolinecarboxylate (synthesized according to the method similar to that in Example 1 (2))

Melting point 70–71° C. Elemental analysis for $C_{23}H_{33}NO_6$ Calculated: C, 65.85; H, 7.93; N, 3.34. Found: C, 65.64; H, 7.79; N, 3.45. $^1$H-NMR(CDCl$_3$) δ: 0.95 (9H, s), 0.96 (3H, t, J=7.2 Hz), 1.34–1.52 (5H, m), 1.65–1.80 (2H, m), 3.63 (3H, s), 3.89–3.96 (4H, m), 4.00 (3H, s), 4.42 (2H, q, J=7.2 Hz), 7.19 (1H, d, J=8.8 Hz), 8.28 (1H, d, J=8.8 Hz).

(4) 4-Butoxy-5,6-dimethoxy-2-neopentyl-1-oxo-1,2-dihydro-3-isoquinolinecarboxylic acid (synthesized according to the method similar to that in Example 4 (3))

Melting point 144–145.5° C. Elemental analysis for $C_{21}H_{29}NO_6$ ¼$H_2O$ Calculated: C, 63.70; H, 7.51; N, 3.54. Found: C, 63.81; H, 7.28; N, 3.60. $^1$H-NMR(CDCl$_3$) δ: 0.91 (9H, s), 0.95 (3H, t, J=7.2 Hz), 1.37–1.52 (2H, m), 1.72–1.86 (2H, m), 3.87 (3H, s), 3.89–3.97 (2H, m), 4.00 (3H, s), 4.10 (2H, bs), 7.22 (1H, d, J=8.9 Hz), 8.27 (1H, d, J=8.9 Hz).

(5) 4-Butoxy-5,6-dimethoxy-3-hydroxymethyl-2-neopentyl-1(2H)-isoquinolinone (synthesized according to the method similar to that in Example 4 (4))

Melting point 140–141° C. Elemental analysis for $C_{21}H_{31}NO_5$ ¼$H_2O$ Calculated: C, 66.03; H, 8.31; N, 3.67. Found: C, 66.13; H, 8.22; N, 3.77. $^1$H-NMR(CDCl$_3$) δ: 0.97 (9H, s), 1.00 (3H, t, J=7.2 Hz), 1.46–1.64 (2H, m), 1.75–1.80 (2H, m), 2.39 (1H, s), 3.84 (3H, s), 3.86 (2H, t, J=7.0 Hz), 3.98 (3H, s), 4.17 (2H, bs), 4.86 (2H, bs), 7.11 (1H, d, J=9.0 Hz), 8.20 (1H, d, J=9.0 Hz).

(6) 4-Butoxy-3-chloromethyl-5,6-dimethoxy-2-neopentyl-1(2H)-isoquinolinone (synthesized according to the method similar to that in Example 4 (5))

$^1$H-NMR(CDCl$_3$) δ: 0.98 (9H, s), 1.02 (3H, t, J=7.4 Hz), 1.47–1.64 (2H, m), 1.76–1.87 (2H, m), 3.85 (3H, s), 3.89 (2H, t, J=6.2 Hz), 3.99 (3H, s), 4.12 (2H, bs), 4.92 (2H, bs), 7.24 (1H, d, J=8.8 Hz), 8.28 (1H, d, J=8.8 Hz).

(7) 2-{(4-Butoxy-5,6-dimethoxy-2-neopentyl-1-oxo-1,2-dihydro-3-isoquinolinyl)methyl}-1H-isoindole-1,3(2H)-dione (synthesized according to the method similar to that in Example 4 (6))

Melting point 122–123° C. Elemental analysis for $C_{29}H_{34}N_2O_6$ Calculated: C, 68.76; H, 6.76; N, 5.53. Found: C, 68.72; H, 6.71; N, 5.58. $^1$H-NMR(CDCl$_3$) δ: 0.95 (3H, t, J=7.4 Hz), 0.99 (9H, s), 1.41–1.53 (2H, m), 1.75–1.89 (2H, m), 3.86 (3H, s), 3.94–3.95 (4H, m), 3.99 (3H, s), 5.13 (2H, bs), 7.15 (1H, d, J=9.0 Hz), 7.67–7.84 (4H, m), 8.25 (1H, d, J=9.0 Hz).

(8) Tert-butyl(4-butoxy-5,6-dimethoxy-2-neopentyl-1-oxo-1,2-dihydro-3-isoquinolinyl)methylcarbamate (synthesized according to the method similar to that in Example 1 (6))

Elemental analysis for $C_{26}H_{40}N_2O_6$ Calculated: C, 65.52; H, 8.46; N, 5.88. Found: C, 65.17; H, 8.30; N, 5.89. $^1$H-NMR(CDCl$_3$) δ: 0.98 (9H, s), 0.99 (3H, t, J=7.3 Hz), 1.45 (9H, s), 1.46–1.55 (2H, m), 1.74–1.84 (2H, m), 3.80 (2H, t, J=6.2 Hz), 3.85 (3H, s), 3.99 (3H, s), 4.14 (2H, bs), 4.56 (2H, d, J=5.6 Hz), 4.67 (1H, bs), 7.15 (1H, d, J=9.0 Hz), 8.26 (1H, d, J=9.0 Hz).

(9) 3-(Aminomethyl)-4-butoxy-5,6-dimethoxy-2-neopentyl-1(2H)-isoquinolinone hydrochloride (synthesized according to the method similar to that in Example 1 7))

Melting point 156–157° C. Elemental analysis for $C_{21}H_{33}N_2O_4Cl$ Calculated: C, 61.08; H, 8.05; N, 6.78. Found: C, 60.71; H, 8.05; N, 6.78. $^1$H-NMR(DMSO-$d_6$) δ: 0.88 (9H, s), 0.97 (3H, t, J=7.3 Hz), 1.43–1.54 (2H, m), 1.76–1.83 (2H, m), 3.76 (3H, s), 3.79 (2H, bs), 3.94 (3H, s), 4.07 (2H, bs), 4.22 (2H, s), 7.40 (1H, d, J=9.0 Hz), 8.11 (1H, d, J=9.0 Hz), 8.52 (3H, bs).

Example 70

3-(Aminomethyl)-4-butoxy-6,7-dimethoxy-2-neopentyl-1(2H)-isoquinolinone hydrochloride (1) 2-(Ethoxycarbonyl)-4,5-dimethoxybenzoic acid (synthesized according to the method similar to that in Example 69 (1))

Melting point 130–131° C. Elemental analysis for $C_{12}H_{14}O_6$ ¼$H_2O$ Calculated: C, 55.70; H, 5.65. Found: C, 56.06; H, 5.53. $^1$H-NMR(CDCl$_3$) δ: 1.39 (3H, t, J=7.2 Hz), 3.98 (6H, s), 4.40 (2H, q, J=7.2 Hz), 7.22 (1H, s), 7.50 (1H, s), 8.01 (1H, s).

(2) Ethyl 6,7-dimethoxy-4-hydroxy-2-neopentyl-1-oxo-1,2-dihydro-3-isoquinolinecarboxylate (synthesized according to the method similar to that in Example 69 (2))

Elemental analysis for $C_{19}H_{25}NO_6$ Calculated: C, 62.80; H, 6.93; N, 3.85. Found: C, 62.58; H, 6.89; N, 3.82. $^1$H-NMR(CDCl$_3$) δ: 0.85 (9H, s), 1.47 (3H, t, J=7.2 Hz), 4.04 (6H, s), 4.47 (2H, q, J=7.2 Hz), 4.55 (2H, bs), 7.49 (1H, s), 7.85 (1H, s), 11.04 (1H, s).

(3) Ethyl 4-butoxy-6,7-dimethoxy-2-neopentyl-1-oxo-1,2-dihydro-3-isoquinolinecarboxylate (synthesized according to the method similar to that in Example 1 (2))

$^1$H-NMR(CDCl$_3$) δ: 0.94 (9H, s), 1.02 (3H, t, J=7.3 Hz), 1.44 (3H, t, J=7.3 Hz), 1.49–1.67 (2H, m), 1.74–1.87 (2H, m), 3.96 (2H, t, J=6.4 Hz), 4.01 (3H, s), 4.02 (3H, s), 4.14 (2H, bs), 4.42 (2H, q, J=7.1 Hz), 7.15 (1H, s), 7.83 (1H, s).

(4) 4-Butoxy-6,7-dimethoxy-2-neopentyl-1-oxo-1,2-dihydro-3-isoquinolinecarboxylic acid (synthesized according to the method similar to that in Example 4 (3))

Melting point 209–210° C. Elemental analysis for $C_{21}H_{29}NO_6$ Calculated: C, 64.43; H, 7.47; N, 3.58. Found: C, 64.14; H, 7.34; N, 3.46. $^1$H-NMR(CDCl$_3$) δ: 0.91 (9H, s), 1.01 (3H, t, J=7.2 Hz), 1.44–1.65 (2H, m), 1.74–1.88 (2H, m), 3.92 (3H, s), 4.03–4.18 (7H, m), 6.60 (1H, s), 7.31 (1H, s).

(5) 4-Butoxy-6,7-dimethoxy-3-hydroxymethyl-2-neopentyl-1(2H)-isoquinolinone (synthesized according to the method similar to that in Example 4 (4))

Melting point 142–143° C. Elemental analysis for $C_{21}H_{31}NO_5$ ¼$H_2O$ Calculated: C, 66.03; H, 8.31; N, 3.67. Found: C, 66.32; H, 8.46; N, 3.83. $^1$H-NMR(CDCl$_3$) δ: 0.95 (9H, s), 1.03 (3H, t, J=7.3 Hz), 1.55–1.67 (2H, m), 1.77–1.87 (2H, m), 3.65 (1H, bs), 3.80 (2H, t, J=6.2 Hz), 3.95 (3H, s), 4.02 (3H, s), 4.22 (2H, bs), 4.84 (2H, bs), 6.76 (1H, s), 7.57 (1H, s).

(6) 4-Butoxy-3-chloromethyl-6,7-dimethoxy-2-neopentyl-1(2H)-isoquinolinone (synthesized according to the method similar to that in Example 4 (5))

$^1$H-NMR(CDCl$_3$) δ: 1.00 (9H, s), 1.05 (3H, t, J=7.3 Hz), 1.58–1.73 (2H, m), 1.82–1.93 (2H, m), 3.97 (2H, t, J=6.4 Hz), 4.02 (6H, s), 4.21 (2H, bs), 4.90 (2H, bs), 7.12 (1H, s), 7.82 (1H, s).

(7) 2-{(4-Butoxy-6,7-dimethoxy-2-neopentyl-1-oxo-1,2-dihydro-3-isoquinolinyl)methyl}-1H-isoindole-1,3(2H)-dione (synthesized according to the method similar to that in Example 4 (6))

Melting point 210–212° C. Elemental analysis for $C_{29}H_{34}N_2O_6$ Calculated: C, 68.76; H, 6.76; N, 5.53. Found: C, 68.61; H, 6.65; N, 5.55. $^1$H-NMR(CDCl$_3$) δ: 1.01 (3H, t, J=7.4 Hz), 1.02 (9H, s), 1.49–1.67 (2H, m), 1.82–1.96 (2H, m), 3.99 (3H, s), 4.00 (3H, s), 4.03 (2H, t, J=6.6 Hz), 4.10 (2H, bs), 5.07 (2H, s), 7.13 (1H, s), 7.68–7.83 (5H, m).

(8) Tert-butyl(4-butoxy-6,7-dimethoxy-2-neopentyl-1-oxo-1,2-dihydro-3-isoquinolinyl)methylcarbamate (synthesized according to the method similar to that in Example 1 (6))

Melting point 197–198° C. Elemental analysis for $C_{26}H_{40}N_2O_6$ ½$H_2O$ Calculated: C, 64.31; H, 8.51; N, 5.77. Found: C, 64.68; H, 8.43; N, 5.62. $^1$H-NMR(CDCl$_3$) δ: 1.00 (9H, s), 1.04 (3H, t, J=7.2 Hz), 1.46 (9H, s), 1.55–1.70 (2H, m), 1.79–1.93 (2H, m), 3.86 (2H, t, J=6.4 Hz), 4.00 (3H, s), 4.05 (3H, s), 4.10 (2H, bs), 4.56 (2H, d, J=5.4 Hz), 4.80 (1H, bs), 7.03 (1H, s), 7.77 (1H, s).

(9) 3-(Aminomethyl)-4-butoxy-6,7-dimethoxy-2-neopentyl-1(2H)-isoquinolinone hydrochloride (synthesized according to the method similar to that in Example 1 (7))

Melting point 231–233° C. Elemental analysis for $C_{21}H_{33}N_2O_4Cl$ $H_2O$ Calculated: C, 58.53; H, 8.19; N, 6.50. Found: C, 58.77; H, 8.23; N, 6.61. $^1$H-NMR(DMSO-d$_6$) δ: 0.90 (9H, s), 1.00 (3H, t, J=7.3 Hz), 1.53–1.65 (2H, m), 1.77–1.88 (2H, m), 3.90 (3H, s), 3.94 (3H, s), 3.95 (2H, t, J=7.8 Hz), 4.09 (2H, bs), 4.22 (2H, s), 7.10 (1H, s), 7.65 (1H, s), 8.56 (3H, bs).

Example 71

5-(Aminomethyl)-4-butoxy-6-neopentylthieno[2,3-c]pyridin-7(6H)-one hydrochloride (1) 3-(Ethoxycarbonyl)-2-thiophenecarboxylic acid (synthesized according to the method similar to that in Example 69 (1))

Melting point 80–81° C. Elemental analysis for $C_8H_8O_4S$ Calculated: C, 47.99; H, 4.03. Found: C, 47.91; H, 3.79. $^1$H-NMR(CDCl$_3$) δ: 1.46 (3H, t, J=7.1 Hz), 4.50 (2H, q, J=7.1 Hz), 7.57 (1H, d, J=5.3 Hz), 7.63 (1H, d, J=5.3 Hz).

(2) Ethyl 4-hydroxy-6-neopentyl-7-oxo-6,7-dihydrothieno[2,3-c]pyridin-5-carboxylate (synthesized according to the method similar to that in Example 69 (2))

Melting point 95.5–97° C. Elemental analysis for $C_{15}H_{19}NO_4S$ Calculated: C, 58.23; H, 6.19; N, 4.53. Found: C, 58.12; H, 6.01; N, 4.48. $^1$H-NMR(CDCl$_3$) δ: 0.85 (9H, s), 1.46 (3H, t, J=7.2 Hz), 4.47 (2H, q, J=7.2 Hz), 4.53 (2H, bs), 7.55 (1H, d, J=5.1 Hz), 7.72 (1H, d, J=5.1 Hz), 10.66 (1H, s).

(3) Ethyl 4-butoxy-6-neopentyl-7-oxo-6,7-dihydrothieno[2,3-c]pyridine-5-carboxylate (synthesized according to the method similar to that in Example 1 (2))

Melting point 74–74.5° C. Elemental analysis for $C_{19}H_{27}NO_4S$ Calculated: C, 62.44; H, 7.45; N, 3.83. Found: C, 62.48; H, 7.70; N, 3.89. $^1$H-NMR(CDCl$_3$) δ: 0.94 (9H, s), 0.99 (3H, t, J=7.3 Hz), 1.43 (3H, t, J=7.2 Hz), 1.49–1.60 (2H, m), 1.70–1.84 (2H, m), 4.00 (2H, t, J=6.6 Hz), 4.14 (2H, bs), 4.41 (2H, q, J=7.2 Hz), 7.32 (1H, d, J=5.2 Hz), 7.72 (1H, d, J=5.2 Hz).

(4) 4-Butoxy-6-neopentyl-7-oxo-6,7-dihydrothieno[2,3-c]pyridine-5-carboxylic acid (synthesized according to the method similar to that in Example 4 (3))

Melting point 111–112° C. Elemental analysis for $C_{17}H_{23}NO_4S$ Calculated: C, 60.51; H, 6.87; N, 4.15. Found: C, 60.53; H, 6.87; N, 4.29. $^1$H-NMR(CDCl$_3$) δ: 0.95 (9H, s), 0.98 (3H, t, J=7.4 Hz), 1.43–1.61 (2H, m), 1.74–1.84 (2H, m), 4.08 (2H, t, J=6.4 Hz), 4.31 (2H, bs), 5.98 (1H, bs), 7.34 (1H, d, J=5.2 Hz), 7.75 (1H, d, J=5.2 Hz).

(5) 4-Butoxy-5-hydroxymethyl-6-neopentylthieno[2,3-c]pyridin-7(6H)-one (synthesized according to the method similar to that in Example 4 (4))

Melting point 110–111° C. Elemental analysis for $C_{17}H_{25}NO_3S$ Calculated: C, 63.13; H, 7.79; N, 4.33. Found:

C, 63.11; H, 7.59; N, 4.44. $^1$H-NMR(CDCl$_3$) δ: 0.97 (9H, s), 1.02 (3H, t, J=7.4 Hz), 1.47–1.68 (2H, m), 1.76–1.89 (2H, m), 3.98 (2H, t, J=6.6 Hz), 4.22 (2H, bs), 4.86 (2H, bs), 7.24 (1H, d, J=5.4 Hz), 7.62 (1H, d, J=5.4 Hz).

(6) 4-Butoxy-5-chloromethyl-6-neopentylthieno[2,3-c]pyridin-7(6H)-one (synthesized according to the method similar to that in Example 4 (5))

$^1$H-NMR(CDCl$_3$) δ: 1.01 (9H, s), 1.02 (3H, t, J=7.3 Hz), 1.52–1.63 (2H, m), 1.78–1.88 (2H, m), 4.01 (2H, t, J=6.4 Hz), 4.20 (2H, bs), 4.89 (2H, bs), 7.30 (1H, d, J=5.2 Hz), 7.69 (1H, d, J=5.2 Hz).

(7) 2-{(4-Butoxy-6-neopentyl-7-oxo-6,7-dihydrothieno{2,3-c}pyridin-5-yl)methyl}-1H-isoindole-1,3(2H)-dione (synthesized according to the method similar to that in Example 4 (6))

Melting point 118–119° C. Elemental analysis for C$_{25}$H$_{28}$N$_2$O$_4$S Calculated: C, 66.35; H, 6.24; N, 6.19. Found: C, 66.26; H, 6.17; N, 6.27. $^1$H-NMR(CDCl$_3$) δ: 0.99 (3H, t, J=7.2 Hz), 1.03 (9H, s), 1.41–1.60 (2H, m), 1.76–1.91 (2H, m), 4.08 (2H, t, J=6.8 Hz), 4.14 (2H, bs), 5.08 (2H, s), 7.30 (1H, d, J=5.0 Hz), 7.67 (1H, d, J=5.0 Hz), 7.69–7.84 (4H, m).

(8) Tert-butyl(4-butoxy-6-neopentyl-7-oxo-6,7-dihydrothieno[2,3-c]pyridin-5-yl)methylcarbamate (synthesized according to the method similar to that in Example 1 (6))

Melting point 131–131.5° C. Elemental analysis for C$_{22}$H$_{34}$N$_2$O$_4$S Calculated: C, 62.53; H, 8.11; N, 6.63. Found: C, 62.47; H, 8.13; N, 6.63. $^1$H-NMR(CDCl$_3$) δ: 1.01 (9H, s), 1.02 (3H, t, J=7.1 Hz), 1.44 (9H, s), 1.46–1.68 (2H, m), 1.75–1.89 (2H, m), 3.93 (2H, t, J=6.4 Hz), 4.17 (2H, bs), 4.56 (2H, d, J=5.2 Hz), 4.70 (1H, bs), 7.27 (1H, d, J=5.5 Hz), 7.68 (1H, d, J=5.5 Hz).

(9) 5-(Aminomethyl)-4-butoxy-6-neopentylthieno[2,3-c]pyridin-7(6H)-one hydrochloride (synthesized according to the method similar to that in Example 1 (7))

Elemental analysis for C$_{17}$H$_{27}$N$_2$O$_2$ClS ¼H$_2$O Calculated: C, 56.18; H, 7.63; N, 7.71. Found: C, 56.01; H, 7.64; N, 7.67. $^1$H-NMR(DMSO-d$_6$) δ: 0.91 (9H, s), 0.97 (3H, t, J=7.4 Hz), 1.45–1.56 (2H, m), 1.73–1.83 (2H, m), 4.01 (2H, t, J=6.2 Hz), 4.13 (2H, bs), 4.23 (2H, bs), 7.47 (1H, d, J=5.1 Hz), 8.16 (1H, d, J=5.1 Hz), 8.53 (3H, bs).

Example 72

6-(Aminomethyl)-7-butoxy-5-neopentylthieno[3,2-c]pyridin-4(5H)-one hydrochloride (1) 2-(Ethoxycarbonyl)-3-thiophenecarboxylic acid (synthesized according to the method similar to that in Example 69 (1))

Melting point 94–95° C. Elemental analysis for C$_8$H$_8$O$_4$S Calculated: C, 47.99; H, 4.03. Found: C, 47.91; H, 3.79. $^1$H-NMR(CDCl$_3$) δ: 1.28 (3H, t, J=7.0 Hz), 4.28 (2H, q, J=7.0 Hz), 7.32 (1H, d, J=5.1 Hz), 7.89 (1H, d, J=5.1 Hz).

(2) Ethyl 7-hydroxy-5-neopentyl-4-oxo-4,5-dihydrothieno[3,2-c]pyridine-6-carboxylate (synthesized according to the method similar to that in Example 69 (2))

Melting point 110–111° C. Elemental analysis for C$_{15}$H$_{19}$NO$_4$S Calculated: C, 58.23; H, 6.19; N, 4.53. Found: C, 58.28; H, 6.19; N, 4.50. $^1$H-NMR(CDCl$_3$) δ: 0.86 (9H, s), 1.47 (3H, t, J=7.2 Hz), 4.48 (2H, q, J=7.2 Hz), 7.58 (1H, d, J=5.2 Hz), 7.72 (1H, d, J=5.2 Hz), 10.62 (1H, s).

(3) Ethyl 7-butoxy-5-neopentyl-4-oxo-4,5-dihydrothieno[3,2-c]pyridine-6-carboxylate (synthesized according to the method similar to that in Example 1 (2))

$^1$H-NMR(CDCl$_3$) δ: 0.94 (9H, s), 0.99 (3H, t, J=7.5 Hz), 1.43 (3H, t, J=7.2 Hz), 1.43–1.61 (2H, m), 1.70–1.84 (2H, m), 4.07 (2H, t, J=6.6 Hz), 4.14 (2H, bs), 4.41 (2H, q, J=7.2 Hz), 7.41 (1H, d, J=5.3 Hz), 7.68 (1H, d, J=5.3 Hz).

(4) 7-Butoxy-5-neopentyl-4-oxo-4,5-dihydrothieno[3,2-c]pyridine-6-carboxylic acid (synthesized according to the method similar to that in Example 4 (3))

Melting point 137–138° C. Elemental analysis for C$_{17}$H$_{23}$NO$_4$S Calculated: C, 60.51; H, 6.87; N, 4.15. Found: C, 60.66; H, 6.86; N, 4.10. $^1$H-NMR(CDCl$_3$) δ: 0.93 (9H, s), 0.98 (3H, t, J=7.4 Hz), 1.43–1.61 (2H, m), 1.72–1.86 (2H, m), 4.14 (2H, t, J=6.4 Hz), 4.21 (2H, bs), 6.83 (1H, bs), 7.44 (1H, d, J=5.3 Hz), 7.68 (1H, d, J=5.3 Hz).

(5) 7-Butoxy-6-hydroxymethyl-5-neopentylthieno[3,2-c]pyridin-4(5H)-one (synthesized according to the method similar to that in Example 4 (4))

Melting point 102–103° C. Elemental analysis for C$_{17}$H$_{25}$NO$_3$S ½H$_2$O Calculated: C, 61.42; H, 7.88; N, 4.21. Found: C, 61.39; H, 7.61; N, 4.36. $^1$H-NMR(CDCl$_3$) δ: 0.95 (9H, s), 1.02 (3H, t, J=7.2 Hz), 1.47–1.66 (2H, m), 1.75–1.89 (2H, m), 3.10 (1H, bs), 4.04 (2H, t, J=6.5 Hz), 4.15 (2H, bs), 4.83 (2H, bs), 7.22–7.26 (1H, m), 7.52–7.56 (1H, m).

(6) 7-Butoxy-6-chloromethyl-5-neopentylthieno[3,2-c]pyridin-4(5H)-one (synthesized according to the method similar to that in Example 4 (5))

$^1$H-NMR(CDCl$_3$) δ: 1.01 (9H, s), 1.02 (3H, t, J=7.3 Hz), 1.52–1.63 (2H, m), 1.77–1.88 (2H, m), 4.08 (2H, t, J=6.4 Hz), 4.14 (2H, bs), 4.87 (2H, bs), 7.35 (1H, d, J=5.5 Hz), 7.68 (1H, d, J=5.5 Hz).

(7) 2-{(7-Butoxy-5-neopentyl-4-oxo-4,5-dihydrothieno[3,2-c]pyridin-6-yl)methyl}-1H-isoindole-1,3(2H)-dione (synthesized according to the method similar to that in Example 4 (6))

Melting point 136–137° C. Elemental analysis for C$_{25}$H$_{28}$N$_2$O$_4$S Calculated: C, 66.35; H, 6.24; N, 6.19. Found: C, 66.27; H, 6.14; N, 6.22. $^1$H-NMR(CDCl$_3$) δ: 0.99 (3H, t, J=7.2 Hz), 1.02 (9H, s), 1.45–1.60 (2H, m), 1.76–1.90 (2H, m), 4.14 (2H, bs), 4.16 (2H, t, J=6.6 Hz), 5.07 (2H, s), 7.29 (1H, d, J=5.2 Hz), 7.64 (1H, d, J=5.2 Hz), 7.69–7.83 (4H, m).

(8) Tert-butyl(7-butoxy-5-neopentyl-4-oxo-4,5-dihydrothieno[3,2-c]pyridin-6-yl)methylcarbamate (synthesized according to the method similar to that in Example 1 (6))

Melting point 141–142° C. Elemental analysis for C$_{22}$H$_{34}$N$_2$O$_4$S Calculated: C, 62.53; H, 8.11; N, 6.63. Found: C, 62.50; H, 8.08; N, 6.66. $^1$H-NMR(CDCl$_3$) δ: 1.01 (9H, s), 1.02 (3H, t, J=7.1 Hz), 1.44 (9H, s), 1.49–1.64 (2H, m), 1.74–1.88 (2H, m), 4.00 (2H, t, J=6.4 Hz), 4.14 (2H, bs), 4.56 (2H, d, J=5.0 Hz), 4.70 (1H, bs), 7.29 (1H, d, J=5.1 Hz), 7.64 (1H, d, J=5.1 Hz).

(9) 6-(Aminomethyl)-7-butoxy-5-neopentylthieno[3,2-c]pyridin-4(5H)-one hydrochloride (synthesized according to the method similar to that in Example 1 (7))

Melting point 204–206° C. Elemental analysis for C$_{17}$H$_{27}$N$_2$O$_2$ClS Calculated: C, 56.89; H, 7.58; N, 7.80. Found: C, 56.98; H, 7.46; N, 7.61. $^1$H-NMR(DMSO-d$_6$) δ: 0.91 (9H, s), 0.98 (3H, t, J=7.4 Hz), 1.44–1.59 (2H, m), 1.71–1.92 (2H, m), 4.07 (2H, t, J=6.4 Hz), 4.09 (2H, bs), 4.24 (2H, d, J=5.3 Hz), 7.56 (1H, d, J=5.3 Hz), 7.77 (1H, d, J=5.3 Hz), 8.58 (3H, bs).

Example 74

3-(Aminomethyl)-6-bromo-4-butoxy-2-isobutyl-1(2H)-isoquinolinone hydrochloride (1) Ethyl 6-bromo-4-hydroxy-2-isobutyl-1-oxo-1,2-dihydro-3-isoquinolinecarboxylate (synthesized according to the method similar to that in Example 1 (1))

Melting point 74–75° C. Elemental analysis for $C_{16}H_{18}NO_4Br$ Calculated: C, 52.19; H, 4.93; N, 3.80. Found: C, 52.15; H, 4.89; N, 3.85. $^1$H-NMR(CDCl$_3$) δ: 0.82 (6H, d, J=6.6 Hz), 1.46 (3H, t, J=7.2 Hz), 1.78–1.88 (1H, m), 4.39 (2H, d, J=5.6 Hz), 4.49 (2H, q, J=7.2 Hz), 7.78 (1H, dd, J=2.0, 8.4 Hz), 8.30 (1H, d, J=2.0 Hz), 8.31 (1H, d, J=8.4 Hz), 11.14 (1H, s).

(2) Ethyl 6-bromo-4-butoxy-2-isobutyl-1-oxo-1,2-dihydro-3-isoquinolinecarboxylate (synthesized according to the method similar to that in Example 1 (2))

Melting point 88–89° C. Elemental analysis for $C_{20}H_{26}NO_4Br$ Calculated: C, 56.61; H, 6.18; N, 3.30. Found: C, 56.64; H, 6.13; N, 3.38. $^1$H-NMR(CDCl$_3$) δ: 0.90 (6H, d, J=7.0 Hz), 1.01 (3H, t, J=7.4 Hz), 1.44 (3H, t, J=7.2 Hz), 1.48–1.63 (2H, m), 1.72–1.83 (2H, m), 2.05–2.19 (1H, m), 3.88 (2H, d, J=7.4 Hz), 3.95 (2H, t, J=6.4 Hz), 4.46 (2H, q, J=7.2 Hz), 7.65 (1H, dd, J=2.0, 8.6 Hz), 7.88 (1H, d, J=2.0 Hz), 8.29 (1H, d, J=8.6 Hz).

(3) 6-Bromo-4-butoxy-2-isobutyl-1-oxo-1,2-dihydro-3-isoquinolinecarboxylic acid (synthesized according to the method similar to that in Example 4 (3))

Melting point 177–178° C. Elemental analysis for $C_{18}H_{22}NO_4Br$ Calculated: C, 54.56; H, 5.60; N, 3.53. Found: C, 54.57; H, 5.63; N, 3.57. $^1$H-NMR(CDCl$_3$) δ: 0.90 (6H, d, J=6.6 Hz), 1.00 (3H, t, J=7.4 Hz), 1.45–1.63 (2H, m), 1.75–1.89 (2H, m), 2.07–2.23 (1H, m), 4.01 (2H, t, J=6.4 Hz), 4.02 (2H, d, J=8.6 Hz), 6.81 (1H, bs), 7.65 (1H, dd, J=1.8, 8.6 Hz), 7.81 (1H, d, J=1.8 Hz), 8.23 (1H, d, J=8.6 Hz).

(4) 6-Bromo-4-butoxy-3-hydroxymethyl-2-isobutyl-1 (2H)-isoquinolinone (synthesized according to the method similar to that in Example 4 (4))

Melting point 92–93° C. Elemental analysis for $C_{18}H_{24}NO_3Br$ ½$H_2O$ Calculated: C, 55.25; H, 6.43; N, 3.58. Found: C, 55.62; H, 6.35; N, 3.75. $^1$H-NMR(CDCl$_3$) δ: 0.93 (6H, d, J=6.6 Hz), 1.04 (3H, t, J=7.4 Hz), 1.50–1.68 (2H, m), 1.79–1.93 (2H, m), 2.11–2.28 (1H, m), 2.47 (1H, bs), 3.88 (2H, t, J=6.4 Hz), 4.08 (2H, d, J=7.8 Hz), 4.80 (2H, s), 7.55 (1H, d, J=8.6 Hz), 7.80 (1H, s), 8.18 (1H, d, J=8.6 Hz).

(5) 6-Bromo-4-butoxy-3-chloromethyl-2-isobutyl-1(2H)-isoquinolinone (synthesized according to the method similar to that in Example 4 (5)) $^1$H-NMR(CDCl$_3$) δ: 0.95 (6H, d, J=7.0 Hz), 1.05 (3H, t, J=7.2 Hz), 1.52–1.75 (2H, m), 1.86–1.96 (2H, m), 2.04– 2.23 (1H, m), 3.98 (2H, t, J=6.4 Hz), 4.07 (2H, d, J=7.4 Hz), 4.80 (2H, s), 7.63 (1H, dd, J=2.0, 8.4 Hz), 7.88 (1H, d, J=2.0 Hz), 8.29 (1H, d, J=8.4 Hz).

(6) 2-{(6-Bromo-4-butoxy-2-isobutyl-1-oxo-1,2-dihydro-3-isoquinolinyl)methyl}-1H-isoindole-1,3(2H)-dione (synthesized according to the method similar to that in Example 4 (6))

$^1$H-NMR(CDCl$_3$) δ: 0.96 (6H, d, J=7.0 Hz), 1.00 (3H, t, J=7.3 Hz), 1.44–1.58 (2H, m), 1.79–1.95 (2H, m), 2.08–2.22 (1H, m), 3.95–4.05 (4H, m), 5.02 (2H, s), 7.59 (1H, dd, J=2.0, 8.8 Hz), 7.71–7.90 (5H, m), 8.27 (1H, d, J=8.8 Hz).

(7) Tert-butyl(6-bromo-4-butoxy-2-isobutyl-1-oxo-1,2-dihydro-3-isoquinolinyl)methylcarbamate (synthesized according to the method similar to that in Example 1 (6))

Melting point 138–139° C. Elemental analysis for $C_{23}H_{33}N_2O_4Br$ Calculated: C, 57.38; H, 6.91; N, 5.82. Found: C, 57.41; H, 6.79; N, 5.76. $^1$H-NMR(CDCl$_3$) δ: 0.95 (6H, d, J=6.6 Hz), 1.04 (3H, t, J=7.3 Hz), 1.46 (9H, s), 1.53–1.67 (2H, m), 1.80–1.93 (2H, m), 2.05–2.23 (1H, m), 3.85 (2H, t, J=6.6 Hz), 3.98 (2H, d, J=7.6 Hz), 4.41 (2H, d, J=5.4 Hz), 4.73 (1H, bs), 7.59 (1H, dd, J=2.0, 8.6 Hz), 7.82 (1H, d, J=2.0 Hz), 8.26 (1H, d, J=8.6 Hz).

(8) 3-(Aminomethyl)-6-bromo-4-butoxy-2-isobutyl-1 (2H)-isoquinolinone hydrochloride (synthesized according to the method similar to that in Example 1 (7))

Melting point 133–134° C. Elemental analysis for $C_{18}H_{26}N_2O_2BrCl$ ½$H_2O$ Calculated: C, 50.66; H, 6.38; N, 6.56. Found: C, 51.05; H, 6.56; N, 6.68. $^1$H-NMR(DMSO-d$_6$) δ: 0.88 (6H, d, J=7.0 Hz), 1.00 (3H, t, J=7.4 Hz), 1.46–1.65 (2H, m), 1.76–1.91 (2H, m), 1.96–2.10 (1H, m), 3.93 (2H, t, J=6.4 Hz), 3.96 (2H, d, J=7.6 Hz), 4.18 (2H, d, J=4.4 Hz), 7.79 (1H, dd, J=2.0, 8.6 Hz), 7.87 (1H, d, J=2.0 Hz), 8.20 (1H, d, J=8.6 Hz), 8.69 (3H, bs).

Example 75

Methyl 3-(aminomethyl)-4-butoxy-2-isobutyl-1-oxo-1,2-dihydro-6-isoquinolinecarboxylate hydrochloride (1) A mixture of tert-butyl(6-bromo-4-butoxy-2-isobutyl-1-oxo-1,2-dihydro-3-isoquinolinyl)methylcarbamate (synthesized according to the method similar to that in Example 74 (7)) (2.41 g, 5 mmol), 1,3-bis(diphenylphosphino)propane (0.21 g, 0.5 mmol) and triethylamine (0.77 ml, 5.5 mmol) in dimethyl sulfoxide (30 ml) and methanol (20 ml) was stirred under a carbon monoxide atmosphere at room temperature for 10 min. To the obtained mixture was added palladium acetate (0.11 g, 0.5 mmol) and the mixture was stirred with heating under a carbon monoxide atmosphere at 60° C. for 12 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 4-butoxy-3-{{(tert-butoxycarbonyl)amino}methyl}-2-isobutyl-1-oxo-1,2-dihydro-6-isoquinolinecarboxylate (1.92 g, 83.5%) as crystals.

Melting point 148–149° C. Elemental analysis for $C_{25}H_{36}N_2O_6$ Calculated: C, 65.20; H, 7.88; N, 6.08. Found: C, 65.30; H, 7.67; N, 6.17. $^1$H-NMR(CDCl$_3$) δ: 0.97 (6H, d, J=6.8 Hz), 1.05 (3H, t, J=7.3 Hz), 1.47 (9H, S), 1.56–1.71 (2H, m), 1.83–1.93 (2H, m), 2.05–2.25 (1H, m), 3.89 (2H, t, J=6.6 Hz), 3.99 (3H, s), 4.01 (2H, d, J=7.6 Hz), 4.53 (2H, d, J=5.4 Hz), 4.77 (1H, bs), 8.09 (1H, dd, J=1.9, 8.4 Hz), 8.40 (1H, d, J=1.9 Hz), 8.47 (1H, d, J=8.4 Hz).

(2) Methyl 3-(aminomethyl)-4-butoxy-2-isobutyl-1-oxo-1,2-dihydro-6-isoquinolinecarboxylate hydrochloride (synthesized according to the method similar to that in Example 1 (7))

Melting point 135–136° C. Elemental analysis for $C_{20}H_{29}N_2O_4Cl$ Calculated: C, 60.52; H, 7.36; N, 7.06. Found: C, 60.20; H, 7.48; N, 7.02. $^1$H-NMR(DMSO-d$_6$) δ: 0.89 (6H, d, J=6.6 Hz), 1.02 (3H, t, J=7.3 Hz), 1.51–1.70 (2H, m), 1.80–1.92 (2H, m), 1.99–2.11 (1H, m), 3.95–4.01 (7H, m), 4.21 (2H, s), 8.11 (1H, dd, J=1.4, 8.2 Hz), 8.35 (1H, d, J=1.4 Hz), 8.41 (1H, d, J=8.2 Hz), 8.70 (3H, bs).

Example 76

3-(Aminomethyl)-4-butoxy-2-isobutyl-1-oxo-1,2-dihydro-6-isoquinolinecarboxylic acid hydrochloride (1) To a solution of methyl 4-butoxy-3-{{(tert-butoxycarbonyl)amino}methyl}-2-isobutyl-1-oxo-1,2-dihydro-6-isoquinolinecarboxylate (synthesized according to the method similar to that in Example 75 (1)) (1.61 g, 3.5 mmol) in tetrahydrofuran (10 ml) and methanol (10 ml) was added 1N sodium hydroxide (5 ml). The obtained mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diethyl ether to give 4-butoxy-3-{{(tert-butoxycarbonyl)amino}methyl}-2-isobutyl-1-oxo-1,2-dihydro-6-isoquinolinecarboxylic acid (1.54 g, 98.7%) as crystals.

Melting point 185–186° C. Elemental analysis for $C_{24}H_{34}N_2O_6$ Calculated: C, 64.55; H, 7.67; N, 6.27. Found: C, 64.77; H; 7.40; N, 6.10. $^1$H-NMR(CDCl$_3$) δ: 0.96 (6H, d, J=6.6 Hz), 1.07 (3H, t, J=7.4 Hz), 1.49 (9H, S), 1.50–1.72 (2H, m), 1.84–1.98 (2H, m), 2.14–2.21 (1H, m), 3.90 (2H, t, J=6.4 Hz), 4.00 (2H, d, J=6.8 Hz), 4.55 (2H, d, J=5.01 Hz), 5.37 (1H, bs), 8.08–8.13 (1H, m), 8.35–8.46 (2H, m).

(2) 3-(Aminomethyl)-4-butoxy-2-isobutyl-1-oxo-1,2-dihydro-6-isoquinolinecarboxylic hydrochloride (synthesized according to the method similar to that in Example 1 (7))

Melting point 238–239° C. Elemental analysis for $C_{19}H_{27}N_2O_4Cl$ Calculated: C, 59.60; H, 7.11; N, 7.32. Found: C, 59.42; H, 7.04; N, 7.18. $^1$H-NMR(DMSO-d$_6$) δ: 0.89 (6H, d, J=6.6 Hz), 1.01 (3H, t, J=7.4 Hz), 1.50–1.69 (2H, m), 1.80–1.93 (2H, m), 1.99–2.12 (1H, m), 3.97 (2H, t, J=6.4 Hz), 3.99 (2H,d, J=7.6 Hz), 4.21 (2H, s), 8.09 (1H, dd, J=1.4, 8.4 Hz), 8.34 (1H, d, J=1.4 Hz), 8.38 (1H, d, J=8.4 Hz), 8.69 (3H, bs).

Example 77

3-(Aminomethyl)-4-butoxy-2-isobutyl-1-oxo-1,2-dihydro-6-isoquinolinecarboxamide hydrochloride (1) A solution of 4-butoxy-3-{{(tert-butoxycarbonyl)amino}methyl}-2-isobutyl-1-oxo-1,2-dihydro-6-isoquinolinecarboxylic acid (Example 76 (1)) (0.45 g, 3.5 mmol), 1-ethyl-3-(3-dimethylaminopropyl)carbodiimide hydrochloride (0.38 g, 2 mmol) and 1-hydroxybenzotriazole ammonium salt (0.30 g, 2 mmol) in N,N-dimethylformamide (10 ml) was stirred at room temperature for 3 h. The reaction mixture was poured into water and extracted with ethyl acetate. The extract was washed with brine, dried over anhydrous magnesium sulfate and concentrated under reduced pressure. The residue was recrystallized from ethyl acetate-diisopropyl ether to give tert-butyl{(6-aminocarbonyl)-4-butoxy-2-isobutyl-1-oxo-1,2-dihydro-3-isoquinolinyl}methylcarbamate (0.35 g, 79.5%) as crystals.

Melting point 159–160° C. Elemental analysis for $C_{24}H_{35}N_3O_5$ Calculated: C, 64.70; H, 7.92; N, 9.43. Found: C, 64.53; H, 8.01; N, 9.53. $^1$H-NMR(CDCl$_3$) δ: 0.96 (6H, d, J=7.0 Hz), 1.03 (3H, t, J=7.3 Hz), 1.48 (9H, S), 1.49–1.63 (2H, m), 1.80–1.95 (2H, m), 2.10–2.21 (1H, m), 3.87 (2H, t, J=6.4 Hz), 4.00 (2H, d, J=7.2 Hz), 4.52 (2H, d, J=5.6 Hz), 5.07 (1H, bs), 5.99 (1H, bs), 6.48 (1H, bs), 7.75 (1H, d, J=8.0 Hz), 8.10 (1H, s), 8.35 (1H, d, J=8.0 Hz).

(2) 3-(Aminomethyl)-4-butoxy-2-isobutyl-1-oxo-1,2-dihydro-6-isoquinolinecarboxamide hydrochloride (synthesized according to the method similar to that in Example 1 (7))

Melting point 171–173° C. Elemental analysis for $C_{19}H_{28}N_3O_3Cl \cdot H_2O$ Calculated: C, 57.06; H, 7.56; N, 10.51. Found: C, 57.41; H, 7.62; N, 10.59. $^1$H-NMR (DMSO-d$_6$) δ: 0.89 (6H, d, J=7.0 Hz), 1.01 (3H, t, J=7.3 Hz), 1.48–1.66 (2H, m), 1.80–2.07 (3H, m), 3.94–4.00 (4H, m), 4.20 (2H, s), 7.70 (1H, s), 8.04 (1H, dd, J=1.6, 8.4 Hz) 8.22 (1H, d, J=1.6 Hz), 8.33 (1H, d, J=8.4 Hz), 8.35 (1H, s), 8.60 (3H, bs).

Example 78

3-(Aminomethyl)-4-butoxy-2-isobutyl-1-oxo-1,2-dihydro-6-isoquinolinecarbonitrile hydrochloride (1) A solution of tert-butyl{(6-aminocarbonyl)-4-butoxy-2-isobutyl-1-oxo-1,2-dihydro-3-isoquinolinyl}methylcarbamate (Example 77 (1)) (0.54 g, 1.2 mmol) and cyanuric chloride (0.66 g, 3.6 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was recrystallized from ethyl acetate-n-hexane to give tert-butyl(4-butoxy-6-cyano-2-isobutyl-1-oxo-1,2-dihydro-3-isoquinolinyl)methylcarbamate (0.41 g, 80.4%) as crystals.

Melting point 126–127° C. $^1$H-NMR(CDCl$_3$) δ: 9.97 (6H, d, J=6.6 Hz), 1.05 (3H, t, J=7.3 Hz), 1.47 (9H, s), 1.48–1.67 (2H, m), 1.82–1.96 (2H, m), 2.11–2.25 (1H, m), 3.86 (2H, t, J=6.4 Hz), 4.02 (2H, d, J=7.0 Hz), 4.53 (2H, d, J=5.2 Hz), 4.73 (1H, bs), 7.68 (1H, d, J=8.0 Hz), 8.01 (1H, s), 8.50 (1H, d, J=8.0 Hz).

(2) 3-(Aminomethyl)-4-butoxy-2-isobutyl-1-oxo-1,2-dihydro-6-isoquinolinecarbonitrile hydrochloride (synthesized according to the method similar to that in Example 1 (7))

Melting point 135–136° C. $^1$H-NMR(DMSO-d$_6$) δ: 0.89 (6H, d, J=6.6 Hz), 1.00 (3H, t, J=7.2 Hz), 1.41–1.64 (2H, m), 1.81–1.91 (2H, m), 1.99–2.08 (1H, m), 3.93–4.02 (4H, m), 4.20 (2H, s), 7.99 (1H, d, J=8.2 Hz), 8.24 (1H, s), 8.42 (1H, d, J=8.2 Hz), 8.74 (3H, bs).

Example 79

3-(Aminomethyl)-4-butoxy-6-hydroxymethyl-2-isobutyl-1(2H)-isoquinoline hydrochloride (1) To a solution of 4-butoxy-3-{{(tert-butoxycarbonyl)amino}methyl}-2-isobutyl-1-oxo-1,2-dihydro-6-isoquinolinecarboxylic acid (synthesized according to the method similar to that in Example 76 (1)) (0.45 g, 3.5 mmol) and N-methylmorpholine (0.13 ml, 1.2 mmol) in tetrahydrofuran (10 ml) was added ethyl chloroformate (0.12 ml, 1.2 mmol) at 0° C., and the mixture was stirred at 0° C. for 10 min. To the obtained mixture was added sodium tetrahydroborate (0.11 g, 3 mmol) and the mixture was stirred at 0° C. for 1 h. The reaction mixture was poured into water and extracted with ethyl acetate. The extract was washed with brine, dried over anhydrous magnesium sulfate and concentrated under reduced pressure. The residue was recrystallized from ethyl acetate-diisopropyl ether to give tert-butyl(4-butoxy-6-hydroxymethyl-2-isobutyl-1-oxo-1,2-dihydro-3-isoquinolinyl)methylcarbamate (0.33 g, 76.7%) as crystals.

Melting point 153–154° C. Elemental analysis for $C_{24}H_{36}N_2O_5$ Calculated: C, 66.64; H, 8.39; N, 6.48. Found: C, 66.61; H, 8.21; N, 6.44. $^1$H-NMR(CDCl$_3$) δ: 0.95 (6H, d, J=6.6 Hz), 1.01 (3H, t, J=7.4 Hz), 1.40–1.57 (11H, m), 1.78–1.92 (2H, m), 2.11–2.24 (1H, m), 3.80 (2H, t, J=6.8

Hz), 3.97 (2H, d, J=7.8 Hz), 4.50 (2H, d, J=5.4 Hz), 4.82 (2H, s), 5.25 (1H, bs), 7.39–7.51 (2H, m), 8.17–8.21 (1H, m).

(2) 3-(Aminomethyl)-4-butoxy-6-hydroxymethyl-2-isobutyl-1(2H)-isoquinoline hydrochloride (synthesized according to the method similar to that in Example 1 (7))

Elemental analysis for $C_{19}H_{29}N_2O_3Cl \cdot \frac{1}{2}H_2O$ Calculated: C, 60.39; H, 8.00; N, 7.41. Found: C, 60.00; H, 7.07; N, 7.07. $^1$H-NMR(DMSO-$d_6$) δ: 0.87 (6H, d, J=6.4 Hz), 1.00 (3H, t, J=7.1 Hz), 1.51–1.62 (2H, m), 1.82–2.02 (3H, m), 3.91–3.99 (4H, m), 4.69 (2H, d, J=5.2 Hz), 5.30 (2H, s), 5.53 (1H, bs), 7.52–7.62 (1H, m), 7.74 (1H, s), 8.21–8.30 (1H, m), 8.64 (3H, bs).

Example 80

N-{3-(Aminomethyl)-4-butoxy-2-isobutyl-1-oxo-1,2-dihydro-6-isoquinolinyl}-N'-methylurea hydrochloride (1) A solution of 4-butoxy-3-{{(tert-butoxycarbonyl)amino}methyl}-2-isobutyl-1-oxo-1,2-dihydro-6-isoquinolinecarboxylic acid (synthesized according to the method similar to that in Example 76 (1)) (0.45 g, 1 mmol), diphenylphosphoryl azide (0.26 ml, 1.2 mmol) and triethylamine (0.17 ml, 1.2 mmol) in N,N-dimethylformamide (10 ml) was stirred at room temperature for 1 h. The reaction mixture was poured into water and extracted with ethyl acetate. The extract was washed with brine, dried over anhydrous magnesium sulfate and concentrated under reduced pressure. The residue was dissolved in toluene (20 ml) and the mixture was refluxed with stirring for 1 h. To the obtained mixture was added a solution of 2N methylamine in tetrahydrofuran (1 ml, 2 mmol), and the mixture was refluxed with stirring for 1 h. The reaction mixture was poured into water and extracted with ethyl acetate. The extract was washed with brine, dried over anhydrous magnesium sulfate and concentrated under reduced pressure. The residue was recrystallized from tetrahydrofuran-diisopropyl ether to give tert-butyl {4-butoxy-2-isobutyl-6-{{(methylamino)carbony}-amino}-1-oxo-1,2-dihydro-3-isoquinolinyl}methylcarbamate (0.39 g, 83.0%) as an amorphous.

Elemental analysis for $C_{25}H_{38}N_4O_5$ Calculated: C, 63.27; H, 8.07; N, 11.81. Found: C, 62.96; H, 8.35; N, 11.55. $^1$H-NMR(CDCl$_3$) δ: 0.93 (6H, d, J=5.8 Hz), 0.95 (3H, t, J=6.6 Hz), 1.45–1.54 (11H, m), 1.64–1.82 (2H, m), 2.05–2.17 (1H, m), 2.86 (3H, d, J=4.4 Hz), 3.83 (2H, t, J=6.5 Hz), 3.98 (2H, d, J=7.4 Hz), 4.50 (2H, d, J=5.2 Hz), 5.02 (1H, bs), 5.98 (1H, bs), 6.99–7.04 (2H, m), 8.06–8.10 (1H, m), 8.39 (1H, s).

(2) N-{3-(Aminomethyl)-4-butoxy-2-isobutyl-1-oxo-1,2-dihydro-6-isoquinolinyl}-N'-methylurea hydrochloride (synthesized according to the method similar to that in Example 1 (7))

Melting point 181–183° C. Elemental analysis for $C_{20}H_{31}N_4O_3Cl \cdot \frac{1}{2}H_2O$ Calculated: C, 57.20; H, 7.68; N, 13.34. Found: C, 57.13; H, 7.66; N, 13.40. $^1$H-NMR (DMSO-$d_6$) δ: 0.87 (6H, d, J=6.6 Hz), 0.99 (3H, t, J=7.1 Hz), 1.46–1.65 (2H, m), 1.78–2.07 (3H, m), 3.87–3.93 (4H, m), 4.14 (2H, d, J=4.6 Hz), 6.74 (1H, bs), 7.48 (1H, dd, J=2.0, 8.8 Hz), 8.04 (1H, d, J=2.0 Hz), 8.10 (1H, d, J=8.8 Hz), 8.53 (3H, bs), 9.60 (1H, s).

Example 81

Methyl 3-(aminomethyl)-4-butoxy-2-isobutyl-1-oxo-1,2-dihydro-6-isoquinolinylcarbamate hydrochloride (1) Methyl 4-butoxy-3-{{(tert-butoxycarbonyl)amino}-methyl}-2-isobutyl-1-oxo-1,2-dihydro-6-isoquinolinylcarbamate (synthesized according to the method similar to that in Example 80 (1))

Elemental analysis for $C_{25}H_{38}N_4O_5$ Calculated: C, 63.14; H, 7.84; N, 8.84. Found: C, 62.99; H, 7.87; N, 9.01. $^1$H-NMR(CDCl$_3$) δ: 0.95 (6H, d, J=7.0 Hz), 1.03 (3H, t, J=7.1 Hz), 1.46 (9H, s), 1.52–1.67 (2H, m), 1.81–1.95 (2H, m), 2.09–2.23 (1H, m), 3.82 (3H, s), 3.88 (2H, t, J=6.6 Hz), 3.98 (2H, d, J=7.4 Hz), 4.51 (2H, d, J=5.4 Hz), 4.80 (1H, bs), 7.09 (1H, bs), 7.36 (1H, dd, J=2.0, 8.8 Hz), 7.89 (1H, d, J=2.0 Hz), 8.33 (1H, d, J=8.8 Hz).

(2) Methyl 3-(aminomethyl)-4-butoxy-2-isobutyl-1-oxo-1,2-dihydro-6-isoquinolinylcarbamate hydrochloride (synthesized according to the method similar to that in Example 1 (7))

Melting point 166–168° C. Elemental analysis for $C_{20}H_{30}N_3O_4Cl \cdot \frac{1}{4}H_2O$ Calculated: C, 57.69; H, 7.38; N, 10.09. Found: C, 57.59; H, 7.66; N, 10.02. $^1$H-NMR (DMSO-$d_6$) δ: 0.87 (6H, d, J=6.6 Hz), 1.00 (3H, t, J=7.4 Hz), 1.47–1.65 (2H, m), 1.79–2.04 (3H, m), 3.73 (3H, s), 3.89–3.94 (4H, m), 4.15 (2H, d, J=4.6 Hz), 7.63 (1H, dd, J=1.8, 8.8 Hz), 8.03 (1H, d, J=1.8 Hz), 8.17 (1H, d, J=8.8 Hz), 8.62 (3H, bs), 10.28 (1H, s).

Example 82

6-Amino-3-(aminomethyl)-4-butoxy-2-isobutyl-1(2H)-isoquinolinone dihydrochloride (1) A solution of 4-butoxy-3-{{(tert-butoxycarbonyl)amino} methyl}-2-isobutyl-1-oxo-1,2-dihydro-6-isoquinolinecarboxylic acid (synthesized according to the method similar to that in Example 76 (1)) (0.45 g, 1 mmol), diphenylphosphoryl azide (0.26 ml, 1.2 mmol) and triethylamine (0.17 ml, 1.2 mmol) in N,N-dimethylformamide, (10 ml) was stirred at room temperature for 1 h. The reaction mixture was poured into water and extracted with ethyl acetate. The extract was washed with brine, dried over anhydrous magnesium sulfate and concentrated under reduced pressure. The residue was dissolved in toluene (20 ml) and the mixture was refluxed with stirring for 1 h. To the obtained mixture was added 9H-fluorenylmethanol (0.29 g, 1.5 mmol) and the mixture was refluxed with stirring for 1 h. The reaction mixture was poured into water and extracted with ethyl acetate. The extract was washed with brine, dried over anhydrous magnesium sulfate and concentrated under reduced pressure. The residue was purified by silica gel column chromatography and recrystallized from tetrahydrofuran-diisopropyl ether to give 9H-fluoren-9-ylmethyl 4-butoxy-3-{{(tert-butoxycarbonyl)-amino}methyl}-2-isobutyl-1-oxo-1,2-dihydro-6-isoquinolinylcarbamate (0.53 g, 82.8%) as crystals.

Melting point 137–138° C. Elemental analysis for $C_{38}H_{45}N_3O_6$ Calculated: C, 71.34; H, 7.09; N, 6.57. Found: C, 71.09; H, 7.03; N, 6.63. $^1$H-NMR(CDCl$_3$) δ: 0.95 (6H, d, J=7.0 Hz), 1.01 (3H, t, J=7.4 Hz), 1.46 (9H, s), 1.47–1.61 (2H, m), 1.79–1.90 (2H, m), 2.09–2.23 (1H, m), 3.85 (2H, t, J=6.4 Hz), 3.97 (2H, d, J=7.4 Hz), 4.28 (1H, t, J=6.2 Hz), 4.50 (2H, d, J=5.2 Hz), 4.61 (2H, d, J=6.2 Hz), 4.80 (2H, bs), 7.11–7.16 (1H, m), 7.29–7.46 (4H, m), 7.63 (2H, d, J=7.0 Hz), 7.79 (2H, d, J=7.0 Hz), 7.87 (1H, d, J=1.8 Hz), 8.32 (1H, d, J=8.8 Hz).

(2) To a solution of 9H-fluoren-9-ylmethyl 4-butoxy-3-{{(tert-butoxycarbonyl)amino}methyl}-2-isobutyl-1-oxo-1,2-dihydro-6-isoquinolinylcarbamate (0.45 g, 0.7 mmol) in N,N-dimethylformamide (10 ml) was added pyrrolidine (0.5 ml) and the mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl(6-amino-4-butoxy-2-isobutyl-1-oxo-1,2-dihydro-3-isoquinolinyl)methylcarbamate (0.23 g, 79.3%) as crystals.

Melting point 175–176° C. Elemental analysis for $C_{23}H_{35}N_3O_4$ Calculated: C, 66.16; H, 8.45; N, 10.06. Found: C, 66.10; H, 8.74; N, 10.05. $^1$H-NMR(CDCl$_3$) δ: 0.94 (6H, d, J=6.6 Hz), 1.02 (3H, t, J=7.4 Hz), 1.46 (9H, s), 1.50–1.64 (2H, m), 1.77–1.91 (2H, m), 2.05–2.22 (1H, m), 3.82 (2H, t, J=6.6 Hz), 3.93 (2H, d, J=7.2 Hz), 4.16 (2H, s), 4.47 (2H, d, J=5.4 Hz), 4.69 (1H, bs), 6.778–6.83 (2H, m), 8.21 (1H, d, J=9.2 Hz).

(3) 6-Amino-3-(aminomethyl)-4-butoxy-2-isobutyl-1(2H)-isoquinolinone dihydrochloride (synthesized according to the method similar to that in Example 1 (7))

Melting point 245–247° C. Elemental analysis for $C_{18}H_{29}N_3O_2Cl_2$ Calculated: C, 55.38; H, 7.49; N, 10.76. Found: C, 55.02; H, 7.47; N, 10.72. $^1$H-NMR(DMSO-d$_6$) δ: 0.86 (6H, d, J=6.6 Hz), 0.99 (3H, t, J=7.4 Hz), 1.44–1.63 (2H, m), 1.77–2.02 (3H, m), 3.84–3.90 (4H, m), 4.11 (2H, d, J=4.0 Hz), 6.30 (3H, bs), 6.91–7.01 (2H, m), 8.00 (1H, d, J=9.2 Hz), 8.60 (3H, bs).

Example 83

3-(Aminomethyl)-6-bromo-4-butoxy-2-neopentyl-1(2H)-isoquinolinone hydrochloride (1) Ethyl 6-bromo-4-hydroxy-2-neopentyl-1-oxo-1,2-dihydro-3-isoquinolinecarboxylate (synthesized according to the method similar to that in Example 1 (1))

Melting point 105–106° C. Elemental analysis for $C_{17}H_{20}NO_4Br$ Calculated: C, 53.42; H, 5.37; N, 3.66. Found: C, 53.75; H, 5.25; N, 3.61. $^1$H-NMR(CDCl$_3$) δ: 0.84 (9H, s), 1.47 (3H, t, J=7.2 Hz), 4.54 (2H, bs), 7.78 (1H, dd, J=1.8, 8.4 Hz), 8.28 (1H, d, J=1.8 Hz), 8.30 (1H, d, J=8.4 Hz), 10.72 (1H, s).

(2) Ethyl 6-bromo-4-butoxy-2-neopentyl-1-oxo-1,2-dihydro-3-isoquinolinecarboxylate (synthesized according to the method similar to that in Example 1 (2))

Melting point 107.5–108° C. Elemental analysis for $C_{21}H_{28}NO_4Br$ Calculated: C, 57.54; H, 6.44; N, 3.20. Found: C, 57.54; H, 6.48; N, 3.18. $^1$H-NMR(CDCl$_3$) δ: 0.93 (9H, s), 1.02 (3H, t, J=7.3 Hz), 1.44 (3H, t, J=7.2 Hz), 1.44–1.61 (2H, m), 1.73–1.87 (2H, m), 3.94 (2H, t, J=6.6 Hz), 4.06 (2H, bs), 4.43 (2H, q, J=7.2 Hz), 7.65 (1H, dd, J=2.0, 8.6 Hz), 7.89 (1H, d, J=2.0 Hz), 8.28 (1H, d, J=8.6 Hz).

(3) 6-Bromo-4-butoxy-2-neopentyl-1-oxo-1,2-dihydro-3-isoquinolinecarboxylic acid (synthesized according to the method similar to that in Example 4 (3))

Melting point 152–153° C. Elemental analysis for $C_{19}H_{24}NO_4Br$ Calculated: C, 55.62; H, 5.90; N, 3.41. Found: C, 55.58; H, 5.80; N, 3.35. $^1$H-NMR(CDCl$_3$) δ: 0.93 (9H, s), 1.01 (3H, t, J=7.3 Hz), 1.46–1.65 (2H, m), 1.76–1.90 (2H, m), 4.02 (2H, t, J=6.4 Hz), 4.22 (2H, bs), 6.50 (1H, bs), 7.67 (1H, dd, J=2.0, 8.6 Hz), 7.82 (1H, d, J=2.0 Hz), 8.21 (1H, d, J=8.6 Hz).

(4) 6-Bromo-4-butoxy-3-hydroxymethyl-2-neopentyl-1(2H)-isoquinolinone (synthesized according to the method similar to that in Example 4 (4))

Melting point 162–163° C. Elemental analysis for $C_{19}H_{26}NO_3Br$ Calculated: C, 57.58; H, 6.61; N, 3.53. Found: C, 57.60; H, 6.55; N, 3.49. $^1$H-NMR(CDCl$_3$) δ: 0.95 (9H, s), 1.05 (3H, t, J=7.1 Hz), 1.51–1.69 (2H, m), 1.80–1.93 (2H, m), 2.88 (1H, t, J=5.8 Hz), 3.88 (2H, t, J=6.4 Hz), 4.18 (2H, bs), 4.86 (2H, bs), 7.49 (1H, dd, J=1.8, 8.8 Hz), 7.75 (1H, d, J=1.8 Hz), 8.08 (1H, d, J=8.8 Hz).

(5) 6-Bromo-4-butoxy-3-chloromethyl-2-neopentyl-1(2H)-isoquinolinone (synthesized according to the method similar to that in Example 4 (5))

$^1$H-NMR(CDCl$_3$) δ: 0.98 (9H, s), 1.05 (3H, t, J=7.3 Hz), 1.52–1.70 (2H, m), 1.82–1.95 (2H, m), 3.94 (2H, t, J=6.4 Hz), 4.18 (2H, bs), 4.86 (2H, bs), 7.67 (1H, dd, J=1.8, 8.8 Hz), 7.87 (1H, d, J=1.8 Hz), 8.28 (1H, d, J=8.8 Hz).

(6) 2-{(6-Bromo-4-butoxy-2-neopentyl-1-oxo-1,2-dihydro-3-isoquinolinyl)methyl}-1H-isoindole-1,3(2H)-dione (synthesized according to the method similar to that in Example 4 (6))

Melting point 134–136° C. Elemental analysis for $C_{27}H_{29}N_2O_4Br$ Calculated: C, 61.72; H, 5.56; N, 5.33. Found: C, 61.92; H, 5.49; N, 5.32. $^1$H-NMR(CDCl$_3$) δ: 1.02 (9H, s), 1.02 (3H, t, J=7.3 Hz), 1.46–1.65 (2H, m), 1.82–1.96 (2H, m), 4.01 (2H, t, J=6.8 Hz), 4.05 (2H, bs), 5.07 (2H, s), 7.58 (1H, dd, J=2.0, 8.6 Hz), 7.60–7.84 (4H, m), 7.87 (1H, d, J=2.0 Hz), 8.25 (1H, d, J=8.6 Hz).

(7) Tert-butyl(6-bromo-4-butoxy-2-neopentyl-1-oxo-1,2-dihydro-3-isoquinolinyl)methylcarbamate (synthesized according to the method similar to that in Example 1 (6))

Melting point 130–131° C. Elemental analysis for $C_{24}H_{35}N_2O_4Br$ Calculated: C, 58.18; H, 7.12; N, 5.65. Found: C, 58.50; H, 7.09; N, 5.56. $^1$H-NMR(CDCl$_3$) δ: 0.99 (9H, s), 1.04 (3H, t, J=7.4 Hz), 1.45 (9H, s), 1.46–1.68 (2H, m), 1.80–1.93 (2H, m), 3.85 (2H, t, J=6.4 Hz), 4.14 (2H, bs), 4.56 (2H, d, J=5.4 Hz), 4.71 (1H, bs), 7.58 (1H, dd, J=1.8, 8.4 Hz), 7.82 (1H, d, J=1.8 Hz), 8.24 (1H, d, J=8.4 Hz).

(8) 3-(Aminomethyl)-6-bromo-4-butoxy-2-neopentyl-1(2H)-isoquinolinone hydrochloride (synthesized according to the method similar to that in Example 1 (7))

Melting point 114–115° C. Elemental analysis for $C_{19}H_{28}N_2O_2BrCl$ Calculated: C, 52.85; H, 6.54; N, 6.49. Found: C, 52.60; H, 6.62; N, 6.44. $^1$H-NMR(DMSO-d$_6$) δ: 0.90 (9H, s), 1.00 (3H, t, J=7.4 Hz), 1.46–1.64 (2H, m), 1.77–1.90 (2H, m), 3.94 (2H, t, J=6.0 Hz), 4.12 (2H, bs), 4.24 (2H, s), 7.79 (1H, dd, J=1.8, 8.4 Hz), 7.87 (1H, d, J=1.8 Hz), 8.19 (1H, d, J=8.4 Hz), 8.52 (3H, bs).

Example 84

Methyl 3-(aminomethyl)-4-butoxy-2-neopentyl-1-oxo-1,2-dihydro-6-isoquinolinecarboxylate hydrochloride (1) Methyl 4-butoxy-3-{{(tert-butoxycarbonyl)amino}methyl}-2-neopentyl-1-oxo-1,2-dihydro-6-isoquinolinecarboxylate (synthesized according to the method similar to that in Example 75 (1))

Elemental analysis for $C_{26}H_{38}N_2O_6$ Calculated: C, 65.80; H, 8.07; N, 5.90. Found: C, 66.03; H, 8.33; N, 6.05. $^1$H-NMR(CDCl$_3$) δ: 1.00 (9H, s), 10.6 (3H, t, J=7.4 Hz), 1.46 (9H, S), 1.53–1.71 (2H, m), 1.83–1.97 (2H, m), 3.90 (2H, t, J=6.4 Hz), 3.99 (3H, s), 4.14 (2H, bs), 4.59 (2H, d, J=5.4 Hz), 4.79 (1H, bs), 8.06 (1H, dd, J=1.7, 8.4 Hz), 8.38 (1H, d, J=1.7 Hz), 8.43 (1H, d, J=8.4 Hz).

(2) Methyl 3-(aminomethyl)-4-butoxy-2-neopentyl-1-oxo-1,2-dihydro-6-isoquinolinecarboxylate hydrochloride (synthesized according to the method similar to that in Example 1 (7))

Melting point 123–124° C. Elemental analysis for $C_{21}H_{31}N_2O_4Cl$ Calculated: C, 61.38; H, 7.60; N, 6.82. Found: C, 61.08; H, 7.82; N, 6.82. $^1$H-NMR(DMSO-$d_6$) δ: 0.92 (9H, s), 1.02 (3H, t, J=7.3 Hz), 1.55–1.66 (2H, m), 1.79–1.91 (2H, m), 3.95 (3H, s), 3.97 (2H, t, J=6.2 Hz), 4.14 (2H, bs), 4.28 (2H, s), 8.11 (1H, dd, J=1.6, 8.6 Hz), 8.34 (1H, d, J=1.6 Hz), 8.40 (1H, d, J=8.6 Hz), 8.56 (3H, bs).

Example 85

3-(Aminomethyl)-4-butoxy-2-neopentyl-1-oxo-1,2-dihydro-6-isoquinolinecarboxylic acid hydrochloride (1) 4-Butoxy-3-{{(tert-butoxycarbonyl)amino}methyl}-2-neopentyl-1-oxo-1,2-dihydro-6-isoquinolinecarboxylic acid (synthesized according to the method similar to that in Example 76 (1))

Melting point 130–131° C. Elemental analysis for $C_{25}H_{36}N_2O_6$ Calculated: C, 65.20; H, 7.88; N, 6.08. Found: C, 64.92; H, 7.88; N, 6.04. $^1$H-NMR(CDCl$_3$) δ: 0.99 (9H, s), 1.08 (3H, t, J=7.3 Hz), 1.50 (9H, S), 1.56–1.73 (2H, m), 1.85–1.99 (2H, m) 3.90 (2H, t, J=6.2 Hz), 4.14 (2H, bs), 4.61 (2H, d, J=5.2 Hz), 5.64 (1H, bs), 8.31 (1H, d, J=8.4 Hz), 8.28–8.33 (2H, m).

(2) 3-(Aminomethyl)-4-butoxy-2-neopentyl-1-oxo-1,2-dihydro-6-isoquinolinecarboxylic acid hydrochloride (synthesized according to the method similar to that in Example 1 (7))

Melting point 255–257° C. Elemental analysis for $C_{20}H_{29}N_2O_4Cl$ Calculated: C, 60.52; H, 7.36; N, 7.06. Found: C, 60.42; H, 7.35; N, 7.01. $^1$H-NMR(DMSO-$d_6$) δ: 0.92 (9H, s), 1.01 (3H, t, J=7.4 Hz), 1.54–1.66 (2H, m), 1.79–1.92 (2H, m), 3.97 (2H, t, J=6.3 Hz), 4.13 (2H, bs), 4.28 (2H, s), 8.09 (1H, dd, J=1.5, 8.4 Hz), 8.33 (1H, bs), 8.34 (1H, d, J=1.5 Hz), 8.38 (1H, d, J=8.4 Hz), 8.60 (3H, bs).

Example 86

3-(Aminomethyl)-4-butoxy-2-neopentyl-1-oxo-1,2-dihydro-6-isoquinolinecarboxamide hydrochloride (1) Tert-butyl{(6-aminocarbonyl)-4-butoxy-2-neopentyl-1-oxo-1,2-dihydro-3-isoquinolinyl}methylcarbamate (synthesized according to the method similar to that in Example 77 (1))

Melting point 172–173° C. Elemental analysis for $C_{25}H_{37}N_3O_5$ ½(i-Pr)$_2$O Calculated: C, 65.86; H, 8.49; N, 8.23. Found: C, 65.53; H, 8.75; N, 8.17. $^1$H-NMR(CDCl$_3$) δ: 0.99 (9H, s) 1.04 (3H, t, J=7.2 Hz), 1.46 (9H, S), 1.47–1.68 (2H, m), 1.81–1.95 (2H, m), 3.71 (2H, t, J=6.2 Hz), 4.14 (2H, bs), 4.58 (2H, d, J=5.6 Hz), 4.97 (1H, bs), 5.91 (1H, bs), 6.39 (1H, bs), 7.75 (1H, dd, J=1.6, 8.4 Hz), 8.12 (1H, d, J=8.4 Hz), 8.36 (1H, d, J=8.4 Hz).

(2) 3-(Aminomethyl)-4-butoxy-2-neopentyl-1-oxo-1,2-dihydro-6-isoquinolinecarboxamide hydrochloride (synthesized according to the method similar to that in Example 1 (7))

Melting point 237–238° C. Elemental analysis for $C_{20}H_{30}N_3O_3Cl$ ½H$_2$O Calculated: C, 59.32; H, 7.72; N 10.38. Found: C, 59.45; H, 7.63; N, 10.20. $^1$H-NMR (DMSO-$d_6$) δ: 0.91 (9H, s), 1.00 (3H, t, J=7.4 Hz), 1.48–1.67 (2H, m), 1.80–1.92 (2H, m), 3.98 (2H, t, J=6.4 Hz), 4.12 (2H, bs), 4.26 (2H, s), 7.70 (1H, s), 8.04 (1H, dd, J=1.2, 8.2 Hz), 8.22 (1H, d, J=1.2 Hz), 8.33 (1H, d, J=8.2 Hz), 8.37 (1H, s), 8.58 (3H, bs).

Example 87

3-(Aminomethyl)-4-butoxy-2-neopentyl-1-oxo-1,2-dihydro-6-isoquinolinecarbonitrile hydrochloride (1) Tert-butyl(4-butoxy-6-cyano-2-neopentyl-1-oxo-1,2-dihydro-3-isoquinolinyl)methylcarbamate (synthesized according to the method similar to that in Example 78 (7))

Melting point 162–163° C. Elemental analysis for $C_{25}H_{35}N_3O_4$ Calculated: C, 68.00; H, 7.99; N, 9.52. Found: C, 67.97; H, 8.13; N, 9.44. $^1$H-NMR(CDCl$_3$) δ: 1.00 (9H, s), 1.05 (3H, t, J=7.3 Hz), 1.45 (9H, s), 1.53–1.68 (2H, m), 1.82–1.90 (2H, m), 3.86 (2H, t, J=6.6 Hz), 4.17 (2H, bs), 4.58 (2H, d, J=5.4 Hz), 4.70 (1H, bs), 7.68 (1H, dd, J=1.6, 8.8 Hz), 8.00 (1H, d, J=1.6 Hz), 8.49 (1H, d, J=8.2 Hz)

(2) 3-(Aminomethyl)-4-butoxy-2-neopentyl-1-oxo-1,2-dihydro-6-isoquinolinecarbonitrile hydrochloride (synthesized according to the method similar to that in Example 1 (7))

Elemental analysis for $C_{20}H_{28}N_3O_2Cl$ ¼H$_2$O Calculated: C, 62.81; H, 7.51; N, 10.99. Found: C, 62.98; H, 7.75; N, 10.95. $^1$H-NMR(DMSO-$d_6$) δ: 0.91 (9H, s), 1.00 (3H, t, J=7.1 Hz), 1.46–1.64 (2H, m), 1.80–1.92 (2H, m), 3.97 (2H, t, J=6.4 Hz), 4.14 (2H, bs), 4.27 (2H, bs), 7.97 (1H, dd, J=1.2, 8.0 Hz), 8.23 (1H, d, J=1.2 Hz), 8.41 (1H, d, J=8.0 Hz), 8.68 (3H, bs).

Example 88

N-{3-(Aminomethyl)-4-butoxy-2-isobutyl-1-oxo-1,2-dihydro-6-isoquinolinyl}acetamide hydrochloride (1) A solution of tert-butyl(6-amino-4-butoxy-2-isobutyl-1-oxo-1,2-dihydro-3-isoquinolinyl)methylcarbamate (synthesized according to the method similar to that in Example 82 (2)) (0.21 g, 0.5 mmol) and acetyl chloride (0.04 ml, 0.6 mmol) in N,N-dimethylacetamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was recrystallized from ethyl acetate-diisopropyl ether to give tert-butyl{6-(acetylamino)-4-butoxy-2-isobutyl-1-oxo-1,2-dihydro-3-isoquinolinyl}methylcarbamate (0.19 g, 80.8%) as crystals.

Melting point 174–175° C. Elemental analysis for $C_{25}H_{37}N_3O_5$ Calculated: C, 65.34; H, 8.11; N, 9.14. Found: C, 65.32; H, 8.05; N, 9.21. $^1$H-NMR(CDCl$_3$) δ: 0.95 (6H, d, J=6.6 Hz), 1.02 (3H, t, J=7.4 Hz), 1.47 (9H, S), 1.47–1.65 (2H, m), 1.81–1.95 (2H, m), 2.09–2.20 (1H, m), 2.26 (3H, s), 3.88 (2H, t, J=6.6 Hz), 3.98 (2H, d, J=7.4 Hz), 4.51 (2H, d, J=5.6 Hz), 4.82 (1H, bs), 7.35 (1H, d, J=8.0 Hz), 7.71 (1H, bs), 8.17 (1H, s), 8.32 (1H, d, J=8.0 Hz).

(2) N-{3-(Aminomethyl)-4-butoxy-2-isobutyl-1-oxo-1,2-dihydro-6-isoquinolinyl}acetamide hydrochloride (synthesized according to the method similar to that in Example 1 (7))

Melting point 176–177° C. Elemental analysis for $C_{20}H_{30}N_3O_3Cl$ H$_2$O Calculated: C, 58.03; H, 7.79; N, 10.15. Found: C, 58.26; H, 8.11; N, 10.08. $^1$H-NMR (DMSO-$d_6$) δ: 0.87 (6H, d, J=6.6 Hz), 0.99 (3H, t, J=7.3

Hz), 1.50–1.62 (2H, m), 1.79–2.04 (3H, m), 2.14 (3H, s), 3.91 (2H, t, J=6.8 Hz), 3.93 (2H, d, J=7.0 Hz), 4.16 (2H, d, J=5.4 Hz), 7.70 (1H, dd, J=2.0, 8.8 Hz), 8.18 (1H, d, J=8.8 Hz), 8.27 (1H, d, J=2.0 Hz), 8.56 (3H, bs), 10.59 (1H, s).

Example 89

N-{3-(Aminomethyl)-4-butoxy-2-isobutyl-1-oxo-1,2-dihydro-6-isoquinolinyl}propanamide hydrochloride (1) tert-butyl{4-butoxy-2-isobutyl-1-oxo-6-(propionylamino)-1,2-dihydro-3-isoquinolinyl} methylcarbamate (synthesized according to the method similar to that in Example 88 (1))

$^1$H-NMR(CDCl$_3$) δ: 0.95 (6H, d, J=7.0 Hz), 1.01 (3H, t, J=7.2 Hz), 1.28 (3H, t, J=7.6 Hz), 1.46 (9H, S), 1.47–1.67 (2H, m), 1.80–1.94 (2H, m), 2.09–2.27 (1H, m), 2.48 (2H, q, J=7.6 Hz), 3.88 (2H, t, J=6.4 Hz), 3.98 (2H, d, J=7.4 Hz), 4.51 (2H, d, J=5.0 Hz), 4.83 (1H, bs), 7.37 (1H, dd, J=1.8, 8.8 Hz), 7.69 (1H, bs), 8.15 (1H, d, J=1.8 Hz), 8.31 (1H, d, J=8.8 Hz).

(2) N-{3-(Aminomethyl)-4-butoxy-2-isobutyl-1-oxo-1,2-dihydro-6-isoquinolinyl}propanamide hydrochloride (synthesized according to the method similar to that in Example 1 (7))

$^1$H-NMR(DMSO-d$_6$) δ: 0.87 (6H, d, J=7.0 Hz), 1.00 (6H, m), 1.46–1.64 (2H, m), 1.72–2.14 (3H, m), 2.41–2.50 (2H, m), 3.91 (4H, bs), 4.16 (2H, s), 7.72 (1H, d, J=9.0 Hz), 8.18 (1H, d, J=9.0 Hz), 8.27 (1H, s), 8.55 (3H, bs), 10.49 (1H, s).

Example 90

N-{3-(Aminomethyl)-4-butoxy-2-isobutyl-1-oxo-1,2-dihydro-6-isoquinolinyl}-2-methylpropanamide hydrochloride (1) Tert-butyl{4-butoxy-2-isobutyl-6-(isobutyrylamino)-1-oxo-1,2-dihydro-3-isoquinolinyl}methylcarbamate (synthesized according to the method similar to that in Example 88 (1))

$^1$H-NMR(CDCl$_3$) δ: 0.95 (6H, d, J=7.0 Hz), 1.02 (3H, t, J=7.2 Hz), 1.29 (6H, d, J=7.0 Hz), 1.46 (9H, S), 1.47–1.66 (2H, m), 1.80–1.91 (2H, m), 2.09–2.20 (1H, m), 2.53–2.66 (1H, m), 3.89 (2H, t, J=6.6 Hz), 3.98 (2H, d, J=7.4 Hz), 4.51 (2H, d, J=5.6 Hz), 4.79 (1H, bs), 7.41 (1H, dd, J=1.8, 8.8 Hz), 7.62 (1H, bs), 8.15 (1H, d, J=1.8 Hz), 8.32 (1H, d, J=8.8 Hz).

(2) N-{3-(Aminomethyl)-4-butoxy-2-isobutyl-1-oxo-1,2-dihydro-6-isoquinolinyl}-2-methylpropanamide hydrochloride (synthesized according to the method similar to that in Example 1 (7))

Melting point 181–183° C. $^1$H-NMR(DMSO-d$_6$) δ: 0.88 (6H, d, J=6.2 Hz), 1.00 (3H, t, J=7.4 Hz), 1.14 (6H, d, J=6.6 Hz), 1.48–1.64 (2H, m), 1.83–2.12 (3H, m), 2.62–2.78 (1H, m), 3.92–3.95 (4H, m), 4.16 (2H, bs), 7.76 (1H, d, J=8.8 Hz), 8.18 (1H, d, J=8.8 Hz), 8.27 (1H, s), 8.57 (3H, bs), 10.47 (1H, s).

Example 91

N-{3-(Aminomethyl)-4-butoxy-2-isobutyl-1-oxo-1,2-dihydro-6-isoquinolinyl}benzamide hydrochloride (1) Tert-butyl{4-butoxy-6-(benzoylamino)-2-isobutyl-1-oxo-1,2-dihydro-3-isoquinolinyl}methylcarbamate (synthesized according to the method similar to that in Example 88 (1))

$^1$H-NMR(CDCl$_3$) δ: 0.95 (6H, d, J=6.6 Hz), 1.02 (3H, t, J=7.4 Hz), 1.47 (9H, S), 1.48–1.68 (2H, m), 1.82–1.96 (2H, m), 2.07–2.23 (1H, m), 3.92 (2H, t, J=6.8 Hz), 3.98 (2H, d, J=8.8 Hz), 4.52 (2H, d, J=5.4 Hz), 4.89 (1H, bs), 7.45–7.62 (4H, m), 7.90–7.94 (2H, m), 8.25 (1H, bs), 7.56 (1H, bs), 8.27 (1H, d, J=1.8 Hz), 8.32 (1H, d, J=8.8 Hz).

(2) N-{3-(Aminomethyl)-4-butoxy-2-isobutyl-1-oxo-1,2-dihydro-6-isoquinolinyl}benzamide hydrochloride (synthesized according to the method similar to that in Example 1 (7))

$^1$H-NMR(DMSO-d$_6$) δ: 0.89 (6H, d, J=6.6 Hz), 1.01 (3H, t, J=7.3 Hz), 1.49–1.67 (2H, m), 1.83–2.06 (3H, m), 3.93–3.98 (4H, m), 4.19 (2H, s), 7.54–7.68 (3H, m), 7.95–8.03 (3H, m), 8.25 (1H, d, J=8.8 Hz), 8.43 (1H, d, J=1.8 Hz), 8.58 (3H, bs), 10.77 (1H, s).

Example 92

N-{3-(Aminomethyl)-4-butoxy-2-isobutyl-1-oxo-1,2-dihydro-6-isoquinolinyl}cyclopentanecarboxamide hydrochloride (1) Tert-butyl{4-butoxy-6-{(cyclopentylcarbonyl)amino}-2-isobutyl-1-oxo-1,2-dihydro-3-isoquinolinyl} methylcarbamate (synthesized according to the method similar to that in Example 88 (1))

$^1$H-NMR(CDCl$_3$) δ: 0.95 (6H, d, J=7.0 Hz), 1.02 (3H, t, J=7.3 Hz), 1.46 (9H, S), 1.47–1.74 (4H, m), 1.78–2.20 (9H, m), 2.67–2.80 (1H, m), 3.89 (2H, t, J=6.6 Hz), 3.98 (2H, d, J=7.6 Hz), 4.51 (2H, d, J=5.4 Hz), 4.78 (1H, bs), 7.42 (1H, dd, J=2.2, 8.8 Hz), 7.56 (1H, bs), 8.12 (1H, d, J=2.2 Hz), 8.32 (1H, d, J=8.8 Hz).

(2) N-{3-(Aminomethyl)-4-butoxy-2-isobutyl-1-oxo-1,2-dihydro-6-isoquinolinyl}cyclopentanecarboxamide (synthesized according to the method similar to that in Example 1(7))

$^1$H-NMR(DMSO-d$_6$) δ: 0.87 (6H, d, J=6.2 Hz), 0.99 (3H, t, J=7.1 Hz), 1.54–2.11 (11H, m), 2.79–2.92 (1H, m), 3.91–3.95 (4H, m), 4.16 (2H, s), 7.75 (1H, d, J=8.8 Hz), 8.18 (1H, d, J=8.8 Hz), 8.25 (1H, s), 8.55 (3H, bs), 10.49 (1H, s).

Example 93

N-{3-(Aminomethyl)-4-butoxy-2-isobutyl-1-oxo-1,2-dihydro-6-isoquinolinyl}methanesulfonamide hydrochloride (1) Tert-butyl{4-butoxy-2-isobutyl-6-{(methylsulfonyl)amino}-1-oxo-1,2-dihydro-3-isoquinolinyl}methylcarbamate (synthesized according to the method similar to that in Example 88 (1))

$^1$H-NMR(CDCl$_3$) δ: 0.95 (6H, d, J=6.6 Hz), 1.02 (3H, t, J=7.4 Hz), 1.47 (9H, s), 1.47–1.64 (2H, m), 1.79–1.94 (2H, m), 2.10–2.23 (1H, m), 3.11 (3H, s), 3.86 (2H, t, J=6.6 Hz), 3.99 (2H, d, J=7.8 Hz), 4.51 (2H, d, J=5.4 Hz), 4.77 (1H, bs), 7.23 (1H, dd, J=2.0, 8.6 Hz), 7.31 (1H, s), 7.56 (1H, d, J=2.0 Hz), 8.38 (1H, d, J=8.6 Hz).

(2) N-{3-(Aminomethyl)-4-butoxy-2-isobutyl-1-oxo-1,2-dihydro-6-isoquinolinyl}methanesulfonamide (synthesized according to the method similar to that in Example 1 (7))

$^1$H-NMR(DMSO-d$_6$) δ: 0.87 (6H, d, J=6.6 Hz), 0.99 (3H, t, J=7.8 Hz), 1.45–1.64 (2H, m), 1.78–2.09 (3H, m), 3.13 (3H, s), 3.88–3.94 (4H, m), 4.17 (2H, bs), 7.40 (1H, dd, J=2.0, 8.8 Hz), 7.60 (1H, d, J=2.0 Hz), 8.21 (1H, d, J=8.8 Hz), 8.58 (3H, bs), 10.57 (1H, s).

Example 94

N-{3-(Aminomethyl)-4-butoxy-2-isobutyl-1-oxo-1,2-dihydro-6-isoquinolinyl}benzenesulfonamide hydrochloride (1) Tert-butyl{4-butoxy-2-isobutyl-1-oxo-6-{(phenylsulfonyl)amino}-1,2-dihydro-3-isoquinolinyl}methylcarbamate (synthesized according to the method similar to that in Example 88 (1))

Melting point 160–161° C. Elemental analysis for $C_{29}H_{39}N_3O_6S$ Calculated: C, 62.45; H, 7.05; N, 7.53. Found: C, 62.35; H, 6.97; N, 7.50. $^1$H-NMR(CDCl$_3$) δ: 0.93 (6H, d, J=6.6 Hz) 1.02 (3H, t, J=7.3 Hz), 1.46 (9H, s), 1.47–1.63 (2H, m), 1.72–1.90 (2H, m), 2.07–2.20 (1H, m), 3.76 (2H, t, J=6.6 Hz), 3.96 (2H, d, J=7.6 Hz), 4.48 (2H, d, J=5.6 Hz), 4.78 (1H, bs), 7.14 (1H, d, J=8.4 Hz), 7.41–7.58 (4H, m), 7.81–7.99 (3H, m), 8.25 (1H, dd, J=1.4, 8.4 Hz).

(2) N-{3-(Aminomethyl)-4-butoxy-2-isobutyl-1-oxo-1,2-dihydro-6-isoquinolinyl}benzenesulfonamide (synthesized according to the method similar to that in Example 1 (7))

Melting point 166–167° C. Elemental analysis for $C_{24}H_{32}N_3O_4ClS$ ¼$H_2O$ Calculated: C, 57.82; H, 6.57; N, 8.43. Found: C, 57.83; H, 6.49; N, 8.26. $^1$H-NMR(DMSO-d$_6$) δ: 0.84 (6H, d, J=7.4 Hz), 1.01 (3H, t, J=7.4 Hz), 1.43–1.62 (2H, m), 1.75–1.99 (3H, m), 3.76 (2H, t, J=6.6 Hz), 3.89 (2H, d, J=6.8 Hz), 4.11 (2H, bs), 7.35 (1H, dd, J=2.0, 8.6 Hz), 7.53–7.65 (3H, m), 7.83–7.88 (2H, m), 8.13 (1H, d, J=8.6 Hz), 8.52 (3H, bs), 11.18 (1H, s).

Example 95

2-{{3-(Aminomethyl)-4-butoxy-2-neopentyl-1-oxo-1,2-dihydro-6-isoquinolinyl}oxy}acetamide hydrochloride (1) A solution of tert-butyl(4-butoxy-6-hydroxy-2-neopentyl-1-oxo-1,2-dihydro-3-isoquinolinyl)methylcarbamate (Example 59 (1)) (0.43 g, 1 mmol), iodoacetamide (0.22 g, 1.2 mmol) and 1,8-diazabicyclo[5.4.0]-7-undecene (0.18 ml, 1.2 mmol) in N,N-dimethylformamide (10 ml) was stirred at 70° C. for 12 h. The reaction mixture was poured into water and extracted with ethyl acetate. The extract was washed with brine, dried over anhydrous magnesium sulfate and concentrated under reduced pressure. The residue was recrystallized from ethyl acetate-diisopropyl ether to give tert-butyl{6-(2-amino-2-oxoethyl)-4-butoxy-2-neopentyl-1-oxo-1,2-dihydro-3-isoquinolinyl}-methylcarbamate (0.29 g, 60.4%) as crystals.

Melting point 114–115° C. Elemental analysis for $C_{26}H_{39}N_3O_6$ Calculated: C, 63.78; H, 8.03; N, 8.58. Found: C, 63.61; H, 7.91; N, 8.43. $^1$H-NMR(CDCl$_3$) δ: 0.99 (9H, s), 1.04 (3H, t, J=7.0 Hz), 1.43 (9H, S), 1.45–1.67 (2H, m), 1.79–1.90 (2H, m), 3.85 (2H, t, J=6.6 Hz), 4.14 (2H, bs), 4.56 (2H, d, J=5.4 Hz), 4.57 (1H, bs), 7.07–7.12 (2H, m), 8.36 (1H, d, J=9.4 Hz).

(2) 2-{{3-(Aminomethyl)-4-butoxy-2-neopentyl-1-oxo-1,2-dihydro-6-isoquinolinyl}oxy}acetamide hydrochloride (synthesized according to the method similar to that in Example 1 (7))

Melting point 233–235° C. Elemental analysis for $C_{21}H_{32}N_3O_4Cl$ ½$H_2O$ Calculated: C, 57.99; H, 7.65; N, 9.66. Found: C, 58.18; H, 7.68; N, 9.63. $^1$H-NMR(DMSO-d$_6$) δ: 0.89 (9H, s), 1.00 (3H, t, J=7.3 Hz), 1.50–1.65 (2H, m), 1.77–1.91 (2H, m), 3.92 (2H, t, J=6.4 Hz), 4.07 (2H, bs), 4.22 (2H, d, J=4.4 Hz), 4.64 (2H, s), 7.07 (1H, d, J=2.6 Hz), 7.22 (1H, dd, J=2.6, 8.8 Hz), 7.46 (1H, bs), 7.73 (1H, bs), 8.20 (1H, d, J=8.8 Hz), 8.54 (3H, bs).

Example 96

3-(Aminomethyl)-4-butoxy-6-isopropoxy-2-neopentyl-1(2H)-isoquinolinone hydrochloride (1) Tert-butyl(4-butoxy-6-isopropoxy-2-neopentyl-1-oxo-1,2-dihydro-3-isoquinolinyl)methylcarbamate (synthesized according to the method similar to that in Example 95 (1))

Melting point 130–130.5° C. Elemental analysis for $C_{27}H_{42}N_2O_5$ Calculated: C, 68.32; H, 8.92; N, 5.90. Found: C, 68.28; H, 8.75; N, 5.99. $^1$H-NMR(CDCl$_3$) δ: 0.99 (9H, s), 1.03 (3H, t, J=7.4 Hz), 1.41 (6H, d, J=5.8 Hz), 1.45 (9H, s), 1.46–1.65 (2H, m), 1.79–1.93 (2H, m), 3.86 (2H, t, J=6.4 Hz), 4.14 (2H, bs), 4.55 (2H, d, J=4.8 Hz), 4.64–4.76 (2H, m), 7.00–7.04 (2H, m), 8.31 (1H, d, J=9.6 Hz).

(2) 3-(Aminomethyl)-4-butoxy-6-isopropoxy-2-neopentyl-1(2H)-isoquinolinone hydrochloride (synthesized according to the method similar to that in Example 1 (7))

Melting point 181–182° C. Elemental analysis for $C_{22}H_{35}N_2O_3Cl$ Calculated: C, 64.29; H, 8.58; N, 6.82. Found: C, 64.10; H, 8.80; N, 6.78. $^1$H-NMR(DMSO-d$_6$) δ: 0.90 (9H, s), 1.00 (3H, t, J=7.1 Hz), 1.35 (6H, d, J=6.2 Hz), 1.51–1.62 (2H, m), 1.77–1.90 (2H, m), 3.93 (2H, t, J=6.3 Hz), 4.07 (2H, bs), 4.22 (2H, bs), 4.74–4.86 (1H, m), 7.05 (1H, d, J=2.4 Hz), 7.16 (1H, dd, J=2.4, 8.8 Hz), 8.17 (1H, d, J=8.8 Hz), 8.52 (3H, bs).

Example 97

3-(Aminomethyl)-4-butoxy-2-neopentyl-6-(2,2,2-trifluoroethoxy)-1(2H)-isoquinolinone hydrochloride (1) Tert-butyl{4-butoxy-2-neopentyl-6-(2,2,2-trifluoroethoxy)-1-oxo-1,2-dihydro-3-isoquinolinyl}methylcarbamate (synthesized according to the method similar to that in Example 95 (1))

Melting point 154.5–155° C. Elemental analysis for $C_{26}H_{37}N_2O_5F_3$ Calculated: C, 60.69; H, 7.25; N, 5.44. Found: C, 60.44; H, 7.16; N, 5.48. $^1$H-NMR(CDCl$_3$) δ: 0.99 (9H, s), 1.04 (3H, t, J=7.0 Hz), 1.45 (9H, s), 1.46–1.64 (2H, m), 1.80–1.90 (2H, m), 3.86 (2H, t, J=6.6 Hz), 4.11 (2H, bs), 4.48 (2H, q, J=8.0 Hz), 4.56 (2H, d, J=5.6 Hz), 4.71 (1H, bs), 7.09–7.13 (2H, m), 8.37 (1H, d, J=8.0 Hz).

(2) 3-(Aminomethyl)-4-butoxy-2-neopentyl-6-(2,2,2-trifluoroethoxy)-1(2H)-isoquinolinone hydrochloride (synthesized according to the method similar to that in Example 1 (7))

Melting point 145.5–146° C. Elemental analysis for $C_{21}H_{30}N_2O_3ClF_3$ ½$H_2O$ Calculated: C, 54.84; H, 6.79; N, 6.09. Found: C, 54.75; H, 6.77; N, 6.22. $^1$H-NMR(DMSO-d$_6$) δ: 0.90 (9H, s), 0.99 (3H, t, J=7.3 Hz), 1.47–1.65 (2H, m), 1.78–1.89 (2H, m), 3.95 (2H, t, J=6.4 Hz), 4.08 (2H, bs), 4.24 (2H, bs), 5.02 (2H, q, J=8.8 Hz), 7.18 (1H, d, J=2.6 Hz), 7.32 (1H, dd, J=2.6, 8.8 Hz), 8.24 (1H, d, J=8.8 Hz), 8.52 (3H, bs).

Example 98

3-(Aminomethyl)-4-butoxy-6-(cyclopropylmethoxy)-2-neopentyl-1(2H)-isoquinolinone hydrochloride (1) Tert-butyl{4-butoxy-6-(cyclopropylmethoxy)-2-neopentyl-1-oxo-1,2-dihydro-3-isoquinolinyl}methylcarbamate (synthesized according to the method similar to that in Example 95 (1))

Melting point 154–155° C. Elemental analysis for $C_{28}H_{42}N_2O_5$ ½$H_2O$ Calculated: C, 67.85; H, 8.74; N, 5.65. Found: C, 68.08; H, 8.65; N, 5.47. $^1$H-NMR(CDCl$_3$) δ: 0.36–0.42 (2H, m), 0.65–0.75 (2H, m), 0.99 (9H, s), 1.03 (3H, t, J=7.4 Hz), 1.22–1.37 (1H, m), 1.45 (9H, s), 1.52–1.68 (2H, m), 1.78–1.93 (2H, m), 3.86 (2H, t, J=6.4 Hz), 3.92 (2H, d, J=6.8 Hz), 4.10 (2H, bs), 4.55 (2H, d, J=5.2 Hz), 4.63 (1H, bs), 7.04–7.10 (2H, m), 8.30–8.34 (1H, m).

(2) 3-(Aminomethyl)-4-butoxy-6-(cyclopropylmethoxy)-2-neopentyl-1(2H)-isoquinolinone hydrochloride (synthesized according to the method similar to that in Example 1 (7))

Melting point 203–205° C. Elemental analysis for $C_{23}H_{35}N_2O_3Cl$ Calculated: C, 65.31; H, 8.34; N, 6.62. Found: C, 65.23; H, 8.25; N, 6.71. $^1$H-NMR(DMSO-d$_6$) δ: 0.34–0.42 (2H, m), 0.58–0.67 (2H, m), 0.89 (9H, s), 0.99 (3H, t, J=7.3 Hz), 1.23–1.33 (1H, m), 1.52–1.63 (2H, m), 1.77–1.87 (2H, m), 3.93 (2H, t, J=6.2 Hz), 3.99 (2H, d, J=7.0 Hz), 4.03 (2H, bs), 4.23 (2H, s), 7.06 (1H, d, J=2.4 Hz), 7.19 (1H, dd, J=2.4, 9.0 Hz), 8.18 (1H, d, J=9.0 Hz), 8.50 (3H, bs).

Example 99

3-(Aminomethyl)-4-butoxy-2-neopentyl-6-(2-propynyloxy)-1(2H)-isoquinolinone hydrochloride (1) Tert-butyl{4-butoxy-2-neopentyl-1-oxo-6-(2-propynyloxy)-1,2-dihydro-3-isoquinolinyl}methylcarbamate (synthesized according to the method similar to that in Example 95 (1))

$^1$H-NMR(CDCl$_3$) δ: 0.99 (9H, s), 1.03 (3H, t, J=7.4 Hz), 1.45 (9H, s), 1.53–1.68 (2H, m) 1.80–1.94 (2H, m), 2.57 (1H, t, J=2.2 Hz), 3.87 (2H, t, J=6.4 Hz), 4.10 (2H, bs), 4.56 (2H, d, J=4.8 Hz), 4.63 (1H, bs), 4.82 (2H, d, J=2.2 Hz), 7.11 (1H, dd, J=2.4, 8.8 Hz), 7.19 (1H, d, J=2.4 Hz), 8.35 (1H, d, J=8.8 Hz).

(2) 3-(Aminomethyl)-4-butoxy-2-neopentyl-6-(2propynyloxy)-1(2H)-isoquinolinone hydrochloride (synthesized according to the method similar to that in Example 1 (7)))

Elemental analysis for $C_{22}H_{31}N_2O_3Cl$ ¼$H_2O$ Calculated: C, 64.22; H, 7.72; N, 6.81. Found: C, 64.36; H, 7.73; N, 6.66. $^1$H-NMR(DMSO-d$_6$) δ: 0.90 (9H, s), 1.00 (3H, t, J=7.4 Hz), 1.53–1.64 (2H, m), 1.79–1.91 (2H, m) 3.71 (1H, t, J=2.2 Hz), 3.95 (2H, t, J=6.1 Hz), 4.08 (2H, bs), 4.23 (2H, s), 5.01 (1H, d, J=2.2 Hz), 7.19–7.23 (2H, m), 8.20 (1H, d, J=9.6 Hz), 8.50 (3H, bs).

Example 100

3-(Aminomethyl)-4-butoxy-6-isobutoxy-2-neopentyl-1(2H)-isoquinolinone hydrochloride (1) Tert-butyl(4-butoxy-6-isobutoxy-2-neopentyl-1-oxo-1,2-dihydro-3-isoquinolinyl)methylcarbamate (synthesized according to the method similar to that in Example 95 (1))

$^1$H-NMR(CDCl$_3$) δ: 0.99 (9H, s), 1.04 (3H, t, J=7.2 Hz), 1.06 (6H, d, J=6.4 Hz), 1.45 (9H, s), 1.51–1.69 (2H, m), 1.79–1.93 (2H, m), 2.09–2.22 (1H, m), 3.84 (2H, d, J=6.6 Hz), 3.86 (2H, t, J=6.5 Hz), 4.10 (2H, bs), 4.56 (2H, d, J=5.6 Hz), 4.69 (1H, bs), 7.04–7.08 (2H, m), 8.31 (1H, d, J=9.4 Hz).

(2) 3-(Aminomethyl)-4-butoxy-6-isobutoxy-2-neopentyl-1(2H)-isoquinolinone hydrochloride (synthesized according to the method similar to that in Example 1 (7))

Elemental analysis for $C_{23}H_{37}N_2O_3Cl$ ¼$H_2O$ Calculated: C, 64.32; H, 8.80; N, 6.52. Found: C, 64.31; H, 8.87; N, 6.60. $^1$H-NMR(DMSO-d$_6$) δ: 0.89 (9H, s), 1.00 (3H, t, J=7.0 Hz), 1.02 (6H, d, J=6.6 Hz), 1.50–1.68 (2H, m), 1.77–1.87 (2H, m), 2.03–2.16 (1H, m), 3.92 (2H, d, J=6.6 Hz), 3.93 (2H, t, J=6.2 Hz), 4.04 (2H, bs), 4.23 (2H, s), 7.07 (1H, d, J=2.6 Hz), 7.19 (1H, dd, J=2.6, 8.8 Hz), 8.18 (1H, d, J=8.8 Hz) 8.45 (3H, bs).

Example 101

3-(Aminomethyl)-4-butoxy-6-(cyclopentyloxy)-2-neopentyl-1(2H)-isoquinolinone hydrochloride (1) Tert-butyl{4-butoxy-6-(cyclopentyloxy)-2-neopentyl-1-oxo-1,2-dihydro-3-isoquinolinyl}methylcarbamate (synthesized according to the method similar to that in Example 95 (1))

$^1$H-NMR(CDCl$_3$) δ: 0.99 (9H, s), 1.03 (3H, t, J=7.4 Hz), 1.45 (9H, s), 1.50–1.70 (4H, m), 1.73–1.98 (8H, m), 3.86 (2H, t, J=6.4 Hz), 4.10 (2H, bs), 4.55 (2H, d, J=5.2 Hz), 4.68 (1H, bs), 4.86–4.90 (1H, m), 6.98–7.04 (2H, m), 8.27–8.32 (1H, m).

(2) 3-(Aminomethyl)-4-butoxy-6-(cyclopentyloxy)-2-neopentyl-1(2H)-isoquinolinone hydrochloride (synthesized according to the method similar to that in Example 1 (7))

Elemental analysis for $C_{24}H_{37}N_2O_3Cl$ ¼$H_2O$ Calculated: C, 65.29; H, 8.56; N, 6.34. Found: C, 65.27; H, 8.53; N, 6.18. $^1$H-NMR(DMSO-d$_6$) δ: 0.89 (9H, s), 1.00 (3H, t, J=7.3 Hz), 1.52–2.05 (12H, m), 3.93 (2H, t, J=6.2 Hz), 4.05 (2H, bs), 4.23 (2H, s), 4.99 (1H, bs), 7.04 (1H, d, J=2.4 Hz), 7.13 (1H, dd, J=2.4, 9.0 Hz), 8.16 (1H, d, J=9.0 Hz), 8.51 (3H, bs).

Example 102

3-(Aminomethyl)-4-butoxy-6-(cyclohexylmethoxy)-2-neopentyl-1(2H)-isoquinolinone hydrochloride (1) Tert-butyl{4-butoxy-6-(cyclohexylmethoxy)-2-neopentyl-1-oxo-1,2-dihydro-3-isoquinolinyl}methylcarbamate (synthesized according to the method similar to that in Example 95 (1))

$^1$H-NMR(CDCl$_3$) δ: 0.99 (9H, s), 1.04 (3H, t, J=7.3 Hz), 1.07–1.35 (3H, m), 1.45 (9H, s), 1.51–1.93 (8H, m), 3.83–3.89 (4H, m), 4.10 (2H, bs), 4.55 (2H, d, J=5.2 Hz), 4.63 (1H, bs), 7.03–7.08 (2H, m), 8.31 (1H, d, J=8.4 Hz).

(2) 3-(Aminomethyl)-4-butoxy-6-(cyclohexylmethoxy)-2-neopentyl-1(2H)-isoquinolinone hydrochloride (synthesized according to the method similar to that in Example 1 (7))

Elemental analysis for $C_{26}H_{41}N_2O_3Cl$ Calculated: C, 67.15; H, 8.89; N, 6.02. Found: C, 67.00; H, 8.83; N, 6.03. $^1$H-NMR(DMSO-d$_6$) δ: 0.89 (9H, s), 1.00 (3H, t, J=7.3 Hz), 1.09–1.30 (3H, m), 1.53–1.84 (12H, m), 3.90–3.97 (4H, m), 4.08 (2H, bs), 4.23 (2H, s), 7.06 (1H, d, J=2.3 Hz), 7.18 (1H, dd, J=2.3, 8.8 Hz), 8.18 (1H, d, J=8.8 Hz), 8.47 (3H, bs).

Example 103

3-(Aminomethyl)-4-butoxy-6-(3,3-dimethyl-2-oxobutoxy)-2-neopentyl-1(2H)-isoquinolinone hydrochloride (1) Tert-butyl{4-butoxy-6-(3,3-dimethyl-2-oxobutoxy)-2-neopentyl-1-oxo-1,2-dihydro-3-isoquinolinyl}methylcarbamate (synthesized according to the method similar to that in Example 95 (1))

$^1$H-NMR(CDCl$_3$) δ: 0.98 (9H, s), 1.03 (3H, t, J=7.2 Hz), 1.29 (9H, s), 1.45 (9H, s), 1.51–1.65 (2H, m), 1.76–1.87 (2H, m), 3.87 (2H, t, J=6.4 Hz), 4.10 (2H, bs), 4.54 (2H, d, J=5.2 Hz), 4.69 (1H, bs), 5.01 (2H, s), 6.98 (1H, d, J=2.6 Hz), 7.05 (1H, dd, J=2.6, 8.8 Hz), 8.33 (1H, d, J=8.8 Hz).

(2) 3-(Aminomethyl)-4-butoxy-6-(3,3-dimethyl-2-oxobutoxy)-2-neopentyl-1(2H)-isoquinolinone hydrochloride (synthesized according to the method similar to that in Example 1 (7))

Elemental analysis for C$_{25}$H$_{39}$N$_2$O$_4$Cl ¼H$_2$O Calculated: C, 63.68; H, 8.44; N, 5.94. Found: C, 63.64; H, 8.32; N, 5.99. $^1$H-NMR(DMSO-d$_6$) δ: 0.89 (9H, s), 0.98 (3H, t, J=7.2 Hz), 1.21 (9H, s), 1.48–1.59 (2H, m), 1.73–1.84 (2H, m), 3.90 (2H, t, J=6.5 Hz), 4.05 (2H, bs), 4.21 (2H, s), 5.39 (2H, s), 6.90 (1H, d, J=2.5 Hz), 7.17 (1H, dd, J=2.5, 8.9 Hz), 8.18 (1H, d, J=8.9 Hz), 8.43 (3H, bs).

Example 104

Ethyl {{3-(aminomethyl)-4-butoxy-2-neopentyl-1-oxo-1,2-dihydro-6-isoquinolinyl}oxy}acetate hydrochloride (1) Ethyl {4-butoxy-3-{{(tert-butoxycarbonyl)amino}methyl}-2-neopentyl-1-oxo-1,2-dihydro-6-isoquinolinyl}oxy}acetate (synthesized according to the method similar to that in Example 95 (1))

$^1$H-NMR(CDCl$_3$) δ: 0.98 (9H, s), 1.04 (3H, t, J=7.3 Hz), 1.30 (3H, t, J=7.1 Hz), 1.45 (9H, s), 1.52–1.67 (4H, m), 1.78–1.88 (2H, m), 3.84 (2H, t, J=6.6 Hz), 4.14 (2H, bs), 4.29 (2H, q, J=7.1 Hz), 4.55 (2H, d, J=5.2 Hz), 4.64 (1H, bs), 4.74 (2H, s), 7.02 (1H, d, J=1.5 Hz), 7.08 (1H, dd, J=1.5, 8.8 Hz), 8.33 (1H, d, J=8.8 Hz).

(2) Ethyl {{3-(aminomethyl)-4-butoxy-2-neopentyl-1-oxo-1,2-dihydro-6-isoquinolinyl}oxy}acetate hydrochloride (synthesized according to the method similar to that in Example 1 (7))

Elemental analysis for C$_{23}$H$_{35}$N$_2$O$_5$Cl ½H$_2$O Calculated: C, 59.54; H, 7.82; N, 6.04. Found: C, 59.81; H, 7.70; N, 5.99. $^1$H-NMR(DMSO-d$_6$) δ: 0.89 (9H, s), 1.00 (3H, t, J=7.1 Hz), 1.23 (3H, t, J=7.1 Hz), 1.50–1.61 (4H, m), 1.78–1.91 (2H, m), 3.91 (2H, t, J=6.2 Hz), 4.01 (2H, bs), 4.19 (2H, q, J=7.1 Hz), 4.21 (2H, s), 5.01 (2H, s), 6.99 (1H, d, J=2.6 Hz), 7.22 (1H, dd, J=2.6, 9.0 Hz), 8.20 (1H, d, J=9.0 Hz), 8.42 (3H, bs).

Example 105

3-(Aminomethyl)-4-butoxy-6-(1-methyl-2-oxopropoxy)-2-neopentyl-1(2H)-isoquinolinone hydrochloride (1) Tert-butyl{4-butoxy-6-(1-methyl-2-oxopropoxy)-2-neopentyl-1-oxo-1,2-dihydro-3-isoquinolinyl}methylcarbamate (synthesized according to the method similar to that in Example 95 (1)) 32–11

$^1$H-NMR(CDCl$_3$) δ: 0.99 (9H, s), 1.04 (3H, t, J=7.3 Hz), 1.44 (9H, s), 1.52–1.70 (5H, m), 1.78–1.92 (2H, m), 2.19 (3H, s), 3.89 (2H, t, J=6.4 Hz), 4.11 (2H, bs), 4.57 (2H, d, J=5.4 Hz), 4.73 (1H, bs), 7.08–7.17 (2H, m), 8.38 (1H, d, J=8.8 Hz).

(2) 3-(Aminomethyl)-4-butoxy-6-(1-methyl-2-oxopropoxy)-2-neopentyl-1(2H)-isoquinolinone hydrochloride (synthesized according to the method similar to that in Example 1 (7))

Elemental analysis for C$_{23}$H$_{35}$N$_2$O$_4$Cl Calculated: C, 62.93; H, 8.04; N, 6.38. Found: C, 62.70; H, 8.29; N, 6.39. $^1$H-NMR(DMSO-d$_6$) δ: 0.89 (9H, s), 0.99 (3H, t, J=7.3 Hz), 1.48–1.60 (5H, m), 1.75–1.85 (2H, m), 2.20 (3H, s), 3.83–4.05 (4H, m), 4.21 (2H, bs), 5.15 (2H, q, J=7.0 Hz), 6.90 (1H, d, J=2.6 Hz), 7.18 (1H, dd, J=2.6, 8.8 Hz), 8.19 (1H, d, J=8.8 Hz), 8.45 (3H, bs).

Example 106

3-Aminomethyl-6-bromo-2-isobutyl-4-phenyl-1(2H)-isoquinolinone (1) To a solution of 4-bromophthalic anhydride (50 g, 220 mmol) in benzene (500 mL) was added aluminum chloride (60 g, 450 mmol) by small portions under ice-cooling. The obtained mixture was stirred at room temperature for 24 h. The reaction mixture was poured into ice water and extracted with a mixed solvent of ethyl acetate-tetrahydrofuran (1/1). The extract was washed with brine, dried over anhydrous magnesium sulfate and concentrated under reduced pressure. The residue was purified by silica gel column chromatography and recrystallized from ethyl acetate-diisopropyl ether. The precipitated crystals were collected by filtration to give 2-benzoyl-4-bromobenzoic acid (33 g, 49%) as crystals.

Melting point 185–187° C. $^1$H-NMR(CDCl$_3$) δ: 7.36–7.73 (7H, m), 7.94 (1H, d, J=8.4 Hz).

(2) A mixture of 2-benzoyl-4-bromobenzoic acid (25 g, 82 mmol), potassium carbonate (12 g, 87 mmol), diethyl bromomalonate (22 g, 92 mmol), acetone (450 mL) and N,N-dimethylformamide (8 mL) was stirred at room temperature for 15 h. The solvent was evaporated under reduced pressure. The residue was poured into water and extracted with ethyl acetate. The residue was crystallized from hexane and the crystals were collected by filtration. The obtained crystals were added to a mixture of acetic acid (235 mL) and concentrated hydrochloric acid (360 mL) and the mixture was stirred at 120° C. for 8 h. The reaction mixture was cooled and concentrated. The residue was poured into water and extracted with ethyl acetate. The extract was washed with brine, dried with anhydrous sodium sulfate and concentrated under reduced pressure. The precipitated crystals were collected by filtration, washed with diisopropyl ether and dried to give 6-bromo-4-phenyl-1H-isochromene-3-carboxylic acid (17 g, 60%) as crystals.

Melting point 205–206° C. $^1$H-NMR(CDCl$_3$) δ: 7.20–7.28 (3H, m), 7.47–7.55 (3H, m), 7.77 (1H, dd, J=8.6, 1.8 Hz), 8.26 (1H, d, J=8.6 Hz).

(3) A solution of 6-bromo-4-phenyl-1H-isochromene-3-carboxylic acid (8.0 g, 23 mmol) and isobutylamine (23 mL, 230 mmol) in methanol (120 mL) was stirred at room temperature for 15 h. The solvent was evaporated under reduced pressure, and the residue was acidified with concentrated hydrochloric acid and extracted with ethyl acetate. The extract was washed with brine, dried over anhydrous magnesium sulfate and concentrated under reduced pressure. To the residue was added a solution of 4N hydrogen chloride in ethyl acetate (150 mL) and the mixture was stirred at room temperature for 3 h. The solvent was evaporated under reduced pressure, and the precipitated crystals were collected by filtration with water. The crystals were washed with water and dried to give 6-bromo-2-isobutyl-4-phenyl-1(2H)-isoquinolinone-3-carboxylic acid (8.1 g, 87%) as crystals.

Melting point 233–235° C. $^1$H-NMR(CDCl$_3$) δ: 0.92 (6H, d, J=6.6 Hz), 2.21 (1H, m), 3.99 (2H, d, J=7.6 Hz), 7.32–7.38 (3H, m), 7.42–7.47 (3H, m), 7.60 (1H, dd, J=8.4, 2.0 Hz), 8.26 (1H, d, J=8.4 Hz).

(4) 6-Bromo-2-isobutyl-4-phenyl-1(2H)-isoquinolinone-3-carboxylic acid (12.3 g, 30.7 mmol) was dissolved in tetrahydrofuran (100 ml), and oxalyl chloride (3.2 mL, 36.8 mmol) and N,N-dimethylformamide (5 drops) were added thereto. The mixture was stirred at room temperature for 1 h. The reaction mixture was concentrated under reduced pressure, and the residue was dissolved in tetrahydrofuran (50 mL). The obtained solution was added dropwise to a suspension of sodium tetrahydroborate (4.0 g, 107 mmol) in 1,2-dimethoxyethane (50 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The residue was recrystallized from diethyl ether-n-hexane to give 6-bromo-3-hydroxymethyl-2-isobutyl-4-phenyl-1(2H)-isoquinolinone (10.7 g, 90%) as crystals.

Melting point 176–177° C. $^1$H-NMR(CDCl$_3$) δ: 97 (6H, d, J=6.6 Hz), 2.22 (1H, m), 2.35 (1H, t, J=5.8 Hz), 4.21 (2H, d, J=7.6 Hz), 4.44 (2H, d, J=5.8 Hz), 7.10 (1H, d, J=1.8 Hz), 7.30–7.35 (2H, m), 7.47 (1H, dd, J=8.4, 1.8 Hz), 7.50–7.56 (3H, m), 8.20 (1H, d, J=8.4 Hz).

(5) To a solution of 6-bromo-3-hydroxymethyl-2-isobutyl-4-phenyl-1(2H)-isoquinolinone (8.7 g, 22.5 mmol) and pyridine (5 drops) in tetrahydrofuran (30 mL) and toluene (30 mL) was added thionyl chloride (3.4 mL, 47.3 mmol). The obtained mixture was stirred at room temperature for 3 h. The reaction mixture was concentrated, poured into water and extracted with ethyl acetate. The extract was washed with brine, dried over anhydrous magnesium sulfate and concentrated under reduced pressure to give 6-bromo-3-chloromethyl-2-isobutyl-4-phenyl-1(2H)-isoquinolinone (8.2 g, 90%) as crystals.

Melting point 145–146° C. $^1$H-NMR(CDCl$_3$) δ: 1.01 (6H, d, J=6.6 Hz), 2.22 (1H, m), 4.17 (2H, d, J=7.6 Hz), 4.37 (2H, s), 7.14 (1H, d, J=1.8 Hz), 7.31–7.37 (2H, m), 7.49–7.55 (3H, m), 7.59 (1H, dd, J=8.4, 1.8 Hz), 8.34 (1H, d, J=8.4 Hz).

(7) A solution of 6-bromo-3-chloromethyl-2-isobutyl-4-phenyl-1(2H)-isoquinolinone (10 g, 24.7 mmol) in tetrahydrofuran (20 mL) and a solution of 2M ammonia in ethanol (200 mL) were sealed in a stainless tube and stirred at 140° C. for 5 h. The reaction mixture was cooled and concentrated. The residue was poured into water and extracted with ethyl acetate. The extract was washed with brine, dried over anhydrous magnesium sulfate and concentrated under reduced pressure. The residue was crystallized from diethyl ether and the precipitated crystals were collected by filtration to give 3-aminomethyl-6-bromo-2-isobutyl-4-phenyl-1 (2H)-isoquinolinone (5.6 g, 53%) as crystals.

Melting point 129–130° C. $^1$H NMR (CDCl$_3$) δ: 1.00 (6H, d, J=6.6 Hz), 1.33 (2H, br), 2.12–2.38 (1H, m), 3.65 (2H, s), 4.20 (2H, d, J=7.8 Hz), 7.08 (1H, d, J=1.6 Hz), 7.21–7.35 (2H, m), 7.42–7.60 (4H, m), 8.32 (1H, d, J=9.0 Hz). Elemental analysis for C$_{20}$H$_{21}$BrN$_2$O Calculated: C, 62.35; H, 5.49; N, 7.27. Found: C, 62.36; H, 5.64; N, 7.44.

Example 107

Methyl 3-aminomethyl-2-isobutyl-4-phenyl-1(2H)-isoquinolinone-6-carboxylate hydrochloride (1) To a solution of 3-aminomethyl-6-bromo-2-isobutyl-4-phenyl-1(2H)-isoquinolinone (synthesized according to the method similar to that in Example 106 (7)) (5.6 g, 14.5 mmol) and 4-dimethylaminopyridine (20 mg) in tetrahydrofuran (50 mL) was added di-t-butyl dicarbonate (6.3 g, 2.9 mmol). The obtained mixture was stirred at room temperature for 1 h. The reaction mixture was poured into water and extracted with ethyl acetate. The extract was washed with brine, dried over anhydrous magnesium sulfate and concentrated under reduced pressure. The residue was crystallized from diethyl ether to give 3-tert-butoxycarbonylaminomethyl-6-bromo-2-isobutyl-4-phenyl-1(2H)-isoquinolinone (6.6 g, 94%) as crystals.

$^1$H-NMR(CDCl$_3$) δ: 1.00 (6H, d, J=7.0 Hz), 1.43 (9H, s), 2.23 (1H, m), 4.06 (2H, d, J=7.8 Hz), 4.19 (2H, d, J=5.4 Hz), 4.50 (1H, bs), 7.08 (1H, d, J=2.0 Hz), 7.21–7.25 (2H, m), 7.48–7.56 (4H, m), 8.30 (1H, d, J=8.8 Hz).

(2) A mixture of 3-tert-butoxycarbonylaminomethyl-6-bromo-2-isobutyl-4-phenyl-1(2H)-isoquinolinone (3.0 g, 6.2 mmol), 1,3-bis(diphenylphosphino)propane (0.45 g, 1.1 mol) and triethylamine (0.69 g, 6.8 mmol) in dimethyl sulfoxide (30 ml) and methanol (15 ml) was stirred under a carbon monoxide atmosphere at room temperature for 30 min. Palladium acetate (0.25 g, 1.1 mmol) was added to the resulting mixture and the mixture was stirred under a carbon monoxide atmosphere with heating at 80° C. for 15 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 3-tert-butoxycarbonylaminomethyl-2-isobutyl-4-phenyl-1 (2H)-isoquinolinone-6-carboxylate (1.92 g, 83.5%) as crystals.

Melting point 205–206° C. Elemental analysis for C$_{27}$H$_{32}$N$_2$O$_5$ Calculated: C, 69.81; H, 6.94; N, 6.03. Found: C, 69.71; H, 6.80; N, 6.13. $^1$H-NMR(CDCl$_3$) δ: 1.01 (6H, d, J=6.6 Hz), 1.43 (9H, s), 2.26 (1H, m), 3.85 (3H, s), 4.09 (2H, d, J=7.6 Hz), 4.22 (2H, d, J=5.6 Hz), 4.47 (1H, bs), 7.23–7.28 (2H, m), 7.49–7.56 (3H, m), 7.66 (1H, d, J=1.0 Hz), 8.05 (1H, dd, J=1.7, 8.0 Hz), 8.52 (1H, d, J=8.0 Hz).

(3) To a solution of methyl 3-tert-butoxycarbonylaminomethyl-2-isobutyl-4-phenyl-1(2H)-isoquinolinone-6-carboxylate (0.2 g, 0.43 mmol) in tetrahydrofuran (10 mL) was added a solution of 10% hydrogen chloride in methanol (20 mL). The obtained solution was stirred at room temperature for 15 h. The reaction mixture was concentrated under reduced pressure and the residue was crystallized from diethyl ether to give methyl 3-aminomethyl-2-isobutyl-4-phenyl-1(2H)-isoquinolinone-6-carboxylate hydrochloride (0.17 g, 99%) as crystals.

Elemental analysis for C$_{22}$H$_{24}$N$_2$O$_3$ HCl ¼H$_2$O Calculated: C, 65.18; H, 6.34; N, 6.91. Found: C, 65.08; H, 6.29; N, 6.86. $^1$H-NMR(DMSO-d$_6$) δ: 0.93 (6H, d, J=6.6 Hz), 2.12 (1H, m), 3.80 (3H, s), 3.89 (2H, s), 4.10 (2H, d, J=6.6 Hz), 7.42–7.46 (2H, m), 7.54 (1H, d, J=1.6 Hz), 7.54–7.62 (3H, m), 8.07 (1H, dd, J=8.4 Hz), 8.47 (1H, d, J=8.4 Hz), 8.58 (3H, s).

Example 108

3-Aminomethyl-2-isobutyl-4-phenyl-1(2H)-isoquinolinone-6-carboxylic acid hydrochloride (1) To a solution of methyl 3-tert-butoxycarbonylaminomethyl-2-isobutyl-4-phenyl-1(2H)-isoquinolinone-6-carboxylate (synthesized according to the method similar to that in Example 107 (2)) (0.28 g, 0.6 mmol) in tetrahydrofuran (10 ml) and methanol (10 ml) was added 1N sodium hydroxide (5 ml). The obtained mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diethyl ether to give 3-tert-butoxycarbonylaminomethyl-2-isobutyl-4-phenyl-1(2H)-isoquinolinone-6-carboxylic acid (1.54 g, 98.7%) as crystals.

Elemental analysis for $C_{26}H_{30}N_2O_5$ Calculated: C, 69.31; H, 6.71; N, 6.22. Found: C, 69.17; H, 6.59; N, 6.27.
$^1$H-NMR(CDCl$_3$) δ: 0.96 (6H, d, J=6.6 Hz), 1.07 (3H, t, J=7.4 Hz), 1.49 (9H, s), 1.50–1.72 (2H, m), 1.84–1.98 (2H, m), 2.14–2.21 (1H, m), 3.90 (2H, t, J=6.4 Hz), 4.00 (2H, d, J=6.8 Hz), 4.55 (2H, d, J=5.0 Hz), 5.37 (1H, bs), 8.08–8.13 (1H, m), 8.35–8.46 (2H, m).

(2) To a solution of 3-tert-butoxycarbonylaminomethyl-2-isobutyl-4-phenyl-1(2H)-isoquinolinone-6-carboxylic acid (0.15 g, 0.33 mmol) in tetrahydrofuran (6 mL) was added a solution of 4N hydrogen chloride in dioxane (10 mL). The obtained solution was stirred at room-temperature for 15 h. The reaction mixture was concentrated under reduced pressure, and the residue was crystallized from diethyl ether to give 3-aminomethyl-2-isobutyl-4-phenyl-1(2H)-isoquinolinone-6-carboxylic acid hydrochloride (0.09 g, 69%) as crystals.

$^1$H-NMR(DMSO-d$_6$) δ: 0.89 (6H, d, J=6.6 Hz), 1.01 (3H, t, J=7.4 Hz), 1.50–1.69 (2H, m), 1.80–1.93 (2H, m), 1.99–2.12 (1H, m), 3.97 (2H, t, J=6.4 Hz), 3.99 (2H, d, J=7.6 Hz), 4.21 (2H, s), 8.09 (1H, dd, J=1.4, 8.4 Hz), 8.34 (1H, d, J=1.4 Hz), 8.38 (1H, d, J=8.4 Hz), 8.69 (3H, bs).

Example 109

3-Aminomethyl-2-isobutyl-4-phenyl-1(2H)-isoquinolinone-6-carboxamide hydrochloride [3-(aminomethyl)-2-isobutyl-1-oxo-4-phenyl-1,2-dihydro-6-isoquinolinecarboxamide hydrochloride]

(1) A solution of 3-tert-butoxycarbonylaminomethyl-2-isobutyl- 4-phenyl-1(2H)-isoquinolinone-6-carboxylic acid (synthesized according to the method similar to that in Example 108 (1)) (0.6 g, 1.3 mmol), 1-ethyl-3-(3-dimethylaminopropyl)carbodiimide hydrochloride (0.5 g, 2.6 mmol) and 1-hydroxybenzotriazole ammonium salt (0.4 g, 2.6 mmol) in N,N-dimethylformamide (3 ml) was stirred at room temperature for 3 h. The reaction mixture was poured into water and extracted with ethyl acetate. The extract was washed successively with saturated aqueous sodium hydrogencarbonate solution and brine, dried over anhydrous magnesium sulfate and concentrated under reduced pressure. The residue was crystallized from diethyl ether-n-hexane to give 3-tert-butoxycarbonylaminomethyl-2-isobutyl-4-phenyl-1(2H)-isoquinolinone-6-carboxamide (0.5 g, 86%) as crystals.

$^1$H-NMR(CDCl$_3$) δ: 1.00 (6H, d, J=6.6 Hz), 1.43 (9H, s), 2.24 (1H, m), 4.08 (2H, d, J=7.2 Hz), 4.20 (2H, d, J=5.4 Hz), 4.68 (1H, bs), 5.73 (1H, bs), 6.08 (1H, bs), 7.24–7.29 (2H, m), 7.38 (1H, d, J=2.0 Hz), 7.47–7.56 (3H, m), 7.74 (1H, dd, J=8.8, 2.0 Hz), 8.45 (1H, d, J=8.8 Hz).

(2) To a solution of 3-tert-butoxycarbonylaminomethyl-2-isobutyl-4-phenyl-1(2H)-isoquinolinone-6-carboxamide (0.15 g, 0.33 mmol) in tetrahydrofuran (6 mL) was added a solution of 4N hydrogen chloride in dioxane (10 mL). The obtained solution was stirred at room temperature for 6 h. The reaction mixture was concentrated under reduced pressure, and the residue was crystallized from diethyl ether to give 3-aminomethyl-2-isobutyl-4-phenyl-1(2H)-isoquinolinone-6-carboxamide hydrochloride (0.11 g, 85%) as crystals.

Melting point 240–242° C. $^1$H-NMR(DMSO-d$_6$) δ: 0.92 (6H, d, J=6.6 Hz), 2.11 (1H, m), 3.87 (2H, d, J=5.6 Hz), 4.10 (2H, d, J=7.2 Hz), 7.39 (1H, d, 1.4 Hz), 7.40–7.43 (2H, m), 7.56–7.62 (4H, m), 8.00 (1H, dd, J=8.4, 1.4 Hz), 8.16 (1H, s), 8.37 (1H, d, J=8.4 Hz), 8.61 (3H, bs).

Example-110

3-Aminomethyl-6-benzyloxycarbonylamino-2-isobutyl-4-phenyl-1(2H)-isoquinolinone hydrochloride (1) A solution of 3-tert-butoxycarbonylaminomethyl-2-isobutyl-4-phenyl-1(2H)-isoquinolinone-6-carboxy acid (synthesized according to the method similar to that in Example 108 (1)) (0.5 g, 1.1 mmol), diphenylphosphoryl azide (0.28 ml, 1.3 mmol) and triethylamine (0.18 ml, 1.3 mmol) in N,N-dimethylformamide (5 ml) was stirred at room temperature for 2 h. The reaction mixture was poured into water and extracted with ethyl acetate. The extract was washed with brine, dried over anhydrous magnesium sulfate and concentrated under reduced pressure. The residue was dissolved in toluene (20 ml) and the mixture was stirred with heating at 100° C. for 2 h. To the obtained mixture was added benzyl alcohol (0.14 ml, 1.3 mmol) and the mixture was stirred with heating at 100° C. for 1 h. The reaction mixture was cooled, poured into water and extracted with ethyl acetate. The extract was washed with brine, dried over anhydrous magnesium sulfate and concentrated under reduced pressure. The residue was crystallized from diisopropyl ether to give 6-benzyloxycarbonylamino-3-tert-butoxycarbonylaminomethyl-2-isobutyl-4-phenyl-1(2H)-isoquinolinone (0.47 g, 77%) as crystals.

$^1$H-NMR(CDCl$_3$) δ: 0.99 (6H, d, J=6.6 Hz), 1.42 (9H, s), 2.23 (1H, m), 4.05 (2H, d, J=7.6 Hz), 4.18 (2H, d, J=5.2 Hz), 4.47 (1H, bs), 5.13 (2H, s), 6.75 (1H, d, J=1.8 Hz), 6.76 (1H, s), 7.21–7.26 (2H, m), 7.34–7.75 (5H, m), 7.45–7.56 (3H, m), 7.65 (1H, dd, J=8.8, 1.8 Hz), 8.41 (1H, d, J=8.8 Hz).

(2) To a solution of 6-benzyloxycarbonylamino-3-tert-butoxycarbonylaminomethyl-2-isobutyl-4-phenyl-1(2H)-isoquinolinone (0.07 g, 0.13 mmol) in tetrahydrofuran (2 mL) was added a solution, of 4N hydrogen chloride in ethyl acetate (10 mL). The obtained solution was stirred at room temperature for 5 h. The reaction mixture was concentrated under reduced pressure and the residue was crystallized from diethyl ether to give 3-aminomethyl-6-benzyloxycarbonylamino-2-isobutyl-4-phenyl-1(2H)-isoquinolinone hydrochloride (0.05 g, 81%) as crystals.

$^1$H-NMR(DMSO-d$_6$) δ: 0.91 (6H, d, J=6.6 Hz), 2.08 (1H, m), 3.84 (2H, s), 4.03 (2H, d, J=7.4 Hz), 5.08 (2H, s), 7.22 (1H, d, J=1.8 Hz), 7.35–7.37 (7H, s), 7.54–7.58 (2H, m), 7.64 (1H, dd, J=8.8, 1.8 Hz), 8.24 (1H, d, J=8.8 Hz), 8.44 (3H, s), 10.16 (1H, s).

Example 111

6-Amino-3-aminomethyl-2-isobutyl-4-phenyl-1(2H)-isoquinolinone dihydrochloride

(1) To a mixed solution of 6-benzyloxycarbonylamino-3-tert-butoxycarbonylaminomethyl-2-isobutyl-4-phenyl-1(2H)-isoquinolinone (synthesized according to the method similar to that in Example 110 (1)) (0.45 g, 0.81 mmol) in tetrahydrofuran (20 ml) and ethanol (20 ml) was added 5% palladium-carbon (0.1 g). The obtained mixture was hydrogenated, at ambient temperature and atmospheric pressure. The catalyst was filtered off and the filtrate was concentrated under reduced pressure. The precipitated crystals were collected by filtration to give 6-amino-3-tert-butoxycarbonylaminomethyl-2isobutyl-4-phenyl-1(2H)-isoquinolinone (0.31 g, 87.0%) as crystals.

$^1$H-NMR(CDCl$_3$) δ: 0.99 (6H, d, J=6.8, Hz), 1.42 (9H, s), 2.22 (1H, m), 3.94 (2H, bs), 4.02 (2H, d, J=7.4 Hz), 4.15 (2H, d, J=5.4 Hz), 4.40 (1H, bs), 6.12 (1H, d, J=2.2 Hz), 6.78 (1H, dd, J=8.8, 2, 2 Hz), 7.21–7.26 (2H, m), 7.44–7.53 (3H, m), 8.27 (1H, d, J=8.8 Hz).

(2) 6-Amino-3-aminomethyl-2-isobutyl-4-phenyl-1(2H)-isoquinolinone dihydrochloride was synthesized from 6-amino-3-tert-butoxycarbonylaminomethyl-2-isobutyl-4-phenyl-1(2H)-isoquinolinone according to the method similar to that in Example 110 (2).

$^1$H-NMR(DMSO-d$_6$) δ: 0.90 (6H, d, J=6.6 Hz), 2.05 (1H, m), 3.76 (2H, bs), 3.99 (2H, d, J=6.6 Hz), 5.44 (3H, bs), 6.00 (1H, d, J=2.0 Hz), 6.84 (1H, dd, t, J=8.8, 2.0 Hz), 7.34–7.38 (2H, m), 7.50–7.59 (3H, m), 8.03 (1H, d, J=8.8 Hz), 8.48 (3H, bs).

Example 112

6-Acetylamino-3-aminomethyl-2-isobutyl-4-phenyl-1(2H)-isoquinolinone hydrochloride

(1) A mixture of 6-amino-3-tert-butoxycarbonylaminomethyl-2-isobutyl-4-phenyl-1(2H)-isoquinolinone (synthesized according to the method similar to that in Example 111 (1)) (0.1 g, 0.24 mmol), acetyl chloride (38 mg, 0.48 mmol), sodium hydrogencarbonate (81 mg, 0.96 mmol), water (0.5 ml) and ethyl acetate (5 ml) was stirred at room temperature for 2 h. The reaction mixture was extracted with ethyl acetate. The extract was washed with brine, dried over anhydrous magnesium sulfate and concentrated under reduced pressure. The residue was crystallized from diisopropyl ether to give 6-acetylamino-3-tert-butoxycarbonylaminomethyl-2-isobutyl-4-phenyl-1(2H)-isoquinolinone (80 mg, 73%) as crystals.

$^1$H-NMR(CDCl$_3$) δ: 0.87 (6H, d, J=7.0 Hz), 1.42 (9H, s), 2.10 (3H, s), 2.23 (1H, m), 4.05 (2H, d, J=7.4 Hz), 4.19 (2H, d, J=5.6 Hz), 4.60 (1H, bs), 6.95 (1H, s), 7.24–7.28 (2H, m), 7.37 (1H, s), 7.47–7.55 (3H, m), 7.69 (1H, d, J=8.8 Hz), 8.37 (1H, d, J=8.8 Hz).

(2) 6-Acetylamino-3aminomethyl-2-isobutyl-4-phenyl-1(2H)-isoquinolinone hydrochloride was synthesized from 6-acetylamino-3-tert-butoxycarbonylaminomethyl-2-isobutyl-4-phenyl-1(2H)-isoquinolinone according to the method-similar to that in Example 110 (2).

$^1$H-NMR(DMSO-d$_6$) δ: 0.91 (6H, d, J=6.6 Hz) 1.98 (3H, s), 2.08 (1H, m), 3.84 (2H, s), 4.03 (2H, d, J=7.0 Hz), 7.19 (1H, d, J=1.8 Hz), 7.35–7.39 (2H, m), 7.49–7.58 (3H, m), 7.86 (1H, dd, J=8.8, 1.8 Hz), 8.25 (1H, d, J=8.8 Hz), 8.45 (3H, bs), 10.28 (1H, s).

The compounds of the following Examples 113 to 130 were synthesized according to the method similar to that in Example 106.

Example 113

3-(Aminomethyl)-6-chloro-2-ethyl-4-phenyl-1(2H)-isoquinolinone

Melting point 126–127° C. $^1$H-NMR (CDCl$_3$) δ: 1.39 (2H, br), 1.42 (3H, t, J=7.0 Hz), 3.64 (2H, s), 4.43 (2H, q, J=7.0 Hz), 6.91 (1H, d, J=2.2 Hz), 7.23–7.31 (2H, m), 7.38 (1H, dd, J=2.2 and 8.4 Hz), 7.45–7.57 (3H, m), 8.41 (1H, d, J=8.4 Hz). Elemental analysis for C$_{18}$H$_{17}$ClN$_2$O.0.125H$_2$O Calculated: C, 68.62; H, 5.51; N, 8.89. Found: C, 68.61; H, 5.40; N, 8.84.

Example 114

3-(Aminomethyl)-6-chloro-4-phenyl-2-propyl-1(2H)-isoquinolinone

$^1$H-NMR (CDCl$_3$) δ: 1.04 (3H, t, J=7.4 Hz), 1.17 (2H, br), 1.71–1.93 (2H, m), 3.63 (2H, s), 4.28 (2H, t, J=7.6 Hz), 6.90 (1H, d, J=2.2 Hz), 7.21–7.32 (2H, m), 7.37 (1H, dd, J=2.2 and 8.4 Hz), 7.41–7.58 (3H, m), 8.40 (1H, d, J=8.4 Hz). Elemental analysis for C$_{19}$H$_{19}$ClN$_2$O Calculated: C, 69.83; H, 5.86; N, 8.57. Found: C, 69.97; H, 5.90; N, 8.49.

Example 115

3-(Aminomethyl)-2-butyl-6-chloro-4-phenyl-1(2H)-isoquinolinone

$^1$H-NMR (CDCl$_3$) δ: 1.00 (3H, t, J=7.4 Hz), 1.23 (2H, br), 1.38–1.60 (2H, m), 1.68–1.84 (2H, m), 3.63 (2H, s), 4.33 (2H, t, J=7.6 Hz), 6.90 (1H, d, J=2.0 Hz), 7.22–7.31 (2H, m), 7.38 (1H, dd, J=2.0 and 8.8 Hz), 7.45–7.58 (3H, m), 8.41 (1H, d, J=8.8 Hz). Elemental analysis for C$_{20}$H$_{21}$ClN$_2$O Calculated: C, 70.48; H, 6.21; N, 8.22. Found: C, 70.27; H, 6.18; N, 8.09.

Example 116

3-(Aminomethyl)-6-bromo-2-methyl-4-phenyl-1(2H)-isoquinolinone

$^1$H-NMR (CDCl$_3$) δ: 1.30 (2H, br), 3.66 (2H, s), 3.84 (3H, s), 7.10 (1H, d, J=2.0 Hz), 7.20–7.32 (2H, m), 7.45–7.59 (4H, m), 8.33 (1H, d, J=8.8 Hz). Elemental analysis for C$_{17}$H$_{15}$BrN$_2$O Calculated: C, 59.49; H, 4.41; N, 8.16. Found: C, 59.61; H, 4.65; N, 7.78.

Example 117

3-(Aminomethyl)-6-chloro-2-pentyl-4-phenyl-1(2H)-isoquinolinone

$^1$H-NMR (CDCl$_3$) δ: 0.93 (3H, t, J=7.4 Hz), 1.20–1.53 (6H, m), 1.70–1.90 (2H, m), 3.63 (2H, s), 4.31 (2H, t, J=8.0 Hz), 6.90 (1H, d, J=2.2 Hz), 7.22–7.31 (2H, m), 7.37 (1H, dd, J=2.2 and 8.4 Hz), 7.45–7.58 (3H, m), 8.40 (1H, d, J=8.4 Hz). Elemental analysis for C$_{21}$H$_{23}$ClN$_2$O Calculated: C, 71.07; H, 6.53; N, 7.89. Found: C, 70.82; H, 6.34; N, 7.72.

Example 118

3-(Aminomethyl)-6-chloro-2-isobutyl-4-phenyl-1 (2H)-isoquinolinone

Melting point 123–124° C. $^1$H-NMR (CDCl$_3$) δ: 1.00 (6H, d, J=6.6 Hz), 1.18 (2H, br), 2.12–2.38 (1H, m), 3.66 (2H, s), 4.20 (2H, d, J=7.4 Hz), 6.90 (1H, d, J=1.6 Hz), 7.21–7.31 (2H, m), 7.37 (1H, dd, J=1.6 and 8.4 Hz), 7.45–7.58 (3H, m), 8.40 (1H, d, J=8.4 Hz). Elemental analysis for C$_{20}$H$_{21}$ClN$_2$O Calculated: C, 70.48; H, 6.21; N, 8.22. Found: C, 70.35; H, 6.07; N, 8.10.

Example 119

3-(Aminomethyl)-6-chloro-2-(cyclohexylmethyl)-4-phenyl-1(2H)-isoquinolinone $^1$H-NNR (CDCl$_3$) δ: 1.00–1.47 (8H, m), 1.56–2.00 (5H, m), 3.66 (2H, s), 4.21 (2H, d, J=6.8 Hz), 6.90 (1H, d, J=2.0 Hz), 7.22–7.32 (2H, m), 7.37 (1H, dd, J=2.0 and 8.8 Hz), 7.47–7.58 (3H, m), 8.40 (1H, d, J=8.8 Hz). Elemental analysis for C$_{23}$H$_{25}$ClN$_2$O Calculated: C, 72.52; H, 6.62; N, 7.35. Found: C, 72.34; H, 6.76; N, 7.21.

Example 120

3-(Aminomethyl)-6,7-dichloro-4-(4-fluorophenyl)-2-isobutyl-1(2H)-isoquinolinone hydrochloride $^1$H-NMR (CDCl$_3$, free base) δ: 0.99 (6H, d, J=6.8 Hz), 1.36 (2H, br), 2.10–2.35 (1H, m), 3.65 (2H, s), 4.20 (2H, d, J=7.6 Hz), 6.99 (1H, s), 7.24 (4H, d, J=7.4 Hz), 8.53 (1H, s). Elemental analysis for C$_{20}$H$_{19}$Cl$_2$N$_2$OF.HCl.H$_2$O Calculated: C, 53.65; H, 4.95; N, 6.26. Found: C, 53.69; H, 4.84; N, 5.96.

Example 121

3-(Aminomethyl)-6,7-dichloro-2-isobutyl-4-phenyl-1(2H)-isoquinolinone $^1$H-NMR (CDCl$_3$) δ: 1.00 (6H, d, J=7.0 Hz), 1.13 (2H, br), 2.10–2.36 (1H, m), 3.65 (2H, s), 4.20 (2H, d, J=7.4 Hz), 7.02 (1H, s), 7.20–7.32 (2H, m), 7.45–7.59 (3H, m), 8.54 (1H, s). Elemental analysis for C$_{20}$H$_{20}$Cl$_2$N$_2$O Calculated: C, 64.01; H, 5.37; N, 7.46. Found: C, 63.71; H, 5.39; N, 7.23.

Example 122

3-(Aminomethyl)-6-chloro-2-neopentyl-4-phenyl-1(2H)-isoquinolinone

Melting point 173–174° C. $^1$H-NMR (CDCl$_3$) δ: 1.02 (9H, s), 1.23 (2H, br), 3.71 (2H, s), 4.30 (2H, br), 6.90 (1H, d, J=2.2 Hz), 7.20–7.30 (2H, m), 7.37 (1H, dd, J=2.2 and 8.4 Hz), 7.42–7.68 (3H, m), 8.39 (1H, d, J=8.4 Hz). Elemental analysis for C$_{21}$H$_{23}$ClN$_2$O Calculated: C, 71.07; H, 6.53; N, 7.89. Found: C, 70.89; H, 6.54; N, 7.61.

Example 123

3-(Aminomethyl)-2-isobutyl-4-phenyl-1(2H)-isoquinolinone

Melting point 129–130° C. $^1$H-NMR (CDCl$_3$) δ: 1.01 (6H, d, J=7.0 Hz), 1.23 (2H, br), 2.17–2.40 (1H, m), 3.68 (2H, s), 4.22 (2H, d, J=7.8 Hz), 6.90–7.00 (1H, m), 7.23–7.34 (2H, m), 7.38–7.57 (5H, m), 8.44–8.52 (1H, m). Elemental analysis for C$_{20}$H$_{22}$N$_2$O Calculated: C, 78.40; H, 7.24; N, 9.14. Found: C, 78.30; H, 7.50; N, 9.06.

Example 124

3-(Aminomethyl)-4-(4-chlorophenyl)-2-isobutyl-1(2H)-isoquinolinone

Melting point 119–120° C. $^1$H-NMR (CDCl$_3$) δ: 1.00 (6H, d, J=6.6 Hz), 1.15 (1H, br), 1.61 (1H, br), 2.14–2.39 (1H, m), 3.67 (2H, s), 4.21 (2H, d, J=7.8 Hz), 6.88–6.97 (1H, m), 7.20–7.29 (2H, m), 7.40–7.56 (4H, m), 8.43–8.52 (1H, m). Elemental analysis for C$_{20}$H$_{21}$ClN$_2$O Calculated: C, 70.48; H, 6.21; N, 8.22. Found: C, 70.36; H, 6.40; N, 8.19.

Example 125

3-(Aminomethyl)-4-(4-methylphenyl)-2-isobutyl-1(2H)-isoquinolinone hydrochloride Melting point 178–180° C. (dec.) $^1$H-NMR (CDCl$_3$, free base) δ: 1.00 (6H, d, J=6.6 Hz), 1.48 (2H, br), 2.18–2.37 (1H, m), 2.46 (3H, s), 3.69 (2H, s), 4.22 (2H, d, J=7.8 Hz), 6.95–7.04 (1H, m), 7.17 (2H, d, J=8.0 Hz), 7.31 (2H, d, J=7.0 Hz), 7.37–7.53 (2H, m), 8.43–8.53 (1H, m). Elemental analysis for C$_{21}$H$_{24}$N$_2$O.HCl.0.5H$_2$O Calculated: C, 68.93; H, 7.16; N, 7.66. Found: C, 69.25; H, 7.11; N, 7.30.

Example 126

3-(Aminomethyl)-6-fluoro-2-isobutyl-4-phenyl-1(2H)-isoquinolinone $^1$H-NMR (CDCl$_3$) δ: 1.00 (6H, d, J=6.6 Hz), 1.12 (2H, br), 2.15–2.38 (1H, m), 3.67 (2H, s), 4.20 (2H, d, J=7.4 Hz), 6.56 (1H, dd, J=2.6 and 10.6 Hz), 7.13 (1H, dt, J=2.6 and 8.8 Hz), 7.23–7.33 (2H, m), 7.41–7.57 (3H, m), 8.48 (1H, dd, J=5.8 and 8.8 Hz). Elemental analysis for C$_{20}$H$_{21}$FN$_2$O.0.25H$_2$O Calculated: C, 73.04; H, 6.59; N, 8.52. Found: C, 73.32; H, 6.72; N, 8.43.

Example 127

3-(Aminomethyl)-2-isobutyl-6-methoxy-4-phenyl-1(2H)-isoquinolinone $^1$H-NMR (CDCl$_3$) δ: 1.00 (6H, d, J=6.6 Hz), 1.26 (2H, br), 2.15–2.38 (1H, m), 3.65 (2H, s), 3.67 (3H, s), 4.18 (2H, d, J=7.2 Hz), 6.30 (1H, d, J=2.4 Hz), 7.02 (1H, dd, J=2.4 and 8.8 Hz), 7.23–7.34 (2H, m), 7.39–7.57 (3H, m), 8.41 (1H, d, J=8.8 Hz). Elemental analysis for C$_{21}$H$_{24}$N$_2$O$_2$ Calculated: C, 74.97; H, 7.19; N, 8.33. Found: C, 74.73; H, 7.40; N, 8.32.

Example 128

3-(Aminomethyl)-6-ethoxy-2-isobutyl-4-phenyl-1(2H)-isoquinolinone

$^1$H-NMR (CDCl$_3$) δ: 1.00 (6H, d, J=7.0 Hz), 1.21 (2H, br), 1.33 (3H, t, J=7.0 Hz), 2.13–2.38 (1H, m), 3.65 (2H, s), 3.88 (2H, q, J=7.0 Hz), 4.18 (2H, d, J=7.4 Hz), 6.29 (1H, d, J=2.6 Hz), 7.01 (1H, dd, J=2.6 and 8.8 Hz), 7.22–7.32 (2H, m), 7.41–7.55 (3H, m), 8.39 (1H, d, J=8.8 Hz). Elemental analysis for C$_{22}$H$_{26}$N$_2$O$_2$ Calculated: C, 75.40; H, 7.48; N, 7.99. Found: C, 75.43; H, 7.69; N, 8.17.

Example 129

3-(Aminomethyl)-2-isobutyl-4-phenyl-6-propoxy-1(2H)-isoquinolinone

$^1$H-NMR (CDCl$_3$) δ: 0.95 (3H, t, J=7.4 Hz), 0.99 (6H, d, J=7.0 Hz), 1.32 (2H, br), 1.61–1.82 (2H, m), 2.13–2.38 (1H, m), 3.64 (2H, s), 3.77 (2H, t, J=6.6 Hz), 4.18 (2H, d, J=7.4 Hz), 6.28 (1H, d, J=2.6 Hz), 7.01 (1H, dd, J=2.6 and 9.2 Hz), 7.22–7.31 (2H, m), 7.42–7.56 (3H, m), 8.39 (1H, d, J=9.2 Hz). Elemental analysis for C$_{23}$H$_{28}$N$_2$O$_2$ Calculated: C, 75.79; H, 7.74; N, 7.69. Found: C, 75.81; H, 7.45; N, 7.56.

Example 130

3-(Aminomethyl)-2-isobutyl-6,7-dimethoxy-4-phenyl-1(2H)-isoquinolinone

$^1$H-NMR (CDCl$_3$) δ: 1.01 (6H, d, J=6.6 Hz), 1.34 (2H, br), 2.15–2.40 (1H, m), 3.66 (5H, s), 4.01 (3H, s), 4.21 (2H, d, J=7.4 Hz), 6.28 (1H, s), 7.25–7.35 (2H, m), 7.40–7.57 (3H, m), 7.87 (1H, s). Elemental analysis for C$_{22}$H$_{26}$N$_2$O$_3$·0.5H$_2$O Calculated: C, 70.38; H, 7.25; N, 7.46. Found: C, 70.56; H, 7.36; N, 7.39.

Example 131

3-(Aminomethyl)-2-isobutyl-4-phenyl-1(2H)-isoquinolinone-6-carbonitrile hydrochloride

(1) A solution of 3-tert-butoxycarbonylaminomethyl-2-isobutyl-4-phenyl-1(2H)-isoquinolinone-6-carboxamide (synthesized according to the method similar to that in Example 109 (1)) (0.3 g, 0.67 mmol) and cyanuric chloride (0.37 g, 2 mmol) in N,N-dimethylformamide (3 mL) was stirred at 0° C. for 1 h. The reaction mixture was poured into water and extracted with ethyl acetate. The extract was washed successively with water, 10% aqueous citric acid solution, saturated aqueous sodium hydrogencarbonate solution and brine, dried over anhydrous magnesium sulfate and concentrated under reduced pressure. The residue was purified by silica gel column chromatography to give a amorphous solid of tert-butyl(6-cyano-2-isobutyl-4-phenyl-1-oxo-1,2-dihydro-3-isoquinolinyl)methylcarbamate (0.28 g, 97%).

$^1$H-NMR(CDCl$_3$) δ: 1.01 (6H, d, J=7.0 Hz), 1.43 (9H, s), 2.24 (1H, m), 4.09 (2H, d, J=7.0 Hz), 4.23 (2H, d, J=5.4 Hz), 4.43 (1H, bs), 7.21–7.29 (3H, m), 7.51–7.59 (3H, m), 7.65 (1H, dd, J=1.4, 8.0 Hz), 8.55 (1H, d, J=8.0 Hz).

(2) 3-(Aminomethyl)-2-isobutyl-4-phenyl-1(2H)-isoquinolinone-6-carbonitrile hydrochloride was synthesized from tert-butyl(6-cyano-2-isobutyl-4-phenyl-1-oxo-1,2-dihydro-3-isoquinolinyl)methylcarbamate in the same manner as in Example 1 (7).

$^1$H-NMR(DMSO-d$_6$) δ: 0.93 (6H, d, J=6.6 Hz), 2.11 (1H, m), 3.89 (2H, s), 4.11 (2H, d, J=7.4 Hz), 7.22 (1H, d, J=1.6 Hz), 7.42–7.46 (2H, m), 7.58–7.61 (3H, m), 7.97 (1H, dd, J=1.6, 8.4 Hz), 8.48 (1H, d, J=8.4 Hz), 8.67 (3H, bs).

Example 132

3-(Aminomethyl)-4-phenyl-6-(1-pyrrolidinylcarbonyl)-2-isobutyl-1(2H)-isoquinolinone hydrochloride

(1) A mixture of 3-tert-butoxycarbonylaminomethyl-2-isobutyl-4-phenyl-1(2H)-isoquinolinone-6-carboxylic acid (synthesized according to the method similar to that in Example 108 (1)) (100 mg, 0.22 mmol), hydrochloric acid 1-ethyl-3-(3-dimethylaminopropyl)carbodiimide hydrochloride(63 mg, 0.33 mmol), 1-hydroxy-7-azabenzotriazole (30 mg, 0.22 mmol), pyrrolidine (31 mg, 0.44 mmol) and N,N-dimethylformamide (3 mL) was stirred at room temperature for 3 h. The reaction mixture was poured into 10% aqueous citric acid solution and extracted with ethyl acetate. The extract was dried over anhydrous magnesium sulfate and concentrated under reduced pressure. The residue was purified by silica gel column chromatography to give 3-(tert-butoxycarbonylaminomethyl)-2-isobutyl-4-phenyl-6-(1-pyrrolidinylcarbonyl)-1(2H)-isoquinolinone (70 mg, 64%) as an amorphous solid.

$^1$H-NMR(CDCl$_3$) δ: 1.01 (6H, d, J=6.6 Hz), 1.43 (9H, s), 1.79–1.99 (4H, m), 2.25 (1H, m), 3.21 (2H, t, J=6.2 Hz), 3.57 (2H, t, J=6.8 Hz), 4.09 (2H, d, J=7.6 Hz), 4.21 (2H, d, J=6.0 Hz), 4.44 (1H, bs), 7.08 (1H, d, J=1.6 Hz), 7.21–7.27 (2H, m), 7.45–7.51 (3H, m), 7.56 (1H, dd, J=8.4, 1.6 Hz), 8.50 (1H, d, J=8.4 Hz).

(2) 3-(Aminomethyl)-2-isobutyl-4-phenyl-6-(1-pyrrolidinylcarbonyl)-1(2H)-isoquinolinone hydrochloride was synthesized from 3-(tert-butoxycarbonylaminomethyl)-2-isobutyl-4-phenyl-6-(1-pyrrolidinylcarbonyl)-1(2H)-isoquinolinone in the same manner as in Example 1 (7).

$^1$H-NMR(DMSO-d$_6$) δ: 0.93 (6H, d, J=6.6 Hz), 1.70–1.90 (4H, m), 2.11 (1H, m), 3.20 (2H, t, J=6.4 Hz), 3.90 (2H, t, J=6.2 Hz), 3.88 (2H, s), 4.09 (2H, d, J=7.4 Hz), 6.96 (1H, d, J=1.6 Hz), 7.39–7.44 (2H, m), 7.56–7.164 (3H, m), 7.69 (1H, dd, J=8.4, 1.6 Hz), 8.37 (1H, d, J=8.4 Hz), 8.55 (3H, bs).

The compounds of the following Examples 133 to 141 were synthesized according to the method similar to that in Example 132.

Example 133

3-Aminomethyl-N-benzyl-2-isobutyl-4-phenyl-1(2H)-isoquinolinone-6-carboxamide hydrochloride

$^1$H-NMR(DMSO-d$_6$) δ: 0.93 (6H, d, J=6.6 Hz), 2.11 (1H, m), 3.88 (2H, s), 4.09 (2H, d, J=6.6 Hz), 4.36 (2H d, J=6.0 Hz), 7.22–7.34 (5H, m), 7.40–7.45 (3H, m), 7.57–7.60 (3H, m), 8.04 (1H, d, J=8.4 Hz), 8.41 (1H, d. J=8.4 Hz), 8.52 (3H, bs), 9.28 (1H, t, J=6.0 Hz).

Example 134

3-Aminomethyl-2-isobutyl-N-methyl-4-phenyl-1(2H)-isoquinolinone-6-carboxamide hydrochloride

$^1$H-NMR(DMSO-d$_6$) δ: 0.93 (6H, d, J=6.6 Hz), 2.11 (1H, m), 2.72 (3H, d, J=4.8 Hz), 3.87 (2H, s), 4.09 (2H, d, J=6.8 Hz), 7.39–7.43 (3H, m), 7.54–7.60 (3H, m), 7.95 (1H, dd, J=8.6, 1.6 Hz), 8.39 (1H, d, J=8.6 Hz), 8.60 (3H, bs), 8.64 (1H, t, J=4.8 Hz).

Example 135

3-Aminomethyl-N-cyclopropyl-2-isobutyl-4-phenyl-1(2H)-isoquinolinone-6-carboxamide hydrochloride $^1$H-NMR(DMSO-d$_6$) δ: 0.49–0.59 (2H, m), 0.62–0.71 (2H, m), 0.92 (6H, d, J=6.6 Hz), 2.11 (1H, m), 2.73 (1H, m), 3.88 (2H, s), 4.08 (2H, d, J=7.0 Hz), 7.39 (1H, d, J=1.4 Hz), 7.40–7.43 (2H, m), 7.58–7.61 (3H, m), 7.94 (1H, dd, J=8.4, 1.4 Hz), 8.37 (1H, d, J=8.4 Hz), 8.46 (3H, bs), 8.66 (1H, t, J=4.0 Hz).

Example 136

3-Aminomethyl-2-isobutyl-4-phenyl-N-propyl-1(2H)-isoquinolinone-6-carboxamide hydrochloride $^1$H-NMR(DMSO-d$_6$) δ: 0.83 (3H, t, J=7.4 Hz), 0.92 (6H, d, J=6.6 Hz), 1.40–1.60 (2H, m), 2.11 (1H, m), 3.15 (2H, m), 3.88 (2H, s), 4.08 (2H, d, J=7.0 Hz), 7.39 (1H, d, J=1.6 Hz), 7.39–7.43 (2H, m), 7.57–7.60 (3H, m), 7.97 (1H, dd, J=8.4, 1.6 Hz), 8.39 (1H, d, J=8.4 Hz), 8.45 (3H, bs), 8.66 (1H, t, J=4.8 Hz).

Example 137

3-Aminomethyl-N-ethyl-2-isobutyl-4-phenyl-1(2H)-isoquinolinone-6-carboxamide hydrochloride $^1$H-NMR(DMSO-d$_6$) δ: 0.92 (6H, d, J=6.6 Hz), 1.07 (3H, t, J=7.0), 2.11 (1H, m), 3.15–3.29 (2H, m), 3.87 (2H, s), 4.08 (2H, d, J=7.0 Hz), 7.38–7.43 (3H, m), 7.55–7.63 (3H, m), 7.97 (1H, dd, J=8.4, 1.8 Hz), 8.38 (1H, d, J=8.4 Hz), 8.45 (3H, bs), 8.68 (1H, t, J=5.0 Hz).

Example 138

3-Aminomethyl-N,N-dimethyl-2-isobutyl-4-phenyl-1(2H)-isoquinolinone-6-carboxamide hydrochloride $^1$H-NMR(DMSO-d$_6$) δ: 0.93 (6H, d, J=6.6 Hz), 2.11 (1H, m), 2.78 (3H, s), 2.91 (3H, s), 3.88 (2H, s), 4.08 (2H, d, J=7.4 Hz), 6.84 (1H, d, J=1.0 Hz), 7.39–7.43 (2H, m), 7.54–7.61 (4H, m), 8.37 (1H, d, J=8.6 Hz), 8.50 (3H, bs).

Example 139

Ethyl N-[(3-aminomethyl-2-isobutyl-4-phenyl-1(2H)-isoquinolinone-6-yl)carbonyl]glycinate hydrochloride $^1$H-NMR(DMSO-d$_6$) δ: 0.93 (6H, d, J=6.6 Hz), 117 (3H, t, J=7.2 Hz), 2.11 (1H, m), 3.88 (2H, s), 3.94 (2H, d, J=5.6 Hz), 4.08 (2H, g, J=7.2 Hz), 4.08 (2H, d, J=7.0 Hz), 7.39–7.43 (3H, m), 7.57–7.60 (3H, m), 8.00 (1H, dd, J=8.4, 1.6 Hz), 8.43 (1H, d, J=8.4 Hz), 8.43 (3H, bs), 9.15 (1H, t, J=5.6 Hz).

Example 140

3-(Aminomethyl)-6-[(4-hydroxypiperidin-1-yl)carbonyl]-2-isobutyl-4-phenyl-1(2H)-isoquinolinone hydrochloride $^1$H-NMR(DMSO-d$_6$) δ: 0.93 (6H, d, J=6.6 Hz), 1.20–1.80 (6H, m), 2.11 (1H, m), 2.90–3.30 (2H, m), 3.67 (1H, m), 3.89 (2H, s), 4.07 (2H, d, J=6.4 Hz), 4.80 (1H, bs), 6.83 (1H, m), 7.40–7.43 (2H, m), 7.54–7.61 (4H, m), 8.38 (1H, d, J=8.4 Hz), 8.46 (3H, bs).

Example 141

3-Aminomethyl-N-(2,2,2-trifluoroethyl)-2-isobutyl-4-phenyl-1(2H)-isoquinolinone-6-carboxamide hydrochloride $^1$H-NMR(DMSO-d$_6$) δ: 0.93 (6H, d, J=6.6 Hz), 2.12 (1H, m), 3.89 (2H, s), 4.00–4.10 (4H, m), 7.39–7.44 (3H, m), 7.57–7.61 (3H, m), 8.02 (1H, dd, J=8.6, 1.4 Hz), 8.44 (1H, d, J=8.4 Hz), 8.46 (3H, bs), 9.31 (1H, t, J=6.3 Hz).

Example 142

3-Aminomethyl-4-(4-fluorophenyl)-2-isobutyl-1(2H)-isoquinolinone-6-carboxamide hydrochloride (1) To a solution of 4-bromophthalic anhydride (50 g, 220 mmol) in fluorobenzene (300 mL) was added aluminum chloride (60 g, 450 mmol) by small portions under ice-cooling. The obtained mixture was stirred at room temperature for 15 h. The reaction mixture was poured into ice water and extracted with ethyl acetate. The extract was washed with 1N hydrochloric acid and brine, dried over anhydrous magnesium sulfate and concentrated under reduced pressure. The residue was crystallized from ethyl acetate-diisopropyl ether and the precipitated crystals were collected by filtration. The crystals were recrystallized from ethyl acetate to give a solid of a mixture (9:1)(7 g, 10%) of 2-(4-fluorobenzoyl)-4-bromobenzoic acid and 2-(4-fluorobenzoyl)-5-bromobenzoic acid. (2-(4-fluorobenzoyl)-4-bromobenzoic acid: $^1$H-NMR(CDCl$_3$) δ: 7.06–7.17 (2H, m), 7.50 (1H, d, J=2.0 Hz), 7.69–7.79 (3H, m), 7.95 (1H, d, J=8.4 Hz).

(2) A solid of 6-bromo-4-(4-fluorophenyl)-1H-isochromene-3-carboxylic acid (5.5 g, 69%) was obtained from 2-(4-fluorobenzoyl)-4-bromobenzoic acid (7 g, 22 mmol) in the same manner as in Example 106 (2).

$^1$H-NMR(CDCl$_3$) δ: 7.21–7.27 (5H, m), 7.79 (1H, dd, J=8.4, 1.8 Hz), 8.27 (1H, d, J=8.6 Hz).

(3) 6-Bromo-4-(4-fluorophenyl)-2-isobutyl-1(2H)-isoquinolinone-3-carboxylic acid (5.3 g, 85%) was obtained as crystals from 6-bromo-4-(4-fluorophenyl)-1H-isochromene-3-carboxylic acid (5.4 g, 14.9 mmol) in the same manner as in Example 106 (3).

$^1$H-NMR(CDCl$_3$) δ: 0.94 (6H, d, J=7.0 Hz), 2.28 (1H, m), 4.02 (2H, d, J=7.4 Hz), 7.12–7.25 (3H, m), 7.33–7.41 (2H, m), 7.61 (1H, dd, J=8.4, 1.8 Hz), 8.34 (1H, d, J=8.4 Hz).

(4) 6-Bromo-4-(4-fluorophenyl)-3-hydroxymethyl-2-isobutyl-1(2H)-isoquinolinone (4.9 g, 96%) was obtained as crystals from 6-bromo-4-(4-fluorophenyl)-2-isobutyl-1(2H)-isoquinolinone-3-carboxylic acid (5.3 g, 12.6 mmol) in the same manner as in Example 106 (4).

Melting point 194–196° C. $^1$H-NMR(CDCl$_3$) δ: 0.98 (6H, d, J=7.0 Hz), 1.94 (1H, t, J=6.0 Hz), 2.21 (1H, m), 4.20 (2H, d, J=7.4 Hz), 4.44 (2H, d, J=5.6 Hz), 7.09 (1H, d, J=1.8 Hz), 7.18–7.34 (4H, m), 7.52 (1H, dd, J=8.6, 1.8 Hz), 8.26 (1H, d, J=8.6 Hz).

(5) 6-Bromo-3-chloromethyl-4-(4-fluorophenyl)-2-isobutyl-1(2H)-isoquinolinone (4.5 g, 90%) was obtained as crystals from 6-bromo-4-(4-fluorophenyl)-3-hydroxymethyl-2-isobutyl-1(2H)-isoquinolinone (4.8 g, 11.9 mmol) in the same manner as in Example 106 (5).

¹H-NMR(CDCl₃) δ: 1.01 (6H, d, J=7.0 Hz), 2.21 (1H, m), 4.17 (2H, d, J=7.2 Hz), 4.36 (2H, s), 7.11 (1H, d, J=1.8 Hz), 7.19–7.36 (4H, m), 7.60 (1H, dd, J=8.4, 1.8 Hz), 8.34 (1H, d, J=8.4 Hz).

(6) 3-(Tert-butoxycarbonylaminomethyl)-6-bromo-4-(4-fluorophenyl)-2-isobutyl-1(2H)-isoquinolinone (4.5 g, 86%) was obtained as crystals from 6-bromo-3-chloromethyl-4-(4-fluorophenyl)-2-isobutyl-1(2H)-isoquinolinone (4.5 g, 10.6 mmol) in the same manner as in Example 106 (6), (7).

¹H NMR (CDCl₃) δ: 0.99 (6H, d, J=7.0 Hz), 1.43 (9H, s), 2.19 (1H, m), 4.05 (2H, d, J=7.2 Hz), 4.18 (2H, d, J=5.0 Hz), 4.43 (1H, bs), 7.05 (1H, d, J=1.8 Hz), 7.21–7.24 (4H, m), 7.56 (1H, dd, J=8.6, 1.8 Hz), 8.31 (1H, d, J=8.6 Hz).

(7) Methyl 3-(tert-butoxycarbonylaminomethyl)-4-(4-fluorophenyl)-2-isobutyl-1(2H)-isoquinolinone-6-carboxylate (1.4 g, 33%) was obtained as crystals from 3-(tert-butoxycarbonylaminomethyl)-6-bromo-4-(4-fluorophenyl)-2-isobutyl-1(2H)-isoquinolinone (4.5 g, 8.9 mmol) in the same-manner as in Example 107 (2).

¹H-NMR(CDCl₃) δ: 1.00 (6H, d, J=7.0 Hz), 1.43 (9H, s), 2.24 (1H, m), 3.87 (3H, s), 4.08 (2H, d, J=7.4 Hz), 4.21 (2H, d, J=5.0 Hz), 4.45 (1H, bs), 7.22–7.26 (4H, m), 7.62 (1H, d, J=2.0 Hz), 8.05 (1H, dd, J=8.4, 2.0 Hz), 8.52 (1H, d, J=8.4 Hz).

(8) 3-(tert-Butoxycarbonylaminomethyl)-4-(4-fluorophenyl)-2-isobutyl-1(2H)-isoquinolinone-6-carboxylic acid (1.1 g, 92%) was obtained as a solid from methyl 3-(tert-butoxycarbonylaminomethyl)-4-(4-fluorophenyl)-2-isobutyl-1(2H)-isoquinolinone-6-carboxylate (1.2 g, 2.5 mmol) in the same manner as in Example 108 (1).

¹H-NMR(DMSO-d₆) δ: 0.91 (6H, d, J=6.6 Hz), 1.38 (9H, s), 2.17 (2H, m), 3.93 (2H, d, J=7.6 Hz), 3.99 (2H, d, J=4.4 Hz), 7.33 (1H, bs), 7.37–7.48 (4H, m), 7.51 (1H, d, J=1.4H), 8.00 (1H, dd, J=8.4, 1.4 Hz), 8.40 (1H, d, J=8.4 Hz).

(9) 3-(Tert-butoxycarbonylaminomethyl)-4-(4-fluorophenyl)-2-isobutyl-1(2H)-isoquinolinone-6-carboxamide (0.57 g, 95%) was obtained as a solid from 3-(tert-butoxycarbonylaminomethyl)-4-(4-fluorophenyl)-2-isobutyl-1(2H)-isoquinolinone-6-carboxylic acid (0.6 g, 1.3 mmol) in the same manner as in Example 109 (1).

¹H-NMR(CDCl₃) δ: 1.00 (6H, d, J=7.0 Hz), 1.44 (9H, s), 2.26 (2H, m), 4.07 (2H, d, J=6.8 Hz), 4.20 (2H, d, J=4.8 Hz), 4.62 (1H, bs), 5.12 (1H, bs), 6.03 (1H, bs), 7.22–7.26 (4H, m), 7.38 (1H, s), 7.74 (1H, d, J=8.0 Hz), 8.44 (1H, bs).

(10) To a solution of 3-(tert-butoxycarbonylaminomethyl)-4-(4-fluorophenyl)-2-isobutyl-1(2H)-isoquinolinone-6-carboxamide (0.5 g, 1.1 mmol) in tetrahydrofuran (2 mL) was added a solution of 4N hydrogenchloride in ethyl acetate (10 mL). The obtained solution was stirred at room temperature for 3 h. The reaction mixture was concentrated under reduced pressure and the residue was crystallized from diethyl ether to give 3-aminomethyl-4-(4-fluorophenyl)-2-isobutyl-1(2H)-isoquinolinone-6-carboxamide hydrochloride (0.37 g, 85%) as crystals.

Melting point 218–220° C. ¹H-NMR(DMSO-d₆) δ: 0.92 (6H, d, J=6.6 Hz), 2.10 (1H, m), 3.86 (2H, d, J=4.6 Hz), 4.08 (2H, d, J=7.4 Hz), 7.36–7.46 (5H, m), 7.59 (1H, s), 8.00 (1H, dd, J=8.4, 1.6 Hz), 8.17 (1H, s), 8.37 (1H, d, J=8.4 Hz), 8.55 (3H, bs).

Example 143

Methyl 3-aminomethyl-4-(4-fluorophenyl)-2-isobutyl-1(2H)-isoquinolinone-6-carboxylate hydrochloride This compound was synthesized from methyl 3-(tert-butoxycarbonylaminomethyl)-4-(4-fluorophenyl)-2-isobutyl-1(2H)-isoquinolinone-6-carboxylate in the same manner as in Example 142(10).

¹H-NMR(DMSO-d₆) δ: 0.93 (6H, d, J=6.6 Hz), 2.11 (1H, m), 3.81 (3H, s), 3.88 (2H, s), 4.08 (2H, d, J=7.8 Hz), 7.39–7.52 (5H, m), 8.08 (1H, dd, J=8.4, 1.6 Hz), 8.46 (1H, d, J=8.4 Hz), 8.50 (3H, s).

Example 144

3-Aminomethyl-4-(4-fluorophenyl)-2-isobutyl-1(2H)-isoquinolinone-6-carboxylic acid hydrochloride This compound was synthesized from 3-(tert-butoxycarbonylaminomethyl)-4-(4-fluorophenyl)-2-isobutyl-1(2H)-isoquinolinone-6-carboxylic acid in the same manner as in Example 142(10).

¹H-NMR(DMSO-d₆) δ: 0.93 (6H, d, J=6.6 Hz), 2.14 (1H, m), 3.89 (2H, s), 4.08 (1H, s, J=7.8 Hz), 7.39–7.52 (5H, m), 8.06 (1H, dd, J=8.4, 1.6 Hz), 8.44 (1H, d, J=8.4 Hz), 8.50 (3H, bs).

Example 145

3-Aminomethyl-2-isobutyl-4-phenyl-1(2H)-isoquinolinone-6-carboxamide [3-(aminomethyl)-2-isobutyl-1-oxo-4-phenyl-1,2-dihydro-6-isoquinolinecarboxamide]

To a solution of 3-aminomethyl-2-isobutyl-4-phenyl-1(2H)-isoquinolinone-6-carboxamide hydrochloride (2.04 g, 5 mmol) in water (20 mL) was added 1N sodium hydroxide (10 ml) and the obtained mixture was stirred at room temperature for 10 min. The reaction mixture was poured into water and extracted with ethyl acetate. The extract was washed with brine, dried over anhydrous magnesium sulfate and concentrated under reduced pressure. The obtained crystals were recrystallized from ethyl acetate to give 3-aminomethyl-2-isobutyl-4-phenyl-1(2H)-isoquinolinone-6-carboxamide (0.87 g, 82.9%) as crystals.

Melting point 208° C. Elemental analysis for C₂₁H₂₃N₃O₂. Calculated: C, 72.18; H, 6.63; N, 12.03. Found: C, 72.10; H, 6.56; N, 11.88. ¹H-NMR(CDCl₃) δ: 1.01 (6H, d, J=6.6 Hz), 1.42 (2H, bs), 2.20–2.34 (1H, m), 3.68 (2H, s), 4.23 (2H, d, J=7.6 Hz), 5.72 (1H, bs), 6.01 (1H, bs), 5.89 (1H, bs), 7.26–7.31 (2H, m), 7.20 (1H, d, J=2.2 Hz), 7.46–7.57 (3H, m), 7.79 (1H, dd, J=1.8, 8.4 Hz), 8.54 (1H, d, J=8.4 Hz).

| Powder X-ray crystal diffraction data | |
|---|---|
| Diffraction angle: 2θ(°) (angstrom) | spacing: d value |
| 5.98 | 14.8 |
| 7.88 | 11.2 |

-continued

Powder X-ray crystal diffraction data

Diffraction angle: 2θ(°)
(angstrom) | spacing: d value
--- | ---
8.44 | 10.5
17.1 | 5.19

Recrystallization from ethyl acetate in the same manner gave crystals in a different crystal form.

Powder X-ray crystal diffraction data

Diffraction angle: 2θ(°)
(angstrom) | spacing: d value
--- | ---
7.22 | 11.4
9.80 | 9.02
12.1 | 7.32
13.5 | 6.53
17.9 | 4.94
19.6 | 4.52
20.6 | 4.30
21.8 | 4.08

Example 146

3-(Aminomethyl)-4-butoxy-2-cyclopropylmethyl-1-oxo-1,2-dihydro-6-isoquinolinecarboxamide hydrochloride (1) A solution of 4-bromophthalic anhydride (22.70 g, 100 mmol) and ethyl 2-(cycloproplylmethylamino)acetate (18.87 g, 120 mmol) in tetrahydrofuran (150 mL) was stirred at room temperature for 1 h. The reaction mixture was poured into water and extracted with ethyl acetate. The extract was washed with brine, dried over anhydrous magnesium sulfate and concentrated under reduced pressure. The residue was dissolved in N,N-dimethylformamide (150 mL), and potassium carbonate (14.82 g, 100 mmol) and ethyl iodide (9.6 mL, 120 mmol) were added thereto. The mixture was stirred at room temperature for 12 h. The reaction mixture was poured into water and extracted with ethyl acetate. The extract was washed with brine, dried over anhydrous magnesium sulfate and concentrated under reduced pressure. The residue was dissolved in ethanol (150 mL) and 20% sodium ethoxide ethanol solution (68.10 g, 200 mmol) was added thereto. The mixture was stirred at room temperature for 1 h. The reaction mixture was poured into 1N hydrochloric acid (300 mL) and extracted with ethyl acetate. The extract was washed with brine, dried over anhydrous magnesium sulfate and concentrated under reduced pressure. The residue was purified by silica gel column chromatography and the component eluted earlier was concentrated to give ethyl 7-bromo-2-cyclopropylmethyl-4-hydroxy-1-oxo-1,2-dihydro-3-isoquinolinecarboxylate (11.14 g, 30.4%) as crystals.

Melting point 105–105.5° C. Elemental analysis for $C_{16}H_{16}NO_4Br$ Calculated: C, 52.48; H, 4.40; N, 3.82. Found: C, 52.50; H, 4.31; N, 3.80. $^1$H-NMR(CDCl$_3$) δ: 0.32–0.54 (4H, m), 0.97–1.14 (1H, m), 1.47 (3H, t, J=7.2 Hz), 4.34 (2H, d, J=7.0 Hz), 4.45 (2H, d, J=7.2 Hz), 7.85 (1H, dd, J=2.0, 8.6 Hz), 8.02 (1H, d, J=8.6 Hz), 8.59 (1H, d, J=2.6 Hz), 11.25 (1H, s).

The component eluted later was concentrated to give ethyl 6-bromo-2-cyclopropylmethyl-4-hydroxy-1-oxo-1,2-dihydro-3-isoquinolinecarboxylate (11.02 g, 30.1%) as crystals.

Melting point 64–65° C. Elemental analysis for $C_{16}H_{16}NO_4Br$ Calculated: C, 52.48; H, 4.40; N, 3.82. Found: C, 52.36; H, 4.31; N, 3.87. $^1$H-NMR(CDCl$_3$) δ: 0.32–0.54 (4H, m), 0.97–1.13 (1H, m), 1.48 (3H, t, J=7.2 Hz), 4.33 (2H, d, J=6.6 Hz), 4.52 (2H, d, J=7.2 Hz), 7.78 (1H, dd, J=2.0, 8.5 Hz), 8.29 (1H, d, J=8.5 Hz), 8.30 (1H, d, J=2.0 Hz), 11.16 (1H, s).

(2) To a solution of ethyl 6-bromo-2-cyclopropylmethyl-4-hydroxy-1-oxo-1,2-dihydro-3-isoquinolinecarboxylate (7.32 g, 20 mmol), 1-butanol (2.7 mL, 30 mmol) and tributylphosphine (10.0 mL, 40 mmol) in tetrahydrofuran (100 mL) was added 1,1'-(azodicarbonyl)dipiperidine (10.09 g, 40 mmol) and the mixture was stirred at room temperature for 3 h. The reaction mixture was concentrated under reduced pressure and the residue was purified, by silica gel column chromatography to give ethyl 6-bromo-4-butoxy-2-cyclopropylmethyl-1-oxo-1,2-dihydro-3-isoquinolinecarboxylate (7.24 g, 85.8%) as an oil.

$^1$H-NMR(CDCl$_3$) δ: 0.39–0.57 (4H, m), 1.02 (3H, t, J=7.1 Hz), 1.13–1.31 (1H, m), 1.45 (3H, t, J=7.2 Hz), 1.46–1.63 (2H, m), 1.73–1.87 (2H, m), 3.90 (2H, d, J=7.0 Hz), 3.96 (2H, t, J=6.6 Hz), 4.47 (2H, q, J=7.2 Hz), 7.65 (1H, dd, J=2.0, 8.6 Hz), 7.78 (1H, d, J=2.0 Hz), 8.29 (1H, dd, J=5.4, 8.6 Hz).

(3) To a solution of ethyl 6-bromo-4-butoxy-2-cyclopropylmethyl-1-oxo-1,2-dihydro-3-isoquinolinecarboxylate (7.18 g, 17 mmol) in tetrahydrofuran (20 mL) and ethanol (20 mL) was added an aqueous solution (10 mL) of sodium hydroxide (2.04 g, 51 mmol). The obtained mixture was refluxed under heating for 12 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals was recrystallized from ethyl acetate-diisopropyl ether to give 6-bromo-4-butoxy-2-cyclopropylmethyl-1-oxo-1,2-dihydro-3-isoquinolinecarboxylic acid (6.41 g, 95.7%) as crystals.

Melting point 166–167° C. Elemental analysis for $C_{18}H_{20}NO_4Br$ Calculated: C, 54.84; H, 5.11; N, 3.55. Found: C, 54.78; H, 4.98; N, 3.27. $^1$H-NMR(CDCl$_3$) δ: 0.41–0.57 (4H, m), 1.00 (3H, t, J=7.4 Hz), 1.22–1.35 (1H, m), 1.45–1.63 (2H, m), 1.75–1.89 (2H, m), 3.98–4.08 (4H, m), 7.63 (1H, dd, J=1.8, 8.8 Hz), 7.68 (1H, bs), 7.82 (1H, d, J=1.8 Hz), 8.24 (1H, d, J=8.8 Hz).

(4) To a solution of 6-bromo-4-butoxy-2-cyclopropylmethyl-1-oxo-1,2-dihydro-3-isoquinolinecarboxylic acid (6.31 g, 16 mmol) in tetrahydrofuran (50 mL were added oxalyl chloride (1.7 mL, 19.2 mmol) and N,N-dimethylformamide (2 drops), and the mixture was stirred at room temperature for 1 h. The reaction mixture was concentrated under reduced pressure and the residue was dissolved in tetrahydrofuran (20 mL). The obtained solution was added dropwise to a suspension of sodium tetrahydroborate (2.11 g, 56 mmol) in 1,2-dimethoxyethane (30 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-bromo-4-butoxy-2-cyclopropylmethyl-3-hydroxymethyl-1(2H)-isoquinolinone (5.87 g, 96.5%) as crystals.

Melting point 111–112° C. Elemental analysis for $C_{18}H_{22}NO_3Br$ Calculated: C, 56.85; H, 5.83; N, 3.68. Found: C, 56.69; H, 5.67; N, 3.59. $^1$H-NMR(CDCl$_3$) δ: 0.42–0.58 (4H, m), 1.04 (3H, t, J=7.1 Hz), 1.12–1.25 (1H, m), 1.49–1.68 (2H, m), 1.79–1.93 (2H, m), 2.48 (1H, bs), 3.88 (2H, t, J=6.6 Hz), 4.19 (2H, d, J=6.6 Hz), 4.83 (2H, s), 7.56 (1H, dd, J=2.0, 8.6 Hz), 7.79 (1H, d, J=2.0 Hz), 8.20 (1H, d, J=8.8 Hz).

(5) To a solution of 6-bromo-4-butoxy-2-cyclopropylmethyl-3-hydroxymethyl-1(2H)-isoquinolinone (5.70 g, 15 mmol) in toluene (50 mL) was added thionyl chloride (2.2 mL, 30 mmol). The obtained mixture was refluxed under heating for 2 h. The reaction mixture was poured into saturated aqueous sodium hydrogencarbonate solution, and extracted with ethyl acetate. The extract was washed with brine, dried over anhydrous magnesium sulfate and concentrated under reduced pressure to give 6-bromo-4-butoxy-3-chloromethyl-2-cyclopropylmethyl-1(2H)-isoquinolinone (5.72 g, 95.7%) as crystals.

$^1$H-NMR(CDCl$_3$) δ: 0.44–0.61 (4H, m), 1.02–1.30 (4H, m), 1.53–1.68 (2H, m), 1.71–1.97 (2H, m), 4.00 (2H, t, J=6.4 Hz), 4.21 (2H, d, J=6.6 Hz), 4.84 (2H, s), 7.63 (1H, dd, J=1.8, 8.4 Hz), 7.88 (1H, d, J=1.8 Hz), 8.29 (1H, d, J=8.4 Hz).

(6) A solution of 6-bromo-4-butoxy-3-chloromethyl-2-cyclopropylmethyl-1(2H)-isoquinolinone (5.58 g, 14 mmol) and potassium phthalimide (3.89 g, 21 mmol) in N,N-dimethylformamide (50 mL) was stirred at room temperature for 5 h. The reaction mixture was poured into water and extracted with ethyl acetate. After washing the extract with water, the extract was dried over anhydrous magnesium sulfate and concentrated under reduced pressure. The obtained crystals were recrystallized from tetrahydrofuran-n-hexane to give 2-[(6-bromo-4-butoxy-2-cyclopropylmethyl-1-oxo-1,2-dihydro-3-isoquinolinyl)methyl]-1H-isoindole-1,3(2H)-dione (6.57 g, 94.7%) as crystals.

Melting point 156–157° C. Elemental analysis for $C_{26}H_{25}N_2O_4Br$ Calculated: C, 61.30; H, 4.95; N, 5.50. Found: C, 61.39; H, 5.06; N, 5.47. $^1$H-NMR(CDCl$_3$) δ: 0.45–0.50 (4H, m), 0.97–1.08 (4H, m), 1.44–1.61 (1H, m), 1.79–1.93 (2H, m), 3.99 (2H, t, J=6.7 Hz), 4.16 (2H, d, J=6.2 Hz), 5.07 (2H, s), 7.59 (1H, dd, J=2.0, 8.8 Hz), 7.71–7.85 (4H, m) 7.86 (1H, d, J=2.0 Hz), 8.27 (1H, d, J=8.8 Hz).

(7) To a solution of 2-[(6-bromo-4-butoxy-2-cyclopropylmethyl-1-oxo-1,2-dihydro-3-isoquinolinyl)methyl]-1H-isoindole-1,3(2H)-dione (6.62 g, 13 mmol) in ethanol (50 mL) was added hydrazine monohydrate (0.13 mL, 2.7 mmol). The obtained mixture was refluxed under heating for 1 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (30 mL) and di-t-butyl dicarbonate (4.5 mL, 19.5 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-n-hexane to give tert-butyl(6-bromo-4-butoxy-2-cyclopropylmethyl-1-oxo-1,2-dihydro-3-isoquinolinyl)methylcarbamate (4.41 g, 70.8%) as crystals.

Melting point 118–119° C. Elemental analysis for $C_{23}H_{31}N_2O_4Br$ Calculated: C, 57.62; H, 6.52; N, 5.84. Found: C, 57.79; H, 6.37; N, 5.71. $^1$H-NMR(CDCl$_3$) δ: 0.50–0.55 (4H, m), 1.05 (3H, t, J=7.3 Hz), 1.13–1.26 (1H, m), 1.46 (9H, s), 1.47–1.68 (2H, m), 1.80–1.94 (2H, m), 3.86 (2H, t, J=6.5 Hz), 4.09 (2H, d, J=7.0 Hz), 4.53 (2H, d, J=5.6 Hz), 4.79 (1H, bs), 7.58 (1H, dd, J=2.0, 8, 6 Hz), 7.82 (1H, d, J=2.0 Hz), 8.26 (1H, d, J=8.6 Hz).

(8) A mixture of tert-butyl(6-bromo-4-butoxy-2-cyclopropylmethyl- 1-oxo-1,2-dihydro-3-isoquinolinyl)-methylcarbamate (4.08 g, 8.5 mmol), 1,3-bis(diphenylphosphino)propane (0.35 g, 0.85 mmol) and triethylamine (1.3 mL, 9.4 mmol) in dimethyl sulfoxide (60 mL) and methanol (40 mL) was stirred under a carbon monoxide atmosphere at room temperature for 30 min. To the obtained mixture was added palladium acetate (0.19 g, 0.85 mmol) and the mixture was stirred under a carbon monoxide atmosphere at 70° C. for 15 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 4-butoxy-3-[[(tert-butoxycarbonyl)amino]methyl]-2-cyclopropylmethyl-1-oxo-1,2-dihydro-6-isoquinolinecarboxylate (3.41 g, 87.7%) as crystals.

Melting point 139–140° C. Elemental analysis for $C_{25}H_{34}N_2O_6$ Calculated: C, 65.48; H, 7.47; N, 6.11. Found: C, 65.59; H, 7.53; N, 6.13. $^1$H-NMR(CDCl$_3$) δ: 0.52–0.55 (4H, m), 1.06 (3H, t, J=7.4 Hz), 1.15–1.30 (1H, m), 1.46 (9H, s), 1.53–1.68 (2H, m), 1.83–1.97 (2H, m), 3.91 (2H, t, J=6.4 Hz), 3.99 (3H, s), 3.91 (2H, d, J=6.6 Hz), 4.56 (2H, d, J=5.4 Hz), 4.81 (1H, bs), 8.09 (1H, dd, J=1.6, 8.4 Hz), 8.40 (1H, d, J=1.6 Hz), 8.48 (1H, d, J=8.4 Hz,).

(9) To a solution of methyl 4-butoxy-3-[[(tert-butoxycarbonyl)amino]methyl]-2-cyclopropylmethyl-1-oxo-1,2-dihydro-6-isoquinolinecarboxylate (2.98 g, 6.5 mmol) in tetrahydrofuran (10 mL) and methanol (10 mL) was added 1N sodium hydroxide (10 mL). The obtained mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 4-butoxy-3-[[(tert-butoxycarbonyl)amino]methyl]-2-cyclopropylmethyl-1-oxo-1,2-dihydro-6-isoquinolinecarboxylic acid (2.62 g, 90.7%) as crystals.

Melting point 197–198° C. Elemental analysis for $C_{24}H_{32}N_2O_6$ Calculated: C, 64.85; H, 7.26; N, 6.30. Found: C, 64.95; H, 7.26; N, 6.29. $^1$H-NMR(CDCl$_3$) δ: 0.51–0.53 (4H, m), 1.07 (3H, t, J=7.3 Hz), 1.13–1.30 (1H, m), 1.50 (9H, s), 1.53–1.72 (2H, m), 1.85–1.99 (2H, m), 3.91 (2H, t, J=6.2 Hz), 4.09 (2H, d, J=6.6 Hz), 4.56 (2H, d, J=5.0 Hz), 4.47 (1H, bs), 8.08 (1H, d, J=8.5 Hz), 8.30 (1H, bs), 8.39 (1H, d, J=8.5 Hz).

(10) A solution 4-butoxy-3-[[(tert-butoxycarbonyl)amino] methyl]-2-cyclopropylmethyl-1-oxo-1,2-dihydro-6-isoquinolinecarboxylic acid (0.89 g, 2 mmol), 1-ethyl-3-(3-dimethylaminopropyl)carbodiimide hydrochloride (0.77 g, 4 mmol) and 1-hydroxybenzotriazole ammonium salt (0.61 g, 4 mmol) in N,N-dimethylformamide (10 mL) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give 4-butoxy-3-[[(tert-butoxycarbonyl) amino]methyl]-2-cyclopropylmethyl-1-oxo-1,2-dihydro-6-isoquinolinecarboxamide (0.82 g, 93.2%) as crystals.

Melting point 202–203° C. Elemental analysis for $C_{24}H_{33}N_3O_5$ Calculated: C, 64.99; H, 7.50; N, 9.47. Found:

C, 64.89; H, 7.68; N, 9.42. $^1$H-NMR(CDCl$_3$) δ: 0.52–0.56 (4H, m), 1.03 (3H, t, J=7.1 Hz), 1.18–1.29 (1H, m), 1.48 (9H, s), 1.49–1.66 (2H, m), 1.86–1.94 (2H, m), 3.87 (2H, t, J=6.6 Hz), 4.10 (2H, d, J=6.6 Hz), 4.54 (2H, d, J=5.4 Hz), 5.24 (1H, bs), 6.03 (1H, bs), 6.60 (1H, bs), 7.72 (1H, dd, J=1.6, 8.4 Hz), 8.04 (1H, d, J=1.6 Hz), 8.29 (1H, d, J=8.4 Hz).

(11) To a solution of 4-butoxy-3-[[(tert-butoxycarbonyl)amino]methyl]-2-cyclopropylmethyl-1-oxo-1,2-dihydro-6-isoquinolinecarboxamide (0.27 g, 0.6 mmol) in ethyl acetate (5 mL) was added a solution of 4N hydrogen chloride in ethyl acetate (5 mL) and the obtained solution was stirred at room temperature for 1 h. The reaction mixture was concentrated under reduced pressure, and the precipitated crystals were recrystallized from methanol-diethyl ether to give 3-(aminomethyl)-4-butoxy-2-cyclopropylmethyl-1-oxo-1,2-dihydro-6-isoquinolinecarboxamide hydrochloride (0.21 g, 91.3%) as crystals.

Melting point 164–165° C. Elemental analysis for C$_{19}$H$_{26}$N$_3$O$_3$Cl 0.5H$_2$O Calculated: C, 58.68; H, 7.00; N, 10.81. Found: C, 59.03; H, 6.85; N, 10.82. $^1$H-NMR (DMSO-d$_6$) δ: 0.45–0.49 (4H, m), 1.01 (3H, t, J=7.3 Hz), 1.09–1.21 (1H, m), 1.52–1.63 (2H, m), 1.83–1.99 (2H, m), 3.99 (2H, t, J=5.9 Hz), 4.08 (2H, d, J=6.4 Hz), 4.23 (2H, s), 7.71 (1H, s), 8.05 (1H, d, J=8.2 Hz), 8.23 (1H, s), 8.33 (1H, d, J=8.2 Hz), 8.38 (1H, s), 8.68 (3H, bs).

Example 147

3-(Aminomethyl)-4-butoxy-2-cyclopropylmethyl-6-(1,3-oxazol-5-yl)-1(2H)-isoquinolinone hydrochloride (1) To a solution of 4-butoxy-3-[[(tert-butoxycarbonyl)amino]methyl]-2-cyclopropylmethyl-1-oxo-1,2-dihydro-6-isoquinolinecarboxylic acid (Example 146 (9)) (0.45 g, 3.5 mmol) and N-methylmorpholine (0.13 mL, 1.2 mmol) in tetrahydrofuran (10 mL) was added ethyl chloroformate (0.12 mL, 1.2 mmol) at 0° C. and the mixture was stirred at 0° C. for 10 min. To the obtained mixture were added sodium tetrahydroborate (0.11 g, 3 mmol) and methanol (5 mL), and the mixture was stirred at 0° C. for 1 h. The reaction mixture was poured into water and extracted with ethyl acetate. The extract was washed with brine, dried over anhydrous magnesium sulfate and concentrated under reduced pressure. The precipitated crystals were recrystallized from ethyl acetate-diisopropyl ether to give tert-butyl (4-butoxy-2-cyclopropylmethyl-6-hydroxymethyl-1-oxo-1,2-dihydro-3-isoquinolinyl)methylcarbamate (0.33 g, 76.7%) as crystals.

Melting point 171–172° C. Elemental analysis for C$_{24}$H$_{34}$N$_2$O$_5$ Calculated: C, 66.95; H, 7.96; N, 6.51. Found: C, 66.65; H, 7.82; N, 6.63. $^1$H-NMR(CDCl$_3$) δ: 0.51–0.56 (4H, m), 1.00 (3H, t, J=7.3 Hz), 1.19–1.26 (1H, m), 1.49–1.57 (11H, m), 1.79–1.93 (2H, m), 2.27 (1H, bs), 3.82 (2H, t, J=6.8 Hz), 4.07 (2H, d, J=6.6 Hz), 4.51 (2H, d, J=5.4 Hz), 4.80 (2H, s), 5.53 (1H, s), 7.38 (1H, d, J=8.2 Hz), 7.46 (1H, s), 8.13 (1H, d, J=8.2 Hz).

(2) To a solution of 4 tert-butyl(4-butoxy-2-cyclopropylmethyl-6-hydroxymethyl-1-oxo-1,2-dihydro-3-isoquinolinyl)methylcarbamate (0.45 g, 3.5 mmol) in tetrahydrofuran (10 mL) was added manganese dioxide (0.12 g) and the mixture was stirred at room temperature for 12 h. Manganese dioxide was filtered off, and the filtrate was concentrated under reduced pressure. The residue was purified by silica gel column chromatography to give tert-butyl(4-butoxy-2-cyclopropylmethyl-6-formyl-1-oxo-1,2-dihydro-3-isoquinolinyl)methylcarbamate (0.33 g, 76.7%) as crystals.

Melting point 151–152° C. Elemental analysis for C$_{24}$H$_{32}$N$_2$O$_5$ Calculated: C, 67.27; H, 7.53; N, 6.54. Found: C, 67.08; H, 7.55; N, 6.54. $^1$H-NMR(CDCl$_3$) δ: 0.53–0.56 (4H, m), 1.06 (3H, t, J=7.3 Hz), 1.16–1.28 (1H, m), 1.47 (9H, s), 1.55–1.68 (2H, m), 1.87–1.96 (2H, m), 3.92 (2H, t, J=6.4 Hz), 4.14 (2H, d, J=6.6 Hz), 4.57 (2H, d, J=5.7 Hz), 4.82 (1H, bs), 7.96 (1H, dd, J=1.8, 8.4 Hz), 8.19 (1H, d, J=1.8 Hz), 8.57 (1H, d, J=8.4 Hz), 10.19 (1H, s).

(3) A solution of tert-butyl(4-butoxy-2-cyclopropylmethyl-6-formyl-1-oxo-1,2-dihydro-3-isoquinolinyl)methylcarbamate (0.34 g, 0.8 mmol) p-toluenesulfonylmethyl isocyanide (0.16 g, 0.8 mmol) and potassium carbonate (0.22 g, 1.6 mmol) in methanol (10 mL) was refluxed under heating for 30 min. The reaction mixture was poured into water and extracted with ethyl acetate. The extract was washed with brine, dried over anhydrous magnesium sulfate and concentrated under reduced pressure. The residue was purified by silica gel column chromatography and the precipitated crystals were recrystallized from ethyl acetate-diisopropyl ether to give tert-butyl[4-butoxy-2-cyclopropylmethyl-6-(1,3-oxazol-5-yl)-1-oxo-1,2-dihydro-3-isoquinolinyl]methylcarbamate (0.33 g, 76.7%), as crystals.

Melting point 160–161° C. Elemental analysis for C$_{26}$H$_{33}$N$_3$O$_5$ Calculated: C, 66.79; H, 7.11; N, 8.99. Found: C, 66.63; H, 7.14; N, 9.01. $^1$H-NMR(CDCl$_3$) δ: 0.52–0.56 (4H, m), 1.07 (3H, t, J=7.2 Hz), 1.12–1.26 (1H, m), 1.47 (9H, s), 1.58–1.71 (2H, m), 1.87–1.96 (2H, m), 3.92 (2H, t, J=6.6 Hz), 4.12 (2H, d, J=6.6 Hz), 4.56 (2H, d, J=5.7 Hz), 4.84 (1H, bs), 7.53 (1H, s), 7.75 (1H, dd, J=1.5, 8.4 Hz), 7.97 (1H, d, J=1.5 Hz), 8.02 (1H, s), 8.46 (1H, d, J=8.4 Hz).

(4) To a solution of tert-butyl[4-butoxy-2-cyclopropylmethyl-6-(1,3-oxazol-5-yl)-1-oxo-1,2-dihydro-3-isoquinolinyl]methylcarbamate (0.19 g, 0.4 mmol) in ethyl acetate (5 mL) was added a solution of 4N hydrogen chloride in ethyl acetate (5 mL) and the obtained solution was stirred at room temperature for 1 h. The reaction mixture was concentrated under reduced pressure, and the precipitated crystals were recrystallized from methanol-diethyl ether to give 3-(aminomethyl)-4-butoxy-2-cyclopropylmethyl-6-(1,3-oxazol-5-yl)-1(2H)-isoquinolinone hydrochloride (0.15 g, 93.8%) as crystals.

Melting point 124–126° C. Elemental analysis for C$_{21}$H$_{26}$N$_3$O$_3$Cl 1.25H$_2$O Calculated: C, 59.15; H, 6.74; N, 9.85. Found: C, 59.12; H, 6.58; N, 9.71. $^1$H-NMR(DMSO-d$_6$) δ: 0.46–0.49 (4H, s), 1.03 (3H, t, J=7.2 Hz), 1.15–1.28 (1H, m), 1.54–1.69 (2H, m), 1.83–1.95 (2H, m), 3.99 (2H, t, J=6.2 Hz), 4.08 (2H, d, J=6.6 Hz), 4.23 (2H, d, J=5.4 Hz), 7.99–8.01 (3H, m), 8.36 (1H, d, J=9.2 Hz), 8.63 (1H, s), 8.74 (3H, bs).

Example 148

(E)-3-[3-(Aminomethyl)-4-butoxy-2-cyclopropylmethyl-1-oxo-1,2-dihydro-6-isoquinolinyl]-2-propenamide hydrochloride (1) To a solution of ethyl diethylphosphonoacetate (0.99 mL, 5 mmol) in N,N-dimethylformamide (30 mL) was added. sodium hydride (0.20 g, 5 mmol) (60% in oil) and the mixture was stirred at room temperature for 10 min. To the obtained mixture was added a solution of tert-butyl (4-butoxy-2-cyclopropylmethyl-6-formyl-1-oxo-1,2-dihydro-3-isoquinolinyl)methylcarbamate (Example 2 (2))(2.14 g, 5 mmol) in N,N-dimethylformamide (20 mL) and the mixture was stirred at room temperature for 3 h. The reaction mixture was poured into water and extracted with ethyl acetate. The extract was washed with brine, dried over anhydrous magnesium sulfate and concentrated under reduced pressure. The residue was purified by silica gel column chromatography to give ethyl (E)-3-(4-butoxy-3-[[(tert-butoxycarbonyl)amino]methyl]-2-cyclopropylmethyl-1-oxo-1,2-dihydro-3-isoquinolinyl)-2-propenate (1.92 g, 77.1%) as crystals.

Melting point 166–167° C. Elemental analysis for $C_{28}H_{38}N_2O_6$ Calculated: C, 67.45; H, 7.68; N, 5.62. Found: C, 67.40; H, 7.65; N, 5.44. $^1$H-NMR(CDCl$_3$) δ: 0.51–0.55 (4H, m), 1.06 (3H, t, J=7.1 Hz), 1.14–1.27 (1H, m), 1.37 (3H, t, J=7.2 Hz), 1.46 (9H, s), 1.47–1.69 (2H, m), 1.83–1.97 (2H, m), 3.89 (2H, t, J=6.4 Hz), 4.12 (2H, d, J=6.6 Hz), 4.30 (2H, q, J=7.2 Hz), 4.55 (2H, d, J=5.4 Hz), 4.78 (1H, bs), 6.58 (1H, d, J=15.8 Hz), 7.66 (1H, dd, J=1.8, 8.4 Hz), 7.78 (1H, d, J=1.8 Hz), 7.79 (1H, d, J=15.8 Hz), 8.42 (1H, d, J=8.4 Hz).

(2) To a solution of ethyl (E)-3-(4-butoxy-3-[[(tert-butoxycarbonyl)amino]methyl]-2-cyclopropylmethyl-1-oxo-1,2-dihydro-3-isoquinolinyl)-2-propenate (1.00 g, 2 mmol) in tetrahydrofuran (10 mL) and ethanol (10 mL) was added 1N sodium hydroxide (4 mL). The obtained mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from tetrahydrofuran-diisopropyl ether to give (E)-3-(4-butoxy-3-[[(tert-butoxycarbonyl)amino]methyl]-2-cyclopropylmethyl-1-oxo-1,2-dihydro-3-isoquinolinyl)-2-propenic acid (0.92 g, 97.9%) as crystals.

Melting point 229–230° C. Elemental analysis for $C_{26}H_{34}N_2O_6$ Calculated: C, 66.36; H, 7.28; N, 5.95. Found: C, 66.05; H, 7.22; N, 5.66. $^1$H-NMR(CDCl$_3$) δ: 0.50–0.55 (4H, m), 1.07 (3H, t, J=7.3 Hz), 1.12–1.28 (1H, m), 1.48 (9H, s), 1.49–1.70 (2H, m), 1.84–1.98 (2H, m), 3.89 (2H, t, J=6.6 Hz), 4.10 (2H, d, J=6.6 Hz), 4.55 (2H, d, J=5.0 Hz), 5.12 (1H, bs), 6.59 (1H, d, J=16.0 Hz), 7.64 (1H, d, J=8.2 Hz), 7.73 (1H, s), 7.85 (1H, d, J=16.0 Hz), 8.38 (1H, d, J=8.2 Hz).

(3) A solution of (E)-3-(4-butoxy-3-[[(tert-butoxycarbonyl)amino]methyl]-2-cyclopropylmethyl-1-oxo-1,2-dihydro-3-isoquinolinyl)-2-propenic acid (0.71 g, 1.5 mmol), 1-ethyl-3-(3-dimethylaminopropyl)carbodiimide hydrochloride (0.58 g, 3 mmol) and 1-hydroxybenzotriazole ammonium salt (0.46 g, 3 mmol) in N,N-dimethylformamide (10 mL) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give (E)-3-(4-butoxy-3-[[(tert-butoxycarbonyl)amino]methyl]-2-cyclopropylmethyl-1-oxo-1,2-dihydro-3-isoquinolinyl)-2-propenamide (0.67 g, 95.7%) as crystals.

Melting point 198–199° C. Elemental analysis for $C_{26}H_{35}N_3O_5$ 0.5H$_2$O Calculated: C, 65.87; H, 7.55; N, 8.86. Found: C, 65.86; H, 7.89; N, 8.68. $^1$H-NMR(CDCl$_3$) δ: 0.50–0.54 (4H, m), 1.04 (3H, t, J=7.4 Hz), 1.12–1.26 (1H, m), 1.47 (9H, s), 1.48–1.67 (2H, m), 1.81–1.95 (2H, m), 3.88 (2H, t, J=6.4 Hz), 4.10 (2H, d, J=6.6 Hz), 4.54 (2H, d, J=5.2 Hz), 5.40 (1H, bs); 5.89 (1H, bs), 6.05 (1H, bs), 6.60 (1H, d, J=15.8 Hz), 7.56 (1H, dd, J=1.5, 8.4 Hz), 7.69 (1H, d, J=1.5 Hz), 7.73 (1H, d, J=15.8 Hz), 8.31 (1H, d, J=8.4 Hz).

(4) To a solution of (E)-3-(4-butoxy-3-[[(tert-butoxycarbonyl)amino]methyl]-1-cyclopropylmethyl-1-oxo-1,2-dihydro-3-isoquinolinyl)-2-propenamide (0.38 g, 0.8 mmol) in ethyl acetate (5 mL) was added a solution of 4N hydrogen chloride in ethyl acetate (5 mL) and the obtained solution was stirred at room temperature for 2 h. The reaction mixture was concentrated under reduced pressure, and the precipitated crystals were recrystallized from methanol-diisopropyl ether to give (E)-3-[3-(aminomethyl)-4-butoxy-2-cyclopropylmethyl-1-oxo-1,2-dihydro-6-isoquinolinyl]-2-propenamide hydrochloride (0.31 g, 96.9%) as crystals.

Melting point 188–190° C. Elemental analysis for $C_{21}H_{28}N_3O_3Cl$ 2H$_2$O Calculated: C, 57.07; H, 7.30; N, 9.51. Found: C, 56.82; H, 7.06; N, 9.49. $^1$H-NMR(DMSO-d$_6$) δ: 0.45–0.48 (4H, m), 1.02 (3H, t, J=6.9 Hz), 1.13–1.24 (1H, m), 1.47–1.69 (2H, m), 1.79–1.99 (2H, m), 4.05 (2H, bs), 4.22 (2H, bs), 4.32 (2H, bs), 6.85 (1H, d, J=15.4 Hz), 7.28 (1H, bs), 7.63 (1H, d, J=15.4 Hz), 7.80–7.88 (3H, m), 8.30 (1H, d, J=7.0 Hz), 8.68 (3H, bs).

Example 149

2-[[3-(Aminomethyl)-4-butoxy-2-cyclopropylmethyl-1-oxo-1,2-dihydro-6-isoquinolinyl]oxy]acetamide hydrochloride (1) A solution of 4-fluorophthalic anhydride (24.99 g, 150 mmol) and ethyl 2-(cyclopropylmethylamino)acetate (23.58 g, 150 mmol) in tetrahydrofuran (200 mL) was stirred at room temperature for 1 h. The reaction mixture was poured into water and extracted with ethyl acetate. The extract was washed with brine, dried over anhydrous magnesium sulfate and concentrated under reduced pressure. The residue was dissolved, in N,N-dimethylformamide (200 mL) and potassium carbonate (20.73 g, 150 mmol) and ethyl iodide (14.4 mL, 180 mmol) were added. The mixture was stirred at room temperature for 3 h. The reaction mixture was poured into water and extracted with ethyl acetate. The extract was washed with brine, dried over anhydrous magnesium sulfate and concentrated under reduced pressure. The residue was dissolved in ethanol (300 mL) and a solution of 20% sodium ethoxide ethanol solution (102 g, 300 mmol) was added thereto. The mixture was stirred at room temperature for 1 h. The reaction mixture was poured into 1N hydrochloric acid (300 mL) and extracted with ethyl acetate. The extract was washed with brine, dried over anhydrous magnesium sulfate and concentrated under reduced pressure. The residue was purified by silica gel column chromatography and the component eluted earlier was concentrated to give ethyl 2-cyclopropylmethyl-7-fluoro-4-hydroxy-1-oxo-1,2-dihydro-3-isoquinolinecarboxylate (13.11 g, 28.6%) as crystals.

Melting point 88–89° C. Elemental analysis for $C_{16}H_{16}NO_4F$ Calculated: C, 62.94; H, 5.28; N, 4.59. Found: C, 62.96; H, 5.23; N, 4.61. $^1$H-NMR(CDCl$_3$) δ: 0.34–0.52 (4H, m), 1.04–1.13 (1H, m), 1.48 (3H, t, J=7.2 Hz), 4.35 (2H, d, J=6.9 Hz), 4.51 (2H, d, J=7.2 Hz), 7.44–7.50 (1H, m), 8.09 (1H, dd, J=2.6, 6.2 Hz), 8.19 (1H, dd, J=6.2, 8.4 Hz), 11.36 (1H, s).

The component eluted later was concentrated to give ethyl 2-cyclopropylmethyl-6-fluoro-4-hydroxy-1-oxo-1,2-dihydro-3-isoquinolinecarboxylate (9.34 g, 20.4%) as crystals.

Melting point 61–62° C. Elemental analysis for $C_{16}H_{16}NO_4F$ Calculated: C, 62.94; H, 5.28; N, 4.59. Found: C, 62.75; H, 5.14; N, 4.64. $^1$H-NMR(CDCl$_3$) δ: 0.32–0.54 (4H, m), 1.00–1.16 (1H, m), 1.48 (3H, t, J=7.2 Hz), 4.33 (2H, d, J=7.0 Hz), 4.52 (2H, d, J=7.2 Hz), 7.33–7.43 (1H, m), 7.78 (1H, dd, J=2.6, 9.2 Hz), 8.46 (1H, dd, J=5.4, 8.8 Hz), 11.14 (1H, s).

(2) To a solution of ethyl 2-cyclopropylmethyl-6-fluoro-4-hydroxy-1-oxo-1,2-dihydro-3-isoquinolinecarboxylate (9.16 g, 30 mmol), 1-butanol (3.3 mL, 45 mmol) and tributylphosphine (14.9 mL, 60 mmol) in tetrahydrofuran (100 mL) was added 1,1'-(azodicarbonyl)dipiperidine (15.14 g, 60 mmol) and the mixture was stirred at room temperature for 3 h. The reaction mixture was concentrated under reduced pressure and the residue was purified by silica gel column chromatography to give ethyl 4-butoxy-2-cyclopropylmethyl-6-fluoro-1-oxo-1,2-dihydro-3-isoquinolinecarboxylate (9.24 g, 85.2%) as an oil.

$^1$H-NMR(CDCl$_3$) δ: 0.39–0.57 (4H, m), 1.01 (3H, t, J=7.3 Hz), 1.12–1.21 (1H, m), 1.41–1.62 (5H, m), 1.73–1.87 (2H, m), 3.91 (2H, d, J=6.8 Hz), 3.96 (2H, t, J=6.6 Hz), 4.47 (2H, q, J=7.3 Hz), 7.19–7.30 (1H, m), 8.73 (1H, dd, J=2.4, 9.4 Hz), 8.46 (1H, dd, J=5.4, 8.8 Hz).

(3) To a solution of ethyl 4-butoxy-2-cyclopropylmethyl-6-fluoro-1-oxo-1,2-dihydro-3-isoquinolinecarboxylate (9.03 g, 25 mmol) in tetrahydrofuran (30 mL) and ethanol (30 mL) was added sodium hydroxide (3.00 g, 75 mmol). The obtained mixture was refluxed under heating for 12 h. The reaction mixture was poured into water, acidified with 1N hydrochloric acid and extracted with ethyl acetate. The extract was washed with brine, dried over anhydrous magnesium sulfate and concentrated under reduced pressure. The residue was dissolved in benzyl alcohol (20 mL) and the obtained solution was added dropwise to a solution of sodium hydride (5.0 g, 125 mmol)(60% in oil) in benzyl alcohol (20 mL). The obtained mixture was stirred at 150° C. for 12 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from tetrahydrofuran-diisopropyl ether to give 6-benzyloxy-4-butoxy-2-cyclopropylmethyl-1-oxo-1,2-dihydro-3-isoquinolinecarboxylic acid (7.31 g, 69.4%) as crystals.

Melting point 178–179° C. Elemental analysis for C$_{25}$H$_{27}$NO$_5$ Calculated: C, 71.24; H, 6.46; N, 3.32. Found: C, 71.21; H, 6.68; N, 3.23. $^1$H-NMR(CDCl$_3$) δ: 0.41–0.52 (4H, m), 0.97 (3H, t, J=7.4 Hz), 1.18–1.32 (1H, m), 1.38–1.57 (2H, m), 1.67–1.80 (2H, m), 3.88 (2H, t, J=6.4 Hz), 4.00 (2H, d, J=7.0 Hz), 5.17 (2H, s), 6.55 (1H, bs), 6.98 (1H, d, J=2.5 Hz), 7.16 (1H, dd, J=2.5, 8.8 Hz), 7.30–7.44 (5H, m), 8.25 (1H, d, J=8.8 Hz).

(4) To a solution of 6-benzyloxy-4-butoxy-2-cyclopropylmethyl-1-oxo-1,2-dihydro-3-isoquinolinecarboxylic acid (7.16 g, 17 mmol) in tetrahydrofuran (50 mL) were added oxalyl chloride (1.8 mL, 20.4 mmol) and N,N-dimethylformamide (3 drops), and the mixture was stirred at room temperature for 1 h. The reaction mixture was concentrated under reduced pressure, and the residue was dissolved in tetrahydrofuran (30 mL). The obtained solution was added dropwise to a suspension of sodium tetrahydroborate (2.25 g, 59.5 mmol) in 1,2-dimethoxyethane (50 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-n-hexane to give 6-benzyloxy-4-butoxy-2-cyclopropylmethyl-3-hydroxymethyl-1(2H)-isoquinolinone (1.72 g, 57.1%) as crystals.

Melting point 96–97° C. Elemental analysis for C$_{25}$H$_{29}$NO$_4$ Calculated: C, 73.68; H, 7.17; N, 3.44. Found: C, 73.53; H, 7.10; N, 3.39. $^1$H-NMR(CDCl$_3$) δ: 0.45–0.55 (4H, m), 1.02 (3H, t, J=7.3 Hz), 1.12–1.24 (1H, m), 1.44–1.62 (2H, m), 1.72–1.86 (2H, m), 3.79 (2H, t, J=6.6 Hz), 4.17 (2H, d, J=6.4 Hz), 4.82 (2H, d, J=5.2 Hz), 5.19 (2H, s), 7.05 (1H, d, J=2.6 Hz), 7.11 (1H, dd, J=2.6, 8.8 Hz), 7.31–7.48 (5H, m), 8.28 (1H, d, J=8.8 Hz).

(5) To a suspension of 6-benzyloxy-4-butoxy-2-cyclopropylmethyl-3-hydroxymethyl-1(2H)-isoquinolinone (6.11 g, 15 mmol) in toluene (50 mL) was added thionyl chloride (2.2. mL, 30 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-4-butoxy-3-chloromethyl-2-cyclopropylmethyl-1(2H)-isoquinolinone (6.17 g, 96.7%) as crystals.

$^1$H-NMR(CDCl$_3$) δ: 0.47–0.55 (4H, m), 1.03 (3H, t, J=7.5 Hz), 1.06–1.18 (1H, m), 1.48–1.63 (2H, m), 1.79–1.86 (2H, m), 3.90 (2H, t, J=6.6 Hz), 4.20 (2H, d, J=6.6 Hz), 4.84 (2H, s), 5.22 (2H, s), 7.14–7.26 (2H, m), 7.34–7.47 (5H, m), 8.36 (1H, d, J=9.0 Hz).

(6) A solution of 6-benzyloxy-4-butoxy-3-chloromethyl-2-cyclopropylmethyl-1(2H)-isoquinolinone (5.96 g, 14, mmol) and potassium phthalimide (3.89 g, 21 mmol) in N,N-dimethylformamide (50 mL) was stirred at room temperature for 6 h. The reaction mixture was poured into water and extracted with ethyl acetate. After washing the extract with water, the extract was dried over anhydrous magnesium sulfate and concentrated under reduced pressure. The obtained crystals were recrystallized from ethyl acetate-diisopropyl ether to give 2-[(6-benzyloxy-4-butoxy-2-cyclopropylmethyl-1-oxo-1,2-dihydro-3-isoquinolinyl)methyl]-1H-isoindole-1,3(2H)-dione (7.14 g, 95.1%) as crystals.

Melting point 127–128° C. Elemental analysis for C$_{33}$H$_{32}$N$_2$O$_5$ Calculated: C, 73.86; H, 6.01; N, 5.22. Found: C, 73.73; H, 5.79; N, 5.22. $^1$H-NMR(CDCl$_3$) δ: 0.43–0.48 (4H, m), 0.97 (3H, t, J=7.3 Hz), 1.01–1.04 (1H, m), 1.37–1.55 (2H, m), 1.71–1.86 (2H, m), 3.89 (2H, t, J=6.8 Hz), 4.15 (2H, d, J=6.2 Hz), 5.06 (2H, s), 5.20 (2H, s), 7.12–7.17 (2H, m), 7.30–7.46 (5H, m), 7.70–7.86 (4H, m), 8.32–8.38 (1H, m).

(7) To a solution of 2-[(6-benzyloxy-4-butoxy-2-cyclopropylmethyl-1-oxo-1,2-dihydro-3-isoquinolinyl)methyl]-1H-isoindole-1,3(2H)-dione (6.97 g, 13 mmol) in ethanol (50 mL) was added hydrazine monohydrate (1.9 mL, 39 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (50 mL) and di-t-butyl dicarbonate (4.5 mL, 19.5 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-n-hexane to give tert-butyl(6-benzyloxy-4-butoxy-2-cyclopropylmethyl-1-oxo-1,2-dihydro-3-isoquinolinyl)methylcarbamate (6.34 g, 96.4%) as crystals.

Melting point 106–107° C. Elemental analysis for C$_{30}$H$_{38}$N$_2$O$_5$ 0.25H$_2$O Calculated: C, 70.50; H, 7.59; N, 5.48. Found: C, 70.61; H, 7.48; N, 5.45. $^1$H-NMR(CDCl$_3$) δ: 0.49–0.52 (4H, m), 1.02 (3H, t, J=7.3 Hz), 1.15–1.26 (1H, m), 1.46 (9H, s), 1.51–1.62 (2H, m), 1.72–1.87 (2H, m), 3.77 (2H, t, J=6.5 Hz), 4.08 (2H, d, J=5.6 Hz), 4.51 (2H, d, J=5.6

Hz), 4.79 (1H, bs), 5.21 (2H, s), 7.07 (1H, d, J=2.6 Hz), 7.14 (1H, dd, J=2.6, 8.8 Hz), 7.33–7.49 (5H, m), 8.34 (1H, d, J=8.8 Hz).

(8) A suspension of tert-butyl(6-benzyloxy-4-butoxy-2-cyclopropylmethyl-1-oxo-1,2-dihydro-3-isoquinolinyl)-methylcarbamate (6.08 g, 12 mmol) and 5% palladium carbon (2.0 g), in tetrahydrofuran (30 mL) and ethanol (30 mL) was stirred under a hydrogen atmosphere at room temperature for 2 h. The catalyst was filtered off and the filtrate was concentrated under reduced pressure. The obtained crystals were recrystallized from tetrahydrofuran-diisopropyl ether to give tert-butyl (4-butoxy-2-cyclopropylmethyl-6-hydroxy-1-oxo-1,2-dihydro-3-isoquinolinyl)methylcarbamate (4.87 g, 97.6%) as crystals.

Melting point 164–166° C. Elemental analysis for $C_{23}H_{32}N_2O_5$ Calculated: C, 66.32; H, 7.74; N, 6.73. Found: C, 66.16; H, 7.69; N, 6.82. $^1$H-NMR(CDCl$_3$) δ: 0.48–0.52 (4H, m), 0.96 (3H, t, J=7.4 Hz), 1.13–1.26 (1H, m), 1.45–1.58 (11H, m), 1.69–1.84 (2H, m), 3.83 (2H, t, J=6.2 Hz), 4.12 (2H, d, J=6.6 Hz), 4.53 (2H, d, J=5.2 Hz), 4.89 (1H, bs), 7.06–7.12 (2H, m), 8.25 (1H, d, J=8.4 Hz), 9.24 (1H, bs).

(9) A solution of tert-butyl(4-butoxy-2-cyclopropylmethyl-6-hydroxy-1-oxo-1,2-dihydro-3-isoquinolinyl)methylcarbamate (0.42 g, 1 mmol), 2-iodoacetamide (0.27 g, 1.5 mmol) and 1,8-diazabicyclo[5.4.0]-7-undecene (0.22 mL, 1.5 mmol) in N,N-dimethylformamide (10 mL) was stirred at 80° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(2-amino-2-oxoethoxy)-4-butoxy-2-cyclopropylmethyl-1-oxo-1,2-dihydro-3-isoquinolinyl]-methylcarbamate (0.36 g, 76.6%) as crystals.

Melting point 209–210° C. Elemental analysis for $C_{25}H_{35}N_3O_6$ Calculated: C, 63.41; H, 7.45; N, 8.87. Found: C, 63.05; H, 7.31; N, 8.61. $^1$H-NMR(CDCl$_3$) δ: 0.48–0.56 (4H, m), 1.04 (3H, t, J=7.2 Hz), 1.15–1.26 (1H, m), 1.46 (9H, s), 1.48–1.69 (2H, m), 1.80–1.91 (2H, m), 3.86 (2H, t, J=6.4 Hz), 4.09 (2H, d, J=6.6 Hz), 4.53 (2H, d, J=5.6 Hz), 4.62 (2H, s), 4.86 (1H, bs), 5.89 (1H, bs), 6.62 (1H, bs), 7.06–7.12 (2H, m), 8.36 (1H, d, J=9.2 Hz).

(10) To a solution of tert-butyl[6-(2-amino-2-oxoethoxy)-4-butoxy-2-cyclopropylmethyl-1-oxo-1,2-dihydro-3-isoquinolinyl]methylcarbamate (0.28 g, 0.6 mmol) in ethyl acetate (5 mL) was added a-solution of 4N hydrogen chloride in ethyl acetate (5 mL) and the obtained solution was stirred at room temperature for 2 h. The reaction mixture was concentrated under reduced pressure, and the precipitated crystals were recrystallized from methanol-diisopropyl ether to give 2-[[3-(aminomethyl)-4-butoxy-2-cyclopropylmethyl-1-oxo-1,2-dihydro-6-isoquinolinyl]oxy]acetamide hydrochloride (0.23 g, 92.0%) as crystals.

Melting point 133–134° C. Elemental analysis for $C_{20}H_{28}N_3O_4Cl$ 1.5H$_2$O Calculated: C, 54.98; H, 7.15; N, 9.62. Found: C, 54.84; H, 6.90; N, 9.54. $^1$H-NMR(DMSO d$_6$) δ: 0.43–0.46 (4H, m), 1.00 (3H, t, J=7.1 Hz), 1.12–1.21 (1H, m), 1.50–1.63 (2H, m), 1.81–1.92 (2H, m), 3.93 (2H, t, J=6.1 Hz), 4.04 (2H, d, J=6.2 Hz), 4.18 (2H, s), 4.64 (2H, s), 7.23 (1H, d, J=8.8 Hz), 7.47 (1H, s), 7.75 (1H, s), 8.21 (1H, d, J=8.8 Hz), 8.68 (3H, s).

Example 150

2-[[3-(Aminomethyl)-4-butoxy-2-isobutyl-1-oxo-1,2-dihydro-6-isoquinolinyl]oxy]acetamide hydrochloride (1) A solution of 4-fluorophthalic anhydride (24.99 g, 150 mmol) and ethyl 2-(isobutylamino)acetate (23.88 g, 150 mmol) in tetrahydrofuran (200 mL) was stirred at room temperature for 1 h. The reaction mixture was poured into water and extracted with ethyl acetate. The extract was washed with brine, dried over anhydrous magnesium sulfate and concentrated under reduced pressure. The residue was dissolved in N,N-dimethylformamide (200 mL), and potassium carbonate (20.73 g, 150 mmol) and ethyl iodide (14.4 mL, 180 mmol) were added thereto. The mixture was stirred at room temperature for 3 h. The reaction mixture was poured into water and extracted with ethyl acetate. The extract was washed with brine, dried over anhydrous magnesium sulfate and concentrated under reduced pressure. The residue was dissolved in ethanol (300 mL) and a solution of 20% sodium ethoxide ethanol solution (102 g, 300 mmol) was added thereto. The mixture was stirred at room temperature for 1 h. The reaction mixture was poured into 1N hydrochloric acid (300 mL) and extracted with ethyl acetate. The extract was washed with brine, dried over anhydrous magnesium sulfate and concentrated under reduced pressure. The residue was purified by silica gel column chromatography and the component eluted earlier was concentrated to give ethyl 7-fluoro-4-hydroxy-2-isobutyl-1-oxo-1,2-dihydro-3-isoquinolinecarboxylate (19.2 g, 41.7%) as crystals.

Melting point 104–105° C. Elemental analysis for $C_{16}H_{18}NO_4F$ Calculated: C, 62.53; H, 5.90; N, 4.56. Found: C, 62.81; H, 5.99; N, 4.67. $^1$H-NMR(CDCl$_3$) δ: 0.82 (6H, d, J=6.6 Hz), 1.46 (3H, t, J=7.2 Hz,), 1.76–1.89 (1H, m), 4.41 (2H, d, J=7.2 Hz), 4.49 (2H, d, J=7.2 Hz), 7.43–7.50 (1H, m), 8.08–8.21 (2H, m), 11.34 (1H, s).

The component eluted later was concentrated to give ethyl 6-fluoro-4-hydroxy-2-isobutyl-1-oxo-1,2-dihydro-3-isoquinolinecarboxylate (13.41 g, 29.1%) as crystals.

Melting point 91–92° C. Elemental analysis for $C_{16}H_{18}NO_4F$ Calculated: C, 62.53; H, 5.90; N, 4.56. Found: C, 62.73; H, 5.83; N, 4.53. $^1$H-NMR(CDCl$_3$) δ: 0.82 (6H, d, J=6.6 Hz), 1.46 (3H, t, J=7.2 Hz), 1.74–1.86 (1H, m), 4.40 (2H, d, J=7.5 Hz), 4.49 (2H, d, J=7.2 Hz), 7.34–7.42 (1H, m), 7.75–7.80 (1H, m), 8.45–8.51 (1H, m), 11.12 (1H, s).

(2) To a solution of ethyl 6-fluoro-4-hydroxy-2-isobutyl-1-oxo-1,2-dihydro-3-isoquinolinecarboxylate (9.22 g, 30 mmol), 1-butanol (3.3 mL, 45 mmol) and tributylphosphine (14.9 mL, 60 mmol) in tetrahydrofuran (100 mL) was added 1,1'-(azodicarbonyl)dipiperidine (15.14 g, 60 mmol) and the mixture was stirred at room temperature for 3 h. The reaction mixture was concentrated under reduced pressure, and the residue was purified by silica gel column chromatography to give ethyl 4-butoxy-6-fluoro-2-isobutyl-1-oxo-1,2-dihydro-3-isoquinolinecarboxylate (9.25 g, 84.9%) as an oil.

$^1$H-NMR(CDCl$_3$) δ: 0.91 (6H, d, J=6.6 Hz), 1.01 (3H, t, J=7.4 Hz), 1.45 (3H, t, J=7.2 Hz), 1.46–1.66 (2H, m), 1.74–1.84 (2H, m), 2.05–2.18 (1H, m), 3.88 (2H, d, J=7.8 Hz), 3.95 (2H, t, J=6.6 Hz), 4.46 (2H, q, J=7.2 Hz), 7.27–7.29 (1H, m), 7.34–7.38 (1H, m), 8.44–8.48 (1H, m).

(3) To a solution of ethyl 4-butoxy-6-fluoro-2-isobutyl-1-oxo-1,2-dihydro-3-isoquinolinecarboxylate (9.09 g, 25 mmol) in tetrahydrofuran (30 mL) and ethanol (30 mL) was added sodium hydroxide (3.00 g, 75 mmol). The obtained mixture was refluxed under heating for 12 h. The reaction mixture was poured into water, acidified with 1N hydrochloric acid and extracted with ethyl acetate. The extract was washed with brine, dried over anhydrous magnesium sulfate and concentrated under reduced pressure. The residue was dissolved in benzyl alcohol (20 mL) and the obtained solution was added dropwise to a solution of sodium hydride (5.0 g, 125 mmol)(60% in oil) in benzyl alcohol (20 mL). The obtained mixture was stirred at 150° C. for 12 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from tetrahydrofuran-diisopropyl ether to give 6-benzyloxy-4-butoxy-2-isobutyl-1-oxo-1,2-dihydro-3-isoquinolinecarboxylic acid (9.32 g, 88.1%) as crystals.

Melting point 151–152° C. Elemental analysis for $C_{25}H_{29}NO_5$ Calculated: C, 70.90; H, 6.90; N, 3.31. Found: C, 70.89; H, 6.91; N, 3.37. $^1$H-NMR(CDCl$_3$) δ: 0.85 (6H, d, J=7.0 Hz), 0.98 (3H, t, J=7.3 Hz), 1.39–1.58 (2H, m), 1.67–1.81 (2H, m), 2.06–2.19 (1H, m), 3.89 (2H, t, J=6.6 Hz), 3.95 (2H, d, J=7.8 Hz), 5.16 (2H, s) 6.96 (1H, d, J=2.6 Hz), 7.17 (1H, dd, J=2.6, 9.0 Hz), 7.32–7.45 (5H, m), 8.23 (1H, d, J=9.0 Hz).

(4) To a solution of 6-benzyloxy-4-butoxy-2-isobutyl-1-oxo-1,2-dihydro-3-isoquinolinecarboxylic acid (7.62 g, 18 mmol) in tetrahydrofuran (50 mL) were added oxalyl chloride (1.9 mL, 21.6 mmol) and N,N-dimethylformamide (2 drops), and the mixture was stirred at room temperature for 1 h. The reaction mixture was concentrated under reduced pressure and the residue was dissolved in tetrahydrofuran (30 mL). The obtained solution was added dropwise to a suspension of sodium tetrahydroborate (2.38 g, 63 mmol) in 1,2-dimethoxyethane (50 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-benzyloxy-4-butoxy-3-hydroxymethyl-2-isobutyl-1(2H)-isoquinolinone (7.11 g, 96.5%) as crystals.

Melting point 90–91° C. Elemental analysis for $C_{25}H_{31}NO_4 \cdot 0.25H_2O$ Calculated: C, 72.53; H, 7.67; N, 3.38. Found: C, 72.86; H, 7.71; N, 3.31. $^1$H-NMR(CDCl$_3$) δ: 0.92 (6H, d, J=6.6 Hz), 1.02 (3H, t, J=7.1 Hz), 1.48–1.60 (2H, m), 1.72–1.85 (2H, m), 2.11–2.25 (1H, m), 2.44 (1H, bs), 3.79 (2H, t, J=6.4 Hz), 4.05 (2H, d, J=7.4 Hz), 4.79 (2H, d, J=5.4 Hz), 5.19 (2H, s), 7.06–7.13 (2H, m), 7.34–7.45 (4H, m), 8.28 (1H, d, J=8.4 Hz).

(5) To a suspension of 6-benzyloxy-4-butoxy-3-hydroxymethyl-2-isobutyl-1(2H)-isoquinolinone (6.96 g, 17 mmol) in toluene (50 mL)) was added thionyl chloride (2.5 mL, 34 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-4-butoxy-3-chloromethyl-2-isobutyl-1(2H)-isoquinolinone (6.90 g, 94.8%) as crystals.

$^1$H-NMR(CDCl$_3$) δ: 0.95 (6H, d, J=7.0 Hz), 1.03 (3H, t, J=7.3 Hz), 1.47–1.65 (2H, m), 1.76–1.90 (2H, m), 2.09–2.23 (1H, m), 3.88 (2H, t, J=6.4 Hz), 4.05 (2H, d, J=7.2 Hz), 4.80 (2H, s), 5.21 (2H, s), 7.13–7.47 (7H, m) 8.36 (1H, d, J=8.8 Hz).

(6) A solution of 6-benzyloxy-4-butoxy-3-chloromethyl-2-isobutyl-1(2H)-isoquinolinone (6.85 g, 16 mmol) and potassium phthalimide (4.44 g, 24 mmol) in N,N-dimethylformamide (50 mL) was stirred at room temperature for 6 h. The reaction mixture was poured into water and extracted with ethyl acetate. After washing the extract with water, the extract was dried over anhydrous magnesium sulfate and concentrated under reduced pressure. The residue was purified by silica gel column chromatography to give 2-[(6-benzyloxy-4-butoxy-2-isobutyl-1-oxo-1,2-dihydro-3-isoquinolinyl)methyl]-1H-isoindole-1,3(2H)-dione (7.08 g, 82.2%) as an amorphous.

$^1$H-NMR(CDCl$_3$) δ: 0.93–1.01 (,9H, m), 1.41–1.55 (2H, m), 1.71–1.85 (2H, m), 2.05–2.22 (1H, m), 3.89 (2H, t, J=6.9 Hz), 4.01 (2H, d, J=7.2 Hz), 5.01 (2H, s), 5.20 (2H, s), 7.13–7.17 (2H, m), 7.30–7.46 (5H, m), 7.68–7.87 (2H, m), 8.32–8.36 (1H, m).

(7) To a solution of 2-[(6-benzyloxy-4-butoxy-2-isobutyl-1-oxo-1,2-dihydro-3-isoquinolinyl)methyl]-1H-isoindole-1,3(2H)-dione (7.00 g, 13 mmol) in ethanol (50 mL) was added hydrazine monohydrate (1.9 mL, 39 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (50 mL) and di-t-butyl dicarbonate (4.5 mL, 19.5 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-n-hexane to give tert-butyl (6-benzyloxy-4-butoxy-2-isobutyl-1-oxo-1,2-dihydro-3-isoquinolinyl)methylcarbamate (6.44 g, 97.4%) as crystals.

Melting point 104–105° C. Elemental analysis for $C_{30}H_{40}N_2O_5$ Calculated: C, 70.84; H, 7.93; N, 5.51. Found: C, 70.85; H, 7.70; N, 5.48. $^1$H-NMR(CDCl$_3$) δ: 0.94 (6H, d, J=7.0 Hz), 1.02 (3H, t, J=7.3 Hz), 1.46–1.62 (11H, m), 1.72–1.86 (2H, m), 2.05–2.22 (1H, m), 3.75 (2H, t, J=6.6 Hz), 3.96 (2H, d, J=7.6 Hz), 4.48 (2H, d, J=5.4 Hz), 4.73 (1H, bs), 5.21 (2H, s), 7.08 (1H, d, J=2.6 Hz), 7.15 (1H, dd, J=2.6, 8.8 Hz), 7.30–7.47 (5H, m), 8.34 (1H, d, J=8.8 Hz).

(8) A suspension of tert-butyl(6-benzyloxy-4-butoxy-2-isobutyl-1-oxo-1,2-dihydro-3-isoquinolinyl)methylcarbamate (6.10 g, 12 mmol) and 5% palladium carbon (2.0 g) in tetrahydrofuran (30 mL) and ethanol (30 mL) was stirred under a hydrogen atmosphere at room temperature for 2 h. The catalyst was filtered off and the filtrate was concentrated under reduced pressure. The obtained crystals were recrystallized from ethyl acetate-diisopropyl ether to give tert-butyl (4-butoxy-6-hydroxy-2-isobutyl-1-oxo-1,2-dihydro-3-isoquinolinyl)methylcarbamate (4.86 g, 96.8%) as crystals.

Melting point 185–186° C. Elemental analysis for $C_{23}H_{34}N_2O_5$ Calculated: C, 66.00; H, 8.19; N, 6.69. Found: C, 66.02; H, 8.14; N, 6.73. $^1$H-NMR(CDCl$_3$) δ: 0.95 (6H, d, J=6.6 Hz), 0.96 (3H, t, J=7.0 Hz), 1.46–1.58 (11H, m), 1.72–1.85 (2H, m), 2.06–2.25 (1H, m), 3.82 (2H, t, J=6.6 Hz), 4.00 (2H, d, J=6.8 Hz), 4.51 (2H, d, J=4.8 Hz), 4.84 (1H, bs), 7.09–7.13 (2H, m), 8.27 (1H, d, J=9.6 Hz), 8.98 (1H, bs).

(9) A solution of tert-butyl(4-butoxy-6-hydroxy-2-isobutyl-1-oxo-1,2-dihydro-3-isoquinolinyl)methylcarbamate (0.42 g, 1 mmol), 2-iodoacetamide (0.27 g, 1.5 mmol) and 1,8-diazabicyclo[5.4.0]-7-undecene (0.22 mL, 1.5 mmol) in N,N-dimethylformamide (10 mL) was stirred at 80° C. for 10 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl[6-(2-amino-2-oxoethoxy)-4-butoxy-2-isobutyl-1-oxo-1,2-dihydro-3-isoquinolinyl]methylcarbamate (0.37 g, 78.7%) as crystals.

Melting point 180–181° C. Elemental analysis for $C_{25}H_{37}N_3O_6$ Calculated: C, 63.14; H, 7.84; N, 8.84. Found: C, 62.90; H, 7.71; N, 8.98. $^1$H-NMR(CDCl$_3$) δ: 0.95 (6H, d, J=6.6 Hz), 1.04 (3H, t, J=7.3 Hz), 1.46 (9H, s), 1.51–1.67 (2H, m), 1.80–1.94 (2H, m), 2.05–2.23 (2H, m), 3.84 (2H, t, J=6.6 Hz), 3.98 (2H, d, J=7.2 Hz), 4.51 (2H, d, J=5.6 Hz), 4.62 (2H, s), 4.76 (1H, bs), 5.84 (1H, bs), 6.59 (1H, bs), 7.07–7.13 (2H, m), 8.37 (1H, d, J=9.2 Hz).

(10) To a solution of tert-butyl[6-(2-amino-2-oxoethoxy)-4-butoxy-2-isobutyl-1-oxo-1,2-dihydro-3-isoquinolinyl] methylcarbamate (0.29 g, 0.6 mmol) in ethyl acetate (5 mL) was added, a solution of 4N hydrogen chloride in ethyl acetate (5 mL) and the obtained solution was stirred at room temperature for 2 h. The reaction mixture was concentrated under reduced pressure, and the precipitated crystals were recrystallized from methanol-diisopropyl ether to give 2-[[3-(aminomethyl)-4-butoxy-2-isobutyl-1-oxo-1,2-dihydro-6-isoquinolinyl]oxy]acetamide hydrochloride (0.23 g, 92.0%) as crystals.

Melting point 248–250° C. Elemental analysis for $C_{20}H_{30}N_3O_4Cl$ 0.5H$_2$O Calculated: C, 57.07; H, 7.42; N, 9.98. Found: C, 57.22; H, 7.67; N, 9.73. $^1$H-NMR(DMSO-d$_6$) δ: 0.87 (6H, d, J=6.6 Hz), 0.99 (3H, t, J=7.3 Hz), 1.47 (9H, s), 1.47–1.65 (2H, m), 1.73–2.04 (3H, m), 3.88–3.95 (4H, m), 4.17 (2H, s), 4.64 (2H, s), 7.06 (1H, d, J=2.5 Hz), 7.23 (1H, dd, J=2.5, 8.8 Hz), 7.46 (1H, s), 7.73 (1H, s), 8.20 (1H, d, J=9.2 Hz), 8.62 (3H, s).

Example 151

(E)-3-[3-(Aminomethyl)-4-butoxy-2-isobutyl-1-oxo-1,2-dihydro-6-isoquinolinyl]-2-propenamide hydrochloride (1) To a solution of ethyl diethylphosphonoacetate (1.4 mL, 7 mmol) in N,N-dimethylformamide (30 mL) was added sodium hydride (0.28 g, 7 mmol) (60% in oil) and the mixture was stirred at room temperature for 10 min. To the obtained mixture was added a solution of tert-butyl (4-butoxy-6-formyl-2-isobutyl-1-oxo-1,2-dihydro-3-isoquinolinyl)methylcarbamate (3.01 g, 7 mmol) in N,N-dimethylformamide (10 mL) and the mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl (E)-3-(4-butoxy-3-[[(tert-butoxycarbonyl)amino]methyl]-2-isobutyl-1-oxo-1,2-dihydro-6-isoquinolinyl)-2-propenate (3.11 g, 88.9%) as crystals.

$^1$H-NMR(CDCl$_3$) δ: 0.96 (6H, d, J=6.6 Hz), 1.06 (3H, t, J=7.2 Hz), 1.37 (3H, t, J=7.2 Hz), 1.47 (9H, s), 1.53–1.68 (2H, m), 1.84–1.94 (2H, m), 2.12–2.22 (1H, m), 3.87 (2H, t, J=6.6 Hz), 3.99 (2H, d, J=7.5 Hz), 4.30 (2H, q, J=7.2 Hz), 4.52 (2H, d, J=5.7 Hz), 4.78 (1H, bs), 6.58 (1H, d, J=16.0 Hz), 7.65 (1H, dd, J=1.5, 8.1 Hz), 7.79 (1H, d, J=1.5 Hz), 7.79 (1H, d, J=16.0 Hz), 8.41 (1H, d, J=8.1 Hz).

(2) To a solution of ethyl (E)-3-(4-butoxy-3-[[(tert-butoxycarbonyl)amino]methyl]-2-isobutyl-1-oxo-1,2-dihydro-6-isoquinolinyl)-2-propenate (1.00 g, 2 mmol) in tetrahydrofuran (10 mL) and ethanol (10 mL) was added 1N sodium hydroxide (4 mL). The obtained mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give (E)-3-(4-butoxy-3-[[(tert-butoxycarbonyl)amino]methyl]-2-isobutyl-1-oxo-1,2-dihydro-6-isoquinolinyl)-2-propenic acid (0.89 g, 94.7%) as crystals.

Melting point 207–209° C. Elemental analysis for $C_{26}H_{36}N_2O_6$ Calculated: C, 66.08; H, 7.68; N, 5.93. Found: C, 65.85; H, 7.52; N, 5.91. $^1$H-NMR(CDCl$_3$) δ: 0.96 (6H, d, J=6.6 Hz), 1.07 (3H, t, J=7.3 Hz), 1.49 (9H, s), 1.49–1.69 (2H, m), 1.83–1.97 (2H, m), 2.05–2.24 (1H, m), 3.88 (2H, t, J=6.4 Hz), 3.99 (2H, d, J=7.2 Hz), 4.53 (2H, d, J=5.6 Hz), 5.16 (1H, bs), 6.58 (1H, d, J=16.0 Hz), 7.62 (1H, d, J=8.2 Hz), 7.71 (1H, s), 7.84 (1H, d, J=16.0 Hz), 8.36 (1H, d, J=8.2 Hz).

(3) A solution of (E)-3-(4-butoxy-3-[[(tert-butoxycarbonyl)amino]methyl]-2-isobutyl-1-oxo-1,2-dihydro-3-isoquinolinyl)-2-propenic acid (0.47 g, 1 mmol), 1-ethyl-3-(3-dimethylaminopropyl)carbodiimide hydrochloride (0.38 g, 2 mmol) and 1-hydroxybenzotriazole ammonium salt (0.30 g, 2 mmol) in N,N-dimethylformamide (10 mL) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from ethyl acetate-n-hexane to give (E)-3-(4-butoxy-3-[[(tert-butoxycarbonyl)amino]methyl]-2-isobutyl-1-oxo-1,2-dihydro-3-isoquinolinyl)-2-propenamide (0.41 g, 87.2%) as crystals.

Melting point 149–150° C. Elemental analysis for $C_{26}H_{37}N_3O_5$ 0.5H$_2$O Calculated: C, 64.98; H, 7.97; N, 8.74. Found: C, 64.71; H, 7.68; N, 8.56. $^1$H-NMR(CDCl$_3$) δ: 0.96 (6H, d, J=6.6 Hz), 1.01 (3H, t, J=7.4 Hz), 1.47 (9H, s), 1.49–1.67 (2H, m), 1.81–1.95 (2H, m), 2.09–2.21 (1H, m), 3.86 (2H, t, J=6.5 Hz), 3.99 (2H, d, J=7.2 Hz), 4.52 (2H, d, J=5.6 Hz), 4.95 (1H, bs), 5.86 (1H, bs), 6.01 (1H, bs), 6.60 (1H, d, J=16.2 Hz), 7.58 (1H, d, J=8.5 Hz), 7.71 (1H, s), 7.74 (1H, d, J=16.2 Hz), 8.33 (1H, d, J=8.4 Hz).

(4) To a solution of (E)-3-(4-butoxy-3-[[(tert-butoxycarbonyl)amino]methyl]-2-isobutyl-1-oxo-1,2-dihydro-3-isoquinolinyl)-2-propenamide (0.14 g, 0.3 mmol) in ethyl acetate (5 mL) was added a solution of 4N hydrogen chloride in ethyl acetate (5 mL) and the obtained solution was stirred at room temperature for 2 h. The reaction mixture was concentrated under reduced pressure, and the precipitated crystals were recrystallized from methanol-diisopropyl ether to give (E)-3-[3-(aminomethyl)-4-butoxy-2-isobutyl-1-oxo-1,2-dihydro-6-isoquinolinyl]-2-propenamide hydrochloride (0.11 g, 91.7%) as crystals.

Melting point 223–225° C. Elemental analysis for $C_{21}H_{30}N_3O_3Cl$ 0.5H$_2$O Calculated: C, 60.49; H, 7.49; N, 10.08. Found: C, 60.37; H, 7.77; N, 9.73. $^1$H-NMR(DMSO-d$_6$) δ: 0.89 (6H, d, J=6.6 Hz), 1.01 (3H, t, J=7.2 Hz), 1.48–1.66 (2H, m), 1.82–2.08 (3H, m), 3.93–3.99 (4H, m), 4.18 (2H, d, J=4.8 Hz), 6.84 (1H, d, J=16.1 Hz), 7.28 (1H, bs), 7.64 (1H, d, J=16.1 Hz), 7.76 (1H, bs), 7.80–7.87 (2H, m), 8.29 (1H, d, J=8.0 Hz), 8.64 (3H, bs).

Example 152

(E)-3-[3-(Amninomethyl)-4-butoxy-2-isobutyl-1-oxo-1,2-dihydro-6-isoquinolinyl]-2-propenamide (1) To a suspension of (E)-3-[3-(aminomethyl)-4-butoxy-2-isobutyl-1-oxo-1,2-dihydro-6-isoquinolinyl]-2-propenamide hydrochloride (2.04 g, 5 mmol) in water (20 mL) was added 1N sodium hydroxide (20 mL). The obtained mixture was stirred at room temperature for 10 min. The reaction mixture was poured into water and extracted with ethyl acetate. The extract was washed with brine, dried over anhydrous magnesium sulfate and concentrated under reduced pressure. The obtained crystals were recrystallized from ethyl acetate to give (E)-3-[3-(aminomethyl)-4-butoxy-2-isobutyl-1-oxo-1,2-dihydro-6-isoquinolinyl]-2-propenamide (1.02 g, 85.0%) as crystals.

Melting point 173–175° C. Elemental analysis for $C_{21}H_{29}N_3O_3$ Calculated: C, 67.90; H, 7.87; N, 11.31. Found: C, 67.73; H, 7.90; N, 11.03. $^1$H-NMR(CDCl$_3$) δ: 0.96 (6H, d, J=6.6 Hz), 1.05 (3H, t, J=7.3 Hz), 1.42 (2H, bs), 1.47–1.69 (2H, m), 1.81–1.95 (1H, m), 3.89 (2H, t, J=6.4 Hz), 4.01 (2H, s), 4.10 (2H, d, J=7.4 Hz), 5.89 (1H, bs), 6.04 (1H, bs), 6.65 (1H, d, J=15.6 Hz), 7.62 (1H, dd, J=1.4, 8.4 Hz), 7.76 (1H, d, J=1.4 Hz), 7.78 (1H, d, J=15.6 Hz), 8.39 (1H, d, J=8.4 Hz).

| Powder X-ray crystal diffraction data | |
|---|---|
| Diffraction angle: 2θ(°) (angstrom) | spacing: d value |
| 8.62 | 10.2 |
| 9.98 | 8.86 |
| 17.4 | 5.09 |
| 23.0 | 3.87 |
| 21.9 | 4.06 |
| 26.3 | 3.38 |
| 24.2 | 3.68 |

Example 153

3-(Aminomethyl)-4-butoxy-2-isobutyl-6-(1,3-oxazol-5-yl)-1(2H)-isoquinolinone hydrochloride (1) A solution of tert-butyl(4-butoxy-6-formyl-2-isobutyl-1-oxo-1,2-dihydro-3-isoquinolinyl)methylcarbamate (0.34 g, 0.8 mmol), p-toluenesulfonylmethyl isocyanide (0.16 g, 0.8 mmol) and potassium carbonate (0.22 g, 1.6 mmol) in methanol (10 mL) was refluxed under heating for 30 min. The reaction mixture was poured into water and extracted with ethyl acetate. The extract was washed with brine, dried over anhydrous magnesium sulfate and concentrated under reduced pressure. The residue was purified by silica gel column chromatography and the precipitated crystals were recrystallized from ethyl acetate-diisopropyl ether to give tert-butyl[4-butoxy-2-isobutyl-6-(1,3-oxazol-5-yl)-1-oxo-1,2-dihydro-3-isoquinolinyl]-methylcarbamate (0.34 g, 91.9%) as crystals.

Melting point 152–153° C. Elemental analysis for $C_{26}H_{35}N_3O_5$ Calculated: C, 66.50; H, 7.51; N, 8.95. Found: C, 66.25; H, 7.57; N, 9.00. $^1$H-NMR(CDCl$_3$) δ: 0.97 (6H, d, J=7.0 Hz), 1.07 (3H, t, J=7.3 Hz), 1.47 (9H, s), 1.55–1.73 (2H, m), 1.84–1.98 (2H, m), 2.12–2.26 (1H, m), 3.91 (2H, t, J=6.4 Hz), 4.00 (2H, d, J=7.4 Hz), 4.54 (2H, d, J=5.4 Hz), 4.81 (1H, bs), 7.53 (1H, d, J=0.8 Hz), 7.72–7.78 (1H, m), 7.97 (1H, s), 8.01 (1H, d, J=0.8 Hz), 8.45 (1H, dd, J=1.4, 8.4 Hz).

(2) To a solution of tert-butyl[4-butoxy-2-isobutyl-6-(1,3-oxazol-5-yl)-1-oxo-1,2-dihydro-3-isoquinolinyl]methylcarbamate (0.28 g, 0.6 mmol) in ethyl acetate (5 mL) was added a solution of 4N hydrogen chloride in ethyl acetate (5 ml) and the obtained solution was stirred at room temperature for 1 h. The reaction mixture was concentrated under reduced pressure, and the precipitated crystals were recrystallized from methanol-diisopropyl ether to give 3-(aminomethyl)-4-butoxy-2-isobutyl-6-(1,3-oxazol-5-yl)-1(2H)-isoquinolinone hydrochloride (0.22 g, 91.7%) as crystals.

Melting point 211–213° C. $^1$H-NMR(DMSO-d$_6$) δ: 0.90 (6H, d, J=6.6 Hz), 1.03 (3H, t, J=7.3 Hz), 1.55–1.67 (2H, m), 1.84–1.93 (2H, m), 2.02–2.12 (1H, m), 3.96–4.01 (4H, m), 4.20 (2H, d, J=5.4 Hz), 8.00–8.02 (3H, m), 8.36 (1H, d, J=9.0 Hz), 8.64 (1H, s), 8.82 (3H, bs).

Example 154

2-[[3-(Aminomethyl)-4-(2-fluorophenyl)-2-isobutyl-1-oxo-1,2-dihydro-6-isoquinolinyl]oxy]acetamide (1) To a suspension of 4-benzyloxyphthalic anhydride (25.42 g, 100 mmol) in methanol (200 mL) was added 28% sodium methoxide methanol solution (21.22 g, 110 mmol) and the mixture was stirred at room temperature for 1 h. The reaction mixture was poured into 1N hydrochloric acid (150 mL) and extracted with ethyl acetate. The extract was washed with brine, dried over anhydrous magnesium sulfate and concentrated under reduced pressure. The residue was dissolved in N,N-dimethylformamide (200 mL) and methyl 2-(isobutylamino)acetate (17.42 g, 120 mmol), 1-ethyl-3-(3-dimethylaminopropyl)carbodiimide hydrochloride (23.00 g, 120 mmol) and 1-hydroxybenzotriazole (18.34 g, 120 mmol) were added, and the mixture was stirred at room temperature for 3 h. The reaction mixture was poured into water and extracted with ethyl acetate. The extract was washed with brine, dried over anhydrous magnesium sulfate and concentrated under reduced pressure. The residue was dissolved in methanol (50 mL) and a solution of 28% sodium methoxide methanol solution (38.59 g, 200 mmol) was added thereto. The mixture was stirred at room temperature for 1 h. The reaction mixture was poured into 1N hydrochloric acid (200 mL) and extracted with ethyl acetate. The extract was washed with brine, dried over anhydrous magnesium sulfate and concentrated under reduced pressure. The residue was purified by silica gel column chromatography and the component eluted earlier was concentrated to give methyl 7-benzyloxy-4-hydroxy-2-isobutyl-1-oxo-1,2-dihydro-3-isoquinolinecarboxylate (4.76 g, 12.1%) as an oil.

$^1$H-NMR(CDCl$_3$) δ: 0.82 (6H, d, J=6.6 Hz), 1.78–1.87 (1H, m), 3.99 (3H, s), 4.39 (2H, d, J=7.5 Hz), 5.25 (2H, s), 7.25–7.48 (6H, m), 7.96–7.98 (1H, m), 8.10 (1H, d, J=8.7 Hz), 11.34 (1H, s).

The component eluted later was concentrated to give methyl 6-benzyloxy-4-hydroxy-2-isobutyl-1-oxo-1,2-dihydro-3-isoquinolinecarboxylate (21.41 g, 54.4%) as crystals.

Melting point 109–110° C. Elemental analysis for $C_{22}H_{23}NO_5$ Calculated: C, 69.28; H, 6.08; N, 3.67. Found: C, 69.28; H, 5.93; N, 3.48. $^1$H-NMR(CDCl$_3$) δ: 0.81 (6H, d, J=6.6 Hz), 1.66–1.85 (1H, m), 4.00 (3H, s), 4.35 (2H, d, J=7.5 Hz), 5.21 (2H, s), 7.31 (1H, dd, J=2.6, 8.8 Hz), 7.38–7.49 (5H, m), 7.60 (1H, d, J=2.6 Hz), 8.38 (1H, d, J=8.8 Hz), 11.12 (1H, s).

(2) To a solution of methyl 6-benzyloxy-4-hydroxy-2-isobutyl-1-oxo-1,2-dihydro-3-isoquinolinecarboxylate (7.86 g, 20 mmol) in N,N-dimethylformamide (100 mL) was added sodium hydride (0.96 g, 24 mmol) (60% in oil) at 0° C. and the mixture was stirred at 0° C. for 30 min. To the obtained mixture was added N-phenyltrifluoromethanesulfonimide (8.57 g, 24 mmol) and the mixture was stirred at room temperature for 3 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 6-benzyloxy-2-isobutyl-1-oxo-4-trifluoromethanesulfonyloxy-1,2-dihydro-3-isoquinolinecarboxylate (10.50 g, 100%) as an oil.

$^1$H-NMR(CDCl$_3$) δ: 0.88 (6H, d, J=7.0 Hz), 1.92–2.05 (1H, m), 3.99 (3H, s), 5.19 (2H, s), 7.23–7.48 (2H, m), 8.37 (1H, d, J=9.2 Hz).

(3) A mixture of methyl 6-benzyloxy-2-isobutyl-1-oxo-4-trifluoromethanesulfonyloxy-1,2-dihydro-3-isoquinolinecarboxylate (10.50 g, 20 mmol), 2-fluorophenylboronic acid (3.36 g, 24 mmol) and sodium carbonate (5.30 g, 50 mmol) in toluene (50 mL), ethanol (10 mL) and water (10 mL) was stirred under an argon atmosphere at room temperature for 30 min. To the obtained mixture was added tetrakis(triphenylphosphine)palladium (1.16 g, 1 mmol) and the mixture was refluxed under heating under an argon atmosphere for 12 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 6-benzyloxy-4-(2-fluorophenyl)-2-isobutyl-1-oxo-1,2-dihydro-3-isoquinolinecarboxylate (6.06 g, 65.9%) as crystals.

Melting point 106–107° C. Elemental analysis for C$_{28}$H$_{26}$NO$_4$F Calculated: C, 73.19; H, 5.70; N, 3.05. Found: C, 73.18; H, 5.83; N, 2.86. $^1$H-NMR(CDCl$_3$) δ: 0.91 (3H, d, J=6.6 Hz), 0.92 (3H, d, J=7.0 Hz), 2.05–2.19 (1H, m), 3.47 (3H, s), 3.86 (1H, dd, J=7.6, 13.8 Hz), 4.08 (1H, dd, J=7.6, 13.8 Hz), 4.98 (2H, s), 6.50–6.52 (1H, m), 7.13–7.50 (10H, m), 8.43 (1H, d, J=8.8 Hz).

(4) To a solution of methyl 6-benzyloxy-4-(2-fluorophenyl)-2-isobutyl-1-oxo-1,2-dihydro-3-isoquinolinecarboxylate (0.46 g, 1 mmol) in methanol (30 mL) was added an aqueous solution (3 mL) of lithium hydroxide monohydrate (0.42 g, 10 mmol). The obtained mixture was refluxed under heating for 12 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-benzyloxy-4-(2-fluorophenyl)-2-isobutyl-1-oxo-1,2-dihydro-3-isoquinolinecarboxylic acid (0.41 g, 93.2%) as crystals.

Melting point 178–179° C. Elemental analysis for C$_{27}$H$_{24}$NO$_4$F 0.25H$_2$O Calculated: C, 72.07; H, 5.49; N, 3.11. Found: C, 72.28; H, 5.20; N, 2.80. $^1$H-NMR(CDCl$_3$) δ: 0.85 (6H, d, J=6.8 Hz), 2.09–2.23 (1H, m), 3.75–3.96 (2H, m), 4.38 (1H, bs), 4.98 (2H, s), 6.49–6.51 (1H, m), 7.10–7.48 (10H, m), 8.30 (1H, d, J=8.8 Hz).

(5) To a solution of 6-benzyloxy-4-(2-fluorophenyl)-2-isobutyl-1-oxo-1,2-dihydro-3-isoquinolinecarboxylic acid (4.90 g, 11 mmol) in tetrahydrofuran (50 mL) were added oxalyl chloride (1.1 mL, 13.2 mmol) and N,N-dimethylformamide (3 drops), and the mixture was stirred at room temperature for 1 h. The reaction mixture was concentrated under reduced pressure and the residue was dissolved in tetrahydrofuran (30 mL). The obtained solution was added dropwise to a suspension of sodium tetrahydroborate (1.46 g, 38.5 mmol) in 1,2-dimethoxyethane (30 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-benzyloxy-4-(2-fluorophenyl)-3-hydroxymethyl-2-isobutyl-1(2H)-isoquinolinone (4.38 g, 92.4%) as crystals.

Melting point 191–192° C. Elemental analysis for C$_{27}$H$_{26}$NO$_3$F 0.25H$_2$O Calculated: C, 74.38; H, 6.13; N, 3.21. Found: C, 74.52; H, 6.20; N, 3.16. $^1$H-NMR(CDCl$_3$) δ: 0.87 (6H, d, J=6.6 Hz), 1.85 (1H, bs), 2.18–2.32 (1H, m), 4.08–4.29 (2H, m), 4.44 (2H, s), 4.94 (2H, s), 6.38 (1H, d, J=2.3 Hz), 7.09 (1H, dd, J=2.3, 8.6 Hz), 7.18–7.36 (7H, m), 7.43–7.54 (1H, m), 8.36 (1H, d, J=8.6 Hz).

(6) To a suspension of 6-benzyloxy-4-(2-fluorophenyl)-3-hydroxymethyl-2-isobutyl-1(2H)-isoquinolinone (4.31 g, 10 mmol) in toluene (50 mL) was added thionyl chloride (1.5 mL, 20 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-4-(2-fluorophenyl)-2-isobutyl-1(2H)-isoquinolinone (4.29 g, 95.3%) as crystals.

$^1$H-NMR(CDCl$_3$) δ: 0.98 (3H, d, J=6.6 Hz), 1.01 (3H, d, J=6.8 Hz), 2.15–2.26 (1H, m), 3.94 (1H, dd, J=7.9, 13.1 Hz), 4.31 (1H, d, J=12.4 Hz), 4.35 (1H, dd, J=7.9, 13.1 Hz), 4.43 (1H, d, J=12.4 Hz), 4.95 (2H, s), 6.36–6.38 (1H, m), 7.12–7.35 (9H, m), 7.45–7.56 (1H, m), 8.41 (1H, d, J=8.8 Hz).

(7) A solution of 6-benzyloxy-3-chloromethyl-4-(2-fluorophenyl)-2-isobutyl-1(2H)-isoquinolinone (4.27 g, 9.5 mmol) and potassium phthalimide (2.65 g, 14.3 mmol) in N,N-dimethylformamide (100 mL) was stirred at room temperature for 6 h. The reaction mixture was poured into water and extracted with ethyl acetate. After washing the extract with water, the extract was dried over anhydrous magnesium sulfate and concentrated under reduced pressure. The residue was purified by silica gel column chromatography to give 2-[[6-benzyloxy-4-(2fluorophenyl)-2-isobutyl-1-oxo-1,2-dihydro-3-isoquinolinyl]methyl]-1H-isoindole-1,3(2H)-dione (5.07 g, 95.3%) as an amorphous.

$^1$H-NMR(CDCl$_3$) δ: 1.00 (3H, d, J=6.6 Hz), 1.01 (3H, d, J=6.8 Hz), 2.12–2.27 (1H, m), 3.94 (1H, dd, J=7.3, 14.8 Hz), 4.33 (1H, dd, J=7.3, 13.9 Hz), 4.57 (1H, d, J=15.6 Hz), 4.92 (1H, d, J=15.6 Hz), 4.93 (2H, s), 6.34 (1H, d, J=2.6 Hz), 7.01–7.45 (10H, m), 7.66–7.76 (4H, m), 8.40 (1H, d, J=8.8 Hz).

(8) To a solution of 2-[[6-benzyloxy-4-(2-fluorophenyl)-2-isobutyl-1-oxo-1,2-dihydro-3-isoquinolinyl]methyl]-1H-isoindole-1,3(2H)-dione (5.05 g, 9 mmol) in ethanol (50 mL) was added hydrazine monohydrate (1.3 mL, 27 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (50 mL) and di-t-butyl dicarbonate (3.1 mL, 13.5 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-n-hexane to give tert-butyl[6-benzyloxy-4-(2-fluorophenyl)-2-isobutyl-1-oxo-1,2-dihydro-3-isoquinolinyl]methylcarbamate (4.27 g, 89.5%) as crystals.

Melting point 138–139° C. Elemental analysis for $C_{32}H_{35}N_2O_4F$ Calculated: C, 72.43; H, 6.65; N, 5.28. Found: C, 72.27; H, 6.38; N, 5.22. $^1$H-NMR(CDCl$_3$) δ: 0.99 (6H, d, J=7.0 Hz), 1.43 (9H, s), 2.16–2.30 (1H, m), 3.83–3.94 (1H, m), 3.99–4.38 (3H, m), 4.58 (1H, bs), 4.95 (2H, s), 6.33 (1H, d, J=2.4 Hz), 7.11 (1H, dd, J=2.4, 9.0 Hz), 7.16–7.38 (8H, m), 7.43–7.54 (1H, m), 8.39 (1H, d, J=9.0 Hz).

(9) A suspension of tert-butyl[6-benzyloxy-4-(2-fluorophenyl)-2-isobutyl-1-oxo-1,2-dihydro-3-isoquinolinyl]methylcarbamate (3.98 g, 7.5 mmol) and 5% palladium carbon (1.5 g) in ethanol (50 mL) was stirred under a hydrogen atmosphere at room temperatures for 2 h. The catalyst was filtered off and the filtrate was concentrated under reduced pressure. The obtained crystals were recrystallized from tetrahydrofuran-diisopropyl ether to give tert-butyl[4-(2-fluorophenyl)-6-hydroxy-2-isobutyl-1-oxo-1,2-dihydro-3-isoquinolinyl]methylcarbamate (3.11 g, 94.2%) as crystals.

Melting point 163–164° C. Elemental analysis for $C_{25}H_{29}N_2O_4F$ 0.5H$_2$O Calculated: C, 66.80; H, 6.73; N, 6.23. Found: C, 66.80; H, 6.93; N, 6.28. $^1$H-NMR(CDCl$_3$) δ: 0.96 (6H, d, J=6.6 Hz), 1.42 (9H, s), 2.11–2.28 (1H, m), 3.82–3.92 (1H, m), 4.02–4.21 (2H, m), 4.28–4.38 (1H, m), 4.60 (1H, bs), 6.37 (1H, d, J=2.2 Hz), 7.08 (1H, dd, J=2.2, 8.8 Hz), 7.13–7.23 (4H, m), 7.34–7.47 (1H, m), 8.28 (1H, d, J=8.8 Hz).

(10) A solution of tert-butyl[4-(2-fluorophenyl)-6-hydroxy-2-isobutyl-1-oxo-1,2-dihydro-3-isoquinolinyl]methylcarbamate (0.44 g, 1 mmol), 2-iodoacetamide (0.37 g, 2 mmol) and 1,8-diazabicyclo[5.4.0]-7-undecene (0.30 mL, 2 mmol) in N,N-dimethylformamide (10 mL) was stirred at 80° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl [6-(2-amino-2-oxoethoxy)-4-(2-fluorophenyl)-2-isobutyl-1-oxo-1,2-dihydro-3-isoquinolinyl]methylcarbamate (0.30 g, 61.2%) as crystals.

Melting point 186–188° C. Elemental analysis for $C_{27}H_{32}N_3O_5F$ 0.25H$_2$O Calculated: C, 64.59; H, 6.52; N, 8.37. Found: C, 64.74; H, 6.32; N, 7.97. $^1$H-NMR(CDCl$_3$) δ: 0.99 (3H, d, J=7.0 Hz), 1.00 (3H, d, J=6.8 Hz), 1.43 (9H, s), 2.15–2.32 (1H, m), 3.85–4.00 (4H, m), 4.35 (2H, s), 4.59 (1H, bs), 5.70 (1H, bs), 6.29 (1H, d, J=2.4 Hz), 6.50 (1H, bs), 7.07 (1H, dd, J=2.4, 9.0 Hz), 7.21–7.37 (3H, m), 7.46–7.58 (1H, m), 8.44 (1H, d, J=9.0 Hz).

(11) To a solution of tert-butyl[6-(2-amino-2-oxoethyl)-4-(2-fluorophenyl)-2-isobutyl-1-oxo-1,2-dihydro-3-isoquinolinyl]methylcarbamate (0.25 g, 0.5 mmol) in ethyl acetate (5 mL) was added a solution of 4N hydrogen chloride in ethyl acetate (5 mL), and the obtained solution was stirred at room temperature for 2 h. The reaction mixture was concentrated under reduced pressure. The residue was poured into saturated aqueous sodium hydrogencarbonate solution and extracted with ethyl acetate. The extract was washed with brine, dried over anhydrous magnesium sulfate and concentrated under reduced pressure. The residue was purified by silica gel column chromatography to give 2-[[3-(aminomethyl)-4-(2-fluorophenyl)-2-isobutyl-1-oxo-1,2-dihydro-6-isoquinolinyl]oxy]acetamide (0.02 g, 10.0%) as an amorphous.

$^1$H-NMR(CDCl$_3$) δ: 1.00 (3H, d, J=6.6 Hz), 1.02 (3H, d, J=6.6 Hz), 1.66 (2H, bs), 2.18–2.32 (1H, m), 4.07–4.28 (3H, m), 4.35 (2H, s), 5.77 (1H, bs), 6.27 (1H, d, J=2.6 Hz), 6.51 (1H, bs), 7.05 (1H, dd, J=2.6, 8.8 Hz), 7.22–7.35 (3H, m), 7.45–7.56 (1H, m), 8.44 (1H, d, J=8.8 Hz).

Example 155

3-(Aminomethyl)-4-(2-fluorophenyl)-2-isobutyl-1 (2H)-isoquinolinone-6-carboxamide hydrochloride (1) To a solution of tert-butyl[4-(2-fluorophenyl)-6-hydroxy-2-isobutyl-1-oxo-1,2-dihydro-3-isoquinolinyl)methylcarbamate (Example 8(9)) (2.42 g, 5.5 mmol) in N,N-dimethylformamide (30 mL) was added sodium hydride (0.33 g, 8.3 mmol) (60% in oil) at 0° C. and the mixture was stirred at 0° C. for 30 min. To the obtained mixture was added N-phenyltrifluoromethanesulfonimide (2.97 g, 8.3 mmol) and the mixture was stirred at room temperature for 1 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl[4-(2-fluorophenyl)-2-isobutyl-1-oxo-6-trifluoromethanesulfonyloxy-1,2-dihydro-3-isoquinolinyl]methylcarbamate (2.91 g, 92.4%) as an amorphous.

$^1$H-NMR(CDCl$_3$) δ: 1.00 (3H, d, J=6.6 Hz), 1.01 (3H, d, J=7.0 Hz), 1.46 (9H, s), 2.17–2.31 (1H, m), 3.89–3.99 (1H, m), 4.07–4.27 (2H, m), 4.33–4.44 (1H, m), 4.59 (1H, bs), 6.79 (1H, d, J=2.2 Hz), 7.21–7.44 (1H, m), 7.48–7.60 (1H, m), 8.57 (1H, d, J=8.8 Hz).

(2) A mixed solution of tert-butyl[4-(2-fluorophenyl)-2-isobutyl-1-oxo-6-trifluoromethanesulfonyloxy-1,2-dihydro-3-isoquinolinyl]methylcarbamate (2.86 g, 5 mmol), 1,1'-bis(diphenylphosphino)ferrocene (0.14 g, 0.25 mmol), triethylamine (0.77 mL, 5.5 mmol) and palladium acetate (56 mg, 0.25 mmol) in tetrahydrofuran (20 mL) and methanol (20 mL) was stirred with heating at 100° C. under a carbon monoxide atmosphere at 5 atm for 1 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 3-[[(tert-butoxycarbonyl)amino]methyl]-4-(2-fluorophenyl)-2-isobutyl-1-oxo-1,2-dihydro-6-isoquinolinecarboxylate (2.23 g, 92.5%) as crystals.

Melting point 180–181° C. Elemental analysis for $C_{27}H_{31}N_2O_5F$ Calculated: C, 67.20; H, 6.48; N, 5.81. Found: C, 66.95; H, 6.55; N, 5.75. $^1$H-NMR(CDCl$_3$) δ: 1.00 (3H, d, J=6.6 Hz), 1.01 (3H, d, J=6.6 Hz), 1.43 (9H, s), 2.19–2.33 (1H, m), 3.86 (3H, s), 3.89–4.43 (4H, m), 4.62 (1H, bs), 7.23–7.38 (3H, m), 7.47–7.58 (1H, m), 7.46 (1H, d, J=1.5 Hz), 8.06 (1H, dd, J=1.5, 8.4 Hz), 8.53 (1H, d, J=8.4 Hz).

(3) To a solution of methyl 3-[[(tert-butoxycarbonyl)amino]methyl]-4-(2-fluorophenyl)-2-isobutyl-1-oxo-1,2-dihydro-6-isoquinolinecarboxylate (1.93 g, 4 mmol) in tetrahydrofuran (10 mL) and methanol (10 mL) was added 1N sodium hydroxide (8 mL). The obtained mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-isopropyl ether to give 3-[[(tert-butoxycarbonyl)amino]methyl]-4-(2-fluorophenyl)-2-isobutyl-1-oxo-1,2-dihydro-6-isoquinolinecarboxylic acid (1.77 g, 94.7%) as crystals.

Melting point 213–214° C. Elemental analysis for $C_{26}H_{29}N_2O_5F$ Calculated: C, 66.65; H, 6.24; N, 5.98. Found: C, 66.51; H, 6.50; N, 5.99. $^1$H-NMR(CDCl$_3$) δ: 1.00 (3H, d, J=6.8 Hz), 1.01 (3H, d, J=6.6 Hz), 1.45 (9H, s), 2.19–2.32 (1H, m), 4.84 (1H, bs), 7.22–7.34 (3H, m), 7.46–7.57 (1H, m), 7.65 (1H, s), 8.05 (1H, d, J=8.4 Hz), 8.51 (1H, d, J=8.4 Hz).

(4) A solution of 3-[[(tert-butoxycarbonyl)amino]methyl]-4-(2-fluorophenyl)-2-isobutyl-1-oxo-1,2-dihydro-6-isoquinolinecarboxylic acid (0.70 g, 1.5 mmol), 1-ethyl-3-(3-dimethylaminopropyl)carbodiimide hydrochloride (0.58 g, 3 mmol) and 1-hydroxybenzotriazole ammonium salt (0.46 g, 3 mmol) in N,N-dimethylformamide (10 mL) was stirred at room temperature for 3 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give 3-[[(tert-butoxycarbonyl)amino]methyl]-4-(2-fluorophenyl)-2-isobutyl-1-oxo-1,2-dihydro-6-isoquinolinecarboxamide (0.67 g, 95.7%) as crystals.

Melting point 232–233° C. Elemental analysis for $C_{26}H_{30}N_3O_4F$ Calculated: C, 66.79; H, 6.47; N, 8.99. Found: C, 66.39; H, 6.75; N, 8.93. $^1$H-NMR(CDCl$_3$) δ: 0.99 (3H, d, J=6.6 Hz), 1.01 (3H, d, J=6.6 Hz), 1.44 (9H, s), 2.22–2.30 (1H, m), 3.92–4.19 (3H, m), 4.32–4.40 (1H, m), 4.69 (1H, bs), 5.78 (1H, bs), 6.10 (1H, bs), 7.23–7.35 (3H, m), 7.40 (1H, d, J=1.5 Hz), 7.47–7.54 (1H, m), 7.77 (1H, dd, J=1.5, 8.4 Hz), 8.49 (1H, d, J=8.4 Hz).

(5) To a solution of 3-[[(tert-butoxycarbonyl)amino]methyl]-4-(2-fluorophenyl)-2-isobutyl-1-oxo-1,2-dihydro-6-isoquinolinecarboxamide (0.37 g, 0.8 mmol) in ethyl acetate (5 mL) was added a solution of 4N hydrogen chloride in ethyl acetate (5 ml) and the obtained solution was stirred at room temperature for 1 h. The reaction mixture was concentrated under reduced pressure, and the precipitated crystals were recrystallized from methanol-diethyl ether to give 3-(aminomethyl)-4-(2-fluorophenyl)-2-isobutyl-1(2H)-isoquinolinone-6-carboxamide hydrochloride (0.30 g, 93.8%) as crystals.

Melting point 216–218° C. Elemental analysis for $C_{21}H_{23}N_3O_2ClF \cdot 2H_2O$ Calculated: C, 57.34; H, 6.19; N, 9.55. Found: C, 57.41; H, 5.93; N, 9.71. $^1$H-NMR(DMSO-d$_6$) δ: 0.92 (3H, d, J=6.6 Hz), 0.93 (3H, d, J=6.6 Hz), 2.01–2.16 (1H, m), 3.62–3.80 (1H, m), 4.02–4.23 (3H, m), 7.43–7.66 (6H, m), 8.03 (1H, d, J=8.4 Hz), 8.21 (1H, bs), 8.38 (1H, d, J=8.4 Hz), 8.72 (3H, bs).

Example 156

3-(Aminomethyl)-4-(2-fluorophenyl)-2-isobutyl-1(2H)-isoquinolinone-6-carbonitrile hydrochloride (1) A solution of 3-[[(tert-butoxycarbonyl)amino]methyl]-4-(2-fluorophenyl)-2-isobutyl-1-oxo-1,2-dihydro-6-isoquinolinecarboxamide (Example 10 (4)) (0.23 g, 0.5 mmol) and cyanuric chloride (0.28 g, 1.5 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was recrystallized from ethyl acetate-n-hexane to give tert-butyl[6-cyano-4-(2-fluorophenyl)-2-isobutyl-1-oxo-1,2-dihydro-3-isoquinolinyl]methylcarbamate (0.19 g, 86.4%) as crystals.

Melting point 191–192° C. Elemental analysis for $C_{26}H_{28}N_3O_3F$ Calculated: C, 69.47; H, 6.28; N, 9.35. Found: C, 69.37; H, 6.42; N, 9.24. $^1$H-NMR(CDCl$_3$) δ: 1.00 (3H, d, J=6.6 Hz), 1.01 (3H, d, J=7.0 Hz), 1.43 (9H, s), 2.18–2.32 (1H, m), 3.89–4.05 (1H, m), 4.07–4.44 (3H, m), 4.58 (1H, bs), 7.20–7.40 (4H, m), 7.50–7.61 (1H, m), 7.67 (1H, dd, J=1.6, 8.2 Hz), 8.56 (1H, d, J=8.2 Hz).

(2) To a solution of tert-butyl[6-cyano-4-(2-fluorophenyl)-2-isobutyl-1-oxo-1,2-dihydro-3-isoquinolinyl]methylcarbamate (0.13 g, 0.3 mmol) in ethyl acetate (5 mL) was added a solution of 4N hydrogen chloride in ethyl acetate (5 mL) and the obtained solution was stirred at room temperature for 1 h. The reaction mixture was concentrated under reduced pressure, and the precipitated crystals were recrystallized from methanol-diethyl ether to give 3-(aminomethyl)-4-(2-fluorophenyl)-2-isobutyl-1(2H)-isoquinolinone-6-carbonitrile hydrochloride (0.11 g, 91.7%) as crystals.

Melting point 228–230° C. $^1$H-NMR(DMSO-d$_6$) δ: 0.92 (3H, d, J=6.6 Hz), 0.94 (3H, d, J=6.6 Hz), 1.99–2.19 (1H, m), 3.76–3.83 (1H, m), 3.96–4.22 (3H, m), 7.30 (1H, d, J=1.4 Hz), 7.41–7.72 (4H, m), 7.99 (1H, dd, J=1.4, 8.4 Hz), 8.49 (1H, d, J=8.4 Hz), 8.74 (3H, bs).

Example 157

2-[[3-(Aminomethyl)-4-(3-fluorophenyl)-2-isobutyl-1-oxo-1,2-dihydro-6-isoquinolinyl]oxy]acetamide hydrochloride (1) A mixture of methyl 6-benzyloxy-2-isobutyl-1-oxo-4-trifluoromethanesulfonyloxy-1,2-dihydro-3-isoquinolinecarboxylate (10.26 g, 20 mmol), 3-fluorophenylboronic acid (3.36 g, 24 mmol) and sodium carbonate (5.30 g, 50 mmol) in toluene (50 mL), ethanol (10 mL) and water (10 mL) was stirred under an argon atmosphere at room temperature for 30 min. To the obtained mixture was added tetrakis(triphenylphosphine)palladium (1.16 g, 1 mmol) and the mixture was refluxed under heating under an argon atmosphere for 12 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 6-benzyloxy-4-(3-fluorophenyl)-2-isobutyl-1-oxo-1,2-dihydro-3-isoquinolinecarboxylate (6.31 g, 68.7%) as crystals.

Melting point 127–128° C. Elemental analysis for $C_{28}H_{26}NO_4F$ Calculated: C, 73.19; H, 5.70; N, 3.05. Found: C, 73.03; H, 5.63; N, 2.77. $^1$H-NMR(CDCl$_3$) δ: 0.91 (6H, d, J=7.0 Hz), 2.04–2.19 (1H, m), 3.50 (3H, s), 3.8–4.00 (2H, m), 4.99 (2H, s), 6.57 (1H, d, J=2.4 Hz), 6.96–7.21 (4H, m), 7.24–7.46 (6H, m), 8.43 (1H, d, J=8.8 Hz).

(2) To a solution of methyl 6-benzyloxy-4-(3-fluorophenyl)-2-isobutyl-1-oxo-1,2-dihydro-3-isoquinolinecarboxylate (5.97 g, 13 mmol) in tetrahydrofuran (50 mL) and methanol (50 mL) was added an aqueous solution (10 mL) of lithium hydroxide monohydrate (1.64 g, 39 mmol). The obtained mixture was refluxed under heating for 12 h. The reaction mixture was poured into water, acidified with 1N hydrochloric acid and extracted with ethyl acetate. The extract was washed with brine, dried over anhydrous magnesium sulfate and concentrated under reduced pressure.

The residue was dissolved in tetrahydrofuran (50 mL), and oxalyl chloride (1.0 mL, 12 mmol) and N,N-dimethylformamide (3 drops) were added thereto. The mixture was stirred at room temperature for 1 h. The reaction mixture was concentrated under reduced pressure and the residue was dissolved in tetrahydrofuran (30 mL). The obtained solution was added dropwise to a suspension of sodium tetrahydroborate (1.32 g, 35 mmol) in 1,2-dimethoxyethane (30 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The residue was purified by silica gel column chromatography to give 6-benzyloxy-4-(3-fluorophenyl)-3-hydroxymethyl-2-isobutyl-1 (2H)-isoquinolinone (1.39 g, 32.2%) as crystals.

Melting point 146–146.5° C. Elemental analysis for $C_{27}H_{26}NO_3F$ Calculated: C, 75.15; H, 6.07; N, 3.25. Found: C, 74.87; H, 6.06; N, 3.12. $^1$H-NMR(CDCl$_3$) δ: 0.94 (6H, d, J=6.6 Hz), 2.11–2.28 (1H, m), 2.58 (1H, bs), 4.16 (2H, d, J=7.6 Hz), 4.41 (2H, d, J=5.8 Hz), 4.91 (2H, s), 6.31 (1H, d, J=2.2 Hz), 6.95–7.37 (9H, m), 7.44–7.52 (1H, m), 8.25 (1H, d, J=8.8 Hz).

(3) To a suspension of 6-benzyloxy-4-(3-fluorophenyl)-3-hydroxymethyl-2-isobutyl-1(2H)-isoquinolinone (3.88 g, 9 mmol) in toluene (30 mL) was added thionyl chloride (1.3 mL, 18 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-4-(3-fluorophenyl)-2-isobutyl-1(2H)-isoquinolinone (3.71 g, 91.8%) as an oil.

$^1$H-NMR(CDCl$_3$) δ: 0.99 (6H, d, J=6.6 Hz), 2.13–2.31 (1H, m), 4.14 (2H, d, J=7.2 Hz), 4.35 (2H, s), 4.96 (2H, s), 6.37 (1H, d, J=2.2 Hz), 6.98–7.32 (9H, m), 7.42–7.53 (1H, m), 8.40 (1H, d, J=8.8 Hz).

(4) A solution of 6-benzyloxy-3-chloromethyl-4-(3-fluorophenyl)-2-isobutyl-1(2H)-isoquinolinone (3.60 g, 8 mmol) and potassium phthalimide (2.22 g, 12 mmol) in N,N-dimethylformamide (30 ml) was stirred at room temperature for 6 h. The reaction mixture was poured into water and extracted with ethyl acetate. After washing the extract with water, the extract was dried over anhydrous magnesium sulfate and concentrated under reduced pressure. The obtained crystals were recrystallized from ethyl acetate-diisopropyl ether to give 2-[[6-benzyloxy-4-(3-fluorophenyl)-2-isobutyl-1-oxo-1,2-dihydro-3-isoquinolinyl]methyl]-1H-isoindole-1,3(2H)-dione (3.95 g, 88.2%) as crystals.

$^1$H-NMR(CDCl$_3$) δ: 0.98 (6H, d, J=6.6 Hz), 2.10–2.27 (1H, m), 4.03 (2H, d, J=4.4 Hz), 4.75 (2H, s), 4.92 (2H, s), 6.32 (1H, d, J=2.6 Hz), 6.98–7.14 (4H, m), 7.21–7.40 (6H, m), 7.68–7.78 (4H, m), 8.38 (1H, d, J=8.8 Hz).

(5) To a solution of 2-[[6-benzyloxy-4-(3-fluorophenyl)-2-isobutyl-1-oxo-1,2-dihydro-3-isoquinolinyl]methyl]-1H-isoindole-1,3(2H)-dione (3.92 g, 7 mmol) in ethanol (50 mL) was added hydrazine monohydrate (1.0 mL, 21 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (30 mL) and di-t-butyl dicarbonate (2.4 mL, 10.5 mol) was added. The obtained mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[(6-benzyloxy-4-(3-fluorophenyl)-2-isobutyl-1-oxo-1,2-dihydro-3-isoquinolinyl)methylcarbamate (3.47 g, 93.5%) as crystals.

Melting point 180–181° C. Elemental analysis for $C_{32}H_{35}N_2O_4F$ Calculated: C, 72.43; H, 6.65; N, 5.28. Found: C, 72.30; H, 6.48; N, 5.32. $^1$H-NMR(CDCl$_3$) δ: 0.98 (6H, d, J=6.6 Hz), 1.43 (9H, s), 2.15–2.28 (1H, m), 4.02 (2H, d, J=7.4 Hz), 4.16 (2H, d, J=5.0 Hz), 4.94 (2H, s), 6.31 (1H, d, J=2.6 Hz), 6.89– 7.35 (9H, m), 7.41–7.52 (1H, m), 8.36 (1H, d, J=8.8 Hz).

(6) A suspension of tert-butyl[6-benzyloxy-4-(3-fluorophenyl)-2-isobutyl-1-oxo-1,2-dihydro-3-isoquinolinyl]methylcarbamate (3.18 g, 6 mmol) and 5% palladium carbon (1.0 g) in tetrahydrofuran (20 mL) and ethanol (20 mL) was stirred, under a hydrogen atmosphere at room temperature for 2 h. The catalyst was filtered off and the filtrate was concentrated under reduced pressure. The obtained crystals were recrystallized from ethyl acetate-n-hexane to give tert-butyl[4-(3-fluorophenyl)-6-hydroxy-2-isobutyl-1-oxo-1,2-dihydro-3-isoquinolinyl]methylcarbamate (2.54 g, 96.2%) as crystals.

Melting point 161–163° C. Elemental analysis for $C_{25}H_{29}N_2O_4F$ Calculated: C, 68.16; H, 6.64; N, 6.36. Found: C, 67.91; H, 6.89; N, 6.38. $^1$H-NMR(CDCl$_3$) δ: 0.96 (6H, d, J=6.6 Hz), 1.42 (9H, s), 2.14–2.24 (1H, m), 4.01 (2H, d, J=5.7 Hz), 4.18 (2H, d, J=4.5 Hz), 4.52 (1H, bs), 6.34 (1H, d, J=2.1 Hz), 6.94–7.13 (4H, m), 7.38–7.46 (1H, m), 7.87 (1H, bs), 8.26 (1H, d, J=8.4 Hz).

(7) A solution of tert-butyl[(4-(3-fluorophenyl)-6-hydroxy-2-isobutyl-1-oxo-1,2-dihydro-3-isoquinolinyl)methylcarbamate (0.44 g, 1 mmol), 2-iodoacetamide (0.37 g, 2 mmol) and 1,8-diazabicyclo[5.4.0]-7-undecene (0.3 mL, 2 mmol) in N,N-dimethylacetamide (10 mL) was stirred at 70° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(2-amino-2-oxoethoxy)-4-(3-fluorophenyl)-2-isobutyl-1-oxo-1,2-dihydro-3-isoquinolinyl]methylcarbamate (0.21 g, 42.9%) as crystals.

Melting point 241–242° C. Elemental analysis for $C_{27}H_{32}N_3O_5F$ 0.25H$_2$O Calculated: C, 64.59; H, 6.52; N, 8.37. Found: C, 64.61; H, 6.66; N, 8.07. $^1$H-NMR(CDCl$_3$) δ: 0.99 (6H, d, J=6.6 Hz), 1.43 (9H, s), 2.19–2.34 (1H, m), 4.04 (2H, d, J=7.0 Hz), 4.35 (2H, s), 4.86 (1H, bs), 6.15 (1H, bs), 6.31 (1H, d, J=2.6 Hz), 6.59 (1H, bs), 6.99–7.25 (4H, m), 7.45–7.54 (1H, m), 8.42 (1H, d, J=9.2 Hz).

(8) To a solution of tert-butyl[6-(2-amino-2-oxoethoxy)-4-(3-fluorophenyl)-2-isobutyl-1-oxo-1,2-dihydro-3-isoquinolinyl]methylcarbamate (0.15 g, 0.3 mmol) in ethyl acetate (5 mL) was added a solution of 4N hydrogen chloride in ethyl acetate (5 mL), and the obtained solution was stirred at room temperature for 2 h. The reaction mixture was concentrated under reduced pressure, and crystallized from ethyl acetate-diisopropyl ether to give 2-[[3-(aminomethyl)-4-(3-fluorophenyl)-2-isobutyl-1-oxo-1,2-dihydro-6-isoquinolinyl]oxy]acetamide hydrochloride (0.12 g, 92.3%) as crystals.

Melting point 209–210° C. $^1$H-NMR(DMSO-d$_6$) δ: 0.91 (6H, d, J=6.6 Hz), 1.99–2.18 (1H, m), 3.84 (2H, bs), 3.94–4.08 (2H, m), 4.39 (2H, s), 6.29 (1H, d, J=2.2 Hz), 7.18–7.41 (5H, m), 8.27 (1H, d, J=9.2 Hz), 8.59 (3H, bs).

Example 158

3-(Aminomethyl)-4-(3-fluorophenyl)-2-isobutyl-1(2H)-isoquinolinone-6-carboxamide hydrochloride

(1) To a solution of tert-butyl[4-(3-fluorophenyl)-6-hydroxy-2-isobutyl-1-oxo-1,2-dihydro-3-isoquinolinyl]methylcarbamate (Example 11 (6)) (1.76 g, 4 mol) in N,N-dimethylformamide (20 mL) was added sodium hydride (0.19 g, 4.8 mmol)(60% in oil) at 0° C. and the mixture was stirred at 0° C. for 30 min. To the obtained mixture was added N-phenyltrifluoromethanesulfonimide (1.71 g, 4.8 mmol) and the mixture was stirred at room temperature, for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl[4-(3-fluorophenyl)-2-isobutyl-1-oxo-6-trifluoromethanesulfonyloxy-1,2-dihydro-3-isoquinolinyl]methylcarbamate (2.30 g, 100%) as an oil.

$^1$H-NMR(CDCl$_3$) δ: 0.99 (6H, d, J=6.6 Hz), 1.43 (9H, s), 2.14–2.28 (1H, m), 4.08 (2H, d, J=9.0 Hz), 4.23 (2H, d, J=5.6 Hz), 4.50 (1H, bs), 6.80 (1H, d, J=2.6 Hz), 6.96–7.08 (2H, m), 7.18–7.59 (3H, m), 8.55 (1H, d, J=8.8 Hz).

(2) A mixed solution of tert-butyl[4-(3-fluorophenyl)-2-isobutyl-1-oxo-6-trifluoromethanesulfonyloxy-1,2-dihydro-3-isoquinolinyl]methylcarbamate (2.29 g, 4 mmol), 1,1'-bis(diphenylphosphino)ferrocene (0.11 g, 0.2 mmol), triethylamine (0.6 mL, 4.4 mmol) and palladium acetate (45 mg, 0.2 mmol) in tetrahydrofuran (20 mL) and methanol (20 mL) was stirred with heating at 100° C. under a carbon monoxide atmosphere at 5 atm for 1 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 3-[[(tert-butoxycarbonyl)amino]methyl]-4-(3-fluorophenyl)-2-isobutyl-1-oxo-1,2-dihydro-6-isoquinolinecarboxylate (1.76 g, 91.2%) as crystals.

Melting point 206–208° C. Elemental analysis for C$_{27}$H$_{31}$N$_2$O$_5$F Calculated: C, 67.20; H, 6.48; N, 5.81. Found: C, 66.96; H, 6.63; N, 5.59. $^1$H-NMR(CDCl$_3$) δ: 1.00 (6H, d, J=6.6 Hz), 1.44 (9H, s), 2.18–2.30 (1H, m), 3.87 (3H, s), 4.08 (2H, d, J=7.2 Hz), 4.21 (2H, d, J=5.1 Hz), 4.54 (1H, bs), 6.99–7.08 (2H, m), 7.18–7.27 (1H, m), 7.62 (1H, d, J=1.2 Hz), 8.04 (1H, dd, J=1.2, 8.4 Hz), 8.50 (1H, d, J=8.4 Hz).

(3) To a solution of methyl 3-[[(tert-butoxycarbonyl)amino]methyl]-4-(3-fluorophenyl)-2-isobutyl-1-oxo-1,2-dihydro-6-isoquinolinecarboxylate (1.45 g, 3 mmol) in tetrahydrofuran (10 mL) and methanol (10 ml) was added 1N sodium hydroxide (6 mL). The obtained mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The residue was crystallized from ethyl acetate-n-hexane to give 3-[[(tert-butoxycarbonyl)amino]methyl]-4-(3-fluorophenyl)-2-isobutyl-1-oxo-1,2-dihydro-6-isoquinolinecarboxylic acid (1.34 g, 95.7%) as crystals.

Melting point 206–207° C. Elemental analysis for C$_{26}$H$_{29}$N$_2$O$_5$F Calculated: C, 66.65; H, 6.24; N, 5.98. Found: C, 66.39; H, 6.33; N, 5.63. $^1$H-NMR(CDCl$_3$) δ: 0.99 (6H, d, J=6.6 Hz), 1.48 (9H, s), 2.10–2.29 (1H, m), 4.05 (2H, d, J=7.4 Hz), 4.17 (2H, d, J=4.4 Hz), 5.49 (1H, bs), 7.05–7.27 (3H, m), 7.44–7.58 (2H, m), 7.86–7.90 (1H, m), 8.36 (1H, d, J=8.4 Hz).

(4) A solution of 3-[[(tert-butoxycarbonyl)amino]methyl]-4-(3-fluorophenyl)-2-isobutyl-1-oxo-1,2-dihydro-6-isoquinolinecarboxylic acid (1.17 g, 2.5 mmol), 1-ethyl-3-(3-dimethylaminopropyl)carbodiimide hydrochloride (0.96 g, 5 mol) and 1-hydroxybenzotriazole ammonium salt (0.76 g, 5 mmol) in N,N-dimethylformamide (10 mL) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give 3-[[(tert-butoxycarbonyl)amino]methyl]-4-(3-fluorophenyl)-2-isobutyl-1-oxo-1,2-dihydro-6-isoquinolinecarboxamide (0.81 g, 69.8%) as crystals.

Melting point 147–149° C. Elemental analysis for C$_{26}$H$_{30}$N$_3$O$_4$F 0.5H$_2$O Calculated: C, 65.53; H, 6.56; N, 8.82. Found: C, 65.91; H, 6.44; N, 8.87. $^1$H-NMR(CDCl$_3$) δ: 1.00 (6H, d, J=7.0 Hz), 1.44 (9H, s), 2.14–2.30 (1H, m), 4.07 (2H, d, J=7.4 Hz), 4.19 (2H, d, J=5.6 Hz), 4.73 (1H, bs), 5.77 (1H, bs), 6.11 (1H, bs), 6.98–7.25 (3H, m), 7.37 (1H, d, J=1.8 Hz), 7.45–7.56 (1H, m), 7.72 (1H, dd, J=1.8, 8.4 Hz), 8.42 (1H, d, J=8.4 Hz).

(5) To a solution of 3-[[(tert-butoxycarbonyl)amino]methyl]-4-(3-fluorophenyl)-2-isobutyl-1-oxo-1,2-dihydro-6-isoquinolinecarboxamide (0.28 g, 0.6 mmol) in ethyl acetate (5 mL) was added a solution of 4N hydrogen chloride in ethyl acetate (5 mL) and the obtained solution was stirred at room temperature for 1 h. The reaction mixture was concentrated under reduced pressure, and the precipitated crystals were recrystallized from methanol-diethyl ether to give 3-(aminomethyl)-4-(3-fluorophenyl)-2-isobutyl-1(2H)-isoquinolinone-6-carboxamide hydrochloride (0.22 g, 91.7%) as crystals.

Melting point 292–293° C. Elemental analysis for C$_{21}$H$_{23}$N$_3$O$_2$ClF 0.5H$_2$O Calculated: C, 61.09; H, 5.86; N, 10.18. Found: C, 60.79; H, 6.09; N, 10.04. $^1$H-NMR (DMSO-d$_6$) δ: 0.93 (6H, d, J=6.6 Hz), 2.02–2.19 (1H, m), 3.87 (2H, bs), 4.00–4.20 (2H, m), 7.26–7.45 (4H, m), 7.58–7.69 (2H, m), 8.01 (1H, dd, J=1.6, 8.4 Hz), 8.19 (1H, bs), 8.38 (1H, d, J=8.4 Hz), 8.61 (3H, bs).

Example 159

(E)-3-[3-(Aminomethyl)-2-isobutyl-1-oxo-4-phenyl-1,2-dihydro-6-isoquinolinyl]]-2-propenamide hydrochloride

(1) To a solution of 3-[[(tert-butoxycarbonyl)amino]methyl]-2-isobutyl-1-oxo-4-phenyl-1,2-dihydro-6-isoquinolinecarboxylic acid (6.31 g, 14 mmol) and N-methylmorpholine (1.8 mL, 16.8 mmol) in tetrahydrofuran (50 mL) was added ethyl chloroformate (1.6 mL, 16.8 mmol) at 0° C. and the mixture was stirred at 0° C. for 10 min. To the obtained mixture were added sodium tetrahydroborate (1.59 g, 42 mmol) and methanol (5 mL) and the mixture was stirred at 0° C. for 1 h. The reaction mixture was poured into water and extracted with ethyl acetate. The extract was washed with brine, dried over anhydrous magnesium sulfate and concentrated under reduced pressure. The precipitated crystals were recrystallized from ethyl acetate-diisopropyl ether to give tert-butyl(6-hydroxymethyl-2-isobutyl-1-oxo-4-phenyl-1,2-dihydro-3-isoquinolinyl)methylcarbamate (4.73 g, 77.4%) as crystals.

Melting point 169–170° C. Elemental analysis for C$_{26}$H$_{32}$N$_2$O$_4$ Calculated: C, 71.53; H, 7.39; N, 6.42. Found: C, 71.25; H, 7.49; N, 6.35. $^1$H-NMR(CDCl$_3$) δ: 0.99 (6H, d, J=6.6 Hz), 1.43 (9H, s), 2.04 (1H, bs), 2.16–2.29 (1H, m), 4.06 (2H, d, J=7.4 Hz), 4.18 (2H, d, J=5.4 Hz), 4.64 (2H, d, J=6.0 Hz), 4.66 (1H, bs), 6.89 (1H, s), 7.22–7.27 (2H, m), 7.49–7.54 (4H, m), 8.38 (1H, d, J=8.0 Hz).

(2) To a solution of tert-butyl(6-hydroxymethyl-2-isobutyl-1-oxo-4-phenyl-1,2-dihydro-3-isoquinolinyl)methylcarbamate (4.58 g, 10.5 mmol) in tetrahydrofuran (50 mL) was added manganese dioxide (13.7 g) and the mixture was stirred at room temperature for 12 h. Manganese dioxide was filtered off and the filtrate was concentrated under reduced pressure. The residue was purified by silica gel column chromatography to give tert-butyl(6-formyl-2-isobutyl-1-oxo-4-phenyl-1,2-dihydro-3-isoquinolinyl)methylcarbamate (4.12 g, 90.4%) as crystals.

Melting point 183–184° C. Elemental analysis for C$_{26}$H$_{30}$N$_2$O$_4$ Calculated: C, 71.87; H, 6.96; N, 6.45. Found: C, 71.79; H, 6.84; N, 6.36. $^1$H-NMR(CDCl$_3$) δ: 1.02 (6H, d, J=6.6 Hz), 1.43 (9H, s), 2.19–2.32 (1H, m), 4.10 (2H, d, J=7.4 Hz), 4.24 (2H, d, J=5.6 Hz), 4.51 (1H, bs), 7.26–7.30 (2H, m), 7.44 (1H, d, J=1.4 Hz), 7.51–7.59 (3H, m), 7.92 (1H, dd, J=1.4, 8.2 Hz), 8.59 (1H, d, J=8.2 Hz), 9.95 (1H, s).

(3) To a solution of ethyl diethylphosphonoacetate (1.0 mL, 5 mmol) in N,N-dimethylformamide (20 mL) was added sodium hydride (0.20 g, 5 mmol) (60% in oil), and the mixture was stirred at room temperature for 10 min. To the obtained mixture was added a solution of tert-butyl (6-formyl-2-isobutyl-1-oxo-4-phenyl-1,2-dihydro-3-isoquinolinyl)methylcarbamate (2.17 g, 5 mmol) in N,N-dimethylformamide (20 mL) and the mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give ethyl (E)-3-[3-[[(tert-butoxycarbonyl)amino]methyl]-2-isobutyl-1-oxo-4-phenyl-1,2-dihydro-6-isoquinolinyl]-2-propenate (2.03 g, 71.7%) as an amorphous.

Melting point 147–148° C. Elemental analysis for C$_{30}$H$_{36}$N$_2$O$_5$ Calculated: C, 71.40; H, 7.19; N, 5.55. Found: C, 71.37; H, 7.15; N, 5.43. $^1$H-NMR(CDCl$_3$) δ: 1.01 (6H, d, J=7.0 Hz), 1.31 (3H, t, J=7.3 Hz), 1.43 (9H, s), 2.18–2.31 (1H, m), 4.08 (2H, d, J=7.4 Hz), 4.13–4.28 (4H, m), 4.53 (1H, bs), 6.37 (1H, d, J=16.2 Hz), 7.00 (1H, d, J=1.4 Hz), 7.18–7.28 (2H, m), 7.44–7.67 (5H, m), 8.44 (1H, d, J=8.0 Hz).

(4) To a solution of ethyl (E)-3-[3-[[(tert-butoxycarbonyl)amino]methyl]-2-isobutyl-1-oxo-4-phenyl-1,2-dihydro-6-isoquinolinyl]-2-propenate (0.70 g, 1.4 mmol) in tetrahydrofuran (10 mL) and ethanol (10 mL) was added 1N sodium hydroxide (3 mL). The obtained mixture was stirred at room temperature for 1 h. The reaction mixture was poured into water, acidified with 1N hydrochloric acid and extracted with ethyl acetate. The extract was washed with brine, dried over magnesium sulfate and concentrated under reduced pressure. The obtained crystals were recrystallized from ethyl acetate-n-hexane to give (E)-3-[3-[[(tert-butoxycarbonyl)amino]methyl]-2-isobutyl-1-oxo-4-phenyl-1,2-dihydro-6-isoquinolinyl]-2-propenic acid (0.56 g, 84.8%) as crystals.

Melting point 172–173° C. Elemental analysis for C$_{28}$H$_{32}$N$_2$O$_5$ Calculated: C, 70.27; H, 7.16; N, 5.85. Found: C, 70.08; H, 6.80; N, 5.65. $^1$H-NMR(CDCl$_3$) δ: 0.99 (6H, d, J=6.6 Hz), 1.48 (9H, s), 2.16–2.24 (1H, m), 4.06 (2H, d, J=7.2 Hz), 4.15 (2H, d, J=4.0 Hz), 5.62 (1H, bs), 6.27 (1H, d, J=16.0 Hz), 6.82 (1H, s), 7.33–7.40 (3H, m), 7.48–7.58 (3H, m), 8.28 (1H, d, J=8.8 Hz).

(5) A solution of (E)-3-[3-[[(tert-butoxycarbonyl)amino]methyl]-2-isobutyl-1-oxo-4-phenyl-1,2-dihydro-6-isoquinolinyl]-2-propenic acid (0.33 g, 0.7 mmol), 1-ethyl-3-(3-dimethylaminopropyl)carbodiimide hydrochloride (0.27 g, 1.4 mmol) and 1-hydroxybenzotriazole ammonium salt (0.21 g, 1.4 mmol) in N,N-dimethylformamide (10 mL) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give (E)-3-[3-[[(tert-butoxycarbonyl)amino]methyl]-2-isobutyl-1-oxo-4-phenyl-1,2-dihydro-6-isoquinolinyl]-2-propenamide (0.31 g, 93.9%) as crystals.

Melting point 146–147° C. Elemental analysis for C$_{28}$H$_{33}$N$_3$O$_4$ 0.25H$_2$O Calculated: C, 70.05; H, 7.03; N, 8.75. Found: C, 70.08; H, 7.09; N, 8.64. $^1$H-NMR(CDCl$_3$) δ: 1.00 (6H, d, J=6.6 Hz), 1.44 (9H, s), 2.16–2.24 (1H, m), 4.07 (2H, d, J=7.4 Hz), 4.19 (2H, d, J=5.6 Hz), 4.96 (1H, bs), 5.75 (1H, bs), 6.38 (1H, d, J=15.6 Hz), 6.94 (1H, s), 7.26–7.30 (2H, m), 7.40–7.56 (5H, m), 8.29 (1H, d, J=8.4 Hz).

(6) A solution of (E)-3-[3-[[(tert-butoxycarbonyl)amino]methyl]-2-isobutyl-1-oxo-4-phenyl-1,2-dihydro-6-isoquinolinyl]-2-propenamide (0.24 g, 0.5 mmol) in ethyl acetate, (5 mL) was added a solution of 4N hydrogen chloride in ethyl acetate (5 mL), and the obtained solution was stirred at room temperature for 2 h. The reaction mixture was concentrated under reduced pressure, and the precipitated crystals were recrystallized from methanol-diisopropyl ether to give (E)-3-[3-(aminomethyl)-2-isobutyl-1-oxo-4-phenyl-1,2-dihydro-6-isoquinolinyl]-2-propenamide hydrochloride (0.20 g, 95.2%) as crystals.

Melting point 223–225° C. Elemental analysis for C$_{23}$H$_{26}$N$_3$O$_2$Cl 1.5H$_2$O Calculated: C, 62.93; H, 6.66; N, 9.57. Found: C, 63.15; H, 6.66; N, 9.34. $^1$H-NMR(DMSO-d$_6$) δ: 0.92 (6H, d, J=6.9 Hz), 2.06–2.16 (1H, m), 3.87 (2H, d, J=4.8 Hz), 4.08 (2H, s), 6.56 (1H, d, J=16.0 Hz), 7.19 (1H, bs), 7.31 (1H, d, J=16.0 Hz), 7.42–7.44 (2H, m), 7.54–7.63 (3H, m), 7.69 (1H, bs), 7.78 (1H, dd, J=1.2, 8.8 Hz), 8.35 (1H, d, J=8.8 Hz), 8.62 (3H, bs).

Example 160

(E)-3-[3-(Aminomethyl)-2-isobutyl-1-oxo-4-phenyl-1,2-dihydro-6-isoquinolinyl]-2-propenamide (1) (E)-3-[3-(Aminomethyl)-2-isobutyl-1-oxo-4-phenyl-1,2-dihydro-6-isoquinolinyl]-2-propenamide hydrochloride (Example 159 (6)) (0.13 g, 0.3 mmol) was dissolved in water (10 mL) and saturated aqueous potassium carbonate solution (10 mL) was added. The mixture was extracted with ethyl acetate. The extract was washed with brine, dried over anhydrous magnesium sulfate and concentrated under reduced pressure. The precipitated crystals were recrystallized from ethyl acetate-diisopropyl ether to give (E)-3-[3-(aminomethyl)-2-isobutyl-1-oxo-4-phenyl-1,2-dihydro-6-isoquinolinyl]-2-propenamide (0.06 g, 54.5%) as crystals.

Melting point 228–230° C. $^1$H-NMR(CDCl$_3$) δ: 1.00 (6H, d, J=7.0 Hz), 1.47 (2H, bs), 2.19–2.33 (1H, m), 3.69 (2H, s), 4.22 (2H, d, J=7.0 Hz), 5.70 (2H, bs), 6.43 (1H, d, J=15.8 Hz), 6.99 (1H, d, J=1.5 Hz), 7.25–7.29 (2H, m), 7.47–7.55 (4H, m), 7.58 (1H, dd, J=1.5, 8.4 Hz), 8.44 (1H, d, J=8.4 Hz).

Recrystallization from ethanol-ethyl acetate gave crystals in a different crystal form.

Melting point 275–276° C.

| Powder X-ray crystal diffraction data | |
|---|---|
| Diffraction angle: 2θ(°) (angstrom) | spacing: d value |
| 8.66 | 10.2 |
| 13.6 | 6.50 |
| 17.5 | 5.07 |
| 21.4 | 4.15 |

Example 161

2-[[3-(Aminomethyl)-2-isobutyl-1-oxo-4-phenyl-1,2-dihydro-6-isoquinolinyl]oxy]acetamide hydrochloride (1) To a suspension of 4-benzyloxyphthalic anhydride (2.54 g, 10 mmol) in ethanol (30 mL) was added 20% sodium ethoxide ethanol solution (3.74 g, 11 mmol) and the mixture was stirred at room temperature for 1 h. The reaction mixture was poured into 1N hydrochloric acid (150 mL) and extracted with ethyl acetate. The extract was washed with brine, dried over anhydrous magnesium sulfate and concentrated under reduced pressure. The residue was dissolved in N,N-dimethylformamide (200 mL) and tert-butyl 2-(isobutylamino)acetate (2.25 g, 12 mmol), 1-ethyl-3-(3-dimethylaminopropyl)carbodiimide hydrochloride (2.30 g, 12 mmol) and 1-hydroxybenzotriazole (1.84 g, 12 mmol) were added and the mixture was stirred at room temperature for 3 h. The reaction mixture was poured into water and extracted with ethyl acetate. The extract was washed with brine, dried over anhydrous magnesium sulfate and concentrated under reduced pressure. The residue was dissolved in ethanol (30 mL) and a solution (6.80 g, 20 mmol) of 20% sodium ethoxide in ethanol was added thereto. The mixture was stirred at room temperature for 1 h. The reaction mixture was poured into 1N hydrochloric acid (20 mL) and extracted with ethyl acetate. The extract was washed with brine, dried over anhydrous magnesium sulfate and concentrated under reduced pressure. The residue was purified by silica gel column chromatography and the component eluted earlier was concentrated to give tert-butyl 7-benzyloxy-4-hydroxy-2-isobutyl-1-oxo-1,2-dihydro-3-isoquinolinecarboxylate (0.40 g, 9.5%) as an oil.

$^1$H-NMR(CDCl$_3$) δ: 0.82 (6H, d, J=6.6 Hz), 1.78–1.87 (1H, m), 3.99 (3H, s), 4.39 (2H, d, J=7.5 Hz), 5.25 (2H, s), 7.25–7.48 (6H, m), 7.96–7.98 (1H, m), 8.10 (1H, d, J=8.7 Hz), 11.34 (1H, s).

The component eluted later was concentrated to give tert-butyl 6-benzyloxy-4-hydroxy-2-isobutyl-1-oxo-1,2-dihydro-3-isoquinolinecarboxylate (1.51 g, 35.7%) as crystals.

Melting point 133–134° C. Elemental analysis for C$_{25}$H$_{29}$NO$_5$ Calculated: C, 70.90; H, 6.90; N, 3.31. Found: C, 70.84; H, 6.85; N, 3.11. $^1$H-NMR(CDCl$_3$) δ: 0.81 (6H, d, J=6.6 Hz), 1.64 (9H, s), 1.73–1.84 (1H, m) 4.38 (2H, d, J=7.4 Hz), 5.21 (2H, s), 7.29 (1H, dd, J=2.4, 8.8 Hz), 7.35–7.51 (5H, m), 7.58 (1H, d, J=2.4 Hz), 8.37 (1H, d, J=8.8 Hz), 11.17 (1H, s).

(2) To a solution of tert-butyl 6-benzyloxy-4-hydroxy-2-isobutyl-1-oxo-1,2-dihydro-3-isoquinolinecarboxylate (6.35 g, 15 mmol) in N,N-dimethylformamide (50 mL) was added sodium hydride (0.72 g, 18 mmol) (60% in oil) at 0° C. and the mixture was stirred at 0° C. for 30 min. To the obtained mixture was added N-phenyltrifluoromethanesulfonimide (6.43 g, 18 mmol) and the mixture was stirred at room temperature for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl 6-benzyloxy-2-isobutyl-1-oxo-4-trifluoromethanesulfonyloxy-1,2-dihydro-3-isoquinolinecarboxylate (6.62 g, 81.2%) as an oil.

$^1$H-NMR(CDCl$_3$) δ: 0.89 (6H, d, J=6.6 Hz), 1.64 (9H, s), 2.04–2.15 (1H, m), 4.03 (2H, d, J>7.4 Hz), 5.18 (2H, s), 7.20–7.56 (7H, m), 8.34 (1H, d, J=9.2 Hz).

(3) A mixed solution of tert-butyl 6-benzyloxy-2-isobutyl-1-oxo-4-trifluoromethanesulfonyloxy-1,2-dihydro-3-isoquinolinecarboxylate (6.52 g, 12 mmol), phenylboronic acid (1.76 g, 14.4 mmol) and sodium carbonate (3.18 g, 30 mmol) in toluene (50 mL), ethanol (10 mL) and water (10 mL) was stirred under an argon atmosphere at room temperature for 10 min. To the obtained mixture was added tetrakis(triphenylphosphine)-palladium (0.69 g, 0.6 mmol) and the mixture was refluxed under heating under an argon atmosphere for 10 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl 6-benzyloxy-2-isobutyl-1-oxo-4-phenyl-1,2-dihydro-3-isoquinolinecarboxylate (5.01 g, 86.4%) as crystals.

Melting point 138–139° C. Elemental analysis for C$_{31}$H$_{33}$NO$_4$ Calculated: C, 76.99; H, 6.88; N, 2.90 Found: C, 77.04; H, 6.80; N, 2.70. $^1$H-NMR(CDCl$_3$) δ: 0.94 (6H, d, J=6.9 Hz), 1.15 (9H, s), 2.17–2.27 (1H, m), 3.98 (2H, d, J=7.5 Hz), 4.95 (2H, s), 6.53 (1H, d, J=2.4 Hz), 7.13 (1H, dd, J=2.4, 8.8 Hz), 7.25–7.36 (6H, m), 7.40–7.45 (4H, m), 8.41 (1H, d, J=8.8 Hz).

(4) A solution of tert-butyl 6-benzyloxy-2-isobutyl-1-oxo-4-phenyl-1,2-dihydro-3-isoquinolinecarboxylate (9.03 g, 25 mmol) in trifluoroacetic acid (30 mL) was stirred at room temperature for 3 h. The reaction mixture was concentrated under reduced pressure and the obtained crystals were recrystallized from ethyl acetate-diisopropyl ether to give 6-benzyloxy-2-isobutyl-1-oxo-4-phenyl-1,2-dihydro-3-isoquinolinecarboxylic acid (3.50 g, 82.0%) as crystals.

$^1$H-NMR(CDCl$_3$) δ: 0.85 (6H, d, J=6.6 Hz), 2.09–2.14 (1H, m), 3.83 (2H, d, J=7.5 Hz), 4.96 (2H, s), 6.58 (1H, d, J=2.4 Hz), 7.09–7.44 (11H, m), 8.29 (1H, d, J=8.7 Hz).

(5) To a solution of 6-benzyloxy-2-isobutyl-1-oxo-4-phenyl-1,2-dihydro-3-isoquinolinecarboxylic acid (3.42 g, 8 mmol) in tetrahydrofuran (30 mL) were added oxalyl chloride (0.84 mL, 9.6 mmol) and N,N-dimethylformamide (3 drops), and the mixture was stirred at room temperature for 1 h. The reaction mixture was concentrated under reduced pressure and the residue was dissolved in tetrahydrofuran (20 mL). The obtained solution was added dropwise to a suspension of sodium tetrahydroborate (1.06 g, 28 mmol) in 1,2-dimethoxyethane (20 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from tetrahydrofuran-diisopropyl ether to give 6-benzyloxy-3-hydroxymethyl-2-isobutyl-4-phenyl-1(2H)-isoquinolinone (2.92 g, 88.5%) as crystals.

$^1$H-NMR(CDCl$_3$) δ: 0.96 (6H, d, J=6.6 Hz), 2.16–2.40 (2H, m), 4.18 (2H, d, J=7.5 Hz), 4.43 (2H, s), 4.89 (2H, s), 6.37 (1H, d, J=2.4 Hz), 7.00 (1H, dd, J=2.4, 9.0 Hz), 7.21–7.34 (7H, m), 7.44–7.52 (3H, m), 8.30 (1H, d, J=9.0 Hz).

(6) To a suspension of 6-benzyloxy-3-hydroxymethyl-2-isobutyl-4-phenyl-1(2H)-isoquinolinone (2.89 g, 7 mmol) in toluene (30 mL) was added thionyl chloride (1.0 mL, 14 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-2-isobutyl-4-phenyl-1(2H)-isoquinolinone (2.61 g, 86.4%) as crystals.

$^1$H-NMR(CDCl$_3$) δ: 1.00 (6H, d, J=7.0 Hz), 2.12–2.31 (1H, m), 4.16 (2H, d, J=7.4 Hz), 4.37 (2H, s), 4.93 (2H, s), 6.41 (1H, d, J=2.3 Hz), 7.13 (1H, dd, J=2.3, 9.0 Hz), 7.19–7.35 (7H, m), 7.45–7.54 (3H, m), 8.41 (1H, d, J=9.0 Hz).

(7) A solution of 6-benzyloxy-3-chloromethyl-2-isobutyl-4-phenyl-1(2H)-isoquinolinone (2.59 g, 6 mmol) and potassium phthalimide (1.67 g, 9 mmol) in N,N-dimethylformamide (30 mL) was stirred at room temperature for 6 h. The reaction mixture was poured into water and extracted with ethyl acetate. After washing the extract with water, the extract was dried over anhydrous magnesium sulfate and concentrated under reduced pressure. The obtained crystals were recrystallized from ethyl acetate-diisopropyl ether to give 2-[(6-benzyloxy-2-isobutyl-1-oxo-4-phenyl-1,2-dihydro-3-isoquinolinyl)methyl]-1H-isoindole-1,3(2H)-dione (3.04 g, 93.5%) as crystals.

Melting point 113–114° C. Elemental analysis for C$_{35}$H$_{30}$N$_2$O$_4$ 0.25H$_2$O Calculated: C, 76.83; H, 5.62; N, 5.12. Found: C, 76.68; H, 5.79; N, 4.93. $^1$H-NMR(CDCl$_3$) δ: 0.99 (6H, d, J=6.4 Hz), 2.14–2.28 (1H, m), 4.04 (2H, d, J=8.4 Hz), 4.76 (2H, s), 4.91 (2H, s), 6.36 (1H, d, J=2.6 Hz), 7.10 (1H, dd, J=2.6, 8.8 Hz), 7.20–7.39 (10H, m), 7.66–7.76 (4H, m), 8.39 (1H, d, J=8.8 Hz).

(8) To a solution of 2-[(6-benzyloxy-2-isobutyl-1-oxo-4-phenyl-1,2-dihydro-3-isoquinolinyl)methyl]-1H-isoindole-1,3(2H)-dione (2.98 g, 5.5 mmol) in ethanol (30 mL) was added hydrazine monohydrate (0.8 mL, 16.5 mmol). The obtained mixture was refluxed under heating for 1 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (20 mL) and di-t-butyl dicarbonate, (1.9 mL, 8.3 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl(6-benzyloxy-2-isobutyl-1-oxo-4-phenyl-1,2-dihydro-3-isoquinolinyl)methylcarbamate (2.29 g, 81.2%) as crystals.

Melting point 141–142° C. Elemental analysis for C$_{32}$H$_{35}$N$_2$O$_4$ Calculated: C, 74.97; H, 7.08; N, 5.46. Found: C, 74.60; H, 7.13; N, 5.45. $^1$H-NMR(CDCl$_3$) δ: 0.99 (6H, d, J=7.0 Hz), 1.42 (9H, s), 2.16–2.30 (1H, m), 4.03 (2H, d, J=7.4 Hz), 4.17 (2H, d, J=5.6 Hz), 4.45 (1H, bs), 4.92 (2H, s), 6.35 (1H, d, J=2.4 Hz), 7.09 (1H, dd, J=2.4, 9.0 Hz), 7.17–7.37 (7H, m), 7.47–7.52 (3H, m), 8.38 (1H, d, J=9.0 Hz).

(9) A suspension of tert-butyl(6-benzyloxy-2-isobutyl-1-oxo-4-phenyl-1,2-dihydro-3-isoquinolinyl)methylcarbamate (2.05 g, 4 mmol) and 5% palladium carbon (0.6 g) in tetrahydrofuran (10 mL) and ethanol (10 mL) was stirred under a hydrogen atmosphere at room temperature for 2 h. The catalyst was filtered off and the filtrate was concentrated under reduced pressure. The obtained crystals were recrystallized from ethyl acetate-diisopropyl ether to give tert-butyl(6-hydroxy-2-isobutyl-1-oxo-4-phenyl-1,2-dihydro-3-isoquinolinyl)methylcarbamate (1.56 g, 92.3%) as crystals.

Melting point 218–219° C. Elemental analysis for C$_{25}$H$_{30}$N$_2$O$_4$ Calculated: C, 71.07; H, 7.16; N, 6.63. Found: C, 70.85; H, 7.10; N, 6.62. $^1$H-NMR(CDCl$_3$) δ: 0.97 (6H, d, J=6.8 Hz), 1.42 (9H, s), 2.14–2.24 (1H, m), 4.02 (2H, d, J=7.2 Hz), 4.18 (2H, d, J=5.4 Hz), 4.47 (1H, bs), 6.33 (1H, d, J=2.4 Hz), 7.03 (1H, dd, J=2.4, 8.8 Hz), 7.20–7.27 (2H, m), 7.43–7.46 (3H, m), 7.97 (1H, bs), 8.30 (1H, d, J=8.8 Hz).

(10) A solution of tert-butyl(6-hydroxy-2-isobutyl-1-oxo-4-phenyl-1,2-dihydro-3-isoquinolinyl)methylcarbamate (0.63 q, 1.5 mmol), 2-iodoacetamide (0.43 g, 2.3 mmol) and 1,8-diazabicyclo[5.4.0]-7-undecene (0.34 mL, 2.3 mmol) in N,N-dimethylformamide (10 mL) was stirred at 80° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl 6-(2-amino-2-oxoethoxy)-2-isobutyl-1-oxo-4-phenyl-1,2-dihydro-3-isoquinolinyl]methylcarbamate (0.32 g, 44.4%) as crystals.

Melting point 226–227° C. Elemental analysis for C$_{27}$H$_{33}$N$_3$O$_5$ Calculated: C, 67.62; H, 6.94; N, 8.76 Found: C, 67.36; H, 6.73; N, 8.60. $^1$H-NMR(DMSO-d$_6$) δ: 0.89 (6H, d, J=6.6 Hz), 1.38 (9H, s), 2.07–2.21 (1H, m), 3.88 (2H, d, J=6.6 Hz), 3.95 (2H, d, J=4.0 Hz), 4.34 (2H, s), 6.30 (1H, d, J=2.4 Hz), 7.13 (1H, dd, J=2.4, 8.8 Hz), 7.34–7.52 (8H, m), 8.24 (1H, d, J=8.8 Hz).

(11) To a solution of tert-butyl[6-(2-amino-2-oxoethoxy)-2-isobutyl-1-oxo-4-phenyl-1,2-dihydro-3-isoquinolinyl]methylcarbamate (0.24 g, 0.5 mmol) in ethyl acetate (5 mL) was added a solution of 4N hydrogen chloride in ethyl acetate (5 mL) and the obtained solution was stirred at room temperature for 2 h. The reaction mixture was concentrated under reduced pressure, and the precipitated crystals were recrystallized from methanol-diethyl ether to give 2-[[3-(aminomethyl)-2-isobutyl-1-oxo-4-phenyl-1,2-dihydro-6-isoquinolinyl]oxy]acetamide hydrochloride (0.19 g, 95.0%) as crystals.

Melting point 185–186° C. Elemental analysis for C$_{22}$H$_{26}$N$_3$O$_3$Cl 0.5H$_2$O Calculated: C, 62.23; H, 6.44; N, 9.75. Found: C, 62.18; H, 6.40; N, 9.89. $^1$H-NMR(DMSO-d$_6$) δ: 0.91 (6H, d, J=6.6 Hz), 2.01–2.18 (1H, m), 3.37 (2H, bs), 3.85 (2H, bs), 4.05 (2H, d, J=6.8 Hz), 4.36 (2H, s), 6.30 (1H, d, J=2.0 Hz), 7.19 (1H, dd, J=2.0, 8.8 Hz), 7.36–7.40 (2H, m), 7.52–7.58(3H, m), 8.28 (1H, d, J=8.8 Hz), 8.55 (3H, s).

Example 162

2-[[3-(Aminomethyl)-2-isobutyl-1-oxo-4-phenyl-1,2-dihydro-6-isoquinolinyl]oxy]acetamide (1) To a solution of tert-butyl[6-(2-amino-2-oxoethoxy)-2-isobutyl-1-oxo-4-phenyl-1,2-dihydro-3-isoquinolinyl]methylcarbamate (0.38 g, 0.8 mmol) in ethyl acetate (5 mL) was added a solution of 4N hydrogen chloride in ethyl acetate (5 mL) and the obtained solution was stirred at room temperature for 2 h. The reaction, mixture was concentrated under reduced pressure, and the residue was suspended in 1N aqueous sodium hydroxide solution. The suspension was stirred at room temperature for 10 min, and the reaction mixture was poured into water and extracted with ethyl acetate. The extract was washed with brine, dried over anhydrous magnesium sulfate and concentrated under reduced pressure. The precipitated crystals were recrystallized from ethyl acetate-diisopropyl ether to give 2-[[3-(aminomethyl)-2-isobutyl-1-oxo-4-phenyl-1,2-dihydro-6-isoquinolinyl]oxy]acetamide (0.19 g, 63.3%) as crystals.

Melting point 161–163° C. Elemental analysis for $C_{22}H_{25}N_3O_3$ 0.25$H_2O$ Calculated: C, 68.82; H, 6.69; N, 10.94. Found: C, 69.02; H, 6.71; N, 10.80. $^1$H-NMR(CDCl$_3$) δ: 0.99 (6H, d, J=7.0 Hz), 1.29 (2H, bs), 2.18–3.66 (2H, s), 4.19 (2H, d, J=7.4 Hz), 4.32 (2H, s), 5.81 (1H, bs), 6.30 (1H, d, J=2.4 Hz), 6.51 (1H, bs), 7.03 (1H, dd, J=2.4, 8.8 Hz), 7.24–7.29 (2H, m), 7.44–7.56 (3H, m), 8.43 (1H, d, J=8.8 Hz), 8.55 (3H, s).

Example 163

(E)-3-[3-(Aminomethyl)-4-butoxy-2-neopentyl-1-oxo-1,2-dihydro-6-isoquinolinyl]-2-propenamide hydrochloride (1) To a solution of 4-butoxy-3-[[(tert-butoxycarbonyl)amino]methyl]-2-neopentyl-1-oxo-1,2-dihydro-6-isoquinolinecarboxylic acid (4.60 g, 10 mmol) and N-methylmorpholine (1.3 mL, 12 mmol) in tetrahydrofuran (30 mL) was added ethyl chloroformate (1.2 mL, 12 mmol) at 0° C. and the mixture was stirred at 0° C. for 10 min. To the obtained mixture were added sodium tetrahydroborate (1.13 g, 30 mmol) and methanol (5 mL), and the mixture was stirred at 0° C. for 10 h. The reaction mixture was poured into water and extracted with ethyl acetate. The extract was washed with brine, dried over anhydrous magnesium sulfate and concentrated under reduced pressure. The precipitated crystals were recrystallized from ethyl acetate-diisopropyl ether to give tert-butyl(4-butoxy-6-hydroxymethyl-2-neopentyl-1-oxo-1,2-dihydro-3-isoquinolinyl)methylcarbamate (2.89 g, 64.8%) as crystals.

Melting point 92–93° C. Elemental analysis for $C_{25}H_{38}N_2O_5$ Calculated: C, 67.24; H, 8.58; N, 6.27. Found: C, 67.09; H, 8.43; N, 6.25. $^1$H-NMR(CDCl$_3$) δ: 0.98 (9H, s), 1.01 (3H, t, J=7.4 Hz), 1.46–1.63 (11H, m), 1.77–1.92 (2H, m), 2.80 (1H, bs), 3.85 (2H, t, J=6.8 Hz), 4.14 (2H, bs), 4.56 (2H, d, J=5.0 Hz), 4.82 (2H, s), 5.15 (1H, bs), 7.42 (1H, d, J=8.4 Hz), 7.53 (1H, s), 8.19 (1H, d, J=8.4 Hz).

(2) To a solution of tert-butyl(4-butoxy-2-cyclopropylmethyl-6-formyl-1-oxo-1,2-dihydro-3-isoquinolinyl)methylcarbamate (2.27 g, 6.2 mmol) in tetrahydrofuran (30 mL) was added manganese dioxide (8.1 g) and the mixture was stirred at room temperature for 12 h. Manganese dioxide was filtered off and the mother liquor was concentrated under reduced pressure. The residue was purified by silica gel column chromatography to give tert-butyl(4-butoxy-6-formyl-2-neopentyl-1-oxo-1,2-dihydro-3-isoquinolinyl)methylcarbamate (2.52 g, 91.6%) as crystals.

Melting point 149–150° C. Elemental analysis for $C_{25}H_{38}N_2O_5$ 0.25$H_2O$ Calculated: C, 66.87; H, 8.19; N, 6.24. Found: C, 67.09; H, 8.15; N, 6.05. $^1$H-NMR(CDCl$_3$) δ: 1.01 (9H, s), 1.06 (3H, t, J=7.4 Hz), 1.45 (9H, s), 1.52–1.71 (2H, m), 1.84–1.98 (2H, m), 3.91 (2H, t, J=6.4 Hz), 4.18 (2H, bs), 4.61 (2H, d, J=5.4 Hz), 4.72 (1H, bs), 7.96 (1H, dd, J=1.7, 8.4 Hz), 7.53 (1H, d, J=1.7 Hz), 8.55 (1H, d, J=8.4 Hz), 10.19 (1H, s).

(3) To a solution of ethyl diethylphosphonoacetate (1.1 mL, 5.5 mmol) in N,N-dimethylformamide (30 mL) was added sodium hydride (0.22 g, 5.5 mmol) (60% in oil), and the mixture was stirred at room temperature for 10 min. To the obtained mixture was added a solution of tert-butyl (4-butoxy-6-formyl-2-neopentyl-1-oxo-1,2-dihydro-3-isoquinolinyl)methylcarbamate (2.45 g, 5.5 mmol) in N,N-dimethylformamide (10 mL) and the mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl (E)-3-[4-butoxy-3-[[(tert-butoxycarbonyl)amino]methyl]-2-neopentyl-1-oxo-1,2-dihydro-6-isoquinolinyl]-2-propenate (2.03 g, 71.7%), as an amorphous.

$^1$H-NMR(CDCl$_3$) δ: 1.00 (9H, s), 1.06 (3H, t, J=7.4 Hz), 1.37 (3H, t, J=7.2 Hz), 1.45 (9H, s), 1.51–1.66 (2H, m), 1.82–1.93 (2H, m), 3.88 (2H, t, J=6.6 Hz), 4.14 (2H, bs), 4.30 (2H, q, J=7.2 Hz), 4.58 (2H, d, J=5.2 Hz), 4.71 (1H, bs), 6.58 (1H, d, J=16.2 Hz), 7.65 (1H, dd, J=1.6, 8.4 Hz), 7.77 (1H, d, J=1.6 Hz), 7.79 (1H, d, J=16.2 Hz), 8.39 (1H, d, J=8.4 Hz).

(4) To a solution of ethyl (E)-3-[4-butoxy-3[[(tert-butoxycarbonyl)amino]methyl]-2-neopentyl-1-oxo-1,2-dihydro-6-isoquinolinyl]-2-propenate (0.67 g, 1.3 mmol) in tetrahydrofuran (5 mL) and ethanol (5 mL) as added 1N sodium hydroxide (3 mL). The obtained mixture was stirred at room temperature for 1 h. The reaction mixture was poured into water, acidified with 1N hydrochloric acid and extracted with ethyl-acetate. The extract was washed with brine, dried over anhydrous magnesium sulfate and concentrated under reduced pressure. The obtained crystals were recrystallized from ethyl acetate-n-hexane to give (E)-3-[4-butoxy-3-[[(tert-butoxycarbonyl)amino]methyl]-2-neopentyl-1-oxo-1,2-dihydro-6-isoquinolinyl]-2-propenic acid (0.53 g, 84.1%) as crystals.

Melting point 138–139° C. Elemental analysis for $C_{27}H_{38}N_2O_6$ Calculated: C, 66.64; H, 7.87; N, 5.76. Found: C, 66.57; H, 7.84; N, 5.57. $^1$H-NMR(CDCl$_3$) δ: 0.99 (9H, s), 1.07 (3H, t, J=7.3 Hz), 1.48 (9H, s), 1.49–1.67 (2H, m), 1.83–1.94 (2H, m), 3.88 (2H, t, J=6.6 Hz), 4.14 (2H, bs), 4.59 (2H, d, J=4.8 Hz), 5.32 (1H, bs), 6.57 (1H, d, J=15.7 Hz), 7.58 (1H, d, J=8.5 Hz), 7.68 (1H, s), 7.83 (1H, d, J=15.7 Hz), 8.29 (1H, d, J=8.5 Hz).

(5) A solution of (E)-3-[4-butoxy-3-[[(tert-butoxycarbonyl)amino]methyl]-2-neopentyl-1-oxo-1,2-dihydro-6-isoquinolinyl]-2-propenic acid (0.34 g, 0.7 mmol), 1-ethyl-3-(3-dimethylaminopropyl)carbodiimide hydrochloride (0.27 g, 1.4 mmol) and 1-hydroxybenzotriazole ammonium salt (0.21 g, 1.4 mmol) in N,N-dimethylformamide (10 mL) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give (E)-3-[4-butoxy-3-[[(tert-butoxycarbonyl)amino]methyl]-2-neopentyl-1-oxo-1,2-dihydro-6-isoquinolinyl]-2-propenamide (0.29 g, 87.9%) as crystals.

Melting point 121–122° C. Elemental analysis for $C_{27}H_{39}N_3O_5$ 0.5$H_2O$ Calculated: C, 65.56; H, 8.15; N, 8.50. Found: C, 66.18; H, 8.06; N, 8.59. $^1$H-NMR(CDCl$_3$) δ: 0.99 (9H, s), 1.05 (3H, t, J=7.2 Hz), 1.46 (9H, s), 1.53–1.65 (2H, m), 1.83–1.93 (2H, m), 3.88 (2H, t, J=6.5 Hz), 4.18 (2H, bs), 4.58 (2H, d, J=4.8 Hz), 4.92 (1H, bs), 5.74 (1H, bs), 5.91 (1H, bs), 6.60 (1H, d, J=15.6 Hz), 7.58 (1H, dd, J=1.5, 8.4 Hz), 7.73 (1H, d, J=1.5 Hz), 7.75 (1H, d, J=15.6 Hz), 8.31 (1H, d, J=8.4 Hz).

(6) To a solution of (E)-3-[4-butoxy-3-[[(tert-butoxycarbonyl)amino]methyl]-2-neopentyl-1-oxo-1,2-dihydro-6-isoquinolinyl]-2-propenamide (0.24 g, 0.5 mmol) in ethyl acetate (5 mL) was added a solution of 4N hydrogen chloride in ethyl acetate (5 mL) and the obtained solution was stirred at room temperature for 2 h. The reaction mixture was concentrated under reduced pressure, and the precipitated crystals were recrystallized from methanol-diethyl ether to give (E)-3-[3-(aminomethyl)-4-butoxy-2-neopentyl-1-oxo-1,2-dihydro-6-isoquinolinyl]-2-propenamide hydrochloride (0.19 g, 90.5%) as crystals.

Melting point 187–188° C. Elemental analysis $C_{22}H_{32}N_3O_3Cl$ 0.75$H_2O$ Calculated: C, 60.68; H, 7.75; N, 9.65. Found: C, 60.53; H, 7.74; N, 9.73. $^1$H-NMR(DMSO-d$_6$) δ: 0.91 (9H, s), 1.01 (3H, t, J=7.3 Hz), 1.52–1.63 (2H, m), 1.82–1.93 (2H, m), 3.96 (2H, t, J=6.3 Hz), 4.12 (2H, bs), 4.24 (2H, bs), 4.91 (1H, bs), 6.84 (1H, d, J=15.8 Hz), 7.29 (1H, bs), 7.63 (1H, d, J=15.8 Hz), 7.81 (1H, d, J=8.4 Hz), 7.87 (1H, bs), 8.29 (1H, d, J=8.4 Hz), 8.58 (3H, bs).

Example 164

2-[[3-(Aminomethyl)-2-isobutyl-1-oxo-4-(4,4,4-trifluorobutoxy)-1,2-dihydro-6-isoquinolinyl]oxy]acetamide hydrochloride (1) A solution of 4-benzyloxyphthalic anhydride (4.07 g, 16 mmol) and ethyl 2-(isobutylamino)acetate (2.86 g, 18 mmol) in tetrahydrofuran (30 mL) was stirred at room temperature for 1 h. The reaction mixture was poured into water and extracted with ethyl acetate. The extract was washed with brine, dried over anhydrous magnesium sulfate and concentrated under reduced pressure. The residue was dissolved in N,N-dimethylformamide (30 mL), and potassium carbonate (2.21 g, 16 mmol) and ethyl iodide (1.5 mL, 19.2 mmol) were added thereto. The mixture was stirred at room temperature for 3 h. The reaction mixture was poured into water and extracted with ethyl acetate. The extract was washed with brine, dried over anhydrous magnesium sulfate and concentrated under reduced pressure. The residue was dissolved in ethanol (50 mL), and a solution (10.9 g, 32 mmol) of 20% sodium ethoxide in ethanol was added thereto. The mixture was stirred at room temperature for 1 h. The reaction mixture was poured into 1N hydrochloric acid (70 mL) and extracted with ethyl acetate. The extract was washed with brine, dried over anhydrous magnesium sulfate and concentrated under reduced pressure. The residue was purified by silica gel column chromatography and the component eluted earlier was concentrated to give ethyl 7-benzyloxy-4-hydroxy-2-isobutyl-1-oxo-1,2-dihydro-3-isoquinolinecarboxylate (4.21 g, 66.6%) as an oil.

$^1$H-NMR(CDCl$_3$) δ: 0.82 (6H, d, J=6.6 Hz), 1.45 (3H, t, J=7.1 Hz), 1.77–1.91 (1H, m), 4.42–4.52 (4H, m), 7.31–7.58(6H, s), 7.97 (1H, d, J=2.6 Hz), 8.10 (1H, d, J=8.8 Hz), 11.45 (1H, s).

The component eluted later was concentrated to give ethyl 6-benzyloxy-4-hydroxy-2-isobutyl-1-oxo-1,2-dihydro-3-isoquinolinecarboxylate (0.80 g, 12.7%) as crystals.

Melting point 92–93° C. Elemental analysis for $C_{23}H_{25}NO_5$ Calculated: C, 69.86; H, 6.37; N, 3.54. Found: C, 69.68; H, 6.20; N, 3.51. $^1$H-NMR(CDCl$_3$) δ: 0.81 (6H, d, J=6.6 Hz), 1.46 (3H, t, J=7.22 Hz), 1.73–1.87 (1H, m), 4.39 (2H, d, J=7.2 Hz), 4.48 (2H, q, J=7.2 Hz), 5.21 (2H, s), 7.28–7.49 (6H, m), 7.60 (1H, d, J=2.6 Hz), 8.38 (1H, d, J=8.8 Hz), 11.23 (1H, s).

(2) To a solution of ethyl 6-benzyloxy-4-hydroxy-2-isobutyl-1-oxo-1,2-dihydro-3-isoquinolinecarboxylate (5.93 g, 15 mmol), 4,4,4-trifluorobutanol (2.31 g, 18 mmol) and tributylphosphine (7.5 ml, 30 mmol) in tetrahydrofuran (50 mL) was added 1,1'-(azodicarbonyl)dipiperidine (7.57 g, 30 mmol) and the mixture was stirred at room temperature for 3 h. The reaction mixture was concentrated under reduced pressure and the residue was purified by silica gel column chromatography to give ethyl 6-benzyloxy-2-isobutyl-1-oxo-4-(4,4,4-trifluorobutoxy)-1,2-dihydro-3-isoquinolinecarboxylate (6.71 g, 88.5%) as an oil.

$^1$H-NMR(CDCl$_3$) δ: 0.89 (6H, d, J=6.6 Hz), 1.43 (3H, t, J=7.2 Hz), 1.90–2.37 (5H, m), 3.83–3.92 (4H, m), 4.43 (2H, q, J=7.2 Hz), 5.22 (2H, s), 7.03 (1H, d, J=2.4 Hz), 7.21 (1H, dd, J=2.4, 9.0 Hz), 7.33–7.46 (5H, m), 8.37 (1H, d, J=9.0 Hz).

(3) To a solution of ethyl 6-benzyloxy-2-isobutyl-1-oxo-4-(4,4,4-trifluorobutoxy)-1,2-dihydro-3-isoquinolinecarboxylate (6.57 g, 13 mmol) in ethanol (50 mL) was added an aqueous solution (20 mL) of sodium hydroxide (2.08 g, 52 mmol). The obtained mixture was refluxed under heating for 12 h. The reaction mixture was poured into water acidified with 1N hydrochloric acid and extracted with ethyl acetate. The extract was washed with brine, dried over anhydrous magnesium, sulfate and concentrated under reduced pressure. The obtained, crystals were recrystallized from ethyl acetate-n-hexane to give 6-benzyloxy-2-isobutyl-1-oxo-4-(4,4,4-trifluorobutoxy)-1,2-dihydro-3-isoquinolinecarboxylic acid (4.89 g, 78.7%) as crystals.

Melting point 130–131° C. $^1$H-NMR(CDCl$_3$) δ: 0.85 (6H, d, J=6.4 Hz), 1.92–2.39 (5H, m), 3.89–3.93 (4H, m), 5.16 (2H, s), 6.79 (1H, d, J=2.6 Hz), 7.71 (1H, dd, J=2.6, 8.8 Hz), 7.32–7.41 (5H, m), 8.18 (1H, d, J=8.8 Hz).

(4) 6-Benzyloxy-2-isobutyl-1-oxo-4-(4,4,4-trifluorobutoxy)-1,2-dihydro-3-isoquinolinecarboxylic acid (4.77 g, 10 mmol) was dissolved in tetrahydrofuran (50 mL), and oxalyl chloride (1.1 mL, 12 mmol) and N,N-dimethylformamide (3 drops) were added. The mixture was stirred at room temperature for 1 h. The reaction mixture was concentrated under reduced pressure and the residue was dissolved in tetrahydrofuran (20 mL). The obtained solution was added dropwise to a suspension of sodium tetrahydroborate (1.32 g, 35 mmol) in 1,2-dimethoxyethane (50 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-n-hexane to give 6-benzyloxy-3-hydroxymethyl-2-isobutyl-4-(4,4,4-trifluorobutoxy)-1(2H)-isoquinolinone-(4.02 g, 84.6%) as crystals.

Melting point 112–113° C. Elemental analysis for $C_{25}H_{28}NO_4F_3$ Calculated: C, 65.67; H, 5.94; N, 2.95. Found: C, 65.77; H, 6.21; N, 3.03. $^1$H-NMR(CDCl$_3$) δ: 0.91 (6H, d, J=6.6 Hz), 1.97–2.43 (5H, m), 2.56 (1H, bs), 3.83 (2H, t, J=6.2 Hz), 4.03 (2H, d, J=7.4 Hz), 4.76 (2H, d, J=5.6 Hz), 5.20 (2H, s), 6.94 (1H, d, J=2.2 Hz), 7.12 (1H, dd, J=2.2, 8.8 Hz), 7.30–7.45 (5H, m), 8.27 (1H, d, J=8.8 Hz).

(5) To a solution of 6-benzyloxy-3-hydroxymethyl-2-isobutyl-4-(4,4,4-trifluorobutoxy)-1(2H)-isoquinolinone (3.80 g, 8 mmol) in toluene (30 mL) was added thionyl chloride (1.2 mL, 16 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-2-isobutyl-4-(4,4,4-trifluorobutoxy)-1(2H)-isoquinolinone (3.4 g, 88.8%) as an oil.

$^1$H-NMR(CDCl$_3$) δ: 0.95 (6H, d, J=6.6 Hz), 2.00–2.46 (5H, m), 3.91 (2H, t, J=6.2 Hz), 4.04 (2H, d, J=7.6 Hz), 4.76 (2H, s), 5.23 (2H, s), 7.02 (1H, d, J=2.6 Hz), 7.12–7.46 (6H, m), 8.38 (1H, d, J=8.8 Hz).

(6) A solution of 6-benzyloxy-3-chloromethyl-2-isobutyl-4-(4,4,4-trifluorobutoxy)-1(2H)-isoquinolinone (3.37 g, 7 mmol) and potassium phthalimide (1.94 g, 10.5 mmol) in N,N-dimethylformamide (30 mL) was stirred at room temperature for 6 h. The reaction mixture was poured into water and extracted with ethyl acetate. After washing the extract with water, and the extract was dried over anhydrous magnesium sulfate and concentrated under reduced pressure. The obtained crystals were recrystallized from ethyl acetate-n-hexane to give 2-[[6-benzyloxy-2-isobutyl-1-oxo-4-(4,4,4-trifluorobutoxy)-1,2-dihydro-3-isoquinolinyl]methyl]-1H-isoindole-1,3(2H)-dione (3.91 g, 94.4%) as crystals.

Melting point 131–132° C. Elemental analysis for C$_{33}$H$_{31}$N$_2$O$_5$F$_3$ Calculated: C, 66.88; H, 5.27; N, 4.73. Found: C, 67.25; H, 5.21; N, 4.84. $^1$H-NMR(CDCl$_3$) δ: 0.95 (6H, d, J=6.6 Hz), 1.95–2.40 (5H, m), 3.93 (2H, t, J=6.4 Hz), 4.05 (2H, d, J=7.8 Hz), 4.97 (2H, s), 5.21 (2H, s), 6.98 (1H, d, J=2.6 Hz), 7.16 (1H, dd, J=2.6, 8.8 Hz), 7.28–7.45 (5H, m), 7.68–7.87 (4H, m), 8.35 (1H, d, J=8.8 Hz).

(7) To a solution of 2-[[6-benzyloxy-2-isobutyl-1-oxo-4-(4,4,4-trifluorobutoxy)-1,2-dihydro-3-isoquinolinyl]methyl]-1H-isoindole-1,3(2H)-dione (3.85 g, 6.5 mmol) in ethanol (30 mL) was added hydrazine monohydrate (0.95 mL, 19.5 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (30 mL) and di-t-butyl dicarbonate (2.2 mL, 9.8 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl[6-benzyloxy-2-isobutyl-1-oxo-4-(4,4,4-trifluorobutoxy)-1,2-dihydro-3-isoquinolinyl]-methylcarbamate (0.36 g, 87.8%) as crystals.

Melting point 117–118° C. Elemental analysis for C$_{32}$H$_{37}$N$_2$O$_5$F$_3$ Calculated: C, 64.04; H, 6.63; N, 4.98. Found: C, 64.33; H, 6.75; N, 5.00. $^1$H-NMR(CDCl$_3$) δ: 0.94 (6H, d, J=7.0 Hz), 1.46 (9H, s), 1.98–2.44 (5H, m), 3.78 (2H, t, J=6.2 Hz), 3.93 (2H, d, J=7.8 Hz), 4.46 (2H, d, J=5.2 Hz), 4.72 (1H, bs), 5.22 (2H, s), 6.97 (1H, d, J=2.4 Hz), 7.16 (1H, dd, J=2.4, 9.0 Hz), 7.31–7.46 (5H, m), 8.34 (1H, d, J=9.0 Hz).

(8) A suspension of tert-butyl[6-benzyloxy-2-isobutyl-1-oxo-4-(4,4,4-trifluorobutoxy)-1,2-dihydro-3-isoquinolinyl]methylcarbamate (3.09 g, 5.5 mmol) and 5% palladium carbon (1.0 g) in tetrahydrofuran (20 mL) and ethanol (20 mL) was stirred under a hydrogen atmosphere at room temperature for 2 h. The catalyst was filtered off and the filtrate was concentrated under reduced pressure. The residue was purified by silica gel column chromatography to give tert-butyl[6-hydroxy-2-isobutyl-1-oxo-4-(4,4,4-trifluorobutoxy)-1,2-dihydro-3-isoquinolinyl]methylcarbamate (2.48 g, 95.4%) as crystals.

Melting point 173–174° C. Elemental analysis for C$_{23}$H$_{31}$N$_2$O$_5$F$_3$ Calculated: C, 58.47; H, 6.61; N, 5.93. Found: C, 58.61; H, 6.66; N, 5.84. $^1$H-NMR(CDCl$_3$) δ: 0.95 (6H, d, J=7.0 Hz), 1.47 (9H, s), 2.03–2.45 (5H, m), 3.88 (2H, t, J=5.9 Hz), 3.98 (2H, d, J=7.4 Hz), 4.49 (2H, d, J=4.6 Hz), 4.77 (1H, bs), 7.08–7.14 (2H, m), 8.26 (1H, d, J=8.8 Hz), 8.86 (1H, bs).

(9) A solution of tert-butyl[6-hydroxy-2-isobutyl-4-(4,4,4-trifluorobutoxy)-1-1,2-dihydro-3-isoquinolinyl]methylcarbamate (0.47 g, 1 mmol), iodoacetamide (0.27 g, 1.5 mmol) and 1,8-diazabicyclo[5.4.0]-7-undecene (0.22 mL, 1.5 mmol) in N,N-dimethylformamide (10 mL) was stirred at 70° C. for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(2-amino-2-oxoethoxy)-2-isobutyl-4-(4,4,4-trifluorobutoxy)-1-oxo-1,2-dihydro-3-isoquinolinyl]methylcarbamate (0.25 g, 48.1%) as crystals.

Melting point 184–186° C. Elemental analysis for C$_{25}$H$_{34}$N$_3$O$_6$F$_3$ Calculated: C, 56.70; H, 6.47; N, 7.94. Found: C, 56.43; H, 6.55; N, 7.87. $^1$H-NMR(CDCl$_3$) δ: 0.96 (6H, d, J=6.6 Hz), 1.47 (9H, s), 2.05–2.23 (2H, m), 2.32–2.52 (2H, m), 3.91 (2H, t, J=6.4 Hz), 3.96 (2H, d, J=7.6 Hz), 4.49 (2H, d, J=5.9 Hz), 4.62 (2H, s), 4.74 (1H, bs), 5.81 (1H, bs), 6.54 (1H, bs), 7.00 (1H, d, J=2.6 Hz), 7.10 (1H, dd, J=2.6, 8.8 Hz), 8.38 (1H, d, J=8.8 Hz).

(10) To a solution of tert-butyl[6-(2-amino-2-oxoethoxy)-2-isobutyl-4-(4,4,4-trifluorobutoxy)-1-oxo-1,2-dihydro-3-isoquinolinyl]methylcarbamate (0.18 g, 0.35 mmol) in ethyl acetate (5 mL) was added a solution of 4N hydrogen, chloride in ethyl acetate (5 mL) and the obtained solution was stirred at room temperature for 2 h. The reaction mixture was concentrated under reduced pressure, and the precipitated crystals were recrystallized from methanol-diisopropyl ether to give 2-[[3-(aminomethyl)-2-isobutyl-1-oxo-4-(4,4,4-trifluorobutoxy)-1,2-dihydro-6-isoquinolinyl]oxy]acetamide hydrochloride (0.15 g, 93.8%) as crystals.

Melting point 147–148° C. Elemental analysis for C$_{20}$H$_{27}$N$_3$O$_4$ClF$_3$ H$_2$O Calculated: C, 49.64; H, 6.04; N, 8.68. Found: C, 49.73; H, 5.97; N, 8.60. $^1$H-NMR(DMSO-d$_6$) δ: 0.88 (6H, d, J=6.6 Hz), 1.96–2.13 (3H, m), 2.56–2.71 (2H, m), 3.93–4.02 (4H, m), 4.15 (2H, d, J=4.2 Hz), 4.67 (2H, s), 7.05 (1H, d, J=2.4 Hz), 7.24 (1H, dd, J=2.4, 8.8 Hz), 7.49 (1H, bs), 7.76 (1H, bs), 8.20 (1H, d, J=8.8 Hz), 8.73 (3H, s).

Example 165

2-[[3-(Aminomethyl)-4-(4-fluorophenyl)-2-isobutyl-1-oxo-1,2-dihydro-6-isoquinolinyl]oxy]acetamide hydrochloride (1) A mixed solution of methyl 6-benzyloxy-2-isobutyl-1-oxo-4-trifluoromethanesulfonyloxy-1,2-dihydro-3-isoquinolinecarboxylate (7.70 g, 15 mmol), 4-fluorophenylboronic acid (2.52 g, 18 mmol) and sodium carbonate (3.97 g, 37.5 mmol) in toluene (50 mL), methanol (10 mL) and water (10 mL) was stirred under an argon atmosphere at room temperature for 30 min. To the obtained mixture was added tetrakis(triphenylphosphine)palladium (0.87 g, 0.9 mmol) and the mixture was refluxed under heating under an argon atmosphere for 12 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 6-benzyloxy-4-(4-fluorophenyl)-2-isobutyl-1-oxo-1,2-dihydro-3-isoquinolinecarboxylate (5.16 g, 74.9%) as crystals.

Melting point 118–119° C. Elemental analysis for $C_{28}H_{26}NO_4F$ Calculated: C, 73.19; H, 5.70; N, 3.05. Found: C, 72.92; H, 5.79; N, 2.97. $^1$H-NMR(CDCl$_3$) δ: 0.92 (6H, d, J=6.6 Hz), 2.02–2.21 (1H, m), 3.49 (3H, s), 3.93 (2H, d, J=7.8 Hz), 4.99 (2H, s), 6.54 (1H, d, J=2.4 Hz), 7.07–7.40 (10H, m), 8.43 (1H, d, J=8.8 Hz).

(2) To a solution of methyl 6-benzyloxy-4-(4-fluorophenyl)-2-isobutyl-1-oxo-1,2-dihydro-3-isoquinolinecarboxylate (5.05 g, 11 mmol) in methanol (30 mL) was added an aqueous solution (10 mL) of lithium hydroxide monohydrate (1.38 g, 33 mmol). The obtained mixture was refluxed under heating for 12 h. The reaction mixture was poured into water, and, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-benzyloxy-4-(4-fluorophenyl)-2-isobutyl-1-oxo-1,2-dihydro-3-isoquinolinecarboxylic acid (3.94 g, 80.5%) as crystals.

Melting point 236–237° C. Elemental analysis for $C_{27}H_{24}NO_4F$ Calculated: C, 72.80; H, 5.43; N, 3.14. Found: C, 72.41; H, 5.28; N, 3.02. $^1$H-NMR(CDCl$_3$) δ: 0.86 (6H, d, J=6.6 Hz), 2.10–2.24 (1H, m), 3.89 (2H, d, J=7.4 Hz), 4.99 (2H, s), 6.52 (1H, d, J=2.2 Hz), 7.04–7.16 (3H, m), 7.24–7.37 (7H, m), 8.25 (1H, d, J=9.2 Hz).

(3) To a solution of 6-benzyloxy-4-(4-fluorophenyl)-2-isobutyl-1-oxo-1,2-dihydro-3-isoquinolinecarboxylic acid (3.79 g, 8.5 mmol) in tetrahydrofuran (30 mL) were added oxalyl chloride (0.9 mL, 10.2 mmol) and N,N-dimethylformamide (3 drops), and the mixture was stirred at room temperature for 1 h. The reaction mixture was concentrated under reduced pressure and the residue was dissolved in tetrahydrofuran (20 mL). The obtained solution was added dropwise to a suspension of sodium tetrahydroborate (1.13 g, 30 mmol) in 1,2-dimethoxyethane (30 mL) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The residue was purified by silica gel column chromatography to give 6-benzyloxy-4-(4-fluorophenyl)-3-hydroxymethyl-2-isobutyl-1(2H)-isoquinolinone (3.31 g, 90.2%) as crystals.

Melting point 143–144° C. Elemental analysis for $C_{27}H_{26}NO_3F$ Calculated: C, 75.15; H, 6.07; N, 3.25. Found C, 75.04; H, 6.28; N, 3.22. $^1$H-NMR(CDCl$_3$) δ: 0.94 (6H, d, J=6.6 Hz), 2.11–2.25 (1H, m), 2.70 (1H, bs), 4.16 (2H, d, J=7.8 Hz), 4.41 (2H, d, J=5.4 Hz), 4.89 (2H, s), 6.28 (1H, d, J=2.4 Hz), 6.93–6.98 (1H, m), 7.13–7.34 (9H, m), 8.20–8.26 (1H, m).

(4) To a suspension of 6-benzyloxy-4-(4-fluorophenyl)-3-hydroxymethyl-2-isobutyl-1(2H)-isoquinolinone (3.24 g, 7.5 mmol) in toluene (50 mL) was added thionyl chloride (1.1 mL, 15 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-4-(4-fluorophenyl)-2-isobutyl-1(2H)-isoquinolinone (3.18 g, 94.4%) as crystals.

$^1$H-NMR(CDCl$_3$) δ: 0.99 (6H, d, J=7.0 Hz), 2.13–2.31 (1H, m), 4.14 (2H, d, J=7.6 Hz), 4.35 (2H, s), 4.95 (2H, s), 6.35 (1H, d, J=2.6 Hz), 7.11–7.38 (10H, m), 8.41 (1H, d, J=8.8 Hz).

(5) A solution of 6-benzyloxy-3-chloromethyl-4-(4-fluorophenyl)-2-isobutyl-1(2H)-isoquinolinone (3.15 g, 7 mmol) and potassium phthalimide (1.94 g, 10.5 mmol) in N,N-dimethylformamide (100 mL) was stirred at room temperature for 6 h. The reaction mixture was poured into water and extracted with ethyl acetate. After washing the extract with water, the extract was dried over anhydrous magnesium sulfate and concentrated under reduced pressure. The residue was crystallized from ethyl acetate-diisopropyl ether to give 2-[[6-benzyloxy-4-(4-fluorophenyl)-2-isobutyl-1-oxo-1,2-dihydro-3-isoquinolinyl]methyl]-1H-isoindole-1,3(2H)-dione (3.42 g, 87.2%) as crystals.

Melting point 198–199° C. Elemental analysis for $C_{35}H_{29}N_2O_4F$ Calculated: C, 74.98; H, 5.21; N, 5.00. Found: C, 74.83; H, 5.01; N, 4.82. $^1$H-NMR(CDCl$_3$) δ: 0.98 (6H, d, J=6.6 Hz), 2.13–2.27 (1H, m), 4.02 (2H, d, J=7.4 Hz), 4.94 (2H, s), 6.31 (1H, d, J=2.6 Hz), 7.02–7.14 (3H, m), 7.20–7.38 (7H, m), 7.66–7.78 (4H, m), 8.39 (1H, d, J=9.2 Hz).

(6) To a solution of 2-[[6-benzyloxy-4-(4-fluorophenyl)-2-isobutyl-1-oxo-1,2-dihydro-3-isoquinolinyl]methyl]-1H-isoindole-1,3(2H)-dione (3.36 g, 6 mmol) in ethanol (30 mL) was added hydrazine monohydrate (0.9 mL, 18 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (20 mL) and di-t-butyl dicarbonate (2.1 mL, 9 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl[6-benzyloxy-4-(4-fluorophenyl)-2-isobutyl-1-oxo-1,2-dihydro-3-isoquinolinyl]methylcarbamate (3.16 g, 99.4%) as crystals.

Melting point 184–185° C. Elemental analysis for $C_{32}H_{35}N_2O_4F$ Calculated: C, 72.43; H, 6.65; N, 5.28. Found: C, 72.07; H, 6.52; N, 5.18. $^1$H-NMR(CDCl$_3$) δ: 0.98 (6H, d, J=6.6 Hz), 1.42 (9H, s), 2.14–2.27 (1H, m), 4.02 (2H, d, J=6.9 Hz), 4.15 (2H, d, J=5.4 Hz), 4.52 (1H, bs), 4.94 (2H, s), 6.29 (1H, d, J=2.4 Hz), 7.06–7.11 (1H, m), 7.16–7.36 (9H, m), 8.34–8.38 (1H, m).

(7) A suspension of tert-butyl[6-benzyloxy-4-(4-fluorophenyl)-2-isobutyl-1-oxo-1,2-dihydro-3-isoquinolinyl]methylcarbamate (2.65 g, 5 mmol) and 5% palladium carbon (0.8 g) in ethanol (20 mL) and tetrahydrofuran (20 mL) was stirred under a hydrogen atmosphere at room temperature for 2 h. The catalyst was filtered off and the filtrate was concentrated under reduced pressure. The obtained crystals were recrystallized from tetrahydrofuran-diisopropyl ether to give tert-butyl[4-(4-fluorophenyl)-6-hydroxy-2-isobutyl-1-oxo-1,2-dihydro-3-isoquinolinyl]methylcarbamate (3.11 g, 94.2%) as crystals.

Melting point 229–230° C. Elemental analysis for $C_{25}H_{29}N_2O_4F$ Calculated: C, 68.16; H, 6.64; N, 6.36. Found: C, 67.98; H, 6.88; N, 6.20. $^1$H-NMR(CDCl$_3$) δ: 0.95 (6H, d, J=6.6 Hz), 1.42 (9H, s), 2.11–2.24 (1H, m) 4.00 (1H, d, J=7.4 Hz), 4.16 (2H, d, J=3.6 Hz), 4.49 (1H, bs), 6.33 (1H, d, J=2.4 Hz), 7.03 (1H, dd, J=2.4, 9.0 Hz), 7.06–7.18 (4H, m), 7.90 (1H, bs), 8.26 (1H, d, J=9.0 Hz), (8) A solution of tert-butyl[4-(4-fluorophenyl)-6-hydroxy-2-isobutyl-1-oxo-1,2-dihydro-3-isoquinolinyl]methylcarbamate (0.44 g, 1 mmol), 2-iodoacetamide (0.37 g, 2 mmol) and 1,8-diazabicyclo[5.4.0]-7-undecene (0.30 mL, 2 mmol) in N,N-dimethylformamide (10 mL) was stirred at 80° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl [6-(2-amino-2-oxoethoxy)-4-(4-fluorophenyl)-2-isobutyl-1-oxo-1,2-dihydro-3-isoquinolinyl]methylcarbamate (0.24 g, 49.0%) as crystals.

Melting point 218–219° C. Elemental analysis for $C_{27}H_{32}N_3O_5F$ Calculated: C, 65.18; H, 6.48; N, 8.45. Found: C, 64.84; H, 6.75; N, 8.25. $^1$H-NMR(CDCl$_3$) δ: 0.99 (6H, d, J=7.0 Hz), 1.43 (9H, s), 2.13–2.30 (1H, m), 4.04 (2H, d, J=7.6 Hz), 4.17 (2H, d, J=5.6 Hz), 4.35 (2H, s), 4.54 (1H, bs), 5.75 (1H, bs), 6.28 (1H, d, J=2.5 Hz), 6.49 (1H, bs), 7.04 (1H, dd, J=2.5, 9.0 Hz), 7.21–7.24 (4H, m), 8.42 (1H, d, J=9.0 Hz).

(9) To a solution of tert-butyl[6-(2-amino-2-oxoethoxy)-4-(4-fluorophenyl)-2-isobutyl-1-oxo-1,2-dihydro-3-isoquinolinyl]methylcarbamate (0.20 g, 0.4 mmol) in ethyl acetate (5 mL) was added a solution of 4N hydrogen chloride in ethyl acetate (5 mL) and the obtained solution was stirred at room temperature for 2 h. The reaction mixture was concentrated under reduced pressure, and the residue was crystallized from ethyl acetate-diisopropyl, ether to give 2-[[3-(aminomethyl)-4-(4-fluorophenyl)-2-isobutyl-1-oxo-1,2-dihydro-6-isoquinolinyl]oxy]acetamide hydrochloride (0.16 g, 94.1%) as crystals.

Melting point 189–190° C. Elemental analysis for $C_{22}H_{25}N_3O_3FCl$ Calculated: C, 65.18; H, 6.48; N, 8.45. Found: C, 64.84; H, 6.75; N, 8.25. $^1$H-NMR(DMSO-d$_6$) δ: 0.91 (6H, d, J=6.6 Hz), 1.99–2.18 (1H, m), 3.84 (2H, bs), 4.04 (2H, d, J=6.6 Hz), 4.38 (2H, s), 6.29 (1H, d, J=2.0 Hz), 7.20 (1H, dd, J=2.0, 9.0 Hz), 7.34 (1H, bs), 7.38–7.43 (4H, m), 7.56 (1H, bs), 8.27 (1H, d, J=9.0 Hz), 8.53 (3H, bs).

Example 166

3-(Aminomethyl)-2-isobutyl-6-(5-methyl-1,3,4-oxadiazol-3-yl)-4-phenyl-1(2H)-isoquinolinone (1) A mixture of methyl 3-{[((tert-butoxycarbonyl)amino]methyl}-2-isobutyl-1-oxo-4-phenyl-1,2-dihydro-6-isoquinolinecarboxylate (0.24 g, 0.53 mmol), hydrazine monohydrate (0.65 mL, 13.3 mmol) and methanol (6 mL) was stirred in a sealed tube at 75° C. The reaction mixture was concentrated under reduced pressure and to the residue was added methanol-water (1:1, 4 mL) to allow precipitation of a solid. This solid was collected by filtration, washed with water and dried in vacuo to give tert-butyl[6-(hydrazinocarbonyl)-2-isobutyl-1-oxo-4-phenyl-1,2-dihydro-3-isoquinolinyl]methylcarbamate (0.23 g, 94%) as a colorless solid.

$^1$H-NMR(CDCl$_3$) δ: 1.00 (6H, d, J=7.0 Hz), 1.43 (9H, s), 2.15–2.35 (1H, m), 4.08 (2H, d, J=7.0 Hz), 4.20 (2H, d, J=5.2 Hz), 4.70 (1H, br), 7.20–7.30 (3H, m), 7.45–7.55 (3H, m), 7.69 (1H, d, J=5.4 Hz), 8.43 (1H, d, J=8.6 Hz).

(2) A mixture of tert-butyl[6-(hydrazinocarbonyl)-2-isobutyl-1-oxo-4-phenyl-1,2-dihydro-3-isoquinolinyl]methylcarbamate (0.23 g, 0.50 mmol), triethyl orthoacetate (2.0 mL, 10.9 mmol) and n-butanol (10 mL) was refluxed under heating for 20 min. To the reaction mixture was added 1,8-diazabicyclo[5.4.0]-7-undecene (0.075 mL, 0.50 mmol) and the mixture was refluxed under heating for 1 h. To this reaction mixture was added acetic acid (0.040 mL, 0.70 mmol) and the mixture was concentrated under reduced pressure. The residue was partitioned between water (10 mL) and ethyl acetate (30 mL), and the organic layer was washed with water (20 mL), dried over anhydrous magnesium sulfate (9 g) and concentrated under reduced pressure. The residue was purified by silica gel column chromatography (n-hexane:ethyl acetate=2:1 (v/v)) to give tert-butyl [2-isobutyl-6-(5-methyl-1,3,4-oxadiazol- 3-yl)-1-oxo-4-phenyl-1,2-dihydro-3-isoquinolinyl]methylcarbamate (0.22 g, 91%) as a colorless powder.

$^1$H-NMR(CDCl$_3$) δ: 1.02 (6H, d, J=7.2 Hz), 1.43 (9H, s), 2.15–2.35 (1H, m), 2.57 (3H, s), 4.10 (2H, d, J=7.2 Hz), 4.22 (2H, d, J=5.4 Hz), 4.57 (1H, br), 7.20–7.35 (2H, m), 7.50–7.65 (4H, m), 8.05 (1H, dm, J=8.4 Hz), 8.58 (1H, dd, J=2.8, 8.4 Hz).

(3) To tert-butyl[2-isobutyl-6-(5-methyl-1,3,4-oxadiazol-3-yl)-1-oxo-4-phenyl-1,2-dihydro-3-isoquinolinyl]methylcarbamate (0.20 g, 0.41 mmol) was added a solution (4 mL) of 4N hydrogen chloride in ethyl acetate and the mixture was stirred at room temperature for 17 h. The reaction mixture was concentrated under reduced pressure and to the residue was added diisopropyl ether (5 mL). The precipitated powder was collected by filtration. To this powder was added saturated aqueous sodium hydrogencarbonate (30 mL) and the mixture was extracted twice with a solution (25 mL) of ethyl acetate-tetrahydrofuran (1:1). The organic layers were combined and the mixture was washed with saturated brine (25 mL), dried over anhydrous magnesium sulfate (15 g) and concentrated under reduced pressure. The residue was purified by silica gel column chromatography (ethyl acetate: methanol=20:1, (v/v)) and recrystallized from n-hexane-ethyl acetate (5:1) to give the title compound (0.11 g, 72%) as pale-yellow crystals.

Elemental analysis for $C_{23}H_{24}N_4O_2$, Calculated: C, 71.11; H, 6.23; N, 14.42. Found: C, 71.09; H, 6.28; N, 14.37. $^1$H-NMR(CDCl$_3$) δ: 1.02 (6H, d, J=6.6 Hz), 2.15–2.40 (1H, m), 2.57 (3H, s), 3.69 (2H, bs), 4.24 (2H, d, J=7.4 Hz), 7.25–7.35 (2H, m), 7.45–7.60 (2H, m), 7.62 (1H, d, J=1.0 Hz), 8.05 (1H, dd, J=1.6, 8.4 Hz), 8.59 (1H, d, J=8.4 Hz). Melting point 179–181° C.

Example 167

6-Acetyl-3-(aminomethyl)-2-isobutyl-4-phenyl-1(2H)-isoquinolinone hydrochloride (1) To a mixture of 3-{[(tert-butoxycarbonyl)amino]methyl}-2-isobutyl-1-oxo-4-phenyl-1,2-dihydro-6-isoquinolinecarboxylic acid (0.81 g, 1.8 mmol), N,O-dimethylhydroxylamine hydrochloride (0.211 g, 2.16 mmol), 1-hydroxy-1H-benzotriazole monohydrate (0.365 g, 2.7 mmol), 1-ethyl-3-(3-dimethylaminopropyl)-carbodiimide hydrochloride (0.517 g, 2.7 mmol) and N,N-dimethylformamide (10 mL) was added triethylamine (0.301 mL, 2.16 mmol), and the mixture was stirred at room temperature for 17 h. The reaction mixture was poured into 0.1 M aqueous citric acid solution (100 mL) and extracted 3 times with ethyl acetate (50 mL). The organic layers were combined, washed once with 0.1 M aqueous citric acid solution (50 mL), twice with saturated aqueous sodium hydrogencarbonate (50 mL) and once with saturated brine (50 mL), dried over anhydrous magnesium sulfate (15 g), and concentrated under reduced pressure. The residue was purified by silica gel column chromatography (n-hexane:ethyl acetate=3:4 (v/v)) to give tert-butyl(2-isobutyl-6-{[methoxy(methyl)amino]carbonyl}-1-oxo-4-phenyl-1,2-dihydro-3-isoquinolinyl)methylcarbamate (0.83 g, 94%) as a colorless, solid.

$^1$H-NMR(CDCl$_3$) δ: 1.02 (6H, d, J=7.0 Hz), 1.43 (9H, s), 2.15–2.35 (1H, m), 3.27 (3H, s), 3.42 (3H, s), 4.09 (2H, d, J=7.2 Hz), 4.21 (2H, d, J=5.4 Hz), 4.43 (1H, br), 7.20–7.30 (3H, m), 7.45–7.55 (3H, m), 7.69 (1H, dd, J=1.6, 8.2 Hz), 8.50 (1H, d, J=8.2 Hz).

(2) Tert-butyl(2-isobutyl-6-{[methoxy(methyl)amino]carbonyl}-1-oxo-4-phenyl-1,2-dihydro-3-isoquinolinyl)methylcarbamate (0.175 g, 0.355 mmol) was dissolved in tetrahydrofuran (5 mL) and a solution (0.15 mL, 0.43 mmol) of 3 M methyl magnesium bromide in diethyl ether was added dropwise under ice-cooling. This mixture was stirred at room temperature for 1 h and quenched with saturated aqueous ammonium chloride solution (5 mL). The whole was extracted with ethyl acetate (10 mL), and the organic layer was washed once each with 0.1 M aqueous citric acid solution (10 mL), saturated aqueous sodium hydrogencarbonate (10 mL) and saturated brine (10 mL), dried over anhydrous magnesium sulfate (12 g) and concentrated under reduced pressure. The residue was purified by silica gel column chromatography (n-hexane:ethyl acetate=5:2 (v/v)) to give tert-butyl(6-acetyl-2-isobutyl-1-oxo-4-phenyl-1,2-dihydro-3-isoquinolinyl)methylcarbamate (0.132 g, 83%) as a colorless powder.

$^1$H-NMR(CDCl$_3$) δ: 1.01 (6H, d, J=7.2 Hz), 1.43 (9H, s), 2.15–2.35 (1H, m), 2.27 (3H, s), 4.10 (2H, d, J=7.2 Hz), 4.23 (2H, d, J=5.4 Hz), 4.49 (1H, br), 7.20–7.30 (2H, m), 7.45–7.65 (4H, m), 7.96 (1H, dd, J=1.8, 8.4 Hz), 8.54 (1H, d, J=8.4 Hz).

(3) Tert-butyl(6-acetyl-2-isobutyl-1-oxo-4-phenyl-1,2-dihydro-3-isoquinolinyl)methylcarbamate (0.10 g, 0.22 mmol) was dissolved in ethyl acetate (4 mL) and a solution (1 mL) of 4N hydrogen chloride in ethyl acetate was added thereto. The mixture was stirred at room temperature for 17 h. The reaction mixture was concentrated under reduced pressure and the residue was precipitated from ethyl acetate-diisopropyl ether (1:10) to give the title compound (0.084 g, 98%) as a pale-yellow powder.

Elemental analysis for $C_{22}H_{24}N_2O_2$ HCl $H_2O$, Calculated:C, 65.58; H, 6.75; N, 6.95. Found: C, 66.25; H, 6.73; N, 6.83. $^1$H-NMR(CD$_3$OD) δ: 1.02 (6H, d, J=6.6 Hz), 2.10–2.30 (1H, m), 2.50 (3H, s), 4.05–4.20 (4H, m), 7.35–7.45 (2H, m), 7.55–7.70 (4H, m), 8.15 (1H, dd, J=1.4, 8.4 Hz), 8.53 (1H, d, J=8.4 Hz). Melting point 179° C. (decomposition)

Example 168

3-(Aminomethyl)-2-isobutyl-6-(1,3-oxazol-5-yl)-4-phenyl-1(2H)-isoquinolinone hydrochloride (1) Tert-Butyl (6-formyl-2-isobutyl-1-oxo-4-phenyl-1,2-dihydro-3-isoquinolinyl)methylcarbamate (0.20 g, 0.45 mmol) was dissolved in methanol (10 mL) and p-toluene sulfonylmethylisocyanide (0.088 g, 0.45 mmol) and potassium carbonate (0.125 g, 0.90 mmol) were added.

This mixture was refluxed under heating for 30 min and the reaction mixture was partitioned between saturated aqueous sodium hydrogencarbonate (50 mL) and ethyl acetate-tetrahydrofuran (1:1 (v/v), 50 mL). The organic layer was washed once each with saturated aqueous sodium hydrogencarbonate (50 mL) and saturated brine (50 mL), dried over anhydrous magnesium sulfate (12 g) and concentrated under reduced pressure. The residue was purified by silica gel column chromatography (n-hexane:ethyl acetate=2:1 (v/v)) to give tert-butyl [2-isobutyl-6-(1,3-oxazol-5-yl)-1-oxo-4-phenyl-1,2-dihydro-3-isoquinolinyl]methylcarbamate (0.16 g, 75%) as a colorless solid.

$^1$H-NMR(CDCl$_3$) δ: 1.02 (6H, d, J=7.0 Hz), 1.43 (9H, s), 2.15–2.40 (1H, m), 4.09 (2H, d, J=7.2 Hz), 4.22 (2H, d, J=5.6 Hz), 4.51 (1H, br), 7.20 (1H, d, J=1.4 Hz), 7.20–7.35 (2H, m), 7.31 (1H, s), 7.45–7.60 (3H, m), 7.70 (1H, dd, J=1.4, 8.4 Hz), 7.86 (1H, s), 8.51 (1H, d, J=8.4 Hz).

(2) Tert-butyl[2-isobutyl-6-(1,3-oxazol-5-yl)-1-oxo-4-phenyl-1,2-dihydro-3-isoquinolinyl]methylcarbamate (0.14 g, 0.30 mmol) was dissolved in methanol (4 mL) and a solution (10 mL) of 4N hydrogen chloride in ethyl acetate were added thereto. This mixture was stirred at room temperature for 1 h and the precipitated crystals were collected by filtration to give the title compound (0.084 g, 69%) as a colorless powder.

$^1$H-NMR(DMSO-d$_6$) δ: 0.93 (6H, d, J=6.6 Hz), 2.10–2.20 (1H, m), 3.80–4.10 (4H, m), 7.16 (1H, d, J=1.6 Hz), 7.40–7.50 (2H, m), 7.55–7.65 (3H, m), 7.95–8.00 (1H, m), 8.30 (3H, br), 8.40 (1H, d, J=8.84 Hz), 8.43 (1H, s). Melting point 217° C. (decomposition)

Example 169

3-(Aminomethyl)-2-isobutyl-4-phenyl-6-(2H-tetrazol-5-yl)-1(2H)-isoquinolinone hydrochloride (1) To a solution (30 mL) of tert-butyl(6-cyano-2-isobutyl-1-oxo-4-phenyl-1,2-dihydro-3-isoquinolinyl)methylcarbamate (0.86 g, 2.0 mmol) in toluene were added sodium azide (0.16 g, 2.5 mmol) and triethylamine hydrochloride (0.28 g, 2.5 mmol) and the mixture was stirred at 90° C. for 24 h. The reaction mixture was poured into water (100 mL), acidified with 1N hydrochloric acid and extracted twice with ethyl acetate (50 mL). The extracts were combined and washed with saturated brine (15 mL), dried over anhydrous magnesium sulfate (12 g) and concentrated under reduced pressure. The residue was recrystallized from tetrahydrofuran-diisopropyl ether (1:5) to give tert-butyl [2-isobutyl-1-oxo-4-phenyl-6-(2H-tetrazol-5-yl)-1,2-dihydro-3-isoquinolinyl]methylcarbamate (0.36 g, 37%) as colorless crystals.

$^1$H-NMR(CDCl$_3$) δ: 1.00 (6H, d, J=6.6 Hz), 1.45 (9H, s), 2.15–2.35 (1H, m), 4.15 (2H, bd, J=7.4 Hz), 4.22 (2H, bd, J=5.0 Hz), 7.25–7.50 (6H, m), 7.73 (1H, bs), 8.05 (1H, dm, J=8.4 Hz), 8.44 (1H, d, J=8.4 Hz).

(2) Tert-butyl[2-isobutyl-1-oxo-4-phenyl-6-(2H-tetrazol-5-yl)-1,2-dihydro-3-isoquinolinyl]methylcarbamate (0.15 g, 0.32 mmol) was dissolved in tetrahydrofuran (4 mL) and a solution (4 mL) of 4N hydrogen chloride in ethyl acetate was added thereto. This mixture was stirred at room temperature for 17 h, and the precipitated crystals were collected by filtration to give the title compound (0.13 g, 97%) as colorless crystals.

Elemental analysis for $C_{21}H_{22}N_6O$ HCl 0.5$H_2O$ Calculated:C, 57.60; H, 5.98; N, 19.19. Found: C, 57.41; H, 5.96; N, 18.73. $^1$H-NMR(DMSO-d$_6$) δ: 0.94 (6H, d, J=6.6 Hz), 2.10–2.20 (1H, m), 3.90 (2H, bs), 4.10 (2H, d, J=6.6 Hz), 7.40–7.50 (2H, m), 7.55–7.65 (3H, m), 7.69 (1H, d, J=1.5

Hz), 8.23 (1H, dd, J=1.5, 8.1 Hz), 8.52 (3H, br), 8.54 (1H, d, J=8.1 Hz). Melting point 218–220° C.

Example 170

3-(Aminomethyl)-2-isobutyl-6-(methylsulfanyl)-4-phenyl-1(2H)-isoquinolinone hydrochloride (1) A mixture of 3-(aminomethyl)-6-bromo-2-isobutyl-4-phenyl-1(2H)-isoquinolinone (0.19 g, 0.50 mmol), sodium thiomethoxide (0.043 g, 0.60 mmol) and dimethylsulfide (2 mL) was stirred at 70° C. for 2 h. To the reaction mixture was added another sodium thiomethoxide (0.043 g, 0.60 mmol), and the resulting mixture was stirred at 70° C. for 2 h. The reaction mixture was partitioned between water (100 mL) and ethyl acetate (25 mL) and the aqueous layer was extracted with ethyl acetate (25 mL). The extracts were combined and washed once each with saturated aqueous sodium hydrogencarbonate (25 mL) and saturated brine (25 mL), dried over anhydrous magnesium sulfate (12 g) and concentrated under reduced pressure. The residue was purified by silica gel column chromatography (n-hexane:ethyl acetate=1:5 (v/v)) to give 3-(aminomethyl)-2-isobutyl-6-(methylsulfanyl)-4-phenyl-1(2H)-isoquinolinone (0.16 g, 88%) as an oil.

$^1$H-NMR(CDCl$_3$) δ: 1.00 (6H, d, J=6.6 Hz), 2.15–2.35 (1H, m), 2.32 (3H, s), 3.66 (2H, bs), 4.19 (2H, d, J=7.8 Hz), 6.69 (1H, d, J=1.8 Hz), 7.20–7.30 (3H, m), 7.45–7.55 (3H, m), 8.36 (1H, d, J=8.4 Hz).

(2) 3-(Aminomethyl)-2-isobutyl-6-(methylsulfanyl)-4-phenyl-1(2H)-isoquinolinone (0.13 g, 0.37 mmol) was dissolved in ethyl acetate (3 mL) and a solution (1 mL) of 4N hydrogen chloride in ethyl acetate was added thereto. The mixture was stirred for 5 min and concentrated under reduced pressure. The obtained residue was crystallized from ethyl acetate-diisopropyl ether (1:2) to give the title compound (0.14 g, 95%) as colorless crystals.

Elemental analysis for C$_{21}$H$_{24}$N$_2$OS HCl, Calculated:C, 64.85; H, 6.48; N, 7.20. Found: C, 64.79; H, 6.55; N, 6.99. $^1$H-NMR(DMSO-d$_6$) δ: 0.91 (6H, d, J=6.6 Hz), 1.95–2.20 (1H, m), 2.34 (3H, s), 3.86 (2H, bs), 4.00–4.15 (2H, m), 6.59 (1H, d, J=1.8 Hz), 7.35–7.65 (6H, m), 8.23 (1H, d, J=8.4 Hz), 8.46 (1H, bs). Melting point 252–255° C.

Example 171

2-{[3-(Aminomethyl)-2-isobutyl-1-oxo-4-phenyl-1,2-dihydro-6-isoquinolinyl]sulfanyl}acetamide A solution (2 mL) of 2-mercaptoacetamide (0.27 g, 3.0 mmol) in N,N-dimethylformamide was ice-cooled under a nitrogen atmosphere and sodium hydride (0.12 g, 3.0 mmol) (60% in oil) was added thereto. The resulting mixture was stirred under ice-cooling for 30 min. To the obtained suspension was added 3-(aminomethyl)-6-bromo-2-isobutyl-4-phenyl-1(2H)-isoquinolinone (1.06 g, 2.74 mmol), and the mixture was stirred at 80° C. for 24 h. The reaction mixture was partitioned between water (100 mL) and ethyl acetate (50 mL), and the aqueous layer was extracted twice with ethyl acetate (50 mL). The extracts were combined and washed with saturated brine (20 mL), dried over anhydrous magnesium sulfate (12 g) and concentrated under reduced pressure. The residue was purified by silica gel column chromatography (ethyl acetate:methanol=1:0–10:1 (v/v)) and recrystallized from n-hexane-ethyl acetate (1:1) to give the title compound (0.54 g, 50%) as a colorless powder.

Elemental analysis for C$_{22}$H$_{25}$N$_3$O$_2$S, Calculated:C, 66.81; H, 6.37; N, 10.62. Found: C, 66.40; H, 6.41; N, 10.26. $^1$H-NMR(CDCl$_3$) δ: 0.99 (6H, d, J=6.6 Hz), 2.20–2.30 (1H, m), 3.52 (2H, s), 3.66 (2H, bs), 4.19 (2H, d, J=7.4 Hz), 5.39 (1H, bs), 6.41 (1H, bs), 6.79 (1H, d, J=1.8 Hz), 7.20–7.35 (3H, m), 7.45–7.55 (3H, m), 8.36 (1H, d, J=8.6 Hz). Melting point 218–220° C.

Example 172

3-(Aminomethyl)-2-isobutyl-6-(methylsulfinyl)-4-phenyl-1(2H)-isoquinolinone

To a mixture of 3-(aminomethyl)-2-isobutyl-6-(methylsulfanyl)-4-phenyl-1(2H)-isoquinolinone (0.18 g, 0.52 mmol), conc. sulfuric acid (0.0168 mL, 0.31 mmol), methanol (2 mL) and water (5 mL) was added Oxone® (0.19 g, 0.31 mmol), and the mixture was stirred at room temperature for 30 min. The reaction mixture was poured into saturated, aqueous sodium hydrogencarbonate (50 mL) and extracted 3 times with ethyl acetate (25 mL). The extracts were combined, washed with saturated brine (10 mL), dried over anhydrous magnesium sulfate (9 g) and concentrated under reduced pressure. The residue was purified by silica gel column chromatography (ethyl acetate:methanol=10:1 (v/v)). The resulting oil was solidified from diisopropyl ether (1 mL) to give the title compound (0.081 g, 42%) as a pale-yellow powder.

Elemental analysis for C$_{21}$H$_{24}$N$_2$O$_2$S 2H$_2$O, Calculated: C, 62.35; H, 6.98; N, 6.93. Found: C, 62.27; H, 6.58; N, 6.36. $^1$H-NMR(CDCl$_3$) δ: 1.01 (6H, d, J=6.6 Hz), 2.20–2.35 (1H, m), 2.66 (3H, s), 3.69 (2H, bs), 4.24 (2H, d, J=7.4 Hz), 7.20–7.35 (3H, m), 7.45–7.55 (3H, m), 7.64 (1H, dd, J=1.8, 8.6 Hz), 8.63 (1H, d, J=8.6 Hz). Melting point 167° C. (decomposition)

Example 173

3-(Aminomethyl)-2-isobutyl-6-(methylsulfonyl)-4-phenyl-1(2H)-isoquinolinone hydrochloride (1) A mixture of tert-butyl(6-bromo-2-isobutyl-1-oxo-4-phenyl-1,2-dihydro-3-isoquinolinyl)methylcarbamate (0.24 g, 0.5 mmol), sodium thiomethoxide (0.080 g, 1.1 mmol) and N,N-dimethylformamide (4 mL) was stirred at 85° C. for 1 h, and the reaction mixture was poured into water (50 mL) and extracted twice with ethyl acetate (25 mL). The extracts were combined, washed with saturated aqueous sodium hydrogencarbonate (15 mL) and saturated brine (15 mL), dried over anhydrous magnesium sulfate (12 g) and concentrated under reduced pressure. The residue was purified by silica gel column chromatography (n-hexane:ethyl acetate=4:1 (v/v)) to give tert-butyl[2-isobutyl-6-(methylsulfanyl)-1-oxo-4-phenyl-1,2-dihydro-3-isoquinolinyl]methylcarbamate (0.17 g, 73%) as a colorless powder.

$^1$H-NMR(CDCl$_3$) δ: 1.00 (6H, d, J=6.6 Hz), 1.43 (9H, s), 2.15–2.35 (1H, m), 2.32 (3H, s), 4.06 (2H, d, J=7.8 Hz), 4.19 (2H, d, J=6.0 Hz), 4.46 (1H, br), 6.68 (1H, d, J=1.8 Hz), 7.20–7.35 (3H, m), 7.40–7.60 (3H, m), 8.34 (1H, d, J=8.4 Hz).

(2) To a solution (5 mL) of tert-butyl[2-isobutyl-6-(methylsulfanyl)-1-oxo-4-phenyl-1,2-dihydro-3-isoquinolinyl]methylcarbamate (0.17 g, 0.37 mmol) in dichloromethane was added m-chloroperbenzoic acid (0.13 g, 7.7 mmol) under ice-cooling, and the mixture was stirred at room temperature for 1 h. The reaction mixture was washed once with 5% aqueous sodium thiosulfate solution (15 mL) and twice with saturated aqueous sodium hydrogencarbonate (15 mL), and partitioned using a PTFE tube. The organic layer was concentrated under reduced pressure. The residue was purified by silica gel column chromatography (n-hexane:ethyl acetate=2:1 (v/v)) to give tert-butyl[2-isobutyl-6-(methylsulfonyl)-1-oxo-4-phenyl-1,2-dihydro- 3-isoquinolinyl]methylcarbamate (0.16 g, 93%) as a colorless oil.

$^1$H-NMR(CDCl$_3$) δ: 1.01 (6H, d, J=6.6 Hz), 1.43 (9H, s), 2.15–2.35 (1H, m), 2.99 (3H, s), 4.12 (2H, d, J=6.9 Hz), 4.24 (2H, d, J=6.0 Hz), 4.42 (1H, br), 7.30–7.35 (2H, m), 7.50–7.60 (4H, m), 7.94 (1H, dd, J=1.8, 8.4 Hz), 8.66 (1H, d, J=8.4 Hz).

(3) A mixture of tert-butyl[2-isobutyl-6-(methylsulfonyl)-1-oxo-4-phenyl-1,2-dihydro-3-isoquinolinyl]methylcarbamate (0.16 g, 0.33 mmol) and a solution (5 mL) of 4N hydrogen chloride in ethyl acetate was stirred for 1 h and concentrated under reduced pressure. The obtained residue was precipitated from ethyl acetate-diisopropyl ether (1:10) to give, the title compound (0.12 g, 87%) as a colorless powder.

Elemental analysis for C$_{21}$H$_{24}$N$_2$O$_3$S HCl H$_2$O 0.25IPE, Calculated:C, 58.18; H, 6.62; N, 6.03. Found: C, 58.15; H, 6.87; N, 5.89. $^1$H-NMR(DMSO-d$_6$) δ: 0.93 (6H, d, J=6.6 Hz), 2.05–2.20 (1H, m), 3.22 (3H, s), 3.90 (2H, bs), 4.11 (2H, bd, J=6.6 Hz), 7.40–7.50 (3H, m), 7.55–7.70 (3H, m), 8.09 (1H, dd, J=1.8, 8.4 Hz), 8.57 (1H, d, J=8.4 Hz), 8.60 (1H, br). Melting point 209° C. (decomposition)

Example 174

3-(Aminomethyl)-2-isobutyl-6-(methanesulfonylamino)-4-phenyl-1(2H)-isoquinolinone hydrochloride This compound was synthesized according to the method similar to that in Example 88 from 6-amino-3-(tert-butoxycarbonylaminomethyl)-2-isobutyl-4-phenyl-1(2H)-isoquinolinone (synthesized according to the method similar to that in Example 111 (1)).

$^1$H-NMR(DMSO-d$_6$) δ: 0.91 (6H, d, J=6.6 Hz), 2.08 (1H, m), 2.98 (3H, s), 3.85 (2H, s), 4.03 (2H, d, J=6.2 Hz), 6.75 (1H, d, J=1.8 Hz), 7.36–7.44 (3H, m), 7.54–7.58 (3H, m), 7.77 (1H, d, J=8.8 Hz), 8.46 (3H, bs), 10.29 (1H, bs).

Example 175

3-(Aminomethyl)-2-isobutyl-6-(methoxycarbonylamino)-4-phenyl-1(2H)-isoquinolinone hydrochloride This compound was synthesized according to the method similar to that in Example 88 from 6-amino-3-(tert-butoxycarbonylaminomethyl)-2-isobutyl-4-phenyl-1(2H)-isoquinolinone (synthesized according to the method similar to that in Example 111 (1)).

$^1$H-NMR(DMSO-d$_6$) δ: 0.91 (6H, d, J=6.6 Hz), 2.08 (1H, m), 3.59 (3H, s), 3.85 (2H, s), 4.02 (2H, d, J=6.6 Hz), 7.22 (1H, d, J=1.8 Hz), 7.34–7.38 (2H, m), 7.54–7.63 (5H, m), 8.23 (1H, d, J=8.8 Hz), 8.40 (3H, bs), 10.04 (1H, s).

Example 176

3-(Aminomethyl)-2-isobutyl-6-(dimethanesulfonylamino)-4-phenyl-1(2H)-isoquinolinone hydrochloride This compound was synthesized according to the method similar to that in Example 88 from 6-amino-3-(tert-butoxycarbonylaminomethyl)-2-isobutyl-4-phenyl-1(2H)-isoquinolinone (synthesized according to the method similar to that in Example 111 (1)).

$^1$H-NMR(DMSO-d$_6$) δ: 0.93 (6H, d, J=6.6 Hz), 2.11 (1H, m), 3.34 (3H, s), 3.44 (2H, s), 3.90 (2H, s), 4.08 (2H, d, J=7.4 Hz), 6.86 (1H, d, J=1.8 Hz), 7.41–7.45 (2H, m), 7.57–7.60 (3H, m), 7.73 (1H, dd, J=8.4, 1.8 Hz), 8.43 (1H, d, J=8.4 Hz), 8.44 (3H, bs).

Example 177

N-{3-(Aminomethyl)-2-isobutyl-1-oxo-4-phenyl-1,2-dihydro-6-isoquinolinyl}-N'-methylurea hydrochloride This compound was synthesized according to the method similar to that in Example 80 from 3-(tert-butoxycarbonylaminomethyl)-2-isobutyl-4-phenyl-1(2H)-isoquinolinone-6-carboxylic acid (synthesized according to the method similar to that in Example 108 (1)).

$^1$H-NMR(DMSO-d$_6$) δ: 0.90 (6H, d, J=6.6 Hz), 2.07 (1H, m), 2.56 (3H, s), 3.81 (2H, s), 4.00 (2H, d, J=7.0 Hz), 6.17 (1H, bs), 6.98 (1H, d, J=2.0 Hz), 7.34–7.38 (2H, m), 7.54–7.67 (4H, m), 8.17 (1H, d, J=8.8 Hz), 8.39 (3H, bs), 9.13 (1H, s).

Example 178

N-{3-(Aminomethyl)-2-isobutyl-1-oxo-4-phenyl-1,2-dihydro-6-isoquinolinyl}-N',N'-dimethylurea hydrochloride This compound was synthesized according to the method similar to that in Example 80 from 3-(tert-butoxycarbonylaminomethyl)-2-isobutyl-4-phenyl-1(2H)-isoquinolinone-6-carboxylic acid (synthesized according to the method similar to that in Example 108 (1)).

$^1$H-NMR(DMSO-d$_6$) δ: 0.91 (6H, d, J=6.6 Hz), 2.07 (1H, m), 2.86 (6H, s), 3.81 (2H, s), 4.02 (2H, d, J=7.0 Hz), 7.13 (1H, s), 7.34–7.38 (2H, m), 7.54–7.57 (3H, m), 7.69 (1H, d, J=8.8 Hz), 8.17 (1H, d, J=8.8 Hz), 8.41 (3H, bs), 8.68 (1H, s).

Example 179

N-{3-(Aminomethyl)-2-isobutyl-1-oxo-4-phenyl-1,2-dihydro-6-isoquinolinyl}urea hydrochloride This compound was synthesized according to the method similar to that in Example 80 from 3-(tert-butoxycarbonylaminomethyl)-2-isobutyl-4-phenyl-1(2H)-isoquinolinone-6-carboxylic acid (synthesized according to the method similar to that in Example 108 (1)).

$^1$H-NMR(DMSO-d$_6$) δ: 0.91 (6H, d, J=6.6 Hz), 2.07 (1H, m), 3.82 (2H, d, J=4.0 Hz), 4.02 (2H, d, J=7.2 Hz), 5.96 (1H, bs), 6.70 (1H, bs), 6.51 (1H, d, J=1.8 Hz), 7.35–7.39 (2H, m), 7.51–7.59 (3H, m), 7.79 (1H, dd, J=8.8, 1.8 Hz), 8.18 (1H, d, J=8.8 Hz), 8.44 (3H, bs), 9.10 (1H, s).

Example 180

(E)-3-[3-(Aminomethyl)-4-(4-fluorophenyl)-2isobutyl-1-oxo-1,2-dihydro-6-isoquinolinyl]-2-propenamide hydrochloride (1) To a solution of tert-butyl[4-(4-fluorophenyl)-6-hydroxy-2-isobutyl-1-oxo-1,2-dihydro-3-isoquinolinyl]methylcarbamate (2.00 g, 3.5 mmol) in N,N-dimethylformamide (30 ml) was added sodium hydride (0.19 g, 4.8 mmol) (60% in oil), at 0° C., and the mixture was stirred at 0° C. for 10 min. To the obtained mixture was added N-phenyltrifluoromethanesulfonimide (1.71 g, 4.8 mmol) and the mixture was stirred at room temperature for 3 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl[4-(4-fluorophenyl)-2-isobutyl-1-oxo-6-trifluoromethanesulfonyloxy-1,2-dihydro-3-isoquinolinyl]methylcarbamate (2.02 g, 88.2%) as an oil.

$^1$H-NMR(CDCl$_3$) δ: 0.99 (6H, d, J=6.6 Hz), 1.43 (9H, s), 2.14–2.28 (1H, m), 4.07 (2H, d, J=7.6 Hz), 4.22 (2H, d, J=5.8 Hz), 4.47 (1H, bs), 6.80 (1H, d, J=2.4 Hz), 7.22–7.44 (5H, m), 8.55 (1H, d, J=8.6 Hz).

(2) A suspension of tert-butyl[4-(4-fluorophenyl)-2-isobutyl-1-oxo-6-trifluoromethanesulfonyloxy-1,2-dihydro-3-isoquinolinyl]methylcarbamate (2.00 g, 3.5 mmol), butyl acrylate (0.76 ml, 5.3 mmol), sodium hydrogencarbonate (0.45 g, 5.5 mmol), tetrabutylammonium chloride (0.11 g, 0.4 mmol) and palladium acetate (90 mg, 0.4 mmol) in N,N-dimethylformamide (30 ml) was stirred with heating at 100° C. under an argon atmosphere for 24 h. The reaction mixture was poured into water and extracted with ethyl acetate. After washing the extract with water, the extract was dried over anhydrous magnesium sulfate and concentrated under reduced pressure. The residue was purified by silica gel column chromatography to give butyl (E)-3-[3-[[(tert-butoxycarbonyl)amino]methyl]-4-(4-fluorophenyl)-2-isobutyl-1-oxo-1,2-dihydro-6-isoquinolinyl]-2-propenate as an amorphous.

$^1$H-NMR(CDCl$_3$) δ: 0.95 (3H, t, J=7.7 Hz), 1.00 (6H, d, J=6.6 Hz), 1.34–1.47 ((11H, m), 1.62–1.72 (2H, m), 2.18–2.28 (1H, m), 4.06 (2H, d, J=7.8 Hz), 4.13–4.21 (4H, m), 4.50 (1H, bs), 6.39 (1H, d, J=16.5 Hz), 6.98 (1H, d, J=1.6 Hz), 7.19–7.27 (4H, m), 7.55 (1H, d, J=16.5 Hz), 7.62 (1H, dd, J=1.6, 8.7 Hz), 8.44 (1H, d, J=8.7 Hz).

(3) To a solution of butyl (E)-3-[3-[[(tert-butoxycarbonyl)amino]methyl]-4-(4-fluorophenyl)-2-isobutyl-1-oxo-1,2-dihydro-6-isoquinolinyl]-2-propenate (0.56 g, 1 mmol) in tetrahydrofuran (10 ml) and methanol (10 ml) was added 1N sodium hydroxide (2 ml). The obtained mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give (E)-3-[3-[[(tert-butoxycarbonyl)amino]methyl]-4-(4-fluorophenyl)-2-isobutyl-1-oxo-1,2-dihydro-6-isoquinolinyl]-2-propenic acid (0.36 g, 72.0%) as crystals.

Melting point 201–202° C. Elemental analysis for C$_{28}$H$_{31}$N$_2$O$_5$F 0.25H$_2$O Calculated: C, 67.39; H, 6.36; N, 5.61. Found: C, 67.69; H, 6.27; N, 5.49. $^1$H-NMR(CDCl$_3$) δ: 0.99 (6H, d, J=6.4 Hz), 1.49 (9H, s), 2.11–2.24 (1H, m), 4.04 (2H, d, J=7.2 Hz), 4.13 (2H, d, J=3.0 Hz), 5.74 (1H, bs), 6.28 (1H, d, J=16.4 Hz), 6.77 (1H, s), 7.21–7.34 (5H, m), 7.43 (1H, d, J=16.4 Hz), 8.22 (1H, d, J=8.2 Hz).

(4) A solution of (E)-3-[3-[[(tert-butoxycarbonyl)amino]methyl]-4-(4-fluorophenyl)-2-isobutyl-1-oxo-1,2-dihydro-6-isoquinolinyl]-2-propenic acid (0.20 g, 0.4 mmol), 1-ethyl-3-(3-3-dimethylaminopropyl)carbodiimide hydrochloride (0.15 g, 0.8 mmol) and 1-hydroxybenzotriazole ammonium salt (0.12 g, 0.8 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was purified by silica gel column chromatography to give (E)-3-[3-[[(tert-butoxycarbonyl)amino]methyl]-4-(4-fluorophenyl)-2-isobutyl-1-oxo-1,2-dihydro-6-isoquinolinyl]-2-propenamide (09.13 g, 65.0%) as crystals.

Melting point 161–163° C. $^1$H-NMR(CDCl$_3$) δ: 1.00 (6H, d, J=6.6 Hz), 1.44 (9H, s), 2.16–2.24 (1H, m), 4.07 (2H, d, J=7.4 Hz), 4.19 (2H, d, J=5.6 Hz), 4.96 (1H, bs), 5.75 (1H, bs), 6.38 (1H, d, J=15.6 Hz), 6.94 (1H, s), 7.26–7.30 (2H, m), 7.40–7.56 (5H, m), 8.29 (1H, d, J=8.4 Hz).

(5) (E)-3-[3-[[(Tert-butoxycarbonyl)amino]methyl]-4-(4-fluorophenyl)-2-isobutyl-1-oxo-1,2-dihydro-6-isoquinolinyl]-2-propenamide (0.10 g, 0.2 mmol) was dissolved in a solution of 4N hydrogen chloride in ethyl acetate (5 ml) and, the mixture was stirred at room temperature for 2 h. The reaction mixture was concentrated under reduced pressure, and the residue was crystallized from ethyl acetate to give (E)-3-[3-(aminomethyl)-4-(4-fluorophenyl)-2-isobutyl-1-oxo-1.2-dihydro-6-isoquinolinyl]-2-propenamide hydrochloride (0.08 g, 88.8%) as crystals.

Melting point 255–258° C. Elemental analysis for C$_{23}$H$_{25}$N$_3$O$_2$ClF 0.75H$_2$O Calculated: C, 62.30; H, 6.02; N, 9.48. Found: C, 61.90; H, 6.38; N, 9.31. $^1$H-NMR(DMSO-d$_6$) δ: 0.92 (6H, d, J=6.6 Hz), 1.99–2.19 (1H, m), 3.86 (2H, d, J=4.0 Hz), 4.08 (2H, d, J=7.0 Hz), 6.57 (1H, d, J=15.8 Hz), 7.00 (1H, d, J=1.6 Hz), 7.18 (1H, bs), 7.32–7.51 (5H, m), 7.67 (1H, bs), 7.78 (1H, dd, J=1.6, 8.4 Hz), 8.35 (1H, d, J=8.4 Hz), 8.61 (3H, bs).

Example 181

2-[[3-(Aminomethyl)-2-isobutyl-4-(4-methylphenyl)-1-oxo-1,2-dihydro-6-isoquinolinyl]oxy]acetamide hydrochloride (1) A mixture of methyl 6-benzyloxy-2-isobutyl-1-oxo-4-trifluoromethanesulfonyloxy-1,2-dihydro-3-isoquinolinecarboxylate (9.24 g, 18 mmol), 4-methylphenylboronic acid (2.94 g, 21.6 mmol) and sodium carbonate (2.86 g, 27 mmol) in toluene (50 ml)-methanol (10 ml)-water (10 ml) was stirred under an argon atmosphere at room temperature for 30 min. To the obtained mixture was added tetrakis (triphenylphosphine)palladium (1.04 g, 1 mmol) and the mixture was refluxed under heating under an argon, atmosphere for 10 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 6-benzyloxy-2-isobutyl-4-(4-methylphenyl)-1-oxo-1,2-dihydro-3-isoquinolinecarboxylate (6.91 g, 84.4%) as crystals.

Melting point 142.5–143° C. Elemental analysis for C$_{29}$H$_{29}$N$_4$ Calculated: C, 76.46; H, 6.42; N, 3.07. Found: C, 76.35; H, 6.40; N, 2.86. $^1$H-NMR(CDCl$_3$) δ: 0.92 (6H, d, J=6.6 Hz), 2.04–2.20 (1H, m), 2.43 (3H, s), 3.47 (3H, s), 3.93 (2H, d, J=7.6 Hz), 4.97 (2H, s), 6.65 (1H, d, J=22.6 Hz), 7.11–7.37 (10H, m), 8.42 (1H, d, J=8.8 Hz).

(2) To a suspension of methyl 6-benzyloxy-2-isobutyl-4-(4-methylphenyl)-1-oxo-1,2-dihydro-3-isoquinolinecarboxylate (6.83 g, 15 mmol) in methanol (50 ml) was added an aqueous solution (20 ml) of lithium hydroxide monohydrate (1.89 g, 45 mmol). The obtained mixture was refluxed under heating for 24 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals was recrystallized from ethyl acetate-diisopropyl ether to give 6-benzyloxy-2-isobutyl-4-(4-methylphenyl)-3-isoquinolinecarboxylic acid (5.78 g, 87.3%) as crystals.

Melting point 153–154° C. $^1$H-NMR(CDCl$_3$) δ: 0.85 (6H, d, J=6.6 Hz), 2.03–2.21 (1H, m), 2.42 (3H, s), 3.86 (2H, d, J=7.4 Hz), 4.13 (1H, bs), 4.96 (2H, s), 6.61 (1H, d, J=2.4 Hz), 7.10 (1H, dd, J=2.4, 9.0 Hz), 7.13–7.36 (9H, m), 8.28 (1H, d, J=9.0 Hz).

(3) To a mixed solution of 6-benzyloxy-2-isobutyl-4-(4-methylphenyl)-1-oxo-1,2-dihydro-3-isoquinolinecarboxylic acid (5.74 g, 13 mmol) in tetrahydrofuran (50 ml) were added oxalyl chloride (1.4 ml, 15.6 mmol) and N,N-dimethylformamide (3 drops), and the mixture was stirred at room temperature for 1 h. The reaction mixture was concentrated under reduced pressure and the residue was dissolved in tetrahydrofuran (20 ml) The obtained solution was added dropwise to a suspension of sodium tetrahydroborate (1.72 g, 45.5 mmol) in 1,2-dimethoxyethane (50 ml) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-benzyloxy-3-hydroxymethyl-2-isobutyl-4-(4-methylphenyl)-1-(2H)-isoquinolinone (4.41 g, 79.5%) as crystals.

Melting point 74–76° C. $^1$H-NMR(CDCl$_3$) δ: 0.95 (6H, d, J=6.6 Hz), 2.16–2.26 (1H, m), 2.41 (1H, bs), 2.47 (3H, s), 4.17 (2H, d, J=7.5 Hz), 4.43 (2H, s), 4.89 (2H, s), 6.39 (1H, d, J=2.4 Hz), 6.98 (1H, dd, J=2.4, 8.8 Hz), 7.17 (2H, d, J=7.8 Hz), 7.23–7.34 (7H, m), 8.28 (1H, d, J=8.8 Hz).

(4) To a suspension of 6-benzyloxy-3-hydroxymethyl-2-isobutyl-4-(4-methylphenyl)-1(2H)-isoquinolinone (4.28 g, 10 mmol) in toluene (50 ml) was added thionyl chloride (1.5 ml, 20 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-2-isobutyl-4-(4-methylphenyl)-1(2H)-isoquinolinone (4.26 g, 95.5%) as an oil.

$^1$H-NMR(CDCl$_3$) δ: 0.99 (1H, d, J=7.0 Hz), 2.14–2.30 (1H, m), 2.47 (3H, s), 4.15 (2H, d, J=6.8 Hz), 4.39 (2H, s), 4.93 (2H, s), 6.45 (1H, d, J=2.6 Hz), 7.09–7.35 (10H, m), 8.40 (1H, d, J=8.8 Hz).

(5) A solution of 6-benzyloxy-3-chloromethyl-2-isobutyl-4-(4-methylphenyl)-1(2H)-isoquinolinone (4.24 g, 9.5 mmol) and potassium phthalimide (2.65 g, 14.3 mmol) in N,N-dimethylformamide (50 ml) was stirred at room temperature for 6 h. The reaction mixture was poured into water and extracted with ethyl acetate. After washing the extract with water, the extract was dried over anhydrous magnesium sulfate and concentrated under reduced pressure. The residue was purified by silica gel column chromatography to give 2-[[6-benzyloxy-2-isobutyl-4-(4-methylphenyl)-1-oxo-1,2-dihydro-3-isoquinolinyl]methyl]-1H-isoindole-1,3(2H)-dione (5.07 g, 96.0%) as crystals.

Melting point 158–159° C. Elemental analysis for $C_{36}H_{32}N_2O_4$ Calculated: C, 77.68; H, 5.79; N, 5.03. Found: C, 77.89; H, 5.91; N, 4.96. $^1$H-NMR(CDCl$_3$) δ: 0.98 (6H, d, J=6.6 Hz), 2.14–2.28 (1H, m), 2.38 (3H, s), 4.01 (2H, d, J=7.2 Hz), 4.78 (2H, s), 4.92 (2H, s), 6.41 (1H, d, J=2.6 Hz), 7.09 (1H, dd, J=2.6, 8.8 Hz), 7.12–7.19 (4H, m), 7.20–7.35 (5H, m), 7.66–7.76 (4H, m), 8.38 (1H, d, J=8.8 Hz).

(6) To a suspension of 2-[[6-benzyloxy-2-isobutyl-4-(4-methylphenyl)-1-oxo-1,2-dihydro-3-isoquinolinyl]methyl]-1H-isoindole-1,3(2H)-dione (5.01 g, 9 mmol) in ethanol (50 ml) was added hydrazine monohydrate (1.3 ml, 27 mmol). The obtained mixture was refluxed under heating for 1 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (50 ml) and di-t-butyl dicarbonate (3.1 ml, 13.5 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl[6-benzyloxy-2-isobutyl-4-(4-methylphenyl)-1-oxo-1,2-dihydro-3-isoquinolinyl]-methylcarbamate (4.48 g, 94.5%) as crystals.

Melting point 164–164.5° C. Elemental analysis for $C_{33}H_{38}N_2O_4$ Calculated: C, 75.26; H, 7.27; N, 5.32. Found: C, 75.17; H, 7.39; N, 5.17. $^1$H-NMR(CDCl$_3$) δ: 0.98 (6H, d, J=7.0 Hz), 1.42 (9H, s), 2.13–2.27 (1H, m), 2.46 (3H, s), 4.03 (2H, d, J=7.2 Hz), 4.18 (2H, d, J=5.4 Hz), 4.48 (1H, bs), 4.92 (2H, s), 6.38 (1H, d, J=2.6 Hz), 7.05–7.11 (3H, m), 7.22–7.35 (7H, m), 8.37 (1H, d, J=8.8 Hz).

(7) A suspension of tert-butyl[6-benzyloxy-2-isobutyl-4-(4-methylphenyl)-1-oxo-1,2-dihydro-3-isoquinolinyl]methylcarbamate (4.21 g, 8 mmol) and 5% palladium carbon (2.0 g) in ethanol (20 ml) and tetrahydrofuran (20 ml) was stirred under a hydrogen atmosphere at room temperature for 2 h. The catalyst was filtered off and the filtrate was concentrated under reduced pressure. The residue was purified by silica gel column chromatography to give tert-butyl [6-hydroxy-2-isobutyl-4-(4-methylphenyl)-1-oxo-1,2-dihydro-3-isoquinolinyl]methylcarbamate (3.28 g, 94.0%) as crystals.

Melting point 233–234° C. Elemental analysis for $C_{26}H_{32}N_2O_4$ Calculated: C, 71.53; H, 7.39; N, 6.42. Found: C, 71.35; H, 7.35; N, 6.22. $^1$H-NMR(CDCl$_3$) δ: 0.96 (6H, d, J=6.6 Hz), 1.41 (9H, s), 2.12–2.26 (1H, m), 2.41 (3H, s), 4.02 (2H, d, J=7.4 Hz), 4.19 (2H, d, J=5.4 Hz), 4.46 (1H, bs), 6.39 (1H, d, J=2.2 Hz), 7.04 (1H, dd, J=2.2, 8.8 Hz), 7.08 (2H, d, J=8.4 Hz), 7.24 (2H, d, J=8.4 Hz), 7.73 (1H, bs), 8.28 (1H, d, J=8.8 Hz).

(8) A solution of tert-butyl[6-hydroxy-2-isobutyl-4-(4-methylphenyl)-1-oxo-1,2-dihydro-3-isoquinolinyl]methylcarbamate (0.44 g, 1 mmol), 2-iodoacetamide (0.37 g, 2 mmol) and 1,8-diazabicyclo[5.4.0]-7-undecene (0.30 ml, 2 mmol) in N,N-dimethylacetamide (10 ml) was stirred at 80° C. for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(2- amino-2-oxoethoxy)-2-isobutyl-4-(4-methylphenyl)-1-oxo-1,2-dihydro-3-isoquinolinyl]methylcarbamate (0.18 g, 36.7%) as crystals.

Melting point 239–239.5° C. Elemental analysis for $C_{28}H_{35}N_3O_5$ Calculated: C, 68.13; H, 7.15; N, 8.51. Found: C, 67.77; H, 7.09; N, 8.21. $^1$H-NMR(CDCl$_3$), δ: 0.99 (6H, d, J=6.6 Hz), 1.43 (9H, s), 2.15–2.29 (1H, m), 2.47 (3H, s), 4.05 (2H, d, J=7.6 Hz), 4.19 (2H, d, J=5.4 Hz), 4.33 (2H, s), 4.48 (1H, bs), 5.69 (1H, bs), 6.34 (1H, d, J=2.6 Hz), 6.52 (1H, bs), 7.04 (1H, dd, J=2.6, 9.0 Hz), 7.10 (2H, d, J=7.9 Hz), 7.31 (2H, d, J=7.9 Hz), 8.42 (1H, d, J=9.0 Hz).

(9) Tert-butyl[6-(2-amino-2-oxoethoxy)-2-isobutyl-4-(4-methylphenyl)-1-oxo-1,2-dihydro-3-isoquinolinyl]methylcarbamate (0.15 g, 0.3 mmol) was dissolved in a solution of 4N hydrogen chloride in ethyl acetate (5 ml) and the mixture was stirred at room temperature for 2 h. The reaction mixture was concentrated under reduced pressure, and the precipitated crystals were recrystallized from ethyl acetate-diisopropyl ether to give 2-[[3-(aminomethyl)-2-isobutyl-4-(4-methylphenyl)-1-oxo-1,2-dihydro-6-isoquinolinyl]oxy] acetamide hydrochloride (0.11 g, 91.7%) as crystals.

Melting point 278–280° C. Elemental analysis for $C_{23}H_{28}N_3O_3$ 0.5H$_2$O Calculated: C, 62.93; H, 6.66; N, 9.57. Found: C, 62.97; H, 6.53; N, 9.28. $^1$H-NMR(DMSO-d$_6$) δ: 0.90 (6H, d, J=6.6 Hz), 1.99–2.16 (1H, m), 2.43 (3H, s), 3.86 (2H, s), 4.04 (2H, d, J=7.0 Hz), 4.36 (2H, s), 6.34 (1H, d, J=2.6 Hz), 7.19 (1H, dd, J=2.6, 8.8 Hz), 7.25 (2H, d, J=8.2 Hz), 7.35 (1H, bs), 7.37 (2H, d, J=8.2 Hz), 7.57 (1H, bs), 8.27 (1H, d, J=8.8 Hz), 8.48 (3H, s).

Example 182

3-(Aminomethyl)-2-isobutyl-4-(4-methylphenyl)-1 (2H)-isoquinolinone-6-carboxamide hydrochloride (1) To a solution of tert-butyl[6-hydroxy-2-isobutyl-4-(4-methylphenyl)-1-oxo-1,2-dihydro-3-isoquinolinyl] methylcarbamate (Example 181(7)) (2.18 g, 5 mmol) in N,N-dimethylformamide (20 ml) was added sodium hydride (0.30 g, 8.3 mmol) (60% in oil) at 0° C. and the mixture was stirred at 0° C. for 30 min. To the obtained mixture was added N-phenyltrifluoromethanesulfonimide (2.68 g, 8.3 mmol) and the mixture was stirred at room temperature for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl[2-isobutyl-4-(4-methylphenyl)-1-oxo-6-trifluoromethanesulfonyloxy-1,2-dihydro-3-isoquinolinyl]methylcarbamate (2.85 g, 100%) as an oil.

$^1$H-NMR(CDCl$_3$) δ: 0.99 (6H, d, J=7.0 Hz), 1.43 (9H, s), 2.14–2.27 (1H, m), 2.47 (3H, s), 4.09 (2H, d, J=7.4 Hz), 4.24 (2H, d, J=5.8 Hz), 4.45 (1H, t, J=2.6 Hz), 6.86 (1H, d, J=2.6 Hz), 7.12 (2H, d, J=8.2 Hz), 7.13–7.40 (3H, m), 8.54 (1H, d, J=8.8 Hz).

(2) A mixture of tert-butyl[2-isobutyl-4-(4-methylphenyl)-1-oxo-6-trifluorbmethanesulfonyloxy-1,2-dihydro-3-isoquinolinyl]methylcarbamate (2.84 g, 5 mmol), 1,1'-bis(diphenylphosphino)ferrocene (0.14 g, 0.25 mmol), triethylamine (0.77 ml, 5.5 mmol) and palladium acetate (56 mg, 0.25 mmol) in tetrahydrofuran (20 ml)-methanol (20 ml) was stirred with heating at 100° C. under a carbon monoxide atmosphere at 5 atm for 1 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 3-[[(tert-butoxycarbonyl)amino]methyl]-2-isobutyl-4-(4-methylphenyl)-1-oxo-1,2-dihydro-6-isoquinolinecarboxylate (2.11 g, 88.3%) as crystals.

Melting point 193–194.5° C. Elemental analysis for $C_{28}H_{34}N_2O_5$ Calculated: C, 70.27; H, 7.16; N, 5.85. Found: C, 69.97; H, 7.22; N, 5.71. $^1$H-NMR(CDCl$_3$) δ: 1.00 (6H, d, J=6.6 Hz), 1.43 (9H, s), 2.17–2.32 (1H, m), 2.47 (3H, s), 3.86 (3H, s), 4.09 (2H, d, J=7.4 Hz), 4.22 (2H, d, J=5.8 Hz), 4.54 (1H, bs), 7.13 (2H, d, J=7.8 Hz), 7.32 (2H, d, J=7.8 Hz), 7.68 (1H, d, J=1.6 Hz), 8.02 (1H, dd, J=1.6, 8.2 Hz), 8.49 (1H, d, J=8.2 Hz).

(3) To a solution of methyl 3-[[(tert-butoxycarbonyl)amino]methyl]-2-isobutyl-4-(4-methylphenyl)-1-oxo-1,2-dihydro-6-isoquinolinecarboxylate (1.91 g, 4 mmol) in tetrahydrofuran (10 ml)-methanol (10 ml) was added 1N sodium hydroxide (8 ml) and the mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from tetrahydrofuran-isopropyl ether to give 3-[[(tert-butoxycarbonyl)amino]methyl]-2-isobutyl-4-(4-methylphenyl)-1-oxo-1,2-dihydro-6-isoquinolinecarboxylic acid (1.67 g, 90.3%) as crystals.

Melting point 230–231° C. Elemental analysis for $C_{27}H_{32}N_2O_5$ Calculated: C, 69.81; H, 6.94; N, 6.03. Found: C, 69.45; H, 7.09; N, 5.67. $^1$H-NMR(CDCl$_3$) δ: 0.98 (6H, d, J=6.6 Hz), 1.49 (9H, s), 2.07–2.25 (1H, m), 2.48 (3H, s), 4.05 (2H, d, J=7.4 Hz), 4.18 (2H, d, J=4.4 Hz), 5.75 (1H, bs), 7.21 (2H, d, J=7.8 Hz), 7.32 (2H, d, J=7.8 Hz), 7.48 (1H, s), 7.79 (1H, d, J=8.2 Hz), 8.32 (1H, d, J=8.2 Hz).

(4) A solution of 3-[[(tert-butoxycarbonyl)amino]methyl]-2-isobutyl-4-(4-methylphenyl)-1-oxo-1,2-dihydro-6-isoquinolinecarboxylic acid (0.92 g, 2 mmol), 1-ethyl-3-(3-dimethylaminopropyl)carbodiimide hydrochloride (0.77 g, 4 mmol) and 1-hydroxybenzotriazole ammonium salt (0.61 g, 4 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give 3-[[(tert-butoxycarbonyl)amino]methyl]-2-isobutyl-4-(4-methylphenyl)-1-oxo-1,2-dihydro-6-isoqinolinecarboxamide (82 g, 89.1%) as crystals.

Melting point 225–226° C. $^1$H-NMR(CDCl$_3$) δ: 1.00 (6H, d, J=6.6 Hz), 1.43 (9H, s), 2.17–2.28 (1H, m), 246 (3H, s), 4.08 (2H, d, J=7.2 Hz), 4.22 (2H, d, J=5.6 Hz), 4.52 (1H, bs), 5.62 (1H, bs), 6.00 (1H, bs), 7.12 (2H, d, J=7.8 Hz), 7.32 (2H, d, J=7.8 Hz), 7.42 (1H, d, J=1.8 Hz), 7.78 (1H, dd, J=1.8, 8.4 Hz), 8.49 (1H, d, J=8.4 Hz).

(5) A solution of 3-[[(tert-butoxycarbonyl)amino]methyl]-2-isobutyl-4-(4-methylphenyl)-1-oxo-1,2-dihydro-6-isoquinolinecarboxamide (0.42 g, 0.9 mmol) was dissolved in a solution of 4N hydrogen chloride in ethyl acetate (5 ml) and the mixture was stirred at room temperature for 1 h. The reaction mixture was concentrated under reduced pressure, and the precipitated crystals were recrystallized from methanol-diethyl ether to give 3-(aminomethyl)-2-isobutyl-4-(4-methylphenyl)-1 (2H)-isoquinolinone-6-carboxamide hydrochloride (0.34 g, 94.4%) as crystals.

Melting point 286–288° C. Elemental analysis for $C_{22}H_{26}N_3O_3Cl$ 1.25H$_2$O Calculated: C, 62.55; H, 6.80; N, 9.95. Found: C, 62.66; H, 6.93; N, 9.99. $^1$H-NMR(DMSO-$d_6$) δ: 0.92 (6H, d, J=6.6 Hz), 2.02–2.16 (1H, m), 2.45 (3H, s), 3.88 (2H, s), 4.08 (2H, d, J=7.4 Hz), 7.28 (2H, d, J=8.1 Hz), 7.39 (2H, d, J=8.1 Hz), 7.46 (1H, d, J=1.6 Hz), 7.58 (1H, bs), 7.99 (1H, d, J=1.6, 8.2 Hz), 8.16 (1H, bs), 8.36 (1H, d, J=8.2 Hz), 8.49 (3H, bs).

Example 183

3-(Aminomethyl)-2-isobutyl-4-(4-methylphenyl)-1 (2H)-isoquinolinone-6-carbonitrile hydrochloride (1) A solution of 3-[[(tert-butoxycarbonyl)amino]methyl]-2-isobutyl-4-(4-methylphenyl)-1-oxo-1,2-dihydro-6-isoquinolinecarboxamide (Example 3 (4)) (0.37 g, 0.8 mmol) and cyanuric chloride (0.44 g, 2.4 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was, purified by silica gel column chromatography to give tert-butyl[6-cyano-4-(4-methylphenyl)-1-oxo-1,2-dihydro-3-isoquinolinyl]methyl-carbamate (0.32 g, 91.4%) as crystals.

Melting point 156–157° C. Elemental analysis for $C_{27}H_{31}N_3O_3$ Calculated: C, 72.78; H, 7.01; N, 9.43. Found: C, 72.66; H, 7.16; N, 9.46. $^1$H-NMR(CDCl$_3$) δ: 1.00 (6H, d, J=6.6 Hz), 1.43 (9H, s), 2.14–2.29 (1H, m), 2.48 (3H, s), 4.09 (2H, d, J=7.6 Hz), 4.24 (2H, d, J=5.8 Hz), 4.45 (1H, bs), 7.10 (2H, d, J=7.7 Hz), 7.31 (1H, d, J=1.4 Hz), 7.35 (2H, d, J=7.7 Hz), 7.63 (1H, dd, J=1.4, 8.2 Hz), 8.53 (1H, d, J=8.2 Hz).

(2) Tert-butyl[6-cyano-4-(4-methylphenyl)-1-oxo-1,2-dihydro-3-isoquinolinyl]methylcarbamate (0.27 g, 0.6 mmol) was dissolved in a solution of 4N hydrogen chloride in ethyl acetate (5 ml) and the mixture was stirred at room temperature, for 1 h. The reaction mixture was concentrated under reduced pressure, and the precipitated crystals were recrystallized from methanol-diethyl ether to give 3-(aminomethyl)-2-isobutyl-4-(4-methylphenyl)-1(2H)-isoquinolinone-6-carbonitrile hydrochloride (0.22 g, 95.7%) as crystals.

Melting point 278–279° C. $^1$H-NMR(DMSO-$d_6$) δ: 0.92 (6H, d, J=6.6 Hz), 1.99–2.16 (1H, m), 2.45 (3H, s), 3.90 (2H, s), 4.11 (2H, d, J=7.0 Hz), 7.25 (1H, d, J=1.4 Hz), 7.31 (2H, d, J=7.9 Hz), 7.41 (2H, d, J=7.9 Hz), 7.96 (1H, dd, J=1.4, 8.4 Hz), 8.47 (1H, d, J=8.4 Hz), 8.65 (3H, bs).

Example 184

(E)-3-[3-(Aminomethyl)-2-isobutyl-4-(4-methylphenyl)-1-oxo-1,2-dihydro-6-isoquinolinyl]-2-propenamide hydrochloride (1) A suspension of tert-butyl[2-isobutyl-4-(4-methylphenyl)-1-oxo-6-trifluoromethanesulfonyloxy-1,2-dihydro-3-isoquinolinyl]methylcarbamate (Example 182 (1)) (1.42 g, 2.5 mmol), butyl acrylate (0.54 ml, 3.8 mmol), sodium hydrogencarbonate (0.32 g, 3.81 mmol), tetrabutylammonium chloride (83 mg, 0.3 mmol) and palladium acetate (67 mg, 0.3 mmol) in N,N-dimethylformamide (30 ml) was stirred with heating at 100° C. under an argon atmosphere for 20 h. The reaction mixture was poured into water and extracted with ethyl acetate. After washing the extract with water, the extract was dried over anhydrous magnesium sulfate and concentrated under reduced pressure. The residue was purified by silica gel column chromatography to give butyl (E)-3-[3-[[(tert-butoxycarbonyl)amino]methyl]-2-isobutyl-4-(4-methylphenyl)-1-oxo-1,2-dihydro-6-isoquinolinyl]-2-propenate (0.56 g, 40.3%) as an amorphous.

$^1$H-NMR(CDCl$_3$) δ: 0.95 (3H, t, J=7.8 Hz), 1.00 (6H, d, J=6.6 Hz), 1.35–1.47 (11H, m), 1.62–1.71 (2H, m), 2.18–2.29 (1H, m), 2.49 (3H, s), 4.08 (2H, d, J=6.0 Hz), 4.18 (2H, t, J=6.6 Hz), 4.22 (2H, d, J=4.8 Hz), 4.52 (1H, bs), 6.38 (1H, d, J=15.9 Hz), 7.04 (1H, d, J=1.0 Hz), 7.13 (2H, d, J=8.1 Hz), 7.33 (2H, d, J=8.1 Hz), 7.55 (1H, d, J=15.9 Hz), 7.61 (1H, dd, J=1.0, 8.4 Hz), 8.44 (1H, d, J=8.4 Hz).

(2) To a solution of butyl ((E)-3-[3-[[(tert-butoxycarbonyl)amino]methyl]-2-isobutyl-4-(4-methylphenyl)-1-oxo-1,2-dihydro-6-isoquinolinyl]-2-propenate (0.50 g, 0.9 mmol) in tetrahydrofuran (10 ml)-methanol (10 ml) was added 1N sodium hydroxide (2 ml). The obtained mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give (E)-3-[3-[[(tert-butoxycarbonyl)amino]methyl]-2-isobutyl-4-(4-methylphenyl)-1-oxo-1,2-dihydro-6-isoquinolinyl]-2-propenic acid (0.38 g, 84.4%) as crystals.

Melting point 171–173° C. Elemental analysis for $C_{29}H_{34}N_2O_5$ 0.25$H_2O$ Calculated: C, 70.35; H, 7.02; N, 5.66. Found: C, 70.16; H, 6.94; N, 5.49. $^1$H-NMR(CDCl$_3$) δ: 0.99 (6H, d, J=6.6 Hz), 1.48 (9H, s), 2.08–2.29 (1H, m), 2.50 (3H, s), 4.05 (2H, d, J=6.3 Hz), 4.17 (2H, d, J=4.5 Hz), 5.46 (1H, bs), 6.30 (1H, d, J=15.9 Hz), 6.88 (1H, s), 7.20 (2H, d, J=7.6 Hz), 7.34 (2H, d, J=7.6 Hz), 7.41 (1H, d, J=8.6 Hz), 7.47 (1H, d, J=15.9 Hz), 8.29 (1H, d, J=8.6 Hz).

(3) A solution of (E)-3-[3-[[(tert-butoxycarbonyl)amino] methyl]-2-isobutyl-4-(4-methylphenyl)- 1-oxo-1,2-dihydro-6-isoquinolinyl]-2-propenic acid (0.25 g, 0.5 mmol), 1-ethyl-3-(3-dimethylaminopropyl)carbodiimide hydrochloride (0.19 g, 1 mmol) and 1-hydroxybenzotriazole ammonium salt (0.15 g, 1 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was purified by silica gel column chromatography to give (E)-3-[3-[[(tert-butoxycarbonyl)-amino]methyl]-2-isobutyl-4-(4-methylphenyl)-1-oxo-1,2-dihydro-6-isoquinolinyl]-2-propenamide (0.21 g, 84.0%) as crystals.

Melting point 152–154° C. Elemental analysis for $C_{29}H_{35}N_3O_4$ 0.75$H_2O$ Calculated: C, 69.23; H, 7.31; N, 8.35. Found: C, 69.58; H, 7.29; N, 8.01. $^1$H-NMR(CDCl$_3$) δ: 1.00 (6H, d, J=6.6 Hz), 1.43 (9H, s), 2.16–2.28 (1H, m), 2.48 (3H, s), 4.07 (2H, d, J=7.4 Hz), 4.22 (2H, d, J=5.6 Hz), 4.70 (1H, bs), 5.71 (2H, bs), 6.40 (1H, d, J=15.6 Hz), 7.00 (1H, s), 7.12 (2H, d, J=7.8 Hz), 7.32 (2H, d, J=7.8 Hz), 7.44–7.54 (2H, m), 8.36 (1H, d, J=8.4 Hz).

(4) (E)-3-[3-[[(Tert-butoxycarbonyl)amino]methyl-]-2-isobutyl-4-(4-methylphenyl)-1-oxo-1,2-dihydro-6-isoquinolinyl]-2-propenamide (0.15 g, 0.3 mmol) was dissolved in a solution of 4N hydrogen chloride in ethyl acetate (5 ml) and the mixture was stirred at room temperature, for 1 h. The reaction mixture was concentrated under reduced pressure, and the residue was crystallized from ethyl acetate-diisopropyl ether to give (E)-3-[3-(aminomethyl)-2-isobutyl-4-(4-methylphenyl)-1-oxo-1,2-dihydro-6-isoquinolinyl]-2-propenamide hydrochloride (0.12 g, 92.3%) as crystals.

Melting point 264–266° C. Elemental analysis for $C_{24}H_{28}N_3O_2Cl \cdot 1.25H_2O$ Calculated: C, 64.28; H, 6.85; N, 9.37. Found: C, 64.37; H, 6.88; N, 9.08. $^1$H-NMR(DMSO-$d_6$) δ: 0.92 (6H, d, J=6.6 Hz), 2.04–2.16 (1H, m), 3.87 (2 H, d, J=2.4 Hz), 4.08 (2H, d, J=6.9 Hz), 6.56 (1H, d, J=15.9 Hz), 7.00 (1H, d, J=1.2 Hz), 7.18 (1H, bs), 7.25–7.42 (5H, m), 7.67 (1H, bs), 7.77 (1H, dd, J=1.2, 8.7 Hz), 8.34 (1H, d, J=8.7 Hz), 8.53 (3H, bs).

Example 185

2-[[3-(Aminomethyl)-4-(4-chlorophenyl)-2-isobutyl-1-oxo-1,2-dihydro-6-isoquinolinyl]oxy]acetamide hydrochloride (1) A mixed solution of methyl 6-benzyloxy-2-isobutyl-1-oxo-4-trifluoromethanesulfonyloxy-1,2-dihydro-3-isoquinolinecarboxylate (10.27 g, 20 mmol), 4-chlorophenylboronic acid (3.75 g, 24 mmol) and sodium carbonate (5.30 g, 50 mmol) in toluene (50 ml)-methanol (10 ml)-water (10 ml) was stirred under an argon atmosphere at room temperature for 30 min. To the obtained mixture was added tetrakis(triphenylphosphine)palladium (1.15 g, 1 mmol) and the mixture was refluxed under heating under an argon atmosphere for 10 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 6-benzyloxy-4-(4-chlorophenyl)-2-isobutyl-1-oxo-1,2-dihydro-3-isoquinolinecarboxylate (5.21 g, 54.8%) as crystals.

Melting point 165.5–166° C. Elemental analysis for $C_{28}H_{26}NO_4Cl$ Calculated: C, 70.66; H, 5.51; N, 2.94 Found: C, 70.89; H, 5.68; N, 2.78. $^1$H-NMR(CDCl$_3$) δ: 0.91 (6H, d, J=7.0 Hz), 2.03–2.21 (1H, m), 3.50 (3H, s), 3.93 (2H, d, J=7.8 Hz), 4.99 (2H, s), 6.52 (1H, d, J=2.6 Hz), 7.15–7.22 (3H, m), 7.26–7.44 (7H, m), 8.42 (1H, d, J=8.8 Hz).

(2) To a suspension of methyl 6-benzyloxy-4-(4-chlorophenyl)-2-isobutyl-1-oxo-1,2-dihydro-3-isoquinolinecarboxylate (5.00 g, 10.5 mmol) in 1,4-dioxane (50 ml) was added an aqueous solution (20 ml) of lithium hydroxide monohydrate (1.32 g, 31.5 mmol). The obtained mixture was refluxed under heating for 24 h. The reaction mixture was poured into water, acidified with 1N hydrochloric acid and extracted with ethyl acetate. The extract was washed with brine, dried over anhydrous magnesium sulfate and concentrated under reduced pressure. The obtained, crystals were recrystallized from tetrahydrofuran-n-hexane to give 6-benzyloxy-4-(4-chlorophenyl)-2-isobutyl-1-oxo-1,2-dihydro-3-isoquinolinecarboxylic acid (4.69 g, 96.7%) as crystals.

Melting point 200–201° C. Elemental analysis for $C_{27}H_{24}NO_4Cl$ Calculated: C, 70.20; H, 5.24; N, 3.03. Found: C, 70.12; H, 5.28; N, 2.97. $^1$H-NMR(CDCl$_3$) δ: 0.86 (6H, d, J=6.6 Hz), 2.07–2.25 (1H, m), 3.90 (2H, d, J=7.2 Hz), 5.00 (2H, s), 6.51 (1H, d, J=2.4 Hz), 7.14 (1H, dd, J=2.4, 9.0 Hz), 7.21–7.40 (9H, m), 8.25 (1H, d, J=9.0 Hz).

(3) To a mixture of 6-benzyloxy-4-(4-chlorophenyl)-2-isobutyl-1-oxo-1,2-dihydro-3-isoquinolinecarboxylic acid (4.62 g, 10 mmol) and tetrahydrofuran (50 ml) were added oxalyl chloride (1.0 ml, 15.6 mmol) and N,N-dimethylformamide (3 drops), and the mixture was stirred at room temperature for 1 h. The reaction mixture was concentrated under reduced pressure and the residue was dissolved in tetrahydrofuran (20 ml). The obtained solution was added dropwise to a suspension of sodium tetrahydroborate (1.32 g, 35 mmol) in 1,2-dimethoxyethane (30 ml) at 0° C. The obtained mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 6-benzyloxy-4-(4-chlorophenyl)-3-hydroxymethyl-2-isobutyl-1(2H)-isoquinolinone (4.31 g, 96.4%) as crystals.

Melting point 87–88° C.
$^1$H-NMR(CDCl$_3$) δ: 0.95 (6H, d, J=6.6 Hz), 2.11–2.28 (1H, m), 2.39 (1H, bs), 4.16 (2H, d, J=7.6 Hz), 4.41 (2H, d, J=5.4 Hz), 4.92 (2H, s), 6.29 (1H, d, J=2.4 Hz), 7.00 (1H, dd, J=2.4, 9.0 Hz), 7.21–7.38 (7H, m), 7.45 (2H, d, J=8.4 Hz), 8.27 (1H, d, J=8.8 Hz).

(4) To a suspension of 6-benzyloxy-4-(4-chlorophenyl)-3-hydroxymethyl-2-isobutyl-1(2H)-isoquinolinone (4.25 g, 9.5 mmol) in toluene (50 ml) was added thionyl chloride (1.4 ml, 19 mmol). The obtained mixture was refluxed under heating for 2 h. The reaction mixture was poured into saturated aqueous sodium hydrogencarbonate solution and extracted with ethyl acetate. The extract was washed with brine, dried over anhydrous magnesium sulfate and concentrated under reduced pressure to give 6-benzyloxy-3-chloromethyl-4-(4-chlorophenyl)-2-isobutyl-1(2H)-isoquinolinone (3.98 g, 89.8%) as an oil.
$^1$H-NMR(CDCl$_3$) δ: 0.99 (6H, d, J=7.0 Hz), 2.13–2.30 (1H, m), 4.14 (2H, d, J=7.6 Hz), 4.34 (2H, s), 4.96 (2H, s), 6.34 (1H, d, J=2.2 Hz), 7.06–7.38 (8H, m), 7.44–7.50 (2H, m), 8.41 (1H, d, J=8.8 Hz).

(5) A solution of 6-benzyloxy-3-chloromethyl-4-(4-chlorophenyl)-2-isobutyl-1(2H)-isoquinolinone (3.96 g, 8.5 mmol) and potassium phthalimide (2.37 g, 12.8 mmol) in N,N-dimethylformamide (40 ml) was stirred at room temperature for 6 h. The reaction mixture was poured into water and extracted with ethyl acetate. After washing the extract with water, the extract was dried over anhydrous magnesium sulfate and concentrated under reduced pressure. The residue was purified by silica gel column chromatography to give 2-[[6-benzyloxy-4-(4-chlorophenyl)-2-isobutyl-1-oxo-1,2-dihydro-3-isoquinolinyl]methyl]-1H-isoindole-1,3(2H)-dione (4.72 g, 96.3%) as crystals.

Melting point 182–183° C. Elemental analysis for $C_{35}H_{29}N_2O_4Cl$ Calculated: C, 72.85; H, 5.07; N, 4.85. Found: C, 72.95; H, 5.19; N, 4.70. $^1$H-NMR(CDCl$_3$) δ: 0.98 (6H, d, J=6.6 Hz), 2.09–2.31 (1H, m), 4.00 (2H, d, J=7.2 Hz), 4.74 (2H, s), 4.93 (2H, s), 6.29 (1H, d, J=2.6 Hz), 7.11 (1H, dd, J=2.6, 8.8 Hz), 7.19–7.41 (9H, m), 7.66–7.79 (4H, m), 8.38 (1H, d, J=8.8 Hz).

(6) To a suspension of 2-[[6-benzyloxy-4-(4-chlorophenyl)-2-isobutyl-1-oxo-1,2-dihydro-3-isoquinolinyl]methyl]-1H-isoindole-1,3(2H)-dione (4.61 g, 8 mmol) in ethanol (50 ml) was added hydrazine monohydrate (1.2 ml, 24 mmol). The obtained mixture was refluxed under heating for 1 h. The reaction mixture was poured into saturated aqueous sodium hydrogencarbonate solution and extracted with ethyl acetate. The extract was washed with brine, dried over anhydrous magnesium sulfate and concentrated under reduced pressure. The residue was dissolved in tetrahydrofuran (50 ml) and di-t-butyl dicarbonate (2.8 ml, 12 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give tert-butyl[6-benzyloxy-4-(4-chlorophenyl)-2- isobutyl-1-oxo-1,2-dihydro-3-isoquinolinyl]methylcarbamate (4.16 g, 95.2%) as crystals.

Melting point 186–187° C. Elemental analysis for $C_{32}H_{35}N_2O_4Cl$ Calculated: C, 70.25; H, 6.45; N, 5.12. Found: C, 70.17; H, 6.43; N, 5.00. $^1$H-NMR(CDCl$_3$) δ: 0.98 (6H, d, J=6.6 Hz), 1.42 (9H, s), 2.14–2.28 (1H, m), 4.02 (2H, d, J=7.6 Hz), 4.15 (2H, d, J=5.2 Hz), 4.46 (1H, bs), 4.95 (2H, s), 6.28 (1H, d, J=2.6 Hz), 7.07–7.16 (3H, m), 7.22–7.37 (5H, m), 7.42–7.49 (2H, m), 8.37 (1H, d, J=8.8 Hz).

(7) Tert-butyl[6-benzyloxy-4-(4-chlorophenyl)-2-isobutyl-1-oxo-1,2-dihydro-3-isoquinolinyl]methylcarbamate (0.54 g, 1 mmol) was suspended in 48% aqueous solution (20 ml) of hydrogen bromide and the obtained mixture was refluxed under heating for 3 h. The reaction mixture was neutralized with 1N sodium hydroxide aqueous solution and extracted with ethyl acetate. The extract was washed with brine, dried over anhydrous magnesium sulfate and concentrated under reduced pressure. The residue was dissolved in tetrahydrofuran (10 ml) and di-t-butyl dicarbonate (0.28 ml, 1 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-(4-chlorophenyl)-6-hydroxy-2-isobutyl-1-oxo-1,2-dihydro-3-isoquinolinyl]methylcarbamate (0.32 g, 71.1%) as crystals.

Melting point 220–221° C. $^1$H-NMR(CDCl$_3$) δ: 0.95 (6H, d, J=6.6 Hz), 1.42 (9H, s), 2.08–2.29 (1H, m), 4.01 (2H, d, J=7.0 Hz), 4.13 (2H, d, J=5.6 Hz), 4.50 (1H, bs), 6.33 (1H, d, J=2.4 Hz), 7.03 (1H, dd, J=2.4, 8.8 Hz), 7.03 (2H, d, J=8.2 Hz), 7.40 (2H, d, J=8.2 Hz), 7.93 (1H, bs), 8.26 (1H, d, J=8.8 Hz).

(8) To a solution of tert-butyl[4-(4-chlorophenyl)-6-hydroxy-2-isobutyl-1-oxo-1,2-dihydro-3-isoquinolinyl]methylcarbamate (0.45 g, 1 mmol) in N,N-dimethylformamide (10 ml) was added sodium hydride (48 mg, 1.2 mmol) (60% in oil) at 0° C., and the mixture was stirred at 0° C. for 10 min. To the obtained mixture was added 2-iodoacetamide (0.22 g, 1.2 mmol) and the mixture was stirred at 0° C. for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl[6-(2-amino-2-oxoethoxy)-4-(4-chlorophenyl)-2-isobutyl-1-oxo-1,2-dihydro-3-isoquinolinyl]methylcarbamate (0.27 g, 52.9%) as crystals.

Melting point 241–242° C. Elemental analysis for $C_{27}H_{32}N_3O_5Cl$ Calculated: C, 63.09; H, 6.27; N, 8.17. Found: C, 63.07; H, 6.32; N, 8.22. $^1$H-NMR(CDCl$_3$) δ: 0.99 (6H, d, J=6.6 Hz), 1.43 (9H, s), 2.10–2.28 (1H, m), 4.04 (2H, d, J=7.4 Hz), 4.17 (2H, d, J=5.4 Hz), 4.35 (2H, s), 4.56 (1H, bs), 5.79 (1H, bs), 6.28 (1H, d, J=2.4 Hz), 6.50 (1H, bs), 7.04 (1H, dd, J=2.4, 9.0 Hz), 7.17–7.24 (2H, m), 7.47–7.53 (2H, m), 8.41 (1H, d, J=9.0 Hz).

(9) Tert-butyl[6-(2-amino-2-oxoethoxy)-4-(4-chlorophenyl)-2-isobutyl-1-oxo-1,2-dihydro-3-isoquinolinyl]methylcarbamate (0.20 g, 0.4 mmol) was dissolved in a solution of 4N hydrogen chloride in ethyl acetate (5 ml) and the mixture was stirred at room temperature for 2 h. The reaction mixture was concentrated under reduced pressure, and the precipitated crystals were recrystallized from ethyl acetate-diisopropyl ether to give 2-[[3-(aminomethyl)-4-(4-chlorophenyl)-2-isobutyl-1-oxo-1,2-dihydro-6-isoquinolinyl]oxy]acetamide hydrochloride (0.16 g, 88.9%) as crystals.

Melting point 260–262° C. $^1$H-NMR(DMSO-d$_6$) δ: 0.91 (6H, d, J=6.6 Hz), 1.99–2.18 (1H, m) 3.84 (2H, bs), 4.03 (2H, d, J=7.4 Hz), 4.39 (2H, s), 6.31 (1H, d, J=2.4 Hz), 7.21 (1H, dd, J=2.4, 9.0 Hz), 7.36 (1H, bs), 7.40 (2H, d, J=8.4 Hz), 7.59 (1H, bs), 7.62 (2H, d, J=8.4 Hz), 8.27 (1H, d, J=9.0 Hz), 8.51 (3H, s).

Example 186

3-(Aminomethyl)-4-(4-chlorophenyl)-2-isobutyl-1(2H)-isoquinolinone-6-carboxamide hydrochloride (1) To a solution of tert-butyl[6-hydroxy-4-(4-chlorophenyl)-2-isobutyl-1-oxo-1,2-dihydro-3-isoquinolinyl]methylcarbamate (Example 185(7)) (1.83 g, 4 mmol) in N,N-dimethylformamide (20 ml) was added sodium hydride (0.24 g, 6 mmol) (60% in oil) at 0° C., and the mixture was stirred at 0° C. for 10 min. To the obtained mixture was added N-phenyltrifluoromethanesulfonimide (2.14 g, 6 mmol) and the mixture was stirred at room temperature for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give tert-butyl[4-(4-chlorophenyl)-2-isobutyl-1-oxo-6-trifluoromethanesulfonyloxy-1,2-dihydro-3-isoquinolinyl]methylcarbamate (2.36 g, 100%) as an oil.

$^1$H-NMR(CDCl$_3$) δ: 0.98 (6H, d, J=7.0 Hz), 1.43 (9H, s), 2.04–2.26 (1H, m), 4.07 (2H, d, J=7.4 Hz), 4.21 (2H, d, J=5.4 Hz), 4.50 (1H, bs), 6.81 (1H, d, J=2.6 Hz), 7.17–7.26 (2H, m), 7.50–7.57 (3H, m), 8.54 (1H, d, J=8.8 Hz).

(2) A mixed solution of tert-butyl[4-(4-chlorophenyl)-2-isobutyl-1-oxo-6-trifluoromethanesulfonyloxy-1,2-dihydro-3-isoquinolinyl]methylcarbamate (2.35 g, 4 mmol), 1,1'-bis(diphenylphosphino)ferrocene (0.11 g, 0.2 mmol), triethylamine (0.6 ml, 4.4 mmol) and palladium acetate (45 mg, 0.2 mmol) in tetrahydrofuran (20 ml)-methanol (20 ml) was stirred with heating at 100° C. under a carbon monoxide atmosphere at 5 atm for 2 h. The reaction mixture was poured into water and extracted with ethyl acetate. After washing the extract with water, the extract was dried over anhydrous magnesium sulfate and concentrated under reduced pressure. The residue was purified by silica gel column chromatography to give methyl 3-[[(tert-butoxycarbonyl)amino]methyl]-4-(4-chlorophenyl)-2-isobutyl-1-oxo-1,2-dihydro-6-isoquinolinecarboxylate (1.71 g, 85.9%) as crystals.

Melting point 205–207° C. Elemental analysis for $C_{27}H_{31}N_2O_5Cl$ Calculated: C, 64.99; H, 6.26; N, 5.61. Found: C, 64.91; H, 6.44; N, 5.34. $^1$H-NMR(CDCl$_3$) δ: 1.00 (6H, d, J=6.6 Hz), 1.44 (9H, s), 2.14–2.30 (1H, m), 3.87 (3H, s), 4.08 (2H, d, J=7.2 Hz), 4.20 (2H, d, J=5.6 Hz), 4.55 (1H, bs), 7.19–7.25 (2H, m), 7.49–7.56 (2H, m), 7.61 (1H, d, J=1.5 Hz), 8.03 (1H, dd, J=1.5, 8.5 Hz), 8.49 (1H, d, J=8.5 Hz).

(3) To a solution of methyl 3-[[(tert-butoxycarbonyl)amino]methyl]-4-(4-chlorophenyl)-2-isobutyl-1-oxo-1,2-dihydro-6-isoquinolinonecarboxylate (1.50 g, 3 mmol) in tetrahydrofuran (10 ml)-methanol (10 ml) was added 1N sodium hydroxide (6 ml) and the mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from tetrahydrofuran-isopropyl ether to give 3-[[((tert-butoxycarbonyl)amino]methyl]-4-(4-chlorophenyl)-2-isobutyl-1-oxo-1,2-dihydro-6-isoquinolinecarboxylic acid (1.41 g, 97.2%) as crystals.

Melting point 226–227° C. Elemental analysis for $C_{26}H_{29}N_2O_5Cl$ Calculated: C, 64.39; H, 6.03; N, 5.78. Found: C, 64.50; H, 6.36; N, 5.37. $^1$H-NMR(CDCl$_3$) δ: 0.98 (6H, d, J=6.6 Hz), 1.49 (9H, s), 2.10–2.26 (1H, m), 4.04 (2H, d, J=6.6 Hz), 4.14 (2H, s), 5.65 (1H, bs), 7.29 (2H, d, J=8.2 Hz), 7.44 (1H, s), 7.52 (2H, d, J=8.2 Hz), 7.83 (1H, d, J=8.0 Hz), 8.32 (1H, d, J=8.0 Hz).

(4) A solution of 3-[[(tert-butoxycarbonyl)amino]methyl]-4-(4-chlorophenyl)-2-isobutyl-1-oxo-1,2-dihydro-6-isoquinolinecarboxylic acid (1.21 g, 2.5 mmol), 1-ethyl-3-(3-dimethylaminopropyl)carbodiimide hydrochloride (0.96 g, 5 mmol) and 1-hydroxybenzotriazole ammonium salt (0.76 g, 5 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from ethyl acetate-diisopropyl ether to give 3-[[(tert-butoxycarbonyl)amino]methyl]-4-(4-chlorophenyl)-2-isobutyl-1-oxo-1,2-dihydro-6-isoquinolinecarboxamide (1.02 g, 85.0%) as crystals.

Melting point 144–146° C. Elemental analysis for $C_{26}H_{30}N_3O_4Cl$ 0.25H$_2$O Calculated: C, 63.93; H, 6.29; N, 8.60. Found: C, 64.06; H, 6.06; N, 8.53. $^1$H-NMR(CDCl$_3$) δ: 0.99 (6H, d, J=6.6 Hz), 1.45 (9H, s), 2.14–2.26 (1H, m), 4.06 (2H, d, J=6.9 Hz), 4.18 (2H, d, J=4.5 Hz), 4.92 (1H, bs), 5.89 (1H, bs), 6.22 (1H, bs), 7.24 (2H, d, J=8.4 Hz), 7.35 (1H, d, J=1.2 Hz), 7.50 (2H, d, J=8.4 Hz), 7.66 (1H, dd, J=1.2, 8.4 Hz), 8.35 (1H, d, J=8.4 Hz).

(5) 3-[[(Tert-butoxycarbonyl)amino]methyl]-4-(4-chlorophenyl)-2-isobutyl-1-oxo-1,2-dihydro-6-isoquinolinecarboxamide (0.48 g, 1 mmol) was dissolved in a solution of 4N hydrogen chloride in ethyl acetate (5 ml) and the mixture was stirred at room temperature for 1 h. The reaction mixture was concentrated under reduced pressure, and the precipitated crystals were recrystallized from methanol-diethyl ether to give 3-(aminomethyl)-4-(4-chlorophenyl)-2-isobutyl-1(2H)-isoquinolinone-6-carboxamide hydrochloride (0.41 g, 97.6%) as crystals.

Melting point 260–261° C. $^1$H-NMR(DMSO-d$_6$) δ: 0.92 (6H, d, J=6.6 Hz), 1.99–2.17 (1H, m), 3.85 (2H, s), 4.08 (2H, d, J=7.0 Hz), 7.44 (2H, d, J=8.0 Hz), 7.45 (1H, d, J=1.5 Hz), 7.60 (1H, bs), 7.64 (2H, d, J=8.0 Hz), 8.01 (1H, d, J=1.5, 8.4 Hz), 8.19 (1H, bs), 8.38 (1H, d, J=8.4 Hz), 8.56 (3H, bs).

Example 187

3-(Aminomethyl)-4-(4-chlorophenyl)-2-isobutyl-1 (2H)-isoquinolinone-6-carbonitrile hydrochloride (1) A solution of 3-[[(tert-butoxycarbonyl)amino]methyl]-4-(4-chlorophenyl)-2-isobutyl-1-oxo-1,2-dihydro-6-isoquinolinecarboxamide (Example 186 (4)) (0.48 g, 1 mmol) and cyanuric chloride (0.55 g, 3 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-(4-chlorophenyl)-6-cyano-1-oxo-1,2-dihydro-3-isoquinolinyl]methylcarbamate (0.37 g, 80.4%) as crystals.

Melting point 234–235° C. Elemental analysis $C_{26}H_{28}N_3O_3Cl$ Calculated: C, 67.02; H, 6.06; N, 9.02. Found: C, 67.10; H, 6.09; N, 9.07. $^1$H-NMR(CDCl$_3$) δ: 1.00 (6H, d, J=6.6 Hz), 1.43 (9H, s), 2.16–2.30 (1H, m), 4.08 (2H, d, J=7.4 Hz), 4.22 (2H, d, J=5.8 Hz), 4.44 (1H, bs), 7.16–7.23 (2H, m), 7.26 (1H, d, J=1.6 Hz), 7.51–7.58 (2H, m), 7.65 (1H, dd, J=1.6, 8.6 Hz), 8.55 (1H, d, J=8.6 Hz).

(2) Tert-butyl[4-(4-chlorophenyl)-6-cyano-1-oxo-1,2-dihydro-3-isoquinolinyl]methylcarbamate (0.28 g, 0.6 mmol) was dissolved in a solution of 4N hydrogen chloride in ethyl acetate (5 ml) and the mixture was stirred at room temperature for 1 h. The reaction mixture was concentrated under reduced pressure, and the precipitated crystals were recrystallized from methanol-diethyl ether to give 3-(aminomethyl)-4-(4-chlorophenyl)-2-isobutyl-1(2H)-isoquinolinone-6-carbonitrile hydrochloride (0.23 g, 95.8%) as crystals.

Melting point 280–281° C. Elemental analysis for $C_{21}H_{21}N_3OCl$ Calculated: C, 62.69; H, 5.26; N, 10.44. Found: 62.34; H, 5.31; N, 10.45. $^1$H-NMR(DMSO-d$_6$) δ: 0.93 (6H, d, J=6.6 Hz), 1.99–2.19 (1H, m), 3.87 (2H, s), 4.10 (2H, d, J=7.4 Hz), 7.32 (1H, d, J=1.4 Hz), 7.43–7.49 (2H, m), 7.64–7.68 (2H, m), 7.97 (1H, dd, J=1.4, 8.4 Hz), 8.47 (1H, d, J=8.4 Hz), 8.67 (3H, bs).

Example 188

(E)-3-[3-(Aminomethyl)-4-(4-chlorophenyl)-2-isobutyl-1-oxo-1,2-dihydro-6-isoquinolinyl]-2-propenamide hydrochloride (1) A suspension of tert-butyl[4-(4-chlorophenyl)-2-isobutyl-1-oxo-6-trifluoromethanesulfonyloxy-1,2-dihydro-3-isoquinolinyl]methylcarbamate (Example 186 (1)) (2.06 g, 3.5 mmol), butyl acrylate (0.76 ml, 5.3 mmol), sodium hydrogencarbonate (0.45 g, 5.3 mmol), tetrabutylammonium chloride (0.11 g, 0.4 mmol) and palladium acetate (0.09 g, 0.4 mmol) in N,N-dimethylformamide (20 ml) was stirred with heating at 100° C. under an argon atmosphere for 48 h. The reaction mixture was poured into water and extracted with ethyl acetate. After washing the extract with water, the extract was dried over anhydrous magnesium sulfate and concentrated under reduced pressure. The residue was purified by silica gel column chromatography to give butyl (E)-3-[3-[[(tert-butoxycarbonyl)amino]methyl]-4-(4-chlorophenyl)-2-isobutyl-1-oxo-1,2-dihydro-6-isoquinolinyl]-2-propenate (0.48 g, 23.8%) as crystals.

Melting point 149–150° C. Elemental analysis for $C_{32}H_{39}N_2O_5Cl$ 0.25H$_2$O Calculated: C, 67.24; H, 6.97; N, 4.90. Found: C, 67.22; H, 7.01; N, 4.93. $^1$H-NMR(CDCl$_3$) δ: 0.95 (3H, t, J=7.4 Hz), 1.00 (6H, d, J=6.4 Hz), 1.32–1.50 (11H, m), 1.59–1.71 (2H, m), 2.14–2.30 (1H, m), 4.07 (2H, d, J=7.6 Hz), 4.16–4.22 (4H, m), 4.43 (1H, bs), 6.40 (1H, d, J=16.2 Hz), 6.98 (1H, d, J=1.4 Hz), 7.20 (2H, d, J=8.4 Hz), 7.52 (2H, d, J=8.4 Hz), 7.55 (1H, d, J=16.2 Hz), 7.63 (1H, dd, J=1.4, 8.4 Hz), 8.45 (1H, d, J=8.4 Hz).

(2) To a solution of butyl (E)-3-[3-[[(tert-butoxycarbonyl)amino]methyl]-4-(4-chlorophenyl)-2-isobutyl-1-oxo-1,2-dihydro-6-isoquinolinyl]-2-propenate (0.41 g, 0.7 mmol) in tetrahydrofuran (10 ml)-methanol (10 ml) was added 1N sodium hydroxide (2 ml) and the mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give (E)-3-[3-[[(tert-butoxycarbonyl)amino] methyl]-4-(4-chlorophenyl)-2-isobutyl-1-oxo-1,2-dihydro-6-isoquinolinyl]-2-propenic acid (0.34 g, 91.9%) as crystals.

Melting point 147–149° C. Elemental analysis for C$_{28}$H$_{31}$N$_2$O$_5$Cl 0.25H$_2$O Calculated: C, 65.24; H, 6.16; N, 5.43. Found: C, 65.18; H, 6.15; N, 5.31. $^1$H-NMR(CDCl$_3$) δ: 0.99 (6H, d, J=6.4 Hz), 1.48 (9H, s), 2.08–2.28 (1H, m), 4.05 (2H, d, J=5.8 Hz), 4.14 (2H, s), 5.46 (1H, bs), 6.32 (1H, d, J=15.8 Hz), 6.82 (1H, s), 7.26–7.31 (2H, m), 7.42–7.56 (4H, m), 8.28 (1H, d, J=7.8 Hz).

(3) A solution of (E)-3-[3-[[(tert-butoxycarbonyl)amino]methyl]-4-(4-chlorophenyl)-2-isobutyl-1-oxo-1,2-dihydro-6-isoquinolinyl]-2-propenic acid (0.20 g, 0.4 mmol), 1-ethyl-3-(3-dimethylaminopropyl)carbodiimide hydrochloride (0.15 g, 0.8 mmol) and 1-hydroxybenzotriazole ammonium salt (0.12 g, 0.8 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was crystallized from ethyl acetate-n-hexane to give (E)-3-[3-[[(tert-butoxycarbonyl)amino]methyl]-4-(4-chlorophenyl)-2-isobutyl-1-oxo-1,2-dihydro-6-isoquinolinyl]-2-propenamide (0.18 g, 90.0%) as crystals.

Melting point 152–154° C. Elemental analysis for C$_{28}$H$_{32}$N$_3$O$_4$Cl 0.25H$_2$O Calculated: C, 65.36; H, 6.37; N, 8.17. Found: C, 65.30; H, 6.27; N, 7.99. $^1$H-NMR(CDCl$_3$) δ: 0.99 (6H, d, J=6.6 Hz), 1.45 (9H, s), 2.12–2.28 (1H, m), 4.05 (2H, d, J=7.2 Hz), 4.18 (2H, d, J=4.6 Hz), 4.95 (1H, bs), 5.72 (1H, bs), 5.85 (1H, bs), 6.37 (1H, d, J=15.8 Hz), 6.91 (1H, d, J=1.2 Hz), 7.24 (2H, d, J=8.8 Hz), 7.41–7.54 (4H, m), 8.28 (1H, d, J=8.4 Hz).

(4) A solution of (E)-3-[3-[[(tert-butoxycarbonyl)amino]methyl]-4-(4-chlorophenyl)-2-isobutyl-1-oxo-1,2-dihydro-6-isoquinolinyl]-2-propenamide (0.15 g, 0.3 mmol) was dissolved in a solution of 4N hydrogen chloride in ethyl acetate (5 ml) and the mixture was stirred at room temperature for 1 h. The reaction mixture was concentrated under reduced pressure, and the residue was crystallized from ethyl acetate to give (E)-3-[3-(aminomethyl)-4-(4-chlorophenyl)-2-isobutyl-1-oxo-1,2-dihydro-6-isoquinolinyl]-2-propenamide hydrochloride (0.12 g, 92.3%) as crystals.

Melting point 261–263° C. Elemental analysis for C$_{23}$H$_{25}$N$_3$O$_2$Cl$_2$ 0.75H$_2$O Calculated: C, 60.07; H, 5.81; N, 9.14. Found: C, 59.78; H, 6.14; N, 8.75. $^1$H-NMR(DMSO-d$_6$) δ: 0.92 (6H, d, J=6.6 Hz), 1.91–2.21 (1H, m), 3.85 (2H, s), 4.06 (2H, d, J=7.4 Hz), 6.58 (1H, d, J=15.8 Hz), 7.02 (1H, s), 7.19 (1H, bs), 7.34–7.47 (3H, m), 7.62–7.67 (3H, m), 7.79 (1H, d, J=8.0 Hz,) 8.35 (1H, d, J=8.0 Hz), 8.60 (3H, bs).

Example 189

3-(Aminomethyl)-4-butoxy-2-isobutyl-6-(4-methyl-1,3-thiazol-2-yl)-1(2H)-isoquinolinone dihydroxhloride (1) To a suspension of 3-[[(tert-butoxycarbonyl)amino]methyl]-4-butoxy-2-isobutyl-1-oxo-1,2-dihydro-6-isoquinolinecarboxamide (0.44 g, 1 mmol) in toluene (20 ml) was added Lawesson's reagent (0.24 g, 0.6 mmol), and the mixture was refluxed under heating for 1 h. The reaction mixture was purified by silica gel column chromatography to give tert-butyl[6-(aminothiocarbonyl)-4-butoxy-2-isobutyl-1-oxo-1,2-dihydro-3-isoquinolinyl]methylcarbamate (0.18 g, 39.1%) as crystals.

Melting point 189–190° C. Elemental analysis for C$_{24}$H$_{35}$N$_3$O$_4$S Calculated: C, 62.44; H, 7.64; N, 9.10. Found: C, 62.38; H, 7.51; N, 8.89. $^1$H-NMR(CDCl$_3$) δ: 0.93 (6H, d, J=6.6 Hz), 1.02 (3H, t, J=7.3 Hz), 1.50–1.64 (11H, m), 1.80–1.93 (2H, m), 2.04–2.18 (1H, m), 3.83 (2H, t, J=6.8 Hz), 3.96 (2H, d, J=7.4 Hz), 4.48 (2H, d, J=5.6 Hz), 5.37 (1H, bs), 7.67 (1H, d, J=8.3 Hz), 7.83–7.90 (2H, m), 8.05 (1H, d, J=8.3 Hz), 8.31 (1H, bs).

(2) A suspension of tert-butyl[6-(aminothiocarbonyl)-4-butoxy-2-isobutyl-1-oxo-1,2-dihydro-3-isoquinolinyl]methylcarbamate (0.46 g, 1 mmol), bromoacetone (0.20 g, 1.5 mmol) and sodium acetate (0.12 g, 1.5 mmol) in ethanol (10 ml) was refluxed under heating for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-2-isobutyl-6-(4-methyl-1,3-thiazol-2-yl)-1-oxo-1,2-dihydro-3-isoquinolinyl]methylcarbamate (0.36 g, 73.5%) as an amorphous.

Elemental analysis for C$_{27}$H$_{37}$N$_3$O$_4$S Calculated: C, 64.90; H, 7.46; N, 8.41. Found: C, 64.63; H, 7.58; N, 8.26. $^1$H-NMR(CDCl$_3$) δ: 0.98 (6H, d, J=7.0 Hz), 1.07 (3H, t, J=7.3 Hz), 1.47 (9H, s), 1.56–1.75 (2H, m), 1.84–1.98 (2H, m), 2.12–2.26 (1H, m), 2.55 (3H, d, J=0.8 Hz), 3.92 (2H, t, J=6.4 Hz), 4.00 (2H, d, J=7.4 Hz), 4.54 (2H, d, J=5.8 Hz), 4.78 (1H, bs), 6.98 (1H, q, J=0.8 Hz), 8.08 (1H, dd, J=1.8, 8.4 Hz), 8.22 (1H, d, J=1.8 Hz), 8.46 (1H, d, J=8.4 Hz).

(3) Tert-butyl[4-butoxy-2-isobutyl-6-(4-methyl-1,3-thiazol-2-yl)-1-oxo-1,2-dihydro-3-isoquinolinyl]methylcarbamate (0.30 g, 0.6 mmol) was dissolved in a solution of 4N hydrogen chloride in ethyl acetate (5 ml) and the mixture was stirred at room temperature for 1 h. The reaction mixture was concentrated under reduced pressure, and the precipitated crystals were recrystallized from methanol-diisopropyl ether to give 3-(aminomethyl)-4-butoxy-2-isobutyl-6-(4-methyl-1,3-thiazol-2-yl)-1(2H)-isoquinolinone dihydrochloride (0.27 g, 96.4%) as crystals.

Melting point 201–202° C. $^1$H-NMR(DMSO-d$_6$) δ: 0.90 (6H, d, J=6.6 Hz), 1.04 (3H, t, J=7.1 Hz), 1.56–1.74 (2H, m), 1.82–2.12 (3H, m), 2.48 (3H, d, J=0.6 Hz), 3.98–4.02 (4H, m), 4.21 (2H, d, J=5.2 Hz), 7.51 (1H, q, J=0.6 Hz), 8.13 (1H, dd, J=1.6, 8.4 Hz), 8.25 (1H, d, J=1.6 Hz), 8.37 (1H, d, J=8.4 Hz), 8.76 (3H, bs).

Example 190

Ethyl 2-[3-(aminomethyl)-4-butoxy-2-isobutyl-1-oxo-1,2-dihydro-6-isoquinolinyl]-1,3-thiazole-4-carboxylate hydrochloride (1) Tert-butyl[6-(aminothiocarbonyl)-4-butoxy-2-isobutyl-1-oxo-1,2-dihydro-3-isoquinolinyl]methylcarbamate (Example 189 (1)) (1.38 g, 3 mmol) was dissolved in a solution of 4N hydrogen chloride in ethyl acetate (10 ml) and the mixture was stirred at room temperature for 1 h. The reaction mixture was concentrated under reduced pressure and the residue was suspended in tetrahydrofuran (20 ml). To the obtained mixture were added triethylamine (0.84 ml, 6 mmol) and 9-fluorenylmethylchloroformate (1.16 g, 4.5 mmol) and the mixture was stirred at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give 9H-fluoren-9-ylmethyl [6-(aminocarbothioyl)-4-butoxy-2-isobutyl-1-oxo-1,2-dihydro-3-isoquinolinyl]methylcarbamate (1.52 g, 86.9%) as an amorphous.

¹H-NMR(CDCl₃) δ: 0.94–1.00 (9H, m), 1.47–1.59 (2H, m), 1.74–1.83 (2H, m), 2.07–2.18 (1H, m), 3.77 (2H, t, J=6.3 Hz), 3.98 (2H, d, J=6.6 Hz), 4.25 (1H, t, J=6.6 Hz), 4.51–4.53 (4H, m), 5.79 (1H, bs), 7.26–7.41 (4H, m), 7.63–7.66 (3H, m), 7.75 (2H, d, J=7.2 Hz), 7.86 (1H, bs), 7.93 (1H, s), 8.00 (1H,bs), 8.12 (1H, d, J=8.1 Hz).

(2) A solution of 9H-fluoren-9-ylmethyl[6-(aminocarbothioyl)-4-butoxy-2-isobutyl-1-oxo-1,2-dihydro-3-isoquinolinyl]methylcarbamate (0.29 g, 0.5 mmol) and ethyl bromopyruvate (0.19 g, 1 mmol) in ethanol (10 ml) was refluxed under heating for 1 h. The reaction mixture was poured into water and extracted with ethyl acetate. The extract was washed with brine, dried over anhydrous magnesium sulfate and concentrated under reduced pressure. The residue was crystallized from ethyl acetate-diisopropyl ether to give ethyl 2-[4-butoxy-3-[[[(9H-fluoren-9-ylmethoxy)carbony]amino]methyl]-2-isobutyl-1-oxo-1,2-dihydro-6-isoquinolinyl]-1,3-thiazole-4-carboxylate (0.30 g, 90.9%) as crystals.

Melting point 203–203.5° C. Elemental analysis for C₃₉H₄₁N₃O₆S Calculated: C, 68.90; H, 6.08; N, 6.18. Found: C, 68.64; H, 6.10; N, 6.06. ¹H-NMR(CDCl₃) δ: 0.97 (6H, d, J=6.6 Hz), 1.07 (3H, t, J=7.1 Hz), 1.45 (3H, t, J=7.0 Hz), 1.56–1.75 (2H, m), 1.81–1.98 (2H, m), 2.06–2.24 (1H, m), 3.94 (2H, t, J=6.4 Hz), 4.05 (2H, d, J=7.0 Hz), 4.22 (1H, t, J=6.6 Hz), 4.47 (2H, q, J=7.0 Hz), 4.49 (2H, d, J=6.6 Hz), 4.59 (2H, d, J=5.4 Hz), 5.23 (1H, bs), 7.29–7.43 (4H, m), 7.59 (2H, d, J=7.3 Hz), 8.14 (1H, dd, J=1.6, 8.4 Hz), 8.24–8.26 (2H, m), 8.47 (1H, d, J=8.4 Hz).

(3) To a solution of ethyl 2-[4-butoxy-3-[[[(9H-fluoren-9-ylmethoxy)carbony]amino]ethyl]-2-isobutyl-1-oxo-1,2-dihydro-6-isoquinolinyl]-1,3-thiazole-4-carboxylate (1.70 g, 2.5 mmol) in N,N-dimethylformamide (25 ml)-tetrahydrofuran (25 ml) was added pyrrolidine (2 ml), and the mixture was stirred at room temperature for 1 h. The reaction mixture was poured into water and extracted with ethyl acetate. The extract was washed with brine, dried over anhydrous magnesium sulfate and concentrated under reduced pressure. The residue was dissolved in tetrahydrofuran (20 ml) and di-t-butyl dicarbonate (0.89 ml, 4 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl 2-[4-butoxy-3-[[(tert-butoxycarbonyl)amino]methyl]-2-isobutyl-1-oxo-1,2-dihydro-6-isoquinolinyl]-1,3-thiazole-4-carboxylate (1.21 g, 87.1%) as crystals.

Melting point 172–172.5° C. Elemental analysis for C₂₉H₃₉N₃O₆S Calculated: C, 62.45; H, 7.05; N, 7.53. Found: C, 62.50; H, 7.04; N, 7.53. ¹H-NMR(CDCl₃) δ: 0.98 (6H, d, J=6.6 Hz), 1.07 (3H, t, J=7.3 Hz), 1.45 (3H, t, J=7.2 Hz), 1.47 (9H, s), 1.62–1.78 (2H, m), 1.85–1.99 (2H, m), 2.12–2.26 (1H, m), 3.93 (2H, t, J=6.4 Hz), 4.01 (2H, d, J=7.2 Hz), 4.47 (2H, q, J=7.2 Hz), 4.54 (2H, d, J=6.6 Hz), 4.77 (1H, bs), 8.16 (1H, dd, J=1.8, 8.4 Hz), 8.25 (1H, s), 8.28 (1H, d, J=1.8 Hz), 8.49 (1H, d, J=8.4 Hz).

(4) Ethyl 2-[4-butoxy-3-[[(tert-butoxycarbonyl)amino]methyl]-2-isobutyl-1-oxo-1,2-dihydro-6-isoquinolinyl]-1,3-thiazole-4-carboxylate (0.17 g, 0.3 mmol) was dissolved in a solution of 4N hydrogen chloride in ethyl acetate (5 ml), and the mixture was stirred at room temperature for 1 h. The reaction mixture was concentrated under reduced pressure, and the precipitated crystals were recrystallized from ethyl acetate-diisopropyl ether to give ethyl 2-[3-(aminomethyl)-4-butoxy-2-isobutyl-1-oxo-1,2-dihydro-6isoquinolinyl]-1,3-thiazole-4-carboxylate hydrochloride (0.13 g, 92.9%) as crystals.

Melting point 224–226° C. Elemental analysis for C₂₄H₃₂N₃O₄ClS H₂O Calculated: C, 56.29; H, 6.69; N, 8.21. Found: C, 56.00; H, 6.43; N, 7.99. ¹H-NMR(DMSO-d₆) δ: 0.91 (6H, d, J=6.6 Hz),1.05 (3H, t, J=7.1 Hz), 1.36 (3H, t, J=7.2 Hz), 1.57–1.76 (2H, m), 1.83–2.16 (3H, m), 3.98–4.06 (4H, m), 4.22 (2H, d, J=4.6 Hz), 4.37 (2H, q, J=7.2 Hz), 8.20 (1H, dd J=1.4, 8.4 Hz), 8.31 (1H, d, J=1.4 Hz), 8.42 (1H, d, J=8.4 Hz), 8.66 (3H, bs), 8.73 (1H, s).

Example 191

2-[3-(Aminomethyl)-4-butoxy-2-isobutyl-1-oxo-1,2-dihydro-6-isoquinolinyl]-1,3-thiazole-4-carbocylic acid hydrochloride (1) To a solution of ethyl 2-[4-butoxy-3-[[(tert-butoxycarbonyl)amino]methyl]-2-isobutyl-1-oxo-1,2-dihydro-6-isoquinolinyl]-1,3-thiazole-4-carboxylate (1.12 g, 2 mmol) in tetrahydrofuran (10 ml)-ethanol (5 ml) was added 1N sodium hydroxide (4 ml) and the mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 2-[4-butoxy-3-[[(tert-butoxycarbonyl)amino]methyl]-2-isobutyl-1-oxo-1,2-dihydro-6-isoquinolinyl]-1,3-thiazole-4-carboxylic acid (0.97 g, 92.4%) as crystals.

Melting point 195–196° C. Elemental analysis for C₂₇H₃₅N₃O₆S Calculated: C, 61.23; H, 6.66; N, 7.93. Found: C, 61.10; H, 6.71; N, 7.65. ¹H-NMR(CDCl₃) δ: 0.98 (6H, d, J=7.0 Hz), 1.08 (3H, t, J=7.4 Hz), 1.48 (9H, s), 1.57–1.76 (2H, m), 1.85–1.99 (2H, m), 2.13–2.26 (1H, m), 3.93 (2H, t, J=6.2 Hz), 4.02 (2H, d, J=7.2 Hz), 4.56 (2H, d, J=5.6 Hz), 4.92 (1H, bs), 8.11 (1H, dd, J=1.8, 8.4 Hz), 8.24 (1H, d, J=1.8 Hz), 8.36 (1H, s), 8.49 (1H, d, J=8.4 Hz).

(2) 2-[4-Butoxy-3-[[(tert-butoxycarbonyl)amino]methyl]-2-isobutyl-1-oxo-1,2-dihydro-6-isoquinolinyl]-1,3-thiazole-4-carboxylic acid (0.16 g, 0.3 mmol) was dissolved in a solution of 4N hydrogen chloride in ethyl acetate (5 ml) and the mixture was stirred at room temperature for 1 h. The reaction mixture was concentrated under reduced pressure and the residue was crystallized from ethyl acetate to give 2-[3-(aminomethyl)-4-butoxy-2-isobutyl-1-oxo-1,2-dihydro-6-isoquinolinyl]-1,3-thiazole-4-carboxylic acid hydrochloride (0.13 g, 92.9%) as crystals.

Melting point 244–246° C. Elemental analysis for C₂₂H₂₈N₃O₄ClS 0.5H₂O Calculated: C, 55.63; H, 6.15; N, 8.85. Found: C, 55.45; H, 6.49; N, 8.51. ¹H-NMR(DMSO-d₆) δ: 0.91 (6H, d, J=6.6 Hz), 1.04 (3H, t, J=7.2 Hz), 1.60–1.72 (2H, m), 1.84–1.93 (2H, m), 2.00–2.10 (1H, m), 3.99–4.02 (4H, m), 4.22 (2H, s), 8.21 (1H, dd, J=1.5, 8.4 Hz), 8.30 (1H, d, J=1.5 Hz), 8.42 (1H, d, J=8.4 Hz), 8.63 (3H, bs), 8.66 (1H, s).

Example 192

2-[3-(Aminomethyl)-4-butoxy-2-isobutyl-1-oxo-1,2-dihydro-6-isoquinolinyl]-1,3-thiazole-4-carboxamide hydrochloride (1) A solution of 2-[4-butoxy-3-[[(tert-butoxycarbonyl)amino]methyl]-2-isobutyl-1-oxo-1,2-dihydro- 6-isoquinolinyl]-1,3-thiazole-4-carboxylic acid (0.79 g, 1.5 mmol), 1-ethyl-3-(3-dimethylaminopropyl)carbodiimide hydrochloride (0.58 g, 3 mmol) and 1-hydroxybenzotriazole ammonium salt (0.46 g, 3 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give tert-butyl [6-[4-(aminocarbonyl)-1,3-thiazol-2-yl]-4-butoxy-2-isobutyl-1-oxo-1,2-dihydro-3-isoquinolinyl]methylcarbamate (0.74 g, 93.7%) as crystals.

Melting point 195–196° C. Elemental analysis for $C_{27}H_{36}N_4O_4S$ 0.5$H_2O$ Calculated: C, 60.31; H, 6.94; N, 10.42. Found: C, 60.62; H, 7.08; N, 10.19. $^1$H-NMR(CDCl$_3$) δ: 0.98 (6H, d, J=6.8 Hz), 1.07 (3H, t, J=7.2 Hz), 1.48 (9H, s), 1.57–1.98 (4H, m), 2.11–2.28 (1H, m), 3.92 (2H, t, J=6.2 Hz), 4.02 (2H, d, J=7.4 Hz), 4.55 (2H, d, J=5.4 Hz), 4.91 (1H, bs), 5.89 (1H, bs), 7.29 (1H, bs), 8.04–8.09 (1H, m), 8.24–8.25 (1H, m), 8.46–8.51 (2H, m).

(2) Tert-butyl[6-[4-(aminocarbonyl)-1,3-thiazol-2-yl]-4-butoxy-2-isobutyl-1-oxo-1,2-dihydro-3-isoquinolinyl]-methylcarbamate (0.32 g, 0.6 mmol) was dissolve in a solution of 4N hydrogen chloride in ethyl acetate (5 ml) and the mixture was stirred at room temperature for 1 h. The reaction mixture was concentrated under reduced pressure and the residue was crystallized from ethyl acetate to give 2-[3-(aminomethyl)-4-butoxy-2-isobutyl-1-oxo-1,2-dihydro-6-isoquinolinyl]-1,3-thiazole-4-carboxamide hydrochloride (0.26 g, 92.6%) as crystals.

Melting point 274–276° C. Elemental analysis for $C_{22}H_{29}N_4O_3ClS$ 0.5$H_2O$ Calculated: C, 55.74; H, 6.38; N, 11.82. Found: C, 56.13; H, 6.33; N, 11.86. $^1$H-NMR (DMSO-d$_6$) δ: 0.91 (6H, d, J=6.6 Hz), 1.04 (3H, t, J=7.1 Hz), 1.56–1.75 (2H, m), 1.84–2.18 (3H, m), 3.99–4.05 (4H, m), 4.22 (2H, d, J=4.4 Hz), 8.28 (1H, d, J=1.6 Hz), 8.30 (1H, dd, J=1.6, 9.2 Hz), 8.41 (1H, d, J=9.2 Hz), 8.46 (1H, s), 8.71 (3H, bs).

Example 193

2-[3-(Aminomethyl)-4-butoxy-2-isobutyl-1-oxo-1,2-dihydro-6-isoquinolinyl]-1,3-thiazole-4-carbonitrile hydrochloride (1) A solution of tert-butyl[6-[4-(aminocarbonyl)-1,3-thiazol-2-yl]-4-butoxy-2-isobutyl-1-oxo-1,2-dihydro-3-isoquinolinyl]methylcarbamate (0.32 g, 0.6 mmol) and cyanuric chloride (0.33 g, 1.8 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-6-(4-cyano-1,3-thiazol-2-yl)-2-isobutyl-1-oxo-1,2-dihydro-3-isoquinolinyl]methylcarbamate (0.28 g, 93.3%) as crystals.

Melting point 160–161° C. Elemental analysis for $C_{27}H_{34}N_4O_4S$ Calculated: C, 63.5; H, 6.71; N, 10.97. Found: C, 63.47; H, 6.69; N, 10.99. $^1$H-NMR(CDCl$_3$) δ: 0.98 (6H, d, J=6.9 Hz), 1.08 (3H, t, J=7.5 Hz)), 1.48 (9H, s), 1.60–1.72 (2H, m), 1.87–1.97 (2H, m), 2.12–2.24 (1H, m), 3.92 (2H, t, J=6.4 Hz), 4.01 (2H, d, J=7.5 Hz), 4.55 (2H, d, J=5.4 Hz), 4.86 (1H, bs), 8.01 (1H, dd, J=1.8, 8.2 Hz), 8.08 (1H, s), 8.29 (1H, d, J=1.8 Hz), 8.49 (1H, d, J=8.2 Hz).

(2) Tert-butyl[4-butoxy-6-(4-cyano-1,3-thiazol-2-yl)-2-isobutyl-1-oxo-1,2-dihydro-3-isoquinolinyl]methylcarbamate (0.20 g, 0.4 mmol) was dissolved in a solution of 4N hydrogen chloride in ethyl acetate (5 ml) and the mixture was stirred at room temperature for 1 h. The reaction mixture was concentrated under reduced pressure, and the residue was crystallized from ethyl acetate to give 2-[3-(aminomethyl)-4-butoxy-2-isobutyl-1-oxo-1,2-dihydro-6-isoquinolinyl]-1,3-thiazole-4-carbonitrile hydrochloride (0.17 g, 94.4%) as crystals.

Melting point 167–169° C. Elemental analysis for $C_{22}H_{27}N_4O_2ClS$ $H_2O$ Calculated: C, 56.82; H, 6.29; N, 12.05. Found: C, 56.92; H; 6.29; N, 11.95. $^1$H-NMR (DMSO-d$_6$) δ: 0.91 (6H, d, J=6.6 Hz), 1.05 (3H, t, J=7.2 Hz), 1.56–1.74 (2H, m), 1.82–2.18 (3H, m), 3.98–4.05 (4H, m), 4.22 (2H, s), 8.20 (1H, d, J=8.4 Hz), 8.30 (1H, s), 8.42 (1H, d, J=8.4 Hz) 8.70 (3H, bs), 9.06 (1H, s).

Example 194

3-(Aminomethyl)-2-isobutyl-6-(4-methyl-1,3-thiazol-2-yl)-4-phenyl-1(2H)-isoquinolinone (1) To a suspension of 3-[[(tert-butoxycarbonyl)amino]methyl]-2-isobutyl-4-phenyl-1-oxo-1,2-dihydro-6-isoquinolinecarboxamide (4.05 g, 9 mmol) in toluene (50 ml) was added Lawesson's reagent (2.19 g, 5.4 mmol), and the mixture was refluxed under heating for 1 h. The reaction mixture was purified by silica gel column chromatography to give tert-butyl[6-(aminothiocarbonyl)-2-isobutyl-1-oxo-4-phenyl-1,2-dihydro-3-isoquinolinyl)methylcarbamate (3.64 g, 86.9%) as crystals.

Melting point 228–229° C. Elemental analysis for $C_{26}H_{31}N_3O_3S$ Calculated: C, 67.07; H, 6.71; N, 9.02. Found: C, 66.88; H, 6.66; N, 8.85. $^1$H-NMR(CDCl$_3$) δ: 0.98 (6H, d, J=6.6 Hz), 1.44 (9H, s), 2.12–2.29 (1H, m), 4.07 (2H, d, J=6.9 Hz), 4.20 (2H, d, J=5.1 Hz), 4.79 (1H, bs), 7.23–7.27 (2H, m), 7.33 (1H, d, J=1.6 Hz), 7.37 (1H, bs), 7.46–7.56 (3H, m), 7.74 (1H, bs), 7.76 (1H, dd, J=1.6, 8.6 Hz.), 8.29 (1H, d, J=8.6 Hz).

(2) Tert-butyl[6-(aminothiocarbonyl)-2-isobutyl-1-oxo-4-phenyl-1,2-dihydro-3-isoquinolinyl]methylcarbamate (3.26 g, 7 mmol) was dissolved in a solution of 4N hydrogen chloride in ethyl acetate (20 ml) and the mixture was stirred at room temperature for 1 h. The reaction mixture was concentrated under reduced pressure and the residue was suspended in tetrahydrofuran (20 ml). To the obtained mixture were added triethylamine (2.0 ml, 14 mmol) and 9-fluorenylmethyl chloroformate (2.72 g, 10.5 mmol) and the mixture was stirred with heating at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give 9H-fluoren-9-ylmethyl[6-(aminocarbothioyl)-2-isobutyl-1-oxo-4-phenyl-1,2-dihydro-3-isoquinolinyl]methylcarbamate (3.21 g, 78.1%) as an amorphous.

$^1$H-NMR(CDCl$_3$) δ: 0.97 (6H, d, J=6.6 Hz), 2.07–2.24 (1H, m), 4.08 (2H, d, J=7.4 Hz), 4.19 (1H, t, J=6.8 Hz), 4.25 (2H, d, J=2.6 Hz), 4.41 (2H, d, J=6.8 Hz), 5.35 (1H, bs), 7.21–7.60 (13H, m), 7.72–7.76 (3H, m), 8.26 (1H, d, J=8.6 Hz).

(3) A suspension of 9H-fluoren-9-ylmethyl[6-(aminocarbothioyl)-2-isobutyl-1-oxo-4-phenyl-1,2-dihydro-3-isoquinolinyl]methylcarbamate (0.47 g, 0.8 mmol) and bromoacetone (0.22 g, 1.6 mmol) in ethanol (10 ml) was refluxed under heating for 1 h. The reaction mixture was poured into water and extracted with ethyl. acetate. The extract was washed with brine, dried over anhydrous magnesium sulfate and concentrated under reduced pressure. The residue was purified by silica gel column chromatography to give 9H-fluoren-9-ylmethyl [2-isobutyl-6-(4-methyl-1,3-thiazol-2-yl)-1-oxo-4phenyl-1,2-dihydro-3-isoquinolinyl]methylcarbamate (0.41 g, 82.0%) as an amorphous.

Elemental analysis for $C_{39}H_{35}N_3O_3S$ $0.25H_2O$ Calculated: C, 74.32; H, 5.68; N, 6.67. Found: C, 74.36; H, 5.44; N, 6.62. $^1$H-NMR(CDCl$_3$) δ: 1.00 (6H, d, J=6.8 Hz), 2.12–2.29 (1H, m), 2.44 (3H, d, J=0.8 Hz), 4.06 (2H, d, J=7.2 Hz), 4.19 (2H, t, J=6.6 Hz), 4.27 (2H, d, J=5.0 Hz), 4.44 (2H, d, J=6.6 Hz), 4.86 (1H, bs), 6.86 (1H, q, J=0.8 Hz), 7.26–7.44 (7H, m), 7.52–7.57 (5H, m), 7.75 (2H, d, J=7.0 Hz), 8.02 (1H, dd, J=1.8, 8.4 Hz), 8.50 (1H, d, J=8.4 Hz).

(4) To a solution of 9H-fluoren-9-ylmethyl[2-isobutyl-6-(4-methyl-1,3-thiazol-2-yl)-1-oxo-4-phenyl-1,2-dihydro-3-isoquinolinyl]methylcarbamate (0.38 g, 0.6 mmol) in N,N-dimethylformamide (10 ml) was added pyrrolidine (0.5 ml) and the mixture was stirred at room temperature for 1 h. The reaction mixture was poured into water and extracted with ethyl acetate. The residue was purified by silica gel column chromatography to give 3-(aminomethyl)-2-isobutyl-6-(4-methyl-1,3-thiazol-2-yl)-4-phenyl-1(2H)-isoquinolinone (0.13 g, 54.2%) as crystals.

Melting point 162–163° C. Elemental analysis for $C_{24}H_{24}N_3OS$ $0.25H_2O$ Calculated: C, 70.64; H, 6.30; N, 10.30. Found: C, 70.96; H, 6.38; N, 10.16. $^1$H-NMR(CDCl$_3$) δ: 1.02 (6H, d, J=7.0 Hz), 1.35 (2H, bs), 2.13–2.35 (1H, m), 2.45 (3H, d, J=1.2 Hz), 3.69 (2H, s), 4.23 (2H, d, J=7.2 Hz), 6.85 (1H, q, J=1.2 Hz), 7.30–7.35 (2H, m), 7.43 (1H, d, J=1.4 Hz), 7.48–7.59 (3H, m), 8.03 (1H, dd, J=1.4, 8.4 Hz), 8.52 (1H, d, J=8.4 Hz).

Example 195

Ethyl 2-[3-(aminomethyl)-2-isobutyl-1-oxo-4-phenyl-1,2-dihydro-6-isoquinolinyl]-1,3-thiazole-4-carboxylate hydrochloride (1) A solution of 9H-fluoren-9-ylmethyl[6-(aminocarbothioyl)-2-isobutyl-1-oxo-4-phenyl-1,2-dihydro-3-isoquinolinyl]methylcarbamate (Example 194(2)) (2.35 g, 4 mmol) and ethyl bromopyruvate (1.56 g, 8 mmol) in ethanol (20 ml) was refluxed under heating for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl 2-[3-[[[(9H-fluoren-9-ylmethoxy)carbonyl]amino]methyl]-2-isobutyl-1-oxo-4-phenyl-1,2-dihydro-6-isoquinolinyl]-1,3-thiazole-4-carboxylate (1.92 g, 70.3%) as crystals.

Melting point 151–152° C. Elemental analysis for $C_{41}H_{37}N_3O_5S$ Calculated: C, 72.01; H, 5.45; N, 6.14. Found: C, 71.79; H, 5.59; N, 6.02. $^1$H-NMR(CDCl$_3$) δ: 1.00 (6H, d, J=6.6 Hz), 1.41 (3H, t, J=7.2 Hz), 2.16–2.27 (1H, m), 4.07 (2H, d, J=5.7 Hz), 4.19 (1H, t, J=6.6 Hz), 4.28 (2H, d, J=5.4 Hz), 4.38–4.45 (4H, m), 4.86 (1H, bs), 7.28–7.45 (7H, m), 7.75 (2H, d, J=7.1 Hz), 8.11 (1H, s), 8.13 (1H, dd, J=1.8, 8.4 Hz), 8.53 (1H, d, J=8.4 Hz).

(2) To a solution of ethyl 2-[3-[[[(9H-fluoren-9-ylmethoxy)carbonyl]amino]methyl]-2-isobutyl-1-oxo-4-phenyl-1,2-dihydro-6-isoquinolinyl]-1,3-thiazole-4-carboxylate (1.84 g, 2.7 mmol) in N,N-dimethylformamide (20 ml) was added pyrrolidine (1 ml) and the mixture was stirred at room temperature for 1 h. The reaction mixture was poured into water and extracted with ethyl acetate. The extract was washed with brine, dried over anhydrous magnesium sulfate and concentrated under reduced pressure. The residue was dissolved in tetrahydrofuran (20 ml) and di-t-butyl dicarbonate (0.9 ml, 4 mmol) was added thereto. The obtained mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl 2-[3-[[(tert-butoxycarbonyl)amino]methyl]-2-isobutyl-1-oxo-4-phenyl-1,2-dihydro-6-isoquinolinyl]-1,3-thiazole-4-carboxylate (1.41 g, 93.4%) as crystals.

Melting point 170.5–171° C. Elemental analysis for $C_{29}H_{39}N_3O_6S$ Calculated: C, 62.45; H, 7.05; N, 7.53. Found: C, 62.50; H, 7.04; N, 7.53. $^1$H-NMR(CDCl$_3$) δ: 1.02 (6H, d, J=6.6 Hz), 1.41 (3H, t, J=7.0 Hz), 1.44 (9H, s), 2.11–2.38 (1H, m), 4.19 (2H, d, J=7.2 Hz), 4.23 (2H, d, J=5.4 Hz), 4.42(2H, q, J=7.0 Hz), 4.60 (1H, bs) 7.28–7.33 (2H, m), 7.45 (1H, d, J=1.8 Hz), 7.51–7.61 (3H, m), 8.11 (1H, s), 8.13 (1H, dd, J=1.8, 8.4 Hz), 8.52 (1H, d, J=8.4 Hz).

(3) Ethyl 2-[3-[[(tert-butoxycarbonyl)amino]methyl]-2-isobutyl-1-oxo-4-phenyl-1,2-dihydro-6-isoquinolinyl]-1,3-thiazole-4-carboxylate (0.17 g, 0.3 mmol) was dissolved in a solution of 4N hydrogen chloride in ethyl acetate (5 ml) and the mixture was stirred at room temperature for 1 h. The reaction mixture was concentrated under reduced pressure, and the precipitated crystals were recrystallized from methanol-diisopropyl ether to give ethyl 2-[3-(aminomethyl)-2-isobutyl-1-oxo-4-phenyl-1,2-dihydro-6-isoquinolinyl]-1,3-thiazole-4-carboxylate hydrochloride (0.13 g, 92.9%) as crystals.

Melting point 265–267° C. Elemental analysis for $C_{26}H_{28}N_3O_3ClS$ $0.5H_2O$ Calculated: C, 61.59; H, 5.76; N, 8.29. Found: C, 61.75; H, 5.77; N, 8.40. $^1$H-NMR(DMSO-d$_6$) δ: 0.94 (6H, d, J=6.6 Hz), 1.30 (3H, t, J=7.2 Hz), 3.91 (2H, s), 4.11 (2H, d, J=7.2 Hz), 4.30 (2H, q, J=7.2 Hz), 7.46–7.50 (3H, m), 7.60–7.72 (3H, m), 8.15 (1H, dd, J=1.4, 8.4 Hz), 8.48 (1H, d, J=8.4 Hz), 8.59 (1H, s), 8.40 (3H, bs).

Example 196

2-[3-(Aminomethyl)-2-isobutyl-1-oxo-4-phenyl-1,2-dihydro-6-isoquinolinyl]-1,3-thiazole-4-carboxylic acid hydrochloride (1) To a solution of ethyl 2-[3-[[(tert-butoxycarbonyl)amino]methyl]-2-isobutyl-1-oxo-4-phenyl-1,2-dihydro-6-isoquinolinyl]-1,3-thiazole-4-carboxylate (1.12 g, 2 mmol) in tetrahydrofuran (10 ml)-ethanol (10 ml) was added 1N sodium hydroxide (4 ml) and the mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The obtained crystals were recrystallized from ethyl acetate-diisopropyl ether to give 2-[3-[[(tert-butoxycarbonyl)amino]methyl]-2-isobutyl-1-oxo-4-phenyl-1,2-dihydro-6-isoquinolinyl]-1,3-thiazole-4-carboxylic acid (1.02 g, 96.2%) as crystals.

Melting point 213–214° C. Elemental analysis for $C_{29}H_{31}N_3O_5S$ Calculated: C, 65.27; H, 5.86; N, 7.87. Found: C, 65.01; H, 5.65; N, 7.65. $^1$H-NMR(CDCl$_3$) δ: 1.02 (6H, d, J=6.6 Hz), 1.45 (1H, s), 2.18–2.34 (1H, m), 4.10 (2H, d, J=7.4 Hz), 4.23 (2H, d, J=5.2 Hz), 4.88 (1H, bs), 6.40 (1H, bs), 7.33–7.41 (3H, m), 7.47–7.58 (3H, m), 8.03 (1H, dd, J=1.8, 8.4 Hz), 8.21 (1H, s), 8.49 (1H, d, J=8.4 Hz).

(2) 2-[3-[[(Tert-butoxycarbonyl)amino]methyl]-2-isobutyl-1-oxo-4-phenyl-1,2-dihydro-6-isoquinolinyl]-1,3-thiazole-4-carboxylic acid (0.16 g, 0.3 mmol) was dissolved in a solution of 4N hydrogen chloride in ethyl acetate (5 ml) and the mixture was stirred at room temperature for 1 h. The reaction mixture was concentrated under reduced pressure and the residue was crystallized from ethyl acetate to give 2-[3-(aminomethyl)-2-isobutyl-1-oxo-4-phenyl-1,2-dihydro-6-isoquinolinyl]-1,3-thiazole-4-carboxylic acid hydrochloride (0.13 g, 92.9%) as crystals.

Melting point 281–283° C. Elemental analysis for $C_{24}H_{24}N_3O_3ClS\ H_2O$ Calculated: C, 59.07; H, 5.37; N, 8.61. Found: C, 59.32; H, 5.42; N, 8.57. $^1$H-NMR(DMSO-$d_6$) δ: 0.94 (6H, d, J=6.6 Hz), 2.01–2.21 (1H, m), 3.90 (2H, s), 4.10 (2H, d, J=7.8 Hz), 7.45–7.51 (3H, m), 7.56–7.64 (3H, m), 8.41 (1H, dd, J=1.7, 8.4 Hz), 8.48 (1H, d, J=8.4 Hz) 8.53 (1H, s), 8.57 (3H, bs).

Example 197

2-[3-(Aminomethyl)-2-isobutyl-1-oxo-4-phenyl-1,2-dihydro-6-isoquinolinyl]-1,3-thiazole-4-carboxamide hydrochloride (1) A solution of 2-[3-[[(tert-butoxycarbonyl)amino]methyl]-2-isobutyl-1-oxo-4-phenyl-1,2-dihydro-6-isoquinolinyl]-1,3-thiazole-4-carboxylic acid (0.80 g, 1.5 mmol), 1-ethyl-3-(3-dimethylaminopropyl)carbodiimide hydrochloride (0.58 g, 3 mmol) and 1-hydroxybenzotriazole ammonium salt (0.46 g, 3 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give tert-butyl[6-[4-(aminocarbonyl)-1,3-thiazol-2-yl]-2-isobutyl-1-oxo-4-phenyl-1,2-dihydro-3-isoquinolinyl]methylcarbamate (0.75 g, 93.8%) as crystals.

Melting point 248–249° C. Elemental analysis for $C_{29}H_{32}N_4O_4S\ 0.25H_2O$ Calculated: C, 64.84; H, 6.10; N, 10.43. Found: C, 64.98; H, 6.21; N, 10.23. $^1$H-NMR(CDCl$_3$) δ: 1.02 (6H, d, J=6.8 Hz), 1.44 (9H, s), 2.19–2.34 (1H, m), 4.10 (2H, d, J=7.4 Hz), 4.24 (2H, d, J=5.4 Hz), 4.65 (1H, bs), 5.84 (1H, bs), 7.29–7.34 (2H, m), 7.44 (1H, d, J=1.8 Hz), 7.51–7.61 (3H, m), 8.00 (1H, dd, J=1.8, 8.4 Hz), 8.11 (1H, s), 8.52 (1H, d, J=8.4 Hz).

(2) Tert-butyl[6-[4-(aminocarbonyl)-1,3-thiazol-2-yl]-2-isobutyl-1-oxo-4-phenyl-1,2-dihydro-3-isoquinolinyl]-methylcarbamate (0.32 g, 0.6 mmol) was dissolved in a solution of 4N hydrogen chloride in ethyl acetate (5 ml) and the mixture was stirred at room temperature for 1 h. The reaction mixture was concentrated under reduced pressure and the residue was crystallized from ethyl acetate to give 2-[3-(aminomethyl)-2-isobutyl-1-oxo-4-phenyl-1,2-dihydro-6-isoquinolinyl]-1,3-thiazole-4-carboxamide hydrochloride (0.27 g, 96.4%) as crystals.

Melting point 235–237° C. $^1$H-NMR(DMSO-$d_6$) δ: 0.94 (6H, d, J=6.8 Hz), 2.05–2.21 (1H, m), 3.92 (2H, s), 4.10 (2H, d, J=7.8 Hz), 7.39 (1H, d, J=1.6 Hz), 7.45–7.50 (2H, m), 7.60–7.66 (3H, m), 7.70 (1H, bs), 7.79 (1H, bs), 8.28 (1H, d, J=1.6, 8.4 Hz), 8.30 (1H, s), 8.47 (1H, d, J=8.4 Hz), 8.58 (3H, bs).

Example 198

2-[3-(Aminomethyl)-2-isobutyl-1-oxo-4-phenyl-1,2-dihydro-6-isoquinolinyl]-1,3-thiazole-4-carbonitrile hydrochloride (1) A solution of tert-butyl[6-[4-(aminocarbonyl)-1,3-thiazol-2-yl]-2-isobutyl-1-oxo-4-phenyl-1,2-dihydro-3-isoquinolinyl]methylcarbamate (0.32 g, 0.6 mmol) and cyanuric chloride (0.33 g, 1.8 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(4-cyano-1,3-thiazol-2-yl)-2-isobutyl-1-oxo-4-phenyl-1,2-dihydro-3-isoquinolinyl]methylcarbamate (0.28 g, 90.3%) as crystals.

Melting point 209–211° C. Elemental analysis for $C_{29}H_{30}N_4O_3S$ Calculated: C, 67.68; H, 5.88; N, 10.89. Found: C, 67.72; H, 5.92; N, 10.62. $^1$H-NMR(CDCl$_3$) δ: 1.02 (6H, d, J=6.8 Hz), 1.44 (9H, s), 2.19–2.38 (1H, m), 4.10 (2H, d, J=7.8 Hz), 4.24 (2H, d, J=5.6 Hz), 4.58 (1H, bs), 7.28–7.32 (2H, m), 7.49 (1H, d, J=1.4 Hz), 7.52–7.63 (3H, m), 7.95 (1H, s), 7.96 (1H, dd, J=1.4, 8.4 Hz), 8.54 (1H, d, J=8.4 Hz).

(2) Tert-butyl[6-(4-cyano-1,3-thiazol-2-yl)-2-isobutyl-1-oxo-4-phenyl-1,2-dihydro-3-isoquinolinyl]methylcarbamate (0.21 g, 0.4 mmol) was dissolved in a solution of 4N hydrogen chloride in ethyl acetate (5 ml) and the mixture was stirred at room temperature for 1 h. The reaction mixture was concentrated under reduced pressure and the residue was crystallized from ethyl acetate to give 2-[3-aminomethyl)-2-isobutyl-1-oxo-4-phenyl-1,2-dihydro-6-isoquinolinyl]-1,3-thiazole-4-carbonitrile hydrochloride (0.17 g, 94.4%) as crystals.

Melting point 274–276° C. Elemental analysis for $C_{24}H_{23}N_4OClS\ 0.5H_2O$ Calculated: C, 62.67; H, 5.26; N, 12.18. Found: C, 62.57; H, 5.06; N, 12.08. $^1$H-NMR (DMSO-$d_6$) δ: 0.94 (6H, d, J=6.6 Hz), 2.01–2.21 (1H, m), 3.89 (2H, m), 4.11 (2H, d, J=7.2 Hz), 7.45–7.51 (3H, m), 7.61–7.64 (3H, m), 8.14 (1H, dd, J=1.8, 8.4 Hz), 8.48 (1H, d, J=8.4 Hz), 8.62 (3H, bs), 8.95 (1H, s).

Example 199

3-(Aminomethyl)-4-butoxy-2-isobutyl-6-(1H-pyrrol-1-yl)-1(2H)-isoquinolinone dihydrochloride (1) A solution of tert-butyl(6-amino-4-butoxy-2-isobutyl-1-oxo-1,2-dihydro-3-isoquinolinyl)methylcarbamate (0.41 g, 1 mmol) and 2,5-dimethoxytetrahydrofuran (0.19 ml, 1.5 mmol) in acetic acid (10 ml) was stirred at 80° C. for 2 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-2-isobutyl-1-oxo-6-(1H-pyrrol-1-yl)-1,2-dihydro-3-isoquinolinyl]methylcarbamate (0.31 g, 67.4%) as crystals.

Melting point 164–166° C. Elemental analysis for $C_{27}H_{37}N_3O_4$ Calculated: C, 69.35; H, 7.98; N, 8.99. Found: C, 69.29; H, 8.28; N, 8.87. $^1$H-NMR(CDCl$_3$) δ: 0.97 (6H, d, J=6.6 Hz), 1.04 (3H, t, J=7.4 Hz), 1.47 (9H, s), 1.51–1.69 (2H, m), 1.81–1.95 (2H, m), 2.04–2.25 (1H, m), 3.89 (2H, t, J=6.5 Hz), 3.99 (2H, d, J=7.8 Hz), 4.53 (2H, d, J=5.6 Hz), 4.80 (1H, bs), 6.41–6.43 (2H, m), 7.21–7.23 (2H, m), 7.50–7.56 (1H, m), 7.62 (1H, d, J=1.8 Hz), 8.43–8.48 (1H, m).

(2) Tert-butyl[4-butoxy-2-isobutyl-1-oxo-6-(1H-pyrrol-1-yl)-1,2-dihydro-3-isoquinolinyl]methylcarbamate (0.23 g, 0.5 mmol) was dissolved in a solution of 4N hydrogen chloride in ethyl acetate (5 ml) and the mixture was stirred at room temperature for 1 h. The reaction mixture was concentrated under reduced pressure and the obtained crystals were recrystallized from methanol-diethyl ether to give 3-(aminomethyl)-4-butoxy-2-isobutyl- 6-(1H-pyrrol-1-yl)-1 (2H)-isoquinolinone dihydrochloride (0.19 g, 95.0%) as crystals.

Melting point 156–157° C. Elemental analysis for $C_{22}H_{30}N_3O_2Cl$ $0.5H_2O$ Calculated: C, 63.99; H, 7.57; N, 10.18. Found: C, 64.23; H, 7.86; N, 10.25. $^1$H-NMR (DMSO-$d_6$) δ: 0.90 (6H, d, J=6.6 Hz), 1.00 (3H, t, J=7.3 Hz), 1.55–1.66 (2H, m), 1.81–2.13 (3H, m), 3.96–4.03 (4H, m), 4.19 (2H, bs), 6.39 (2H, t, J=2.2 Hz), 7.55 (2H, t, J=2.2 Hz), 7.70 (1H, d, J=2.0 Hz), 7.89 (1H, dd, J=2.0, 8.8 Hz), 8.33 (1H, d, J=8.8 Hz), 8.72 (3H, bs).

Example 200

3-(Aminomethyl)-4-butoxy-2-isobutyl-6-(1H-tetrazol-1-yl)-1(2H)-isoquinolinone hydrochloride (1) To a solution of tert-butyl(6-amino-4-butoxy-2-isobutyl-1-oxo-1,2-dihydro-3-isoquinolinyl)methylcarbamate (0.41 g, 1 mmol) in acetic acid (5 ml) was added trimethyl orthoformate (0.33 ml, 3 mmol) and the mixture was stirred at room temperature for 30 min. To the obtained mixture was added sodium azide (0.10 g, 1.5 mmol) and the mixture was stirred at 80° C. for 2 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-2-isobutyl-1-oxo-6-(1H-tetrazol-1-yl)-1,2-dihydro-3-isoquinolinyl]-methylcarbamate (0.31 g, 66.0%) as crystals.

Melting point 199–200° C. $^1$H-NMR(CDCl$_3$) δ: 0.98 (6H, d, J=6.6 Hz), 1.05 (3H, t, J=7.3 Hz), 1.48 (9H, s), 1.54–1.69 (2H, m), 1.83–1.97 (2H, m), 2.12–2.26 (1H, m), 3.91 (2H, t, J=6.4 Hz), 4.03 (2H, d, J=7.4 Hz), 4.56 (2H, d, J=5.4 Hz), 4.80 (1H, bs), 7.78 (1H, dd, J=2.2, 8.8 Hz), 8.09 (1H, d, J=2.2 Hz), 8.62 (1H, d, J=8.8 Hz), 9.15 (1H, s).

(2) Tert-butyl[4-butoxy-2-isobutyl-1-oxo-6-(1H-tetrazol-1-yl)-1,2-dihydro-3-isoquinolinyl]methylcarbamate (0.24 g, 0.5 mmol) was dissolved in a solution of 4N hydrogen chloride in ethyl acetate (5 ml) and the mixture was stirred at room temperature for 1 h. The reaction mixture was concentrated under reduced pressure and the obtained crystals was crystallized from methanol-diethyl ether to give 3-(aminomethyl)-4-butoxy-2-isobutyl-6-(1H-tetrazol-1-yl)-1(2H)-isoquinolinone hydrochloride (0.19 g, 95.0%) as crystals.

Melting point 177–179° C. Elemental analysis for $C_{19}H_{27}N_6O_2Cl$ $0.5H_2O$ Calculated: C, 54.87; H, 6.79; N, 20.21. Found: C, 55.08; H, 7.19; N, 20.00. $^1$H-NMR (DMSO-$d_6$) δ: 0.91 (6H, d, J=6.6 Hz), 1.01 (3H, t, J=7.3 Hz), 1.43–1.67 (2H, m), 1.82–2.10 (3H, m), 3.98–4.04 (4H, m), 4.23 (2H, bs), 8.17 (1H, dd, J=2.0, 8.6 Hz), 8.23 (1H, d, J=2.0 Hz), 8.52 (1H, d, J=8.6 Hz), 8.73 (3H, bs), 10.38 (1H, s).

Example 201

3-(Aminomethyl)-4-butoxy-2-isobutyl-6-(1H-1,2,3-triazol-1-yl)-1(2H)-isoquinolinone hydrochloride (1) To a solution of tert-butyl(6-amino-4-butoxy-2-isobutyl-1-oxo-1,2-dihydro-3-isoquinolinyl)methylcarbamate (0.41 g, 1 mmol) in methanol (10 ml) was added N'-(2,2-dichloroethylidene)-4-methylbenzenesulfonohydtazide (0.28 g, 1 mmol) and the mixture was stirred at 0° C. for 1 h and at room temperature for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-2-isobutyl- 1-oxo-6-(1H-1,2,3-triazol-1-yl)-1,2-dihydro-3-isoquinolinyl]methylcarbamate (0.21 g, 45.7%) as crystals.

Melting point 190–191° C. Elemental analysis for $C_{25}H_{35}N_5O_4$ Calculated: C, 63.97; H, 7.51; N, 14.91. Found: C, 64.95; H, 7.69; N, 14.63. $^1$H-NMR(CDCl$_3$) δ: 0.98 (6H, d, J=6.6 Hz), 1.04 (3H, t, J=7.0 Hz), 1.48 (9H, s), 1.54–1.69 (2H, m), 1.83–1.97 (2H, m), 2.04–2.24 (1H, m), 3.92 (2H, t, J=6.6 Hz), 4.02 (2H, d, J=7.8 Hz), 4.55 (2H, d, J=5.6 Hz), 4.82 (1H, bs), 7.81 (1H, dd, J=2.2, 8.8 Hz), 7.91 (1H, d, J=1.3 Hz), 8.12 (1H, d, J=1.3 Hz), 8.13 (1H, d, J=2.2 Hz), 8.56 (1H, d, J=8.8 Hz).

(2) tert-butyl[4-butoxy-2-isobutyl-1-oxo-6-(1H-1,2,3-triazol-1-yl)-1,2-dihydro-3-isoquinolinyl]methylcarbamate (0.14 g, 0.3 mmol) was dissolved in a solution of 4N hydrogen chloride in ethyl acetate (5 ml,) and the mixture was stirred at room temperature for 1 h. The reaction mixture was concentrated under reduced pressure to give 3-(aminomethyl)-4-butoxy-2-isobutyl-6-(1H-1,2,3-triazol-1-yl)-1 (2H)-isoquinolinone hydrochloride (81 mg, 62.3%) as an amorphous.

$^1$H-NMR(DMSO-$d_6$) δ: 0.91 (6H, d, J=6.6 Hz), 1.01 (3H, t, J=7.3 Hz), 1.49–1.68 (2H, m), 1.82–2.12 (3H, m), 3.89–4.03 (4H, m), 4.22 (2H, d, J=4.4 Hz), 8.09 (1H, d, J=1.3 Hz), 8.18 (1H, dd, J=2.0, 8.6 Hz), 8.24 (1H, d, J=2.0 Hz), 8.48 (1H, d, J=8.6 Hz), 8.75 (3H, bs), 9.11 (1H, d, J=1.3 Hz).

Example 202

3-(Aminomethyl)-4-butoxy-2-isobutyl-6-(5-oxo-4,5-dihydro-1,2,4-oxadiazol-3-yl)-1(2H)-isoquinolinone hydrochloride (1) A solution of tert-butyl(4-butoxy-6-cyano-2-isobutyl-1-oxo-1,2-dihydro-3-isoquinolinyl)methylcarbamate (0.85 g, 2 mmol), sodium carbonate (0.85 g, 8 mmol) and hydroxylamine hydrochloride (0.42 g, 6 mmol) in ethanol (20 ml) was refluxed with stirring for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-[amino(hydroxyimino)methyl]-4-butoxy-2-isobutyl-1-oxo-1,2-dihydro-3-isoquinolinyl]methylcarbamate (0.81 g, 88.0%) as crystals.

Melting point 209–210° C. Elemental analysis for $C_{24}H_{36}N_4O_5$ Calculated: C, 62.59; H, 7.88; N, 12.16. Found: C, 62.49; H, 7.93; N, 11.98. $^1$H-NMR(CDCl$_3$) δ: 0.95 (6H, d, J=6.6 Hz), 1.02 (3H, t, J=7.3 Hz), 1.49–1.66 (11H, m), 1.78–1.91 (2H, m), 2.09–2.24 (1H, m), 3.68–3.84 (2H, m), 3.98 (2H, t, J=6.6 Hz), 4.51 (2H d, J=4.8 Hz), 5.02 (2H, s), 5.16 (1H, bs), 5.37 (1H, bs), 7.62 (1H, d, J=8.3 Hz), 7.82 (1H, s), 8.25 (1H, d, J=8.3 Hz).

(2) To a solution of tert-butyl[6-[amino(hydroxyimino)methyl]-4-butoxy-2-isobutyl-1-oxo-1,2-dihydro-3-isoquinolinyl]methylcarbamate (0.78 g, 1.7 mmol) in ethyl acetate (10 ml) tetrahydrofuran (10 ml) was added 1,1'-carbonyldiimidazole (0.83 g, 5.1 mmol) and the mixture was stirred at 80° C. for 2 h. The reaction mixture was poured into water and extracted with ethyl acetate. The extract was washed with brine, dried over anhydrous magnesium sulfate and concentrated under reduced pressure. The residue was crystallized from ethyl acetate-diisopropyl ether to give tert-butyl [4-butoxy-2-isobutyl-1-oxo-6-(5-oxo-4,5-dihydro-1,2,4-oxadiazol-3-yl)-1,2-dihydro-3-isoquinolinyl]methylcarbamate (0.54 g, 65.9%) as crystals.

Melting point 223–224° C. Elemental analysis for $C_{25}H_{34}N_4O_6$ 0.25$H_2O$ Calculated: C, 61.15; H, 7.08; N, 11.41 Found: C, 61.00; H, 7.11; N, 11.13. $^1$H-NMR(CDCl$_3$) δ: 0.86 (6H, d, J=6.6 Hz), 0.98 (3H, t, J=7.3 Hz), 1.42 (9H, s), 1.43–1.61 (2H, m), 1.76–1.90 (2H, m), 2.04–2.15 (1H, m), 3.86–3.92 (4H, m), 4.39 (2H, d, J=4.4 Hz), 7.36 (1H, bs), 7.94 (1H, dd, J=1.4, 8.4 Hz), 8.15 (1H, d, J=1.4 Hz), 8.38 (1H, d, J=8.4 Hz).

(3) Tert-butyl[4-butoxy-2-isobutyl-1-oxo-6-(5-oxo-4,5-dihydro-1,2,4-oxadiazol-3-yl)-1,2-dihydro-3-isoquinolinyl]methylcarbamate (0.44 g, 0.9 mmol) was dissolved in a solution of 4N hydrogen chloride in ethyl acetate (10 ml) and the mixture was stirred at room temperature for 3 h. The reaction mixture was concentrated under reduced pressure and the obtained crystals were recrystallized from methanol-diethyl ether to give 3-(aminomethyl)-4-butoxy-2-isobutyl-6-(5-oxo-4,5-dihydro-1,2,4-oxadiazol-3-yl)-1(2H)-isoquinolinone hydrochloride (0.36 g, 94.7%) as crystals.

Melting point 256–258° C. Elemental analysis for $C_{20}H_{27}N_4O_4Cl$ 0.25$H_2O$ Calculated: C, 56.20; H, 6.49; N, 13.11. Found: C, 56.23; H, 6.65; N, 12.98. $^1$H-NMR (DMSO-d$_6$) δ: 0.90 (6H, d, J=6.4 Hz), 1.01 (3H, t, J=7.3 Hz), 1.46–1.64 (2H, m), 1.83–2.16 (3H, m), 3.95–4.02 (4H, m), 4.21 (2H, s), 8.03 (1H, dd, J=1.8, 8.4 Hz), 8.21 (1H, d, J=1.8 Hz), 8.43 (1H, d, J=8.4 Hz), 8.68 (3H, bs).

Example 203

3-(Aminomethyl)-4-butoxy-2-isobutyl-6-(5-methyl-1,2,4-oxadiazol-3-yl)-1(2H)-isoquinolinone hydrochloride (1) A solution of tert-butyl[6-[amino(hydroxyimino)methyl]-4-butoxy-2-isobutyl-1-oxo-1,2-dihydro-3-isoquinolinyl]methylcarbamate (0.46 g, 1 mmol), acetic anhydride (0.14 ml, 1.5 mmol) and a catalytic amount of acetic acid in tetrahydrofuran (10 ml) was refluxed under heating for 10 h. The reaction mixture was poured into water and extracted with ethyl acetate. The extract was washed with brine, dried over anhydrous magnesium sulfate and concentrated under reduced pressure. The residue was crystallized from ethyl acetate-diisopropyl ether to give tert-butyl[4-butoxy-2-isobutyl-6-(5-methyl-1,2,4-oxadiazol-3-yl)-1-oxo-1,2-dihydro-3-isoquinolinyl]methylcarbamate (0.22 g, 45.8%) as crystals.

Melting point 151.5–152° C. Elemental analysis for $C_{26}H_{36}N_4O_6$ Calculated: C, 64.44; H, 7.49; N, 11.56. Found: C, 64.12; H, 7.74; N, 11.54. $^1$H-NMR(CDCl$_3$) δ: 0.98 (6H, d, J=6.6 Hz), 1.05 (3H, t, J=7.3 Hz), 1.47 (9H, s), 1.56–1.68 (2H, m), 1.86–1.95 (2H, m), 2.15–2.24 (1H, m), 2.70 (3H, s), 3.92 (2H, t, J=6.6 Hz), 4.02 (2H, d, J=7.5 Hz), 4.54 (2H, d, J=5.7 Hz), 4.78 (1H, bs), 8.15 (1H, dd, J=1.8, 8.7 Hz), 8.42 (1H, d, J=1.8 Hz), 8.51 (1H, d, J=8.7 Hz).

(2) Tert-butyl[4-butoxy-2-isobutyl-6-(5-methyl-1,2,4-oxadiazol-3-yl)-1-oxo-1,2-dihydro-3-isoquinolinyl]-methylcarbamate (0.15 g, 0.3 mmol) was dissolved in a solution of 4N hydrogen chloride in ethyl acetate (5 ml) and the mixture was stirred at room temperature for 3 h. The reaction mixture was concentrated under reduced pressure and the obtained crystals were recrystallized from methanol-diethyl ether to give 3-(aminomethyl)-4-butoxy-2-isobutyl-6-(5-methyl-1,2,4-oxadiazol-3-yl)-1(2H)-isoquinolinone hydrochloride (0.11 g, 91.7%) as crystals.

Melting point 230–232° C. Elemental analysis for $C_{21}H_{29}N_4O_3Cl$ 0.25$H_2O$ Calculated: C, 59.29; H, 6.99; N, 13.17. Found: C, 59.50; H, 7.02; N, 12.95. $^1$H-NMR (DMSO-d$_6$) δ: 0.90 (6H, d, J=6.6 Hz), 1.03 (3H, t, J=7.3 Hz), 1.52–1.67 (2H, m), 1.70–1.99 (2H, m), 2.02–2.12 (1H, m), 2.73 (3H, s), 3.95–4.02 (4H, m), 4.22 (2H, s), 8.18 (1H, d, J=8.4 Hz), 8.39 (1H, s), 8.45 (1H, d, J=8.4 Hz), 8.67 (3H, bs).

Example 204

3-(Aminomethyl)-4-butoxy-2-isobutyl-6-(1H-tetrazol-5-yl)-1(2H)-isoquinolinone hydrochloride (1) A solution of tert-butyl(4-butoxy-6-cyano-2-isobutyl-1-oxo-1,2-dihydro-3-isoquinolinyl)methylcarbamate (0.85 g, 2 mmol), triethylamine hydrochloride (0.34 g, 2.5 mmol) and sodium azide (0.16 g, 2.5 mmol) in toluene (20 ml) was stirred at 90° C. for 24 h. The reaction mixture was poured into water and extracted with ethyl acetate. The extract was washed with brine, dried over anhydrous magnesium sulfate and concentrated under reduced pressure. The obtained crystals were recrystallized from tetrahydrofuran-diisopropyl ether to give tert-butyl [4-butoxy-2-isobutyl-1-oxo-6-(1H-tetrazol-5-yl)-1,2-dihydro-3-isoquinolinyl]methylcarbamate (0.50 g, 53.2%) as crystals.

Melting point 152–153° C. Elemental analysis for $C_{24}H_{34}N_6O_4$ 0.25$H_2O$ Calculated: C, 60.68; H, 7.32; N, 17.69. Found: C, 60.98; H, 7.20; N, 17.29. $^1$H-NMR(CDCl$_3$) δ: 0.95–1.02 (9H, m), 1.48–1.61 (11H, m), 1.81–1.92 (2H, m), 2.14–2.27 (1H, m), 3.91 (2H, t, J=6.6 Hz), 4.08 (2H, d, J=7.2 Hz), 4.57 (2H, d, J=5.2 Hz), 4.79 (1H, bs), 5.39 (1H, bs), 8.12 (1H, dd, J=1.5, 8.5 Hz), 8.40 (1H, d, J=8.5 Hz), 8.46 (1H, d, J=1.5 Hz).

(2) Tert-butyl[4-butoxy-2-isobutyl-1-oxo-6-(1H-tetrazol-5-yl)-1,2-dihydro-3-isoquinolinyl]methylcarbamate (0.47 g, 1 mmol) was dissolved in a solution of 4N hydrogen chloride in ethyl acetate (5 ml) and the mixture was stirred at room temperature for 1 h. The reaction was concentrated under reduced pressure and the obtained crystals crystallized from methanol-diethyl ether to give 3-(aminomethyl)-4-butoxy-2-isobutyl-6-(1H-tetrazol-5-yl)-1(2H)-isoquinolinone hydrochloride (0.38 g, 92.7%) as crystals.

Melting point 252–254° C. Elemental analysis for $C_{19}H_{27}N_6O_2Cl$ 0.25$H_2O$ Calculated: C, 55.47; H, 6.74; N, 20.43. Found: C, 55.63; H, 6.67; N, 20.21. $^1$H-NMR (DMSO-d$_6$) δ: 0.91 (6H, d, J=7.0 Hz), 1.02 (3H, t, J=7.3 Hz), 1.50–1.69 (2H, m), 1.85–2.10 (3H, m), 3.98–4.02 (4H, m), 4.22 (2H, s), 8.30 (1H, dd, J=1.4, 8.4 Hz), 8.48 (1H, d, J=8.4 Hz), 8.51 (1H, d, J=1.4 Hz), 8.63 (3H, bs).

Example 205

2-(Aminomethyl)-4-isobutyl-5-phenyl[1,7]naphthyridin-8(7H)-one dihydrochloride (1) To a suspension of 3-benzoylpyridin-2-carboxylic acid (2.27 g, 10 mmol) in toluene (20 ml) was added thionyl chloride (0.88 ml, 12 mmol) and the mixture was stirred at 100° C. for 2 h. The reaction mixture was concentrated under reduced pressure and the residue was dissolved in tetrahydrofuran (20 ml). The obtained solution was added dropwise to (isobutylamino)-acetonitrile (1.68 g, 15 mmol) in N,N-dimethylacetamide (20 ml) and the mixture was stirred at 70° C. for 12 h. The reaction mixture was poured into water and extracted with ethyl acetate. The extract was washed with brine, dried over anhydrous magnesium sulfate and concentrated under reduced pressure. To a solution of the residue and acetic anhydride (1.1 ml, 12 mmol) in acetonitrile (6.0 ml, 40 mmol) at 0° C. and the mixture was stirred at room temperature for 15 h. Water was added to the reaction mixture and the mixture was stirred at room temperature for 30 min. The precipitated crystals were collected by filtration. The obtained crystals were recrystallized from tetrahydrofuran-diisopropyl ether to give 7-isobutyl-8-oxo-5-phenyl-7,8-dihydro[1,7]naphthyridine-6-carbonitrile (2.65 g, 87.5%) as crystals.

Melting point 221–222° C. Elemental analysis for $C_{19}H_{17}N_3O$ Calculated: C, 75.23; H, 5.65; N, 13.85. Found: C, 75.20; H, 5.72; N, 13.85. $^1$H-NMR(CDCl$_3$) δ: 1.06 (6H, d, J=7.0 Hz), 2.30–2.51 (1H, m), 4.24 (2H, d, J=7.8 Hz), 7.37–7.46 (2H, m), 7.52–7.61 (4H, m), 7.72 (1H, dd, J=1.8, 8.3 Hz), 9.01 (1H, dd, J=1.8, 8.4 Hz).

(2) A suspension of 7-isobutyl-8-oxo-5-phenyl-7,8-dihydro[1,7]naphthyridine-6-carbonitrile (2.43 g, 8 mmol), Raney-cobalt (2.4 ml) and 25% aqueous ammonia (3.2 ml) in tetrahydrofuran (100 ml) was stirred under a hydrogen atmosphere at 5 atm and 60° C. for 3 h. Raney-cobalt was filtered off and the filtrate was concentrated under reduced pressure. The residue was dissolved in tetrahydrofuran (30 ml) and to the obtained solution was added di-t-butyl dicarbonate (2.3 ml, 10 mmol). The mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl(7-isobutyl-8-oxo-5-phenyl-7,8-dihydro[1,7]naphthyridin-6-yl)methylcarbamate (0.21 g, 6.4%) as crystals.

Melting point 176–177° C. Elemental analysis for $C_{24}H_{29}N_3O_3$ Calculated: C, 70.74; H, 7.17; N, 10.31. Found: 70.59; H, 7.18; N, 10.26. $^1$H-NMR(CDCl$_3$) δ: 1.01 (6H, d, J=6.6 Hz), 1.44 (9H, s), 2.23–2.32 (1H, m), 4.14 (2H, d, J=7.2 Hz), 4.22 (2H, d, J=5.4 Hz), 4.93 (1H, bs), 7.26–7.33 (4H, m), 7.45–7.57 (3H, m), 8.76–8.77 (1H, m).

(3) Tert-butyl(7-isobutyl-8-oxo-5-phenyl-7,8-dihydro[1,7]naphthyridin-6-yl)methylcarbamate (0.16 g, 0.4 mmol) was dissolved in a solution of 4N hydrogen chloride in ethyl acetate (5 ml) and the mixture was stirred at room temperature for 1 h. The reaction mixture was concentrated under reduced pressure and the obtained crystals were recrystallized from methanol-ethyl acetate to give 2-(aminomethyl)-4-isobutyl-5-phenyl[1,7]naphthyridin-8(7H)-one dihydrochloride (0.12 g, 80.0%) as crystals.

Melting point 293° C. $^1$H-NMR(DMSO-d$_6$) δ: 0.94 (6H, d, J=6.6 Hz), 2.06–2.19 (1H, m), 3.91 (2H, d, J=3.9 Hz), 4.14 (2H, d, J=7.2 Hz), 7.41–7.44 (3H, m), 7.50–7.62 (3H, m), 7.71–7.76 (1H, m), 8.79 (3H, bs), 8.88–8.90 (1H, m).

Example 206

3-(Aminomethyl)-2-isobutyl-6-(5-oxo-4,5-dihydro-1,2,4-oxadiazol-3-yl)-4-phenyl-1(2H)-isoquinolinone hydrochloride (1) To a mixture of tert-butyl(6-cyano-2-isobutyl-1-oxo-4-phenyl-1,2-dihydro-3-isquinolinyl)methylcarbamate (0.86 g, 2.0 mmol), hydroxylamine hydrochloride (0.21 g, 3.0 mmol) and ethanol (20 ml) was added potassium t-butoxide (0.34 g, 3.0 mmol) at room temperature and the mixture was stirred at 75–80° C. for 3 h. The reaction mixture was poured into water (100 ml) and the mixture was extracted with ethyl acetate (50 ml). The organic layer was washed with saturated brine (20 ml) and dried over anhydrous magnesium sulfate (6 g). The solvent was evaporated and the residue was purified by silica gel column chromatography (n-hexane-ethyl acetate=1:1 (v/v)) to give tert-butyl{6-[amino(hydroxyimino)methyl]-2-isobutyl-1-oxo-4-phenyl-1,2-dihydroisoquinolin-3-yl}methylcarbamate (0.57 g, 62%) as a colorless powder.

$^1$H-NMR(CDCl$_3$) δ: 0.90 (6H, d, J=6.6 Hz), 1.38 (9H, s), 2.05–2.20 (1H, m), 3.85–4.00 (4H, s), 5.84 (2H, bs), 7.29 (1H, d, J=1.8 Hz), 7.31 (1H, br), 7.35–7.55 (5H, m), 7.55 (1H, dd, J=1.8, 8.4 Hz), 9.83 (1H, s).

(2) Tert-butyl{6-[amino(hydroxyimino)methyl]-2-isobutyl-1-oxo-4-phenyl-1,2-dihydroisoquinolin-3-yl}methylcarbamate (0.25 g, 0.54 mmol) was dissolved in ethyl acetate (10 ml) and N,N'-carbonyldiimidazole (0.26 g, 1.6 mmol) was added. The mixture was refluxed under heating for 3 h. To the reaction mixture were added 0.1 M aqueous citric acid solution (25 ml) and ethyl acetate (50 ml). The organic layer was washed with 0.1 M aqueous citric acid solution (25 ml), and then saturated brine (25 ml), dried over anhydrous magnesium sulfate (12 g) and concentrated under reduced pressure. The residue was recrystallized from diisopropyl ether-ethyl acetate=2:1 (v/v) to give tert-butyl[2-isobutyl-1-oxo-6-(5-oxo-4,5-dihydro-1,2,4-oxadiazol-3-yl)-4-phenyl-1,2-dihydro-3-isoquinolinyl]methylcarbamate (0.24 g, 93%) as a colorless powder.

$^1$H-NMR(CDCl$_3$) δ: 1.01 (6H, d, J=6.6 Hz), 1.44 (9H, s), 2.15–2.35 (1H, m), 4.10 (2H, d, J=7.2 Hz), 4.22 (2H, d, J=5.4 Hz), 4.64 (1H, br), 7.25–7.35 (3H, m), 7.45–7.60 (3H, m), 7.82 (1H, dd, J=1.7, 8.4 Hz), 8.52 (1H, d, J=8.4 Hz).

(3) Tert-butyl[2-isobutyl-1-oxo-6-(5-oxo-4,5-dihydro-1,2,4-oxadiazol-3-yl)-4-phenyl-1,2-dihydro-3-isoquinolinyl]methylcarbamate (0.18 g, 0.37 mmol) was dissolved in ethanol (4 ml) and a solution (4 ml) of 4N hydrogen chloride in ethyl acetate was added. The mixture was stirred at room temperature for 30 min. The reaction mixture was concentrated under reduced pressure, and the residue was washed with diisopropyl ether (2 ml) and recrystallized from ethyl acetate-ethanol (20:1) to give 3-(aminomethyl)-2-isobutyl-6-(5-oxo-4,5-dihydro-1,2,4-oxadiazol-3-yl)-4-phenyl-1(2H)-isoquinolinone hydrochloride (0.12 g, 80%) as a colorless powder.

Elemental analysis for $C_{22}H_{22}N_4O_3$ HCl 0.5H$_2$O, Calculated: C, 60.62; H, 5.55; N, 12.85. Found: C, 61.01; H, 5.49; N, 12.21. $^1$H-NMR(DMSO-d$_6$) δ: 0.93 (6H, d, J=6.6 Hz), 2.00–2.25 (1H, m), 3.88 (2H, s), 4.08 (2H, d, J=7.2 Hz), 7.35–7.45 (3H, m), 7.55–7.65 (3H, m), 7.96 (1H, dd, J=1.8, 8.4 Hz), 8.46 (3H, br), 8.50 (1H, d, J=8.4 Hz).

Melting point 253° C. (decomposition)

Example 207

3-(Aminomethyl)-2-isobutyl-6-(5-oxo-4,5-dihydro-1,2,4-thiadiazol-3-yl)-4-phenyl-1(2H)-isoquinolinone hydrochloride (1) A mixture of tert-butyl{6-[amino(hydroxyimino)methyl]-2-isobutyl-1-oxo-4-phenyl-1,2-dihydroisoquinolin-3-yl}methylcarbamate (0.50 g, 1.1 mmol), acetic acid (5 ml) and acetic anhydride (0.12 ml, 1.3 mmol) was stirred at room temperature for 20 min. To the reaction mixture was added 10% palladium-activated carbon (0.05 g) under a nitrogen atmosphere and the mixture was stirred at room temperature and 1 atm under a hydrogen atmosphere for 12 h. The insoluble material was filtered off and the solvent was evaporated. Diisopropyl ether (2 ml) was added to the residue to give tert-butyl{6-[amino(imino)methyl]-2-isobutyl-1-oxo-4-phenyl-1,2-dihydroisoquinolin-3-yl}methylcarbamate diacetate (0.92 g, 85%) as a brown powder.

$^1$H-NMR(DMSO-d$_6$) δ: 0.90 (6H, d, J=6.6 Hz), 1.38 (9H, s), 1.80 (6H, s), 2.05–2.25 (1H, m), 3.90–4.05 (4H, m), 7.23 (1H, d, J=1.4 Hz), 7.30–7.45 (3H, m), 7.45–7.60 (3H, m), 7.76 (1H, dd, J=1.4, 8.2 Hz), 8.44 (1H, d, J=8.2 Hz), 10.59 (2H, br).

(2) Chlorocarbonylsulfenyl chloride (0.04 ml, 0.45 mmol) was added to a mixture of tert-butyl{6-[ amino(imino)methyl]-2-isobutyl-1-oxo-4-phenyl-1,2-dihydroisoquinolin-3-yl}methylcarbamate diacetate (0.25 g, 0.43 mmol), sodium carbonate (0.40 g, 3.8 mmol), water (5 ml) and tetrahydrofuran (5 ml) while stirring vigorously under ice-cooling. The reaction mixture was stirred for 3 h, warmed to room temperature and stirred for 1 h more. The reaction mixture was added to 1N hydrochloric acid (30 ml) and extracted twice with ethyl acetate (30 ml). The organic layers were combined and washed with 1N hydrochloric acid (10 ml) and then saturated brine (10 ml), dried over anhydrous magnesium sulfate (12 g) and concentrated under reduced pressure. The residue was purified by silica gel column chromatography (n-hexane-ethyl acetate=1:1 (v/v)) to give tert-butyl[2-isobutyl-1-oxo-6-(5-oxo-4,5-dihydro-1,2,4-thiadiazol-3-yl)-4-phenyl-1,2-dihydro-3-isioquinolinyl] methylcarbamate (0.084 g, 39%) as a yellow powder.

$^1$H-NMR(CDCl$_3$) δ: 1.01 (6H, d, J=6.6 Hz), 1.44 (9H, s), 2.15–2.35 (1H, m,), 4.03 (2H, d, J=6.6 Hz), 4.19 (2H, d, J=5.2 Hz), 4.73 (1H, br), 7.25–7.35 (3H, m), 7.50–7.60 (3H, m), 7.97 (1H, dd, J=1.8, 8.4 Hz), 8.53 (1H, d, J=8.4 Hz), 11.44 (1H, bs).

(3) Tert-butyl[2-isobutyl-1-oxo-6-(5-oxo-4,5-dihydro-1,2,4-thiadiazol-3-yl)-4-phenyl-1,2-dihydro-3-isoquinolinyl] methylcarbamate (0.050 g, 0.10 mmol) was dissolved in tetrahydrofuran (3 ml) and a solution (2 ml) of 4N hydrogen chloride in ethyl acetate was added. The mixture was stirred at room temperature for 24 h. The reaction mixture was concentrated under reduced pressure and diisopropyl ether-ethyl acetate (2:1) was added to the residue to give 3-(aminomethyl)-2-isobutyl-6-(5-oxo-4,5-dihydro-1,2,4-thiadiazol-3-yl)-4-phenyl-1(2H)-isoquinolinone hydrochloride (0.041 g, 94%) as a pale-yellow powder.

Elemental analysis for $C_{22}H_{22}N_4O_2S$ HCl 0.75H$_2$O, Calculated: C, 57.89; H, 5.41; N, 12.27. Found: C, 57.95; H, 5.41; N, 11.58. $^1$H-NMR(DMSO-d$_6$) δ: 0.95 (6H, d J=6.6 Hz) 2.00–2.20 (1H, m), 3.93(2H, s), 4.09 (2H, d, J=7.4 Hz), 7.35–7.50 (2H, m), 7.50–7.65 (3H, m), 7.86 (1H, d, J=1.8 Hz) 8.32 (1H, dd, J=1.8, 8.2 Hz), 8.48 (1H, d, J=8.2 Hz), 8.50 (3H, bs).

Melting point 232–237° C.

Example 208

6-Bromo-2-isobutyl-1-oxo-4-phenyl-1,2-dihydroisoquinoline-3-carbonitrile

To a mixture of 2-benzoyl-4-bromobenzoic acid (5.0 g), toluene (65 ml) and dimethylformamide (0.1 ml) was added dropwise thionyl chloride (1.42 ml) under a nitrogen atmosphere, and the mixture was stirred at 50° C. for 1.5 h. The solvent was evaporated and toluene (10 ml) was added to the residue. The mixture was heated to around 90° C. Diisopropylethylamine (4.21 ml) was added to the obtained solution and the mixture was stirred for about 5 min. Isobutylaminoacetonitrile (2.75 g) was added and the mixture was stirred at around the same temperature for 3 h. The reaction mixture was cooled to 25° C. and 1N hydrochloric acid (50 ml) was added and stirred. The organic layer was separated and washed with 10% brine (50 ml). The solvent was evaporated to give 2-benzoyl-4-bromo-(N-cyanomethyl)-N-(isobutyl)benzamide. Acetonitrile (15 ml) and ethanol (15 ml) were added to the residue, and acetic anhydride (1.85 ml) and 1,8-diazabicyclo[5,4,0]-7-undecene (4.90 ml) were successively added dropwise to the mixture below 40° C. The reaction mixture was heated to 50° C. and the mixture was stirred for 1 h. The reaction mixture was cooled to around 25° C. and water (12.5 ml) was added dropwise. The mixture was stirred at the same temperature for 1 h. The precipitated crystals were collected by filtration and washed with 70% ethanol to give the title compound (5.31 g, yield 85%).

$^1$H-NMR(300 MHz, CDCl$_3$) δ: 1.04 (6H, d, J=6.7 Hz), 2.30–2.39(1H, m), 4.15(2H, d, J=7.5 Hz), 7.39–7.44(3H, m), 7.55–7.60(3H, m), 7.76(1H, dd, J=1.9 Hz, 8.6 Hz), 8.39(1H, d, J=8.6 Hz)

Example 209

(3-(Aminomethyl)-6-bromo-2-isobutyl-4-phenylisoquinolin-1(2H)-one

A mixture of 6-bromo-2-isobutyl-1-oxo-4-phenyl-1,2-dihydroisoquinoline-3-carbonitrile (16.0 g), sponge cobalt (manufactured by Kawaken Fine Chemicals Co., Ltd.; trademark: ODHT-60) (4 ml), 25% ammonium hydroxide (2 ml) and tetrahydrofuran. (80 ml) was stirred at 60° C. at a 1 MPa hydrogen pressure for 4 h and the catalyst was filtered off. The solvent was evaporated and acetonitrile (48 ml) was added to the residue. The mixture was heated to about 70° C. The obtained solution was cooled to 25° C. to give crystals, and water (80 ml) was added dropwise. The obtained mixture was cooled to around 5° C. and the mixture was stirred for 1 h. The precipitated crystals were collected by filtration to give the title compound (14.8 g, yield 91.4%).

$^1$H-NMR(CDCl$_3$) δ: 1.00(6H, d, J=6.7 Hz), 1.10(2H, br), 2.25(1H, m), 3.65(2H, s), 4.20(2H, d, J=7.4 Hz), 7.07(1H, d, J=1.9 Hz), 7.08–7.28(2H, m), 7.45–7.54(4H, m), 8.32(1H, d, J=8.6 Hz)

Example 210

3-(Aminomethyl)-2-isobutyl-1-oxo-4-phenyl-1,2-dihydroisoquinoline-6-carbonitrile A mixture of 3-(aminomethyl)-6-bromo-2-isobutyl-4-phenylisoquinolin-1(2H)-one (15.0 g), zinc cyanide (2.74 g), tetrakis(triphenylphosphine)palladium (1.35 g), N-meth ylpyrrolidone (75 ml) and water (0.75 ml), was stirred under a nitrogen atmosphere at an inner temperature of 54–56° C. To the reaction mixture was added dropwise saturated aqueous ammonium chloride-25% ammonium hydroxide-water (4:1:4, 37.5 ml) over 30 min at the same temperature, and the mixture was stirred for 1 h and below 5° C. for 1 h. The obtained crystals were collected by filtration and suspended in acetonitrile (105 ml). The suspension was dissolved at 80° C. To the obtained solution was added activated carbon (0.75 g) and the mixture was stirred for 10 min. The activated carbon was filtered off and washed with acetonitrile (15 ml). The filtrate was combined and cooled to 25° C. to give crystals. Water (120 ml) was added dropwise and the obtained mixture was cooled to 5° C. and stirred for 1 h. The obtained crystals were collected by filtration to give the title compound (9.6 g, yield 74.5%).

$^1$H-NMR(300 MHz, CDCl$_3$) δ: 1.01(6H, d, J=6.8 Hz), 1.13(2H, br), 2.22–2.31(1H, m), 3.69(2H, s), 4.23(2H, d, J=7.5 Hz), 5.55–5.95(2H, br), 7.24–7.28(3H, m), 7.50–7.56 (3H, m), 7.61(1H, dd, J=1.5 Hz, 8.3 Hz), 8.55(1H, d, J=8.3 Hz)

Example 211

3-(Aminomethyl)-2-isobutyl-1-oxo-4-phenyl-1,2-dihydroisoquinoline-6-carboxamide ½ dimethyl sulfoxide solvate A mixture of 3-(aminomethyl)-2-isobutyl-1-oxo-4-phenyl-1,2-dihydroisoquinoline-6-carbonitrile (20.0 g), 2N aqueous sodium-hydroxide solution (6 ml), dimethyl sulfoxide (100 ml) and water (40 ml) was stirred at an inner temperature of 85° C. for 30 min. The reaction mixture was cooled to 40° C., cooled to not higher than 5° C. and stirred for 1 h. The precipitated crystals were collected by filtration and washed twice with water (40 ml) to give the title compound (21.7 g) as pale yellow crystals.

$^1$H-NMR(300 MHz, CDCl$_3$) δ: 1.01(6H, d, J=6.7 Hz), 2.20–2.32(1H, m), 2.62(6H, s; DMSO), 3.68(2H, s), 4.24 (2H, d, J=7.4 Hz), 5.55–5.95(2H, br), 7.25–7.30(2H, m), 7.39(1H, d, J=1.6 Hz), 7.45–7.55(3H, m), 7.79(1H, dd, J=1.5 Hz, 8.3 Hz), 8.54(1H, d, J=8.3 Hz)

Example 212

3-(Aminomethyl)-2-isobutyl-1-oxo-4-phenyl-1,2-dihydroisoquinoline-6-carboxamide

A mixture of 3-(aminomethyl)-2-isobutyl-1-oxo-4-phenyl-1,2-dihydroisoquinoline-6-carboxamide (10 g), methanol (40 ml) and 1N hydrochloric acid (20 ml) was heated to 60° C. 1N Hydrochloric acid (ca. 7 ml) was added to the reaction mixture at around the same temperature to adjust pH to 2.0, and activated, carbon (0.5 g) was added. The mixture was stirred for about 10 min and activated carbon was filtered off. The obtained solution was washed with methanol-water (2:1) (10 ml) and heated again to around 60° with stirring. 5% Ammonium hydroxide was added to the reaction mixture while keeping the same temperature to adjust pH to 7.3, and water (10 ml) was added dropwise. The obtained mixture was cooled to 25° C., ice-cooled and stirred at around 5° C. for 1 h. The precipitated crystals (8.48 g) were collected by filtration, suspended in ethyl acetate (85 ml) and stirred at around 75° C. for 2 h. The obtained mixture was allowed to cool for 1 h, ice-cooled and stirred at around 5° C. for 1 h. The precipitated crystals were collected by filtration and washed with previously-cooled ethyl acetate (17 ml) to give the title compound as crystals (8.02 g).

| Powder X-ray crystal diffraction data | |
|---|---|
| Diffraction angle: 2θ(°) (angstrom) | spacing: d value |
| 8.96 | 9.86 |
| 13.7 | 6.46 |
| 15.9 | 5.56 |
| 16.6 | 5.34 |
| 22.8 | 3.89 |
| 24.4 | 3.65 |
| 24.7 | 3.60 |
| 25.3 | 3.52 |
| 25.7 | 3.46 |

Example 213

7-(Aminomethyl)-6-isobutyl-8-phenyl[1,3]dioxolo[4,5-g]isoquinolin-5(6H)-one

This compound was synthesized according to the method similar to that in Example 106.

$^1$H-NMR(CDCl$_3$) δ: 0.99 (6H, d, J=6.6 Hz), 1.32 (2H, br), 2.26 (1H, m), 3.64 (2H, s), 4.19 (2H, d, J=7.6 Hz), 6.00 (2H, s), 6.29 (1H, s), 7.23–7.28 (2H, m), 7.40–7.54 (3H, m), 7.83 (1H, s).

Example 214

Ethyl 2-[3-(aminomethyl)-2-isobutyl-1-oxo-4-phenyl-1,2-dihydro-6-isoquinolinyl]-4-methyl-1,3-thiazole-5-carboxylate hydrochloride (1) A solution of 9H-fluoren-9-ylmethyl[6-(aminocarbothioyl)-2-isobutyl-1-oxo-4-phenyl-1,2-dihydro-3-isoquinolinyl]methylcarbamate (1.76 g, 3 mmol) and ethyl 2-choloroacetate (0.99 g, 6 mmol) in ethanol (20 ml) was refluxed under heating for 12 h. The reaction mixture was poured into water and extracted with ethyl acetate. The extract was washed with brine, dried over anhydrous magnesium sulfate and concentrated under reduced pressure. The residue was purified by silica gel column chromatography to give ethyl 2-[3-({[(9H-fluoren-9-ylmethoxy)carbonyl]amino}methyl)-2-isobutyl-1-oxo-4-phenyl-1,2-dihydro-6-isoquinolinyl]-4-methyl-1,3thiazole-5-carboxylate (1.46 g, 69.9%) as crystals.

Melting point 157–158° C. Elemental analysis for C$_{42}$H$_{39}$N$_3$O$_5$S Calculated: C, 72.29; H, 5.63; N, 6.02. Found: C, 72.12; H, 5.69; N, 5.79. $^1$H-NMR(CDCl$_3$) δ: 0.99 (6H, d, J=6.9 Hz), 1.37 (3H, t, J=7.2 Hz), 2.12–2.29 (1H, m), 2.69 (3H, s), 4.08 (2H, d, J=6.0 Hz), 4.21 (1H, t, J=6.9 Hz), 4.26 (2H, d, J=4.8 Hz), 4.33 (2H, q, J=7.2 Hz), 4.44 (2H, d, J=6.9 Hz), 5.23 (1H, bs), 7.26–7.45 (7H, m), 7.51–7.60 (5H, m), 7.75 (2H, d, J=7.5 Hz), 7.97 (1H, d, J=8.4 Hz), 8.46 (1H, d, J=8.4 Hz).

(2) To a solution of ethyl 2-[3-({[(9H-fluoren-9-ylmethoxy)carbonyl]amino}methyl)-2-isobutyl-1-oxo-4-phenyl-1,2-dihydro-6-isoquinolinyl]-4-methyl-1,3-thiazole-5-carboxylate (1.40 g, 2 mmol) in N,N-dimethylformamide (20 ml) was added pyridine (1 ml). The mixture was stirred at room temperature for 1 h. The reaction mixture was poured into water and extracted with ethyl acetate. The extract was washed with brine, dried over anhydrous magnesium sulfate and concentrated under reduced pressure. The residue was dissolved in tetrahydrofuran (20 ml), and di-t-butyl dicarbonate (0.69 ml, 3 mmol) was added thereto. The resulting mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl 2-(3-{[(tert-butoxycarbonyl)amino]methyl}-2-isobutyl-1-oxo-4-phenyl-1,2-dihydro-6-isoquinolinyl)-4-methyl-1,3-thiazole-5-carboxylate (0.88 g, 76.5%) as crystals.

Melting point 201–202° C. Elemental analysis for $C_{30}H_{37}N_3O_5S$ Calculated: C, 66.76; H, 6.48; N, 7.30. Found: C, 66.85; H, 6.56; N, 7.27. $^1$H-NMR(CDCl$_3$) δ: 1.02 (6H, d, J=6.6 Hz), 1.37 (3H, t, J=7.0 Hz), 1.44 (9H, s), 2.18–2.32 (1H, m), 2.71 (3H, s), 4.19 (2H, d, J=7.4 Hz), 4.22 (2H, d, J=5.6 Hz), 4.33 (2H, q, J=7.0 Hz), 4.69 (1H, bs), 7.28–7.34 (2H, m), 7.46 (1H, d, J=1.6 Hz), 7.51–7.62 (3H, m), 8.00 (1H, dd, J=1.6, 8.4 Hz), 8.49 (1H, d, J=8.4 Hz).

(3) Ethyl 2-(3-{[(tert-butoxycarbonyl)amino]methyl}-2-isobutyl-1-oxo-4-phenyl-1,2-dihydro-6-isoquinolinyl)-4-methyl-1,3-thiazole-5-carboxylate (0.14 g, 0.5 mmol) was dissolved in a solution of 4N hydrogen chloride in ethyl acetate (5 ml). The solution was stirred at room temperature for 1 h. The reaction mixture was concentrated under reduced pressure, and the precipitated crystals were recrystallized from methanol-diisopropyl ether to give ethyl 2-[3-(aminomethyl)-2-isobutyl-1-oxo-4-phenyl-1,2-dihydro-6-isoquinolinyl]-4-methyl-1,3-thiazole-5-carboxylate hydrochloride (0.11 g, 91.7%) as crystals.

Melting point 286–287° C. Elemental analysis for $C_{27}H_{30}N_3O_3ClS$ 0.25H$_2$O Calculated: C, 62.78; H, 5.95; N, 8.13. Found: C, 62.94; H, 6.35; N, 8.11. $^1$H-NMR(DMSO-d$_6$) δ: 0.94 (6H, d, J=6.6 Hz) 1.29 (3H, t, J=7.2 Hz), 2.02–2.21 (1H, m), 2.63 (3H, s), 3.90 (2H, s), 4.10 (2H, d, J=7.8 Hz), 4.28 (2H, q, J=7.2 Hz), 7.44–7.52 (3H, m), 7.61–7.65 (3H, m), 8.14 (1H, dd, J=1.6, 8.4 Hz), 8.46 (1H, d, J=8.4 Hz), 8.59 (3H, bs)

Example 215

2-[3-(Aminomethyl)-2-isobutyl-1-oxo-4-phenyl-1,2-dihydro-6-isoquinolinyl]-4-methyl-1,3-thiazole-5-carboxylic acid hydrochloride (1) To a solution of ethyl 2-(3-{[(tert-butoxycarbonyl)amino]methyl}-2-isobutyl-1-oxo-4-phenyl-1,2-dihydro-6-isoquinolinyl)-4-methyl-1,3-thiazole-5-carboxylate (0.69 g, 1.2 mmol) in tetrahydrofuran (10 ml) and ethanol (10 ml) was added 1N sodium hydroxide solution (3 ml). The resulting mixture was stirred at room temperature for 2 h. The reaction mixture was poured into water, acidified with 1N hydrochloric acid and extracted with ethyl acetate. The extract was washed with brine, dried over anhydrous magnesium sulfate and concentrated under reduced pressure. The residue was crystallized from ethyl acetate-n-hexane to give 2-(3-{[(tert-butoxycarbonyl)amino]methyl}-2-isobutyl-1-oxo-4-phenyl-1,2-dihydro-6-isoquinolinyl)-4-methyl-1,3-thiazole-5-carboxylic acid (0.61 g, 93.8%) as crystals.

Melting point 184–186° C. Elemental analysis for $C_{30}H_{33}N_3O_5S$ Calculated: C, 65.79; H, 6.07; N, 7.67. Found: C, 65.60; H, 6.23; N, 7.46. $^1$H-NMR(CDCl$_3$) δ: 1.01 (6H, d, J=6.6 Hz), 1.50 (9H, s), 2.14–2.28 (1H, m), 2.67 (3H, s), 4.08 (2H, d, J=6.6 Hz), 4.17 (2H, s), 5.84 (1H, bs), 7.38–7.44 (2H, m), 7.51–7.71 (5H, m), 8.28 (1H, d, J=8.8 Hz).

(2) 2-(3-{[(Tert-butoxycarbonyl-)amino]methyl}-2-isobutyl-1-oxo-4-phenyl-1,2-dihydro-6-isoquinolinyl)-4-methyl-1,3-thiazole-5-carboxylic acid (0.17 g, 0.3 mmol) was dissolved in a solution of 4N hydrogen chloride in ethyl acetate (5 ml). The solution was stirred at room temperature for 1 h. The reaction mixture was concentrated under reduced pressure, and the residue was crystallized from ethyl acetate to give 2-[3-(aminomethyl)-2-isobutyl-1-oxo-4-phenyl-1,2-dihydro-6-isoquinolinyl]-4-methyl-1,3-thiazole-5-carboxylic acid hydrochloride (0.12 g, 92.3%) as crystals.

Melting point 239–241° C. Elemental analysis for $C_{25}H_{26}N_3O_3ClS$ H$_2$O Calculated: C, 59.82; H, 5.62; N, 8.37. Found: C, 59.64; H, 5.46; N, 8.08. $^1$H-NMR(DMSO-d$_6$) δ: 0.94 (6H, d, J=6.6 Hz), 2.02–2.21 (1H, m), 2.61 (3H, s), 3.91 (2H, s), 4.10 (2H, d, J=8.8 Hz), 7.44–7.49 (3H, m), 7.61–7.66 (3H, m), 8.12 (1H, dd, J=1.4, 8.4 Hz), 8.45 (1H, d, J=8.4 Hz), 8.64 (3H, bs).

Example 216

2-[3-(Aminomethyl)-2-isobutyl-1-oxo-4-phenyl 1,2-dihydro-6-isoquinolinyl]-4-methyl-1,3-thiazole-5-carboxamide hydrochloride (1) A solution of 2-(3-{[(tert-butoxycarbonyl)amino]methyl}-2-isobutyl-1-oxo-4-phenyl-1,2-dihydro-6-isoquinolinyl)-4-methyl-1,3-thiazole-5-carboxylic acid (0.44 g, 0.8 mmol), 1-ethyl-3-(3-dimethylaminopropyl)carbodiimide hydrochloride (0.31 g, 1.6 mmol) and 1-hydroxybenzotriazole ammonium salt (0.24 g, 1.6 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The resulting crystals were recrystallized from ethyl acetate-diisopropyl ether to give tert-butyl{6-[5-(aminocarbonyl)-4-methyl-1,3-thiazol-2-yl]-2-isobutyl-1-oxo-4-phenyl-1,2-dihydro-3-isoquinolinyl}methylcarbamate (0.38 g, 86.4%) as crystals.

Melting point 227–228° C. Elemental analysis for $C_{30}H_{34}N_4O_4S$ Calculated: C, 65.91; H, 6.27; N, 10.25. Found: C, 65.70; H, 6.19; N, 10.35. $^1$H-NMR(CDCl$_3$) δ: 1.01 (6H, d, J=6.4 Hz), 1.45 (9H, s), 2.12–2.31 (1H, m), 2.66 (3H, s), 4.08 (2H, d, J=7.4 Hz), 4.20 (2H, d, J=5.2 Hz), 5.00 (1H, bs), 5.84 (2H, bs), 7.31–7.37 (3H, m), 7.52–7.61 (3H, m), 7.92 (1H, dd, J=1.6, 8.4 Hz), 8.41 (1H, d, J=8.4 Hz)

(2) Tert-butyl{6-[5-(aminocarbonyl)-4-methyl-1,3-thiazol-2-yl]-2-isobutyl-1-oxo-4-phenyl-1,2-dihydro-3-isoquinolinyl}methylcarbamate (0.14 g, 0.25 mmol) was dissolved in a solution of 4N hydrogen chloride in ethyl acetate (5 ml). The solution was stirred at room temperature for 1 h. The reaction was concentrated under reduced pressure, and the resulting crystals were recrystallized from methanol-ethyl acetate to give 2-[3-(aminomethyl)-2-isobutyl-1-oxo-4-phenyl-1,2-dihydro-6-isoquinolinyl]-4-methyl-1,3-thiazole-5-carboxamide hydrochloride (0.11 g, 91.7%) as crystals.

Melting point 222–224° C. $^1$H-NMR(DMSO-d$_6$) δ: 0.94 (6H, d, J=6.6 Hz), 2.02–2.21 (1H, m), 2.56 (3H, s), 3.89 (2H, s), 4.10 (2H, d, J=6.4 Hz), 7.42–7.49 (3H, m), 7.61–7.78 (5H, m), 8.09 (1H, d, J=8.6 Hz), 8.46 (1H, d, J=8.6 Hz), 8.54 (3H, bs).

Example 217

2-[3-(Aminomethyl)-2-isobutyl-1-oxo-4-phenyl-1,2-dihydro-6-isoquinolinyl]-4-methyl-1,3-thiazole-5-carbonitrile hydrochloride (1) A solution of tert-butyl{6-[5-(aminocarbonyl)-4-methyl-1,3-thiazol-2-yl]-2-isobutyl-1-oxo-4-phenyl-1,2-dihydro-3-isoquinolinyl}methylcarbamate (0.16 g, 0.3 mmol) and cyanuric chloride (0.17 g, 0.9 mmol) in N,N-dimethylformamide (10 mmol) was stirred at 0° C. for 1 h. The resulting reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(5-cyano-4-methyl-1,3-thiazol-2-yl)-2-isobutyl-1-oxo-4-phenyl-1,2-dihydro-3-isoquinolinyl]methylcarbamate (0.15 g, 93.8%) as crystals.

Melting point 209–211° C. Elemental analysis for $C_{30}H_{32}N_4O_3S$ Calculated: C, 68.16; H, 6.10; N, 10.60. Found: C, 68.17; H, 5.99; N, 10.70. $^1$H-NMR(CDCl$_3$) δ: 1.04 (6H, d, J=6.6 Hz), 1.44 (9H, s), 2.14–2.36 (1H, m), 2.61 (3H, s), 4.10 (2H, d, J=7.2 Hz), 4.23 (2H, d, J=5.4 Hz), 4.63 (1H, bs), 7.27–7.32 (2H, m), 7.42 (1H, d, J=1.5 Hz), 7.53–7.60 (3H, m), 7.97 (1H, dd, J=1.5, 8.4 Hz), 8.52 (1H, d, J=8.4 Hz).

(2) Tert-butyl[6-(5-cyano-4-methyl-1,3-thiazol-2-yl)-2-isobutyl-1-oxo-4-phenyl-1,2-dihydro-3-isoquinolinyl]methylcarbamate (0.21 g, 0.4 mmol) was dissolved in a solution of 4N hydrogen chloride in ethyl acetate (5 ml). The solution was stirred at room temperature for 1 h. The reaction mixture was concentrated under reduced pressure, and the residue was crystallized from ethyl acetate to give 2-[3-(aminomethyl)-2-isobutyl-1-oxo-4-phenyl-1,2-dihydro-6-isoquinolinyl]-4-methyl-1,3-thiazole-5-carbonitrile hydrochloride (0.11 g, 91.7%) as crystals.

Melting point 284–285° C. Elemental analysis for $C_{25}H_{25}N_4OClS$ 0.25H$_2$O Calculated: C, 63.95; H, 5.47; N, 11.93. Found: C, 64.00; H, 5.45; N, 11.73. $^1$H-NMR (DMSO-d$_6$) δ: 0.94 (6H, d, J=6.6 Hz), 2.06–2.21 (1H, m), 2.54 (3H, s), 3.89 (2H, s) 4.11 (2H, d, J=7.6 Hz), 7.44–7.49 (2H, m), 7.52 (1H, d, J=1.5 Hz), 7.60–7.63 (3H, m), 8.11 (1H, dd, J=1.5, 8.4 Hz), 8.48 (1H, d, J=8.4 Hz), 8.63 (3H, bs).

Example 218

Ethyl 2-[3-(aminomethyl)-4-butoxy-2-isobutyl-1-oxo-1,2-dihydro-6-isoquinolinyl]-4-methyl-1,3-thiazole-5-carboxylate hydrochloride (1) A solution of 9H-fluoren-9-ylmethyl[6-(aminocarbothioyl)-4-butoxy-2-isobutyl-1-oxo-1,2-dihydro-3-isoquinolinyl]methylcarbamate (2.33 g, 4 mmol) and ethyl 2-chloroacetate (1.32 g, 8 mmol) in ethanol (20 ml) was refluxed under heating for 10 h. The resulting reaction mixture was poured into water and extracted with ethyl acetate. The extract was washed with brine, dried over anhydrous magnesium sulfate and concentrated under reduced pressure. The residue was purified by silica gel column chromatography to give ethyl 2-[4-butoxy-3-({[(9H-fluoren-9-ylmethoxy)carbonyl]amino}methyl)-2-isobutyl-1-oxo-1,2-dihydro-6-isoquinolinyl]-4methyl-1,3-thiazole-5-carboxylate (1.81 g, 65.3%) as crystals.

Melting point 203–204° C. Elemental analysis for $C_{40}H_{43}N_3O_6S$ Calculated: C, 69.24; H, 6.25; N, 6.06. Found: C, 69.08; H, 6.11; N, 5.99. $^1$H-NMR(CDCl$_3$) δ: 0.97 (6H, d, J=6.6 Hz), 1.07 (3H, t, J=7.2 Hz), 1.42 (3H, t, J=7.2 Hz), 1.58–1.75 (2H, m), 1.84–1.97 (2H, m), 2.04–2.23 (1H, m), 2.81 (3H, s), 3.92 (2H, t, J=6.4 Hz), 4.00 (2H, d, J=7.2 Hz), 4.23 (1H, t, J=6.8 Hz), 4.39 (2H, q, J=7.2 Hz) 4.49 (2H, d, J=6.8 Hz), 4.59 (2H, d, J=5.6 Hz), 5.29 (1H, bs), 7.28–7.43 (4H, m), 7.60 (2H, d, J=7.4 Hz), 7.75 (2H, d, J=7.0 Hz), 8.05 (1H, dd, J=1.8, 8.4 Hz), 8.24 (1H, d, J=1.8 Hz), 8.44 (1H, d, J=8.4 Hz).

(2) To a solution of ethyl 2-[4-butoxy-3-({[(9H-fluoren-9-ylmethoxy)carbonyl]amino}methyl)-2-isobutyl-1-oxo-1,2-dihydro-6-isoquinolinyl]-4-methyl-1,3-thiazole-5-carboxylate (1.73 g, 2.5 mmol) in N,N-dimethylformamide (20 ml) and tetrahydrofuran (10 ml) was added pyrrolidine (2 ml). The resulting mixture was stirred at room temperature for 1 h. The reaction was poured into water and extracted with ethyl acetate. The extract was washed with brine, dried over anhydrous magnesium sulfate and concentrated under reduced pressure. The residue was dissolved in tetrahydrofuran (20 ml), and di-t-butyl dicarbonate (0.9 ml, 3.8 mmol) was added thereto. The resulting mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give ethyl 2-(4-butoxy-3-{[(tert-butoxycarbonyl)amino]methyl}-2-isobutyl-1-oxo-1,2-dihydro-6-isoquinolinyl)-4-methyl-1,3-thiazole-5-carboxylate (1.15 g, 80.4%) as crystals.

Melting point 145.5–147° C. Elemental analysis for $C_{30}H_{41}N_3O_6S$ Calculated: C, 63.02; H, 7.23; N, 7.35. Found: C, 63.00; H, 7.30; N, 7.28. $^1$H-NMR(CDCl$_3$) δ: 0.97 (6H, d, J=6.6 Hz), 1.08 (3H, t, J=7.3 Hz), 1.41 (3H, t, J=7.2 Hz), 1.47 (9H, s), 1.57–1.76 (2H, m), 1.85–1.99 (2H, m), 2.08–2.24 (1H, m), 2.81 (3H, s), 3.92 (2H, t, J=6.4 Hz), 4.00 (2H, d, J=7.8 Hz), 4.38 (2H, q, J=7.2 Hz), 4.54 (2H, d, J=5.6 Hz), 4.87 (1H, bs), 8.05 (1H, dd, J=1.8, 8.6 Hz), 8.26 (1H, d, J=1.8 Hz), 8.46 (1H, d, J=8.6 Hz).

(3) Ethyl 2-(4-butoxy-3-{[(tert-butoxycarbonyl)amino]methyl}-2-isobutyl-1-oxo-1,2-dihydro-6-isoquinolinyl)-4-methyl-1,3-thiazole-5-carboxylate (0.17 g, 0.3 mmol) was dissolved in a solution of 4N hydrogen chloride in ethyl; acetate (5 ml). The solution was stirred at room temperature for 1 h. The reaction mixture was concentrated under reduced pressure, and the residue was crystallized from ethyl acetate to give ethyl 2-[3-(aminomethyl)-4-butoxy-2-isobutyl-1-oxo-1,2-dihydro-6-isoquinolinyl]-4-methyl-1,3-thiazole-5-carboxylate hydrochloride (0.14 g, 93.3%) as crystals.

Melting point 250–254° C. Elemental analysis for $C_{25}H_{34}N_3O_4ClS$ Calculated: C, 59.10; H, 6.75; N, 8.27.Found: C, 58.90; H, 6.84; N, 8.25. $^1$H-NMR(DMSO-d$_6$) δ: 0.90 (6H, d, J=6.6 Hz), 1.05 (3H, t, J=7.1 Hz), 1.33 (3H, t, J=7.0 Hz), 1.57–1.76 (2H, m), 1.82–1.95 (2H, m), 1.00–2.18 (1H, m), 2.74 (3H, s), 3.97–4.00 (4H, m), 4.21 (2H, s), 4.33 (2H, q, J=7.0 Hz), 8.18 (1H, d, J=8.4 Hz), 8.32 (1H, s), 8.39 (1H, d, J=8.4 Hz), 8.67 (3H, bs).

Example 219

2-[3-(Aminomethyl)-4-butoxy-2-isobutyl-1-oxo-1,2-dihydro-6-isoquinolinyl]-4-methyl-1,3-thiazaole-5-carboxylic acid hydrochloride (1) To a solution of ethyl 2-(4-butoxy-3-{[(tert-butoxycarbonyl)amino]methyl}-2-isobutyl-1-oxo-1,2-dihydro-6-isoquinolinyl)-4-methyl-1,3-thiazole-5-carboxylate (0.91 g, 1.6 mmol) in tetrahydrofuran (5 ml) and ethanol (5 ml) was added 1N sodium hydroxide solution (3 ml). The resulting mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The resulting crystals were recrystallized from ethyl acetate-diisopropyl ether to give 2-(4-butoxy-3-{[(tert-butoxycarbonyl)amino]methyl}-2-isobutyl-1-oxo-1,2-dihydro-6-isoquinolinyl)-4-methyl-1,3-thiazole-5-carboxylic acid (0.78 g, 89.7%) as crystals.

Melting point 107–109° C. Elemental analysis for $C_{28}H_{37}N_3O_6S$ 0.5$H_2O$ Calculated: C, 60.85; H, 6.93; N, 7.60. Found: C, 60.73; H, 6.92; N, 7.41. $^1$H-NMR(CDCl$_3$) δ: 0.96 (6H, d, J=6.6 Hz), 1.11 (3H, t, J=7.3 Hz), 1.52 (9H, s), 1.60–1.78 (2H, m), 1.87–2.01 (2H, m), 2.04–2.21 (1H, m), 2.82 (3H, s), 3.89–3.98 (4H, m), 4.54 (2H, d, J=4.8 Hz), 5.71 (1H, bs), 7.91 (1H, d, J=8.3 Hz), 8.10 (1H, s), 8.29 (1H, d, J=8.3 Hz).

(2) 2-(4-Butoxy-3-{[(tert-butoxycarbonyl)amino]methyl}-2-isobutyl-1-oxo-1,2-dihydro-6-isoquinolinyl)-4-methyl-1,3-thiazole-5-carboxylic acid (0.16 g, 0.3 mmol) was dissolved in a solution of 4N hydrogen chloride in ethyl acetate (5 ml). The solution was stirred at room temperature for 1 h. The reaction mixture was concentrated under reduced pressure, and the residue was crystallized from ethyl acetate to give 2-[3-(aminomethyl)-4-butoxy-2-isobutyl-1-oxo-1,2-dihydro-6-isoquinolinyl]-4-methyl-1,3-thiazole-5-carboxylic acid hydrochloride (0.13 g, 92.9%) as crystals.

Melting point 275–276° C. Elemental analysis for. Calcd for $C_{23}H_{30}N_3O_4ClS$ 0.25$H_2O$ Calculated: C, 57.01; H, 6.34; N, 8.67. Found: C, 57.03; H, 6.28; N, 8.51. $^1$H-NMR (DMSO-d$_6$) δ: 0.90 (6H, d, J=6.6 Hz), 1.05 (3H, t, J=7.4, Hz), 1.59–1.72 (2H, m), 1.83–1.91 (2H, m), 1.99–2.16 (1H, m), 2.72 (3H, s), 3.98–4.06 (4H, m), 4.21 (2H, s), 8.18 (1H, d, J=8.1 Hz), 8.31 (1H, s) 8.39 (1H, d, J=8.1 Hz), 8.65 (3H, bs).

Example 220

2-[3-(Aminomethyl)-4-butoxy-2-isobutyl-1-oxo-1,2-dihydro-6-isoquinolinyl]-4-methyl-1,3-thiazole-5-carboxamide hydrochloride (1) A solution of 2-(4-butoxy-3-{[(tert-butoxycarbonyl)amino]methyl}-2-isobutyl-1-oxo-1,2-dihydro-6-isoquinolinyl)-4-methyl-1,3-thiazole-5-carboxylic acid (0.60 g, 1.1 mmol), 1-ethyl,-3-(3-dimethylaminopropyl)carbodiimide hydrochloride (0.42 g, 2.2 mmol) and 1-hydroxybenzotriazole ammonium salt (0.33 g, 2.2 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The resulting crystals were recrystallized from tetrahydrofuran-diisopropyl ether to give tert-butyl{6-[5-(-aminocarbonyl)-4-methyl-1,3-thiazol-2-yl]-4-butoxy-2-isobutyl-1-oxo-1,2-dihydro-3-isoquinolinyl}methylcarbamate (0.58 g, 96.7%) as crystals.

Melting point 233.5–234° C. Elemental analysis for $C_{28}H_{38}N_4O_4S$ Calculated: C, 61.97; H, 7.06; N, 10.32. Found: C, 61.95; H, 7.07; N, 10.19. $^1$H-NMR(CDCl$_3$) δ: 0.97 (6H, d, J=6.6 Hz), 1.07 (3H, t, J=7.3 Hz), 1.49 (9H, s), 1.55–1.71 (2H, m), 1.80–1.98 (2H, m), 2.05–2.24 (1H, m), 2.78 (3H, s), 3.91 (2H, t, J=6.4 Hz), 3.99 (2H, d, J=7.4 Hz), 4.53 (2H, d, J=5.0 Hz), 5.05 (1H, bs), 5.94 (2H, bs), 7.98 (1H, dd, J=1.6, 8.6 Hz), 8.19 (1H, d, J=1.6 Hz), 8.42 (1H, d, J=8.6 Hz).

(2) Tert-butyl{6-[5-(aminocarbonyl)-4-methyl-1,3-thiazol-2-yl]-4-butoxy-2-isobutyl-1-oxo-1,2-dihydro-3-isoquinolinyl}methylcarbamate (0.22 g, 0.4 mmol) was dissolved in a solution of 4N hydrogen chloride in ethyl acetate (5 ml). The solution was stirred at room temperature for 1 h. The reaction mixture was concentrated under reduced pressure, and the residue was crystallized from ethyl acetate to give 2-[3-(aminomethyl)-4-butoxy-2-isobutyl-1-oxo-1,2-dihydro-6-isoquinolinyl]-4-methyl-1,3-thiazole-5-carboxamide hydrochloride (0.18 g, 94.7%) as crystals.

Melting point 270–271° C. Elemental analysis for $C_{23}H_{31}N_4O_3ClS$ Calculated: C, 57.67; H, 6.52; N, 11.70. Found: 57.37; H, 6.46; N, 11.62. $^1$H-NMR(DMSO-d$_6$) δ: 0.90 (6H, d, J=6.6 Hz), 1.05 (3H, t, J=7.1 Hz), 1.56–1.74 (2H, m), 1.82–2.18 (3H, m), 2.67 (3H, s), 3.97–4.00 (4H, m), 4.21 (2H, s) 7.77 (2H, bs), 8.27 (1H, d, J=1.5 Hz), 8.39 (1H, dd, J=1.5, 8.4 Hz), 8.39 (1H, d, J=8.4 Hz), 8.66 (3H, bs).

Example 221

2-[3-(Aminomethyl)-4-butoxy-2-isobutyl-1-oxo-1,2-dihydro-6-isoquinolinyl]-4-methyl-1,3-carbonitrile hydrochloride (1) A solution of tert-butyl{6-[5-(aminocarbonyl)-4-methyl-1,3-thiazol-2-yl]-4-butoxy-2-isobutyl-1-oxo-1,2-dihydro-3-isoquinolinyl}methylcarbamate (0.33 g, 0.6 mmol) and cyanuric chloride (0.33 g, 1.8 mmol) in N,N-dimethylformamide (10 mmol) was stirred for 1 h at 0° C. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-6-(5-cyano-4-methyl-1,3-thiazol-2-yl)-2-isobutyl-1-oxo-1,2-dihydro-3-isoquinolinyl]methylcarbamate (0.25 g, 80.6%) as crystals.

Melting point 148.5–149.5° C. Elemental analysis for $C_{28}H_{36}N_4O_4S$ Calculated: C, 64.10; H, 6.92; N, 10.68. Found: C, 64.04; H, 6.96; N, 10.63. $^1$H-NMR(CDCl$_3$) δ: 0.98 (6H, d, J=6.6 Hz), 1.08 (3H, t, J=7.3 Hz), 1.47 (9H, s), 1.57–1.75 (2H, m), 1.84–1.98 (2H, m), 2.08–2.28 (1H, m), 2.72 (3H, s), 3.91 (2H, t, J=6.4 Hz), 4.01 (2H, d, J=7.4 Hz), 4.54 (2H, d, J=5.6 Hz), 4.80 (1H, bs), 8.02 (1H, dd, J=1.8, 8.2 Hz), 8.24. (1H, d, J=1.8 Hz), 8.48 (1H, d, J=8.2 Hz).

(2) Tert-butyl[4-butoxy-6-(5-cyano-4-methyl-1,3-thiazol-2-yl)-2-isobutyl-1-oxo-1,2-dihydro-3-isoquinolinyl]methylcarbamate (0.21 g, 0.4 mmol) was dissolved in a solution of 4N hydrogen chloride in ethyl acetate (5 ml). The solution was stirred at room temperature for 1 h. The reaction mixture was concentrated under reduced pressure and the residue was crystallized from ethyl acetate-diisopropyl ether to give 2-[3-(aminomethyl)-4-butoxy-2-isobutyl-1-oxo-1,2-dihydro-6-isoquinolinyl]-4-methyl-1,3-thiazole-5-carbonitrile hydrochloride (0.17 g, 94.4%) as crystals.

Melting point 166–168° C. Elemental analysis for $C_{23}H_{29}N_4O_2ClS$ 0.5$H_2O$ Calculated: C, 58.77; H, 6.63; N, 11.92. Found: C, 58.58; H, 6.45; N, 11.91. $^1$H-NMR (DMSO-d$_6$) δ: 0.90 (6H, d, J=6.6 Hz), 1.04 (3H, t, J=7.4 Hz), 1.55–1.73 (2H, m), 1.82–1.95 (2H, m), 1.98–2.16 (1H, m), 2.66 (3H, s), 3.98–4.01 (4H, m), 4.22 (2H, s), 8.17 (1H, dd, J=8.4 Hz), 8.30 (1H, d, J=1.8 Hz), 8.42 (1H, d, J=8.4 Hz), 8.69 (3H, bs).

Example 222

3-(Aminomethyl)-6-(4-amino-1,3-thiazol-2-yl)-2-isobutyl-4-phenyl-1(2H)-isoquinolinone dihydrochloride (1) A solution of 2-(3-{[(tert-butoxycarbonyl)amino]methyl}-2-isobutyl-1-oxo-4-phenyl- 1,2-dihydro-6-isoquinolinyl)-1,3-thiazole-4-carboxylic acid (1.60 g, 3 mmol), diphenylphosphoryl azide (0.78 ml, 3.6 mmol) and triethylamine (0.50 ml, 3.6 mmol) in N,N-dimethylformamide (10 ml) was stirred at room temperature for 1 h. The reaction mixture was poured into water and extracted with ethyl acetate. The extract was washed with brine dried over anhydrous magnesium sulfate and concentrated under reduced pressure. The residue was dissolved in toluene (20 ml) and refluxed for 1 h. To the resulting mixture was added 9-fluorenylmethanol (0.88 g, 4.5 mmol), and the mixture was stirred at 100° C. for 3 h. The reaction mixture was poured into water and extracted with ethyl acetate. The extract was washed with brine, dried over anhydrous magnesium sulfate and concentrated under reduced pressure. The residue was purified by silica gel column chromatography to give 9H-fluoren-9-ylmethyl 2-(3-{[(tert-butoxycarbonyl)amino]methyl}-2-isobutyl-1-oxo-4-phenyl-1,2-dihydro-6-isoquinolinyl)-1,3-thiazol-4-ylcarbamate (1.12 g, 51.4%) as an amorphous solid.

$^1$H-NMR(CDCl$_3$) δ: 1.01 (6H, d, J=6.6 Hz), 1.44 (9H, s), 2.19–2.32 (1H, m), 4.07 (2H, d, J=6.6 Hz), 4.11–4.22 (3H, m), 4.45 (2H, s), 4.63 (1H, bs), 7.24–7.56 (13H, m), 7.77 (2H, d, J=7.5 Hz), 7.88 (1H, d, J=7.8 Hz), 7.97 (1H, bs), 8.47 (1H, d, J=7.8 Hz).

(2) To a solution of 9H-fluoren-9-ylmethyl 2-(3-{[(tert-butoxycarbonyl)amino]methyl}-2-isobutyl-1-oxo-4-phenyl-1,2-dihydro-6-isoquinolinyl)-1,3-thiazol-4-ylcarbamate (1.09 g, 1.5 mmol) in N,N-dimethylformamide (20 ml) was added pyrrolidine (1 ml). The mixture was stirred at room temperature for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(4-amino-1,3 2-yl)-2-isobutyl-1-oxo-4-phenyl-1,2-dihydro-3-isoquinolinyl]methylcarbamate (0.59 g, 78.7%) as crystals.

Melting point 195–196° C. Elemental analysis for C$_{28}$H$_{32}$N$_4$O$_3$S 0.25H$_2$O Calculated: C, 66.05; H, 6.43; N, 11.00 Found: C, 66.20; H, 6.54; N, 10.96. $^1$H-NMR(CDCl$_3$) δ: 1.01 (6H, d, J=6.6 Hz), 1.43 (9H, s), 1.98–2.35 (1H, m), 4.08 (2H, d, J=7.8 Hz), 4.14 (2H, bs), 4.21 (2H, d, J=5.8 Hz), 4.58 (1H, bs), 5.95 (1H, s), 7.27–7.31 (2H, m), 7.42 (1H, d, J=1.6 Hz), 7.48–7.59 (3H, m), 7.91 (1H, dd, J=1.6, 8.2 Hz), 8.47 (1H, d, J=8.2 Hz).

(3) Tert-butyl[6-(4-amino-1,3-thiazol-2-yl)-2-isobutyl-1-oxo-4-phenyl-1,2-dihydro-3-isoquinolinyl]methylcarbamate (0.14 g, 0.5 mmol) was dissolved in a solution of 4N hydrogen chloride in ethyl acetate (5 ml). The solution was stirred at room temperature for 1 h. The reaction was concentrated under reduced pressure, and the residue was crystallized from ethyl acetate to give 3-(aminomethyl)-6-(4-amino-1,3-thiazol-2yl)-2-isobutyl-4-phenyl-1(2H)-isoquinolinone dihydrochloride (0.13 g, 92.9%) as crystals.

Melting point 230° C. $^1$H-NMR(DMSO-d$_6$) δ: 0.94 (6H, d, J=6.2 Hz), 1.99–2.21 (1H, m), 3.87 (2H, s), 4.10 (2H, d, J=8.2 Hz), 5.48 (3H, bs), 7.10 (1H, s), 7.16–7.62 (6H, m), 8.03 (1H, d, J=8.4 Hz), 8.44 (1H, d, J=8.4 Hz), 8.67 (3H, bs).

Example 223

N-{2-[3-(Aminomethyl)-2-isobutyl-1-oxo-4-phenyl-1,2-dihydro-6-isoquinolinyl]-1,3-thiazol-4-yl}acetamide hydrochloride (1) A solution of tert-butyl[6-(4-amino-1,3-thiazol-2-yl)-2-isobutyl-1-oxo-4-phenyl-1,2-dihydro-3-isoquinolinyl]methylcarbamate (0.20 g, 0.4 mmol) and acetyl chloride (0.04 ml, 0.6 mmol) in N,N-dimethylacetamide (10 ml) was stirred at room temperature for 2 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl{6-[4-(acetylamino)-1,3-thiazol-2-yl]-2-isobutyl-1-oxo-4-phenyl-1,2-dihydro-3-isoquinolinyl}methylcarbamate (0.18 g, 85.7%) as crystals.

Melting point 227–228° C. Elemental analysis for C$_{30}$H$_{34}$N$_4$O$_4$S Calculated: C, 65.91; H, 6.27; N, 10.25. Found: C, 65.66; H, 6.44; N, 10.17. $^1$H-NMR(CDCl$_3$) δ: 0.99 (6H, d, J=6.6 Hz), 1.47 (9H, s), 2.18–2.39 (4H, m), 4.10 (2H, bs), 4.19 (2H, bs), 7.06–7.38 (4H, m), 7.41–7.56 (3H, m), 7.61 (1H, s), 8.13 (1H, bs), 8.69 (1H, bs).

(2) Tert-butyl{6-[4-(acetylamino)-1,3-thiazol-2-yl]-2-isobutyl-1-oxo-4-phenyl-1,2-dihydro-3-isoquinolinyl}methylcarbamate (0.14 g, 0.25 mmol) was dissolved in a solution of 4N hydrogen chloride in ethyl acetate (5 ml). The solution was stirred at room temperature for 1 h. The reaction was concentrated under reduced pressure, and the residue was crystallized from ethyl acetate to give N-{2-[3-(aminomethyl)-2-isobutyl-1-oxo-4-phenyl-1,2-dihydro-6-isoquinolinyl]-1,3-thiazol-4-yl}acetamide hydrochloride (0.11 g, 91.7%) as crystals.

Melting point 242–244° C. Elemental analysis for C$_{25}$H$_{27}$N$_4$O$_2$ClS 2H$_2$O Calculated: C, 57.85; H, 6.02; N, 10.79. Found: C, 57.70; H, 5.69; N, 10.69. $^1$H-NMR (DMSO-d$_6$) δ: 0.93 (6H, d, J=6.6 Hz), 1.99–2.18 (4H, m), 3.86 (2H, s), 4.10 (2H, d, J=6.3 Hz), 7.45–7.48 (3H, m), 7.54–7.66 (4H, m), 8.05 (1H, d, J=8.6 Hz), 8.46 (1H, d, J=8.6 Hz), 8.65 (3H, bs), 11.03 (1H, s)

Example 224

Methyl 2-{[3-(aminomethyl)-2-isobutyl-1oxo-4-phenyl-1,2-dihydro-6-isoquinolinyl]-oxy}-2-methylpropanoate hydrochloride (1) To a solution of tert-butyl[6-hydroxy-2-isobutyl-4-phenyl-1-oxo-1,2-dihydro-3-isoquinolinyl]methylcarbamate (0.42 g, 1 mmol) in N,N-dimethylformamide (10 ml) was added sodium hydride (48 mg, 1.2 mmol) (60% in oil). The resulting mixture was stirred at 0° C. for 10 min. To the mixture was added methyl 2-bromoisobutyrate (0.22 g, 1.2 mmol), and the mixture was stirred at room temperature for 12 h. The reaction mixture was poured into water and extracted with ethyl acetate. The extract was washed with brine, dried over anhydrous magnesium sulfate and concentrated under reduced pressure. The residue was purified by silica gel column chromatography to give methyl 2-[(3-{[(tert-butoxycarbonyl)amino]methyl}-2-isobutyl-1-oxo-4-phenyl-1,2-dihydro-6-isoquinolinyl)oxy]-2-methylpropanoate (0.31 g, 59.6%) as crystals.

Melting point 207–209° C. Elemental analysis for C$_{30}$H$_{38}$N$_2$O$_6$ 0.25H$_2$O Calculated: C, 68.35; H, 7.36; N, 5.31. Found: C, 68.39; H, 7.54; N, 5.31. $^1$H-NMR(CDCl$_3$) δ: 0.99 (6H, d, J=6.6 Hz), 1.42 (9H, s), 1.51 (6H, s), 2.11–2.31 (1H, m) 3.53 (3H, s) 4.04 (2H, d, J=7.4 Hz), 4.18 (2H, d, J=5.4 Hz), 4.42 (1H, bs), 6.14 (1H, d, J=2.5 Hz), 6.94 (1H, dd, J=2.5, 8.8 Hz), 7.19–7.24 (2H, m), 7.46–7.57 (3H, m), 8.35 (1H, d, J=8.8 Hz).

(2) Methyl 2-[(3-{[(tert-butoxycarbonyl)amino]methyl-}-2-isobutyl-1-oxo-4-phenyl-1,2-dihydro-6-isoquinolinyl)oxy]-2-methylpropanoate (0.16 g, 0.3 mmol) was dissolved in a solution of 4N hydrogen chloride in ethyl acetate (5 ml). The solution was stirred at room temperature for 1 h. The reaction was concentrated under reduced pressure, and the precipitated crystals were recrystallized from ethyl acetate-diisopropyl ether to give methyl 2-{[3-(aminomethyl)-2-isobutyl-1-oxo-4-phenyl-1,2-dihydro-6-isoquinolinyl]oxy}-2-methylpropanoate hydrochloride(0.10 g, 71.4%) as crystals.

Melting point 236–237° C. Elemental analysis for $C_{25}H_{31}N_2O_4Cl$ 1.25$H_2O$ Calculated: C, 62.36; H, 7.01; N, 5.82. Found: C, 62.32; H, 6.73; N, 5.58. $^1$H-NMR(DMSO-$d_6$) δ: 0.91 (6H, d, J=6.6 Hz) 1.44 (6H, s), 1.99–2.18 (1H, m), 3.45 (3H, s), 3.84 (2H, s), 4.05 (2H, d, J=7.0 Hz), 5.99 (1H, d, J=2.4 Hz), 7.02 (1H, dd, J=2.4, 8.8 Hz), 7.34–7.39 (2H, m), 7.55–7.62 (3H, m), 8.23 (1H, d, J=8.8 Hz), 8.57 (3H, bs).

Example 225

2-{[3-(Aminomethyl)-2-isobutyl-1-oxo-4-phenyl-1,2-dihydro-6-isoquinolinyl]oxy}-2-methylpropanoic acid hydrochloride (1) To a solution of methyl 2-[(3-{[(tert-butoxycarbonyl)amino]methyl}-2-isobutyl-1-oxo-4-phenyl-1,2-dihydro-6-isoquinolinyl)oxy]-2-methylpropanoate (0.37 g, 0.7 mmol) in tetrahydrofuran (10 ml) and methanol (10 ml) was added 1N sodium hydroxide solution (2 ml). The mixture was stirred at room temperature for 1 h. The reaction mixture was poured into water acidified with 1N hydrochloric acid and extracted with ethyl acetate. The extract was washed with brine, dried over anhydrous magnesium sulfate and concentrated under reduced pressure. The resulting crystals were crystallized from ethyl acetate-diisopropyl ether to give 2-[(3-{[(tert-butoxycarbonyl)amino]methyl}-2-isobutyl-1-oxo-4-phenyl-1,2-dihydro-6-isoquinolinyl)oxy]-2-methylpropanoic acid (0.32 g, 91.4%) as crystals.

Melting point 219–220° C. Elemental analysis for $C_{29}H_{36}N_2O_6$ Calculated: C, 68.48; H, 7.13; N, 5.51. Found: C, 68.48; H, 7.19; N, 5.28. $^1$H-NMR(CDCl$_3$) δ: 0.98 (6H, d, J=6.6 Hz), 1.42 (9H, s), 1.59 (6H, s), 2.16–2.32 (1H, m), 4.07 (2H, d, J=7.4 Hz), 4.19 (2H, d, J=5.2 Hz), 4.58 (1H, bs), 6.41 (1H, d, J=2.4 Hz), 6.97 (1H, dd, J=2.4, 8.8 Hz), 7.14–7.22 (2H, m), 7.41–7.56 (3H, m), 8.30 (1H, d, J=8.8 Hz).

(2) 2-[(3-{[(Tert-butoxycarbonyl)amino]methyl}-2-isobutyl-1-oxo-4-phenyl-1,2-dihydro-6-isoquinolinyl)oxy]-2-methylpropanoic acid (0.13 g, 0.25 mmol) was dissolved in a solution of 4N hydrogen chloride in ethyl acetate (5 ml). The solution was stirred at room temperature for 1 h. The reaction mixture was concentrated under reduced pressure, and the residue was crystallized from ethyl acetate to give 2-{[3-(aminomethyl)-2-isobutyl-1-oxo-4-phenyl-1,2-dihydro-6-isoquinolinyl]oxy}-2-methylpropanoic acid hydrochloride (0.10 g, 90.9%) as crystals.

Melting point 256–257° C. Elemental analysis for $C_{24}H_{29}N_2O_4Cl$ 0.5$H_2O$ Calculated: C, 63.50; H, 6.66; N, 6.17. Found: C, 63.25; H, 6.66; N, 5.86. $^1$H-NMR(DMSO-$d_6$) δ: 0.91 (6H, d, J=6.6 Hz) 1.44 (6H, s), 1.99–2.14 (1H, m), 3.86 (2H, s), 4.03 (2H, d, J=6.9 Hz), 6.17 (1H, d, J=2.2 Hz), 7.01 (1H, dd, J=2.2, 8.7 Hz), 7.34–7.37 (2H, m), 7.49–7.58 (3H, m), 8.22 (1H, d, J=8.7 Hz), 8.49 (3H, bs).

Example 226

2-{[3-(Aminomethyl)-2-isobutyl-1-oxo-4-phenyl-1,2-dihydro-6-isoquinolinyl]oxy}-2-methylpropanamide hydrochloride (1) A solution of 2-[(3-{[(tert-butoxycarbonyl)amino]methyl}-2-isobutyl-1-oxo-4-phenyl-1,2-dihydro-6-isoquinolinyl)oxy]-2-methylpropanoic acid (0.20 g, 0.4 mmol), 1-ethyl-3-(3-dimethylaminopropyl)carbodiimide hydrochloride (0.15 g, 0.8 mmol) and 1-hydroxybenzotriazole ammonium salt (0.12 g, 0.8 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The resulting crystals were recrystallized from ethyl acetate-diisopropyl ether to give tert-butyl[6-(2-amino-1,1-dimethyl-2-oxoethoxy)-2-isobutyl-1-oxo-4-phenyl-1,2-dihydro-3-isoquinolinyl]methylcarbamate (0.19 g, 95.0%) as crystals.

Melting point 219–220° C. Elemental analysis for $C_{29}H_{37}N_3O_5$ 0.25$H_2O$ Calculated: C, 68.01; H, 7.38; N, 8.21. Found: C, 68.04; H, 7.46; N, 7.97. $^1$H-NMR(CDCl$_3$) δ: 1.00 (6H, d, J=6.4 Hz), 1.42 (9H, s), 1.46 (6H, s), 2.12–2.31 (1H, m), 4.05 (2H, d, J=7.2 Hz), 4.20 (2H, d, J=5.4 Hz), 4.45 (1H, bs), 5.36 (1H, bs), 6.34 (1H, bs), 6.39 (1H, d, J=2.6 Hz), 7.03 (1H, dd, J=2.6, 8.8 Hz), 7.20–7.25 (2H, m), 7.48–7.58 (3H, m), 8.39 (1H, d, J=8.8 Hz).

(2) Tert-butyl[6-(2-amino-1,1-dimethyl-2-oxoethoxy)-2-isobutyl-1-oxo-4-phenyl-1,2-dihydro-3-isoquinolinyl]methylcarbamate (0.15 g, 0.3 mmol) was dissolved in a solution of 4N hydrogen chloride in ethyl acetate (5 ml). The solution was stirred at room temperature for 1 h. The reaction was concentrated under reduced pressure, and the residue was crystallized from ethyl acetate to give 2-{[3-(aminomethyl)-2-isobutyl-1-oxo-4-phenyl-1,2-dihydro-6-isoquinolinyl]oxy}-2-methylpropanamide hydrochloride (0.12 g, 92.3%) crystals.

Melting point 182–184° C. Elemental analysis for $C_{24}H_{30}N_3O_3Cl$ AcOEt Calculated: C, 63.21; H, 7.20; N, 7.90. Found: C, 63.31; H, 7.47; N, 8.11. $^1$H-NMR(DMSO-$d_6$) δ: 0.91 (6H, d, J=6.6 Hz), 1.38 (6H, s), 1.99–2.18 (1H, m), 3.85 (2H, s), 4.04 (2H, d, J=6.8 Hz), 6.27 (1H, d, J=2.2 Hz), 7.04 (1H, dd, J=2.2, 8.8 Hz), 7.17 (1H, bs), 7.34–7.38 (2H, m), 7.44 (1H, bs), 7.54–7.61 (3H, m), 8.22 (1H, d, J=8.8 Hz), 8.55 (3H, bs).

Example 227

6-Acetyl-3-(aminomethyl)-4-butoxy-2-isobutyl-1(2H)-isoquinolinone hydrochloride (1) A solution of 4-butoxy-3{[(tert-butoxycarbonyl)amino]methyl}-2-isobutyl-1-oxo-1,2-dihydro-6-isoquinolinecarboxylic acid (4.46 g, 10 mmol), N,O-dimethylhydroxyamine hydrochloride (1.17 g, 12 mmol), 1-ethyl-3-(3-dimethylaminopropyl)carbodiimide hydrochloride (2.30 g, 12 mmol), 1-hydroxybenzotriazole (1.84 g, 12 mmol) and triethylamine (1.7 ml, 12 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The resulting crystals were recrystallized from ethyl acetate-diisopropyl ether to give tert-butyl(4butoxy-2-isobutyl-6-{[methoxy(methyl)amino]carbonyl}-1-oxo-1,2-dihydro-3-isoquinolinyl)methylcarbamate (4.15 g, 84.9%) as crystals.

Melting point 142–143° C. Elemental analysis for $C_{26}H_{39}N_3O_6$ Calculated: C, 63.78; H, 8.03; N, 8.58. Found: C, 63.59; H, 8.10; N, 8.58. $^1$H-NMR(CDCl$_3$) δ: 0.97 (6H, d, J=6.9 Hz), 1.02 (3H, t, J=7.0 Hz), 1.47 (9H, s), 1.48–1.62 (2H, m), 1.79–1.93 (2H, m), 2.12–2.26 (1H, m), 3.41 (3H, s), 3.54 (3H, s), 3.88 (2H, t, J=6.5 Hz), 4.01 (2H, d, J=7.6 Hz), 4.53 (2H, d, J=5.6 Hz), 4.74 (1H, bs), 7.74 (1H, dd, J=1.4, 8.6 Hz), 7.99 (1H, d, J=1.4 Hz), 8.46 (1H, d, J=8.6 Hz).

(2) To a solution of tert-butyl(4-butoxy-2-isobutyl-6{[methoxy(methyl)amino]carbonyl}-1-oxo-1,2-dihydro-3-isoquinolinyl)methylcarbamate (0.49 g, 1 mmol) in tetrahydrofuran (10 ml) was added 1N methylmagnesium bromide tetrahydrofuran solution (5 ml) at 0° C. The mixture was stirred at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl(6-acetyl-4-butoxy-2-isobutyl-1-oxo-1,2-dihydro-3-isoquinolinyl)methylcarbamate (0.37 g, 84.1%) as crystals.

Melting point 161–162° C. Elemental analysis for $C_{25}H_{36}N_2O_5$ Calculated: C, 67.54; H, 8.16; N, 6.30. Found: C, 67.30; H, 8.14; N, 6.21. $^1$H-NMR(CDCl$_3$) δ: 0.97 (6H, d, J=6.6 Hz), 1.06 (3H, t, J=7.2 Hz), 1.47 (9H, s), 1.53–1.72 (2H, m), 1.82–1.97 (2H, m), 2.12–2.25 (1H, m), 2.71 (3H, s), 3.90 (2H, t, J=6.5 Hz), 4.01 (2H, d, J=7.4 Hz), 4.54 (2H, d, J=5.6 Hz), 4.78 (1H, bs), 8.01 (1H, dd, J=2.0, 8.4 Hz), 8.28 (1H, d, J=2.0 Hz), 8.49 (1H, d, J=8.4 Hz).

(3) Tert-butyl(6-acetyl-4-butoxy-2-isobutyl-1-oxo-1,2-dihydro-3-isoquinolinyl)methylcarbamate (0.13 g, 0.3 mmol) was dissolved in a solution of 4N hydrogen chloride in ethyl acetate (5 ml). The solution was stirred at room temperature for 1 h. The reaction was concentrated under reduced pressure, and the precipitated crystals were recrystallized from methanol-diisopropyl ether to give 6-acetyl-3-(aminomethyl)-4-butoxy-2-isobutyl-1(2H)-isoquinolinone hydrochloride (0.10 g, 90.9%) as crystals.

Melting point 171.5–173° C. Elemental analysis for $C_{20}H_{29}N_2O_3Cl$ Calculated: C, 63.06; H, 7.67; N, 7.35. Found: C, 62.77; H, 7.77; N, 7.26. $^1$H-NMR(DMSO-d$_6$) δ: 0.89 (6H, d, J=6.6 Hz), 1.02 (3H, t, J=7.4 Hz), 1.52–1.70 (2H, m), 1.84–2.16 (3H, m), 2.72 (3H, s), 3.92–4.01 (4H, m), 4.20 (2H, s), 8.12 (1H, d, J=8.2 Hz), 8.26 (1H, s), 8.39 (1H, d, J=8.2 Hz), 8.70 (3H, bs).

The compounds of following Examples 228 to 252 were synthesized according to the method similar to that in Example 214 (2) from the N-Boc intermediates.

Example 228

(E)-3-[3-(Aminomethyl)-4-(4-chlorophenyl)-2-isobutyl-1-oxo-1,2-dihydro-6-isoquinolyl]-2-propenoic acid hydrochloride Melting point 268–270° C. Elemental analysis for $C_{23}H_{24}N_2O_3Cl_2$ 0.5H$_2$O Calculated: C, 60.53; H, 5.52; N, 6.14. Found: C, 60.49; H, 5.75; N, 5.81. $^1$H-NMR(DMSO-d$_6$) δ: 0.92 (6H, d, J=6.6 Hz), 2.04–2.18 (1H, m), 3.86 (2H, s), 4.07 (2H, d, J=6.6 Hz), 6.52 (1H, d, J=15.9 Hz), 7.09 (1H, s), 7.44 (2H, d, J=8.1 Hz), 7.56 (1H, d, J=15.9 Hz), 7.64 (2H, d, J=8.1 Hz), 7.96 (1H, d, J=8.7 Hz), 8.33 (1H, d, J=8.7 Hz), 8.53 (3H, bs).

Example 229

Methyl 3-(aminomethyl)-4-(4-chlorophenyl)-2-isobutyl-1-oxo-1,2-dihydro-6-isoquinolinecarboxylate hydrochloride Melting point 177–179° C. Elemental analysis for $C_{22}H_{24}N_2O_3Cl_2$ 0.25H$_2$O Calculated: C, 60.07; H, 5.61; N, 6.37. Found: C, 60.00; H, 5.89; N, 6.24. $^1$H-NMR(DMSO-d$_6$) δ: 0.93 (6H, d, J=6.6 Hz), 2.02–2.18 (1H, m), 3.82 (3H, s), 3.88 (2H, s), 4.08 (2H, d, J=7.0 Hz), 7.46 (2H, d, J=8.4 Hz), 7.61 (1H, d, J=1.6 Hz), 7.68 (2H, d, J=8.4 Hz), 8.08 (1H, dd, J=1.6, 8.4 Hz), 8.46 (1H, d, J=8.4 Hz), 8.52 (3H, bs).

Example 230

(Aminomethyl)-4-(4-chlorophenyl)-2-isobutyl-1-oxo-1,2-dihydro-6-isoquinolinecarboxylic acid hydrochloride Melting point 263–265° C. $^1$H-NMR(DMSO-d$_6$) δ: 0.93 (6H, d, J=6.6 Hz), 1.99–2.18 (1H, m), 3.88 (2H, s), 4.08 (2H, d, J=7.0 Hz), 7.46 (2H, d, J=8.4 Hz), 7.51 (1H, d, J=1.4 Hz), 7.67 (2H, d, J=8.4 Hz), 8.06 (1H, dd, J=1.4, 8.2 Hz), 8.44 (1H, d, J=8.2 Hz), 8.46 (3H, bs).

Example 231

3-(Aminomethyl)-2-isobutyl-1-oxo-4-phenyl-1,2-dihydro-6-isoquinolinecarbothioamide hydrochloride Melting point 257–259° C. Elemental analysis for $C_{21}H_{24}N_3OClS$ 0.5H$_2$O Calculated: C, 61.37; H, 6.13; N, 10.22. Found: C, 61.04; H, 5.99; N, 9.85. $^1$H-NMR(DMSO-d$_6$) δ: 0.92 (6H, d, J=6.6 Hz), 1.99–2.18 (1H, m), 3.88 (2H, s), 4.06 (2H, d, J=7.2 Hz), 7.37–7.43 (3H, m), 7.56–7.59 (3H, m), 7.85 (1H, dd, J=1.5, 8.4 Hz), 8.32 (1H, d, J=8.4 Hz), 8.52 (3H, bs), 9.67 (1H, bs), 10.02 (1H, bs).

Example 232

3-(Aminomethyl)-6-(benzyloxy)-4-(4-chlorophenyl)-2-isobutyl-1(2H)-isoquinolinone hydrochloride Melting point 162–164° C. Elemental analysis for $C_{27}H_{28}N_2O_3Cl_2$ 0.25H$_2$O Calculated: C, 66.46; H, 5.89; N, 5.74. Found: C, 66.26; H, 5.87; N, 5.49. $^1$H-NMR(DMSO-d$_6$) δ: 0.90 (6H, d, J=6.6 Hz), 1.98–2.13 (1H, m), 3.82 (2H, s), 4.03 (2H, d, J=7.0 Hz), 5.04 (2H, s), 6.26 (1H, d, J=2.6 Hz), 7.23–7.59 (8H, m), 7.61 (2H, d, J=8.4 Hz), 8.25 (1H, d, J=8.8 Hz), 8.52 (3H, bs).

Example 233

3-(Aminomethyl)-4-(4-chlorophenyl)-6-hydroxy-2-isobutyl-1(2H)-isoquinolinone hydrochloride Melting point 247–249° C. $^1$H-NMR(DMSO-d$_6$) δ: 0.90 (6H, d, J=7.0 Hz), 1.99–2.13 (1H, m), 3.82 (2H, s), 3.99 (2H, d, J=7.4 Hz), 6.19 (1H, d, J=2.2 Hz), 6.99 (1H, dd, J=2.2, 8.8

Hz), 7.40 (2H, d, J=8.4 Hz), 7.63 (2H, d, J=8.4 Hz), 8.16 (1H, d, J=8.8 Hz), 8.42 (3H, bs), 10.30 (1H, s).

Example 234

(E)-3-[3-(Aminomethyl)-2-isobutyl-4-(4-methylphenyl)-1-oxo-1,2-dihydro-6-isoquinolinyl]-2-propenoic acid hydrochloride Melting point 230–231° C. Elemental analysis for $C_{25}H_{27}N_2O_3Cl\ H_2O$ Calculated: C, 64.78; H, 6.57; N, 6.30. Found: C, 64.73; H, 6.63; N, 5.86. $^1$H-NMR(DMSO-d$_6$) δ: 0.92 (6H, d, J=6.6 Hz), 2.06–2.18 (1H, m), 2.45 (3H, s), 3.89 (2H, s), 4.07 (2H, d, J=6.6 Hz), 6.47 (1H, d, J=16.0 Hz), 7.05 (1H, d, J=1.2 Hz), 7.29 (2H, d, J=8.1 Hz), 7.40 (2H, d, J=8.1 Hz), 7.49 (1H, d, J=16.0 Hz), 7.94 (1H, dd, J=1.2, 8.1 Hz), 8.33 (1H, d, J=8.1 Hz), 8.50 (3H, bs).

Example 235

Methyl 3-(aminomethyl)-2-isobutyl-4-(4-methylphenyl)-1-oxo-1,2-dihydro-6-isoquinolinecarboxylate hydrochloride Melting point 254–256° C. Elemental analysis for $C_{23}H_{27}N_2O_3Cl\ 0.25H_2O$ Calculated: C, 65.86; H, 6.61; N, 6.68. Found: C, 66.03; H, 6.67; N, 6.50. $^1$H-NMR(DMSO-d$_6$) δ: 0.92 (6H, d, J=6.6 Hz), 2.06–2.16 (1H, m), 2.45 (3H, s), 3.81 (3H, s), 3.89 (2H, s), 4.10 (2H, d, J=6.9 Hz), 7.31 (2H, d, J=7.8 Hz), 7.41 (2H, d, J=7.8 Hz), 7.57 (1H, s), 8.06 (1H, d, J=8.3 Hz), 8.45 (1H, d, J=8.3 Hz), 8.57 (3H, bs).

Example 236

3-(Aminomethyl)-2-isobutyl-4-(4-methylphenyl)-1-oxo-1,2-dihydro-6-isoquinolinecarboxylic acid hydrochloride Melting point 259–261° C. Elemental analysis for $C_{22}H_{25}N_2O_3Cl\ 0.75\ H_2O$ Calculated: C, 63.76; H, 6.45; N, 6.76. Found: C, 63.66; H, 6.49; N, 6.50. $^1$H-NMR(DMSO-d$_6$) δ: 0.92 (6H, d, J=6.6 Hz), 1.99–2.14 (1H, m), 2.45 (3H, s), 3.89 (2H, s), 4.09 (2H, d, J=7.4 Hz), 7.31 (2H, d, J=7.9 Hz), 7.42 (2H, d, J=7.9 Hz), 7.57 (1H, d, J=1.4 Hz), 8.05 (1H, dd, J=1.4, 8.4 Hz), 8.43 (1H, d, J=8.4 Hz), 8.53 (3H, bs).

Example 237

3-(Aminomethyl)-4-butoxy-2-isobutyl-1-oxo-1,2-dihydro-6-isoquinolinecarbothioamide hydrochloride Melting point 200–202° C. $^1$H-NMR(DMSO-d6) δ: 0.88 (6H, d, J=6.6 Hz), 1.00 (3H, t, J=7.3 Hz), 1.49–1.67 (2H, m), 1.79–2.08 (3H, m), 3.95–4.01 (4H, m), 4.19 (2H, bs), 7.98 (1H, dd, J=1.5, 8.5 Hz), 8.20 (1H, d, J=1.5 Hz), 8.28 (1H, d, J=8.5 Hz), 8.51 (3H, bs), 9.87 (1H, bs), 10.20 (3H, bs).

Example 238

3-(Aminomethyl)-6-(benzyloxy)-2-isobutyl-4-(4-methylphenyl)-1(2H)-isoquinolinone hydrochloride Melting point 244–246° C. Elemental analysis for $C_{28}H_{31}N_2O_2Cl$ Calculated: C, 72.63; H, 6.75; N, 6.05. Found: C, 72.31; H, 6.84; N, 5.93. $^1$H-NMR(DMSO-d$_6$) δ: 0.89 (6H, d, J=6.6 Hz), 1.98–2.18 (1H, m), 2.43 (3H, s), 3.84 (2H, s), 4.02 (2H, d, J=7.4 Hz), 5.01 (2H, s), 6.31 (1H, d, J=2.2 Hz), 7.18–7.38 (10H, m), 8.24 (1H, d, J=8.8 Hz), 8.45 (3H, bs).

Example 239

3-(Aminomethyl)-6-hydroxy-2-isobutyl-4-(4-methylphenyl)-1(2H)-isoquinolinone hydrochloride Melting point 255–256° C. $^1$H-NMR(DMSO-d6) δ: 0.90 (6H, d, J=7.0 Hz), 1.99–2.13 (1H, m), 2.42 (3H, s), 3.83 (2H, s), 4.02 (2H, d, J=7.4 Hz), 6.23 (1H, d, J=2.4 Hz), 6.99 (1H, d, J=2.4, 8.6 Hz), 7.25 (2H, d, J=8.1 Hz), 7.37 (2H, d, J=8.1 Hz), 8.15 (1H, d, J=8.6 Hz), 8.50 (3H, bs), 10.27 (1H, s).

Example 240

(E)-3-[3-(Aminomethyl)-4-(4-fluorophenyl)-2-isobutyl-1-oxo-1,2-dihydro-6-isoquinolinyl]-2-propenoic acid hydrochloride Melting point 255–256° C. $^1$H-NMR(DMSO-d$_6$) δ: 0.93 (6H, d, J=6.6 Hz), 1.99–2.18 (1H, m), 3.87 (2H, s), 4.08 (2H, d, J=7.0 Hz), 6.50 (1H, d, J=16.2 Hz), 7.07 (1H, d, J=1.2 Hz), 7.36–7.48 (4H, m), 7.55 (1H, d, J=16.2 Hz), 7.95 (1H, dd, J=1.2, 8.0 Hz), 8.33 (1H, d, J=8.0 Hz), 8.59 (3H, bs).

Example 241

3-(Aminomethyl)-6-(benzyloxy)-4-(4-fluorophenyl)-2-isobutyl-1(2H)-isoquinolinone hydrochloride Melting point 226–227° C. Elemental analysis for $C_{27}H_{28}N_2O_2ClF$ Calculated: C, 69.44; H, 6.04; N, 6.00. Found: C, 69.44; H, 5.89; N, 6.12. $^1$H-NMR(DMSO-d$_6$) δ: 0.90 (6H, d, J=6.6 Hz), 1.99–2.14 (1H, m), 3.83 (2H, s), 4.04 (2H, d, J=7.4 Hz), 5.04 (2H, s), 6.26 (1H, d, J=2.6 Hz), 7.23–7.44 (10H, m), 8.25 (1H, d, J=8.8 Hz), 8.56 (3H, bs).

Example 242

3-(Aminomethyl)-4-(4-fluorophenyl)-6-hydroxy-2-isobutyl-1(2H)-isoquinolinone hydrochloride Melting point 249–251° C. Elemental analysis for $C_{20}H_{22}N_2O_2ClF\ 1.5H_2O$ Calculated: C, 59.48; H, 6.24; N, 6.94. Found: C, 59.21; H, 5.99; N, 6.68. $^1$H-NMR(-DMSO-d$_6$) δ: 0.91 (6H, d, J=6.6 Hz) 1.98–2.16 (1H, m), 3.82 (2H, d, J=7.0 Hz), 4.03 (2H, d, J=7.0 Hz), 6.19 (1H, d, J=2.2 Hz), 6.98 (1H, bs), 7.01 (1H, d, J=2.2, 8.8 Hz) 7.34–7.48 (4H, m), 8.16 (1H, d, J=8.8 Hz), 8.61 (3H, bs).

Example 243

Methyl 3-(aminomethyl)-4-(3-fluorophenyl)-2-isobutyl-1-oxo-1,2-dihydro-6-isoquinolinecarboxylate hydrochloride Melting point 177–179° C. Elemental analysis for $C_{22}H_{24}N_2O_3ClF\ 0.5H_2O$ Calculated: C, 61.75; H, 5.89; N, 6.55. Found: C, 61.55; H, 6.04; N, 6.34. $^1$H-NMR(DMSO-d$_6$) δ: 0.93 (6H, d, J=6.6 Hz), 2.04–2.18 (1H, m), 3.81 (3H, s), 3.89 (2H, s), 3.89 (2H, d, J=7.8 Hz), 7.27–7.47 (3H, m), 7.51 (1H, d, J=1.3 Hz), 7.62–7.70 (1H, m), 8.08 (1H, dd, J=1.3, 8.4 Hz), 8.46 (1H, d, J=8.4 Hz), 8.59–8.67 (3H, m).

Example 244

3-(Aminomethyl)-4-(3-fluorphenyl)-2-isobutyl-1-oxo-1,2-dihydro-6-isoquinolinecarboxylic acid hydrochloride Melting point 252–254° C. Elemental analysis for $C_{21}H_{22}N_2O_3ClF$ $0.75H_2O$ Calculated: C, 60.29; H, 5.66; N, 6.70. Found: C, 60.29; H, 5.97; N, 6.53. $^1$H-NMR(DMSO-$d_6$) δ: 0.93 (6H, d, J=6.6 Hz), 1.99–2.18 (1H, m), 3.89 (2H,bs), 4.04–4.17 (2H, m), 7.27–7.52 (4H, m), 7.60–7.71 (1H, m), 8.06 (1H, dd, J=1.2, 8.4 Hz), 8.44 (1H, d, J=8.4 Hz), 8.63 (3H, bs).

Example 245

3-(Aminomethyl)-6-(benzyloxy)-4-(3-fluorophenyl)-2-isobutyl-1(2H)-isoquinolinone hydrochloride Melting point 178–180° C. Elemental analysis for $C_{27}H_{28}N_2O_2ClF$ $0.25H_2O$ Calculated: C, 68.78; H, 6.09; N, 5.94. Found: C, 68.57; H, 6.20; N, 5.84. $^1$H-NMR(DMSO-$d_6$) δ: 0.90 (6H, d, J=6.6 Hz), 1.99–2.11 (1H, m), 3.77–3.90 (2H, m), 3.96–4.13 (2H, m), 5.04 (2H, s), 6.26 (1H, d, J=2.4 Hz), 7.16–7.43 (9H, m), 7.57–7.65 (1H, m), 8.25 (1H, d, J=8.7 Hz), 8.60 (3H, bs).

Example 246

3-(Aminomethyl)-4-(3-fluorophenyl)-6-hydroxy-2-isobutyl-1(2H)-isoquinolinone hydrochloride Melting point 226–227° C. Elemental analysis for $C_{20}H_{22}N_2O_2ClF$ $1.5H_2O$ Calculated: C, 59.48; H, 6.24; N, 6.94. Found: C, 59.28; H, 6.09; N, 6.85. $^1$H-NMR(DMSO-$d_6$) δ: 0.91 (6H, d, J=6.6 Hz), 1.98–2.12 (1H, m), 3.82 (2H, bs), 3.92–4.14 (2H, m), 6.20 (1H, d, J=2.4 Hz), 7.02 (1H, d, J=2.4, 8.6 Hz), 7.20–7.41 (3H, m), 7.56–7.67 (1H, m), 8.16 (1H, d, J=8.6 Hz), 8.60 (3H, bs).

Example 247

Methyl {[3-(aminomethyl)-2-isobutyl-1-oxo-4-phenyl-1,2-dihydro-6-isoquinolinyl]oxy}acetate hydrochloride Melting point 228–229° C. Elemental analysis for $C_{23}H_{27}N_2O_4Cl$ $0.25H_2O$ Calculated: C, 63.44; H, 6.37; N, 6.43. Found: C, 63.53; H, 6.27; N, 6.30. $^1$H-NMR(DMSO-$d_6$) δ: 0.91(6H, d, J=6.6 Hz), 1.99–2.18 (1H, m), 3.60 (3H, s), 3.86 (2H, s), 4.04 (2H, d, J=7.2 Hz), 4.71 (2H, s), 6.13 (1H, d, J=2.4 Hz), 7.20 (1H, dd, J=2.4, 8.8 Hz), 7.34–7.39 (2H, m), 7.54–7.60 (3H, m), 8.26 (1H, d, J=8.8 Hz), 8.47 (3H, bs).

Example 248

{[3-(Aminomethyl)-2-isobutyl-1-oxo-4-phenyl-1,2-dihydro-6-isoquinolinyl]oxy}acetic acid hydrochloride Melting point 255–257° C. Elemental analysis for $C_{22}H_{25}N_2O_4Cl$ $0.5H_2O$ Calculated: C, 62.04; H, 6.15; N, 6.58. Found: C, 62.15; H, 6.28; N, 6.36. $^1$H-NMR(DMSO-$d_6$) δ: 0.91 (6H, d, J=6.6 Hz), 1.99–2.18 (1H, m), 3.86 (2H, s), 4.05 (2H, d, J=7.6 Hz), 4.61 (2H, s), 6.20 (1H, d, J=2.2 Hz), 7.18 (1H, dd, J=2.2, 8.8 Hz), 7.35–7.40 (2H, m), 7.52–7.63 (3H, m), 8.26 (1H, d, J=8.8 Hz), 8.55 (3H, bs).

Example 249

Methyl 3-(aminomethyl)-4-(2-fluorophenyl)-2-isobutyl-1-oxo-1,2-dihydro-6-isoquinolinecarboxylate hydrochloride Melting point 243–245° C. Elemental analysis for $C_{22}H_{24}N_2O_3ClF$ $1.0H_2O$ Calculated: C, 63.23; H, 6.27; N, 6.70. Found: C, 63.08; H, 5.89; N, 6.46. $^1$H-NMR(DMSO-$d_6$) δ: 0.92 (3H, d, J=6.3 Hz), 0.94 (3H, d, J=5.7 Hz), 2.04–2.18 (1H, m), 3.77–3.80 (1H, m), 3.81 (3H, s), 3.97–4.05 (2H, m), 4.13–4.21 (1H, m), 7.44–7.58 (4H, m), 7.64–7.72 (1H, m), 8.10 (1H, dd, J=1.6, 8.7 Hz), 8.48 (1H, d, J=8.7 Hz), 8.66 (3H, bs).

Example 250

3-(Aminomethyl)-4-(2-fluorophenyl)-2-isobutyl-1-oxo-1,2-dihydro-6-isoquinolinecarboxylic acid hydrochloride Melting point 222–224° C. Elemental analysis for $C_{21}H_{22}N_2O_3ClF$ $0.75H_2O$ Calculated: C, 60.29; H, 5.66; N, 6.70. Found: C, 60.37; H, 5.76; N, 6.31. $^1$H-NMR(DMSO-$d_6$) δ: 0.92 (3H, d, J=6.6 Hz), 0.94 (3H, d, J=6.6 Hz), 2.05–2.17 (1H, m), 3.77–3.84 (1H, m), 3.95–4.22 (3H, m), 7.42–7.73 (5H, m), 8.08 (1H, dd, J=1.4, 8.2 Hz), 8.45 (1H, d, J=8.2 Hz), 8.66 (3H, bs).

Example 251

3-(Aminomethyl)-6-(benzyloxy)-4-(2-fluorophenyl)-2-isobutyl-1(2H)-isoquinolinone hydrochloride Melting point 144–145° C. Elemental analysis for $C_{27}H_{28}N_2O_2ClF$ $0.5H_2O$ Calculated: C, 68.13; H, 6.14; N, 5.89. Found: C, 68.08; H, 6.43; N, 5.83. $^1$H-NMR(DMSO-$d_6$) δ: 0.89 (3H, d, J=6.6 Hz), 0.91 (3H, d, J=6.6 Hz), 1.99–2.16 (1H, m), 3.69–4.18 (4H, m), 5.04 (2H, s), 6.26 (1H, d, J=2.0 Hz), 7.22–7.47 (9H, m), 7.59–7.68 (1H, m), 8.26 (1H, d, J=8.8 Hz), 8.52 (3H, bs).

Example 252

3-(Aminomethyl)-4-(2-fluorophenyl)-6-hydroxy-2-isobutyl-1(2H)-isoquinolinone hydrochloride Melting point 259–260° C. Elemental analysis for $C_{20}H_{22}N_2O_2Cl$ Calculated: C, 63.74; H, 5.88; N, 7.43. Found: C, 63.38; H, 5.71; N, 7.43. $^1$H-NMR(DMSO-$d_6$) δ: 0.89 (3H, d, J=6.6 Hz), 0.91 (3H, d, J=6.6 Hz), 2.01–2.18 (1H, m), 3.68–4.16 (4H, m), 6.20 (1H, d, J=2.4 Hz), 7.02 (1H, dd, J=2.4, 8.6 Hz), 7.37–7.67 (4H, m), 8.17 (1H, d, J=8.6 Hz), 8.55 (3H, bs), 10.37 (3H, bs).

Example 253

3-(Aminomethyl)-6-(benzyloxy)-2-isobutyl-4-(2-thienyl)-1(2H)-isoquinolinone hydrochloride (1) A mixture of methyl 6-(benzyloxy)-2-isobutyl-1-oxo-4-trifluoromethanesulfonyloxy-1,2-dihydro-3-isoquinolinecarboxylate (10.26 g, 20 mmol), 2-thiopheneboronic acid (3.07 g, 24 mmol), sodium carbonate (5.30 g, 50 mmol), toluene (50 ml), methanol (10 ml) and water (10 ml) was stirred at room temperature for 30 min under an argon atmosphere. To the resulting mixture was added tetrakis (triphenylphosphine)palladium (1.16 g, 1 mmol), the mixture was refluxed under heating for 10 h under an argon atmosphere. The reaction mixture was poured into water and extracted with ethyl acetate. The extract was washed with brine, dried over anhydrous magnesium sulfate and concentrated under reduced pressure. The residue was purified by silica gel column chromatography to give methyl 6-(benzyloxy)-2-isobutyl-1-oxo-4-(2-thienyl)-1,2-dihydro-3-isoquinolinecarboxylate (2.11 g, 23.6%) as crystals.

Melting point 143–144° C. Elemental analysis for $C_{26}H_{25}NO_4S$ Calculated: C, 69.78; H, 5.63; N, 3.13. Found: C, 69.77; H, 5.76; N, 3.15. $^1$H-NMR(CDCl$_3$) δ: 0.92 (6H, d, J=7.0 Hz), 2.05–2.21 (1H, m), 3.59 (3H, s), 3.92 (2H, d, J=7.8 Hz), 5.02 (2H, s), 6.85 (1H, d, J=2.6 Hz), 6.98 (1H, dd, J=1.2, 3.4 Hz), 7.10 (1H, dd, J=3.4, 5.1 Hz), 7.17 (1H, dd, J=2.4, 9.1 Hz), 7.29–7.42 (5H, m), 7.46 (1H, dd, J=1.2, 5.1 Hz), 8.39 (1H, d, J=9.1 Hz).

(2) To a suspension of methyl 6-(benzyloxy)-2-isobutyl-1-oxo-4-(2-thienyl)-1,2-dihydro-3-isoquinolinecarboxylate (2.01 g, 4.5 mmol) in methanol (30 ml) was added a solution of lithium hydroxide monohydrate (0.57 g, 13.5 mmol) in water (10 ml). The resulting mixture was refluxed under heating for 48 h. The reaction mixture was poured into water, acidified with 1N hydrochloric acid and extracted with ethyl acetate. The extract was washed with brine, dried over anhydrous magnesium sulfate and concentrated under reduced pressure. The resulting crystals were recrystallized from ethyl acetate-n-hexane to give 6-(benzyloxy)-2-isobutyl-1-oxo-4-(2-thienyl)-1,2-dihydro-3-isoquinolinecarboxylic acid (1.71 g, 87.7%) as crystals.

Melting point 171–172° C. Elemental analysis for $C_{25}H_{23}NO_4S$ 0.3$H_2O$ Calculated: C, 68.41; H, 5.42; N, 3.19. Found: C, 68.51; H, 5.84; N, 2.93. $^1$H-NMR(CDCl$_3$) δ: 0.87 (6H, d, J=6.6 Hz), 2.13–2.26 (1H, m), 3.89 (2H, d, J=7.4 Hz), 5.00 (2H, s), 6.79 (1H, d, J=1.8 Hz), 7.08–7.13 (3H, m), 7.27–7.45 (5H, m), 7.46–7.48 (1H, m), 8.26 (1H, dd, J=1.4, 9.0 Hz).

(3) To a solution of 6-(benzyloxy)-2-isobutyl-1-oxo-4-(2-thienyl)-1,2-dihydro-3-isoquinolinecarboxylic acid (1.52 g, 3.5 mmol) in tetrahydrofuran (20 ml) were added oxalyl chloride (0.37 ml, 4.2 mmol) and N,N-dimethylformamide (2 drops). The reaction mixture was stirred at room temperature for 1 h. The reaction mixture was concentrated under reduced pressure, and the residue was dissolved in tetrahydrofuran (10 ml). The solution was added dropwise to a suspension of sodium tetrahydroborate (0.47 g, 12.3 mmol) in 1,2-dimethoxyethane (20 ml) at 0° C., and the mixture was stirred at 0° C. for 1 h. The reaction mixture was poured into 1N hydrochloric acid and extracted with ethyl acetate. The extract was washed with brine, dried over anhydrous magnesium sulfate and concentrated under reduced pressure. The residue was purified by silica gel column chromatography to give 6-(benzyloxy)-3-(hydroxymethyl)-2-isobutyl-4-(2-thienyl)-1(2H)-isoquinolinone (1.36 g, 92.5%) as crystals.

Elemental analysis for $C_{25}H_{25}NO_3S$ Calculated: C, 71.57; H, 6.01; N, 3.34. Found: C, 71.32; H, 6.08; N, 3.25. $^1$H-NMR(CDCl$_3$) δ: 0.96 (6H, d, J=7.0 Hz), 2.11–2.35 (1H, m), 4.18 (2H, d, J=7.4 Hz), 4.53 (2H, d, J=6.2 Hz), 4.94 (2H, s), 6.55 (1H, d, J=2.2 Hz), 7.00–7.05 (2H, m), 7.18 (1H, dd, J=3.5, 5.2 Hz), 7.23–7.38 (5H, m), 7.48 (1H, dd, J=1.0, 5.2 Hz), 8.30 (1H, d, J=9.0 Hz).

(4) To a suspension of 6-(benzyloxy)-3-(hydroxymethyl)-2-isobutyl-4-(2-thienyl)-1(2H)-isoquinolinone (1.26 g, 3 mmol) in toluene (20 ml) was added thionyl chloride (0.44 ml, 6 mmol). The resulting mixture was refluxed for 2 h. The reaction mixture was added to a saturated sodium hydrogen carbonate solution and extracted with ethyl acetate. The extract was washed with brine, dried over anhydrous magnesium sulfate and concentrated under reduced pressure to give 6-(benzyloxy)-3-(chloromethyl)-2-isobutyl-4-(2-thienyl)-1(2H)-isoquinolinone (1.30 g, 100%) as an oil.

$^1$H-NMR(CDCl$_3$) δ: 1.00 (6H, d, J=6.6 Hz), 2.12–2.31 (1H, m), 4.14 (2H, bs), 4.48 (2H, s), 4.99 (2H, s), 6.61 (1H, d, J=2.6 Hz) 7.05 (1H, dd, J=1.6, 3.5 Hz), 7.11–7.38 (7H, m), 7.51 (1H, dd, J=1.6, 5.1 Hz), 8.38 (1H, d, J=8.8 Hz).

(5) A solution of 6-(benzyloxy)-3-(chloromethyl)-2-isobutyl-4-(2-thienyl)-1(2H)-isoquinolinone (1.31 g, 3 mmol) and potassium phthalimide (0.83 g, 4.5 mmol) in N,N-dimethylformamide (20 ml) was stirred at room temperature for 3 h. The reaction mixture was poured into water and extracted with ethyl acetate. The extract was washed with brine, dried over anhydrous magnesium sulfate and concentrated under reduced pressure. The residue was purified by silica gel column chromatography to give 2-{[6-(benzyloxy)-2-isobutyl-1-oxo-4-(2-thienyl)-1,2-dihydro-3-isoquinolinyl]methyl}-1H-isoindole-1,3(2H)-dione (1.42 g, 86.6%) as an amorphous solid.

$^1$H-NMR(CDCl$_3$) δ: 0.98 (6H, d, J=6.6 Hz), 2.12–2.25 (1H, m), 4.02 (1H, d, J=6.6 Hz), 4.87 (2H, d, J=3.2 Hz), 4.97 (2H, s), 6.55 (1H, d, J=2.2 Hz), 7.01 (1H, dd, J=1.3, 3.5 Hz), 7.08–7.14 (2H, m) 7.28–7.39 (5H, m) 7.43 (1H, dd, J=1.3, 5.3, Hz), 7.68–7.80 (4H, m), 8.36 (1H, d, J=9.2 Hz).

(6) To a suspension of 2-{[6-(benzyloxy)-2-isobutyl-1-oxo-4-(2-thienyl)-1,2-dihydro-3-isoquinolinyl]methyl}-1H-isoindole-1,3(2H)-dione (1.37 g, 2.5 mmol) in ethanol (20 ml) was added hydrazine monohydrate (0.36 ml, 7.5 mmol). The mixture was refluxed for 1 h. The reaction mixture was poured into a saturated sodium hydrogencarbonate solution and extracted with ethyl acetate. The extract was washed with brine, dried over anhydrous magnesium sulfate and concentrated under reduced pressure. The residue was dissolved in tetrahydrofuran (20 ml), and then di-t-butyl dicarbonate (0.69 ml, 3 mmol) was added thereto. The resulting mixture was refluxed for 1 h. The reaction mixture was poured into water and extracted with ethyl acetate. The extract was washed with brine, dried over anhydrous magnesium sulfate and concentrated under reduced pressure. The resulting crystals were recrystallized from ethyl acetate-diisopropyl ether to give tert-butyl[6-(benzyloxy)-2-isobutyl-1-oxo-4-(2-thienyl)-1,2-dihydro-3-isoquinolinyl]methylcarbamate (1.19 g, 92.2%) as crystals.

Melting point 176–177° C. Elemental analysis for $C_{30}H_{34}N_2O_4S$ Calculated: C, 69.47; H, 6.61; N, 5.40. Found: C, 69.44; H, 6.68; N, 5.36. $^1$H-NMR(CDCl$_3$) δ: 0.98 (6H, d, J=7.0 Hz), 1.43 (9H, s), 2.14–2.28 (1H, m), 4.05 (2H, bs), 4.30 (2H, d, J=5.0 Hz), 4.56 (1H, bs), 4.98 (2H, s), 6.55 (1H, d, J=2.6 Hz), 6.94 (1H, dd; J=1.2, 3.5 Hz), 7.10 (1H, dd, J=2.6, 8.8 Hz), 7.17 (1H, dd, J=3.5, 5.4 Hz), 7.26–7.39 (5H, m), 7.48 (1H, dd, J=1.2, 5.4 Hz), 8.35 (1H, d, J=8.8 Hz).

(7) Tert-butyl[6-(benzyloxy)-2-isobutyl-1-oxo-4-(2-thienyl)-1,2-dihydro-3-isoquinolinyl]methylcarbamate (0.15 g, 0.3 mmol) was dissolved in a solution of 4N hydrogen chloride in ethyl acetate (5 ml). The solution was stirred at room temperature for 1 h. The reaction mixture was concentrated under reduced pressure, and the precipitated crystals were recrystallized from ethyl acetate-diisopropyl ether to give 3-(aminomethyl)-6-(benzyloxy)-2-isobutyl-4-(2-thienyl)-1(2H)-isoquinolinone hydrochloride (0.11 g, 84.6%) as crystals.

Melting point 139–141° C. Elemental analysis for $C_{25}H_{27}N_2O_2ClS$ $0.5H_2O$ Calculated: C, 64.71; H, 6.08; N, 6.04. Found: C, 65.01; H, 6.18; N, 5.74. $^1$H-NMR(DMSO-$d_6$) δ: 0.89 (6H, d, J=6.6 Hz), 1.99–2.09 (1H, m), 3.98; (2H, bs), 4.08 (2H, bs), 5.06 (2H,bs), 6.49 (1H, d, J=2.2 Hz), 7.20–7.41(8H, m), 7.85 (1H, dd, J=1.1, 5.1 Hz), 8.23 (1H, d, J=9.0 Hz), 8.59 (3H, bs).

Example 254

3-(Aminomethyl)-6-hydroxy-2-isobutyl-4-(2-thienyl)-1(2H)-isoquinolinone hydrochloride (1) A suspension of tert-butyl[6-(benzyloxy)-2-isobutyl-1-oxo-4-(2-thienyl)-1,2-dihydro-3-isoquinolinyl]methylcarbamate (1.04 g, 2 mmol) and 5% palladium carbon (1.0 g) in ethanol (10 ml) and tetrahydrofuran (10 ml) was stirred under a hydrogen atmosphere at room temperature for 2 h. The catalyst was filtered off and the filtrate was concentrated under reduced pressure. The residue was purified by silica gel column chromatography to give tert-butyl[6-hydroxy-2-isobutyl-1-oxo-4-(2-thienyl)-1,2-dihydro-3-isoquinolinyl]methylcarbamate (0.82 g, 96.5%) as crystals.

Melting point 216–217° C. Elemental analysis for $C_{23}H_{28}N_2O_4S$ Calculated: C, 64.46; H, 6.59; N, 6.54. Found: C, 64.38; H, 6.60; N, 6.33. $^1$H-NMR(CDCl$_3$) δ: 0.97 (6H, d, J=6.6 Hz), 1.43 (9H, s), 2.13–2.25 (1H, m), 4.04 (2H, bs), 4.30 (2H, d, J=5.2 Hz), 4.57 (1H, bs), 6.53 (1H, d, J=2.4 Hz), 6.97 (1H, d, J=2.8 Hz), 7.03 (1H, dd, J=2.4, 8.8 Hz), 7.13 (1H, dd, J=2.8, 5.6 Hz), 7.40 (1H, bs), 7.42 (1H, d, J=5.6 Hz), 8.28 (1H, d, J=8.8 Hz).

(2) Tert-butyl[6-hydroxy-2-isobutyl-1-oxo-4-(2-thienyl)-1,2-dihydro-3-isoquinolinyl]methylcarbamate (0.15 g, 0.35 mmol) was dissolved in a solution of 4N hydrogen chloride in ethyl acetate solution (5 ml.) The solution was stirred at room temperature for 2 h. The reaction mixture was concentrated under reduce pressure, and the residue was crystallized from ethyl acetate-diisopropyl ether to give 3-(aminomethyl)-6-hydroxy-2-isobutyl-4-(2-thienyl)-1(2H)-isoquinolinone hydrochloride (0.10 g, 83.3%) as crystals.

Melting point 249–251° C. Elemental analysis for $C_{18}H_{21}N_2O_2ClS$ $H_2O$ Calculated: C, 56.46; H, 6.05; N, 7.32. Found: C, 56.54; H, 6.35; N, 7.06. $^1$H-NMR(DMSO-$d_6$) δ: 0.90 (6H, d, J=6.6 Hz), 1.99–2.12 (1H, m), 3.98 (2H, bs), 4.08 (2H, bs), 6.41 (1H, d, J=2.3 Hz), 7.03 (1H, dd, J=2.3, 8.6 Hz), 7.06 (1H, bs), 7.26–7.29 (2H, m), 7.82 (1H, dd, J=2.8, 3.8 Hz), 8.14 (1H, d, J=8.6 Hz), 8.67 (3H, bs).

Example 255

2-{[3-(Aminomethyl)-2-isobutyl-1-oxo-4-(2-thienyl)-1,2-dihydro-6-isoquinolinyl]oxy}acetamide hydrochloride (1) A solution of tert-butyl[6-hydroxy-2-isobutyl-1-oxo-4-(2-thienyl)-1,2-dihydro-3-isoquinolinyl]methylcarbamate (0.43 g, 1 mmol), and 2-iodoacetamide (0.37 g, 2 mmol) and 1,8-diazabicyclo[5.4.0]-7-undecene (0.30 ml, 2 mmol) in N,N-dimethylacetamide (10 ml) was stirred at 80° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(2-amino-2-oxoethoxy)-2-isobutyl-1-oxo-4-(2-thienyl)-1,2-dihydro-3-isoquinolinyl]methylcarbamate (0.19 g, 39.6%) as crystals.

Melting point 219–221° C. Elemental analysis for $C_{25}H_{31}N_3O_5S$ $0.25H_2O$ Calculated: C, 61.27; H, 6.48; N, 8.57. Found: C, 61.02; H, 6.38; N, 8.37. $^1$H-NMR(CDCl$_3$) δ: 0.99 (6H, d, J=6.6 Hz), 1.44 (9H, s), 2.16–2.26 (1H, m), 4.07 (2H, bs), 4.31 (2H, d, J=6.0 Hz), 4.39 (2H, s), 4.61 (1H, bs), 5.72 (1H, bs), 6.50 (1H, d, J=2.5 Hz), 6.51 (1H, bs), 7.01 (1H, dd, J=1.2, 3.6 Hz), 7.06 (1H, dd, J=2.5, 8.9 Hz), 7.20 (1H, dd, J=3.6, 5.4 Hz), 7.51 (1H, dd, J=1.2, 5.4 Hz), 8.40 (1H, d, J=8.9 Hz).

(2) Tert-butyl[6-(2-amino-2-oxoethoxy)-2-isobutyl-1-oxo-4-(2-thienyl)-1,2-dihydro-3-isoquinolinyl]methylcarbamate (0.14 g, 0.3 mmol) was dissolved in a solution of 4N hydrogen chloride in ethyl acetate (5 ml). The solution was stirred at room temperature for 2 h. The reaction was concentrated under reduced pressure to give 2-{[3-(aminomethyl)-2-isobutyl-1-oxo-4-(2-thienyl)-1,2-dihydro-6-isoquinolinyl] oxy}acetamide hydrochloride (0.11 g, 91.7%) as an amorphous solid.

$^1$H-NMR(DMSO-$d_6$) δ: 0.90 (6H, d, J=6.6 Hz), 1.99–2.14 (1H, m), 3.98–4.09 (4H, m), 4.41 (2H, s), 6.50 (1H, d, J=2.6 Hz), 7.21 (1H, dd, J=2.6, 9.0 Hz), 7.26–7.30 (2H, m), 7.35 (1H, bs), 7.60 (1H, bs), 7.83 (1H, dd, J=2.6, 4.0 Hz), 8.26 (1H, d, J=9.0 Hz), 8.63 (3H, s).

Example 256

Methyl 3-(aminomethyl)-2-isobutyl-1-oxo-4-(2-thienyl)-1,2-dihydro-6-isoquinolinecarboxylate hydrochloride (1) To a solution of tert-butyl[6-hydroxy-2-isobutyl-1-oxo-4-(2-thienyl)-1,2-dihydro-3-isoquinolinyl]methylcarbamate (1.07 g, 2.5 mmol) in N,N-dimethylformamide (10 ml) was added sodium hydride (0.12 g, 3 mmol) (60% in oil) at 0° C., and then the mixture was stirred at 0° C. for 30 min. To the mixture was added N-phenyltrifluoromethanesulfonimide (1.07 g, 3 mmol), and the resulting mixture was stirred at room temperature for 2 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[2-isobutyl-1-oxo-4-(2-thienyl)-6-trifluoromethanesulfonyloxy-1,2-dihydro-3-isoquinolinyl]methylcarbamate (1.40 g, 100%) as an oil.

$^1$H-NMR(CDCl$_3$) δ: 0.99 (6H, d, J=6.6 Hz), 1.44 (9H, s), 2.15–2.27 (1H, m), 4.11 (2H, bs), 4.35 (2H, d, J=5.2 Hz), 4.58 (1H, bs), 7.00–7.06 (2H, m), 7.20–7.45 (2H, m), 7.53 (1H, dd, J=1.2, 5.3 Hz), 8.52 (1H, d, J=8.4 Hz).

(2) A mixture of tert-butyl[2-isobutyl-1-oxo-4-(2-thienyl)-6-trifluoromethanesulfonyloxy-1,2-dihydro-3-isoquinolinyl]methylcarbamate (1.40 g, 2.5 mmol), 1,1'-bis(diphenylphosphino)ferrocene (66 mg, 0.12 mmol), triethylamine (0.39 ml, 2.8 mmol) and palladium acetate (27 mg, 0.12 mmol) in tetrahydrofuran (20 ml) and methanol (20 ml) was stirred at 100° C. under a carbon monoxide atmosphere at 5 atom for 3 h. The reaction mixture was poured into water and extracted with ethyl acetate. The extract was washed with brine, dried over anhydrous magnesium sulfate and concentrated under reduced pressure. The residue was purified by silica gel column chromatography to give methyl 3-{[(tert-butoxycarbonyl)amino]methyl}-2-isobutyl-1-oxo-4-(2-thienyl)-1,2-dihydro-6-isoquinolinecarboxylate (1.02 g, 87.2%) as crystals.

Melting point 170–171° C. Elemental analysis for $C_{25}H_{30}N_2O_5S$ Calculated: C, 63.81; H, 6.43; N, 5.95. Found: C, 63.68; H, 6.68; N, 5.68. $^1$H-NMR(CDCl$_3$) δ: 1.01

(6H, d, J=7.0 Hz), 1.44 (9H, s), 2.17–2.31 (1H, m), 3.88 (3H, s), 4.10 (2H, d, J=7.4 Hz), 4.34 (2H, d, J=5.8 Hz), 4.64 (1H, bs) 7.05 (1H, dd, J=1.1, 3.4 Hz), 7.21 (1H, dd, J=3.4, 5.2 Hz), 7.52 (1H, dd, J=1.1, 5.2 Hz), 7.82 (1H, d, J=1.3 Hz), 8.04 (1H, dd, J=1.3, 8.4 Hz), 8.48 (1H, dd, J=0.8, 8.4 Hz).

(3) Methyl 3-{[(tert-butoxycarbonyl)amino]methyl}-2-isobutyl-1-oxo-4-(2-thienyl)-1,2-dihydro-6-isoquinolinecarboxylate (0.14 g, 0.3 mmol) was dissolved in a solution of 4N hydrogen chloride in ethyl acetate (5 ml). The solution was stirred at room temperature for 2 h. The reaction mixture was concentrated under reduced pressure, and the residue was crystallized from ethyl acetate-diisopropyl ether to give methyl 3-(aminomethyl)-2-isobutyl-1-oxo-4-(2-thienyl)-1,2-dihydro-6-isoquinolinecarboxylate hydrochloride (0.11 g, 91.7%) as crystals.

Melting point 227–229° C. Elemental analysis for $C_{20}H_{23}N_2O_3ClS$ 0.25$H_2O$ Calculated: C, 58.39; H, 5.76; N, 6.81. Found: C, 58.28; H, 6.09; N, 6.41. $^1$H-NMR(DMSO-$d_6$) δ: 0.92 (6H, d, J=6.6 Hz), 1.99–2.18 (1H, m), 3.35 (2H, s), 3.84 (3H, s), 4.03 (2H, bs), 7.29–7.33 (2H, m), 7.72 (1H, d, J=1.4 Hz), 7.88 (1H, dd, J=2.6, 4.0 Hz), 8.08 (1H, dd, J=1.4, 8.4 Hz), 8.44 (1H, d, J=8.4 Hz), 8.69 (3H, bs).

Example 257

3-(Aminomethyl)-2-isobutyl-1-oxo-4-(2-thienyl)-1,2-dihydro-6-isoquinolinecarboxylic acid hydrochloride (1) To a solution of methyl 3-{[(tert-butoxycarbonyl) amino]methyl}-2-isobutyl-1-oxo-4-(2-thienyl)-1,2-dihydro-6-isoquinolinecarboxylate (0.85 g, 1.8 mmol) in tetrahydrofuran (10 ml) and methanol (10 ml) was added 1N sodium hydroxide solution (4 ml). The resulting mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The resulting crystals were recrystallized from tetrahydrofuran-diisopropyl ether to give 3-{[(tert-butoxycarbonyl)amino]methyl}-2-isobutyl-1-oxo-4-(2-thienyl)-1,2-dihydro-6-isoquinolinecarboxylic acid (0.79 g, 96.3%) as crystals.

Melting point 224–226° C. Elemental analysis for $C_{24}H_{28}N_2O_5S$ Calculated: C, 63.14; H, 6.18; N, 6.14. Found: C, 63.00; H, 6.04; N, 5.94. $^1$H-NMR(CDCl$_3$) δ: 0.99 (6H, d, J=6.6 Hz), 1.49 (9H, s), 2.12–2.26 (1H, m), 4.05 (2H, d, J=6.4 Hz), 4.30 (2H, d, J=4.4 Hz), 5.61 (1H, bs), 7.09 (1H, d, J=3.5 Hz), 7.21 (1H, dd, J=3.5, 5.2 Hz), 7.53 (1H, dd, J=0.9, 5.2 Hz), 7.65 (1H, s), 7.91 (1H, d, J=8.6 Hz), 8.36 (1H, d, J=8.6 Hz).

(2) 3-{[(Tert-butoxycarbonyl)amino]methyl}-2-isobutyl-1-oxo-4-(2-thienyl)-1,2-dihydro-6-isoquinolinecarboxylic acid (0.14 g, 0.3 mmol) was dissolved in a solution of 4N hydrogen chloride in ethyl acetate (5 ml). The solution was stirred at room temperature for 1 h. The reaction mixture was concentrated under reduced pressure, and the residue was crystallized from ethyl acetate-diisopropyl ether to give 3-(aminomethyl)-2-isobutyl-1-oxo-4-(2-thienyl)-1,2-dihydro-6-isoquinolinecarboxylic acid hydrochloride (0.10 g, 90.9%) as crystals.

Melting point 208–210° C. Elemental analysis for $C_{19}H_{21}N_2O_3ClS$ $H_2O$ Calculated: C, 55.54; H, 5.64; N, 6.82. Found: C, 55.37; H, 5.74; N, 6.60. $^1$H-NMR(DMSO-$d_6$) δ: 0.92 (6H, d, J=6.8 Hz), 1.99–2.19 (1H, m), 3.33 (2H, s), 4.04 (2H, s), 7.28–7.32 (2H, m), 7.72 (1H, d, J=1.4 Hz), 7.86–7.89 (1H, m), 8.06 (1H, dd, J=1.7, 8.2 Hz), 8.41 (1H, d, J=8.2 Hz), 8.60 (3H, bs).

Example 258

3-(Aminomethyl)-2-isobutyl-1-oxo-4-(2-thienyl)-1,2-dihydro-6-isoquinolinecarboxamide hydrochloride (1) A solution of 3-{[(tert-butoxycarbonyl)amino]methyl}-2-isobutyl-1-oxo-4-(2-thienyl)-1,2-dihydro-6-isoquinolinecarboxylic acid (0.59 g, 1.3 mmol), 1-ethyl-3-(3-dimethylaminopropyl)carbodiimide hydrochloride (0.50 g, 2.6 mmol) and 1-hydroxybenzotriazole ammonium salt (0.40 g, 2.6 mmol) in N,N-dimethylformamide (10 ml) was stirred at room temperature for 2 h. The reaction mixture was poured into water and extracted with ethyl acetate. The extract was washed with brine, dried over anhydrous magnesium sulfate and concentrated under reduced pressure. The resulting crystals were recrystallized from tetrahydrofuran-diisopropyl ether to give tert-butyl[6-(aminocarbonyl)-2-isobutyl-1-oxo-4-(2-thienyl)-1,2-dihydro-3-isoquinolinyl]methylcarbamate (0.56 g, 94.9%) as crystals.

Melting point 248–250° C. Elemental analysis for $C_{24}H_{29}N_3O_4S$ Calculated: C, 63.27; H, 6.42; N, 9.22. Found: C, 62.99; H, 6.62; N, 9.00. $^1$H-NMR(CDCl$_3$) δ: 0.99 (6H, d, J=7.0 Hz), 1.46 (9H, s), 2.14–2.27(1H, m), 4.08 (2H, d, J=7.4 Hz), 4.31 (2H, d, J=5.4 Hz), 5.01 (1H, bs), 6.23 (2H, bs), 7.06 (1H, d, J=2.6 Hz), 7.17 (1H, dd, J=2.6, 5.2 Hz), 7.48 (1H, d, J=5.2 Hz), 7.52 (1H, d, J=1.7 Hz), 7.73 (1H, dd, J=1.7, 8.4 Hz), 8.38 (1H, d, J=8.4 Hz).

(2) Tert-butyl[6-(aminocarbonyl)-2-isobutyl-1-oxo-4-(2-thienyl)-1,2-dihydro-3-isoquinolinyl]methylcarbamate (0.23 g, 0.5 mmol) was dissolved in a solution of 4N hydrogen chloride in ethyl acetate (5 ml). The solution was stirred at room temperature for 1 h. The reaction was concentrated under reduced pressure, and the precipitated crystals were crystallized from methanol-diethyl ether to give 3-(aminomethyl)-2-isobutyl-1-oxo-4-(2-thienyl)-1,2-dihydro-6-isoquinolinecarboxamide hydrochloride (0.18 g, 94.7%) as crystals.

Melting point 246–248° C. Elemental analysis for $Cl_{19}H_{22}N_3O_3ClS$ 0.75$H_2O$ Calculated: C, 56.29; H, 5.84; N, 10.36. Found: C, 56.19; H, 5.97; N, 10.22. $^1$H-NMR (DMSO-$d_6$) δ: 0.92 (6H, d, J=6.6 Hz), 2.02–2.18 (1H, m), 3.43 (2H, bs), 4.02 (2H, bs), 7.29–7.33 (2H, m), 7.61–7.63 (2H, m), 7.84–7.87 (1H, m), 8.01 (1H, dd, J=1.5, 8.4 Hz), 8.19 (1H, bs), 8.35 (1H, d, J=8.4 Hz), 8.60 (3H, bs).

Example 259

3-(Aminomethyl)-2-isobutyl-1-oxo-4-(2-thienyl)-1,2-dihydro-6-isoquinolinecarbonitrile hydrochloride (1) A solution of tert-butyl[6-(aminocarbonyl)-2-isobutyl-1-oxo-4-(2-thienyl)-1,2-dihydro-3-isoquinolinyl]methylcarbamate (0.23 g, 0.5 mmol) and cyanuric chloride (0.28 g, 1.5 mmol) in N,N-dimethylformamide (10 mmol) was stirred at 0° C. for 1 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl [6-cyano-2-isobutyl-1-oxo-4-(2-thienyl)-1,2-dihydro-3-isoquinolinyl]methylcarbamate (0.20 g, 95.2%) as crystals.

Melting point 189–190° C. Elemental analysis for $C_{24}H_{27}N_3O_3S$ Calculated: C, 65.88; H, 6.22; N, 9.60.

Found: C, 65.96; H, 6.14; N, 9.51. $^1$H-NMR(CDCl$_3$) δ: 1.00 (6H, d, J=7.0 Hz), 1.44 (9H, s), 2.14–2.31 (1H, m), 4.10 (2H, bs), 4.36 (2H, bs), 4.57 (1H, bs), 7.03 (1H, dd, J=1.2, 3.6 Hz), 7.23 (1H, dd, J=3.6, 5.1 Hz), 7.46 (1H, d, J=1.5 Hz), 7.55 (1H, dd, J=1.2, 5.1 Hz), 7.65 (1H, dd, J=1.5, 8.2 Hz), 8.52 (1H, d, J=8.2 Hz).

(2) Tert-butyl[6-cyano-2-isobutyl-1-oxo-4-(2-thienyl)-1,2-dihydro-3-isoquinolinyl]methylcarbamate (0.17 g, 0.4 mmol) was dissolved in a solution of 4N hydrogen chloride in ethyl acetate (5 ml). The solution was stirred at room temperature for 1 h. The reaction was concentrated under reduced pressure, and the residue was crystallized from ethyl acetate diisopropyl ether to give 3-(aminomethyl)-2-isobutyl-1-oxo-4-(2-thienyl)-1,2-dihydro-6-isoquinolinecarbonitrile hydrochloride (0.14 g, 93.3%) as crystals.

Melting point 202–203° C. $^1$H-NMR(DMSO-d$_6$) δ: 0.92 (6H, d, J=6.6 Hz), 2.06–2.16 (1H, m), 3.98–4.09 (4H, m), 7.29–7.33 (2H, m), 7.41 (1H, s), 7.87–7.91 (1H, m), 7.98 (1H, dd, J=1.1, 8.4 Hz), 8.46 (1H, d, J=8.4 Hz), 8.69 (3H, bs).

Example 260

3-(Aminomethyl)-4-butoxy-2-isobutyl-6-(2-pyridyl)-1(2H)-isoquinolinone dihydrochloride (1) A solution of tert-butyl(6-bromo-4-butoxy-2-isobutyl-1-oxo-1,2-dihydro-3-isoquinolinyl)methylcarbamate (0.48 g, 1 mmol), tri-n-butyl(2-pyridyl)tin (0.37 g, 1 mmol) and tetrakis(triphenylphosphine)palladium (58 mg, 0.05 mmol) in N,N-dimethylformamide (10 ml) was stirred at 100° C. for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-2-isobutyl-1-oxo-6-(2-pyridyl)-1,2-dihydro-3-isoquinolinyl]methylcarbamate (0.36 g, 75.0%) as crystals.

Melting point 123–124° C. Elemental analysis for C$_{28}$H$_{37}$N$_3$O$_4$ Calculated: C, 70.12; H, 7.78; N, 8.76. Found: C, 69.91; H, 8.07; N, 8.71. $^1$H-NMR(CDCl$_3$) δ: 0.98 (6H, d, J=6.6 Hz), 1.05 (3H, t, J=7.3 Hz), 1.47 (9H, s), 1.53–1.72 (2H, m), 1.84–1.97 (2H, m), 2.05–2.27 (1H, m), 3.94 (2H, t, J=6.4 Hz), 4.01 (2H, d, J=7.8 Hz), 4.55 (2H, d, J=5.4 Hz), 4.82 (1H, bs), 7.28–7.37 (1H, m), 7.77–7.85 (2H, m), 8.13 (1H, dd, J=1.8, 8.4 Hz), 8.32 (1H, d, J=1.8 Hz), 8.50 (1H, d, J=8.4 Hz), 8.74–8.78 (1H, m).

(2) Tert-butyl[4-butoxy-2-isobutyl-1-oxo-6-(2-pyridyl)-1,2-dihydro-3-isoquinolinyl]methylcarbamate (0.31 g, 0.65 mmol) was dissolved in a solution of 4N hydrogen chloride in ethyl acetate (5 ml). The solution was stirred at room temperature for 2 h. The reaction was concentrated under reduced pressure to give 3-(aminomethyl)-4-butoxy-2-isobutyl-6-(2-pyridyl)-1(2H)-isoquinolinone dihydrochloride (0.27 g, 93.1%) as an amorphous solid.

Elemental analysis for C$_{23}$H$_{31}$N$_3$O$_2$Cl$_2$ H$_2$O Calculated: C, 58.72; H, 7.07; N, 8.93. Found: C, 59.20; H, 7.46; N, 8.91. $^1$H-NMR(DMSO-d$_6$) δ: 0.91 (6H, d, J=6.3 Hz), 1.01 (3H, t, J=7.2 Hz), 1.56–1.64 (2H, m), 1.87–1.95 (2H, m), 1.99–2.18 (1H, m), 4.02–4.06 (4H, m), 4.23 (2H, bs), 7.73 (1H, bs), 8.27–8.28 (3H, m), 8.42–8.44 (2H, m), 8.46 (4H, bs).

Example 261

3-(Aminomethyl)-4-butoxy-2-isobutyl-6-(2-thienyl)-1(2H)-isoquinolinone hydrochloride (1) A solution of tert-butyl(6-bromo-4-butoxy-2-isobutyl-1-oxo-1,2-dihydro-3-isoquinolinyl)methylcarbamate (0.48 g, 1 mmol), tri-n-butyl(2-thienyl)tin (0.32 ml, 1 mmol) and tetrakis(triphenylphosphine)palladium (58 mg, 0.05 mmol) in tetrahydrofuran (20 ml) was refluxed for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-2-isobutyl-1-oxo-6-(2-thienyl)-1,2-dihydro-3-isoquinolinyl]methylcarbamate (0.22 g, 45.8%) as crystals.

Melting point 130–131° C. Elemental analysis for C$_{27}$H$_{36}$N$_2$O$_4$S Calculated: C, 66.91; H, 7.49; N, 5.78. Found: C, 66.85; H, 7.56; N, 5.70. $^1$H-NMR(CDCl$_3$) δ: 0.97 (6H, d, J=6.6 Hz), 1.06 (3H, t, J=7.3 Hz), 1.47 (9H, s), 1.55–1.73 (2H, m), 1.83–1.97 (2H, m), 2.05–2.25 (1H, m), 3.91 (2H, t, J=6.4 Hz), 3.99 (2H, d, J=7.4 Hz), 4.53 (2H, d, J=5.6 Hz), 4.75 (1H, bs), 7.15 (1H, dd, J=3.6, 5.2 Hz), 7.39 (1H, dd, J=1.1, 5.2 Hz), 7.48 (1H, dd, J=1.1, 3.6 Hz), 7.75 (1H, dd, J=1.6, 8.4 Hz), 7.90 (1H, d, J=1.6 Hz), 8.40 (1H, d, J=8.4 Hz).

(2) Tert-butyl[4-butoxy-2-isobutyl-1-oxo-6-(2-thienyl)-1,2-dihydro-3-isoquinolinyl]methylcarbamate (0.15 g, 0.3 mmol) was dissolved in a solution of 4N hydrogen chloride in ethyl acetate (5 ml). The solution was stirred at room temperature for 2 h. The reaction was concentrated under reduced pressure, and the resulting crystals were recrystallized from methanol-diisopropyl ether to give 3-(aminomethyl)-4-butoxy-2-isobutyl-6-(2-thienyl)-1(2H)-isoquinolinone hydrochloride (0.11 g, 91.7%) as crystals.

Melting point 167–170° C. $^1$H-NMR(DMSO-d$_6$), δ: 0.89 (6H, d, J=6.6 Hz), 1.03 (3H, t, J=7.3 Hz), 1.56–1.73 (2H, m), 1.82–2.11 (3H, m), 3.95–4.01 (4H, m), 4.20 (2H, s), 7.24 (1H, dd, J=3.7, 5.1 Hz), 7.72–7.76 (2H, m), 7.90 (1H, d, J=1.6 Hz), 7.96 (1H, dd, J=1.66, 8.4 Hz), 8.30 (1H, d, J=8.4 Hz), 8.64 (3H, bs).

Example 262

3-(Aminomethyl)-4-butoxy-6-(2-furyl)-2-isobutyl-1(2H)-isoquinolinone hydrochloride (1) A solution of tert-butyl(6-bromo-4-butoxy-2-isobutyl-1-oxo-1,2-dihydro-3-isoquinolinyl)methylcarbamate (0.48 g, 1 mmol), tri-n-butyl(2-furyl)tin (0.31 ml, 1 mmol) and tetrakis(triphenylphosphine)palladium (58 mg, 0.05 mmol) in tetrahydrofuran (20 ml) was refluxed at 80° C. for 12 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-6-(2-furyl)-2-isobutyl-1-oxo-1,2-dihydro-3-isoquinolinyl]methylcarbamate (0.35 g, 76.1%) as crystals.

Melting point 157–158° C. Elemental analysis for C$_{27}$H$_{36}$N$_2$O$_5$ Calculated: C, 69.21; H, 7.74; N, 5.98. Found: C, 68.88; H, 7.98; N, 5.75. $^1$H-NMR(CDCl$_3$) δ: 0.97 (6H, d, J=6.6 Hz), 1.06 (3H, t, J=7.3 Hz), 1.47 (9H, s), 1.57–1.70 (2H, m), 1.86–1.95 (2H, m), 2.14–2.23 (1H, m), 3.91 (2H, t, J=6.6 Hz), 3.99 (2H, d, J=7.2 Hz), 4.53 (2H, d, J=5.7 Hz), 4.78 (1H, bs), 6.54 (1H, dd, J=1.5, 3.3 Hz), 6.85 (1H, dd, J=0.6, 3.3 Hz), 7.56 (1H, dd, J=0.6, 1.5 Hz), 7.76 (1H, dd, J=1.5, 8.4 Hz), 7.97 (1H, d, J=1.5 Hz), 8.40 (1H, d, J=8.4 Hz).

(2) Tert-butyl[4-butoxy-6-(2-furyl)-2-isobutyl-1-oxo-1,2-dihydro-3-isoquinolinyl]methylcarbamate (0.28 g, 0.6 mmol) was dissolved in a solution of 4N hydrogen chloride in ethyl acetate (5 ml). The solution was stirred at room temperature for 2 h. The reaction was concentrated under reduced pressure, and the residue was crystallized from ethyl acetate-diisopropyl ether to give 3-(aminomethyl)-4-butoxy-6-(2-furyl)-2-isobutyl-1(2H)-isoquinolinone hydrochloride (0.22 g, 91.7%) as crystals.

Melting point 189–191° C. Elemental analysis for $C_{22}H_{29}N_2O_3Cl$ 1.75$H_2O$ Calculated: C, 60.54; H, 7.51; N, 6.42. Found: C, 60.46; H, 7.07; N, 6.33. $^1$H-NMR(DMSO-$d_6$) δ: 0.88 (6H, d, J=6.6 Hz), 1.02 (3H, t, J=7.3 Hz), 1.51–1.69 (2H, m), 1.81–2.08 (3H, m), 3.93–3.99 (4H, m), 4.18 (2H, d, J=4.8 Hz), 6.99 (1H, dd, J=1.8, 3.3 Hz), 7.23 (1H, d, J=3.3 Hz), 7.90–7.97 (3H, m), 8.28 (1H, d, J=8.8 Hz), 8.75 (3H, bs).

Example 263

3-(Aminomethyl)-4-butoxy-2-isobutyl-6-phenyl-1(2H)-isoquinolinone hydrochloride (1) A mixture of tert-butyl(6-bromo-4-butoxy-2-isobutyl-1-oxo-1,2-dihydro-3-isoquinolinyl)methylcarbamate (0.48 g, 1 mmol), phenylboric acid (0.15 g, 1.2 mmol), sodium carbonate (0.26 g, 2.5 mmol), toluene (10 ml), ethanol (2 ml) and water (2 ml) was stirred at room temperature under an argon atmosphere for 30 min. To the resulting mixture was added tetrakis(triphenylphosphine)palladium (58 mg, 0.05 mmol), and then the mixture was refluxed under an argon atmosphere for 10 h. The reaction mixture was poured into water and extracted with ethyl acetate. The extract was washed with brine, dried over anhydrous magnesium sulfate and concentrated under reduced pressure. The residue was purified by silica gel column chromatography to give tert-butyl(4-butoxy-2-isobutyl-1-oxo-6-phenyl-1,2-dihydro-3-isoquinolinyl)methylcarbamate (0.42 g, 89.4%) as crystals.

Melting point 155–159° C. Elemental analysis for $C_{29}H_{38}N_2O_4$ Calculated: C, 72.77; H, 8.00; N, 5.85. Found: C, 72.52; H, 7.81; N, 5.73. $^1$H-NMR(CDCl$_3$) δ: 0.98 (6H, d, J=6.6 Hz), 1.03 (3H, t, J=7.3 Hz), 1.47 (9H, s), 1.48–1.69 (2H, m), 1.81–1.95 (2H, m), 2.13–2.26 (1H, m), 3.92 (2H, t, J=6.6 Hz), 4.02 (2H, d, J=7.4 Hz), 4.55 (2H, d, J=5.4 Hz), 4.78 (1H, bs), 7.39–7.56 (3H, m), 7.66–7.75 (3H, m), 7.89 (1H, d, J=1.4 Hz), 8.49 (1H, d, J=8.6 Hz).

(2) Tert-butyl(4-butoxy-2-isobutyl-1-oxo-6-phenyl-1,2-dihydro-3-isoquinolinyl)methylcarbamate (0.34 g, 0.7 mmol) was dissolved in a solution of 4N hydrogen chloride in ethyl acetate (5 ml). The solution was stirred at room temperature for 1 h. The reaction was concentrated under reduced pressure, and the residue was crystallized from methanol-diisopropyl ether to give 3-(aminomethyl)-4-butoxy-2-isobutyl-6-phenyl-1(2H)-isoquinolinone hydrochloride (0.28 g, 96.6%) as crystals.

Melting point 180–181° C. Elemental analysis for $C_{24}H_{31}N_2O_2Cl$ Calculated: C, 69.46; H, 7.53; N, 6.75. Found: C, 69.15; H, 7.70; N, 6.81. $^1$H-NMR(DMSO-$d_6$) δ: 0.90 (6H, d, J=6.6 Hz), 1.00 (3H, t, J=7.4 Hz), 1.51–1.69 (2H, m), 1.80–2.12 (3H, m), 3.90–4.05 (4H, m), 4.22 (2H, s), 7.45–7.62 (3H, m), 7.77–7.82 (2H, m), 7.91–7.95 (2H, m), 8.37 (1H, d, J=8.8 Hz), 8.71 (3H, bs).

Example 264

3-(Aminomethyl)-4-butoxy-2-isobutyl-6-[(E)-2-(1,3-thiazol-4-yl)ethenyl]-1(2H)-isoquinolinone hydrochloride (1) A mixture of triphenyl(1,3-thiazol-4-ylmethyl)phosphonium chloride (0.44 g, 1.1 mmol), potassium carbonate (15 g, 1.1 mmol) and tert-butyl(4-butoxy-6-formyl-2-isobutyl-1-oxo-1,2-dihydro-3-isoquinolinyl)methylcarbamate (0.47 g, 1.1 mol) in N,N-dimethylformamide (10 ml) was stirred at room temperature for 10 h. The reaction mixture was poured into water and extracted with ethyl acetate. The extract was washed with brine, dried over anhydrous magnesium sulfate and concentrated under reduced pressure. The resulting crystals were recrystallized from ethyl acetate-diisopropyl ether to give tert-butyl{4-butoxy-2-isobutyl-1-oxo-6-[(E)-2-(1,3-thiazol-4-yl)ethenyl]-1,2-dihydro-3-isoquinolinyl}methylcarbamate (0.46 g, 80.7%) as crystals.

Melting point 141–142° C. Elemental analysis for $C_{29}H_{37}N_3O_4S$ 0.55$H_2O$ Calculated: C, 65.39; H, 7.19; N, 7.89. Found: C, 65.58; H, 7.33; N, 8.11. $^1$H-NMR(CDCl$_3$) δ: 0.97 (6H, d, J=7.0 Hz), 1.06 (3H, t, J=7.3 Hz), 1.47 (9H, s), 1.48–1.69 (2H, m), 1.83–1.97 (2H, m), 2.11–2.25 (1H, m), 3.89 (2H, t, J=6.6 Hz), 3.99 (2H, d, J=7.4 Hz), 4.52 (2H, d, J=5.4 Hz), 4.77 (1H, bs), 7.31 (1H, d, J=16.0 Hz), 7.32 (1H, d, J=16.0 Hz), 7.32 (1H, d, J=1.8 Hz), 7.62–7.74 (3H, m), 8.39 (1H, d, J=8.8 Hz), 8.87 (1H, d, J=1.4 Hz).

(2) Tert-butyl{4-butoxy-2-isobutyl-1-oxo-6-[(E)-2-(1,3-thiazol-4-yl)ethenyl]-1,2-dihydro-3-isoquinolinyl}methylcarbamate (0.16 g, 0.3 mmol) was dissolved in a solution of 4N hydrogen chloride in ethyl acetate solution (5 ml). The solution was stirred at room temperature for 1 h. The reaction was concentrated under reduced pressure, and the residue was recrystallized from methanol-diisopropyl ether to give 3-(aminomethyl)-4-butoxy-2-isobutyl-6-[(E)-2-(1,3-thiazol-4-yl-)ethenyl]-1(2H)-isoquinolinone hydrochloride (0.11 g, 84.6%) as crystals.

Melting point 164–166° C. Elemental analysis for $C_{24}H_{30}N_3O_2ClS$ 0.75$H_2O$ Calculated: C, 56.52; H, 6.42; N, 8.24. Found: C, 56.44; H, 6.41; N, 8.21. $^1$H-NMR(DMSO-$d_6$) δ: 0.89 (6H, d, J=6.6 Hz), 1.06 (3H, t, J=7.1 Hz), 1.50–1.68 (2H, m), 1.83–2.10 (3H, m), 3.91–4.00 (4H, m), 4.18 (2H, d, J=4.4 Hz), 7.56 (1H, d, J=16.2 Hz), 7.67 (1H, d, J=16.2 Hz), 7.84 (1H, s), 7.87 (1H, d, J=1.8 Hz), 7.94 (1H, dd, J=1.8, 8.6 Hz), 8.26 (1H, d, J=8.6 Hz), 8.69 (3H, bs), 9.22 (1H, s).

Example 265

3-(Aminomethyl)-4-butoxy-2-isobutyl-6-[2-(1,3-thiazol-4-yl)ethyl]-1(2H)-isoquinolinone hydrochloride (1) A suspension of tert-butyl{4-butoxy-2-isobutyl-1-oxo-6-[(E)-2-(1,3-thiazol-4-yl)ethenyl]-1,2-dihydro-3-isoquinolinyl}methylcarbamate (0.21 g, 0.4 mmol) and 5% palladium carbon (0.2 g) in tetrahydrofuran (10 ml) was stirred under a hydrogen atmosphere at room temperature for 2 h. The catalyst was filtered off, and the filtrate was concentrated under reduced pressure. The residue was purified by silica gel column chromatography to give tert-butyl{4-butoxy-2-isobutyl-1-oxo-6-[2-(1,3-thiazol-4-yl)ethyl]-1,2-dihydro-3-isoquinolinyl}methylcarbamate (0.20 g, 95.2%) as crystals.

Melting point 103–104° C. Elemental analysis for $C_{29}H_{39}N_2C_4S$ 0.5$H_2O$ Calculated: C, 65.14; H, 7.54; N, 7.86. Found: C, 65.34; H, 7.53; N, 8.12. $^1$H-NMR(CDCl$_3$) δ: 0.95 (6H, d, J=7.0 Hz), 1.04 (3H, t, J=7.3 Hz), 1.46 (9H, s), 1.46–1.65 (2H, m), 1.77–1.91 (2H, m), 2.09–2.24 (1H, m), 3.22 (4H, s) 3.79 (2H, t, J=6.6 Hz), 3.89 (2H, d, J=7.2 Hz), 4.50 (2H, d, J=5.6 Hz), 4.70 (1H, bs), 6.86 (1H, d, J=2.0 Hz), 7.33 (1H, dd, J=1.6, 8.2 Hz), 7.44 (1H, d, J=1.6 Hz), 8.33 (1H, d, J=8.2 Hz), 8.78 (1H, d, J=2.0 Hz).

(2) Tert-butyl{4-butoxy-2-isobutyl-1-oxo-6-[2-(1,3thiazol-4-yl)ethyl]-1,2-dihydro-3-isoquinolinyl}methylcarbamate (0.16 g, 0.3 mmol) was dissolved in absolution of 4N hydrogen chloride in ethyl acetate (5 ml). The solution was stirred at room temperature for 1 h. The reaction was concentrated under reduced pressure to give 3-(aminomethyl)-4-butoxy-2-isobutyl-6-[2-(1,3-thiazol-4-yl)ethyl]-1(2H)-isoquinolinone hydrochloride (0.13 g, 92.9%) as an amorphous solid.

Elemental analysis for C$_{24}$H$_{32}$N$_3$O$_2$ClS 2.5H$_2$O Calculated: C, 56.85; H, 7.35; N, 8.29. Found: C, 56.80; H, 7.20; N, 8.13. $^1$H-NMR(DMSO-d$_6$) δ: 0.87 (6H, d, J=6.6 Hz), 1.00 (3H, t, J=7.3 Hz), 1.48–1.67 (2H, m), 1.77–1.87 (2H, m), 1.96–2.05 (1H, m), 3.16–3.21 (4H, m), 3.84 (2H, t, J=6.3 Hz), 3.94 (2H, d, J=6.0 Hz), 4.15 (2H, d, J=5.1 Hz), 7.35–7.38 (1H, m), 7.49–7.51 (2H, m), 8.18 (1H, d, J=8.7 Hz), 8.56 (3H, bs), 9.11–9.18 (1H, m).

Example 266

6-Amino-3-(aminomethyl)-2–4-butoxy-2neopentyl-1 (2H)-isoquinolinone dihydrochloride (1) 9H-Fluoren-9-ylmethyl 4-butoxy-3-{[(tert-butoxycarbonyl)amino]methyl}-2-neopentyl-1-oxo-1,2-dihydro-6-isoquinolinylcarbamate (1.14 g, 87.7%) as an amorphous solid. [synthesized according to the method similar to that in Example 82(1) from 4-butoxy-3-{[(tert-butoxycarbonyl) amino]methyl}-2-neopentyl-1-oxo-1,2-dihydro-6-isoquinolinecarboxylic acid (0.92 g, 2 mmol)]

$^1$H-NMR(CDCl$_3$); δ: 0.99 (9H, s), 1.01 (3H, t, J=7.4 Hz), 1.44 (9H, s), 1.45–1.62 (2H, m), 1.79–1.90 (2H, m), 3.86 (2H, t, J=6.4 Hz), 4.10 (2H, bs), 4.29 (1H, t, J=6.4 Hz), 4.54–4.62 (4H, m), 4.72 (1H, bs), 7.10 (1H, bs), 7.26–7.46 (5H, m), 7.63 (2H, d, J=7.3 Hz), 7.79 (2H, d, J=7.3 Hz), 8.78 (1H, s), 8.32 (1H, d, J=8.8 Hz).

(2) Tert-butyl(6-amino-4-butoxy-2-neopentyl-1-oxo-1,2-dihydro-3-isoquinolinyl)methylcarbamate (0.66 g, 90.4%) as an amorphous solid. [synthesized according to the method similar to that in Example 82(2) from 9H-fluoren-9-ylmethyl 4-butoxy-3-{[(tert-butoxycarbonyl)amino]methyl}-2-neopentyl-1-oxo-1,2-dihydro-6-isoquinolinylcarbamate (1.11 g, 1.7 mmol)]

$^1$H-NMR(CDCl$_3$) δ: 0.98 (9H, s), 1.02 (3H, t, J=7.4 Hz), 1.44 (9H, s), 1.50–1.60 (2H, m), 1.70–1.88 (2H, m), 3.83 (2H, t, J=6.5 Hz), 4.19 (2H, bs), 4.53 (2H, d, J=5.4 Hz), 4.67 (1H, bs), 6.78–6.81 (2H, m), 8.20 (1H, d, J=9.0 Hz).

(3) 6-amino-3-(aminomethyl)-4-butoxy-2-neopentyl-1 (2H)-isoquinolinone dihydrochloride (0.19 g, 95.0%) as an amorphous solid. [synthesized according to the method similar to that in Example 82(3) from tert-butyl(6-amino-4-butoxy-2-neopentyl-1-oxo-1,2-dihydro-3-isoquinolinyl)methylcarbamate (0.21 g, 0.5 mmol)]

Elemental analysis for C$_{19}$H$_{31}$N$_3$O$_2$Cl$_2$ Calculated: C, 56.43; H, 7.73; N, 10.39. Found: C, 56.71; H, 8.05; N, 10.00. $^1$H-NMR(DMSO-d$_6$) δ: 0.88 (9H, s), 1.02. (3H, t, J=6.2 Hz), 1.48–1.59 (2H, m), 1.77–1.91 (2H, m), 3.88 (2H, t, J=5.9 Hz); 4.00 (2H, bs), 4.19 (2H, bs), 6.53 (3H, bs), 6.98–7.04 (2H, m), 8.03 (1H, d, J=8.4 Hz), 8.54 (3H, bs).

Example 267

N-[3-(Aminomethyl)-4-butoxy-2-neopentyl-1-oxo-1, 2-dihydro-6-isoquinolinyl]acetamide hydrochloride (1) Tert-butyl[6-(acetylamino)-4-butoxy-2-neopentyl-1-oxo-1,2-dihydro-3-isoquinolinyl]methylcarbamate (0.30 g, 63.8%) as crystals. [synthesized according to the method similar to that in Example 88(1) from tert-butyl(6-amino-4-butoxy-2-neopentyl-1-oxo-1,2-dihydro-3-isoquinolinyl)methylcarbamate (0.43 g, 1 mmol)]

Melting point 120–121° C. $^1$NMR(CDCl$_3$) δ: 0.99 (9H, s), 1.01 (3H, t, J=7.0 Hz), 1.45 (9H, s), 1.4–1.66 (2H, m), 1.79–1.93 (2H, m), 2.26 (3H, s), 3.88 (2H, t, J=6.6 Hz) 4.14 (2H, bs), 4.56 (2H, d, J=5.6 Hz), 4.86 (1H, bs), 7.34 (1H, d, J8.6 Hz), 7.88 (1H, bs), 8.15 (1H, s), 8.28 (1H, d, J=8.6 Hz).

(2) N-[3-(Aminomethyl)-4-butoxy-2-neopentyl-1-oxo-1, 2-dihydro-6-isoquinolinyl]acetamide (0.19 g, 95.0%) as crystals. [synthesized according to the method similar, to that in Example 88(2) from tert-butyl[6-(acetylamino)-4-butoxy-2-neopentyl-1-oxo-1,2-dihydro-3-isoquinolinyl]methylcarbamate (0.24 g, 0.5 mmol)]

Melting point 191–193° C. Elemental analysis for C$_{21}$H$_{32}$N$_3$O$_3$Cl 0.5H$_2$O Calculated: C, 60.20; H, 7.94; N, 10.03. Found: C, 60.43; H, 8.07; N, 9.90. $^1$H-NMR(DMSO-d$_6$) δ: 0.90 (9H, s), 0.99 (3H, t, J=6.2 Hz), 1.43–1.67 (2H, m), 1.72–1.93 (2H, m), 2.13 (3H, s), 3.92 (2H, s), 4.05 (2H, bs), 4.22 (2H, s), 7.70 (1H, d, J=8.6 Hz), 8.08 (1H, d, J=8.6 Hz), 8.27 (1H, s), 8.52 (3H, bs), 10.63 (1H, s).

Example 268

3-(Aminomethyl)-7-(benzyloxy)-2-isobutyl-4-phenyl-1(2H)-isoquinolinone hydrochloride.

(1) Ethyl 7-(benzyloxy)-2-isobutyl-1-oxo-4-trifluoromethanesulfonyloxy-1,2-dihydro-3-isoquinolinecarboxylate (24.01 g, 91.0%) as crystals. [synthesized according to the method similar to that in Example 154(2) from ethyl 7-(benzyloxy)-4-hydroxy-2-isobutyl-1-oxo-1,2-dihydro-3-isoquinolinecarboxylate (19.77 g, 50 mmol)] $^1$H-NMR (CDCl$_3$) δ: 0.90 (6H, d, J=6.6 Hz), 1.44 (3H, t, J=7.1 Hz), 1.96–2.07 (1H, m), 4.12 (2H, d, J=7.2 Hz), 4.45 (2H, q, J=7.1 Hz), 5.21 (2H, s), 7.30–7.48 (6H, m), 7.74 (1H, d, J=9.0 Hz); 7.96 (1H, d, J=9.0 Hz).

(2) Ethyl 7-(benzyloxy)-2-isobutyl-1-oxo-4-phenyl-1,2-dihydro-3-isoquinolinecarboxylate (16.21 g, 79.1%) as crystals. [synthesized according to the method similar to that in Example 154(3) from ethyl 7-(benzyloxy)-2-isobutyl-1-oxo-4-trifluoromethanesulfonyloxy-1,2-dihydro-3-isoquinolinecarboxylate (23.74 g, 45 mmol) and phenylboronic acid (6.58 g, 54 mmol)]

Melting point 107–108° C. Elemental analysis for C$_{29}$H$_{29}$NO$_4$ Calculated: C, 76.46; H, 6.42; N, 3.07. Found: C, 76.45; H, 6.54; N, 3.06. $^1$H-NMR(CDCl$_3$) δ: 0.87 (3H, d, J=7.2 Hz), 0.94 (6H, d, J=6.6 Hz), 2.05–2.23 (1H, m), 3.93 (2H, q, J=7.2 Hz), 4.05 (2H, d, J=7.4 Hz), 5.21 (2H, s), 7.13–7.50 (12H, m), 8.03 (1H, d, J=2.2 Hz).

(3) 7-(Benzyloxy)-2-isobutyl-1oxo-4-phenyl-1,2-dihydro-3-isoquinolinecarboxylic acid (11.21 g, 74.9%) as an amorphous; solid. [synthesized according to the method similar to that in Example 154(4) from ethyl 7-(benzyloxy)-2-isobutyl-1oxo-4-phenyl-1,2-dihydro-3-isoquinolinecarboxylate (15.94 g, 35 mmol)]

$^1$H-NMR(CDCl$_3$) δ: 0.90 (6H, d, J=6.8 Hz), 2.14–2.28 (1H, m), 4.01 (2H, d, J=7.8 Hz), 5.15 (2H, s), 7.11–7.48 (12H, m), 7.66 (1H, d, J=1.8 Hz).

(4) 7-(Benzyloxy)-3-(hydroxymethyl)-2-isobutyl-4-phenyl-1(2H)-isoquinolinone (9.31 g, 90.1%) as crystals. [synthesized according to the method similar to that in Example 154(5) from 7-(benzyloxy)-2-isobutyl-1-oxo-4-phenyl-1,2-dihydro-3-isoquinolinecarboxylic acid (10.69 g, 25 mmol)]

Melting point 125–126° C. Elemental analysis for $C_{27}H_{27}NO_3$ 0.5$H_2O$ Calculated: C, 76.75; H, 6.68; N, 3.32. Found: C, 76.36; H, 6.46; N, 3.24. $^1$H-NMR(CDCl$_3$) δ: 0.99 (6H, d, J=7.0 Hz), 2.05 (1H, bs), 2.20–2.34 (1H, m), 4.25 (2H, d, J=7.2 Hz), 4.46 (2H, d, J=3.6 Hz), 5.11 (2H, s), 6.92 (1H, d, J=8.8 Hz), 7.11 (1H, dd, J=2.6, 8.8 Hz), 7.29–7.56 (10H, m), 7.91 (1H, d, J=2.6 Hz).

(5) 7-(Benzyloxy)-3-(chloromethyl)-2-isobutyl-4-phenyl-1(2H)-isoquinolinone (7.44 g, 86.2%) as an oil. [synthesized according to the method similar to that in Example 154(6) from 7-(benzyloxy)-3-(hydroxymethyl)-2-isobutyl-4-phenyl-1(2H)-isoquinolinone (8.27 g, 20 mmol)]

$^1$H-NMR(CDCl$_3$) δ: 1.02 (6H, d, J=7.0 Hz), 2.16–2.31 (1H, m), 4.20 (2H, d, J=7.4 Hz), 4.42 (2H, s), 5.20 (2H, s), 6.96 (1H, d, J=8.8 Hz,) 7.13–7.54 (11H, m), 8.01 (1H, d, J=2.8 Hz).

(6) 2-{[7-(Benzyloxy)-2-isobutyl-1-oxo-4-phenyl-1,2-dihydro-3-isoquinolinolinyl]methyl}-1H-isoindolone-1,3(2H)-dione (8.74 g, 94.8%) as an amorphous solid. [synthesized according to the method similar to that in Example 154(7) from 7-(benzyloxy)-3-(chloromethyl)-2-isobutyl-4-phenyl-1(2H)-isoquinolinone (7.34 g, 17 mmol)]

$^1$H-NMR(CDCl$_3$) δ: 1.01 (6H, d, J=6.6 Hz), 2.17–2.31 (1H, m), 4.08 (2H, d, J=7.0 Hz), 4.78 (2H, s), 5.19 (2H, s), 6.92 (1H, d, J=9.0 Hz), 7.17 (1H, dd, J=2.8, 9.0 Hz), 7.21–7.49 (10H, m), 7.66–7.78 (4H, m), 7.98 (1H, d, J=2.8 Hz).

(7) Tert-butyl[7-(benzyloxy)-2-isobutyl-1-oxo-4-phenyl-1,2-dihydro-3-isoquinolinyl]methylcarbamate (7.56 g, 92.2%) as crystals. [synthesized according to the method similar to that in Example 154(8) from 2-{[7-(benzyloxy)-2-isobutyl-1-oxo-4-phenyl-1,2-dihydro-3-isoquinolinyl]methyl}-1H-isoindolone-1,3(2H)-dione (8.68 g, 16 mmol)]

Melting point 181–182° C. Elemental analysis for $C_{32}H_{36}N_2O_4$ Calculated: C, 74.97; H, 7.08; N, 5.46. Found: C, 74.94; H, 7.14; N, 5.31. $^1$H-NNR(CDCl$_3$) δ: 1.0 (6H, d, J=6.8 Hz), 1.43 (9H, s), 2.20–2.31 (1H, m), 4.08 (2H, d, J=7.4 Hz), 4.19 ((2H, d, J=5.2 Hz), 4.55 (1H, bs), 5.16 (2H, s), 6.89 (1H, d, J=8.8 Hz), 7.15 (1H, dd, J=2.8, 8.8 Hz), 7.24–7.55 (10H, m), 7.96 (1H, d, J=2.88 Hz).

(8) 3-(Aminomethyl)-7-(benzyloxy)-2-isobutyl-4-phenyl-1(2H)-isoquinolinone hydrochloride (0.21 g, 95.5%) as crystals. [synthesized according to the method similar to that in Example 214(3) from tert-butyl[-7-(benzyloxy)-2-isobutyl-1-oxo-4-phenyl-1,2-dihydro-3-isoquinolinyl]methylcarbamate (0.26 g, 0.5 mmol)]

Melting point 242–243° C. Elemental analysis for $C_{27}H_{29}N_2O_2Cl$ Calculated: C, 72.23; H, 6.51; N, 6.24. Pound: C, 71.99; H, 6.54; N, 6.05. $^1$H-NMR(DMSO-d$_6$) δ: 0.92 (6H, d, J=6.6 Hz), 1.99–2.19 (1H, m), 3.85 (2H, d, J=4.8 Hz), 4.09 (2H, s), 5.26 (2H, s), 6.85 (1H, d, J=8.8 Hz), 7.33–7.57 (11H, m), 7.85 (1H, d, J=2.6 Hz), 8.58 (3H, bs).

Example 269

3-(Aminomethyl)-7-hydroxy-2-isobutyl-4-phenyl-1(2H)-isoquinolinone hydrochloride (1) Tert-butyl(7-hydroxy-2-isobutyl-1-oxo-4-phenyl-1,2-dihydro-3-isoquinolinyl)methylcarbamate (5.75 g, 97.3%) as crystals. [synthesized according to the method similar to that in Example 154(9) from tert-butyl[7-(benzyloxy)-2-isobutyl-1-oxo-4-phenyl-1,2-dihydro-3-isoquinolinyl]methylcarbamate (7.14 g, 14 mmol)]

Melting point 232–233° C. Elemental analysis for $C_{25}H_{30}N_2O_4$ Calculated: C, 71.07; H, 7.16; N, 6.63. Found: C, 70.81; H, 7.22; N, 6.35. $^1$H-NMR(CDCl$_3$) δ: 1.02 (6H, d, J=7.0 Hz), 1.42 (9H, s), 2.21–2.35 (1H, m), 4.11 (2H, d, J=7.2 Hz), 4.22 (2H, d, J=5.2 Hz), 4.52 (1H, bs), 6.91 (1H, d, J=8.8 Hz), 7.16 (1H, dd, J=2.6, 8.8 Hz), 7.23–7.28 (2H, m), 7.44–7.55 (3H, m), 8.52 (1H, d, J=2.8 Hz), 8.90 (1H, s).

(2) 3-(Aminomethyl)-7-hydroxy-2-isobutyl-4-phenyl-1(2H)-isoquinolinone hydrochloride (0.17 g, 94.4%) as crystals. [synthesized according to the method similar to that in Example 214(3) from tert-butyl(7-hydroxy-2-isobutyl-1-oxo-4-phenyl-1,2-dihydro-3-isoquinolinyl)methylcarbamate (0.21 g, 0.5 mmol)]

Melting point 259–261° C. Elemental analysis for $C_{20}H_{23}N_2O_2Cl$ 0.25$H_2O$ Calculated: C, 66.11; H, 6.52; N, 7.71. Found: C, 66.00; H, 6.51; N, 7.53. $^1$H-NMR(DMSO-d$_6$) δ: 0.91 (6H, d, J=6.6 Hz), 2.00–2.16 (1H, m), 3.85 (2H, s), 4.05 (2H, d, J=7.0 Hz), 6.76 (1H, d, J=8.8 Hz), 7.13 (1H, dd, J=2.8, 8.8 Hz), 7.35–7.39 (2H, m), 7.47–7.60 (2H, m), 7.68 (1H, d, J=2.8 Hz), 8.48 (3H, bs), 10.27 (1H, bs).

Example 270

3-(Aminomethyl)-7-ethoxy-2-isobutyl-4-phenyl-1(2H)-isoquinolinone hydrochloride (1) Tert-butyl(7-ethoxy-2-isobutyl-1-oxo-4-phenyl-1,2-dihydro-3-isoquinolinyl)methylcarbamate (0.39 g, 86.7%) as crystals. [synthesized according to the method similar to that in Example 154(10) from tert-butyl(7-hydroxy-2-isobutyl-1-oxo-4-phenyl-1,2-dihydro-3-isoquinolinyl)methylcarbamate (0.42 g, 1 mmol) and 2-iodoethane (0.12 ml, 1.5 mmol)]

Melting point 163–164° C. Elemental analysis for $C_{27}H_{34}N_2O_4$ Calculated: C, 71.97; H, 7.61; N, 6.22. Found: C, 71.67; H, 7.41; N, 6.28. $^1$H-NMR(CDCl$_3$) δ: 1.01 (6H, d, J=6.6 Hz), 1.42 (9H, s), 1.44 (3H, t, J=7.4 Hz), 2.19–2.35 (1H, m), 4.06–4.21 (6H, m) 4.48 (1H, bs), 6.88 (1H, d, J=9.0 Hz), 7.09 (1H, dd, J=2.7, 9.0 Hz), 7.23–7.27 (2H, m), 7.46–7.53 (3H, m), 7.86 (1H, d, J=2.6 Hz).

(2) 3-(Aminomethyl)-7-ethoxy-2-isobutyl-4-phenyl-1(2H)-isoquinolinone hydrochloride (0.18 g, 66.7%) as crystals. [synthesized according to the method similar to that in Example 214(3) from tert-butyl(7-ethoxy-2-isobutyl-1-oxo-4-phenyl-1,2-dihydro-3-isoquinolinyl)methylcarbamate (0.32 g, 0.07 mmol)]

Melting point 154–155° C. Elemental analysis for $C_{22}H_{27}N_2O_2Cl$ 0.25$H_2O$ Calculated: C, 67.51; H, 7.08; N, 7.16. Found: C, 67.30; H, 7.04; N, 7.10. $^1$H-NMR(DMSO-d$_6$) δ: 0.92 (6H, d, J=6.6 Hz), 1.37 (3H, t, J=6.8 Hz), 2.01–2.19 (1H, m), 3.86 (2H, s), 4.07–4.20 (4H, m), 6.83 (1H, d, J=9.0 Hz), 7.27 (1H, dd, J=2.8, 9.0 Hz), 7.37–7.41 (2H, m), 7.54–7.57 (3H, m), 7.73 (1H, d, J=2.8 Hz), 8.53 (3H, s).

Example 271

3-(Aminomethyl)-2-isobutyl-7-(2-methoxyethoxy)-4-phenyl-1(2H)-isoquinolinone hydrochloride (1) Tert-butyl[2-isobutyl-7-(2-methoxyethoxy)-1-oxo-4-phenyl-1,2-dihydro-3-isoquinolinyl]methylcarbamate (0.34 g, 70.8%) as crystals. [synthesized according to the method similar to that in Example 154(10) from tert-butyl(7-hydroxy-2-isobutyl-1-oxo-4-phenyl-1,2-dihydro-3-isoquinolinyl)methylcarbamate (0.42 g, 1 mmol) and bromoethyl methyl ether (0.14 ml, 1.5 mmol)]

Melting point 124–125° C. Elemental analysis for $C_{28}H_{36}N_2O_5$ Calculated: C, 69.98; H, 7.55; N, 5.83. Found: C, 69.81; H, 7.37; N, 5.96. $^1$H-NMR(CDCl$_3$) δ: 1.00 (6H, d, J=6.6 Hz), 1.42 (9H, s), 2.19–2.35 (1H, m), 3.45 (3H, s), 3.74–3.80 (2H, m), 4.08 (2H, d, J=7.0 Hz), 4.19–4.27 (4H, m), 4.51 (1H, bs), 6.89 (1H, d, J=8.6 Hz), 7.16 (1H, dd, J=2.8, 8.6 Hz), 7.19–7.27 (2H, m), 7.47–7.52 (3H, m), 7.86 (1H, d, J=2.8 Hz).

(2) 3-(Aminomethyl)-2-isobutyl-7-(2-methoxyethoxy)-4-phenyl-1(2H)-isoquinolinone hydrochloride (0.21 g, 84.0%) as crystals. [synthesized according to the method similar to that in Example 214(3) from tert-butyl[2-isobutyl-7-(2-methoxyethoxy)-1-oxo-4-phenyl-1,2-dihydro-3-isoquinolinyl]methylcarbamate (0.28 g, 0.6 mmol)]

Melting point 148–149° C. Elemental analysis for $C_{23}H_{29}N_2O_3Cl$ 0.5H$_2$O Calculated: C, 64.85; H, 7.10; N, 6.58. Found: C, 65.25; H, 7.21; N, 6.73. $^1$H-NMR(DMSO-d$_6$) δ: 0.92 (6H, d, J=6.2 Hz), 1.99–2.21 (1H, m), 3.31 (3H, s), 3.63–3.69 (2H, m), 3,86 (2H, s), 4.07–4.10 (2H, m), 4.22 (2H, s), 6.84 (1H, d, J=9.2 Hz), 7.28–7.40 (3H, m), 7.54–7.62 (3H, m), 7.74 (1H, s), 8.56 (3H, s).

Example 272

2-{[3-(Aminomethyl)-2-isobutyl-1-oxo-4-phenyl-1,2-dihydro-7-isoquinolinyl]oxy}acetamide hydrochloride (1) Tert-butyl[7-(2-amino-2-oxoethoxy)-2-isobutyl-1-oxo-4-phenyl-1,2-dihydro-3-isoquinolinyl]methylcarbamate (0.19 g, 40.4%) as crystals. [synthesized according to the method similar to that in Example 154(10) from tert-butyl (7-hydroxy-2-isobutyl-1-oxo-4-phenyl-1,2-dihydro-3-isoquinolinyl)methylcarbamate (0.42 g, 1 mmol) and 2-iodoacetamide (0.27 g, 1.5 mmol)]

Melting point 211–212° C. Elemental analysis for $C_{27}H_{33}N_3O_5$ Calculated: C, 67.62; H, 6.94; N, 8.76. Found: C, 67.38; H, 6.69; N, 8.87. $^1$H-NMR(CDCl$_3$) δ: 1.00 (6H, d, J=6.6 Hz), 1.43 (9H, s), 2.18–2.34 (1H, m), 4.08 (2H, d, J=7.4 Hz), 4.20 (2H, d, J=5.4 Hz), 4.51 (1H, bs), 4.58 (2H, s), 5.86 (1H, bs), 6.57 (1H, bs), 6.94 (1H, d, J=8.8 Hz), 7.13 (1H, d, J=8.8 Hz), 7.23–7.27 (2H, m), 7.49–7.52 (3H, m), 7.90 (1H, s).

(2) 2-{[3-(Aminomethyl)-2-isobutyl-1-oxo-4-phenyl-1,2-dihydro-7-isoqulinolinyl]oxy}acetamide hydrochloride (0.11 g, 91.2%) as crystals. [synthesized according to the method similar to that in Example 214(3) from tert-butyl[7-(2-amino-2-oxoethoxy)-2-isobutyl-1-oxo-4-phenyl-1,2-dihydro-3-isoquinolinyl]methylcarbamate (0.14 g, 0.3 mmol)] Melting point 244–245° C.

Elemental analysis for $C_{22}H_{26}N_3O_3Cl$ 1.75H$_2$O Calculated: C, 59.06; H, 6.65; N, 9.39. Found: C, 59.21; H, 6.52.; N, 9.33. $^1$H-NMR(DMSO-d$_6$) δ: 0.92 (6H, d, J=6.6 Hz), 1.99–2.19 (1H, m), 3.85 (2H, d, J=4.2 Hz), 4.09 (2H, d, J=7.0 Hz), 4.58 (2H, s), 6.85 (1H, d, J=8.8 Hz), 7.33 (1H, dd, J=2.6, 8.8 Hz), 7.36–7.41 (2H, m), 7.56–7.60 (3H, m), 7.69 (1H, bs), 7.72 (1H, d, J=2.6 Hz), 8.64 (3H, s).

Example 273

3-(Aminomethyl)-2-isobutyl-1-oxo-4-phenyl-1,2-dihydro-7-isoquinolinecarboxamide hydrochloride (1) Tert-butyl(2-isobutyl-1-oxo-4-phenyl-7-trifluoromethanesulfonyloxy-1,2-dihydro-3-isoquinolinyl)methylcarbamate (5.01 g, 90.4%) as an amorphous solid. [synthesized according to the method similar to that in Example 155(1) from tert-butyl(7-hydroxy-2-isobutyl-1-oxo-4-phenyl-1,2-dihydro-3-isoquinolinyl)methylcarbamate (4.22 g, 10 mmol)]

$^1$H-NMR(CDCl$_3$) δ: 1.01 (6H, d, J=6.6 Hz), 1.43 (9H, s), 2.20–2.29 (1H, m), 4.09 (2H, d, J=7.5 Hz), 4.23 (2H, d, J=5.4 Hz), 4.46 (1H, bs), 7.06 (1H, d, J=9.0 Hz), 7.22–7.27 (2H, m), 7.36 (1H, dd, J=2.7, 9.0 Hz), 7.42–7.56 (3H, m), 8.34 (1H, d, J=2.7 Hz).

(2) Methyl 3-{[(tert-butoxycarbonyl)amino]methyl}-2-isobutyl-1-oxo-4-phenyl-1,2-dihydro-7-isoquinolinecarboxylate (3.11 g, 74.4%) as crystals. [synthesized according to the method similar to that in Example 155(2) from tert-butyl(2-isobutyl-1-oxo-4-phenyl-7-trifluoromethanesulfonyloxy-1,2-dihydro-3-isoquinolinyl)methylcarbamate (4.99 g, 9 mmol)]

Melting point 134–135° C. Elemental analysis for $C_{27}H_{32}N_2O_5$ Calculated: C, 69.81; H, 6.94; N, 6.03. Found: C, 69.46; H, 7.04; N, 5.81. $^1$H-NMR(CDCl$_3$) δ: 1.01 (6H, d, J=6.6 Hz), 1.43 (9H, s), 2.05–2.28 (1H, m), 3.93 (3H, s), 4.10 (2H, d, J=7.5 Hz), 4.22 (2H, d, J=5.4 Hz), 4.61 (1H, bs), 6.98 (1H, d, J=8.7 Hz), 7.24–7.28 (2H, m), 7.46–7.57 (3H, m), 8.02 (1H, dd, J=1.8, 8.7 Hz), 9.10 (1H, d, J=1.8 Hz).

(3) 3-{[(Tert-butoxycarbonyl)amino]methyl}-2-isobutyl-1-oxo-4-phenyl-1,2-dihydro-7-isoquinolinecarboxylic acid (2.49 g, 92.2%) as crystals. [synthesized according to the method similar to that in Example 155(3) from methyl 3-{[(tert-butoxycarbonyl)amino]methyl}-2-isobutyl-1-oxo-4-phenyl-1,2-dihydro-7-isoquinolinecarboxylate (2.79 g, 6 mmol)]

Melting point 246° C. Elemental analysis for $C_{26}H_{30}N_2O_5$ 0.25H$_2$O Calculated: C, 68.62; H, 6.76; N, 6.16. Found: C, 68.88; H, 6.83; N, 5.87. $^1$H-NMR(CDCl$_3$) δ: 0.91 (6H, d, J=6.6 Hz), 1.38 (9H, s), 2.12–2.26 (1H, m), 3.91 (2H, d, J=6.6 Hz), 3.99 (2H, d, J=4.2 Hz), 6.99 (1H, d, J=8.8 Hz), 7.34 (1H, bs), 7.39–7.42 (2H, m), 7.46–7.56 (3H, m), 8.09 (1H, dd, J=2.0, 8.8 Hz), 8.87 (1H, d, J=2.0 Hz).

(4) Tert-butyl[7-(aminocarbonyl)-2-isobutyl-1-oxo-4-phenyl-1,2-dihydro-3-isoquinolinyl]methylcarbamate (0.86 g, 95.6%) as crystals. [synthesized according to the method similar to that in Example 155(4) from 3-{[(tert-butoxycarbonyl)amino]methyl}-2-isobutyl-1-oxo-4-phenyl-1,2-dihydro-7-isoquinolinecarboxylic acid (0.90 g, 2 mmol)]

Melting point 232–233° C. Elemental analysis for $C_{26}H_{31}N_3O_4$ 0.5H$_2$O Calculated: C, 68.10; H, 7.03; N, 9.16. Found: C, 68.31; H, 7.07; N, 8.75. $^1$H-NMR(CDCl$_3$) δ: 0.99 (6H, d, J=6.6 Hz), 1.43 (9H, s), 2.10–2.24 (1H, m), 4.08 (2H, d, J=7.0 Hz), 4.22 (2H, d, J=5.2 Hz), 4.76 (1H, bs), 5.96 (1H, bs), 6.74 (1H, bs), 7.02 (1H, d, J=8.6 Hz), 7.25–7.30 (2H, m), 7.45–7.56 (3H, m), 8.05 (1H, dd, J=1.4, 8.6 Hz), 8.78 (1H, d, J=1.4 Hz).

(5) 3-(Aminomethyl)-2-isobutyl-1-oxo-4-phenyl-1,2-dihydro-7-isoquinolinecarboxamide hydrochloride (0.18 g, 94.7%) as crystals. [synthesized according to the method similar to that in Example 155(5) from tert-butyl[7-(aminocarbonyl)-2-isobutyl-1-oxo-4-phenyl-1,2-dihydro-3-isoquinolinyl]methylcarbamate (0.23 g, 0.5 mmol)]

Melting point 254–256° C. Elemental analysis for $C_{21}H_{24}N_3O_2Cl$ H$_2$O Calculated: C, 63.87; H, 6.38; N, 10.64. Found: C, 63.76; H, 6.29; N, 10.30. $^1$H-NMR (DMSO-$d_6$) δ: 0.94 (6H, d, J=6.6 Hz), 2.04–2.19 (1H, m), 3.89 (2H, d, J=34.4 Hz), 4.13 (2H, d, J=7.0 Hz), 6.94 (1H, d, J=8.6 Hz), 7.37–7.44 (2H, m), 7.54–7.64 (4H, m), 8.16 (1H, dd, J=1.8, 8.6 Hz), 8.30 (1H, bs), 8.67 (3H, bs), 8.85 (1H, d, J=1.8 Hz).

Example 274

3-[3-(Aminomethyl)-2-isobutyl-1-oxo-4-phenyl-1,2-dihydro-6-isoquinolinyl]propanamide hydrochloride (1) A suspension of ethyl (E)-3-(3-{[(tert-butoxycarbonyl)amino]methyl}-2-isobutyl-1-oxo-4-phenyl-1,2-dihydro-6-isoquinolinyl)-2-propenoate (0.90 g, 1.8 mmol) and 5% palladium carbon (0.5 g) in ethanol (10 ml) and tetrahydrofuran (10 ml) was stirred under a hydrogen atmosphere at room temperature for 2 h. The catalyst was filtered off, and the filtrate was concentrated under reduced pressure. The residue was purified by silica gel column chromatography to give ethyl 3-(3-{[(tert-butoxycarbonyl)amino]methyl}-2-isobutyl-1-oxo-4-phenyl-1,2-dihydro-6-isoquinolinyl)propanoate (0.82 g, 90.1%) as an amorphous solid. $^1$H-NMR (CDCl$_3$) δ: 0.99 (6H, d, J=6.6 Hz), 1.19 (3H, t, J=7.1 Hz), 1.42 (9H, s), 2.18–2.29 (1H, m), 2.51 (2H, t, J=7.8 Hz), 2.90 (2H, t, J=7.8 Hz), 4.01–4.12 (4H, m), 4.19 (2H, d, J=5.6 Hz), 4.40 (1H, bs), 6.74 (1H, d, J=1.6 Hz), 7.21–7.26 (2H, m), 7.31 (1H, dd, J=1.6, 8.4 Hz), 7.46–7.53 (3H, m), 8.39 (1H, d, J=8.4 Hz).

(2) To a solution of ethyl 3-(3-{[(tert-butoxycarbonyl)amino]methyl}-2-isobutyl-1-oxo-4-phenyl-1,2-dihydro-6-isoquinolinyl)propanoate (0.61 g, 1.2 mmol) in tetrahydrofuran (5 ml) and ethanol (5 ml) was added 1N sodium hydroxide solution (3 ml). The resulting mixture was stirred at room temperature for 1 h. The reaction mixture was poured into water, acidified with 1N hydrochloric acid and extracted with ethyl acetate. The extract was washed with brine, dried over anhydrous magnesium sulfate and concentrated under reduced pressure. The resulting crystals were recrystallized from ethyl acetate-diisopropyl ether to give 3-(3-{[(tert-butoxycarbonyl)amino]methyl}-2-isobutyl-1-oxo-4-phenyl-1,2-dihydro-6-isoquinolinyl)propanoic acid (0.52 g, 91.2%) as crystals.

Melting point 182–183° C. Elemental analysis for $C_{28}H_{34}N_2O_5$ Calculated: C, 70.12; H, 7.36; N, 5.84. Found: C, 70.21; H, 7.55; N, 5.68. $^1$H-NMR(CDCl$_3$) δ: 0.98 (6H, d, J=6.9 Hz), 1.42 (9H, s), 2.15–2.27 (1H, m), 2.58 (2H, t, J=7.8 Hz), 2.91 (2H, t, J=7.8 Hz), 4.06 (2H, d, J=6.0 Hz), 4.19 (2H, d, J=5.2 Hz), 4.53 (1H, bs), 6.76 (1H, s), 7.22–7.25 (2H, m), 7.31 (1H, d, J=8.8 Hz), 7.46–7.52 (3H, m), 8.37 (1H, d, J=8.8 Hz).

(3) A solution of 3-(3-{[(tert-butoxycarbonyl)amino]methyl}-2-isobutyl-1-oxo-4-phenyl-1,2-dihydro-6-isoquinolinyl)propanoic acid (0.33 g, 0.7 mmol), 1-ethyl-3-(3-dimethylaminopropyl)carbodiimide hydrochloride (0.27 g, 1.4 mmol) and 1-hydroxybenzotriazole ammonium salt (0.21 g, 1.4 mmol) in N,N-dimethylformamide (10 ml) was stirred at room temperature for 2 h. The resulting reaction mixture was poured into water and extracted with ethyl acetate. The extract was washed with brine, dried over anhydrous magnesium sulfate and concentrated under reduced pressure. The residue was purified by silica gel column chromatography to give tert-butyl[6-(3-amino-3-oxopropyl)-2-isobutyl-1-oxo-4-phenyl-1,2-dihydro-3-isoquinolinyl]methylcarbamate (0.31 g, 93.9%) as crystals.

Melting point 239–240° C. Elemental analysis for $C_{28}H_{35}N_3O_4 \cdot 0.25H_2O$ Calculated: C, 69.76; H, 7.42; N, 8.72. Found: C, 69.54; H, 7.41; N, 8.58. $^1$H-NMR(CDCl$_3$) δ: 0.99 (6H, d, J=6.6 Hz), 1.42 (9H, s), 2.13–2.29 (1H, m), 2.43 (2H, t, J=8.0 Hz), 2.92 (2H, t, J=8.0 Hz), 4.05 (2H, d, J=7.4 Hz), 4.19 (2H, d, J=5.2 Hz), 4.54 (1H, bs), 5.42 (2H, bs), 6.75 (1H, d, J=1.4 Hz), 7.21–7.30 (3H, m), 7.21–7.30 (3H, m), 7.46–7.57 (3H, m), 8.33–8.37 (1H, m).

(4) 3-[3-(Aminomethyl)-2-isobutyl-1-oxo-4-phenyl-1,2-dihydro-6-isoquinolinyl]propanamide hydrochloride (0.20 g, 95.3%) as crystals. [synthesized according to the method similar to that in Example 214(3) from tert-butyl[6-(3-amino-3-oxopropyl)-2-isobutyl-1-oxo-4-phenyl-1,2-dihydro-3-isoquinolinyl]methylcarbamate (0.24 g, 0.5 mmol)]

Melting point 186–187° C. $^1$H-NMR(DMSO-$d_6$) δ: 0.91 (6H, d, J=6.6 Hz), 2.02–2.16 (1H, m), 2.26 (2H, t, J=7.2 Hz), 2.76 (2H, t, J=7.2 Hz), 3.86 (2H, s), 4.08 (2H, s), 6.72 (1H, s), 6.75 (1H, bs), 7.29 (1H, bs), 7.38–7.40 (2H, m), 7.45 (1H, d, J=8.4 Hz), 7.55–7.59 (3H, m), 8.25 (1H, d, J=8.4 Hz), 8.57 (3H, bs).

Example 275

2-(2-{[3-(Aminomethyl)-4-butoxy-2-isobutyl-1-oxo-1,2-dihydro-6-isoquinolinyl]oxy}ethyl)-1H-isoindolone-1,3(2H)-dione hydrochloride To a solution of tert-butyl(4-butoxy-6-hydroxy-2-isobutyl-1-oxo-4-1,2-dihydro-3-isoquinolinyl)methylcarbamate (2.09 g, 5 mmol), N-(2-hydroxyethyl)phthalimide (1.15 g, 6 mmol) and tri-n-butylphosphine (2.5 ml, 10 mmol) in tetrahydrofuran (30 ml) was added 1,1'-(azodicarbonyl)dipiperidine (2.52 g, 10 mmol), and the mixture was stirred at room temperature for 6 h. The reaction mixture was concentrated under reduced pressure, and the residue was purified by silica gel column chromatography. The resulting crystals were dissolved in a solution of 4N hydrogen chloride in ethyl acetate (5 ml). The solution was stirred at room temperature for 2 h. The reaction mixture was concentrated under reduced pressure, and the residue was crystallized from methanol-diisopropyl ether to give 2-(2-{[3-(aminomethyl)-4-butoxy-2-isobutyl-1-oxo-1,2-dihydro-6-isoquinolinyl]oxy}ethyl)-1H-isoindolone-1,3(2H)-dione hydrochloride (0.14 g, 93.3%) as crystals.

Melting point 176–177° C. $^1$H-NMR(DMSO-$d_6$) δ: 0.86 (6H, d, J=6.6 Hz), 0.99 (3H, t, J=7.3 Hz), 1.46–1.64 (2H, m), 1.77–2.06 (3H, m), 3.88–3.94 (4H, m), 4.04 (2H, t, J=5.5 Hz), 4.15 (2H, s), 4.41 (2H, t, J=5.5 Hz), 7.05 (1H, d, J=2.4 Hz), 7.14 (1H, dd, J=2.4, 9.0 Hz) 7.82–7.92 (4H, m), 8.15 (1H, d, J=9.0 Hz), 8.53 (3H, bs).

Example 276

3-[3-(Aminomethyl)-4-butoxy-2-neopentyl-1-oxo-1,2-dihydro-6-isoquinolinyl]propanamide hydrochloride (1) Ethyl 3-(3-{[(tert-butoxycarbonyl)amino]methyl}-4-butoxy-2-neopentyl-1-oxo-1,2-dihydro-6-isoquinolinyl)propanoate (0.68 g, 88.3%) as an oil. [synthesized according to the method similar to that in Example 274(1) from ethyl (E)-3-(3-{[(tert-butoxycarbonyl)amino]methyl}-4-butoxy-2-neopentyl-1-oxo-1,2-dihydro-6-isoquinolinyl)-2-propenoate (0.77 g, 1.5 mmol)]

$^1$H-NMR(CDCl$_3$) δ: 0.99 (9H, s), 1.04 (3H, t, J=7.2 Hz), 1.24 (3H, t, J=7.0 Hz), 1.45 (9H, s), 1.49–1.68 (2H, m), 1.80–1.94 (2H, m), 2.70 (2H, t, J=7.8 Hz), 3.11 (2H, t, J=7.8 Hz), 3.86 (2H, t, J=6.6 Hz), 4.10 (2H, bs), 4.14 (2H, q, J=7.0

Hz), 4.58 (2H, s), 4.62 (1H, bs), 7.35 (1H, dd, J=1.6, 8.2 Hz), 7.51 (1H, d, J=1.6 Hz), 8.33 (1H, d, J=8.4 Hz), (2) 3-(3-{[(Tert-butoxycarbonyl)amino]methyl}-4-butoxy-2-neopentyl-1-oxo-1,2-dihydro-6-isoquinolinyl)propanoic acid (0.40 g, 90.9%) as crystals. [synthesized according to the method similar to that in Example 274(2) from ethyl 3-(3-{[(tert-butoxycarbonyl)amino]methyl}-4-butoxy-2-neopentyl-1-oxo-1,2-dihydro-6-isoquinolinyl)propanoate (0.46 g, 0.9 mmol)]

$^1$H-NMR(CDCl$_3$) δ: 0.98 (9H, s), 1.03 (3H, t, J=7.4 Hz), 1.45 (9H, s), 1.46–1.67 (2H, m), 1.79–1.92 (2H, m), 2.77 (2H, t, J=7.4 Hz), 3.11 (2H, t, J=7.4 Hz), 3.84 (2H, t, J=6.4 Hz), 4.14 (2H, bs), 4.57 (2H, d, J=5 Hz), 4.75 (1H, bs), 7.34 (1H, dd, J=1.6, 8.5 Hz), 7.52 (1H, d, J=1.6 Hz), 8.32 (1H, d, J=8.5 Hz).

(3) Tert-butyl[6-(3-amino-3-oxopropyl)-4-butoxy-2-neopentyl-1-oxo-1,2-dihydro-3-isoquinolinyl]methylcarbamate (0.19 g, 86.4%) as crystals. [synthesized according to the method similar to that in Example 274(3) from 3-(3-{[(tert-butoxycarbonyl)amino]methyl}-4-butoxy-2-neopentyl-1-oxo-1,2-dihydro-6-isoquinolinyl)propanoic acid (0.22 g, 0.45 mmol)]

Melting point 87–88° C. Elemental analysis for C$_{27}$H$_{41}$N$_3$O$_5$ Calculated: C, 66.50; H, 8.47; N, 8.62. Found: C, 66.25; H, 8.35; N, 8.54. $^1$H-NMR(CDCl$_3$) δ: 0.99 (9H, s), 1.04 (3H, t, J=7.4 Hz), 1.45 (9H, s), 1.52–1.72 (2H, m), 1.80–1.94 (2H, m), 2.60 (2H, t, J=7.7 Hz), 3.13 (2H, t, J=7.7 Hz), 3.86 (2H, t, J=6.6 Hz), 4.14 (2H, bs), 4.56 (2H, d, J=5.4 Hz), 4.73 (1H, bs), 5.50 (2H, bs), 7.32 (1H, d, J=8.2 Hz), 7.52 (1H, s), 8.29 (1H, d, J=8.2 Hz).

(4) 3-[3-(Aminomethyl)-4-butoxy-2-neopentyl-1-oxo-1,2-dihydro-6-isoquinolinyl]propanamide hydrochloride (0.11 g, 91.7%) as crystals. [synthesized according to the method similar to that in Example 274(4) from tert-butyl [6-(3-amino-3-oxopropyl)-4-butoxy-2-neopentyl-1-oxo-1,2-dihydro-3-isoquinolinyl]methylcarbamate (0.14 g, 0.3 mmol)]

Melting point 151–153° C. Elemental analysis for C$_{27}$H$_{41}$N$_3$O$_5$Cl Calculated: C, 66.50; H, 8.47; N, 8.62. Found: C, 66.25; H, 8.35; N, 8.54. $^1$H-NMR(DMSO-d$_6$) δ: 0.90 (9H, s), 1.00 (3H, t, J=7.3 Hz), 1.51–1.62 (2H, m), 1.78–1.91 (2H, m), 2.46 (2H, t, J=7.4 Hz), 3.00 (2H, t, J=7.4 Hz), 3.93 (2H, t, J=6.1 Hz), 4.08 (2H, bs), 4.23 (2H, d, J=4.0 Hz), 6.82 (1H, bs), 7.44 (1H, bs), 7.47 (1H, d, J=8.2 Hz), 7.58 (1H, s), 8.17 (1H, d, J=8.2 Hz), 8.53 (3H, bs).

Example 277

[3-(Aminomethyl)-4-butoxy-2-neopentyl-1-oxo-1,2-dihydro-6-isoquinolinyl]acetonitrile hydrochloride (1) To a solution of p-toluenesulfonylmetyl isocyanide (0.94 g, 4.8 mmol) in 1,2-dimethoxyethane (20 ml) were added potassium t-butoxide (0.90 g, 8 mmol) and tert-butyl (4-butoxy-6-formyl-2-neopentyl-1-oxo-1,2-dihydro-3-isoquinolinyl)methylcarbamate (1.78 g, 4 mmol) at – 70° C., and the mixture was stirred at –70° C. for 1 h. To the mixture was added methanol (30 ml), and the mixture was refluxed for 30 min. The reaction mixture was poured into water and extracted with ethyl acetate. The extract was washed with brine, dried over anhydrous magnesium sulfate and concentrated under reduced pressure. The residue was purified by silica gel column chromatography to give tert-butyl[4-butoxy-6-(cyanomethyl)-2-neopentyl-1-oxo-1,2-dihydro-3-isoquinolinyl]methylcarbamate (0.66 g, 36.3%) as an amorphous solid.

$^1$H-NMR(CDCl$_3$) δ: 1.00 (9H, s), 1.04 (3H, t, J=7.4 Hz), 1.45 (9H, s), 1.51–1.66 (2H, m), 1.82–1.92 (2H, m), 3.88 (2H, t, J=6.2 Hz); 3.92 (2H, s), 4.18 (2H, bs), 4.58 (2H, d, J=5.0 Hz), 4.72 (1H, bs), 7.40 (1H, dd, J=1.8, 8.4 Hz), 7.70 (1H, d, J=1.18 Hz), 8.40 (1H, d, J=8.4 Hz).

(2) [3-(Aminomethyl)-4-butoxy-2-neopentyl-1-oxo-1,2-dihydro-6-isoquinolinyl]acetonitrile hydrochloride (0.10 g, 90.9%) as crystals. [synthesized according to the method similar to that in Example 214(3) from tert-butyl[4-butoxy-6-(cyanomethyl)-2-neopentyl-1-oxo-1,2-dihydro-3-isoquinolinyl]methylcarbamate (0.14 g, 0.3 mmol)].

Melting point 169–171° C. Elemental analysis for C$_{21}$H$_{30}$N$_3$O$_2$Cl 0.25H$_2$O Calculated: C, 63.62; H, 7.73; N, 10.60. Found: C, 63.70; H, 7.85; N, 10.59. $^1$H-NMR (DMSO-d$_6$) δ: 0.90 (9H, s), 1.00 (3H, t, J=7.4 Hz), 1.52–1.63 (2H, m), 1.80–1.91 (2H, m), 3.94 (2H, t, J=6.6 Hz), 4.14 (2H, bs), 4.26 (2H, bs), 4.33 (2H, s), 7.57 (1H, dd, J=1.4, 8.0 Hz), 7.78 (1H, d, J=1.4 Hz), 8.29 (1H, d, J=8.0 Hz), 8.54 (3H, bs).

Example 278

2-[3-(Aminomethyl)-4-butoxy-2-neopentyl-1-oxo-1,2-dihydro-6-isoquinolinyl]acetamide hydrochloride (1) To a solution of tert-butyl[4-butoxy-6-(cyanomethyl)-2-neopentyl-1oxo-1,2-dihydro-3-isoquinolinyl] methylcarbamate (0.45 g, 1 mmol) in ethanol (20 ml) was added a solution of potassium hydroxide (0.40 g, 10 mmol) in water (5 ml). The mixture was refluxed for 10 h. The reaction mixture was poured into water, acidified with 1N hydrochloric acid and extracted with ethyl acetate. The extract was washed with brine, dried over anhydrous magnesium sulfate and concentrated under reduced pressure to give crude amorphous solid. A solution of the amorphous solid, 1-ethyl-3-(3-dimethylaminopropyl)carbodiimide hydrochloride (0.19 g, 1 mmol) and 1-hydroxybenzotriazole ammonium salt (0.15 g, 1 mol) in N,N-dimethylformamide (10 ml) was stirred for 2 h at room temperature. The resulting reaction mixture was poured into water and extracted with ethyl acetate. The extract was washed with brine, dried over anhydrous magnesium sulfate and concentrated under reduced pressure. The residue was purified by column chromatography on silica gel to give tert-butyl[6-(2-amino-2-oxoethyl)-4-butoxy-2-neopentyl-1-oxo-1,2-dihydro-3-isoquinolinyl]methylcarbamate. (0.13 g, 54.2%) as crystals.

Melting point 197–198° C. $^1$H-NMR(CDCl$_3$) δ: 0.99 (9H, s), 1.04 (3H, t, J=7.4 Hz), 1.45 (9H, s), 1.46–1.64 (2H, m), 1.80–1.90 (2H, m), 3.74 (2H, s), 3.87 (2H, t, J=6.5 Hz), 4.14 (2H, bs), 4.57 (2H, d, J=5.4 Hz), 4.71 (1H, bs), 5.47 (1H, bs), 5.54 (1H, bs), 7.40 (1H, dd, J=1.4, 8.0 Hz), 7.60 (1H, d, J=1.4 Hz), 8.38 (1H, d, J=8.0 Hz).

(2) Tert-butyl[6-(2-amino-2-oxoethyl)-4-butoxy-2-neopentyl-1-oxo-1,2-dihydro-3-isoquinolinyl]methylcarbamate (95 mg, 0.2 mmol) was dissolved in a solution of 4N hydrogen chloride in ethyl acetate (5 ml). The solution was stirred at room temperature for 2 h. The reaction was concentrated under reduced pressure, and the residue was crystallized from methanol-diisopropyl ether to give 2-[3-(aminomethyl)- 4-butoxy-2-neopentyl-1-oxo-1,2-dihydro-6-isoquinolinyl]acetamide hydrochloride (75 mg, 91.5%) as crystals.

Melting point 163–165° C. $^1$H-NMR(DMSO-$d_6$) δ: 0.90 (9H, s), 1.00 (3H, t, J=7.5 Hz), 1.52–1.59 (2H, m) 1.80–1.90 (2H, m), 3.61 (2H, s), 3.93 (2H, s), 4.02 (2H, bs), 4.24 (2H, s), 7.03 (1H, bs), 7.50 (1H, d, J=8.5 Hz), 7.67 (1H, s), 7.69 (1H, bs), 8.20 (1H, d, J=8.5 Hz).

Example 279

[3-(Aminomethyl)-2-isobutyl-1-oxo-4-phenyl-1,2-dihydro-6-isoquinolinyl]acetonitrile hydrochloride (1) To a mixture of tert-butyl[6-(hydroxymethyl)-2-isobutyl-1-oxo-4-phenyl-1,2-dihydro-3-isoquinolinyl]methylcarbamate (0.33 g, 0.75 mmol), triethylamine (0.18 mL, 1.1 mmol), N,N,N',N'-tetramethyletylenediamine (0.011 mL, 0.075 mmol), toluene (6 mL) and tetrahydrofuran (6 mL) was added dropwise a solution of methanesulfonyl chloride (0.088 mL, 1.1 mmol) in toluene, (4 mL) under ice-cooling. The mixture was stirred under ice-cooling for 30 min, the reaction mixture was poured into 0.1N hydrochloric acid (50 mL) and extracted with ethyl acetate (50 mL). The extract was washed with brine, dried over anhydrous magnesium sulfate and concentrated under reduced pressure to give (3-{[(tert-butoxycarbonyl)amino]methyl}-2-isobutyl-1-oxo-4-phenyl-1,2-dihydroisoquinolin-6-yl)methyl methanesulfonate (0.39 g, 100%) as colorless powder.

$^1$H-NMR (CDCl$_3$) δ: 1.01 (6H, d, J=7.0 Hz), 1.43 (9H, s), 2.15–2.30 (1H, m), 2.91 (3H, s), 4.09 (2H, d, J=7.0 Hz), 4.22 (2H, d, J=6.0 Hz), 4.45 (1H, br), 5.18 (2H, s), 6.93 (1H, d, J=1.0 Hz), 7.15–7.30 (2H, m), 7.45–7.60 (4H, m), 8.51 (1H, d, J=8.6 Hz).

(2) To a mixture of (3-{[(tert-butoxycarbonyl)amino]methyl}-2-isobutyl-1-oxo-4-phenyl- 1,2-dihydroisoquinolin-6-yl)methyl methanesulfonate (39 g, 0.75 mmol) in acetonitrile (5 mL) and tetrahydrofuran (4 mL) were added trimethylsilyl cyanide (0.15 mL, 1.1 mmol) and a solution of 1.0 M tetrabutylammonium fluoride: in tetrahydrofuran (1.1 mL), and then the mixture was stirred at 80° C. for 30 min. The reaction mixture was concentrated under reduced pressure. The residue was purified by silica gel column chromatography (n-hexane:ethyl acetate=5:2 (v/v)) to give tert-butyl[6-(cyanomethyl)-2-isobutyl-1-oxo-4-phenyl-1,2-dihydro-3-isoquinolinyl]methylcarbamate (0.25 g, 75%) as a colorless oil.

$^1$H-NMR (CDCl$_3$) δ: 1.01 (6H, d, J=6.8 Hz), 1.43 (9H, s), 2.15–2.30 (1H, m), 3.71 (2H, s), 4.09 (2H, d, J=6.8 Hz), 4.21 (2H, d, J=5.4 Hz), 4.46 (1H, br), 6.86 (1H, d, J=1.8 Hz), 7.20–7.30(2H, m), 7.43 (1H, dd, J=1.8, 8.4 Hz), 7.50–7.60 (3H, m), 8.49 (1H, d, J=8.4 Hz).

(3) To a solution of tert-butyl[6-(cyanomethyl)-2-isobutyl-1-oxo-4-phenyl-1,2-dihydro-3-isoquinolinyl]methylcarbamate (0.13 g, 0.29 mmol) in ethyl acetate (4 mL) was added a 4N hydrogen chloride ethyl acetate solution (1 mL), and the mixture was stirred at room temperature for 12 h. The reaction was concentrated under reduced pressure, and the residue was crystallized from diisopropyl ether and washed with diisopropyl ether (5 mL×2) to give [3-(aminomethyl)-2-isobutyl-1-oxo-4-phenyl-1,2-dihydro-6-isoquinolinyl]acetonitrile hydrochloride (0.096 g, 88%) as a pale yellow powder.

$^1$H-NMR (DMSO-$d_6$) δ: 0.92 (6H, d, J=6.6 Hz), 1.95–2.20 (1H, m), 3.87 (2H, bs), 4.06 (2H, d, J=5.4 Hz), 4.13 (2H, s), 6.85–6.95 (1H, m), 7.35–7.45 (3H, m), 7.50–7.65 (3H, m), 8.36 (1H, d, J=8.0 Hz), 8.43 (3H, bs).

Melting point: 142–144° C.

Example 280

N-[3-(Aminomethyl)-2-isobutyl-1-oxo-4-phenyl-1,2-dihydro- 6-isoquinolinyl]-N'-methoxyurea hydrochloride (1) To solution of 3-{[(tert-butoxycarbonyl)amino]methyl}-2-isobutyl-1-oxo-4-phenyl-1,2-dihydroisoquinoline-6-carboxylic acid (0.15 g, 0.33 mmol) in N,N-dimethylformamide (5 mL) was added diphenylphosphoryl azide (0.09 mL, 0.40 mmol) and triethylamine (0.056 mL, 0.40 mmol), and the mixture was stirred at room temperature for 2 h. The reaction mixture was poured into water (50 mL) and extracted with ethyl acetate (30 mL×2). The organic layers were combined, washed with water (50 mL) and brine (20 mL), dried, over anhydrous magnesium sulfate and concentrated under reduced pressure. The residue was dissolved in toluene (20 mL), and the solution was refluxed for 1 h. The reaction mixture was allowed to cool to room temperature, and a mixture of O-methylhydroxyamine hydrochloride (0.088 g, 0.40 mmol) and triethylamine (0.056 mL, 0.40 mmol) in N,N-dimethylformamide (2 mL) was added thereto. The resulting reaction mixture was stirred at room temperature for 1 h and then poured into water (100 mL). The organic layer was separated and the aqueous layer was extracted twice with ethyl acetate. The organic layers were combined, washed with 0.1M aqueous citric acid solution (20 mL) and brine (10 mL), dried over anhydrous, magnesium sulfate and concentrated under reduced pressure. The residue was purified by silica gel column chromatography (n-hexane:ethyl acetate=1:1 (v/v)) to give tert-butyl(2-isobutyl-6-{[(methoxyamino)carbonyl]amino}-1-oxo-4-phenyl-1,2-dihydro-3-isoquinolinyl)methylcarbamate (0.13 g, 81%) as a colorless oil.

$^1$H-NMR (CDCl$_3$) δ: 1.00 (6H, d, J=6.9 Hz), 1.43 (9H, s), 2.20–2.35 (1H, m), 3.74 (3H, d, J=0.6 Hz), 4.05 (2H, d, J=6.9 Hz), 4.19 (2H, d, J=5.5 Hz), 4.59 (1H, br), 6.95 (1H, bs), 7.22 (1H, br), 7.25–7.30 (3H, m), 7.45–7.70 (4H, m), 8.40 (1H, d, J=8.7 Hz).

(2) N-[3-(Aminomethyl)-2-isobutyl-1-oxo-4-phenyl-1,2-dihydro-6-isoquinolinyl]-N'-methoxyurea hydrochloride (0.049 g, 46%) as a pale yellow powder[synthesized according to the method similar to that in Example 279

(3) from tert-butyl(2-isobutyl-6-{[(methoxyamino)carbonyl]amino}-1-oxo-4-phenyl-1,2-dihydro-3-isoquinolinyl) methylcarbamate (0.12 g, 0.25 mmol)]

$^1$H-NMR (DMSO-$d_6$) δ: 0.91 (6H, d, J=6.6 Hz), 2.00–2.20 (1H, m), 3.55 (3H, s), 3.83 (2H, bs), 4.02 (2H, d, J=6.6 Hz), 7.25 (1H, d, J=1.8 Hz), 7.30–7.40 (2H, m), 7.50–7.60 (3H, m), 7.82 (1H, dd, J=1.8, 8.8 Hz), 8.21 (1H, d, J=8.8 Hz), 8.39 (3H, bs), 9.29 (1H, s), 9.60 (1H, s). Melting point: 297–299° C.

Example 281

3-(Aminomethyl)-2-isobutyl-1-oxo-4-phenyl-1,2-dihydro-6-isoquinolinecarbohydrazide dihydrochloride (1) A mixture of methyl 3-{[(tert-butoxycarbonyl)amino]methyl}-2-isobutyl-1-oxo-4-phenyl-1,2-dihydroisoquinoline-6-carboxylate (0.12 g, 0.27 mmol) and hydrazine monohydrate (0.65 mL, 13 mmol) in methanol (6 mL) was stirred in a sealed tube at 75° C. for 2 h. The reaction mixture was concentrated, and the residue was recrystallized from water-methanol to give tert-butyl[6-(hydrazinocarbonyl)-2-isobutyl-1-oxo-4-phenyl-1,2-dihydro-3-isoquinolinyl)]methylcarbamate (0.12 g, 96%) as colorless crystals.

$^1$H-NMR (CDCl$_3$) δ: 1.00 (6H, d, J=7.0 Hz), 1.43 (9H, s), 2.20–2.30 (1H, m), 2.48 (3H, br), 4.08 (2H, d, J=7.0 Hz), 4.20 (2H, d, J=5.2 Hz), 4.70 (1H, br), 7.20–7.30 (3H, m), 7.45–7.55 (3H, m), 7.69 (1H, d, J=5.4 Hz), 8.43 (1H, d, J=8.6 Hz).

(2) 3-(Aminomethyl)-2-isobutyl-1-oxo-4-phenyl-1,2-dihydro-6-isoquinolinecarbohydrazide dihydrochloride (0.095 g, 95%) as a pale yellow powder. [synthesized according to the method similar to that in Example 279 (3) from tert-butyl[6-(hydrazinocarbonyl)-2-isobutyl-1-oxo-4-phenyl-1,2-dihydro-3-isoquinolinyl]methylcarbamate (0.11 g, 0.29 mmol)]

$^1$H-NMR (DMSO-d$_6$) δ: 0.93 (6H, d, J=6.6 Hz), 2.00–2.20 (1H, m), 3.88 (2H, bs), 4.09 (2H, d, J=7.0 Hz), 7.35–7.45 (3H, m), 7.55–7.65 (3H, m), 8.00 (1H, dm, J=8.4 Hz), 8.45 (H, d, J=8.4 Hz), 8.56 (3H, bs), 11.62 (1H, bs). Melting point 291–292° C.

Example 282

3-(Aminomethyl)-2-isobutyl-6-(5-methyl-1,3,4-oxadiazol-2-yl)-4-phenyl-1(2H)-isoquinolinone (1) A mixture of tert-butyl[6-(hydrazinocarbonyl)-2-isobutyl-1-oxo-4-phenyl-1,2-dihydro-3-isoquinolinyl]methylcarbamate (0.23 g, 0.50 mmol) and trimethyl orthoacetate (2.0 mL, 11 mmol) in 1-butanol (10 mL) was refluxed for 20 min. To the reaction mixture was added 1,8-diazabicyclo[5.4.0]-7-undecene (0.075 mL, 0.50 mmol), and then the mixture was refluxed for 1 h. The resulting reaction mixture was neutralized with acetic acid (0.040 mL, 0.70 mmol) and concentrated under reduced pressure. The residue was partitioned between water (10 mL) and ethyl acetate (30 mL). The organic layer was washed with water and brine, dried over anhydrous magnesium sulfate and concentrated under reduced pressure. The residue was purified by silica gel column chromatography (n-hexane:ethyl acetate=2:1 (v/v)) to give tert-butyl[2-isobutyl-6-(5-methyl-1,3,4-oxadiazol-2-yl)-1-oxo-4-phenyl-1,2-dihydro-3-isoquinolinyl]methylcarbamate (0.22 g, 91%) as crystals.

$^1$H-NMR (CDCl$_3$) δ: 1.02 (6H, d, J=7.2 Hz), 1.43 (9H, s), 2.15–2.35 (1H, m), 2.57 (3H, s), 4.10 (2H, d, J=7.2 Hz), 4.22 (2H, d, J=5.4 Hz), 4.57 (1H, br), 7.20–7.35 (2H, m), 7.50–7.65 (4H, m), 8.05 (1H, dm, J=8.4 Hz), 8.58 (1H, dd, J=1.4, 8.4 Hz).

(2) A mixture of tert-butyl[2-isobutyl-6-(5-methyl-1,3,4-oxadiazol-2-yl)-1-oxo-4-phenyl-1,2-dihydro-3-isoquinolinyl]methylcarbamate (0.20 g, 0.41 mmol) and 4N hydrogen chloride ethyl acetate solution (4 mL) was stirred for 17 h at room temperature. The reaction mixture was concentrated, the residue was washed with diisopropyl ether (5 mL×2) to give a pale yellow powder. The powder was added to aqueous saturated sodium hydrogencarbonate (30 mL), the resulting mixture was extracted with ethyl acetate-tetrahydrofuran (1:1, v/v, 50 mL×2). The organic layers were combined, washed with brine (25 mL), dried over anhydrous magnesium sulfate and concentrated under reduced pressure. The residue was purified by silica gel column chromatography (ethyl acetate:methanol=20:1 (v/v)) and recrystallized from n-hexane-ethyl acetate to give 3-(aminomethyl)-2-isobutyl-6-(5-methyl-1,3,4-oxadiazol-2-yl)-4-phenyl-1(2H)-isoquinolinone (0.11 g, 72%) as pale yellow crystals.

$^1$H-NMR (CDCl$_3$) δ: 1.02 (6H, d, J=6.6 Hz), 2.15–2.40 (1H, m), 2.57 (3H, s), 3.69 (2H, bs), 4.24 (2H, d, J=7.4 Hz), 7.25–7.35 (2H, m), 7.45–7.60 (3H, m), 7.62 (1H, d, J=1.6 Hz), 8.05 (1H, dd, J=1.6, 8.4 Hz), 8.59 (1H, d, J=8.4 Hz). Melting point: 179–181° C.

Example 283

2-[3-(Aminomethyl)-2-isobutyl-1-oxo-4-phenyl-1,2-dihydro-6-isoquinolinyl]acetamide hydrochloride (1) A mixture of tert-butyl[6-(cyanomethyl)-2-isobutyl-1-oxo-4-phenyl-1,2-dihydro-3-isoquinolinyl]methylcarbamate (0.13 g, 0.29 mmol), 2N potassium hydroxide solution (5 mL) and ethanol (5 mL) was refluxed for 4 h. The reaction mixture was diluted with 0.1N sodium hydroxide solution (100 mL) and washed with ethyl acetate (20 mL×2). The aqueous layer was separated, acidified with 1N hydrochloric acid and extracted with ethylacetate (100 mL×2). The organic layers were combined, washed with brine (20 mL), saturated aqueous sodium hydrogencarbonate (50 mL) and brine (50 mL), dried over, anhydrous magnesium sulfate and concentrated under reduced pressure to give (3-{[(tert-butoxycarbonyl)amino]methyl}-2-isobutyl-1-oxo-4-phenyl-1,2-dihydroisoquinolin-6-yl)acetic acid (0.36 g, 87%) as a pale yellow oil.

$^1$H-NMR (CDCl$_3$) δ: 0.98 (6H, d, J=6.6 Hz), 1.42 (9H, s), 2.15–2.35 (1H, m), 3.60 (2H, s), 3.95–4.25 (4H, m), 4.48 (1H, br), 6.81 (1H, d, J=1.2 Hz), 7.10–7.30 (3H, m), 7.38 (1H, d, J=7.5 Hz), 7.45–7.55 (2H, m), 8.40 (1H, dm, J=7.5 Hz).

(2) A mixture of (3-{[(tert-butoxycarbonyl)amino]methyl}-2-isobutyl-1-oxo-4-phenyl-1,2-dihydroisoquinolin-6-yl)acetic acid (0.15 g, 0.32 mmol), 1-hydroxybenzotriazole ammonium salt (0.074 g, 0.48 mmol) and 1-ethyl-3-(3-dimethylaminopropyl)carbodiimide hydrochloride (0.093 g, 0.48 mmol) in N,N-dimethylformamide (10 mL) was stirred at room temperature for 17 h. The reaction mixture was poured into 0.1N aqueous citric acid solution (50 mL) and extracted with ethyl acetate (25 mL×2). The organic layers were combined, washed with 0.1N aqueous citric acid solution (50 mL), saturated aqueous sodium hydrogencarbonate (50 mL), and brine (50 mL), dried over anhydrous magnesium sulfate and concentrated under reduced pressure. The residue was purified by silica gel column chromatography (ethyl acetate) to give tert-butyl[6-(2-amino-2-oxoethyl)-2-isobutyl-1-oxo-4-phenyl-1,2-dihydro-3-isoquinolinyl]methylcarbamate (0.12 g, 81%) as colorless crystals.

$^1$H-NMR (CDCl$_3$) δ: 1.00 (6H, d, J=6.6 Hz), 1.42 (9H, s), 2.15–2.30 (1H, m), 3.54 (2H, s), 4.00–4.25 (4H, m), 4.44 (1H, br), 5.31 (2H, br), 6.82 (1H, m), 7.20–7.30 (2H, m), 7.35–7.55 (4H, m), 8.46 (1H, dm, J=8.0 Hz).

(3) 2-[3-(Aminomethyl)-2-isobutyl-1-oxo-4-phenyl-1,2-dihydro-6-isoquinolinyl]acetamide hydrochloride (0.090 g, 90%) as pale yellow crystals. [synthesized according to the method similar to that in Example 279 (3) from tert-butyl[6-(2-amino-2-oxoethyl)-2-isobutyl-1-oxo-4-phenyl-1,2-dihydro-3-isoquinolinyl]methylcarbamate (0.11 g, 0.25 mmol)]

$^1$H-NMR (CD$_3$OD) δ: 1.00 (6H, d, J=6.6 Hz), 2.10–2.30 (1H, m), 3.52 (2H, s), 4.05–4.20 (4H, m), 7.00 (1H, d, J=1.2 Hz), 7.35–7.45 (2H, m), 7.50–7.65 (5H, m), 8.37 (1H, d, J=8.0 Hz). Melting point: 231–233° C.

Example 284

2-{[3-(Aminomethyl)-2-isobutyl-1-oxo-4-phenyl-1,2-dihydro-6-isoquinolinyl]methyl}-1H-isoindolone-1,3(2H)-dione hydrochloride (1) To a solution of (3-{[(tert-butoxycarbonyl)amino]methyl}-4-butoxy-2-neopentyl-1-oxo-1,2-dihydro-6-isoquinolinyl)methyl methanesulfonate (1.1 g, 2.11 mmol) in N,N-dimethylformamide (20 mL) was added potassium phthalimide (0.47 g, 2.5 mmol), and the mixture was stirred at room temperature for 17 h. The reaction mixture was poured into water (200 mL) and extracted with ethyl acetate (100 mL×2). The organic layers were combined, washed with 0.2N hydrochloric acid (100 mL), saturated aqueous sodium hydrogencarbonate (50 mL) and brine (50 mL), dried over anhydrous magnesium sulfate and concentrated under reduced pressure. The residue was purified by silica gel column chromatography (n-hexane:ethyl acetate=5:2 (v/v)) to give tert-butyl{6-[(1,3-dioxo-1,3-dihydro-2H-isoindol-2-yl)methyl]-2-isobutyl-1-oxo-4-phenyl-1,2-dihydro-3-isoquinolinyl}methylcarbamate (0.99 g, 84%) as colorless crystals.

$^1$H-NMR (CDCl$_3$) δ: 0.98 (6H, d, J=6.6 Hz), 1.42 (9H, s), 2.10–2.30 (1H, m), 4.05 (2H, d, J=7.4 Hz), 4.20 (2H, d, J=7.4 Hz), 4.42 (1H, br), 4.80 (2H, s), 6.90 (1H, d, J=1.2 Hz), 7.15–7.25 (2H, m), 7.35–7.45 (4H, m), 7.65–7.75 (2H, m), 7.75–7.85 (2H, m), 8.40 (1H, d, J=8.0 Hz).

(2) 2-{[-3-(Aminomethyl)-2-isobutyl-1-oxo-4-phenyl-1,2-dihydro-6-isoquinolinyl]methyl}-1H-isoindolone-1,3(2H)-dione hydrochloride (0.10 g, 100%) as a colorless powder. [synthesized according to the method similar to that in Example 279 (3) from tert-butyl{6-(1,3-dioxo-1,3-dihydro-2H-isoindol-2-yl)methyl]-2-isobutyl-1-oxo-4-phenyl-1,2-dihydro-3-isoquinolinyl}methylcarbamate (0.11 g, 0.20 mmol)]

$^1$H-NMR (DMSO-d$_6$) δ: 0.90 (6H, d, J=6.6 Hz), 1.95–2.20 (1H, m), 3.87 (2H, bs), 4.04 (2H, d, J=5.4 Hz), 4.77 (2H, s), 6.65–6.75 (1H, m), 7.25–7.30 (2H, m), 7.35–7.45 (3H, m), 7.52 (1H, dm, J=8.2 Hz), 7.87 (4H, s), 8.29 (1H, d, J=8.2 Hz), 8.31 (3H, bs). Melting point: 196–199° C.

Example 285

N-{[3-(Aminomethyl)-2-isobutyl-1-oxo-4-phenyl-1,2-dihydro-6-isoquinolinyl]methyl}acetamide hydrochloride (1) A mixture of tert-butyl{6-[(1,3-dioxo-1,3-dihydro-2H-isoindol-2-yl)methyl]-2-isobutyl-1-oxo-4-phenyl-1,2-dihydroisoquinolin-3-yl}methylcarbamate (0.85 g, 1.5 mmol), and hydrazine monohydrate (0.6 mL, 12 mmol) in ethanol (20 mL) and tetrahydrofuran (10 mL) was stirred at room temperature for 17 h. The reaction mixture was filtered, and the filtrate was concentrated. After the residue was dissolved in ethyl acetate (50 mL), the solution was filtrated to remove insoluble material. The filtrate was concentrated to give tert-butyl[6-(aminomethyl)-2-isobutyl-1-oxo-4-phenyl-1,2-dihydro-3-isoquinolinyl]methylcarbamate (0.82 g) as a crude pale yellow oil. To a solution of the crude oil (0.16 g) in tetrahydrofuran (2 mL) was added acetic anhydride (0.034 mL, 0.36 mmol), and then the mixture was stirred at room temperature for 4 h. The reaction mixture was washed with water (4 mL) and concentrated. The residue was purified by silica gel column chromatography (n-hexane:ethyl acetate=4:1 (v/v)) to give tert-butyl{6-[(acetylamino)methyl]-2-isobutyl-1-oxo-4-phenyl-1,2-dihydro-3-isoquinolinyl}methylcarbamate (0.090 g, 63%) as a pale yellow solid.

$^1$H-NMR (CDCl$_3$) δ: 1.00 (6H, d, J=6.6 Hz), 1.43 (9H, s), 1.96 (3H, s), 2.25–2.35 (1H, m), 4.06 (2H, d, J=7.6 Hz), 4.19 (2H, d, J=5.4 Hz), 4.38 (2H, d, J=6.6 Hz), 4.59 (1H, br), 5.84 (1H, br), 6.76 (1H, m), 7.20–7.55 (6H, m), 8.38 (1H, dm, J=8.4 Hz).

(2) N-{[3-(Aminomethyl)-2-isobutyl-1-oxo-4-phenyl-1,2-dihydro-6-isoquinolinyl]methyl}acetamide hydrochloride (0.068 g, 96%) as a pale yellow-powder. [synthesized according to the method similar to that in Example 279 (3) from tert-butyl{6-[(acetylamino)methyl]-2-isobutyl-1-oxo-4-phenyl-1,2-dihydro-3-isoquinolinyl}methylcarbamate (0.082 g, 0.17 mmol)]

$^1$H-NMR (DMSO-d$_6$) δ: 0.91 (6H, d, J=6.6 Hz), 1.75 (3H, s), 1.95–2.20 (1H, m), 3.87 (2H, bs), 4.04 (2H, d, J=6.6 Hz), 4.20 (2H, d, J=6.6 Hz), 6.73 (1H, s), 7:30–7.40 (2H, m), 7.44 (1H, dd, J=1.6, 8.4 Hz), 7.50–7.60 (3H, m), 8.28 (1H, d, J=8.4 Hz), 8.30–8.45 (4H, m). Melting point: 134–139° C.

Example 286

N-{[3-(Aminomethyl)-2-isobutyl-1-oxo-4-phenyl-1,2-dihydro-6-isoquinolinyl]methyl}-2-methylpropanamide hydrochloride (1) To a solution of crude tert-butyl[6-(aminomethyl)-2-isobutyl-1-oxo-4-phenyl-1,2-dihydro-3-isoquinolinyl]methylcarbamate (0.016 g) (Example 285) in tetrahydrofuran (2 mL) was added isobutyryl chloride (0.038 mL, 0.36 mmol) and triethylamine (0.050 mL, 0.36 mmol), and the mixture was stirred at room temperature for 4 h. The reaction mixture was washed with water (4 mL) and concentrated. The residue was purified by silica gel column chromatography (n-hexane:ethyl acetate=4:1 (v/v)) to give tert-butyl{2-isobutyl-6-[(isobutyrylamino)methyl]-1-oxo-4-phenyl-1,2-dihydro-3-isoquinolinyl}methylcarbamate (0.11 g, 75%) as a pale yellow solid.

$^1$H-NMR (CDCl$_3$) δ: 0.99 (6H, d, J=6.6 Hz), 1.07 (6H, d, J=7.0 Hz), 1.43 (9H, s), 2.15–2.35 (2H, m), 4.06 (2H, d, J=7.2 Hz), 4.20 (2H, d, J=5.4 Hz), 4.41 (2H, d, J=6.2 Hz), 4.58 (1H, br), 5.79 (1H, br), 6.77 (1H, d, J=1.2 Hz), 7.20–7.60 (6H, m), 8.38 (1H, dm, J=8.2 Hz).

(2) N-{[3-(Aminomethyl)-2-isobutyl-1-oxo-4-phenyl-1,2-dihydro-6-isoquinolinyl]methyl}-2-methylpropanamide hydrochloride (0.091 g, 98%) as a pale yellow powder. [synthesized according to the method similar to that in Example 279 (3) from tert-butyl{2-isobutyl-6-[(isobutyrylamino)methyl]-1-oxo-4-phenyl-1,2-dihydro-3-isoquinolinyl}methylcarbamate (0.11 g, 0.21 mmol)]

$^1$H-NMR (DMSO-d$_6$) δ: 0.86 (6H, d, J=6.6 Hz), 0.91 (6H, d, J=6.6 Hz), 1.95–2.35 (2H, m), 3.84 (2H, bs), 4.06 (2H, d, J=7.0 Hz), 4.24 (2H, d, J=5.8 Hz), 6.75 (1H, s), 7.30–7.40 (2H, m), 7.43 (1H, dd, J=1.0, 8.4 Hz), 7.45–7.60 (3H, m), 8.27 (1H, bs), 8.27 (1H, d, J=8.4 Hz), 8.52 (3H, bs). Melting point: 189–191° C.

Example 287

Ethyl[3-(aminomethyl)-2-isobutyl-1-oxo-4-phenyl-1,2-dihydro-6-isoquinolinyl]methylcarbamate hydrochloride (1) To a solution of crude tert-butyl[6-(aminomethyl)-2-isobutyl-1-oxo-4-phenyl-1,2-dihydro-3-isoquinolinyl]methylcarbamate (0.16 g) (Example 285) in tetrahydrofuran (2 mL) were added ethyl chloroformate (0.035 mL, 0.36 mmol) and triethylamine (0.050 mL, 0.36 mmol), and the mixture was stirred at room temperature for 4 h. The reaction mixture was washed with water (4 mL) and concentrated. The residue was purified by silica gel column chromatography (n-hexane:ethyl acetate=4:1 (v/v)) to give ethyl (3-{[(tert-butoxycarbonyl)amino]methyl}-2-isobutyl-1-oxo-4-phenyl-1,2-dihydro-6-isoquinolinyl)methylcarbamate (0.13 g, 87%) as pale yellow powder.

$^1$H-NMR (CDCl$_3$) δ: 1.00 (6H, d, J=6.6 Hz), 1.21 (3H, t, J=7.0 Hz), 1.42 (9H, s), 2.15–2.35 (1H, m), 4.07 (2H, d, J=7.8 Hz), 4.09 (2H, q, J=7.0 Hz), 4.19 (2H, d, J=7.4 Hz), 4.31 (2H, d, J=6.6 Hz), 4.49 (1H, br), 4.96 (1H, br), 6.79 (1H, s), 7.20–7.55 (6H, m), 8.42 (1H, d, J=8.4 Hz).

(2) Ethyl[3-(aminomethyl)-2-isobutyl-1-oxo-4-phenyl-1,2-dihydro-6-isoquinolinyl]methylcarbamate hydrochloride (0.092 g, 88%) as a colorless powder. [synthesized according to the method similar to that in Example 279 (3) from ethyl(3-{[(tert-butoxycarbonyl)amino]methyl}-2-isobutyl-1-oxo-4-phenyl-1,2-dihydro-6-isoquinolinyl)methylcarbamate (0.12 g, 0.24 mmol)]

$^1$H-NMR (DMSO-d$_6$) δ: 0.91 (6H, d, J=6.6 Hz), 1.11 (3H, t, J=7.4 Hz), 2.00–2.20 (1H, m), 3.86 (2H, bs), 3.91 (2H, q, J=7.4 Hz), 4.07 (2H, d, J=7.8 Hz), 4.13 (2H, d, J=6.0 Hz), 6.77 (1H, s), 7.30–7.40 (2H, m), 7.45 (1H, dd, J=1.6, 8.2 Hz), 7.50–7.60 (3H, m), 7.64 (1H, d, J=6.0 Hz), 8.28 (1H, d, J=8.2 Hz), 8.55 (3H, bs). Melting point: 184–187° C.

Example 288

N-{[3-(Aminomethyl)-2-isobutyl-1-oxo-4-phenyl-1,2-dihydro-6-isoquinolinyl]methyl}methanesulfoneamide hydrochloride (1) To a solution of crude tert-butyl[6-(aminomethyl)-2-isobutyl-1-oxo-4-phenyl-1,2-dihydro-3-isoquinolinyl]methylcarbamate (0.16 g) (Example 285) in tetrahydrofuran (2 mL) was added methanesulfonyl chloride (0.028 mL, 0.36 mmol) and triethylamine (0.050 mL, 0.36 mmol), and the mixture was stirred at room temperature for 4 h. The reaction mixture was washed with water (4 mL) and concentrated. The residue was purified by silica gel column chromatography (n-hexane:ethyl acetate=2:1 (v/v)) to give tert-butyl (2-isobutyl-6-{[(methylsulfonyl)amino]methyl}-1-oxo-4-phenyl-1,2-dihydro-3-isoquinolinyl)methylcarbamate (0.13 g, 84%) as a pale yellow oil.

$^1$H-NMR (CDCl$_3$) δ: 1.00 (6H, d, J=6.6 Hz), 1.43 (9H, s), 2.15–2.35 (1H, m), 2.80 (3H, s), 4.07 (2H, d, J=7.2 Hz), 4.20 (2H, d, J=5.8 Hz), 4.29 (2H, d, J=6.6 Hz), 4.52 (1H, br), 4.71 (1H, bt, J=5.8 Hz), 6.86 (1H, d, J=1.2 Hz), 7.20–7.30 (2H, m), 7.44 (1H, dd, J=1.6 8.0 Hz), 7.45–7.60 (3H, m), 8.44 (1H, d, J=8.0 Hz).

(2) N-{[3-(Aminomethyl)-2-isobutyl-1-oxo-4-phenyl-1,2-dihydro-6-isoquinolinyl]methyl}methanesulfoneamide hydrochloride (0.097 g, 100%) as a pale yellow powder. [synthesized according to the method similar to that in Example 279 (3) from tert-butyl(2-isobutyl-6-{[(methylsulfonyl)amino]methyl}-1-oxo-4-phenyl-1,2-dihydro-3-isoquinolinyl)methylcarbamate (0.11 g, 0.21 mmol)]

$^1$H-NMR (DMSO-d$_6$) δ: 0.91 (6H, d, J=6.6 Hz), 1.95–2.20 (1H, m), 2.80 (3H, s), 3.86 (2H, bs), 4.07 (2H, d, J=7.0 Hz), 4.14 (2H, d, J=6.2 Hz), 6.88 (1H, s), 7.35–7.45 (2H, m), 7.50–7.65 (4H, m), 7.63 (1H, t, J=6.2 Hz), 8.32 (1H, d, J=8.0 Hz), 8.55 (3H, bs). Melting point: 117–120° C.

Example 289

3,6-Bis(aminomethyl)-2-isobutyl-4-phenyl-1(2H)-isoquinolinone dihydrochloride (1) To a solution of crude tert-butyl[6-(aminomethyl)-2-isobutyl-1-oxo-4-phenyl-1,2-dihydro-3-isoquinolinyl]methylcarbamate (0.16 g)(Example 286) in tetrahydrofuran (2 mL) was added di-t-butyl dicarbonate (0.086 mL, 0.36 mmol), and the mixture was stirred at room temperature for 4 h. The reaction mixture was washed with water (4 mL) and concentrated. The residue was purified by silica gel column chromatography (n-hexane:ethyl acetate=4:1 (v/v)) to give tert-butyl(3-{[(tert-butoxycarbonyl)amino]methyl}-2-isobutyl-1-oxo-4-phenyl-1,2-dihydro-6-isoquinolinyl)methylcarbamate (0.14 g, 93%) as a colorless powder.

$^1$H-NMR (CDCl$_3$) δ: 1.00 (6H, d, J=6.6 Hz), 1.39 (9H, s), 1.42 (9H, s), 2.15–2.35 (1H, m), 4.07 (2H, d, J=7.4 Hz), 4.19 (2H, d, J=6.6 Hz), 4.26 (2H, d, J=6.6 Hz), 4.45 (1H, br), 4.81 (1H, br), 6.81 (1H, d, J=1.1 Hz), 7.20–7.30 (2H, m), 7.30–7.40 (1H, m), 7.45–7.55 (3H, m), 8.42 (1H, d, J=8.0 Hz).

(2) 3,6-Bis(aminomethyl)-2-isobutyl-4-phenyl-1(2H)-isoquinolinone dihydrochloride (0.080 g, 76%) as colorless powder. [synthesized according to the method similar to that in Example 279 (3) from tert-butyl(3-{[(tert-butoxycarbonyl)amino]methyl}-2-isobutyl-1-oxo-4-phenyl-1,2-dihydro-6-isoquinolinyl)methylcarbamate (0.14 g, 0.26 mmol)]

$^1$H-NMR (DMSO-d$_6$) δ: 0.91 (6H, d, J=6.6 Hz), 1.95–2.20 (1H, m), 3.85 (2H, bs), 4.01 (2H, bs), 4.10 (2H, d, J=6.6 Hz), 7.02 (1H, d, J=1.0 Hz), 7.35–7.45 (2H, m), 7.50–7.60 (3H, m), 7.72 (1H, dm, J=8.4 Hz), 8.36 (1H, d, J=8.4 Hz), 8.45 (3H, bs), 8.62 (3H, bs). Melting point: 282–285° C.

Example 290

3-(Aminomethyl)-2-isobutyl-4-phenyl-6-[5-(trifluoromethyl)-1H-1,2,4-triazol-3-yl]-1(2H)-isoquinolinone dihydrochloride (1) A mixture of ethyl trifluoroacetate (0.038 mL, 0.31 mmol) and hydrazine monohydrate (0.026 mL, 0.50 mmol) in tetrahydrofuran (3 mL) was refluxed in a sealed tube for 1 h, the reaction was allowed to cool to room temperature. To the mixture were added tert-butyl{6-[amino(imino)methyl]-2-isobutyl-1-oxo-4-phenyl-1,2-dihydro-3-isoquinolinyl}methylcarbamate diacetate (0.14 g, 0.25 mmol) and sodium hydroxide (0.027 g, 0.55 mmol), and the resulting mixture was refluxed for 3 h. The reaction mixture was partitioned between water (10 mL) and ethyl acetate (30 mL). The organic layer was washed with water and brine, dried over anhydrous magnesium sulfate and concentrated under reduced pressure. The residue was purified by silica gel-column chromatography (n-hexane:ethyl acetate=3:1 (v/v)) to give tert-butyl{2-isobutyl-1-oxo-4-phenyl-6-[5-(trifluoromethyl)-1H-1,2,4-triazol-3-yl]-1,2-dihydro-3-isoquinolinyl}methylcarbamate (0.074 g, 55%) as a colorless powder.

$^1$H-NMR (CDCl$_3$) δ: 1.00 (6H, d, J=6.6 Hz), 1.43 (9H, s), 2.10–2.35 (1H, m), 4.08 (2H, d, J=7.4 Hz), 4.18 (2H, d, J=5.2 Hz), 4.71 (1H, br), 7.20–7.30 (3H, m), 7.35–7.50 (4H, m), 8.02 (1H, dd, J=1.6, 8.6 Hz), 8.46 (1H, d, J=8.6 Hz).

(2) 3-(Aminomethyl)-2-isobutyl-4-phenyl-6-[5-(trifluoromethyl)-1H-1,2,4-triazol-3-yl]-1(2H)-isoquinolinone dihydrochloride (0.063 g, 100%) as yellow crystals. [synthesized according to the method similar to that in Example 279 (3) from tert-butyl{2-isobutyl-1-oxo-4-phenyl-6-[5-(trifluoromethyl)-1H-1,2,4-triazol-2-yl]-1,2-dihydro-3-isoquinolinyl}methylcarbamate (0.065 g, 0.12 mmol)]

$^1$H-NMR (DMSO-d$_6$) δ: 0.94 (6H, d, J=6.6 Hz), 1.72 (1H, br), 2.05–2.20 (1H, m), 3.88 (2H, bs), 4.09 (2H, d, J=7.2 Hz), 7.40–7.50 (2H, m), 7.55–7.70 (4H, m), 8.23 (1H, dd, J=1.6, 8.4 Hz), 8.50 (3H, bs), 8.52 (1H, d, J=8.4 Hz). Melting point: 140–143° C.

Example 291

3-(Aminomethyl)-2-isobutyl-1-oxo-4-phenyl-1,2-dihydro-6-isoquinolinecarboxamidine dihydrochloride This compound was synthesized according to the method similar to that in Example 279 (3) from tert-butyl{6-[amino(imino)methyl]-2-isobutyl-1-oxo-4-phenyl-1,2-dihydro-3-isoquinolinyl}methylcarbamate diacetate.

$^1$H-NMR (DMSO-d$_6$) δ: 0.92 (6H, d, J=6.6 Hz), 2.00–2.20 (1H, m), 3.90 (2H, bs), 4.12 (2H, d, J=7.0 Hz), 7.24 (1H, d, J=1.6 Hz), 7.40–7.50 (2H, m), 7.50–7.65 (3H, m), 7.86 (1H, dd, J=1.6, 8.4 Hz), 8.49 (1H, d, J=8.4 Hz), 8.69 (3H, bs), 9.26 (2H, bs), 9.52 (2H, bs). Melting point: 171–173° C.

Example 292

Methyl 2-[3-(aminomethyl)-2-isobutyl-1-oxo-4-phenyl-1,2-dihydro-6-isoquinolinyl]-1H-imidazole-4-carboxylate dihydrochloride (1) To a mixture of tert-butyl{6-[amino(hydroxyimino)-methyl]-2-isobutyl-1-oxo-4-phenyl-1,2-dihydro-3-isoquinolinyl}methylcarbamate (0.47 g, 1.0 mmol) and triethylamine (0.17 mL, 1.2 mmol) in ethyl acetate (10 mL) was added methylpropionate (0.10 g, 1.2 mmol), and the mixture was stirred at room temperature for 17 h. The reaction mixture was poured into water (5 mL), and the organic layer was separated. The organic layer was dried over anhydrous magnesium sulfate and concentrated under reduced pressure. To the residue was added p-xylene (10 mL), the mixture was refluxed for 40 h. The reaction mixture was diluted with ethyl acetate (100 mL), and the solution was washed with water, dried over anhydrous magnesium sulfate and concentrated under reduced pressure. The residue was purified by silica gel column chromatography (n-hexane:ethyl acetate=1:1 (v/v)) to give methyl 2-(3-{[(tert-butoxycarbonyl)amino]methyl}-2-isobutyl-1-oxo-4-phenyl-1,2-dihydro-6-isoquinolinyl)-1H-imidazole-4-carboxylate (0.22 g, 42%) as an orange powder.

$^1$H-NMR (CDCl$_3$) δ: 0.98 (6H, d, J=6.6 Hz), 1.53 (9H, s), 2.00–2.25 (1H, m), 3.87 (3H, s), 4.00–4.25 (4H, m), 6.37 (1H, br), 7.15–7.25 (1H, m), 7.25–7.55 (7H, m) 7.82 (1H, dm, J=8.4 Hz), 8.23 (1H, d, J=8.4 Hz).

(2) A solution of methyl 2-(3-{[(tert-butoxycarbonyl)amino]methyl}-2-isobutyl-1-oxo-4-phenyl-1,2-dihydro-6-isoquinolinyl)-1H-imidazole-4-carboxylate (0.10 g, 0.19 mmol) in trifluoroacetic acid (3 mL) was stirred at room temperature for 5 min. The reaction mixture was concentrated, and purified by HPLC. The desired fractions were concentrated and then to the residue was added a 4N hydrogen chloride, ethyl acetate solution (1 mL). The mixture was concentrated, and the residue was recrystallized from ethanol-ethyl acetate (10:1, v/v, 2 mL) to give methyl 2-[3-(aminomethyl)-2-isobutyl-1-oxo-4-phenyl-1,2-dihy-dro-6-isoquinolinyl]-1H-imidazole-4-carboxylate dihydrochloride (0.050 g, 53%) as a yellow powder.

$^1$H-NMR (DMSO-d$_6$) δ: 0.93 (6H, d, J=6.6 Hz), 2.00–2.25 (1H, m), 3.77 (3H, s), 3.84 (2H, s), 4.08 (2H, d, J=7.2 Hz), 7.40–7.50 (3H, m), 7.55–7.65 (4H, m), 7.90 (1H, s), 8.20 (1H, dd, J=1.8, 8.4 Hz), 8.43 (1H, d, J=8.4 Hz), 8.51 (3H, bs). Melting point: 266–270° C.

Example 293

Ethyl 3-[3-(aminomethyl)-2-isobutyl-1-oxo-4-phenyl-1,2-dihydro-6-isoquinolinyl]-1,2,4-oxadiazole-5-carboxylate hydrochloride (1) To a mixture of tert-butyl{6-[amino(hydroxyimino)methyl]-2-isobutyl-1-oxo-4-phenyl-1,2-dihydro-3-isoquinolinyl}methylcarbamate (0.23 g, 0.50 mmol) and pyridine (0.043 mL, 0.53 mmol) in toluene (20 mL), was added ethyl chlorooxoacetate (0.059 mL, 0.53 mmol), and the mixture was stirred at room temperature for 1 h and at 80° C. for 1 h. The reaction mixture was partitioned between water (50 mL) and ethyl acetate (50 mL). The organic layer was washed with brine, dried over anhydrous magnesium sulfate and concentrated under reduced pressure. The residue was purified by silica gel column chromatography (n-hexane:ethyl acetate=20:1–1:3 (v/v)) and recrystallized from diisopropyl ether-ethyl acetate (20:1, v/v, 5 mL) to give ethyl 3-(3-{[(tert-butoxycarbonyl)amino]methyl}-2-isobutyl-1-oxo-4-phenyl-1,2-dihydro-6-isoquinolinyl)-1,2,4-oxadiazole-5-carboxylate (0.13 g, 48%) as colorless crystals.

$^1$H-NMR (CDCl$_3$) δ: 1.02 (6H, d, J=6.6 Hz), 1.43 (9H, s), 1.47 (3H, t, J=7.2 Hz), 2.15–2.35 (1H, m), 4.11 (2H, d, J=7.2 Hz), 4.22 (2H, d, J=5.6 Hz), 4.45–4.60 (1H, br), 4.54 (2H, q, J=7.2 Hz), 7.25–7.35 (2H, m), 7.50–7.60 (3H, m), 7.74 (1H, d, J=1.2 Hz), 8.17 (1H, dd, J=1.2, 8.4 Hz), 8.60 (1H, d, J=8.4 Hz).

(2) A solution of ethyl 3-(3-{[(tert-butoxycarbonyl)amino]methyl}-2-isobutyl-1-oxo-4-phenyl-1,2-dihydro-6-isoquinolinyl)-1,2,4-oxadiazole-5-carboxylate (0.070 g, 0.13 mmol) in trifluoroacetic acid (3 mL) was stirred at room temperature for 5 min. The reaction mixture was concentrated, and to the residue was added a solution of 4N hydrogen chloride in ethyl acetate (3 mL). The mixture was concentrated, and the residue was recrystallized from diisopropyl ether-ethyl acetate-methanol (15:40:1, v/v, 5 mL) to give ethyl 3-[3-(aminomethyl)-2-isobutyl-1-oxo-4-phenyl-1,2-dihydro-6-isoquinolinyl]-1,2,4-oxadiazole-5-carboxylate hydrochloride (0.061 g, 100%) as a colorless powder.

$^1$H-NMR (DMSO-d$_6$) δ: 0.94 (6H, d, J=6.6 Hz), 1.34(3H, t, J=7.2 Hz), 2.00–2.20 (1H, m), 3.90 (2H, bs), 4.10 (2H, d, J=5.0 Hz), 4.43 (2H, d, J=7.2 Hz), 7.40–7.50 (2H, m), 7.55–7.70 (4H, m), 8.22 (1H, dd, J=1.4, 8.4 Hz), 8.30–8.60 (3H, br), 8.55 (1H, d, J=8.4 Hz). Melting point: 266–270° C.

Reference Example 1

2-Benzoyl-4-bromobenzoic Acid

A mixture of benzene (2.94 ml), o-dichlorobenzene (20 ml) and aluminum chloride (5.87 g) was cooled to 5° C. and 5-bromophthalic anhydride (5.0 g) was added by small portions while maintaining the temperature of the mixture below 10° C. The mixture was stirred at around 25° C. for 1 h and then at 80° C. for 1 h. The reaction mixture was cooled to around 5° C. and ethyl acetate (40 ml) was added dropwise. Water (20 ml) was added dropwise below 40° C.

The organic layer was separated and 4N hydrochloric acid (20 ml) was added. The mixture was stirred until the precipitated solid was dissolved. The organic layer was separated and washed with water (20 ml). The solvent was evaporated and toluene (30 ml) and ethyl acetate (3 ml) were added to the residue, which was followed by heating to 80° C. The obtained solution was cooled to 25° C. over 30 min and the precipitated crystals were collected by filtration. The crystals were dissolved in a mixture of toluene (30 ml) and ethyl acetate (1.5 ml) by heating and the obtained solution was cooled to 25° C. and then to 5° C. The precipitated crystals were collected by filtration and washed with toluene, to give the title compound (2.81 g, yield 41.8%).

$^1$H-NMR(300 MHz, CDCl$_3$) δ: 7.41–7.46(2H, m), 7.51–7.60(2H, m), 7.69–7.72(3H, m), 7.94(1H, d, J=8.4 Hz)

Reference Example 2

Isobutylaminoacetonitrile

To a mixture of isobutylamine (180.3 g), triethylamine (274.9 g) and ethyl acetate (900 ml) was added dropwise bromoacetonitrile (304.8 g) under ice-cooling below 30° C. over about 2 h. The reaction mixture was adjusted to 25° C. stirred for 3 h and washed with water (900 ml) and 10% brine (900 ml). The solvent was evaporated and the obtained pale-yellow oil was distilled under reduced pressure. The bP$_{10mmHg}$ 82° C. fractions were collected to give the title compound (198.3 g).

$^1$H-NMR(CDCl$_3$), δ: 0.94(6H, d, J=6.6 Hz), 1.17(1H, br), 1.74(1H, m), 2.54(2H, d, J=6.6 Hz), 3.59(2H, s)

Experimental Example 1

1) Preparation of Dipeptidyl Peptidase IV Crude Enzyme Solution

The enzyme activity of dipeptidyl peptidase IV present in human colonic adenocarcinoma-derived cell line Caco-2 cell membrane has been already reported by Yong S. Chung et al. (Cancer Research, vol. 45, pp. 2976–2982, 1985).

A dipeptidyl peptidase IV crude enzyme solution was prepared from culture cell of Caco-2 (ATCC HTB-37). The Caco-2 cells were cultured in D-MEM medium (manufactured by Nissui Pharmaceutical Co., Ltd.) containing 10% FBS (fetal calf serum (manufactured by GIBCO)). The cell extract was prepared by soaking the cells collected by removing the medium in 20 mM phosphate buffer. (pH 7.5) containing 0.5% Triton X-100, extracting for 30 min in an ice bath and separating the supernatant obtained by centrifugation 1500 g for 30 min. The cell extract (22 ml) was applied to a column of Sephadex G-200 (600 ml, manufactured by Pharmacia Corporation) equilibrated with 20 mM Tris-hydrochloride buffer (pH 7.5) and eluted with the same buffer. The elution was fractionated by 10 ml, examined for enzyme activity and 190 ml–280 ml fractions (90 ml) were collected. The same buffer (260 ml) was added for dilution to give a crude enzyme solution (14 mU/ml, 350 ml). One unit of the dipeptidyl peptidase IV enzyme activity was defined as an enzyme amount that produces 1 μmol of p-nitroaniline from glycylprolyl-p-nitroanilide in 1 min.

2) Determination of Caco-2-Derived Dipeptidyl Peptidase IV Inhibitory Activity

The reaction was carried out according to the method of Nagatsu et al. (Analytical Biochemistry, vol. 74, pp. 466–467, 1976) using a 96 well flat-bottomed plate at 37° C. An N,N-dimethylformamide solution (5 μl) containing the test compound was added to a mixture of water (25 μl), 1M Tris-hydrochloride buffer (10 μl, pH 7.5) and 1 mM aqueous glycylprolyl-p-nitroanilide (Gly-Pro-p-NA; manufactured by Backem AG) solution (50 μl) to prepare a mixed solution. The Caco-2-derived dipeptidyl peptidase IV crude enzyme solution (10 μl) obtained in the aforementioned 1) was added to the above-mentioned mixed solution and the enzyme reaction was started at 37° C. The absorbance after 0 h and 3 h was measured using a microplate reader (Multiskan Bichromatic; manufactured by Labsystems) at a wavelength of 405 nm and an increase (ΔODs) was determined. At the same time, an increase (ΔODc) in absorbance of the reaction mixture without the test compound, and an increase (ΔODb) in absorbance of the reaction mixture without the test compound and the enzyme were determined and percent inhibition of dipeptidyl peptidase IV enzyme activity was calculated from the following formula:

{1−[(ΔODs−ΔODb)/(ΔODc−ΔODb)]}×100

The dipeptidyl peptidase IV inhibitory activity of the test compound group is expressed in IC$_{50}$ value (μM) and shown in Table 8.

TABLE 8

| Test compound (Example No.) | IC$_{50}$ value (μM) |
|---|---|
| 95 | 0.28 |
| 109 | 0.36 |
| 112 | 0.25 |

As shown above, the compound of the present invention has a superior dipeptidyl peptidase IV enzyme activity, and is useful as an agent for the prophylaxis or treatment of diabetes and the like.

Experimental Example 2

Determination of Dipeptidyl Peptidase IV Inhibitory Activity in Rat Plasma

The reaction was carried out according to the method of Raymond et al. (Diabetes, vol. 47, pp. 1253–1258, 1998) using a 96 well flat-bottomed plate at 30° C. An N,N-dimethylformamide solution (1 μl) containing the test compound was added to a mixture of water (69 μl), 1M Tris-hydrochloride buffer (10 μl, pH 7.5) and 1 mM aqueous Gly-Pro-p-NA solution (100 μl) to prepare a mixed solution. Plasma (20 μl) prepared from blood of SD rat by a conventional method was added the above-mentioned, mixed solution and the enzyme reaction was started at 30° C. The absorbance after 0 h and 1 h was measured using a microplate reader at a wavelength of 405 nm and an increase (ΔODs) was determined. At the same time, an increase (ΔODc) in absorbance of the reaction mixture without the test compound, and an increase (ΔODb) in absorbance of the reaction mixture without the test compound and the enzyme were determined and percent inhibition of dipeptidyl peptidase IV enzyme activity was calculated from the following formula:

{1−[(ΔODs−ΔODb)/(ΔODc−ΔODb)]}×100

The dipeptidyl peptidase IV inhibitory activity of the test compound group is expressed in IC$_{50}$ value (μM) and shown in Table 9.

TABLE 9

| Test compound (Example No.) | IC$_{50}$ value (μM) |
|---|---|
| 95 | 0.18 |
| 109 | 0.15 |
| 112 | 0.32 |

As shown above, the compound of the present invention has a superior dipeptidyl peptidase IV enzyme activity, and is useful as an agent for the prophylaxis or treatment of diabetes and the like.

Experimental Example 3

Plasma Glucose-lowering Effect and Insulinotropic Effect in Rat

Female Wistar fatty rats (17-week-old, 6 per group) were fasted overnight and blood was drawn from the tail vein. The plasma glucose level before administration of the test compound was measured. Then the test compound (3 mg/kg body weight/5 mL) suspended in 0.5% methyl cellulose was orally administered to the rats using a gastric tube. Oral glucose tolerance test (1 g/kg body weight/5 mL) was started 60 min later. Blood was drawn at 30 min after starting glucose load, and plasma glucose level and insulin level of the serum were measured. The plasma glucose level was measured using an automatic analyzer (HITACHI 7070) and the insulin level was measured using a radio immunoassay kit (trademark: SHIONORIA insulin kit (manufactured by Shionogi & Co., Ltd.)).

The plasma glucose level and insulin level of the test compound group are expressed in a value (%) relative to the control group and shown in Table 10.

TABLE 10

| Test compound (Example No.) | Plasma glucose level (% of control) | insulin level (% of control) |
|---|---|---|
| 95 | 82 | 188 |
| 109 | 73 | 205 |
| 112 | 76 | 255 |

As shown above, the compound of the present invention has a superior plasma glucose level-lowering effect and a superior insulinotropic effect, and is useful as an agent for the prophylaxis or treatment of diabetes and the like.

| Formulation Example 1 (production of capsule) | |
|---|---|
| 1) compound of Example 95 | 30 mg |
| 2) fine cellulose powder | 10 mg |
| 3) lactose | 19 mg |
| 4) magnesium stearate | 1 mg |
| total | 60 mg |

1), 2), 3) and 4) are mixed and filled in gelatin capsules.

| Formulation Example 2 (production of tablet) | |
|---|---|
| 1) compound of Example 95 | 30 g |
| 2) lactose | 50 g |
| 3) corn starch | 15 g |
| 4) calcium carboxymethylcellulose | 44 g |
| 5) magnesium stearate | 1 g |
| total of 1000 tablets | 140 g |

The entire amounts of 1), 2) and 3), and 30 g of 4) are kneaded with water, dried in vacuo and granulated. The granules are mixed with 14 g of 4) and 1 g of 5) and the mixture is compressed with a tableting machine, whereby 1000 tablets containing 30 mg of compound of Example 95 per tablet are obtained.

The compound and the pharmaceutical agent of the present invention show a superior peptidase (preferably dipeptidyl peptidase-IV)-inhibitory activity and are useful as an agent for the prophylaxis or treatment of diabetes and the like.

This application is based on patent application Nos. 2001-27349, 2001-292388 and 2001-382232 filed in Japan, the contents of which are hereby incorporated by reference. All of the references cited herein, including patents, patent applications and publications, are hereby incorporated in their, entireties by reference.

The invention claimed is:
1. A compound of the formula

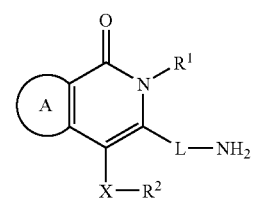

(I)

wherein
ring A is a 5 to 10-membered aromatic ring having 1 to 3 substituent(s) selected from
1) a nitro group;
2) a cyano group;
3) a C$_{1-3}$alkylenedioxy group;
4) a C$_{1-10}$alkyl group or a C$_{2-10}$ alkenyl group, each having 1 to 3 substituent(s) selected from hydroxy group, carboxyl group, alkoxycarbonyl group having 2 to 8 carbon atoms, carbamoyl group, cyano group, amino group, alkanoylamino group having 2 to 8 carbon atoms, alkoxycarbonylamino group having 2 to 8 carbon atoms and alkylsulfonylamino group having 1 to 8 carbon atom(s);
5) an alkoxy group having 1 to 10 carbon atom(s), a cycloalkyloxy group having 3 to 10 carbon atoms or an aralkyloxy group having 7 to 13 carbon atoms, each having 1 to 3 substituent(s) selected from alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms;
6) an acyl group;
7) an optionally substituted amino group;
8) an aryl group having 6 to 14 carbon atoms;
9) an optionally substituted thiol group;

10) an optionally substituted heterocyclic group; and
11) an amidino group;

$R^1$ and $R^2$ are the same or different and each is an optionally substituted hydrocarbon group or an optionally substituted heterocyclic group;

X is a bond, —O—, —S—, —SO—, —$SO_2$— or —$NR^3$— ($R^3$ is a hydrogen atom or an optionally substituted hydrocarbon group); and L is a divalent hydrocarbon group or a salt thereof.

2. The compound of claim 1, wherein the 5 to 10-membered aromatic ring for ring A is a benzene ring.

3. The compound of claim 1, wherein $R^1$ is an alkyl group having 1 to 10 carbon atom(s).

4. The compound of claim 1, wherein $R^1$ is an alkyl group having 4 to 10 carbon atoms.

5. The compound of claim 1, wherein X is a bond or —O—.

6. The compound of claim 1, wherein the divalent hydrocarbon group for L is an alkylene group having 1 to 10 carbon atom(s).

7. The compound of claim 1, wherein $R^2$ is an optionally substituted hydrocarbon group.

8. The compound of claim 1, wherein $R^2$ is an alkyl group having 1 to 10 carbon atom(s), an aryl group having 6 to 14 carbon atoms or an aralkyl group having 7 to 13 carbon atoms, each optionally having 1 to 3 substituent(s) selected from halogen atom, hydroxy group, nitro group, amino group, optionally halogenated alkyl group having 1 to 6 carbon atom(s), alkoxy group having 1 to 6 carbon atom(s), aromatic heterocyclic group and cycloalkyl group having 3 to 10 carbon atoms.

9. The compound of claim 1, which is 2-[3-(aminomethyl)-4-butoxy-2-isobutyl-1-oxo-1,2-dihydro-6-isoquinolyl]-1,3-thiazole-4-carbonitrile, 2-[3-(aminomethyl)-4-butoxy-2-isobutyl-1-oxo-1,2-dihydro-6-isoquinolyl]-1,3-thiazole-4-carboxylic acid, 2-[3-(aminomethyl)-4-butoxy-2-isobutyl-1-oxo-1,2-dihydro-6-isoquinolyl]-1,3-thiazole-4-carboxamide, ethyl 2-[3-(aminomethyl)-4-butoxy-2-isobutyl-1-oxo-1,2-dihydro-6-isoquinolyl]-1,3-thiazole-4-carboxylate, (E)-3-[3-(aminomethyl)-4-butoxy-2-isobutyl-1-oxo-1,2-dihydro-6-isoquinolyl]-2-propenamide, (E)-3-[3-(aminomethyl)-2-isobutyl-4-phenyl-1-oxo-1,2-dihydro-6-isoquinolyl]-2-propenamide, 3-(aminomethyl)-2-isobutyl-1-oxo-4-phenyl-1,2-dihydro-6-isoquinolinecarboxamide, 2-[[3-(aminomethyl)-2-isobutyl-4-phenyl-1-oxo-1,2-dihydro-6-isoquinolyl]oxy]acetamide, or a salt thereof.

10. A crystal of 2-[3-(aminomethyl)-4-butoxy-2-isobutyl-1-oxo-1,2-dihydro-6-isoquinolyl]-1,3-thiazole-4-carbonitrile or a salt thereof.

11. A crystal of 2-[3-(aminomethyl)-4-butoxy-2-isobutyl-1-oxo-1,2-dihydro-6-isoquinolyl]-1,3-thiazole-4-carboxamide or a salt thereof.

12. A crystal of 2-[3-(aminomethyl)-4-butoxy-2-isobutyl-1-oxo-1,2-dihydro-6-isoquinolyl]-1,3-thiazole-4-carboxamide or a salt thereof.

13. A crystal of ethyl 2-[3-(aminomethyl)-4-butoxy-2-isobutyl-1-oxo-1,2-dihydro-6-isoquinolyl]-1,3-thiazole-4-carboxylate or a salt thereof.

14. A crystal of (E)-3-[3-(aminomethyl)-4-butoxy-2-isobutyl-1-oxo-1,2-dihydro-6-isoquinolyl]-2-propenamide or a salt thereof.

15. A crystal of (E)-3-[3-(aminomethyl)-2-isobutyl-4-phenyl-1-oxo-1,2-dihydro-6-isoquinolyl]-2-propenamide or a salt thereof.

16. A crystal of 3-(aminomethyl)-2-isobutyl-1-oxo-4-phenyl-1,2-dihydro-6-isoquinolinecarboxamide or a salt thereof.

17. A crystal of 2-[[3-(aminomethyl)-2-isobutyl-4-phenyl-1-oxo-1,2-dihydro-6-isoquinolyl]oxy]acetamide or a salt thereof.

18. A pharmaceutical composition comprising a compound of the formula

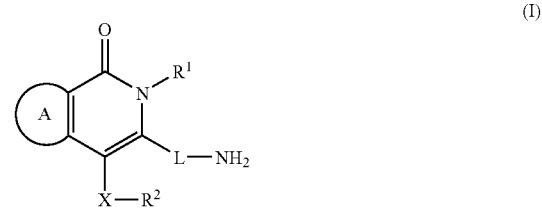

wherein ring A is a 5 to 10-membered aromatic ring having 1 to 3 substituent(s) selected from 1) a nitro group;
2) a cyano group;
3) a $C_{1-3}$ alkylenedioxy group;
4) a $C_{1-10}$ alkyl group or a $C_{2-10}$ alkenyl group, each having 1 to 3 substituent(s) selected from hydroxy group, carboxyl group, alkoxycarbonyl group having 2 to 8 carbon atoms, carbamoyl group, cyano group, amino group, alkanoylamino group having 2 to 8 carbon atoms, alkoxycarbonylamino group having 2 to 8 carbon atoms and alkylsulfonylamino group having 1 to 8 carbon atom(s);
5) an alkoxy group having 1 to 10 carbon atom(s), a cycloalkyloxy group having 3 to 10 carbon atoms or an aralkyloxy group having 7 to 13 carbon atoms, each having 1 to 3 substituent(s) selected from alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms;
6) an acyl group;
7) an optionally substituted amino group;
8) an aryl group having 6 to 14 carbon atoms;
9) an optionally substituted thiol group;
10) an optionally substituted heterocyclic group; and
11) an amidino group;

$R^1$ and $R^2$ are the same or different and each is an optionally substituted hydrocarbon group or an optionally substituted heterocyclic group;

X is a bond, —O—, —S—, —SO—, —$SO_2$— or —$NR^3$— ($R^3$ is a hydrogen atom or an optionally substituted hydrocarbon group); and L is a divalent hydrocarbon group or a salt thereof and a pharmacologically acceptable carrier.

19. A pharmaceutical composition comprising the pharmaceutical composition of claim 19 and a pharmacologically acceptable carrier in combination with at least one member selected from an insulin preparation, an insulin sensitizer, an α-glucosidase inhibitor, a biguanide and an insulin secretagogue.

20. A method of treatment of diabetes in a mammal, which method comprising administering a compound of the formula

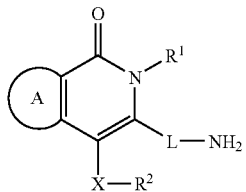

wherein
ring A is a 5 to 10-membered aromatic ring having 1 to 3 substituent(s) selected from
1) a nitro group;
2) a cyano group;
3) a $C_{1-3}$ alkylenedioxy group;
4) a $C_{1-10}$ alkyl group or a $C_{2-10}$ alkenyl group, each having 1 to 3 substituent(s) selected from hydroxy group, carboxyl group, alkoxycarbonyl group having 2 to 8 carbon atoms, carbamoyl group, cyano group, amino group, alkanoylamino group having 2 to 8 carbon atoms, alkoxycarbonylamino group having 2 to 8 carbon atoms and alkylsulfonylamino group having 1 to 8 carbon atom(s);
5) an alkoxy group having 1 to 10 carbon atom(s), a cycloalkyloxy group having 3 to 10 carbon atoms or an aralkyloxy group having 7 to 13 carbon atoms, each having 1 to 3 substituent(s) selected from alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms;
6) an acyl group;
7) an optionally substituted amino group;
8) an aryl group having 6 to 14 carbon atoms;
9) an optionally substituted thiol group;
10) an optionally substituted heterocyclic group; and
11) an amidino group;
$R^1$ and $R^2$ are the same or different and each is an optionally substituted hydrocarbon group or an optionally substituted heterocyclic group;
X is a bond, —O—, —S—, —SO—, —$SO_2$— or —$NR^3$— ($R^3$ is a hydrogen atom or an optionally substituted hydrocarbon group); and
L is a divalent hydrocarbon group, a salt thereof or a prodrug thereof to the mammal.
21. A method of treatment of diabetic complications in a mammal, which method comprising administering a compound of the formula

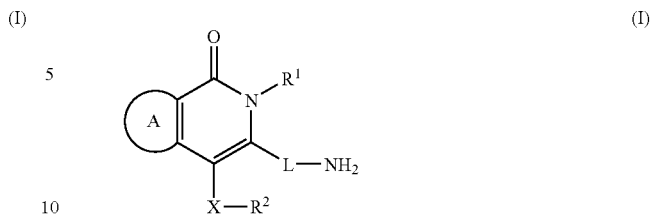

wherein
ring A is a 5 to 10-membered aromatic ring having 1 to 3 substituent(s) selected from
1) a nitro group;
2) a cyano group;
3) a $C_{1-3}$ alkylenedioxy group;
4) a $C_{1-10}$ alkyl group or a $C_{2-10}$ alkenyl group, each having 1 to 3 substituent(s) selected from hydroxy group, carboxyl group, alkoxycarbonyl group having 2 to 8 carbon atoms, carbamoyl group, cyano group, amino group, alkanoylamino group having 2 to 8 carbon atoms, alkoxycarbonylamino group having 2 to 8 carbon atoms and alkylsulfonylamino group having 1 to 8 carbon atom(s);
5) an alkoxy group having 1 to 10 carbon atom(s), a cycloalkyloxy group having 3 to 10 carbon atoms or an aralkyloxy group having 7 to 13 carbon atoms, each having 1 to 3 substituent(s) selected from alkoxy group having 1 to 3 carbon atom(s), alkoxycarbonyl group having 2 to 5 carbon atoms, alkanoyl group having 2 to 5 carbon atoms, cyano group, carbamoyl group, hydroxy group, carboxyl group, amino group, alkanoylamino group having 2 to 5 carbon atoms and cycloalkyl group having 3 to 10 carbon atoms;
6) an acyl group;
7) an optionally substituted amino group;
8) an aryl group having 6 to 14 carbon atoms;
9) an optionally substituted thiol group;
10) an optionally substituted heterocyclic group; and
11) an amidino group;
$R^1$ and $R^2$ are the same or different and each is an optionally substituted hydrocarbon group or an optionally substituted heterocyclic group;
X is a bond, —O—, —S—, —SO—, —$SO_2$— or —$NR^3$— ($R^3$ is a hydrogen atom or an optionally substituted hydrocarbon group); and
L is a divalent hydrocarbon group, a salt thereof or a prodrug thereof to the mammal.

* * * * *

UNITED STATES PATENT AND TRADEMARK OFFICE
CERTIFICATE OF CORRECTION

| | | |
|---|---|---|
| PATENT NO. | : 7,034,039 B2 | Page 1 of 1 |
| APPLICATION NO. | : 10/470805 | |
| DATED | : April 25, 2006 | |
| INVENTOR(S) | : Satoru Oi et al. | |

It is certified that error appears in the above-identified patent and that said Letters Patent is hereby corrected as shown below:

Claim 19, column 306, line 60, please change "19" to -- 18 --.

Signed and Sealed this

Twenty-second Day of May, 2007

JON W. DUDAS
*Director of the United States Patent and Trademark Office*